(12) United States Patent
Luo et al.

(10) Patent No.: US 12,110,290 B2
(45) Date of Patent: *Oct. 8, 2024

(54) TRIAZOLOPYRIDINYL COMPOUNDS AS KINASE INHIBITORS

(71) Applicant: BRISTOL-MYERS SQUIBB COMPANY, Princeton, NJ (US)

(72) Inventors: Guanglin Luo, Newtown, PA (US); Jie Chen, Cambridge, MA (US); Carolyn Diane Dzierba, Medford, MA (US); David B. Frennesson, Naugatuck, CT (US); Junqing Guo, Princeton, NJ (US); Amy C. Hart, Littleton, CO (US); Xirui Hu, Cambridge, MA (US); Michael E. Mertzman, New Hope, PA (US); Matthew Reiser Patton, Cambridge, MA (US); Jianliang Shi, Furlong, PA (US); Steven H. Spergel, Warrington, PA (US); Brian Lee Venables, Durham, CT (US); Yong-Jin Wu, Madison, CT (US); Zili Xiao, East Windsor, NJ (US); Michael G. Yang, Narberth, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/347,703

(22) Filed: Jul. 6, 2023

(65) Prior Publication Data

US 2024/0109888 A1 Apr. 4, 2024

Related U.S. Application Data

(63) Continuation of application No. 17/503,516, filed on Oct. 18, 2021, now Pat. No. 11,767,322.

(60) Provisional application No. 63/093,463, filed on Oct. 19, 2020.

(51) Int. Cl.
   *C07D 471/04* (2006.01)
(52) U.S. Cl.
   CPC .................. *C07D 471/04* (2013.01)
(58) Field of Classification Search
   CPC ................................................... C07D 471/04
   USPC ........................................................ 514/303
   See application file for complete search history.

(56) References Cited

U.S. PATENT DOCUMENTS

| 8,258,122 B2 | 9/2012 | Vidal et al. |
| 8,598,163 B2 | 12/2013 | Claremon et al. |
| 10,913,738 B2 | 2/2021 | Guo et al. |
| 11,440,913 B2 | 9/2022 | Mertzman et al. |
| 11,767,322 B2* | 9/2023 | Luo .................. A61P 29/00 514/303 |
| 2005/0288502 A1 | 12/2005 | Andersen et al. |
| 2007/0191395 A1 | 8/2007 | Kawakami et al. |
| 2011/0105457 A1 | 5/2011 | Taniyama et al. |
| 2015/0322111 A1 | 11/2015 | Borzilleri et al. |
| 2016/0207928 A1 | 7/2016 | Schulze et al. |
| 2018/0317492 A1 | 11/2018 | Tanaka et al. |
| 2019/0389858 A1 | 12/2019 | Maehata et al. |
| 2020/0277296 A1 | 9/2020 | Mertzman et al. |
| 2020/0347071 A1 | 11/2020 | Watterson et al. |
| 2021/0309633 A1 | 10/2021 | Guo et al. |
| 2022/0177462 A1 | 6/2022 | Zhou et al. |
| 2022/0315580 A1 | 10/2022 | Guo et al. |
| 2022/0380335 A1 | 12/2022 | Guo et al. |
| 2022/0380355 A1 | 12/2022 | Chen et al. |

FOREIGN PATENT DOCUMENTS

| EP | 3943488 A1 | 1/2022 |
| WO | 2008107125 A1 | 9/2008 |
| WO | 2010/007099 A1 | 1/2010 |
| WO | 2010007100 A1 | 1/2010 |
| WO | 2010057877 A1 | 5/2010 |
| WO | 2010091067 A2 | 8/2010 |
| WO | 2014198594 A1 | 12/2014 |
| WO | 2016027253 A1 | 2/2016 |
| WO | 2016064957 A1 | 4/2016 |
| WO | 2016064958 A1 | 4/2016 |
| WO | 2018017435 A1 | 1/2018 |
| WO | 2018139436 A1 | 8/2018 |
| WO | 2018148626 A1 | 8/2018 |

(Continued)

OTHER PUBLICATIONS

Bundgaard, H., "Design of Prodrugs", Elsevier, 1985, and Widder, K., et al., "Methods in Enzymology, vol. 112, Drug and Enzyme Targeting", Part A, Academic Press, 1985, vol. 112, pp. 309-396.

(Continued)

*Primary Examiner* — Niloofar Rahmani
(74) *Attorney, Agent, or Firm* — Mary K. VanAtten

(57) ABSTRACT

Compounds having formula (I), and enantiomers, and diastereomers, stereoisomers, pharmaceutically-acceptable salts thereof,

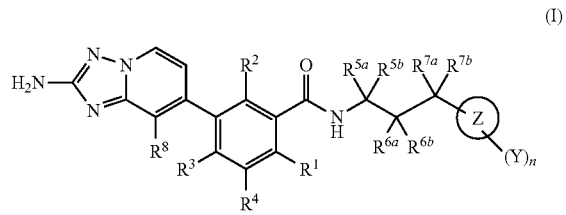

(I)

are useful as kinase modulators, including RIPK1 modulation. All the variables are as defined herein.

14 Claims, No Drawings

(56) References Cited

FOREIGN PATENT DOCUMENTS

| WO | 2018237370 A1 | 12/2018 |
| WO | 2019089442 A1 | 5/2019 |
| WO | 2019147782 A1 | 8/2019 |
| WO | 2020/056072 A1 | 3/2020 |
| WO | 2020056074 A1 | 3/2020 |
| WO | 2020/097400 A1 | 5/2020 |
| WO | 2020/192562 A1 | 10/2020 |
| WO | 2021067654 A1 | 4/2021 |
| WO | 2022052861 A1 | 3/2022 |

OTHER PUBLICATIONS

Bundgaard, Hans, "Design and Application of Prodrugs", Korsgaard-Larsen, P., et al., A Textbook of Drug Design and Development, Harwood Academic Publishers, 1991, pp. 113-191.

Bundgaard, Hans, "Means to Enhance Penetration, Prodrugs as a means to improve the delivery of peptide drugs", Advanced Drug Delivery Reviews, 1992, vol. 8, pp. 1-38.

Cho et al., "Phosphorylation-Driven Assembly of the RIP1-RIP3 Complex Regulates Programmed Necrosis and Virus-Induced Inflammation", Cell vol. 137, pp. 1112-1123 (2009).

Degterev et al., "Chemical inhibitor of nonapoptotic cell death with therapeutic potential for ischemic brain injury", Nat. Chem. Biol., vol. 1, pp. 112-119 (2005).

Degterev et al., "Identification of RIP1 kinase as a specific cellular target of necrostatins", Nat. Chem. Biol. vol. 4, pp. 313-321 (2008).

Duprez et al., "RIP Kinase-Dependent Necrosis Drives Lethal Systemic Inflammatory Response Syndrome", Immunity vol. 35, pp. 908-918 (2011).

Festjens et al., "Necrosis, a well-orchestrated form of cell demise: Signalling cascades, important mediators and concomitant immune response", Biochimica et Biophysica Acta vol. 1757, pp. 1371-1387 (2006).

Golstein et al., "Cell death by necrosis: towards a molecular definition", Trends in Biochemical Sciences vol. 32 No. 1, pp. 37-43.

Harris et al., "Discovery of Small Molecule RIP1 Kinase Inhibitors for the Treatment of Pathologies Associated with Necroptosis", Medicinal Chemistry Letters, vol. 4, pp. 1238-1243 (2013).

He et al., "Receptor Interacting Protein Kinase-3 Determines Cellular Necrotic Response to TNF-a", Cell vol. 137, pp. 1100-1111 (2009).

Holler et al., "Fas triggers an alternative, caspase-8-independent cell death pathway using the kinase RIP as effector molecule", Nature America Inc., Immunol. vol. 1, pp. 489-495 (2009).

ISR-WO-PCT, PCT/US2021-055340 Mailed Jan. 26, 2022.

Ito et al., "RIPK1 mediates axonal degeneration by promoting inflammation and necroptosis in ALS", Science vol. 353, pp. 603-608 (2016).

Kroemer et al., "Classification of cell death: recommendations of the Nomenclature Committee on Cell Death", Cell Death and Differentiation vol. 16, pp. 3-11 (2009).

Li, et al "Combination of 2-methoxy-3 phenylsulfonylaminobenzamide and 2-aminobenzothiazole to discover novel anticancer agents", Bioorganic & Medicinal Chemistry 22 (2014) 3739-3748.

Lin et al., "A Role of RIP3-Mediated Macrophage Necrosis in Atherosclerosis Development", Cell Reports vol. 3, pp. 200-210 (2013).

Miyaura et al. "Palladium-Catalyzed Cross-Coupling Reactions of Organoboron Compounds", Chemical Review, vol. 95, pp. 2457-2483 (1995).

Montalbetti, et al., "Amide bond formation and peptide coupling", Tetrahedron, vol. 61, pp. 10827-10852 (2005).

Moriwaki et al., "RIP3: a molecular switch for necrosis and inflammation", Genes & Development vol. 27, pp. 1640-1649 (2013).

Remington's Pharmaceutical Sciences, 17th Edition, p. 1418, Mack Publishing Company, Easton, PA (1985).

Roychowdhury et al., "Absence of Receptor Interacting Protein Kinase 3 Prevents Ethanol-Induced Liver Injury", Hepatology vol. 57, pp. 1773-1783 (2013).

Schreiber et al. "Necroptosis controls NET generation and mediates complement activation, endothelial damage, and autoimmune vasculitis", PNAS, vol. 114(45), pp. E9618-E9625 (2017).

Sinha et al., "Regioselective synthesis of fluoroaldols. Studies towardfluoroepothilones syntheses via antibody catalysis", Tetrahedron Letters, vol. 43(21), pp. 8243-8246 (2000).

Trichonas et al., "Receptor interacting protein kinases mediate retinal detachment-induced photoreceptor necrosis and compensate for inhibition of apoptosis", Proc. Natl. Acad. Sci. vol. 107, pp. 21695-21700 (2010).

Vandenabeele et al., "Molecular mechanisms of necroptosis: an ordered cellular explosion", Nature, vol. 10, pp. 700-714 (2010).

Vandenabeele et al., "The Role of the Kinases RIP1 and RIP3 in TNF-Induced Necrosis", Science Signaling vol. 3, pp. 1-8 (2010).

Vitner et al., "RIPK3 as a potential therapeutic target for Gaucher's disease", Nature Medicine vol. 20, pp. 204-208 (2014).

Zhang et al., "Receptor-interacting protein (RIP) kinase family", Cellular & Molecular Immunology vol. 7, pp. 243-249 (2010).

Zhang et al., RIP3, an Energy Metabolism Regulator That Switches TNF-Induced Cell Death from Apoptosis to Necrosis, Science vol. 325 pp. 332-336 (2009).

U.S. Office Action of U.S. Appl. No. 17/116,016 mailed Jan. 23, 2024.

* cited by examiner

TRIAZOLOPYRIDINYL COMPOUNDS AS KINASE INHIBITORS

CROSS REFERENCE TO RELATED APPLICATIONS

This application is a continuation application of U.S. patent application Ser. No. 17/503,516 filed Oct. 18, 2021, (now allowed) which is entitled to priority pursuant to 35 U.S.C. § 119(e) to U.S. provisional patent application No. 63/093,463, filed Oct. 19, 2020, which is incorporated herein in its entirety.

FIELD OF THE INVENTION

The present invention relates to novel compounds that inhibit receptor interacting protein kinases and methods of making and using the same. Specifically, the present invention relates to triazolopyridinyl compounds as receptor interacting protein kinase 1 (RIPK1) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) Cell Death Differ 16:3-11). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein P & Kroemer G (2007) Trends Biochem. Sci. 32:37-43; Festjens et al. (2006) Biochim. Biophys. Acta 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al. (2000) Nat. Immunol. 1:489-495; Degterev et al. (2008) Nat. Chem. Biol. 4:313-321). This novel mechanism of cell death is termed "programmed necrosis" or "necroptosis" (Degterev et al., (2005) Nat Chem Biol 1:112-119).

Necroptosis can be triggered by a number of mechanisms including of TNF receptor activation, Toll-like receptor engagement, genotoxic stress and viral infection. Downstream of the various stimuli, the signaling pathway that results in necroptosis is dependent on RIPK1 and RIPK3 kinase activity. (He et al., (2009) Cell 137:1100-1111; Cho et. al., (2009) Cell 137:1112-1123; Zhang et al., (2009) Science 325:332-336).

Dysregulation of the necroptosis signaling pathway has been linked to inflammatory diseases such as macrophage necrosis in atherosclerosis development, virus-induced inflammation, systemic inflammatory response syndrome and ethanol-induced liver injury, neurodegeneration such as detachment of the retina, ischemia, amyotrophic lateral sclerosis (ALS), Gaucher's disease, and AAV (ANCA-associated vasculitis) (Trichonas et al., (2010) Proc. Natl. Acad. Sci. 107, 21695-21700; Lin et al., (2013) Cell Rep. 3, 200-210; Cho et al., (2009) Cell, 137, 1112-1123; Duprez et al., (2011) Immunity 35, 908-918; Roychowdhury et al., Hepatology 57, 1773-1783; Vandenabeele et al., (2010) Nature 10, 700-714; Vandenabeele et al., (2010) Sci. Signalling 3, 1-8; Zhang et al., (2010) Cellular & Mol. Immunology 7, 243-249; Moriwaki et al., (2013) Genes Dev. 27, 1640-1649; Ito et al., (2016) Science 353, 603-608; Vitner et al., (2014) Nature Med. 20, 204-208) (Schreiber et al., (2017) Proc. Natl. Acad. Sci. 114, E9618-E9625).

A potent, selective, small molecule inhibitor of RIPK1 activity would block RIPK1-dependent pro-inflammatory signaling and thereby provide a therapeutic benefit in inflammatory diseases characterized by increased and/or dysregulated RIPK1 kinase activity.

SUMMARY OF THE INVENTION

The present invention provides novel triazolopyridinyl compounds including stereoisomers, tautomers, isotopes, prodrugs, pharmaceutically acceptable salts, salts, or solvates thereof, which are useful as inhibitors of RIPK1. Alternatively, compounds may be useful as a prodrug of an inhibitor of RIPK1.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, isotopes, prodrugs, pharmaceutically acceptable salts, salts, or solvates thereof.

The compounds of the invention may be used in the treatment and/or prophylaxis of conditions associated with aberrant RIPK1 activity.

The compounds of the present invention may be used in therapy.

The compounds of the present invention may be used for the manufacture of a medicament for the treatment and/or prophylaxis of a condition associated with aberrant RIPK1 activity.

In another aspect, the present invention is directed to a method of treating diseases mediated at least partially by RIPK1 including inflammatory diseases, ischemia, neurodegeneration, and Gaucher's disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I) or stereoisomers, tautomers, isotopes, salts, pharmaceutically acceptable salts, solvates, or prodrugs thereof, wherein

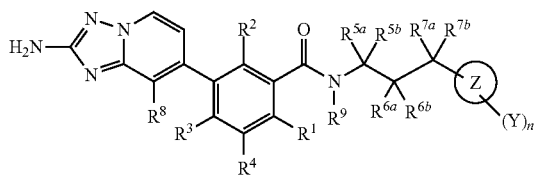

(I)

wherein
$R^1$ is H, $C_{1-3}$ alkyl, $C_{1-3}$ alkoxy, $C_{1-3}$ haloalkyl, $C_{1-3}$ haloalkoxy, $C_{1-3}$ deuteroalkyl, $C_{1-3}$ deuteroalkoxy, halo, or cyclopropyl;
$R^2$ is H, or halo;
$R^3$ is H, halo, or $C_{1-3}$ alkyl or $C_{1-3}$ deuteroalkyl;
$R^4$ is H or F;
$R^{5a}$ and $R^{5b}$ are each, independently, H, deuterium, $C_{1-3}$ alkyl or $C_{1-3}$ haloalkyl; alternatively, $R^{5a}$ and $R^{5b}$ join to form cyclopropyl;
$R^{6a}$ and $R^{6b}$ are each, independently, H, deuterium, OH, F, $C_{1-3}$ alkyl, or C(O)-4-fluorophenyl;
alternatively, $R^{6a}$ and $R^{6b}$ are =O, or join to form cyclopropyl or oxetanyl;
$R^{7a}$ and $R^{7b}$ are each, independently, H, deuterium, OH, OP(O)(OR)$_2$, OC(O)NH$_2$, NH$_2$, F, $C_{1-3}$ alkyl, $C_{1-3}$ alkoxy, OCD$_3$, or $C_{1-3}$ haloalkyl;
alternatively, $R^{7a}$ and $R^{7b}$ are =O, or join to form cyclopropyl or oxetanyl;
R is H or $C_{1-3}$ alkyl;
$R^8$ is H, F, Cl, $C_{1-3}$ alkyl, $C_{1-3}$ alkoxy, $C_{1-3}$ deuteroalkyl, or $C_{1-3}$ deuteroalkoxy;
$R^9$ is H or CH$_3$;
ring Z is phenyl, a 6 membered heteroaryl ring having 1-2 nitrogen atoms, cyclohexyl, cyclopentyl, or cyclobutyl;
Y is F, Cl, $C_{1-3}$ alkyl, $C_{1-3}$ alkoxy, CN, $C_{1-3}$ haloalkyl, $C_{1-3}$ haloalkoxy, $C_{1-3}$ deuteroalkyl, $C_{1-3}$ deuteroalkoxy, C(O)OCH$_3$, or C≡CH;
n is 0, 1, 2, or 3.

Another embodiment provides a compound of Formula (II), or stereoisomers, tautomers, isotopes, salts, pharmaceutically acceptable salts, solvates, or prodrugs thereof, wherein

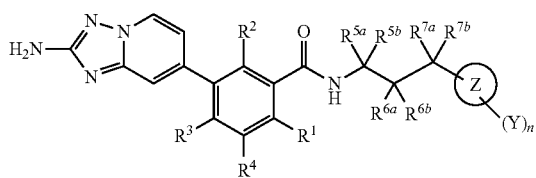

(II)

wherein
$R^1$ is H, $C_{1-3}$ alkyl, $C_{1-3}$ alkoxy, $C_{1-3}$ haloalkyl, $C_{1-3}$ deuteroalkyl, halo, or cyclopropyl;
$R^2$ is H, or halo;
$R^3$ is H, halo, or $C_{1-3}$ alkyl or $C_{1-3}$ deuteroalkyl;
$R^4$ is H or F;
$R^{5a}$ and $R^{5b}$ are each, independently, H, deuterium, $C_{1-3}$ alkyl or $C_{1-3}$ haloalkyl;
$R^{6a}$ and $R^{6b}$ are each, independently, H, deuterium, OH, F, or $C_{1-3}$ alkyl;
alternatively, $R^{6a}$ and $R^{6b}$ are =O, or join to form cyclopropyl or oxetanyl;
$R^{7a}$ and $R^{7b}$ are each, independently, H, deuterium, OH, OP(O)(OR)$_2$, F, $C_{1-3}$ alkyl or $C_{1-3}$ haloalkyl;
alternatively, $R^{7a}$ and $R^{7b}$ are =O, or join to form cyclopropyl or oxetanyl;
R is H or $C_{1-3}$ alkyl;
ring Z is phenyl, a 6 membered heteroaryl ring having 1-2 nitrogen atoms, cyclohexyl, or cyclopentyl;
Y is F, Cl, $C_{1-3}$ alkyl, $C_{1-3}$ alkoxy, CN, or $C_{1-3}$ haloalkyl;
n is 0, 1, 2, or 3.

Another embodiment provides a compound of Formula (I), or stereoisomers, tautomers, isotopes, salts, pharmaceutically acceptable salts, solvates, or prodrugs thereof, wherein
$R^1$ is H, $C_{1-3}$ alkyl, $C_{1-3}$ alkoxy, $C_{1-3}$ haloalkyl, $C_{1-3}$ deuteroalkyl, halo, or cyclopropyl;
$R^2$ is H, or halo;
$R^3$ is H, halo, or $C_{1-3}$ alkyl or $C_{1-3}$ deuteroalkyl;
$R^4$ is H or F;
$R^{5a}$ and $R^{5b}$ are each, independently, H, deuterium, $C_{1-3}$ alkyl or $C_{1-3}$ haloalkyl;
$R^{6a}$ and $R^{6b}$ are each, independently, H, deuterium, OH, F, or $C_{1-3}$ alkyl;
$R^{7a}$ and $R^{7b}$ are each, independently, H, deuterium, OH, F, $C_{1-3}$ alkyl or $C_{1-3}$ haloalkyl;
alternatively, $R^{7a}$ and $R^{7b}$ are =O, or join to form cyclopropyl or oxetanyl;
ring Z is phenyl, a 6 membered heteroaryl ring having 1-2 nitrogen atoms, cyclohexyl, or cyclopentyl;
Y is F, Cl, $C_{1-3}$ alkyl, $C_{1-3}$ alkoxy, CN, or $C_{1-3}$ haloalkyl;
n is 0, 1, or 2.

Another embodiment provides a compound of Formula (I), or stereoisomers, tautomers, isotopes, salts, pharmaceutically acceptable salts, solvates, or prodrugs thereof, wherein
$R^1$ is H, $C_{1-3}$ alkyl, $C_{1-3}$ alkoxy, $C_{1-3}$ haloalkyl, $C_{1-3}$ deuteroalkyl, $C_{1-3}$ deuteroalkoxy, halo, or cyclopropyl;
$R^2$ is H, or halo;
$R^3$ is H, halo, or $C_{1-3}$ alkyl or $C_{1-3}$ deuteroalkyl;
$R^4$ is H or F;
$R^{5a}$ and $R^{5b}$ are each, independently, H, deuterium, $C_{1-3}$ alkyl or $C_{1-3}$ haloalkyl;
$R^{6a}$ and $R^{6b}$ are each, independently, H, deuterium, OH, F, or $C_{1-3}$ alkyl;
$R^{7a}$ and $R^{7b}$ are each, independently, H, deuterium, OH, F, $C_{1-3}$ alkyl or $C_{1-3}$ haloalkyl; alternatively, $R^{7a}$ and $R^{7b}$ are =O, or join to form cyclopropyl or oxetanyl;
ring Z is phenyl, a 6 membered heteroaryl ring having 1-2 nitrogen atoms, cyclohexyl, or cyclopentyl;
Y is F, Cl, $C_{1-3}$ alkyl, $C_{1-3}$ alkoxy, CN, or $C_{1-3}$ haloalkyl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein
$R^1$ is H, $C_{1-2}$ alkyl, $C_{1-2}$ alkoxy, CD$_3$, halo, or cyclopropyl;
$R^2$ is H, or halo;
$R^3$ is H, halo, or $C_{1-2}$ alkyl;
$R^4$ is H or F;
$R^{5a}$ and $R^{5b}$ are each, independently, H, deuterium, $C_{1-2}$ alkyl or $C_{1-2}$ haloalkyl;
$R^{6a}$ and $R^{6b}$ are each, independently, H, deuterium, F, or $C_{1-2}$ alkyl;
$R^{7a}$ and $R^{7b}$ are each, independently, H, deuterium, OH, F, $C_{1-2}$ alkyl or $C_{1-2}$ haloalkyl;
alternatively, $R^{7a}$ and $R^{7b}$ are =O, or join to form cyclopropyl;

Y is F, Cl, $C_{1-2}$ alkyl, $C_{1-2}$ alkoxy, CN, or $C_{1-2}$ haloalkyl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein
$R^1$ is H, $C_{1-2}$ alkyl, $C_{1-2}$ alkoxy, $CD_3$, halo, or cyclopropyl;
$R^2$ is H, or halo;
$R^3$ is H, halo, or $C_{1-2}$ alkyl;
$R^4$ is H or F;
$R^{5a}$ and $R^{5b}$ are each, independently, H, deuterium, $C_{1-2}$ alkyl or $C_{1-2}$ haloalkyl;
$R^{6a}$ and $R^{6b}$ are each, independently, H, deuterium, F, or $C_{1-2}$ alkyl;
$R^{7a}$ and $R^{7b}$ are each, independently, H, deuterium, OH, F, $C_{1-2}$ alkyl, $C_{1-2}$ deuteroalkyl, or $C_{1-2}$ haloalkyl;
alternatively, $R^{7a}$ and $R^{7b}$ are =O, or join to form cyclopropyl:
Y is F, Cl, $C_{1-2}$ alkyl, $C_{1-2}$ alkoxy, CN, or $C_{1-2}$haloalkyl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein
Ring Z is phenyl, pyridinyl, pyrimidinyl, pyrazinyl, or pyridazinyl.

Another embodiment provides a compound of Formula (I) or (II), or stereoisomers, tautomers, isotopes, salts, pharmaceutically acceptable salts, solvates, or prodrugs thereof, wherein
Ring Z is cyclohexyl or cyclopentyl.

Another embodiment provides a compound of Formula (I) or (II), or stereoisomers, tautomers, isotopes, salts, pharmaceutically acceptable salts, solvates, or prodrugs thereof, wherein
$R^1$ is $C_{1-2}$ alkyl, $C_{1-2}$ deuteroalkyl, $C_{1-2}$ haloalkyl, or halo;
$R^2$ is H, or halo;
$R^3$ is H, halo, or $C_{1-2}$ alkyl;
$R^4$ is H or F;
$R^{5a}$ and $R^{5b}$ are each, independently, H, deuterium, $C_{1-2}$ alkyl or $C_{1-3}$ haloalkyl;
$R^{6a}$ and $R^{6b}$ are each, independently, H, deuterium, F, or $C_{1-3}$ alkyl;
$R^{7a}$ and $R^{7b}$ are each, independently, H, deuterium, OH, F, $C_{1-4}$ alkyl or $C_{1-3}$ haloalkyl;
alternatively, $R^{7a}$ and $R^{7b}$ are =O, or join to form cyclopropyl
Y is F, Cl, $C_{1-2}$ alkyl, CN, or $C_{1-2}$haloalkyl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein
$R^1$ is Cl or $CH_3$;
$R^2$ is H, or F;
$R^3$ is H, or F;
$R^4$ is H;
$R^{5a}$ and $R^{5b}$ are each H;
$R^{6a}$ and $R^{6b}$ are each, independently, H, or F;
one of $R^{7a}$ and $R^{7b}$ is H and, the other is OH;
Y is F or Cl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein $R^1$ is Cl or $CH_3$;
$R^2$ is H, or F;
$R^3$ is H, or F;
$R^4$ is H;
$R^{5a}$ and $R^{5b}$ are each H;
$R^{6a}$ and $R^{6b}$ are each, independently, H, or F;
one of $R^{7a}$ and $R^{7b}$ is H, $CH_3$ or $CD_3$; and, the other is OH;
Y is F or Cl;
n is 0, 1, or 2.

Another embodiment provides a compound of Formula (I) or (II), or stereoisomers, tautomers, isotopes, salts, pharmaceutically acceptable salts, solvates, or prodrugs thereof, wherein
$R^{5a}$ and $R^{5b}$ are each H;
$R^{6a}$ and $R^{6b}$ are each, independently, H, or F;
one of $R^{7a}$ and $R^{7b}$ is H and, the other is OH.

Another embodiment provides a compound of Formula (I) or (II), or stereoisomers, tautomers, isotopes, salts, pharmaceutically acceptable salts, solvates, or prodrugs thereof, wherein
$R^{5a}$ and $R^{5b}$ are each H;
$R^{6a}$ and $R^{6b}$ are each, independently, H, or F;
one of $R^{7a}$ and $R^{7b}$ is H, $CH_3$ or $CD_3$; and, the other is OH.

Another embodiment provides a compound of Formula (I) or (II), or stereoisomers, tautomers, isotopes, salts, pharmaceutically acceptable salts, solvates, or prodrugs thereof, wherein
one of $R^{7a}$ and $R^{7b}$ is H and the other is $OP(O)(OR)_2$; and
R is H or $C_{1-3}$ alkyl.

Another embodiment provides a compound of Formula (I) or (II), or stereoisomers, tautomers, isotopes, salts, pharmaceutically acceptable salts, solvates, or prodrugs thereof, wherein
Ring Z is

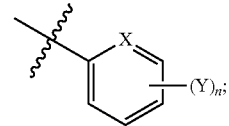

X is CH, N, or C—Y.

Another embodiment provides a compound of Formula (I) or (II), or stereoisomers, tautomers, isotopes, salts, pharmaceutically acceptable salts, solvates, or prodrugs thereof, wherein
Ring Z is pyridinyl.

Another embodiment provides a compound of Formula (I) or (II), or stereoisomers, tautomers, isotopes, salts, pharmaceutically acceptable salts, solvates, or prodrugs thereof, wherein
Ring Z is phenyl.

Another embodiment provides a compound of Formula (I) or (II), or stereoisomers, tautomers, isotopes, salts, pharmaceutically acceptable salts, solvates, or prodrugs thereof, wherein
Ring Z is phenyl, pyridinyl, pyrimidinyl, pyrazinyl, or pyridazinyl.

Another embodiment provides a compound of Formula (I), or stereoisomers, tautomers, isotopes, salts, pharmaceutically acceptable salts, solvates, or prodrugs thereof, wherein the compound is of formula (Ia)

(Ia)

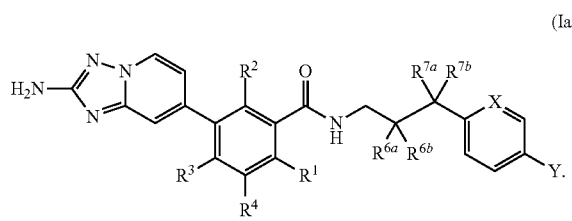

Another embodiment provides a compound of Formula (I), or stereoisomers, tautomers, isotopes, salts, pharmaceutically acceptable salts, solvates, or prodrugs thereof, wherein the compound is of formula (Ib)

(Ib)

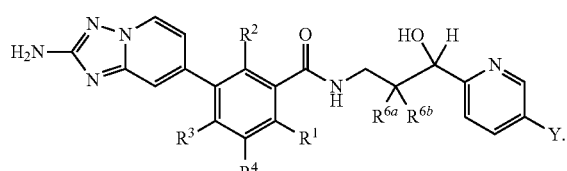

Another embodiment provides a compound of Formula (I), or stereoisomers, tautomers, isotopes, salts, pharmaceutically acceptable salts, solvates, or prodrugs thereof, wherein the compound is of formula (Ic)

(Ic)

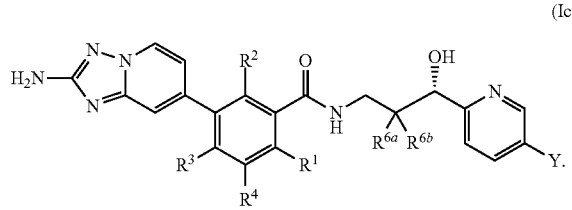

Another embodiment provides a compound of Formula (I), or stereoisomers, tautomers, isotopes, salts, pharmaceutically acceptable salts, solvates, or prodrugs thereof, wherein the compound is of formula (Id)

(Id)

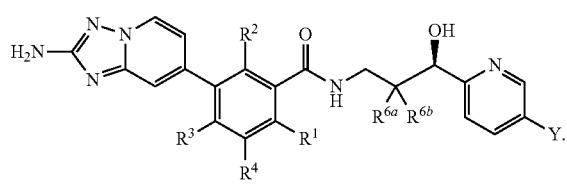

Another embodiment provides a compound of Formula (I), or stereoisomers, tautomers, isotopes, salts, pharmaceutically acceptable salts, solvates, or prodrugs thereof, wherein
$R^8$ is H; and
$R^9$ is H.

Another embodiment provides a compound of Formula (I), or stereoisomers, tautomers, isotopes, salts, pharmaceutically acceptable salts, solvates, or prodrugs thereof, wherein (Ie)

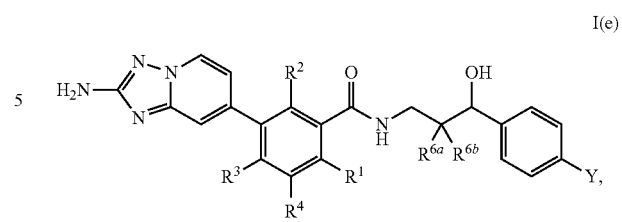

(If)

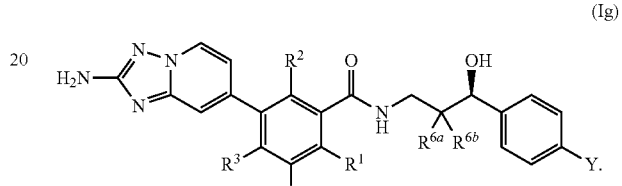

(Ig)

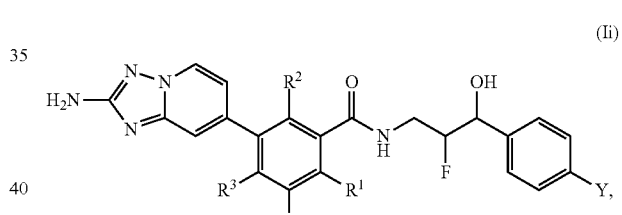

Another embodiment provides a compound of Formula (I), or stereoisomers, tautomers, isotopes, salts, pharmaceutically acceptable salts, solvates, or prodrugs thereof, wherein (Ii)

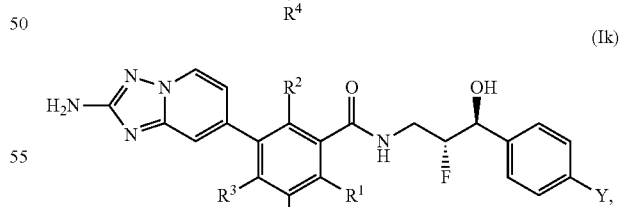

(Ij)

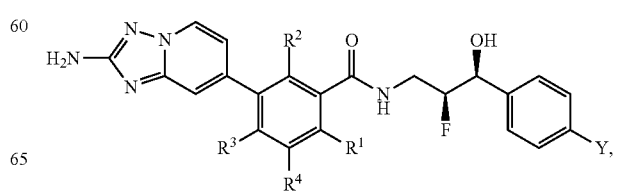

(Ik)

(Il)

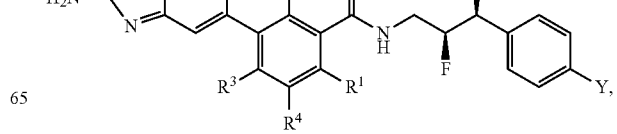

(Im)

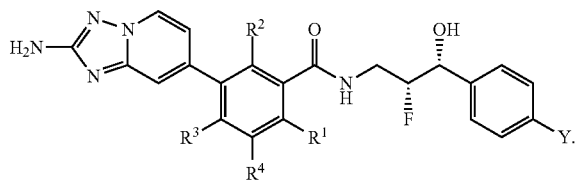

Another embodiment provides a compound of Formula (I), or stereoisomers, tautomers, isotopes, salts, pharmaceutically acceptable salts, solvates, or prodrugs thereof, wherein the compound is of formula (In)

(In)

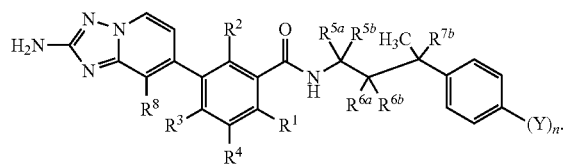

Another embodiment provides a compound of Formula (I), or stereoisomers, tautomers, isotopes, salts, pharmaceutically acceptable salts, solvates, or prodrugs thereof, wherein the compound is of formula (Io)

(Io)

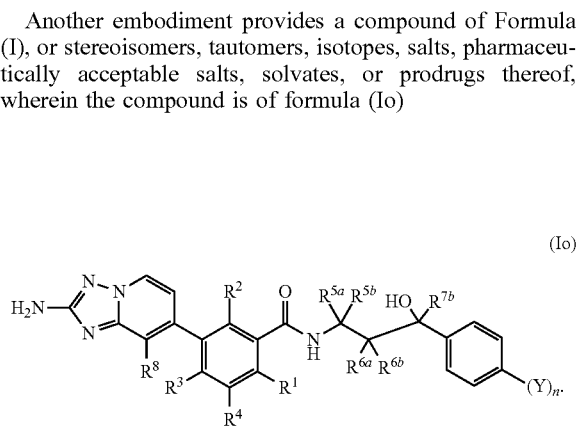

Another embodiment provides a compound of Formula (I), or stereoisomers, tautomers, isotopes, salts, pharmaceutically acceptable salts, solvates, or prodrugs thereof, wherein the compound is of formula I(p)

I(p)

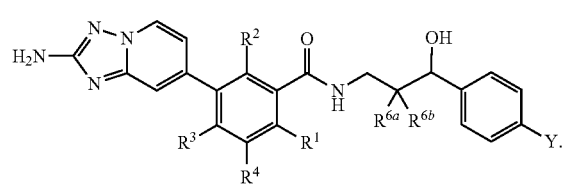

Another embodiment provides a compound of Formula (I), or stereoisomers, tautomers, isotopes, salts, pharmaceutically acceptable salts, solvates, or prodrugs thereof, wherein the compound is of formula (Iq)

(Iq)

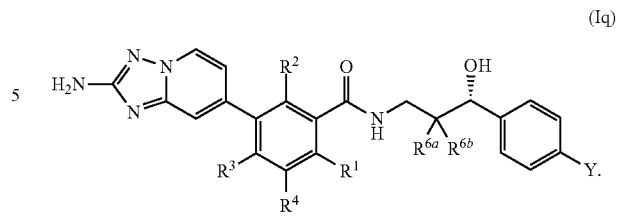

Another embodiment provides a compound of Formula (I), or stereoisomers, tautomers, isotopes, salts, pharmaceutically acceptable salts, solvates, or prodrugs thereof, wherein the compound is of formula (Ir)

(Ir)

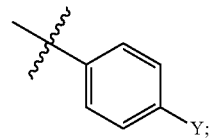

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein wherein Ring Z is and
Y is Cl or F.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein $R^{5a}$ and $R^{5b}$ are H or deuterium;
$R^{6a}$ is F, and $R^{6b}$ is H or F;
$R^{7a}$ is OH, and $R^{7b}$ is H, $CH_3$, or $CD_3$.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein $R^{5a}$ and $R^{5b}$ are H or deuterium;
$R^{6a}$ is F, and $R^{6b}$ F;
$R^{7a}$ is OH, and $R^{7b}$ is H, or $CH_3$.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein $R^{5a}$ and $R^{5b}$ are H;
$R^{6a}$ is F, and $R^{6b}$ is H;
$R^{7a}$ is OH, and $R^{7b}$ is H, $CH_3$, or $CD_3$.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein
$R^{5a}$ and $R^{5b}$ are H;
$R^{6a}$ is F, and $R^{6b}$ is H;
$R^{7a}$ is OH, and $R^{7b}$ is H, $CH_3$, or $CD_3$.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein
$R^1$ is $CH_3$, $CD_3$, $CF_3$, or Cl;
$R^2$ is F;
$R^3$ is H;
$R^4$ is H.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein
$R^{6a}$ and $R^{6b}$ are F;
$R^1$ is $CH_3$, $CD_3$, $CF_3$, or Cl;
$R^2$ is F;
$R^3$ is H;
$R^4$ is H; and
Y is Cl or F.

Another embodiment provides a compound of Formula (I), or stereoisomers, tautomers, isotopes, salts, pharmaceutically acceptable salts, solvates, or prodrugs thereof, wherein the compound is of formula (I), (II), (Ia), (Ib), (Ic), (Id), (Ie), (If), (Ig), (Ii), (Ij), (Ik), (Il), (Im), (In), (Io) (Ip), (Iq), or (Ir) and wherein
$R^{6a}$ is H and $R^{6b}$ is F;
$R^1$ is $CH_3$, $CD_3$, $CF_3$, or Cl;
$R^2$ is F;
$R^3$ is H;
$R^4$ is H; and
Y is Cl or F.

Another embodiment provides a compound of Formula (I), or stereoisomers, tautomers, isotopes, salts, pharmaceutically acceptable salts, solvates, or prodrugs thereof, wherein the compound is selected from the examples.

The present invention is also directed to pharmaceutical compositions useful in treating diseases associated with kinase modulation, including the modulation of receptor interacting protein kinases such as RIPK1, comprising compounds of formula (I), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK1, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases and fibrotic diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I), wherein the disease is inflammatory bowel disease, Crohn's disease or ulcerative colitis, poriasis, systemic lupus erythematosus (SLE), rheumatoid arthritis, multiple sclerosis (MS), transplant rejection, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from systemic lupus erythematosus (SLE), multiple sclerosis (MS), transplant rejection, acute myelogenous leukemia, chronic myelogenous leukemia, metastatic melanoma, Kaposi's sarcoma, multiple myeloma, solid tumors, ocular neovascularization, and infantile haemangiomas, B cell lymphoma, systemic lupus erythematosus (SLE), psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris and asthma, nonalcoholic steatohepatitis (NASH), or ischemia reperfusion.

The present invention also provides a method of treating a condition comprising administering to a patient in need of such treatment a therapeutically-effective amount of a compound of formula (I), wherein the condition is selected from macrophage necrosis in atheroscelerosis development, virus-induced inflammation, systemic inflammatory response syndrome and ethanol-induced liver injury, neurodegeneration such as detachment of the retina, retinal degeneration, wet and dry age-related macular degeneration (AMD), ischemia, amyotrophic lateral sclerosis (ALS), and Gaucher's disease.

The present invention also provides a method of treating a condition comprising administering to a patient in need of such treatment a therapeutically-effective amount of a compound of formula (I), wherein the condition is selected from inflammatory bowel disease, ulcerative colitis, Crohn's disease, psoriasis, rheumatoid arthritis (RA), heart failure, and nonalcoholic steatohepatitis (NASH).

The present invention also provides a method of treating a condition comprising administering to a patient in need of such treatment a therapeutically-effective amount of a compound of formula (I), wherein the condition is selected from inflammatory bowel disease, Crohn's disease, ulcerative colitis, and psoriasis. In another emobiment, the condition is selected from inflammatory bowel disease, Crohn's disease, and ulcerative colitis.

The present invention also provides a method of treating a condition comprising administering to a patient in need of such treatment a therapeutically-effective amount of a compound of formula (I), wherein the condition is selected from nonalcoholic steatohepatitis (NASH), and ischemia reperfusion.

The present invention also provides a method for treating rheumatoid arthritis, comprising administering to a patient in need of such treatment a therapeutically-effective amount of a compound of formula (I), The present invention also provides a method of treating diseases, comprising administering to a patient in need of such treatment a therapeutically-effective amount of a compound of formula (I), or pharmaceutically acceptable salt thereof, in combination with other therapeutic agents.

The present invention also provides the compounds of the present invention or stereoisomers, tautomers, isotopes, salts, pharmaceutically acceptable salts, solvates, or prodrugs thereof, for use in therapy.

In another embodiment, compounds of formula (I), are selected from exemplified examples or combinations of exemplified examples or other embodiments herein.

The present invention also provides the use of the compounds of the present invention or stereoisomers, tautomers, isotopes, salts, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

Unless specifically stated otherwise herein, references made in the singular may also include the plural. For example, "a" and "an" may refer to either one, or one or more.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

Unless otherwise indicated, any carbon or heteroatom with unsatisfied valences is assumed to have hydrogen atoms sufficient to satisfy the valences.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula (I), (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "carbocyclyl" or "carbocyclic" refers to a saturated or unsaturated, or partially unsaturated, monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Carbocycles, can include cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocycle", "heterocyclic", or "heterocyclyl" may be used interchangeably and refer to substituted and unsubstituted aromatic or non-aromatic 3- to 7-membered monocyclic groups, 7- to 11-membered bicyclic groups, and 10- to 15-membered tricyclic groups, in which at least one of the rings has at least one heteroatom (0, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like, including the exemplary groups listed under "heteroaryl". Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "deuteroalkyl" means a substituted alkyl having one or more deuterium atom. For example, the term "deuteroalkyl" includes mono, bi, and trideuteromethyl.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "$CO_2$" is used herein, this is intended to refer to the group

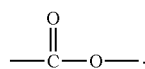

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. In one embodiment, salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, PA, 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. As an example, an alkyl substituent is intended to cover alkyl groups have either hydrogen, deuterium, and/or some combination thereof. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs,* edited by H. Bundgaard, (Elsevier, 1985) and *Methods in Enzymology,* Vol. 112, pp. 309-396, edited by K. Widder, et al. (Academic Press, 1985);

b) *A Textbook of Drug Design and Development,* edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews,* Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

For some examples of the present invention, the absolute stereochemistry of the enantiomers and/or diasteriomers has not been specifically identified. However, the racemic mixtures and all enantiomers and diasteriomers are included in the present invention. Even where the specific enantiomers and/or diastereomers are isolated, but the absolute stereochemistry was not specifically determined and drawn, one of skill in the art can easily identify and draw the structures of the individual stereoisomers or diasteriomers. For example, Example 202, 203, 204 and 205 are represented by the structure:

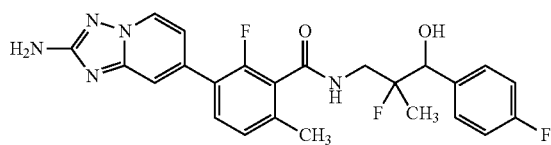 [SMILES: Cc1ccc(-c2ccn3nc(N)nc3c2)c(F)c1C(=O)NCC(C)(F)C(O)c1ccc(F)cc1]

The 4 diasteriomers are:

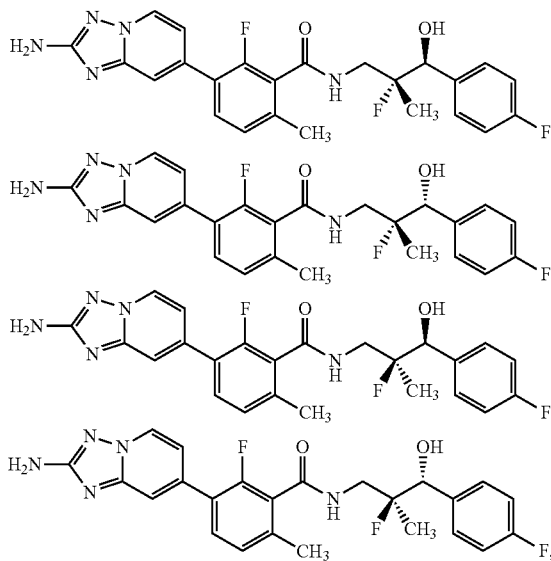

which one of skill in the art is able to identify, even if the structure of each of the examples is not specifically described.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

Utility

The compounds of the invention modulate kinase activity, including the modulation of RIPK1. Accordingly, compounds of formula (I) have utility in treating conditions associated with the modulation of kinase activity, and particularly the selective inhibition of RIPK1 activity. In another embodiment, compounds of formula (I) have advantageous selectivity for RIPK1 activity preferably from at least 10 fold, or alternatively, 20 fold, to over 1,000 fold more selective over other kinases.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as inhibitors of RIPK1, compounds of Formula (I) are useful in treating RIPK1-associated conditions including, but not limited to, inflammatory diseases such as Crohn's disease and ulcerative colitis, inflammatory bowel disease, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, ALS, cerebral ischemias or neurodegenerative disease caused by traumatic injury, oncologic and viral diseases such as metastatic melanoma, Kaposi's sarcoma, multiple myeloma, and HIV infection and CMV retinitis, AIDS; fibrotic conditions such as, nonalcoholic steatohepatitis (NASH); and cardiac conditions such as, ischemia reperfusion; respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, ALS, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. In another aspect, methods of treatment are those wherein the condition is selected from inflammatory bowel disease, Crohn's disease and ulcerative colitis, allograft rejection, rheumatoid arthritis, psoriasis, ankylosing spondylitis, psoriatic arthritis, and pemphigus vulgaris, and nonalcoholic steatohepatitis (NASH), and ischemia reperfusion. In a further aspect, methods of treatment are those wherein the condition is selected from multiple sclerosis, amyotrophic latereal sclerosis, and Alzheimers.

Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK1-associated condition" or "RIPK1-associated disease or disorder" are used herein, each is intended to encompass all of the conditions identified above as if repeated at length, as well as any other condition that is affected by RIPK1 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit RIPK1.

The methods of treating RIPK1 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit RIPK1 and/or treat diseases associated with RIPK1.

Exemplary of such other therapeutic agents include corticosteroids, rolipram, calphostin, cytokine-suppressive antiinflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; anti-inflammatory anti-bodies such as vedolizumab and ustekinumab, anti-infammatory kinase inhibitors such as TYK2 inhibitors, antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, rapamycin (sirolimus or Rapamune) or derivatives thereof, and agonists of FGF21.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK1 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK1 enzyme levels.

Necroptosis is a regulated pathway of cell death that is induced by both inflammatory factors (TNFalpha) as well as viral triggers such as TLR agonists. The process of necroptosis induction occurs following activation and phosphorlylation of RIPK1 to form a complex with RIPK3 (referred to as necrosome). Mixed Lineage Kinase domain-like protein (MLKL) is recruited to RIPK3 and is a downstream target of RIPK3 kinase, leading to MLKL phosphorylation at Thr357 and Ser358. Phosphorylated MLKL (pMLKL) leads to MLKL oligomerization, translocation to the plasma membrane, and subsequent pore formation leading to membrane integrity defects (Moriwaki, K., and F. K. Chan. 2013. RIP3: a molecular switch for necrosis and inflammation. Genes Dev. 27: 1640-1649). Thus, understanding the potency of RIPK1 compounds based on RIPK1 direct binding as well as a functional readout of necroptosis activity (pMLKL) is important for evaluating RIPK1 inhibitor activity and potency.

MLKL Phosphorylation High-Content Assay

HT29-L23 human colorectal adenocarcinoma cells were maintained in RPMI 1640 medium containing 10% heat-inactivated FBS, 1% Penicillin-Streptomycin and 10 mM HEPES. Cells were seeded at 2,000 cells/well in 384 well tissue culture-treated microplates (Greiner #781090-3B) and incubated at 37° C. (5% $CO_2$/95% $O_2$) for 2 d. On the day of the assay, the cells were treated with test compounds at final concentrations of 6.25 to 0.106 µM for 30 min at 37° C. (5% $CO_2$/95% $O_2$). Necroptopsis was induced using a mixture of human TNFα (35 ng/mL) (Peprotech #300-01A), SMAC mimetic (from US 2015/0322111 A1) (700 nM) and Z-VAD (140 nM) (BD pharmingen #51-6936). Following 6 h incubation at 37° C. (5% $CO_2$/95% $O_2$), the cells were fixed with 4% formaldehyde (ACROS 11969-0010) for 15 min at rt, then permeabilized with phosphate buffered saline (PBS) containing 0.2% Triton-X-100 for 10 min. MLKL phosphorylation was detected using anti-MLKL (phospho S358) antibody (Abcam #ab187091) (1:1000 dilution in Blocking Buffer [PBS supplemented with 0.1% BSA]) with ON incubation at 4° C. After washing three times in PBS, goat anti-rabbit Alexa-488 (1:1000 dilution) (Life Technologies, A11008) and Hoechst 33342 (Life Technologies, H3570) (1:2000 dilution) in Blocking Buffer were added for 1 h at rt. Following another three cycles of washes in PBS, the microplates were sealed, and cellular images were acquired in the Cellomics ArrayScan VTI high-content imager equipped with an X1 camera. Fluorescent images were taken using a 10× objective and the 386-23 BGRFRN_BGRFRN and 485-20 BGRFRN_BGRFRN filter sets, for nuclei and MLKL phosphorylation, respectively. The image sets were analyzed using the Compartmental Analysis Bioapplication software (Cellomics). The level of MLKL phosphorylation was quantified as MEAN_CircRingAvgIntenRatio. The maximal inhibitory response was defined by the activity induced by Necls (CAS #: 852391-15-2, 6.25 µM). The IC50 value was defined as the concentration of compound that produces 50% of the maximal inhibition. The data were fitted using the 4-parameter logistic equation to calculate the IC50 and Ymax values.

RIPK1 HTRF Binding Assay

A solution was prepared containing 0.2 nM Anti GST-Tb (Cisbio, 61GSTTLB), 90.6 nM probe and 1 nM His-GST-TVMV-hRIPK1 (1-324) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 mL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Cloning and Baculovirus Expression of RIPK1 Construct

The coding region of human RIPK1 (1-324) flanked by NdeI site at 5' end and stop codon TGA and XhoI site at 3' end was codon optimized and gene synthesized at GenScript USA Inc. (Piscataway, NJ) and subcloned into a modified pFastBac1 vector (Invitrogen, Carlsbad, CA) with N-terminal His-GST-TVMV tag, to generate His-GST-TVMV-hRIPK1 (1-324)-pFB. The fidelity of the synthetic fragment was confirmed by sequencing.

Baculovirus was generated for the construct using the Bac-to-Bac baculovirus expression system (Invitrogen) according to the manufacturer's protocol. Briefly, recombinant bacmid was isolated from transformed DH10Bac *E. coli* competent cells (Invitrogen) and used to transfect *Spodoptera frugiperda* (Sf9) insect cells (Invitrogen). Baculovirus was harvested 72 hours post transfection and a virus stock was prepared by infecting fresh Sf9 cells at a 1/1000 (v/v) ratio for 66 hours.

For large scale protein production, Sf9 cells (Expression System, Davis, CA) grown in ESF921 insect medium (Expression System) at 2×106 cells/ml were infected with virus stock at a 1/100 (v/v) ratio for 66 hours. The production was carried out either at a 10 L scale in a 22 L cellbag (GE Healthcare Bioscience, Pittsburgh, PA) or at a 20 L scale in a 50 L cellbag using WAVE-Bioreactor System 20/50 (GE Healthcare Bioscience). The infected cells were harvested by centrifugation at 2000 rpm for 20 min at 4° C. in a SORVALL® RC12BP centrifuge. The cell pellets was stored at −70° C. before protein was purified.

Purification of his-GST-TVMV-hRIPK1 (1-324)

RIPK1 containing cell paste was resuspended in 50 mM Tris pH 7.5, 150 mM NaCl, 10 mM imidazole, 5% glycerol, 5 mM MgSO4, 1 mM TCEP, 25 U/ml Benzonase, and Complete Protease Inhibitor tablets (1/50 ml, Roche Diagnostics, Indianapolis, IN). The cells were lysed by nitrogen cavitation using an unstirred pressure vessel @ 525 PSI (Parr Instrument Company, Moline, IL). The suspension was clarified by centrifugation at 136,000×g for 40 min, at 4° C. The lysate was decanted from the pellet and passed through a 5 ml NiNTA Superflow cartridge (Qiagen, Valencia, CA) using an AKTA Pure (GE Healthcare). Column was eluted with 10 CV linear gradient into 50 mM Tris 7.5, 150 mM NaCl, 500 mM imidazole, 5% glycerol, 1 mM TCEP. Peak fractions were pooled and loaded directly onto 5 ml GSTrap 4B column (GE Healthcare). Column was washed with 50 mM Tris 7.0, 150 mM NaCl, 5% glycerol, 1 mM DTT and eluted in 10 CV linear gradient into 50 mM Tris 8.0, 150 mM NaCl, 20 mM reduced glutathione, 5% glycerol, 1 mM DTT. Fractions identified by SDS-PAGE as containing RIPK1 were pooled and concentrated using 30 kDa MWCO spin concentrators (Amicon Ultra-15, Millipore, Billerica, MA) and loaded onto a HiLoad 26/600 Superdex 200 column (GE Healthcare) equilibrated in 25 mM Tris 7.5, 150 mM NaCl, 2 mM TCEP, 5% glycerol. The RIPK1 protein eluted as a dimer off the SEC column.

The yield was ~8 mg/L with a purity >95% as determined by Coomassie stain SDS-PAGE gel analysis. LCMS analysis of the protein showed that the protein had lost the N-terminal methionine, had one phosphorylated site, and was partially acetylated. Protein was aliquoted and stored at −80° C.

PI3Kδ HTRF Binding Assay

A solution was prepared containing 0.2 nM Anti GST-Tb (Cisbio, 61GSTTLB), 40 nM probe and 1 nM GST-tagged PIK3Cδ in complex with PIK3R1 (Invitrogen #PV5273) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 mL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Preferred compounds have low to no activity against PI3K, preferably compounds have PIK3 activity of 1p M or greater.

Using these assays, the $IC_{50}$ values of the following compounds were determined. See Table A.

TABLE A

| Example # | RIPK1 IC50 (nM) | pMLKL IC50 (nM) | PIK3CD IC50 μM |
|---|---|---|---|
| 1 | 1.2 | 1.3 | |
| 2 | 2.1 | 1.0 | >15 |
| 3 | 3.9 | 0.6 | >15 |
| 4 | 4.3 | 1.0 | >15 |
| 5 | 6.4 | 2.6 | >15 |
| 6 | 5.8 | 2.3 | >15 |
| 7 | 10 | 13 | >15 |
| 8 | 5.1 | 2.3 | >15 |
| 9 | 6.2 | 2.4 | >15 |
| 10 | 9.4 | 2.5 | >15 |
| 11 | 1.2 | 5.9 | >15 |
| 12 | 3.0 | 9.2 | >15 |
| 13 | 0.6 | 27 | >15 |
| 14 | 1.1 | 1.1 | >15 |
| 15 | 1.5 | 1.7 | >15 |
| 16 | 0.7 | 0.4 | >15 |
| 17 | 1.9 | 2.5 | |
| 18 | 8.9 | | |
| 19 | | 7.7 | >15 |
| 20 | | 3.6 | >15 |
| 21 | 6.4 | 3.1 | |
| 22 | 78 | 411 | |
| 23 | 12 | 61 | >15 |
| 24 | 1.5 | 0.9 | >15 |
| 25 | 3.6 | 4.1 | >15 |
| 26 | 233 | 696 | >15 |
| 27 | 60 | 198 | >15 |
| 28 | 5.1 | 4.9 | 8.8 |
| 29 | 2.2 | 0.7 | >15 |
| 30 | 4.5 | 0.5 | |
| 31 | 2.4 | 0.8 | >15 |
| 32 | 2.2 | | >15 |
| 33 | 1.0 | 0.7 | >15 |
| 34 | 0.8 | 1.0 | >15 |
| 35 | 2.0 | 0.9 | 3.9 |
| 36 | 4.5 | 2.7 | >15 |
| 37 | 21 | 41 | >15 |
| 38 | 4.7 | 6.0 | >15 |
| 39 | 163 | 397 | >15 |
| 40 | 3.8 | 1.5 | >15 |
| 41 | 5.4 | 7.7 | >15 |
| 42 | 1.3 | 2.8 | >15 |
| 43 | 3.2 | 2.6 | 11 |
| 44 | 1.3 | 2.5 | |
| 45 | 3.0 | 7.4 | |
| 46 | 1.9 | 2.4 | |
| 47 | 3.3 | 2.3 | >15 |
| 48 | 4.5 | 2.6 | |
| 49 | 2.5 | 2.6 | |
| 50 | 0.3 | 1.9 | >15 |
| 51 | 3.7 | 1.8 | >15 |
| 52 | 0.3 | 1.1 | >15 |
| 53 | 1.2 | 0.9 | 14 |
| 54 | 2.7 | 1.0 | >15 |
| 55 | 0.3 | 0.9 | >15 |

TABLE A

| Example # | RIPK1 IC50 (nM) | pMLKL IC50 (nM) | PIK3CD IC50 μM |
|---|---|---|---|
| 56 | 4.5 | 0.4 | >15 |
| 57 | 3.1 | 1.9 | >15 |
| 58 | 2.1 | 2.3 | >15 |
| 59 | 2.5 | 1.2 | >15 |
| 60 | 1.0 | 1.3 | >15 |
| 61 |  | 0.8 |  |
| 62 |  | 1.1 |  |
| 63 |  | 1.9 | 13 |
| 64 | 12 | 8.0 | 15 |
| 65 | 28 | 27 | >15 |
| 66 |  | 1.2 | >15 |
| 67 | 4.4 | 1.3 | >15 |
| 68 | 3.6 | 0.6 | >15 |
| 69 | 1.4 | 0.4 | >15 |
| 70 | 11 | 8.1 | >15 |
| 71 | 18 | 21 | >15 |
| 72 | 102 | 89 | 15 |
| 73 | 43 | 73 | >15 |
| 74 | 13 | 8.2 | >15 |
| 75 | 3.2 | 4.3 |  |
| 76 | 1.5 | 3.3 |  |
| 77 | 2.9 | 7.7 |  |
| 78 | 19 | 9.9 |  |
| 79 | 4.8 | 19 |  |
| 80 | 9.0 | 27 |  |
| 81 | 24 | 38 |  |
| 82 | 27 | 26 | 12 |
| 83 | 29 | 17 | 11 |
| 84 | 1.6 | 1.1 | >15 |
| 85 | 2.1 | 0.5 |  |
| 86 | 2.2 | 7.5 |  |
| 87 | 8.6 |  |  |
| 88 | 3.6 | 2.4 |  |
| 89 | 7.7 |  | >15 |
| 90 |  | 15 | >15 |
| 91 |  | 34 | 8.0 |
| 92 |  | 11 | 5.2 |
| 93 |  | 256 | 11 |
| 94 | 3.8 | 4.8 | >15 |
| 95 | 3.0 | 5.9 | >15 |
| 96 |  | 39 | >15 |
| 97 | 1.3 | 6.4 | >15 |
| 98 | 2.8 | 1.2 | >15 |
| 99 | 5.5 | 2.9 | >15 |
| 100 |  | 27 | >15 |
| 101 | 4.8 | 2.9 | >15 |
| 102 |  | 7.6 | >15 |
| 103 |  | 2,064 | >15 |
| 104 |  | 0.3 |  |
| 105 |  | 0.5 |  |
| 106 |  | 0.5 |  |
| 107 |  | 0.4 |  |
| 108 | 6.7 | 1.0 | 7.7 |
| 109 | 4.2 | 1.3 | 8.5 |
| 110 |  |  |  |
| 111 |  |  |  |
| 112 | 3.3 | 0.9 | >15 |
| 113 | 3.5 | 0.9 | >15 |
| 114 | 6.7 | 4.5 | >15 |
| 115 | 3.6 | 1.4 | >15 |
| 116 |  |  |  |
| 117 |  |  |  |
| 118 |  |  |  |
| 119 |  |  |  |
| 120 |  | 1.4 |  |
| 121 |  | 1.0 |  |
| 122 |  |  |  |
| 123 | 5.7 | 0.8 |  |
| 124 |  | 1.4 |  |
| 125 |  | 2.9 |  |
| 126 |  |  |  |
| 127 |  | 9.7 |  |
| 128 | 5.0 | 1.2 |  |
| 129 | 3.5 | 1.7 |  |
| 130 | 7.4 | 2.9 | 4.9 |
| 131 |  |  |  |
| 132 | 8.4 | 1.1 | >15 |
| 133 | 3.8 |  | >15 |
| 134 | 2.9 | 1.5 | >15 |
| 135 | 5.6 | 0.5 | >15 |
| 136 | 5.9 | 1.4 | >15 |
| 137 | 9.7 | 0.9 |  |
| 138 | 11 | 0.2 |  |
| 139 |  | 7.4 | >15 |
| 140 | 0.6 | 13 | >15 |
| 141 | 22 | 38 | >15 |
| 142 | 3.3 | 2.5 | >15 |
| 143 |  | 2.4 | >15 |
| 144 |  | 4.2 | >15 |
| 145 | 21 | 35 | >15 |
| 146 | 0.6 | 2.4 | >15 |
| 147 | 9.4 | 21 | 13 |
| 148 | 8.3 | 17 | 5.0 |
| 149 | 8.2 | 1.3 | >15 |
| 150 | 1.8 | 5.7 | >15 |
| 151 | 2.8 | 0.8 |  |
| 152 | 2.3 | 0.5 | >15 |
| 153 | 4.1 | 8.3 | >15 |
| 154 | 4.7 | 1.4 | >15 |
| 155 | 2.7 | 0.6 | >15 |
| 156 | 5.8 | 0.8 | >15 |
| 157 | 3.1 | 6.7 |  |
| 158 | 3.4 | 3.7 | >15 |
| 159 | 2.5 | 1.9 | >15 |
| 160 | 0.8 | 0.3 | >15 |
| 161 | >15000 | 135 |  |
| 162 | 1.6 | 3.1 |  |
| 163 | 0.3 | 1.3 |  |
| 164 | 2.8 | 2.9 |  |
| 165 | 1.6 | 2.8 |  |
| 166 | 2.1 | 5.1 |  |
| 167 | 15 | 7.8 |  |
| 168 | 0.3 | 1.1 |  |
| 169 | 0.9 | 28 |  |
| 170 | 0.1 | 1.4 |  |
| 171 | 1.6 | 10 |  |
| 172 | 1.3 |  |  |
| 173 | 0.9 | 0.9 |  |
| 174 | 2.8 | 1.4 |  |
| 175 | 2.7 | 7.8 |  |
| 176 | 0.3 | 1.9 |  |
| 177 | 1.8 | 23 |  |
| 178 | 0.9 | 22 |  |
| 179 | 0.3 | 3.7 |  |
| 180 | 2.0 | 10 |  |
| 181 | 1.7 | 0.3 |  |
| 182 | 1.2 | 2.9 |  |
| 183 | 0.4 | 1.0 |  |
| 184 | 4.8 | 0.4 | 1.7 |
| 185 | 0.6 | 1.4 | 12 |
| 186 | 2.9 | 0.2 | 12 |
| 187 | 3.2 | 1.7 | >15 |
| 188 | 6.3 | 0.3 | 9.4 |
| 189 | 11 | 38 | 5.6 |
| 190 | 3.3 | 0.7 | >15 |
| 191 | 2.6 | 1.4 | >15 |
| 192 | 3.5 | 1.2 |  |
| 193 | 8.7 | 15 |  |
| 194 |  | 8.8 |  |
| 195 | 8.4 | 1.0 |  |
| 196 | 14 | 1.0 |  |
| 197 |  | 0.3 |  |
| 198 | 6.4 | 1.3 | >15 |
| 199 | 1.4 | 0.6 | >15 |
| 200 | 4.7 | 0.8 |  |
| 201 | 6.7 | 0.9 |  |
| 202 | 13 | 2.1 |  |
| 203 | 5.6 | 2.7 |  |

TABLE A

| Example # | RIPK1 IC50 (nM) | pMLKL IC50 (nM) | PIK3CD IC50 μM |
|---|---|---|---|
| 204 | 5.8 | 2.7 | |
| 205 | 6.2 | 5.1 | |
| 206 | 7.7 | | |
| 207 | 1.8 | 0.6 | |
| 208 | 2.6 | 0.2 | |
| 209 | | 80 | |
| 210 | | 2.5 | |
| 211 | | 45 | |
| 212 | | 0.8 | |
| 213 | | 13 | |
| 214 | | 0.9 | |
| 215 | 8.7 | 6.6 | |
| 216 | 4.7 | 0.4 | |
| 217 | 18 | 70 | >15 |
| 218 | 15 | 75 | >15 |
| 219 | | 42 | >15 |
| 220 | | 36 | >15 |
| 221 | 3.2 | 0.9 | >15 |
| 222 | 3.2 | 1.0 | >15 |
| 223 | 5.8 | 71 | >15 |
| 224 | 5.2 | 4.1 | >15 |
| 225 | 19 | 3.8 | |
| 226 | 8.3 | 2.2 | |
| 227 | 15 | 0.7 | >15 |
| 228 | 0.9 | 1.0 | >15 |
| 229 | 5.0 | 0.7 | 9.4 |
| 230 | 6.4 | 2.6 | >15 |
| 231 | 2.0 | 1.2 | >15 |
| 232 | 4.5 | 3.0 | >15 |
| 233 | 2.6 | 0.5 | |
| 234 | 8.4 | 3.0 | |
| 235 | 4.3 | 0.6 | |
| 236 | 3.4 | 0.9 | |
| 237 | | 86 | |
| 238 | 16 | 1.9 | >15 |
| 239 | 55 | 26 | >15 |
| 240 | | 3.1 | |
| 241 | 10 | 1.2 | |
| 242 | 9.1 | 1.0 | |
| 243 | 4.7 | 1.2 | |
| 244 | 2.7 | 1.2 | |
| 245 | 19 | 3.7 | |
| 246 | 15 | 2.2 | |
| 247 | 13 | 21 | >15 |
| 248 | 22 | 20 | >15 |
| 249 | 2.1 | 10 | >15 |
| 250 | 13 | 21 | >15 |
| 251 | 16 | | >15 |
| 252 | 7.2 | 2.7 | |
| 253 | 2.4 | 1.2 | |
| 254 | 3.5 | 4.1 | |
| 255 | 17 | 79 | |
| 256 | 3.2 | | |
| 257 | 8.9 | 5.9 | |
| 258 | 12 | 9.1 | >15 |
| 259 | 30 | 69 | >15 |
| 260 | 8.4 | 3.2 | |
| 261 | 40 | 79 | |
| 262 | 14 | 45 | |
| 263 | 21 | 48 | |
| 264 | 6.2 | 1.0 | >15 |
| 265 | 4.1 | 3.6 | >15 |
| 266 | 13 | 2.4 | >15 |
| 267 | 2.8 | 1.0 | >15 |
| 268 | 3.8 | 4.3 | 8.8 |
| 269 | 4.6 | 1.5 | >15 |
| 270 | 11 | 3.1 | >15 |
| 271 | 1.5 | 1.8 | 11 |
| 272 | 6.8 | 11 | >15 |
| 273 | 3.9 | 37 | |
| 274 | 19 | 0.7 | |
| 275 | 6.5 | 1.5 | >15 |
| 276 | 3.7 | 8.4 | |
| 277 | 36 | 69 | >15 |
| 278 | 13 | 38 | >15 |
| 279 | | 8.3 | >15 |
| 280 | 15 | 1.4 | 11 |
| 281 | 7.2 | 1.3 | >15 |
| 282 | 2.2 | 1.1 | >15 |
| 283 | 0.5 | 1.0 | |
| 284 | 3.5 | 1.1 | |
| 285 | | 0.8 | |
| 286 | | 1.0 | |
| 287 | | 0.8 | |
| 288 | | 1.0 | |
| 289 | | 1.7 | |
| 290 | 4.8 | 0.5 | |
| 291 | 1.0 | 2.4 | |
| 292 | 2.4 | 1.0 | |
| 293 | 1.2 | 1.7 | |
| 294 | 1.9 | 1.9 | >15 |
| 295 | 3.3 | 1.4 | >15 |
| 296 | 15 | 22 | 10 |
| 297 | 3.7 | 1.6 | >15 |
| 298 | 2.9 | 0.5 | 8.0 |
| 299 | 16 | 37 | 10 |
| 300 | 9.7 | 0.6 | |
| 301 | 21 | 1.0 | |
| 302 | 2.5 | 1.5 | >15 |
| 303 | 2.4 | 0.4 | >15 |
| 304 | 4.8 | 2.8 | >15 |
| 305 | 1.6 | 0.6 | |
| 306 | 11 | 4.2 | |
| 307 | 9.6 | 14 | |
| 308 | 12 | 9.0 | |
| 309 | 6.2 | 11 | |
| 310 | 5.7 | 20 | |
| 311 | 5.0 | 0.8 | |
| 312 | 5.7 | 0.9 | |
| 313 | | 3.8 | |
| 314 | | 17 | |
| 315 | 6.9 | 0.4 | |
| 316 | 8.5 | 25 | |

Methods of Preparation

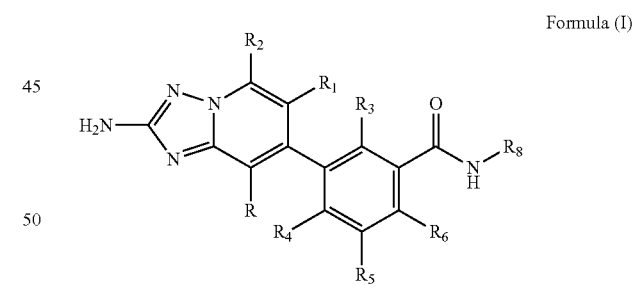

Formula (I)

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "RT" for room temperature, "ON" for overnight, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "m/z" for mass per unit charge, "ESI" for electrospray ionization mass spectroscopy, "HR" for high resolution, "HRMS" for high resolution mass spectrometry, "APCI" for atmospheric pressure chemical ionization, "LCMS" or "LC/MS" for liquid chromatography mass spectrometry, "HPLC" for high pressure liquid chromatography, "RP HPLC" for reverse phase HPLC, "prep" for preparative, "SFC" for supercritical fluid chromatography, "TLC" or "tlc" for thin layer chromatography, "Rf" for retention factor, "UV" for ultraviolet, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
n-BuLi n-butyllithium
i-Bu isobutyl
t-Bu tert-butyl
Ph phenyl
Bn benzyl
BISPIN bis(pinacolato)diboron
Boc tert-butyloxycarbonyl
ACN acetonitrile
AcOH or HOAc acetic acid
BOP benzotriazol-1-yloxytris(dimethylamino)phosphonium hexafluorophosphate
CBz carbobenzyloxy
DAST diethylaminosulfur trifluoride
DCE 1,2 dichloroethane
DCM dichloromethane
DIEA/DIPEA/Hünig's Base diisopropylethylamine
DMAP 4-dimethylaminopyridine
DME 1,2-dimethoxyethane
DMF dimethyl formamide
DMSO dimethyl sulfoxide
EDC/EDCI N-(3-dimthylaminopropyl)-N'-ethylcarbodiimide
Et$_3$N or TEA triethylamine
EtOAc ethyl acetate
Et$_2$O diethyl ether
EtOH ethanol
HCl hydrochloric acid
HATU O-(7-azabenzotriazol-1-yl)-N,N,N',N'-tetramethyluronium hexafluorophosphate
Hex hexane
HOBt or HOBT 1-hydroxybenzotriazole
IBX 2-iodoxybenzoic acid
i-PrOH or IPA isopropanol
KHMDS potassium bis(trimethylsilyl)amide
KOAc potassium acetate
LAH lithium aluminum hydride
LDA lithium diisopropylamide
LG leaving group
LHMDS lithium bis(trimethylsilyl)amide
m-CPBA meta-chloroperoxybenzoic acid
MeCN or ACN acetonitrile
MeOH methanol
MeI iodomethane
MgSO4 magnesium sulfate
NBS N-bromosuccinimide
NCS N-chlorosuccinimide
NH$_4$OAc ammonium acetate
OTf triflate or trifluoromethanesulfonate
Pd$_2$(dba)$_3$ tris(dibenzylideneacetone)dipalladium(O)
Pd(OAc)$_2$ palladium(II) acetate
Pd/C palladium on carbon
PdCl$_2$(dtbpf) [1,1'-Bis(di-tert-butylphosphino)ferrocene]dichloropalladium(II)
Pd(dppf)Cl$_2$ [1,1'-bis(diphenylphosphino)-ferrocene]dichloropalladium(II)
PG protecting group
PTFE polytetrafluoroethylene or Teflon
SiO$_2$ silica oxide or silica gel
S-Phos or SPhos dicyclohexyl(2',6'-dimethoxy-[1,1'-biphenyl]-2-yl)phosphine
TBAI tetra-n-butylammonium iodide
TEA triethyl amine
TFA trifluoroacetic acid
THF Tetrahydrofuran
TMS-Cl trimethylsilyl chloride
X-Phos or XPhos 2-dicyclohexylphosphino-2',4',6'-triisopropylbiphenyl
XPhos Pd G2 2nd generation XPhos precatalyst, chloro(2-dicyclohexylphosphino-2',4',6'-triisopropyl-1,1'-biphenyl)[2-(2'-amino-1,1'-biphenyl)]palladium(II)

The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. The numbering of R groups within the scheme are for illustrative purposes and are not intended to limit the claims. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The following schemes are illustrative for the preparation of the compounds of the present invention. The R groups in the schemes do not necessarily correlate with the R groups elsewhere in the specification, and are not meant to limit the embodiments of the invention.

Scheme 1 illustrates an approach to the synthesis of compounds exemplified by 4. Functionalization of starting material 1 can be achieved through a Suzuki coupling reaction (Miyaura, N. and Suzuki, A. Chemical Reviews, 95:2457-2483, 1995) to provide compounds of the type exemplified by 2. Hydrolysis of the ester in 2 yields a carboxylic acid or carboxylate salt which can be functionalized by amidation (Tetrahedron, 61:10827-10852, 2005) to yield compounds such as 4. Appropriate functionalization of intermediates used in this invention to prepare compounds similar to 4 can be achieved through the Suzuki reaction or simple reactions known to those skilled in the art.

Scheme 2 illustrates an alternative method to access intermediates such as 2. In this scenario, a halobenzene such as 5 can undergo in situ conversion to the boronate. Addition of 1 and aqueous base allows the second coupling to occur. Importantly, this method to access 2 can also be run in reverse. Specifically, 1 can undergo in situ conversion to the boronate and then undergo coupling with halide 5 to produce intermediates exemplified by 2.

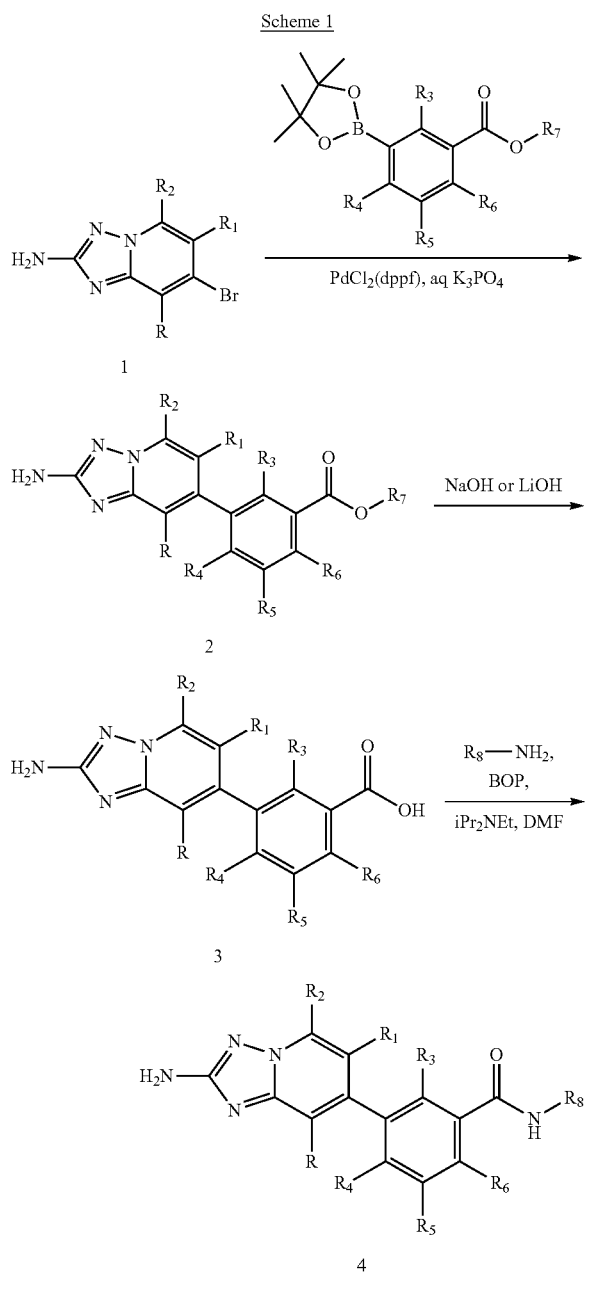

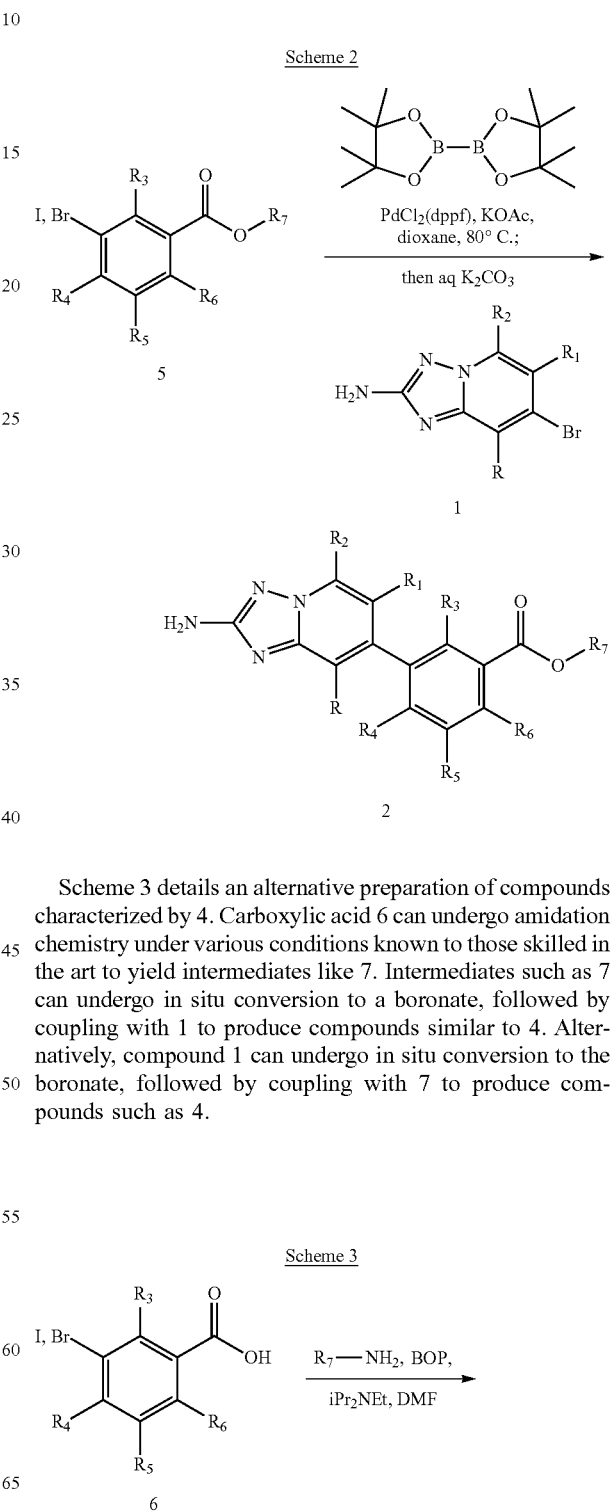

Scheme 3 details an alternative preparation of compounds characterized by 4. Carboxylic acid 6 can undergo amidation chemistry under various conditions known to those skilled in the art to yield intermediates like 7. Intermediates such as 7 can undergo in situ conversion to a boronate, followed by coupling with 1 to produce compounds similar to 4. Alternatively, compound 1 can undergo in situ conversion to the boronate, followed by coupling with 7 to produce compounds such as 4.

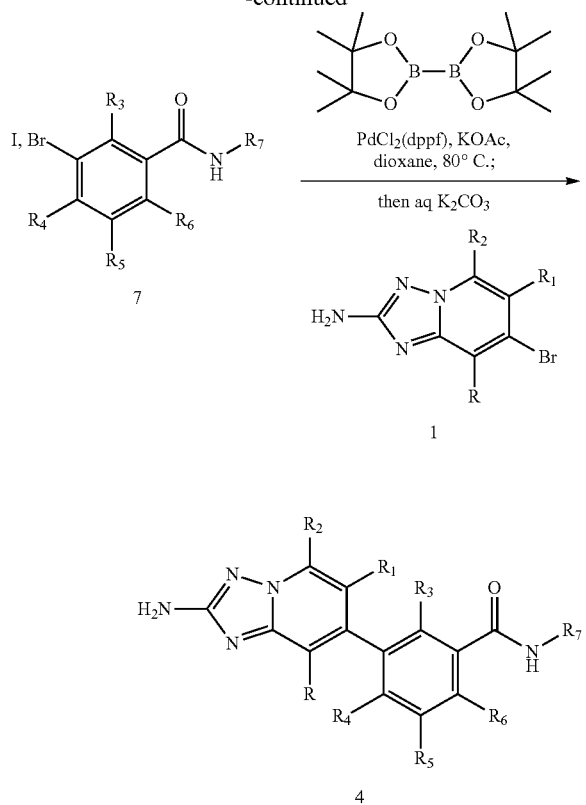

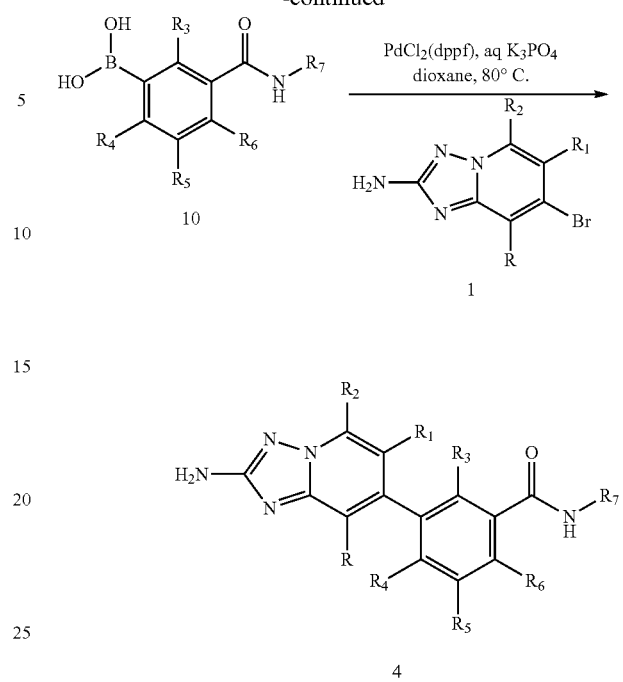

Scheme 4 details another alternative preparation for compounds similar to 4. Boronate esters such as 8 can be hydrolyzed to their acid counterparts. The carboxylic acids can undergo amidation under a variety of conditions known to those skilled in the art to yield compounds such as 10. Suzuki coupling with 1 produces compounds similar to 4.

Scheme 5 illustrates another approach to provide compounds such as 3. In this example, functionalization of N-Boc protected starting material 11 can be achieved through a Suzuki coupling reaction to provide compounds such as 12 directly or a mixture of compounds of the type exemplified by 12 and 13. Intermediates such as 12 and 13, either separately or as a mixture, can be converted to 3 by hydrolysis of the ester followed by subsequent treatment with TFA. Alternatively, intermediates such as 12 and 13 can be treated with TFA first, followed by hydrolysis of the ester, to give compounds exemplified by 3.

Scheme 4

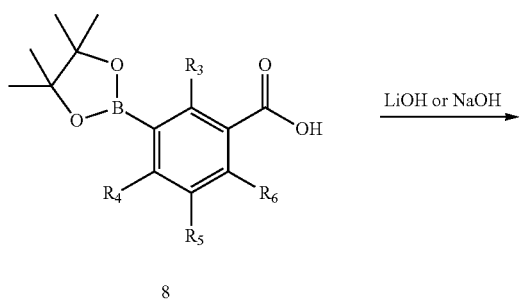

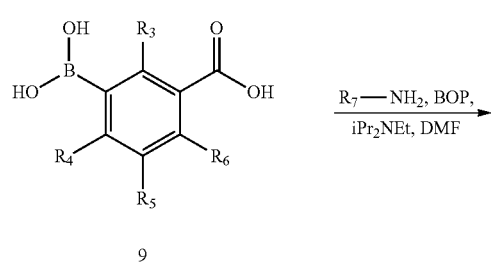

Scheme 5

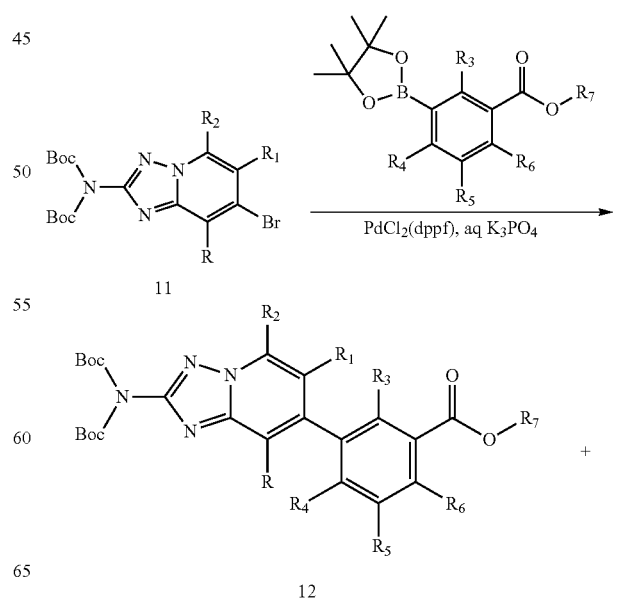

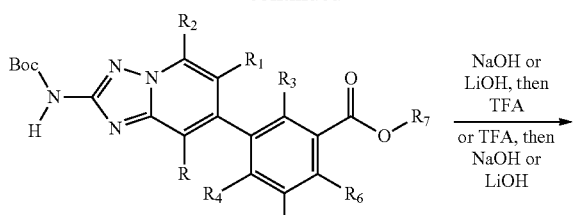
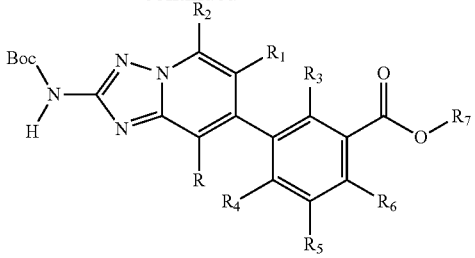

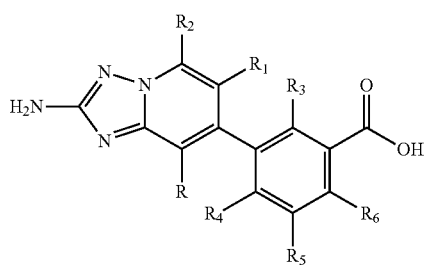

Scheme 6 depicts an alternative method to access intermediates such as 12 and 13. In this scenario, an iodo or bromobenzene such as 5 can undergo in situ conversion to the boronate. Addition of 11 and aqueous base allows the second coupling to occur. Importantly, this method to access either 12 alone or a mixture of 12 and 13 can also be run in reverse. Specifically, 11 can undergo in situ conversion to the boronate and then undergo coupling with halide 5 to produce intermediates exemplified by 12 and 13.

Scheme 7 details an alternative preparation of compounds characterized by 4. Intermediates such as 7 can undergo in situ conversion to a boronate, followed by coupling with 11 to provide a mixture of compounds of the type exemplified by 14 and 15. Alternatively, 11 can undergo in situ conversion to the boronate, followed by coupling with 7 to produce materials such as 14 and 15. Intermediates such as 14 and 15 can be treated with TFA to give compounds similar to 4.

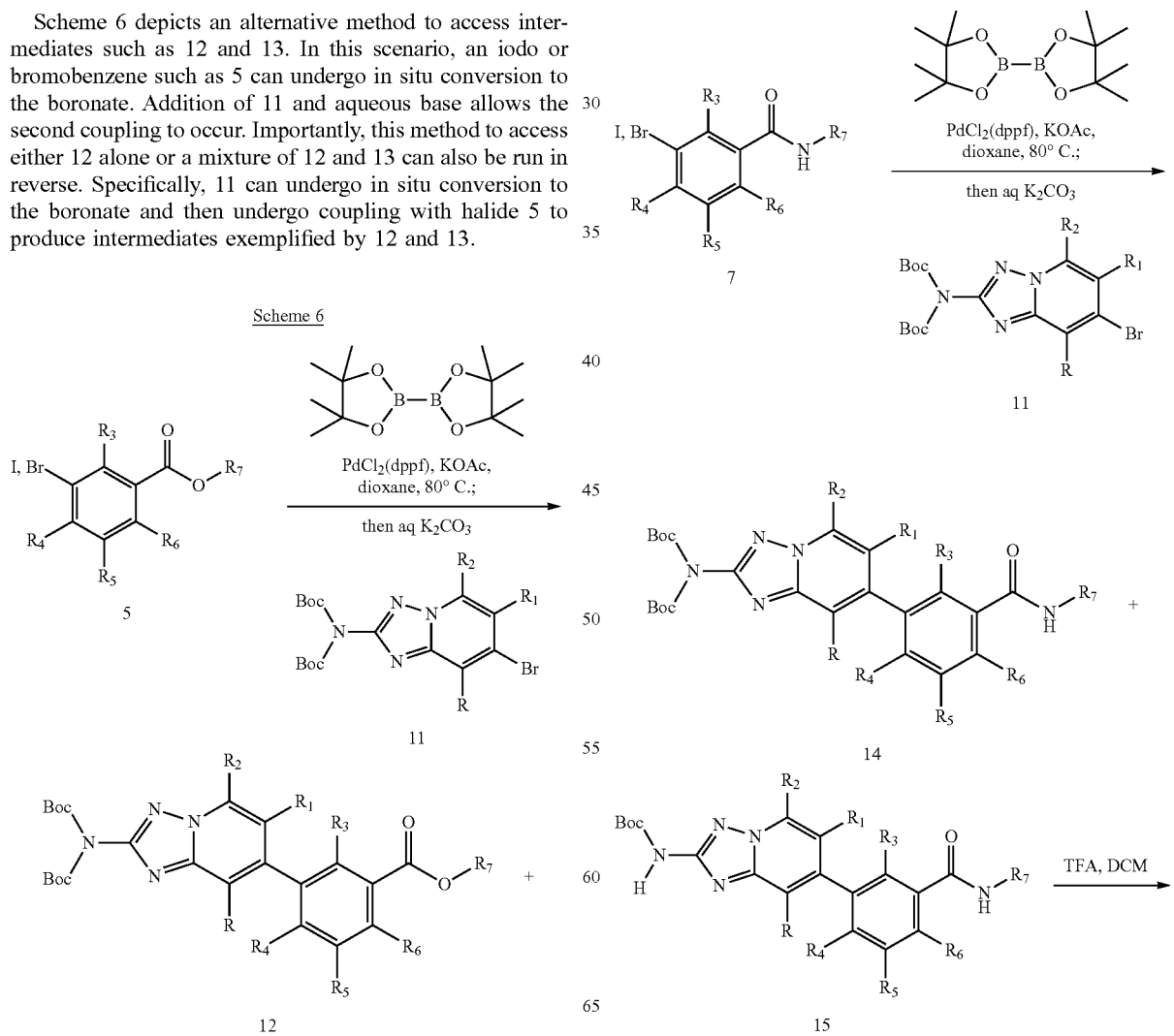

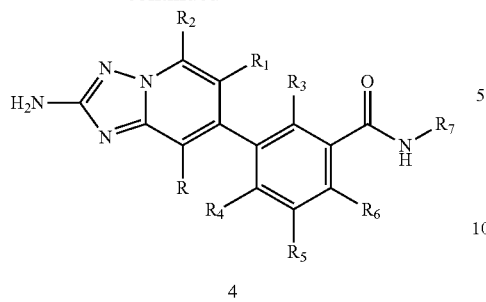

4

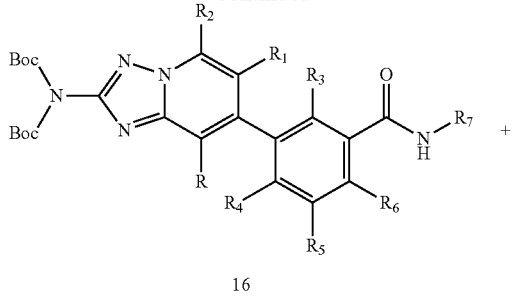

16

Scheme 8 details another preparation of compounds characterized by 4. Compounds such as 11 can undergo in situ conversion to a boronate, followed by Suzuki coupling with carboxylic acid halide 6 to provide either 16 or a mixture of compounds of the type exemplified by 16 and 17. Amides such as 16 and 17 can be treated with TFA either separately or as a mixture to give compounds similar to 4.

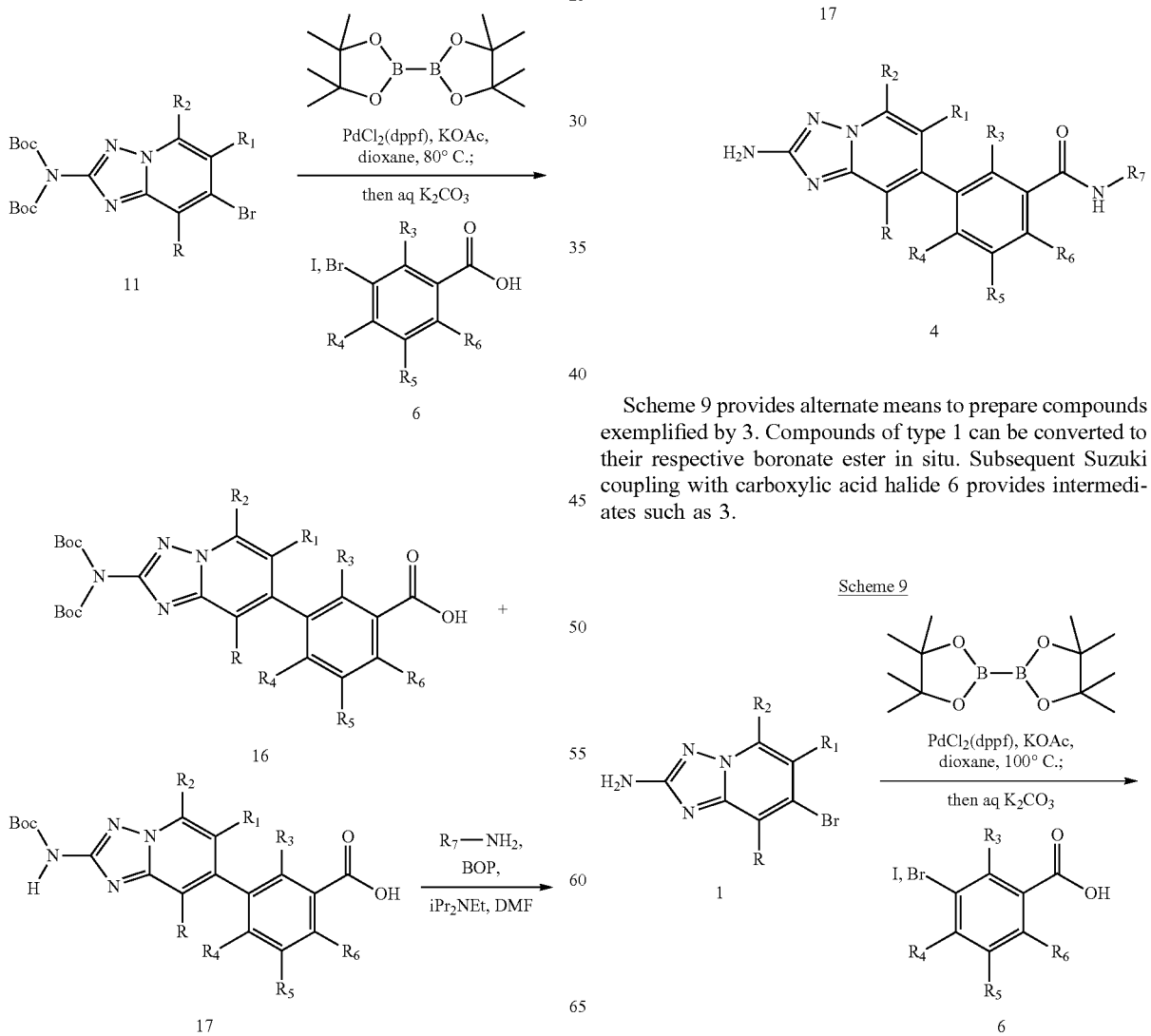

Scheme 9 provides alternate means to prepare compounds exemplified by 3. Compounds of type 1 can be converted to their respective boronate ester in situ. Subsequent Suzuki coupling with carboxylic acid halide 6 provides intermediates such as 3.

Scheme 9

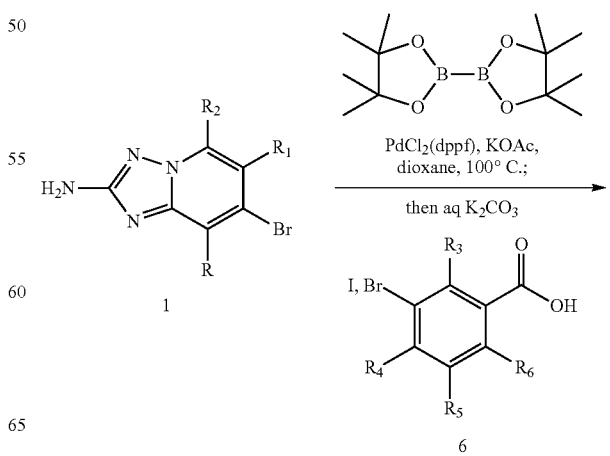

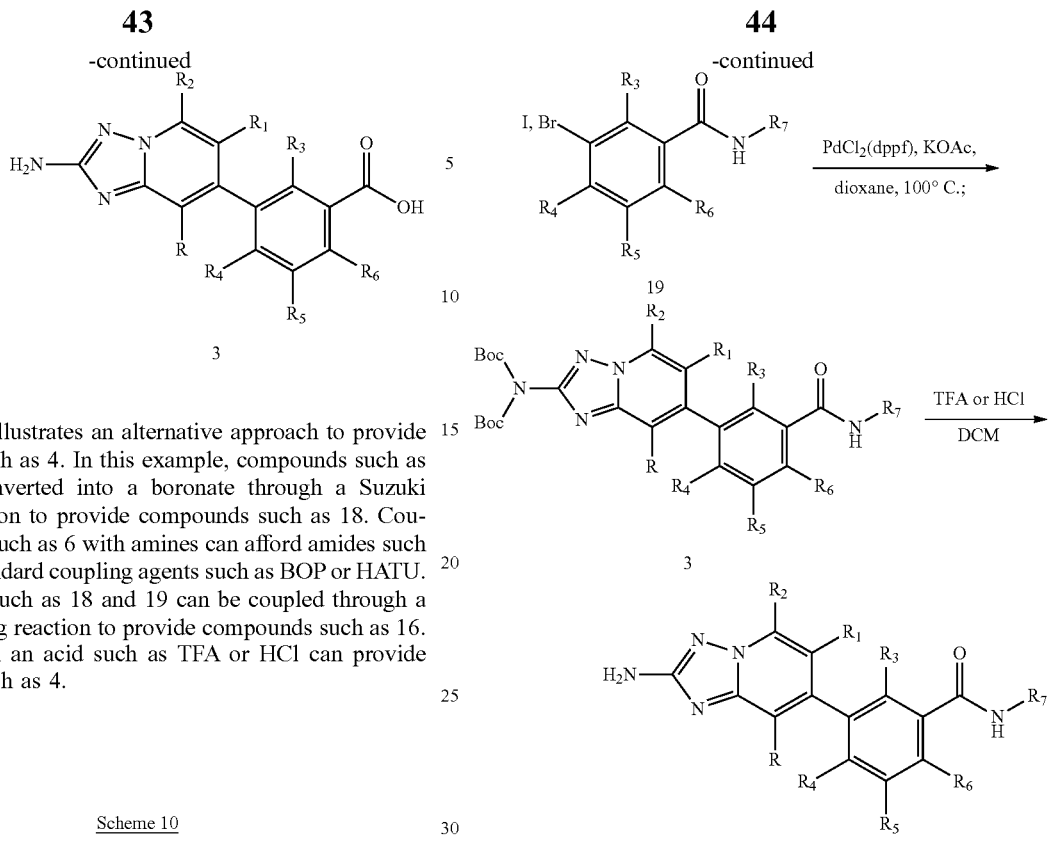

Scheme 10 illustrates an alternative approach to provide compounds such as 4. In this example, compounds such as 11 can be converted into a boronate through a Suzuki coupling reaction to provide compounds such as 18. Coupling of acids such as 6 with amines can afford amides such as 19 using standard coupling agents such as BOP or HATU. Intermediates such as 18 and 19 can be coupled through a Suzuki coupling reaction to provide compounds such as 16. Treatment with an acid such as TFA or HCl can provide compounds such as 4.

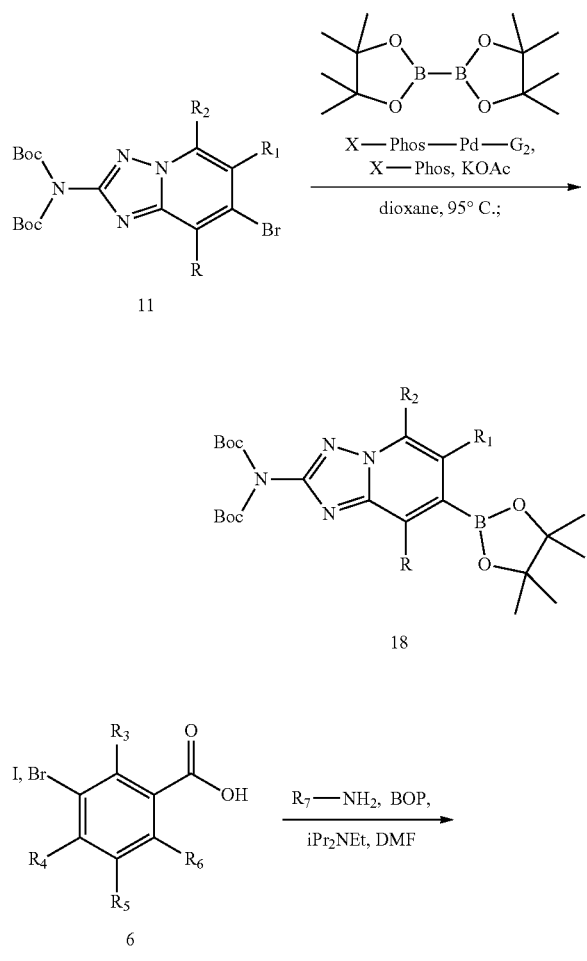

Purification of intermediates and final products was carried out via either normal or reverse phase chromatography. Normal phase chromatography was carried out using pre-packed silica cartridges eluting with either gradients of hexanes and ethyl acetate or dichloromethane and methanol unless otherwise indicated. Reverse phase preparative HPLC or LCMS was typically carried out using C18 columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analytical LCMS injections were used to determine final purity.

Method A: Column: Waters Acquity UPLC BEH C18, 2.1×50 mm, 1.7 μM particles; Mobile phase A: 5:95 acetonitrile:water with 10 mM ammonium acetate; Mobile phase B: 95:5 acetonitrile:water with 10 mM ammonium acetate; Temperature: 50° C.; Gradient: 0-100% B over 3 min, then a 0.75 min hold at 100% B; Flow: 1.11 mL/min; Detection: UV at 220 nm.

Method B: Column: Waters Acquity UPLC BEH C18, 2.1×50 mm, 1.7 m particles; Mobile phase A: 5:95 acetonitrile:water with 0.1% TFA; Mobile phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm.

In a minority of examples analytical HPLC injections were used to determine final purity.

Method A: Column: Sunfire C18, 3.0×150 mm, 3.5 μM particles; Mobile phase A: 5:95 acetonitrile:water with 0.1% TFA; Mobile phase B: 95:5 acetonitrile:water with 0.1% TFA; Gradient: 0-100% B over 10 min; Flow: 1 mL/min; Detection: UV at 220 and 254 nm Method B: Column: Xbridge Phenyl, 3.0×150 mm, 3.5 μM particles; Mobile phase A: 5:95 acetonitrile:water with 0.1% TFA; Mobile phase B: 95:5 acetonitrile:water with 0.1% TFA; Gradient: 0-100% B over 10 min; Flow: 1 mL/min; Detection: UV at 220 and 254 nm Method C: Column: XBridge C18, 3.0×150 mm, 3.5 μM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

Method D: Column: XBridge Phenyl, 3.0×150 mm, 3.5 μM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS (ESI) m/z: [M+H]⁺ BEH C18, 2.11×50 mm, 1.7 m; Mobile phase A: 2:98 water:acetonitrile with 0.1% TFA; Mobile phase B: 98:2 acetonitrile:water with 0.1% TFA; Gradient: 0-100% B over 2 minutes; Flow: 0.8 mL/min; Detection: UV at 220 nm.

Proton NMRs were run with water suppression unless otherwise noted.

Example 1: (S)-5-(2-amino-[1,2,4]triazolo[1,5-a]pyridin-7-yl)-N-(3-(4-chlorophenyl)-3-hydroxypropyl)-4-fluoro-2-methylbenzamide

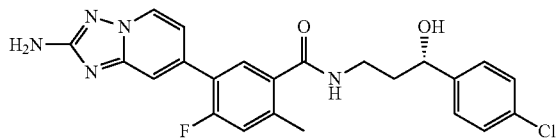 [SMILES: Cc1cc(F)c(-c2ccn3nc(N)nc3c2)cc1C(=O)NCC[C@H](O)c1ccc(Cl)cc1]

1A: methyl 5-(2-((tert-butoxycarbonyl)amino)-[1,2,4]triazolo[1,5-a]pyridin-7-yl)-4-fluoro-2-methylbenzoate: A 100 mL round-bottom flask was charged with a stir bar, [1,1'-bis(di-tert-butylphosphino)ferrocene]dichloropalladium(II) (66.0 mg, 0.102 mmol), N,N-bis-Boc-2-amino-7-bromo-[1,2,4]triazolo[1,5-a]pyridine (1.41 g, 3.40 mmol) and methyl 4-fluoro-2-methyl-5-(4,4,5,5-tetramethyl-1,3,2-dioxaborolan-2-yl)benzoate (1.00 g, 3.40 mmol). The flask was evacuated and backfilled with nitrogen, followed by the addition of 1,4-dioxane (17 mL) and tripotassium phosphate (2M in H₂O) (5.10 mL, 10.2 mmol). The resulting mixture was degassed by bubbling N2 through for 5 min, then the mixture was stirred at 80° C. for 16 h. The crude mixture was purified by flash column chromatography (silica, elution gradient EtOAc in Hex 0% to 25% to 50%) to afford methyl 5-(2-((tert-butoxycarbonyl)amino)-[1,2,4]triazolo[1,5-a]pyridin-7-yl)-4-fluoro-2-methylbenzoate (0.810 g, 2.02 mmol, 60% yield) as the major product, and methyl 5-(2-(di-(tert-butoxycarbonyl)amino)-[1,2,4]triazolo[1,5-a]pyridin-7-yl)-4-fluoro-2-methylbenzoate (0.520 g, 1.04 mmol, 31% yield) as the minor product. 5-(2-((tert-butoxycarbonyl)amino)-[1,2,4]triazolo[1,5-a]pyridin-7-yl)-4-fluoro-2-methylbenzoate: ¹H NMR (500 MHz, CDCl₃) δ 8.63-8.55 (m, 1H), 8.15 (d, J=8.1 Hz, 1H), 7.83 (br s, 1H), 7.76 (s, 1H), 7.20-7.14 (m, 1H), 7.11 (d, J=11.4 Hz, 1H), 3.92 (s, 3H), 2.67 (s, 3H), 1.56 (d, J=0.8 Hz, 9H).

MS ESI m/z 501.1 (M+H)⁺

1B: 5-(2-((tert-butoxycarbonyl)amino)-[1,2,4]triazolo[1,5-a]pyridin-7-yl)-4-fluoro-2-methylbenzoic acid: A 100 mL round-bottom flask was charged with a stir bar and methyl 5-(2-((tert-butoxycarbonyl)amino)-[1,2,4]triazolo[1,5-a]pyridin-7-yl)-4-fluoro-2-methylbenzoate (1.06 g, 2.64 mmol), followed by the addition of THF (11 mL), MeOH (2.2 mL), and sodium hydroxide, 1M aqueous (7.92 mL, 7.92 mmol). The resulting mixture was stirred at RT for 3 h. The reaction mixture was diluted with EtOAc (100 mL) and 1 N aq HCl (100 mL). The mixture was shaken and phases were separated. The organic layer was washed with brine (100 mL), dried with anhydrous MgSO₄ and filtered through celite. The crude 5-(2-((tert-butoxycarbonyl)amino)-[1,2,4]triazolo[1,5-a]pyridin-7-yl)-4-fluoro-2-methylbenzoic acid (1.00 g, 2.59 mmol) thus obtained was used directly in the next step without further purification.

MS ESI m/z 387.0 (M+H)⁺

1C: 5-(2-amino-[1,2,4]triazolo[1,5-a]pyridin-7-yl)-4-fluoro-2-methylbenzoic acid: A 250 mL round-bottom flask was charged with a stir bar and 5-(2-((tert-butoxycarbonyl)amino)-[1,2,4]triazolo[1,5-a]pyridin-7-yl)-4-fluoro-2-methylbenzoic acid (1.00 g, 2.59 mmol), followed by the addition of DCM (6.47 mL) and TFA (6.47 mL). The resulting mixture was stirred at RT for 3 d. The reaction mixture was concentrated in vacuo to afford 5-(2-amino-[1,2,4]triazolo[1,5-a]pyridin-7-yl)-4-fluoro-2-methylbenzoic acid, TFA (850 mg, 2.12 mmol, 82% yield) which was directly subjected to the next step without further purification.

MS ESI m/z 287.3 (M+H)⁺

1: (S)-5-(2-amino-[1,2,4]triazolo[1,5-a]pyridin-7-yl)-N-(3-(4-chlorophenyl)-3-hydroxypropyl)-4-fluoro-2-methylbenzamide: An 8 mL reaction vial was charged with a stir bar, BOP (24.9 mg, 0.0560 mmol), (S)-3-amino-1-(4-chlorophenyl)propan-1-ol, HCl (12.5 mg, 0.0560 mmol) and 5-(2-amino-[1,2,4]triazolo[1,5-a]pyridin-7-yl)-4-fluoro-2-methylbenzoic acid, TFA (15 mg, 0.037 mmol). The vial was evacuated and backfilled with nitrogen, followed by the addition of DMF (375 μL) and DIPEA (65 μL, 0.375 mmol). The resulting mixture was stirred at RT for 16 h. The crude material was purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 16% B, 16-56% B over 20 min, then a 0-min hold at 100% B; Flow Rate: 20 mL/min; Column Temperature: 25 C. Fraction collection was triggered by MS and UV signals. Fractions containing the desired product were combined and dried via centrifugal evaporation to afford (S)-5-(2-amino-[1,2,4]triazolo[1,5-a]pyridin-7-yl)-N-(3-(4-chlorophenyl)-3-hydroxypropyl)-4-fluoro-2-methylbenzamide (7.3 mg, 0.016 mmol, 43% yield).

¹H NMR (500 MHz, DMSO-d6) δ 8.59 (br d, J=6.8 Hz, 1H), 8.37 (br t, J=5.3 Hz, 1H), 7.59-7.50 (m, 2H), 7.37 (s, 4H), 7.26 (br d, J=11.9 Hz, 1H), 7.09 (br d, J=7.0 Hz, 1H), 6.05 (br s, 2H), 5.53-5.42 (m, 1H), 4.70-4.60 (m, 1H), 3.30 (q, J=6.7 Hz, 1H), 2.39 (s, 3H), 1.89-1.80 (m, 2H).

MS ESI m/z 453.9 (M+H)⁺

Example 2: 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide

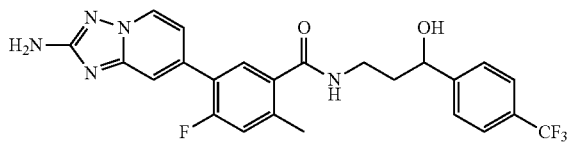 [SMILES: Cc1cc(F)c(-c2ccn3nc(N)nc3c2)cc1C(=O)NCCC(O)c1ccc(C(F)(F)F)cc1]

2A: 3-oxo-3-(4-(trifluoromethyl)phenyl)propanenitrile: To a solution of methyl 4-(trifluoromethyl)benzoate (1.00 g, 4.80 mmol) in dry toluene (4.8 mL) under nitrogen, NaH (0.384 g, 9.60 mmol) was carefully added. Anhydrous acetonitrile (1.25 mL, 24.0 mmol) was added dropwise, and the resulting mixture was heated at 80° C. ON under nitrogen. The resulting slurry was diluted with hexanes, and a solid was isolated by filtration and rinsed with hexanes. The powder solid was then dissolved in water (50 mL) and 1N aqueous HCl (approximately 20 mL) was added with stirring until a precipitate formed. Addition of 1N HCl was ceased when pH=0-1 was achieved. The resulting precipitate was isolated by filtration and allowed to dry under air and then under high vacuum to afford 3-oxo-3-(4-(trifluoromethyl)phenyl)propanenitrile (0.892 g, 4.18 mmol, 62% pure determined by NMR, 54% yield). The product was used as-is in the next step without further purification.

$^1$H NMR (500 MHz, CDCl$_3$) δ 8.05 (d, J=8.1 Hz, 2H), 7.81 (d, J=8.1 Hz, 2H), 4.11 (s, 2H).

2B: 3-amino-1-(4-(trifluoromethyl)phenyl)propan-1-ol: A 20 mL vial was charged with a stir bar and 3-oxo-3-(4-(trifluoromethyl)phenyl)propanenitrile (0.300 g, 1.41 mmol). The flask was evacuated and backfilled with nitrogen, followed by the addition of THF (7 mL). The resulting mixture was cooled to 0° C., and borane dimethyl sulfide complex (1.4 mL, 5M in THF, 7.04 mmol) was slowly added. The reaction mixture was heated to reflux for 16 h. The crude was purified by reverse phase HPLC (Solvent A: 10% acetonitrile, 90% H$_2$O, 0.1% TFA; Solvent B: 90% acetonitrile, 10% H$_2$O, 0.1% TFA; Column: Waters Atlantis 30×100 mm S5; Gradient: 10-70% B) to afford 3-amino-1-(4-(trifluoromethyl)phenyl)propan-1-ol (0.150 g, 0.684 mmol, 49% yield).

1H NMR (500 MHz, DMSO-d6) δ 7.73 (br d, J=7.8 Hz, 2H), 7.57 (br d, J=7.9 Hz, 2H), 4.81 (dd, J=3.8, 2.9 Hz, 1H), 2.88 (br d, J=4.4 Hz, 2H), 2.02-1.70 (m, 2H).
MS ESI m/z 220.05 (M+H)+

2: The title compound was prepared in a similar fashion to the final step described for example 1, substituting 3-amino-1-(4-(trifluoromethyl)phenyl)propan-1-ol for (S)-3-amino-1-(4-chlorophenyl)propan-1-ol, HCl, to afford racemic 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide (11.5 mg, 0.0240 mmol, 32% yield).

$^1$H NMR (500 MHz, DMSO-d$_6$) δ 8.58 (d, J=7.0 Hz, 1H), 8.41 (br t, J=5.5 Hz, 1H), 7.67 (d, J=8.0 Hz, 2H), 7.61-7.50 (m, 4H), 7.25 (d, J=12.0 Hz, 1H), 7.11 (br d, J=7.0 Hz, 1H), 4.74 (dd, J=7.7, 4.9 Hz, 1H), 3.37-3.27 (m, 2H), 2.38 (s, 3H), 1.87 (dt, J=14.6, 7.5 Hz, 2H).
MS ESI m/z 488.0 (M+H)$^+$

Example 3: 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide enantiomer 1

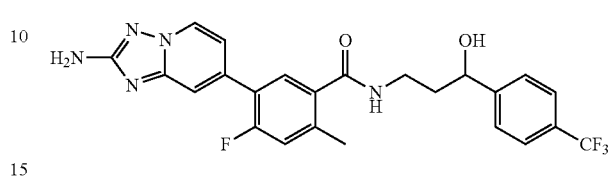

enantiomer 1

Racemic 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide was separated into two individual stereoisomers using SFC chiral chromatography with the following conditions: Column: Chiral OD 30×250 mm. 5 micron; Mobile Phase: 65% CO$_2$/35% IPA w/0.1% DEA; Flow Conditions: 100 mL/min; Detector Wavelength: 220 nm; Injection details: 1.5 mL 9.8 mg dissolved in 3 mL MeOH. Fractions containing the first eluted peak were concentrated to afford 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide enantiomer 1 (2.9 mg, 0.0060 mmol, 8% yield).

$^1$H NMR (500 MHz, DMSO-d$_6$) δ 8.63 (d, J=6.7 Hz, 1H), 8.40 (br t, J=5.3 Hz, 1H), 7.70 (br d, J=7.9 Hz, 2H), 7.63-7.57 (m, 4H), 7.29 (br d, J=11.9 Hz, 1H), 7.12 (br d, J=7.0 Hz, 1H), 4.80-4.75 (m, 1H), 2.42 (s, 3H), 1.95-1.83 (m, 2H).

MS ESI m/z 488.3 (M+H)$^+$

Example 4: 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide enantiomer 2

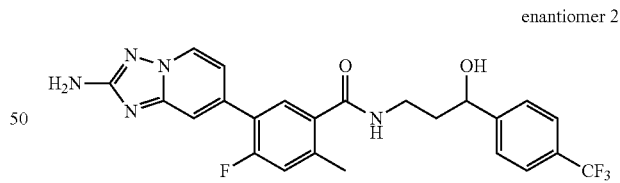

enantiomer 2

The title compound 5-(2-amino-[1,2,4]triazolo[1,5-a]pyridin-7-yl)-4-fluoro-N-(3-hydroxy-3-(4-(trifluoromethyl)phenyl)propyl)-2-methylbenzamide enantiomer 2 (2.7 mg, 0.0060 mmol, 8% yield) was obtained as the second eluting isomer from the chiral SFC purification described for example 3.

$^1$H NMR (500 MHz, DMSO-d$_6$) δ 8.64 (d, J=7.0 Hz, 1H), 8.40 (br t, J=5.5 Hz, 1H), 7.71 (br d, J=8.2 Hz, 2H), 7.63-7.57 (m, 4H), 7.29 (br d, J=11.9 Hz, 1H), 7.12 (br d, J=7.0 Hz, 1H), 4.80-4.75 (m, 1H), 2.42 (s, 3H), 1.96-1.82 (m, 2H).

MS ESI m/z 488.3 (M+H)$^+$

TABLE 1

Compounds in Table 1 were prepared in a similar fashion to examples 2, 3 and 4.

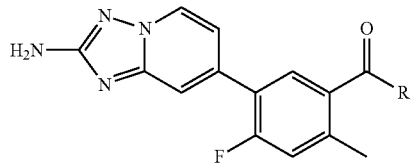

| Ex No | Name | R | M + H⁺ | ¹H NMR (500 MHz, DMSO-d6) δ |
|---|---|---|---|---|
| 5 | 5-(2-amino-[1,2,4]-triazolo[1,5-a]-pyridin-7-yl)-N-(3-(5-chloropyridin-2-yl)-3-hydroxy-propyl)-4-fluoro-2-methylbenzamide | racemate | 455.3 | 8.57 (d, J = 6.9 Hz, 1H), 8.48 (d, J = 1.7 Hz, 1H), 8.40 (br t, J = 5.4 Hz, 1H), 7.88 (dd, J = 8.5, 2.4 Hz, 1H), 7.58-7.47 (m, 3H), 7.25 (d, J = 12.1 Hz, 1H), 7.10 (br d, J = 6.9 Hz, 1H), 6.03 (s, 2H), 4.68 (dt, J = 8.6, 4.4 Hz, 1H), 3.41-3.28 (m, 2H), 2.37 (s, 3H), 2.10-1.97 (m, 1H), 1.91-1.78 (m, 1H) |
| 6 | 5-(2-amino-[1,2,4]-triazolo[1,5-a]-pyridin-7-yl)-N-(3-(5-chloropyridin-2-yl)-3-hydroxy-propyl)-4-fluoro-2-methylbenzamide-enantiomer 1 | enantiomer 1 first eluted | 455.3 | 8.65 (d, J = 7.0 Hz, 1H), 8.54 (br d, J = 1.8 Hz, 1H), 8.40 (br t, J = 5.2 Hz, 1H), 7.92 (dd, J = 8.4, 2.3 Hz, 1H), 7.62-7.55 (m, 3H), 7.29 (br d, J = 11.9 Hz, 1H), 7.15 (br d, J = 7.0 Hz, 1H), 4.71 (br dd, J = 8.1, 3.8 Hz, 1H), 3.44-3.31 (m, 1H), 3.00-2.88 (m, 1H), 2.42 (s, 3H), 2.11-2.02 (m, 1H), 1.90-1.80 (m, 1H) |
| 7 | 5-(2-amino-[1,2,4]-triazolo[1,5-a]-pyridin-7-yl)-N-(3-(5-chloropyridin-2-yl)-3-hydroxy-propyl)-4-fluoro-2-methylbenzamide enantiomer 2 | enantiomer 2 second eluted | 455.3 | 8.63 (d, J = 7.0 Hz, 1H), 8.54 (d, J = 2.1 Hz, 1H), 8.40 (br t, J = 5.3 Hz, 1H), 7.93 (dd, J = 8.2, 2.1 Hz, 1H), 7.61-7.55 (m, 3H), 7.28 (br d, J = 11.6 Hz, 1H), 7.12 (br d, J = 6.7 Hz, 1H), 4.71 (br dd, J = 8.4, 4.1 Hz, 1H), 3.44-3.32 (m, 1H), 2.99-2.89 (m, 1H), 2.42 (s, 3H), 2.11-2.03 (m, 1H), 1.90-1.81 (m, 1H) |
| 8 | 5-(2-amino-[1,2,4]-triazolo[1,5-a]-pyridin-7-yl)-4-fluoro-N-(3-(4-fluorophenyl)-3-hydroxypropyl)-2-methylbenzamide | racemate | 438.3 | 8.65 (br d, J = 6.8 Hz, 1H), 8.39 (br t, J = 5.3 Hz, 1H), 7.65-7.52 (m, 2H), 7.38 (br t, J = 6.3 Hz, 2H), 7.27 (br d, J = 11.9 Hz, 1H), 7.21-7.10 (m, 3H), 4.65 (br t, J = 6.4 Hz, 1H), 3.29 (q, J = 6.6 Hz, 2H), 2.39 (s, 3H), 1.84 (q, J = 6.7 Hz, 2H) |
| 9 | 5-(2-amino-[1,2,4]-triazolo[1,5-a]-pyridin-7-yl)-4-fluoro-N-(3-(4-fluorophenyl)-3-hydroxypropyl)-2-methylbenzamide enantiomer 1 | enantiomer 1 first eluted | 438.3 | 8.65 (d, J = 7.0 Hz, 1H), 8.38 (br t, J = 4.7 Hz, 1H), 7.63-7.58 (m, 2H), 7.40 (br dd, J = 8.1, 5.6 Hz, 2H), 7.29 (br d, J = 11.9 Hz, 1H), 7.18-7.12 (m, 3H), 4.67 (br t, J = 6.3 Hz, 1H), 3.35-3.27 (m, 1H), 2.98-2.90 (m, 1H), 2.42 (s, 3H), 1.89-1.83 (m, 2H) |
| 10 | 5-(2-amino-[1,2,4]-triazolo[1,5-a]-pyridin-7-yl)-4-fluoro-N-(3-(4-fluorophenyl)-3-hydroxypropyl)-2-methylbenzamide enantiomer 2 | enantiomer 2 second eluted | 438.0 | 8.65 (d, J = 6.7 Hz, 1H), 8.38 (br t, J = 5.0 Hz, 1H), 7.63-7.58 (m, 2H), 7.40 (br dd, J = 8.1, 6.0 Hz, 2H), 7.29 (br d, J = 12.2 Hz, 1H), 7.18-7.12 (m, 3H), 4.67 br t, J = 6.4 Hz, 1H), 3.35-3.28 (m, 1H), 2.98-2.90 (m, 1H), 2.42 (s, 3H), 1.86 (q, J = 6.9 Hz, 2H) |

Example 11: 3-(2-amino-[1,2,4]triazolo[1,5-a]pyridin-7-yl)-2-fluoro-6-methyl-N-(4,4,4-trifluoro-3-phenylbutyl)benzamide

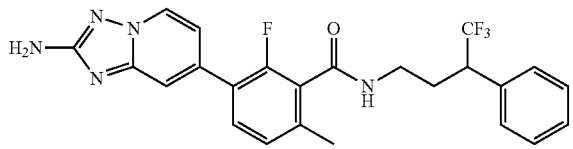 [SMILES: Cc1ccc(-c2ccn3nc(N)nc3c2)c(F)c1C(=O)NCCC(c1ccccc1)C(F)(F)F]

11A: ethyl 3-(N,N-bis-Boc-2-amino-[1,2,4]triazolo[1,5-a]pyridin-7-yl)-2-fluoro-6-methylbenzoate and ethyl 3-(N-Boc-2-amino-[1,2,4]triazolo[1,5-a]pyridin-7-yl)-2-fluoro-6-methylbenzoate: A 100 mL round-bottom flask was charged with a stir bar, [1,1'-bis(di-tert-butylphosphino)ferrocene]dichloropalladium(II) (0.125 g, 0.192 mmol), ethyl 3-bromo-2-fluoro-6-methylbenzoate (1.00 g, 3.83 mmol) and N,N-bis-Boc-2-amino-7-(4,4,5,5-tetramethyl-1,3,2-dioxaborolan-2-yl)-[1,2,4]triazolo[1,5-a]pyridine (2.12 g, 4.60 mmol). The flask was evacuated and backfilled with nitrogen, followed by the addition of 1,4-dioxane (19.2 mL) and tripotassium phosphate, 2M aqueous (5.8 mL, 11.5 mmol). The resulting mixture was stirred at 80° C. for 3 h. The crude mixture was purified by flash column chromatography (silica, elution gradient EtOAc in Hex 0% to 50%) to afford ethyl 3-(N,N-bis-Boc-2-amino-[1,2,4]triazolo[1,5-a]pyridin-7-yl)-2-fluoro-6-methylbenzoate (1.75 g, 3.40 mmol, 89% yield) and ethyl 3-(N-Boc-2-amino-[1,2,4]triazolo[1,5-a]pyridin-7-yl)-2-fluoro-6-methylbenzoate (0.136 g, 0 328 mmol, 9% yield).

ethyl 3-(N,N-bis-Boc-2-amino-[1,2,4]triazolo[1,5-a]pyridin-7-yl)-2-fluoro-6-methylbenzoate: $^1$H NMR (500 MHz, CDCl$_3$) δ 8.56 (d, J=7.3 Hz, 1H), 7.83 (d, J=0.9 Hz, 1H), 7.45 (t, J=7.9 Hz, 1H), 7.28-7.23 (m, 1H), 7.16 (d, J=7.9 Hz, 1H), 4.45 (q, J=7.3 Hz, 2H), 2.46 (s, 3H), 1.48 (s, 18H), 1.41 (t, J=7.3 Hz, 3H).

ethyl 3-(N-Boc-2-amino-[1,2,4]triazolo[1,5-a]pyridin-7-yl)-2-fluoro-6-methylbenzoate: $^1$H NMR (500 MHz, CDCl$_3$) δ 8.56 (d, J=7.2 Hz, 1H), 7.98 (s, 1H), 7.71 (s, 1H), 7.44 (t, J=7.9 Hz, 1H), 7.14 (dd, J=7.6, 2.3 Hz, 2H), 4.45 (q, J=7.1 Hz, 2H), 2.45 (s, 3H), 1.56 (s, 9H), 1.41 (t, J=7.2 Hz, 3H).
MS ESI m/z 415.2 (M+H)$^+$ 11B: ethyl 3-(2-amino-[1,2,4]triazolo[1,5-a]pyridin-7-yl)-2-fluoro-6-methylbenzoate: A 100 mL round-bottom flask was charged with a stir bar and ethyl 3-(N,N-bis-Boc-2-amino-[1,2,4]triazolo[1,5-a]pyridin-7-yl)-2-fluoro-6-methylbenzoate (1.75 g, 3.40 mmol). The flask was evacuated and backfilled with nitrogen, followed by the addition of DCM (8.5 mL) and TFA (8.5 mL). The resulting mixture was stirred at RT for 16 h. The mixture was concentrated in vacuo and the crude was used directly in the next step without further purification.
MS ESI m/z 315.1 (M+H)$^+$ 11C: 3-(2-amino-[1,2,4]triazolo[1,5-a]pyridin-7-yl)-2-fluoro-6-methylbenzoic acid: A 100 mL round-bottom flask was charged with a stir bar, ethyl 3-(2-amino-[1,2,4]triazolo[1,5-a]pyridin-7-yl)-2-fluoro-6-methylbenzoate (1.07 g, 3.23 mmol) and lithium hydroxide monohydrate (0.679 g, 16.2 mmol). The flask was evacuated and backfilled with nitrogen, followed by the addition of THF (35 mL) and H$_2$O (5.8 mL). The resulting mixture was stirred at 60° C. for 3 d. The mixture was concentrated in vacuo. The crude was diluted with 1 N aqueous HCl (100 mL), washed with diethyl ether (50 mL), and the aqueous phase was concentrated in vacuo to obtain 3-(2-amino-[1,2,4]triazolo[1,5-a]pyridin-7-yl)-2-fluoro-6-methylbenzoic acid, HCl (2.00 g, 3.10 mmol, 96% yield).

$^1$H NMR (500 MHz, DMSO-d$_6$) δ 8.76 (d, J=7.0 Hz, 1H), 7.70-7.62 (m, 2H), 7.28 (d, J=8.0 Hz, 2H), 2.39 (s, 3H).
MS ESI m/z 286.8 (M+H)$^+$

11: An 8 mL vial was charged with a stir bar, 4,4,4-trifluoro-3-phenylbutan-1-amine (81.0 mg, 0.397 mmol) and 3-(2-amino-[1,2,4]triazolo[1,5-a]pyridin-7-yl)-2-fluoro-6-methylbenzoic acid, HCl (171 mg, 0.265 mmol). The vial was evacuated and backfilled with nitrogen, followed by the addition of BOP (141 mg, 0.318 mmol), N,N-diisopropylethylamine (0.230 ml, 1.33 mmol) and DMF (2.7 mL). The resulting mixture was stirred at RT for 16 h. The crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 24% B, 24-64% B over 23 min, then a 0-min hold at 100% B; Flow Rate: 20 mL/min; Column Temperature: 25 C. Fraction collection was triggered by MS signals. Fractions containing the desired product were combined and dried via centrifugal evaporation to afford racemic 3-(2-amino-[1,2,4]triazolo[1,5-a]pyridin-7-yl)-2-fluoro-6-methyl-N-(4,4,4-trifluoro-3-phenylbutyl)benzamide (122 mg, 0.259 mmol, 98% yield).

$^1$H NMR (500 MHz, DMSO-d$_6$) δ 8.72 (t, J=5.3 Hz, 1H), 8.61 (d, J=6.7 Hz, 1H), 7.59 (t, J=8.1 Hz, 1H), 7.49 (s, 1H), 7.47-7.38 (m, 5H), 7.23 (d, J=8.2 Hz, 1H), 7.05 (br d, J=7.0 Hz, 1H), 3.72 (td, J=10.1, 3.2 Hz, 1H), 3.28-3.14 (m, 1H), 3.13-3.03 (m, 1H), 2.30 (s, 3H), 2.27-2.09 (m, 2H).
MS ESI m/z 472.3 (M+H)$^+$

Example 12: 3-(2-amino-[1,2,4]triazolo[1,5-a]pyridin-7-yl)-2-fluoro-6-methyl-N-(4,4,4-trifluoro-3-phenylbutyl)benzamide enantiomer 1

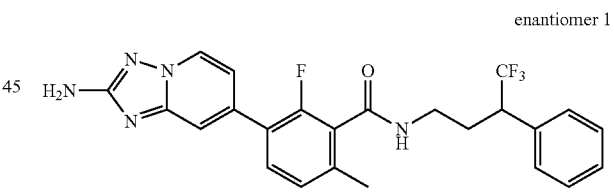

Racemic 3-(2-amino-[1,2,4]triazolo[1,5-a]pyridin-7-yl)-2-fluoro-6-methyl-N-(4,4,4-trifluoro-3-phenylbutyl)benzamide was separated into two individual stereoisomers using SFC chiral chromatography with the following conditions: Column: Chiral OJ 30×250 mm. 5 micron; Mobile Phase: 85% CO2/15% IPA w/0.1% DEA; Flow Conditions: 100 mL/min; Detector Wavelength: 220 nm. Fractions containing the first eluted peak were concentrated to afford 3-(2-amino-[1,2,4]triazolo[1,5-a]pyridin-7-yl)-2-fluoro-6-methyl-N-(4,4,4-trifluoro-3-phenylbutyl)benzamide enantiomer 1 (39.7 mg, 0.0840 mmol, 32% yield).

$^1$H NMR (500 MHz, DMSO-d$_6$) δ 8.73 (t, J=5.5 Hz, 1H), 8.61 (d, J=7.0 Hz, 1H), 7.59 (t, J=8.1 Hz, 2H), 7.49 (s, 1H), 7.47-7.38 (m, 5H), 7.23 (d, J=8.2 Hz, 1H), 7.05 (br d, J=7.0 Hz, 1H), 3.78-3.67 (m, 1H), 3.24-3.15 (m, 1H), 3.12-3.03 (m, 1H), 2.30 (s, 3H), 2.27-2.09 (m, 2H)
MS ESI m/z 472.1 (M+H)$^+$

Example 13: 3-(2-amino-[1,2,4]triazolo[1,5-a]pyridin-7-yl)-2-fluoro-6-methyl-N-(4,4,4-trifluoro-3-phenylbutyl)benzamide enantiomer 2

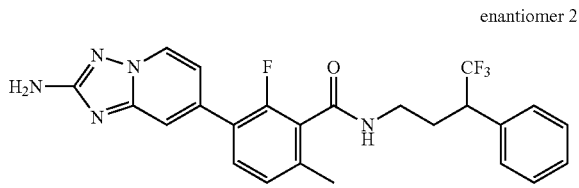 [SMILES: Cc1ccc(-c2ccn3nc(N)nc3c2)c(F)c1C(=O)NCCC(c1ccccc1)C(F)(F)F]

enantiomer 2

The title compound 3-(2-amino-[1,2,4]triazolo[1,5-a]pyridin-7-yl)-2-fluoro-6-methyl-N-(4,4,4-trifluoro-3-phenylbutyl)benzamide enantiomer 2 (39.9 mg, 0.085 mmol, 32% yield) was obtained as the second eluting isomer from the chiral SFC purification described for example 12.

$^1$H NMR (500 MHz, DMSO-$d_6$) δ 8.73 (t, J=5.5 Hz, 1H), 8.61 (d, J=7.0 Hz, 1H), 7.59 (t, J=8.1 Hz, 2H), 7.49 (s, 1H), 7.47-7.38 (m, 5H), 7.23 (d, J=8.2 Hz, 1H), 7.05 (br d, J=7.0 Hz, 1H), 3.78-3.67 (m, 1H), 3.24-3.15 (m, 1H), 3.12-3.03 (m, 1H), 2.30 (s, 3H), 2.27-2.09 (m, 2H).
MS ESI m/z 472.1 (M+H)$^+$

Example 14: 3-(2-amino-[1,2,4]triazolo[1,5-a]pyridin-7-yl)-N-(3-(4-chlorophenyl)-3-hydroxypropyl-1,1,3-$d_3$)-2-fluoro-6-methylbenzamide

14A: 3-amino-1-(4-chlorophenyl)propan-1,3,3-$d_3$-1-ol: A 50 mL round-bottom flask was charged with a stir bar and 3-(4-chlorophenyl)-3-oxopropanenitrile (0.500 g, 2.78 mmol). The flask was evacuated and backfilled with nitrogen, followed by the addition of THF (9.3 mL). The resulting mixture was cooled to 0° C. and lithium aluminum deuteride, 98% isotopic purity (0.351 g, 8.35 mmol) in THF (4.6 mL) was added slowly. The mixture was stirred at RT for 3 h, then quenched by addition of TN aqueous NaOH. The product was extracted with diethyl ether and washed with brine, dried over anhydrous MgSO$_4$, filtered through celite and concentrated in vacuo. The crude material was used as-is in subsequent steps without further purification.
MS ESI m/z 189.2 (M+H)$^+$ 14: The title compound was prepared in a similar fashion to the final step described for example 11, substituting 3-amino-1-(4-chlorophenyl)propan-1,3,3-d3-1-ol for 4,4,4-trifluoro-3-phenylbutan-1-amine in the final step to afford racemic 3-(2-amino-[1,2,4]triazolo[1,5-a]pyridin-7-yl)-N-(3-(4-chlorophenyl)-3-hydroxypropyl-1,1,3-d3)-2-fluoro-6-methylbenzamide (46.1 mg, 0.101 mmol, 38% yield).

$^1$H NMR (500 MHz, DMSO-$d_6$) δ 8.63-8.58 (m, 2H), 7.58 (t, J=8.1 Hz, 1H), 7.49 (s, 1H), 7.43-7.35 (m, 4H), 7.22 (d, J=7.9 Hz, 1H), 7.04 (br d, J=6.7 Hz, 1H), 2.32 (s, 3H), 1.80 (s, 2H).
MS ESI m/z 457.0 (M+H)$^+$

Example 15: 3-(2-amino-[1,2,4]triazolo[1,5-a]pyridin-7-yl)-N-(3-(4-chlorophenyl)-3-methylbutyl)-2-fluoro-6-methylbenzamide

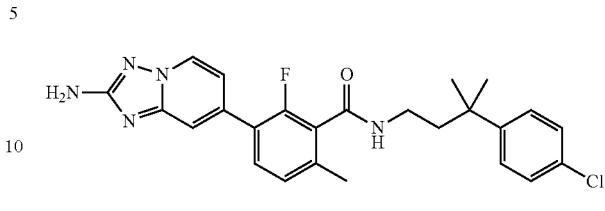

15A: 3-(4-chlorophenyl)-3-methylbutanoic acid: An 8 mL reaction vial was charged with a stir bar and methyl 4-(4-chlorophenyl)-4-methylpentanoate (0.290 g, 1.21 mmol). The vial was evacuated and backfilled with nitrogen, followed by the addition of lithium hydroxide monohydrate (0.152 g, 3.61 mmol), THF (4.5 mL) and H$_2$O (1.5 mL). The resulting mixture was stirred at RT for 16 h. The crude mixture was concentrated in vacuo, diluted with EtOAc (50 mL) and 1N aqueous HCl (50 mL). The aqueous phase was washed with EtOAc (50 mL×2), and the combined organic phase was washed with brine, dried over anhydrous MgSO$_4$ and filtered. The mixture was concentrated in vacuo and used as-is in the next step (100% yield assumed).

MS ESI m/z 224.95 (M–H)$^-$

15B: A 20 mL reaction vial was charged with a stir bar and 4-(4-chlorophenyl)-4-methylpentanoic acid (272 mg, 1.20 mmol). The vial was evacuated and backfilled with nitrogen, followed by the addition of toluene (4 mL), triethylamine (669 μl, 4.80 mmol) and diphenyl phosphoryl azide (516 μl, 2.40 mmol) at 0° C. The resulting mixture was stirred at RT for 16 h, then diluted with EtOAc (30 mL). The organic phase was washed with TN aqueous HCl and brine, dried over anhydrous MgSO$_4$, filtered and concentrated in vacuo. The crude material was dissolved in tert-butanol (574 μl, 60.0 mmol), followed by addition of tin(II) chloride (11.4 mg, 0.0600 mmol). The resulting mixture was stirred at 80° C. for 2 d. The mixture was concentrated in vacuo and redissolved in a mixture of TFA (3 mL) and DCM (6 mL). The resulting mixture was stirred at RT for 16 h. The product was purified by reverse phase preparative HPLC (Solvent A: 10% acetonitrile, 90% H$_2$O, 0.1% TFA; Solvent B: 90% acetonitrile, 10% H$_2$O, 0.1% TFA; Column: Waters Atlantis OBD 30×100 mm S5; Gradient: 10-70% B) to afford 3-(4-chlorophenyl)-3-methylbutan-1-amine, TFA (69.0 mg, 0.221 mmol, 18.5% yield).

MS ESI m/z 197.85 (M+H)$^+$

15: The title compound was prepared in a similar fashion to the final step described for example 11, substituting 3-(4-chlorophenyl)-3-methylbutan-1-amine, TFA for 4,4,4-trifluoro-3-phenylbutan-1-amine in the final step to afford 3-(2-amino-[1,2,4]triazolo[1,5-a]pyridin-7-yl)-N-(3-(4-chlorophenyl)-3-methylbutyl)-2-fluoro-6-methylbenzamide (8.1 mg, 0.0174 mmol, 39% yield).

$^1$H NMR (500 MHz, DMSO-$d_6$) δ 8.60 (d, J=7.0 Hz, 1H), 8.50 (t, J=5.5 Hz, 1H), 7.56 (t, J=8.1 Hz, 1H), 7.48-7.34 (m, 5H), 7.19 (d, J=8.1 Hz, 1H), 7.01 (br d, J=7.0 Hz, 1H), 6.08 (s, 2H), 2.99 (dt, J=11.0, 5.5 Hz, 2H), 2.26 (s, 3H), 1.88-1.81 (m, 2H), 1.31 (s, 6H).
MS ESI m/z 466.0 (M+H)$^+$

Example 16: 3-(2-amino-[1,2,4]triazolo[1,5-a]pyridin-7-yl)-2-fluoro-N-(2-(1-(4-fluorophenyl)cyclopropyl)ethyl)-6-methylbenzamide

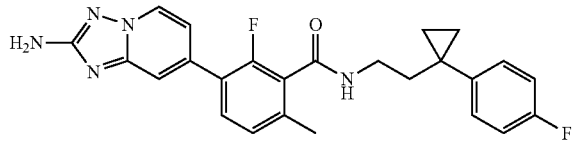 [SMILES: Cc1ccc(-c2ccn3nc(N)nc3c2)c(F)c1C(=O)NCCC1(c2ccc(F)cc2)CC1]

16A: 2-(1-(4-fluorophenyl)cyclopropyl)ethan-1-amine: A 20 mL vial was charged with a stir bar and 2-(1-(4-fluorophenyl)cyclopropyl)acetonitrile (0.250 g, 1.43 mmol). The flask was evacuated and backfilled with nitrogen, followed by the addition of THF (7.1 mL). The resulting mixture was cooled to 0° C., and borane dimethyl sulfide complex (0.86 mL, 5M in THF, 4.28 mmol) was slowly added. The reaction mixture was heated to reflux for 16 h. The crude mixture was purified by reverse phase preparative HPLC (Solvent A: 10% acetonitrile, 90% $H_2O$, 0.1% TFA; Solvent B: 90% acetonitrile, 10% $H_2O$, 0.10% TFA; Column: Waters Atlantis OBD 30×100 mm S5; Gradient 10-100% B) to afford 2-(1-(4-fluorophenyl)cyclopropyl)ethan-1-amine, TFA (135 mg, 0.460 mmol, 32.3% yield).
$^1$H NMR (500 MHz, DMSO-$d_6$) δ 7.41-7.26 (m, 2H), 7.14 (br t, J=8.4 Hz, 2H), 2.76-2.61 (m, 2H), 1.90-1.70 (m, 2H), 0.92-0.64 (m, 4H).
MS ESI m/z 180.1 $(M+H)^+$ 16: The title compound was prepared in a similar fashion to the final step described for example 11, substituting 2-(1-(4-fluorophenyl)cyclopropyl)ethan-1-amine, TFA for 4,4,4-trifluoro-3-phenylbutan-1-amine in the final step to afford 3-(2-amino-[1,2,4]triazolo[1,5-a]pyridin-7-yl)-2-fluoro-N-(2-(1-(4-fluorophenyl)cyclopropyl)ethyl)-6-methylbenzamide (22.3 mg, 0.0498 mmol, 64% yield).
$^1$H NMR (500 MHz, DMSO-$d_6$) δ 8.61 (d, J=6.6 Hz, 1H), 8.55 (t, J=5.5 Hz, 1H), 7.57 (t, J=8.1 Hz, 1H), 7.47 (s, 1H), 7.42-7.35 (m, 2H), 7.20 (d, J=8.1 Hz, 1H), 7.13 (t, J=8.8 Hz, 2H), 7.02 (br d, J=7.0 Hz, 1H), 3.21-3.14 (m, 2H), 2.28 (s, 3H), 1.82-1.73 (m, 2H), 0.77 (br d, J=12.1 Hz, 4H).
MS ESI m/z 448.0 $(M+H)^+$ Example 17: 3-(2-amino-[1,2,4]triazolo[1,5-a]pyridin-7-yl)-N-(3-(4-chlorophenyl)-3-hydroxybutyl)-2-fluoro-6-methylbenzamide

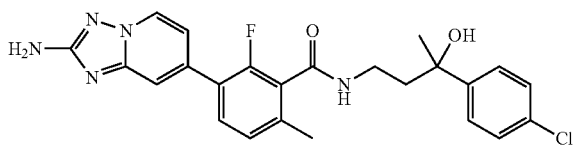 [SMILES: Cc1ccc(-c2ccn3nc(N)nc3c2)c(F)c1C(=O)NCCC(C)(O)c1ccc(Cl)cc1]

17A: 3-(4-chlorophenyl)-3-hydroxybutanenitrile: A 100 mL round-bottom flask was charged with a stir bar. The flask was vacuum-dried twice, followed by the addition of THF (32.3 mL). The flask was cooled to −20° C. and n-BuLi solution (7.8 mL, 2.5 M, 19.4 mmol) was added. A solution of acetonitrile (1.0 mL, 19.4 mmol) in THF (8.1 mL) was dropwise added over 10 min. The resulting mixture was stirred at −20° C. for 1 h, and 1-(4-chlorophenyl)ethan-1-one (2.52 mL, 19.4 mmol) in THF (8.1 mL) was added dropwise over 10 min. The mixture was further stirred at −20° C. for 15 min and allowed to warm to RT over 15 min. The reaction was quenched by addition of saturated aqueous $NH_4Cl$. Most of the starting material remained unreacted as indicated by TLC. The reaction mixture was diluted with EtOAc (200 mL), washed with $H_2O$ (200 mL) and brine (200 mL), dried with anhydrous $MgSO_4$ and filtered through celite. The crude mixture was concentrated in vacuo and purified by flash column chromatography (EtOAc in hexane, gradient 0% to 40%, 40% hold, 40 g silica) to afford 3-(4-chlorophenyl)-3-hydroxybutanenitrile (492 mg, 2.51 mmol, 13.0% yield).
$^1$H NMR (500 MHz, $CDCl_3$) δ 7.45-7.40 (m, 2H), 7.37-7.32 (m, 2H), 2.85-2.74 (m, 2H), 1.74 (s, 3H).

17B: 4-amino-2-(4-chlorophenyl)butan-2-ol, TFA: A 100 mL round-bottom flask was charged with a stir bar and 3-(4-chlorophenyl)-3-hydroxybutanenitrile (0.492 g, 2.51 mmol). The flask was evacuated and backfilled with nitrogen, followed by the addition of THF (12.6 mL). The resulting mixture was cooled to 0° C., and borane dimethyl sulfide complex solution (1.5 mL, 5 M in THF, 7.54 mmol) was slowly added. The resulting mixture was heated to reflux for 16 h. The crude material was purified by reverse phase preparative HPLC (Solvent A: 10% acetonitrile, 90% $H_2O$, 0.1% TFA; Solvent B: 90% acetonitrile, 10% $H_2O$, 0.10% TFA; Column: Waters Atlantis OBD 30×100 mm S5; Gradient: 10-60% B) to afford 4-amino-2-(4-chlorophenyl)butan-2-ol, TFA (0.251 g, 0.800 mmol, 32% yield). The mixture was used as-is in the next step without further purification.
MS ESI m/z 199.8 $(M+H)^+$.

17: The title compound was prepared in a similar fashion to the final step described for example 11, substituting 4-amino-2-(4-chlorophenyl)butan-2-ol, TFA for 4,4,4-trifluoro-3-phenylbutan-1-amine in the final step to afford racemic 3-(2-amino-[1,2,4]triazolo[1,5-a]pyridin-7-yl)-N-(3-(4-chlorophenyl)-3-hydroxybutyl)-2-fluoro-6-methylbenzamide (0.9 mg, 0.0019 mmol, 7% yield).
$^1$H NMR (500 MHz, DMSO-$d_6$) δ 8.60 (d, J=6.6 Hz, 1H), 8.45 (br t, J=5.3 Hz, 1H), 7.56 (br t, J=7.9 Hz, 1H), 7.51-7.44 (m, 2H), 7.38 (d, J=8.1 Hz, 2H), 7.19 (d, J=8.1 Hz, 1H), 7.01 (br d, J=7.0 Hz, 1H), 6.09 (s, 2H), 5.23 (s, 1H), 3.40-3.25 (m, 1H), 2.95 (td, J=11.6, 5.9 Hz, 1H), 2.27 (s, 3H), 2.01-1.88 (m, 2H), 1.46 (s, 3H).
MS ESI m/z 468.3 $(M+H)^+$ Example 18: 3-(2-amino-[1,2,4]triazolo[1,5-a]pyridin-7-yl)-N-(2,2-difluoro-3-(4-fluorophenyl)-3-hydroxybutyl)-2-fluoro-6-methylbenzamide

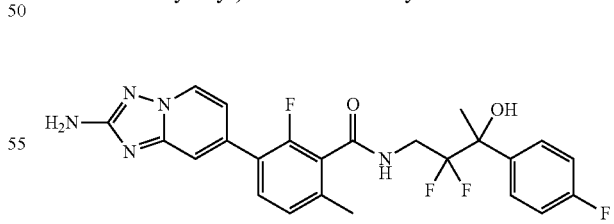

18A: ethyl 2,2-difluoro-3-(4-fluorophenyl)-3-hydroxybutanoate: A mixture of iron (168 mg, 3.00 mmol), 1-(4-fluorophenyl)ethan-1-one (138 mg, 1.00 mmol), ethyl 2-bromo-2,2-difluoroacetate (609 mg, 3.00 mmol), and iodine (50.8 mg, 0.200 mmol) in THF (2 mL) was purged with nitrogen and stirred at 70° C. for 20 h. The reaction was quenched with saturated aqueous $NH_4Cl$ (20 mL). The reaction mixture was extracted with EtOAc (3×20 mL), washed with brine, dried over Na$_2$SO$_4$, filtered and concentrated under reduced pressure. The crude product was purified by flash column chromatography on a silica gel cartridge eluting with 0-60% EtOAc in Hex. The fractions containing the expected product were collected and concentrated under reduced pressure to give ethyl 2,2-difluoro-3-(4-fluorophenyl)-3-hydroxybutanoate (166 mg, 0.633 mmol, 63% yield) as an oil.

$^1$H NMR (500 MHz, CDCl$_3$) δ 7.51 (dd, J=8.5, 5.5 Hz, 2H), 7.06 (t, J=8.7 Hz, 2H), 4.19 (q, J=7.2 Hz, 2H), 1.74 (t, J=1.5 Hz, 3H), 1.17 (t, J=7.2 Hz, 3H).

18B: 2,2-difluoro-3-(4-fluorophenyl)-3-hydroxybutanamide: To a solution of ethyl 2,2-difluoro-3-(4-fluorophenyl)-3-hydroxybutanoate (166 mg, 0.633 mmol) in MeOH (3 mL) at 0° C. was added ammonia (7N in MeOH) (0.36 mL, 2.53 mmol). The mixture was stirred at RT for 5 h and concentrated under reduced pressure to give crude 2,2-difluoro-3-(4-fluorophenyl)-3-hydroxybutanamide which was used as-is in the next step without further purification. MS ESI m/z 231.85 (M−H)$^-$ 18C: 4-amino-3,3-difluoro-2-(4-fluorophenyl)butan-2-ol, HCl salt: To a solution of 2,2-difluoro-3-(4-fluorophenyl)-3-hydroxybutanamide (148 mg, 0.635 mmol) in THF (3 mL) was added borane-methyl sulfide complex (2M in THF) (1.6 mL, 3.17 mmol). The mixture was stirred at 70° C. for 24 h. The reaction was quenched by dropwise addition of methanol (1 mL). The mixture was stirred at RT for 30 min and concentrated under reduced pressure. The crude product was then treated with 1 N aqueous HCl (2 mL) at 65° C. for 1 h, then concentrated under reduced pressure. The residue was triturated with Et$_2$O and the solvent was decanted. The residue was dried under vacuum to give crude 4-amino-3,3-difluoro-2-(4-fluorophenyl)butan-2-ol, HCl salt (104 mg, 0.407 mmol, 64% yield) as a solid.

$^1$H NMR (500 MHz, DMSO-d$_6$) δ 7.57 (br dd, J=8.5, 5.6 Hz, 2H), 7.26-7.18 (m, 2H), 3.08-2.93 (m, 1H), 1.63 (s, 3H). MS ESI m/z 220.0 (M+H)$^+$

18: The title compound was prepared in a similar fashion to the final step described for example 11, substituting 4-amino-3,3-difluoro-2-(4-fluorophenyl)butan-2-ol, HCl for 4,4,4-trifluoro-3-phenylbutan-1-amine in the final step to afford racemic 3-(2-amino-[1,2,4]triazolo[1,5-a]pyridin-7-yl)-N-(2,2-difluoro-3-(4-fluorophenyl)-3-hydroxybutyl)-2-fluoro-6-methylbenzamide (21.0 mg, 0.043 mmol, 58% yield).

$^1$H NMR (500 MHz, DMSO-d$_6$) δ 8.80 (br t, J=6.3 Hz, 1H), 8.64 (d, J=7.0 Hz, 1H), 7.62-7.55 (m, 3H), 7.51 (s, 1H), 7.24-7.16 (m, 3H), 7.09 (br d, J=7.3 Hz, 1H), 4.03-3.86 (m, 2H), 2.27 (s, 3H), 1.63 (s, 3H). MS ESI m/z 488.2 (M+H)$^+$

Example 19: 3-(2-amino-[1,2,4]triazolo[1,5-a]pyridin-7-yl)-N-[4-(4-chlorophenyl)-4-hydroxybutan-2-yl]-2-fluoro-6-methylbenzamide racemate 1

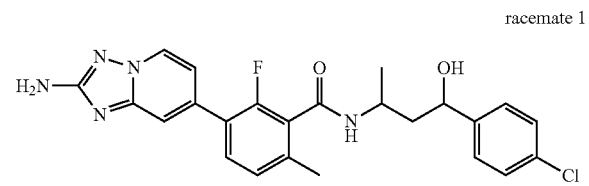 [SMILES: Cc1ccc(-c2ccn3nc(N)nc3c2)c(F)c1C(=O)NC(C)CC(O)c1ccc(Cl)cc1]

racemate 1

19A: 4-(4-chlorophenyl)-4-hydroxybutan-2-one (Ref. Euro. J. Med. Chem. 2009, 44, 1278-1287): To a solution of 4-chlorobenzaldehyde (1.13 g, 8.00 mmol) in acetone (200 mL) was added D-proline (0.184 g, 1.60 mmol). The resulting mixture was stirred at RT overnight for 18 h. DMSO (10 mL) and water (2 mL) were added and the mixture was stirred for another 24 h. Volatiles were removed in vacuo, and the residue was partitioned between EtOAc and water and layers were separated. The organic layer was washed with water, brine, dried with Na$_2$SO$_4$, filtered and concentrated in vacuo. The residue was purified by silica gel column chromatography (gradient 100% Hex to 50% EtOAc in Hex) to afford 4-(4-chlorophenyl)-4-hydroxybutan-2-one (1.18 g, 5.92 mmol, 74% yield) as a colorless oil. Per literature reference, the desired product should be S-configuration at OH position with ~76% ee.

$^1$H NMR (499 MHz, CDCl$_3$) δ 7.37-7.29 (m, 4H), 5.15 (dd, J=8.5, 3.8 Hz, 1H), 3.39 (s, 1H), 2.95-2.75 (m, 2H), 2.22 (s, 3H).

19B: 3-amino-1-(4-chlorophenyl)butan-1-ol: To a solution of 4-(4-chlorophenyl)-4-hydroxybutan-2-one (596 mg, 3.00 mmol) in MeOH (10 mL) was added ammonium acetate (1.85 g, 24.0 mmol) and sodium cyanoborohydride (377 mg, 6.00 mmol). The resulting mixture was stirred at RTON for 18 h. LCMS showed two separate peaks had formed with m/z consistent with the desired product. Volatiles were removed in vacuo, and the residue was partitioned between EtOAc and water and layers were separated. The organic layer was washed with water, brine, dried with Na$_2$SO$_4$, filtered and concentrated in vacuo to afford crude 3-amino-1-(4-chlorophenyl)butan-1-ol (0.60 g, 3.0 mmol, 100% crude yield) as a tan oil which was used as-is in subsequent steps.

MS ESI m/z 200.1 (M+H)$^+$

19: A mixture of lithium 3-(2-amino-[1,2,4]triazolo[1,5-a]pyridin-7-yl)-2-fluoro-6-methylbenzoate (29.2 mg, 0.100 mmol), BOP (66.3 mg, 0.150 mmol), 3-amino-1-(4-chlorophenyl)butan-1-ol (24.0 mg, 0.120 mmol) and Hünig's Base (0.070 mL, 0.40 mmol) in DMF (0.5 mL) was stirred at RT for 5 h. LCMS showed two separate peaks had formed, both with m/z consistent with the desired product. The mixture was diluted with MeOH and filtered. The crude material was purified via preparative LCMS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-min hold at 19% B, 19-59% B over 25 minutes, then a 0-min hold at 100% B; Flow Rate: 20 mL/min; Column Temperature: 25 C. Fraction collection was triggered by MS signals. Fractions containing the first eluting peak with LCMS m/z signal consistent with the desired product were combined and dried via centrifugal evaporation to afford the racemic mixture 3-(2-amino-[1,2,4]triazolo[1,5-a]pyridin-7-yl)-N-[4-(4-chlorophenyl)-4-hydroxybutan-2-yl]-2-fluoro-6-methylbenzamide racemate 1 (11.3 mg, 24.0 µmol, 24% yield) as the first eluting mixture from the preparative HPLC separation. Relative and absolute stereochemistries were not determined.

$^1$H NMR (500 MHz, DMSO-d$_6$) δ 8.62 (d, J=7.0 Hz, 1H), 8.56 (d, J=8.4 Hz, 1H), 7.58 (t, J=8.0 Hz, 1H), 7.50 (s, 1H), 7.39 (s, 4H), 7.23 (d, J=8.1 Hz, 1H), 7.05 (d, J=6.9 Hz, 1H), 6.07 (s, 2H), 5.37 (d, J=4.6 Hz, 1H), 4.63 (q, J=6.6 Hz, 1H), 4.04-3.89 (m, 1H), 2.33 (s, 3H), 1.93 (dt, J=14.5, 7.4 Hz, 1H), 1.63 (dt, J=13.5, 6.6 Hz, 1H), 1.16 (d, J=6.6 Hz, 3H); $^{19}$F NMR (471 MHz, DMSO-d6) δ−121.94. MS ESI m/z 468.2 (M+H)$^+$

Example 20: 3-(2-amino-[1,2,4]triazolo[1,5-a]pyridin-7-yl)-N-[4-(4-chlorophenyl)-4-hydroxybutan-2-yl]-2-fluoro-6-methylbenzamide racemate 2 racemate 2

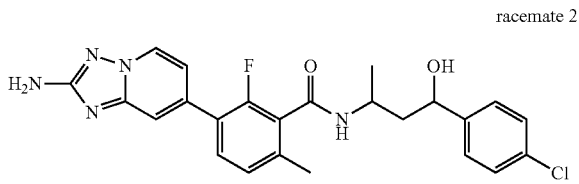 [SMILES: Cc1ccc(-c2ccn3nc(N)nc3c2)c(F)c1C(=O)NC(C)CC(O)c1ccc(Cl)cc1]

The title compound 3-(2-amino-[1,2,4]triazolo[1,5-a]pyridin-7-yl)-N-[4-(4-chlorophenyl)-4-hydroxybutan-2-yl]-2-fluoro-6-methylbenzamide racemate 2 (3.5 mg, 6.8 μmol, 7% yield) was obtained as the second eluting peak with LCMS m/z signal consistent with the desired product from the preparative HPLC purification described for example 19.
$^1$H NMR (500 MHz, DMSO-d$_6$) δ 8.61 (d, J=7.0 Hz, 1H), 8.56 (d, J=8.0 Hz, 1H), 7.59 (t, J=8.1 Hz, 1H), 7.53-7.47 (m, 1H), 7.43-7.31 (m, 4H), 7.25 (d, J=7.9 Hz, 1H), 7.06 (d, J=7.1 Hz, 1H), 6.07 (s, 2H), 5.41 (d, J=4.6 Hz, 1H), 4.70-4.61 (m, 1H), 4.24 (s, 1H), 2.36 (s, 3H), 1.80-1.60 (m, 2H), 1.19 (d, J=6.6 Hz, 3H); $^{19}$F NMR (471 MHz, DMSO-d6) δ −122.00.
MS ESI m/z 468.2 (M+H)$^+$

Example 21: 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 1 diastereomer 1

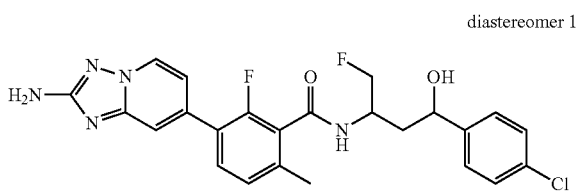 [SMILES: Cc1ccc(-c2ccn3nc(N)nc3c2)c(F)c1C(=O)NC(CF)CC(O)c1ccc(Cl)cc1]

21A: 4-(4-chlorophenyl)-1-fluoro-4-hydroxybutan-2-one (Ref Sinha, S. C.; Duttan, S.; Sun, J. Tetrahedron Lett. 2000, 41, 8243-8246): In an oven-dried 500 mL round-bottomed flask were combined dibutylboron triflate solution 1M in CH$_2$Cl$_2$ (20.0 mL, 20.0 mmol) and Hunig's base (4.2 mL, 24.0 mmol) in CH$_2$Cl$_2$ (100 mL) to give a colorless solution at 0° C. 1-Fluoropropan-2-one (1.52 g, 20.0 mmol) was added dropwise and the color changed to slightly pink. After stirring at 0° C. for 1 h, 4-chlorobenzaldehyde (1.41 g, 10.0 mmol) was slowly added. The reaction was allowed to warm to RT and was stirred ON for 16 h. The reaction mixture was diluted with Et$_2$O and was slowly quenched with water and excess H$_2$O$_2$ (4 mL each). Phases were separated and the organic was concentrated to a residue. The crude residue was purified by silica gel flash column chromatography (gradient 100% Hex to 80% EtOAc in Hex). Product fractions were combined and concentrated to afford 4-(4-chlorophenyl)-1-fluoro-4-hydroxybutan-2-one (720 mg, 3.32 mmol, 33% yield) as a colorless oil.
$^1$H NMR (499 MHz, CDCl$_3$) δ 7.40-7.32 (m, 4H), 5.24 (dt, J=9.3, 2.9 Hz, 1H), 4.90 (d, J=2.4 Hz, 1H), 4.82-4.80 (m, 1H), 3.00-2.91 (m, 2H); $^{19}$F NMR (470 MHz, Chloroform-d) δ −227.74.

21B: 3-amino-1-(4-chlorophenyl)-4-fluorobutan-1-ol: To a solution of 4-(4-chlorophenyl)-1-fluoro-4-hydroxybutan-2-one (720 mg, 3.32 mmol) in MeOH (10 mL) was added ammonium acetate (1.54 g, 19.9 mmol) and sodium cyanoborohydride (313 mg, 4.99 mmol). The resulting mixture was stirred at RT for 72 h. LCMS showed two separate product peaks, both with m/z consistent with the desired product. Volatiles were removed in vacuo and the residue was partitioned between EtOAc and water and the layers were separated. The organic layer was washed with water, brine, dried with Na$_2$SO$_4$, filtered and concentrated in vacuo to give the crude 3-amino-1-(4-chlorophenyl)-4-fluorobutan-1-ol (0.800 g, 3.32 mmol, 100% crude yield) as a light tan oil which was used as-is in subsequent steps.
MS ESI m/z 218.1 (M+H)$^+$ 21C: 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide: A mixture of lithium 3-(2-amino-[1,2,4]triazolo[1,5-a]pyridin-7-yl)-2-fluoro-6-methylbenzoate (292 mg, 1.00 mmol), BOP (663 mg, 1.50 mmol). 3-amino-1-(4-chlorophenyl)-4-fluorobutan-1-ol (435 mg, 2.00 mmol) and Hünig's base (0.70 mL, 4.00 mmol) in DMF (4 mL) was stirred at RT for 18 h. LCMS showed two separate peaks had formed with m/z consistent with the desired product. The mixture was diluted with EtOAc and water and the layers were separated. The aqueous layer was extracted with EtOAc. The combined organic layers were washed with water, brine, dried with Na$_2$SO$_4$, filtered and concentrated in vacuo. The residue was purified by silica gel flash column chromatography (120 g silica, gradient 100% DCM up to 10% MeOH in DCM) to afford two separated enantiomeric mixtures of 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide:
The first eluted, less polar material was the minor isolate 21C-1 (132 mg, 0.272 mmol, 27% yield) and was isolated as a tan oily semisolid. The second eluted, more polar material was the major isolate 21C-2 (164 mg, 0.338 mmol, 34% yield) and was isolated as an off-white solid. Both isolates were mixtures of enantiomers and were further subjected to chiral separation.
21C-1: MS ESI m/z 486.3 (M+H)$^+$
21C-2: MS ESI m/z 486.3 (M+H)$^+$ 21: The isolate 21C-2 (164 mg, 0.338 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 60% CO2/40% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 60% CO2/40% MeOH w/0.1% DEA; Flow Rate: 60 mL/min; Detector Wavelength: 220 nm; Injection details: 900 μL 164.2 mg dissolved in 3 mL MeOH. Fractions containing the first eluting isomer were combined and dried to afford 3-(2-amino-[1,2,4]triazolo[1,5-a]pyridin-7-yl)-N-(-4-(4-chlorophenyl)-1-fluoro-4-hydroxybutan-2-yl)-2-fluoro-6-methylbenzamide diastereomer 1 (21.7 mg, 0.043 mmol, >95% ee, 13% yield). The relative and absolute stereochemistry was not determined.
$^1$H NMR (500 MHz, DMSO-d6) δ 8.83 (d, J=8.2 Hz, 1H), 8.62 (d, J=7.0 Hz, 1H), 7.61 (t, J=8.1 Hz, 1H), 7.51 (s, 1H), 7.40 (q, J=8.5 Hz, 4H), 7.24 (d, J=7.9 Hz, 1H), 7.07 (d, J=6.9 Hz, 1H), 6.08 (s, 2H), 5.52 (d, J=4.4 Hz, 1H), 4.69 (q, J=6.5 Hz, 1H), 4.52 (dd, J=9.8, 4.8 Hz, 1H), 4.49-4.34 (m, 1H), 4.09 (d, J=21.3 Hz, 1H), 2.34 (s, 3H), 2.00-1.88 (m, 1H), 1.84 (dt, J=13.5, 6.5 Hz, 1H); $^{19}$F NMR (471 MHz, DMSO-d6) δ −121.63 (missing one F).
MS ESI m/z 486.3 (M+H)$^+$ Example 22: 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 2 diastereomer 2

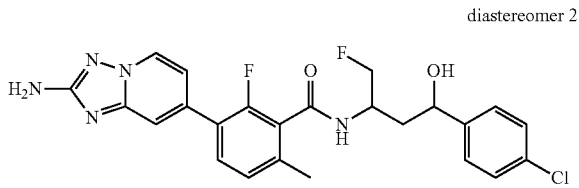 [SMILES: Cc1ccc(-c2ccn3nc(N)nc3c2)c(F)c1C(=O)NC(CF)CC(O)c1ccc(Cl)cc1]

The title compound 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 2 (29.6 mg, 0.060 mmol, >95% ee, 18% yield) was obtained as the second eluting isomer from the chiral SFC purification described for example 21.

$^1$H NMR (500 MHz, DMSO-d$_6$) δ 8.82 (d, J=8.2 Hz, 1H), 8.63 (d, J=7.0 Hz, 1H), 7.61 (t, J=8.1 Hz, 1H), 7.51 (s, 1H), 7.40 (q, J=8.4 Hz, 4H), 7.24 (d, J=8.0 Hz, 1H), 7.06 (d, J=7.0 Hz, 1H), 6.08 (s, 2H), 5.50 (d, J=4.5 Hz, 1H), 4.69 (q, J=6.4 Hz, 1H), 4.57-4.48 (m, 1H), 4.49-4.38 (m, 1H), 4.17-4.02 (m, 1H), 2.34 (s, 3H), 2.00-1.89 (m, 1H), 1.84 (dt, J=13.7, 6.6 Hz, 1H); $^{19}$F NMR (471 MHz, DMSO-d$_6$) δ −121.60.
MS ESI m/z 486.3 (M+H)$^+$

Example 23: 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 3 diastereomer 3

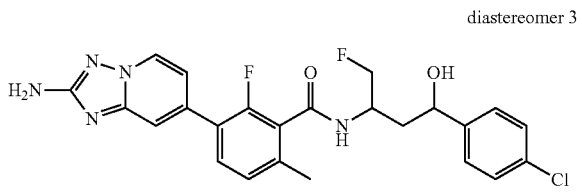 [SMILES: Cc1ccc(-c2ccn3nc(N)nc3c2)c(F)c1C(=O)NC(CF)CC(O)c1ccc(Cl)cc1]

The isolate 21C-1 (132 mg, 0.272 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 65% CO2/35% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 65% CO2/35% MeOH w/0.1% DEA; Flow Rate: 60 mL/min; Detector Wavelength: 220 nm; Injection details: 600 μL 130.2 mg dissolved in 3 mL MeOH. Fractions containing the first eluting isomer were combined and dried to afford 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 3 (10.1 mg, 0.020 mmol, >95% ee 8% yield). The relative and absolute stereochemistry was not determined.

$^1$H NMR (500 MHz, DMSO-d6) δ 8.78 (d, J=7.4 Hz, 1H), 8.62 (d, J=7.0 Hz, 1H), 7.61 (t, J=8.0 Hz, 1H), 7.51 (s, 1H), 7.45-7.33 (m, 4H), 7.26 (d, J=8.0 Hz, 1H), 7.07 (d, J=7.0 Hz, 1H), 6.07 (s, 2H), 4.70 (s, 1H), 4.62-4.32 (m, 3H), 2.37 (s, 3H), 1.92 (s, 1H), 1.76 (d, J=8.6 Hz, 2H); 19F NMR (471 MHz, DMSO-d6) δ −121.69.
MS ESI m/z 486.3 (M+H)$^+$

Example 24: 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 4 diastereomer 4

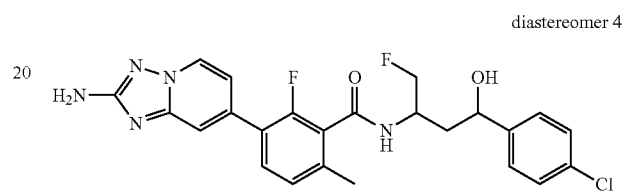

The title compound 3-(2-amino-[1,2,4]triazolo[1,5-a]pyridin-7-yl)-N-(4-(4-chlorophenyl)-1-fluoro-4-hydroxybutan-2-yl)-2-fluoro-6-methylbenzamide diastereomer 4 (9.7 mg, 0.020 mmol, >95% ee, 8% yield): was obtained as the second eluting isomer from the chiral SFC purification described for example 23.

$^1$H NMR (500 MHz, DMSO-d$_6$) δ 8.78 (d, J=7.4 Hz, 1H), 8.62 (d, J=7.1 Hz, 1H), 7.61 (t, J=8.0 Hz, 1H), 7.51 (s, 1H), 7.44-7.34 (m, 4H), 7.26 (d, J=8.0 Hz, 1H), 7.07 (d, J=6.9 Hz, 1H), 6.07 (s, 2H), 4.70 (s, 1H), 4.61-4.35 (m, 3H), 2.37 (s, 3H), 1.91 (s, 1H), 1.76 (d, J=8.4 Hz, 2H); $^{19}$F NMR (471 MHz, DMSO-d$_6$) δ −121.69.
MS ESI m/z 486.3 (M+H)$^+$

Example 25: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 1 diastereomer 1

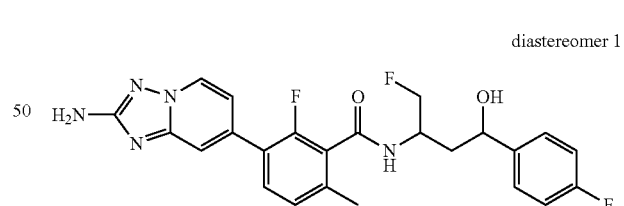

25A: 1-fluoro-4-(4-fluorophenyl)-4-hydroxybutan-2-one (Ref. Sinha, S. C.; Duttan, S.; Sun, J. Tetrahedron Lett. 2000, 41, 8243-8246): In an oven-dried 500 mL round-bottom flask were combined dibutylboron triflate solution, 1M in CH$_2$Cl$_2$ (20.0 mL, 20.0 mmol) and Hünig's base (4.18 mL, 23.94 mmol) in CH$_2$Cl$_2$ (100 mL) to give a colorless solution at 0° C. 1-Fluoropropan-2-one (1.52 g, 20.0 mmol) was added dropwise and the color changed to slightly pink. After stirring at 0° C. for 1 h, 4-fluorobenzaldehyde (1.40 mL, 13.3 mmol) was slowly added. The reaction was allowed to warm to RT and was stirred ON for 16 h. The reaction mixture was diluted with Et$_2$O and slowly quenched with water and H$_2$O$_2$ (4 mL each). Phases were separated and the organic layer was concentrated to a residue. The crude residue was purified by silica gel flash column chromatography (gradient 100% Hex to 80% EtOAc in Hex). Product fractions were combined and concentrated to afford 1-fluoro-4-(4-fluorophenyl)-4-hydroxybutan-2-one (730 mg, 3.65 mmol, 27% yield) as a colorless oil.

$^1$H NMR (499 MHz, CDCl$_3$) δ 7.43-7.30 (m, 2H), 7.12-6.98 (m, 2H), 5.21 (dd, J=9.3, 3.2 Hz, 1H), 4.95-4.72 (m, 2H), 3.00 (ddd, J=17.4, 9.3, 2.4 Hz, 1H), 2.86 (ddd, J=17.4, 3.3, 2.6 Hz, 1H).

25B: 3-amino-1-(4-fluorophenyl)-4-fluorobutan-1-ol: To solution of 1-fluoro-4-(4-fluorophenyl)-4-hydroxybutan-2-one (730 mg, 3.65 mmol) in MeOH (10 mL) was added ammonium acetate (1.69 g, 21.9 mmol) and sodium cyanoborohydride (344 mg, 5.47 mmol). The resulting mixture was stirred at RT for 72 h. LCMS showed two separate product peaks, both with m/z consistent with the desired product. Volatiles were removed in vacuo and the residue was partitioned between EtOAc and water and the layers were separated. The organic layer was washed with water, brine, dried with Na$_2$SO$_4$, filtered and concentrated in vacuo to give the crude product as a tan oil. The residue was purified by silica gel flash column chromatography (gradient 100% DCM to 10% MeOH in DCM) to afford two separate less polar undesired materials and the more polar (silica TLC Rf ~0.2, eluted with 10% MeOH in DCM) desired 3-amino-1-(4-fluorophenyl)-4-fluorobutan-1-ol (220 mg, 1.10 mmol, 30% yield) as a light tan oil.

$^1$H NMR (499 MHz, CD$_3$OD) δ 7.52-7.38 (m, 2H), 7.09 (td, J=8.8, 6.6 Hz, 2H), 4.98 (dd, J=10.0, 3.6 Hz, 1H), 4.81-4.51 (m, 2H), 3.95-3.55 (m, 1H), 2.10-1.86 (m, 2H); $^{19}$F NMR (470 MHz, Methanol-d4) δ−116.77, −230.27, −231.70. $^1$H NMR indicated a diastereomeric ratio of approximately 3:1.

25C: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide: A mixture of lithium 3-(2-amino-[1,2,4]triazolo[1,5-a]pyridin-7-yl)-2-fluoro-6-methylbenzoate (120 mg, 0.409 mmol), BOP (271 mg, 0.614 mmol) 3-amino-4-fluoro-1-(4-fluorophenyl)butan-1-ol (82.3 mg, 0.409 mmol) and Hünig's Base (0.214 mL, 1.23 mmol) in DMF (1 mL) was stirred at RT for 16 h. LCMS showed two separate peaks had formed, both with m/z consistent with the desired product, in roughly a 3:1 ratio. The mixture was diluted with water and EtOAc and the layers were separated. The aqueous layer was extracted with EtOAc. Silica TLC (elution 10% MeOH in DCM) showed two close but separable spots. The combined organic layers were washed with water, brine, dried with Na$_2$SO$_4$, filtered and concentrated in vacuo. The residue was purified by flash column chromatography (24 g silica, gradient 100% DCM to 8% MeOH in DCM) to afford two separated enantiomeric mixtures of 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide. The first eluted, less polar minor isolate 25C-01 (21.7 mg, 0.046 mmol, 11% yield) was obtained as an off-white powder. The second eluted, more polar major isolate 25C-02 (66.2 mg, 0.141 mmol, 35% yield) was also obtained as an off-white powder. Both isolates were mixtures of enantiomers and were further subjected to chiral separation.

25C-01: MS ESI m/z 470.3 (M+H)$^+$
25C-02: MS ESI m/z 470.4 (M+H)$^+$

25: The isolate 25C-02 (66.2 mg, 0.141 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 60% CO2/40% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 60% CO2/40% MeOH w/0.1% DEA; Flow Rate: 60 mL/min; Detector Wavelength: 220 nm; Injection details: 1800 μL 66.2 mg dissolved in 3 mL MeOH. Fractions containing the first eluting isomer were combined and dried to afford 3-(2-amino-[1,2,4]triazolo[1,5-a]pyridin-7-yl)-N-(4-(4-fluorophenyl)-1-fluoro-4-hydroxybutan-2-yl)-2-fluoro-6-methylbenzamide diastereomer 1 (17.9 mg, 0.037 mmol, >95% ee, 26% yield): The relative and absolute stereochemistry was not determined.

$^1$H NMR (500 MHz, DMSO-d6) δ 8.82 (d, J=8.2 Hz, 1H), 8.63 (d, J=7.0 Hz, 1H), 7.61 (t, J=8.0 Hz, 1H), 7.51 (s, 1H), 7.45-7.36 (m, 2H), 7.25 (d, J=8.0 Hz, 1H), 7.18 (dd, J=10.0, 7.8 Hz, 2H), 7.07 (dt, J=6.8, 1.7 Hz, 1H), 6.08 (s, 2H), 5.45 (d, J=4.5 Hz, 1H), 4.70 (q, J=6.5 Hz, 1H), 4.58-4.47 (m, 1H), 4.43 (qd, J=9.3, 4.9 Hz, 1H), 4.10 (d, J=21.3 Hz, 1H), 2.35 (s, 3H), 1.94 (dt, J=14.8, 7.6 Hz, 1H), 1.84 (dt, J=13.4, 6.5 Hz, 1H); $^{19}$F NMR (471 MHz, DMSO-d6) δ−73.42, −115.94, −121.61.

MS ESI m/z 470.4 (M+H)$^+$

Example 26: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 2

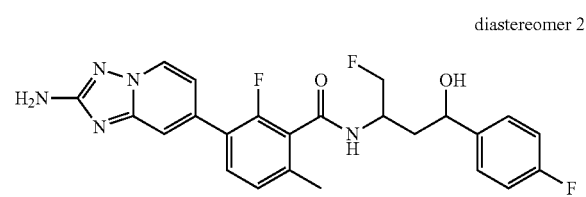

diastereomer 2

The title compound 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 2 (17.6 mg, 0.037 mmol, 26% yield) was obtained as the second eluting isomer from the chiral SFC purification described for example 25.

$^1$H NMR (500 MHz, DMSO-d$_6$) δ 8.84 (d, J=8.3 Hz, 1H), 8.60 (d, J=7.1 Hz, 1H), 7.59 (t, J=8.1 Hz, 1H), 7.50 (s, 1H), 7.39 (dd, J=8.5, 5.6 Hz, 2H), 7.24 (d, J=8.1 Hz, 1H), 7.17 (t, J=8.8 Hz, 2H), 7.07 (d, J=7.0 Hz, 1H), 6.06 (s, 2H), 5.52 (s, 1H), 4.68 (t, J=7.1 Hz, 1H), 4.51 (qd, J=9.4, 4.7 Hz, 1H), 4.46-4.36 (m, 1H), 4.08 (d, J=21.9 Hz, 1H), 2.33 (s, 3H), 1.93 (dt, J=14.8, 7.5 Hz, 1H), 1.83 (dt, J=13.4, 6.6 Hz, 1H); $^{19}$F NMR (471 MHz, DMSO-d6) δ−73.42, −115.94, −121.61.

MS ESI m/z 470.4 (M+H)$^+$

Example 27: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 3 diastereomer 3

The isolate 25C-01 (21.7 mg, 0.046 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 65% CO2/35% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 65% CO2/35% MeOH w/0.1% DEA; Flow Rate: 60 mL/min; Detector Wavelength: 220 nm; Injection details: 720 µL 21.6 mg dissolved in 3 mL MeOH. Fractions containing the first eluting isomer were combined and dried to afford 3-(2-amino-[1,2,4]triazolo[1,5-a]pyridin-7-yl)-N-(4-(4-fluorophenyl)-1-fluoro-4-hydroxybutan-2-yl)-2-fluoro-6-methylbenzamide diastereomer 3 (2.8 mg, 5.96 µmol, >95% ee 13% yield). The relative and absolute stereochemistry was not determined.

$^1$H NMR (500 MHz, DMSO-d6) δ 8.79 (d, J=7.6 Hz, 1H), 8.60 (d, J=7.0 Hz, 1H), 7.59 (t, J=8.0 Hz, 1H), 7.50 (s, 1H), 7.37 (dd, J=8.6, 5.6 Hz, 2H), 7.26 (d, J=8.0 Hz, 1H), 7.14 (t, J=8.8 Hz, 2H), 7.08 (d, J=7.0 Hz, 1H), 6.05 (s, 2H), 5.54 (d, J=4.7 Hz, 1H), 4.69 (d, J=6.6 Hz, 1H), 4.62-4.33 (m, 3H), 2.36 (s, 3H), 1.76 (t, J=6.7 Hz, 2H); $^{19}$F NMR (471 MHz, DMSO-d6) δ−73.60, −116.23, −121.81.
MS ESI m/z 470.4 (M+H)$^+$

Example 28: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 4 diastereomer 4

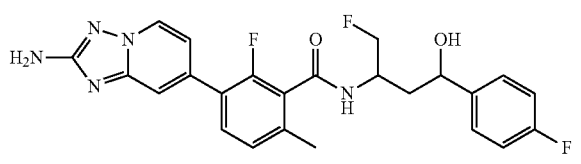

The title compound 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide diastereomer 4 (3.1 mg, 6.6 µmol, 13% yield) was obtained as the second eluting isomer from the chiral SFC purification described for example 27.

$^1$H NMR (500 MHz, DMSO-d$_6$) δ 8.80 (d, J=7.7 Hz, 1H), 8.59 (d, J=6.9 Hz, 1H), 7.59 (t, J=8.0 Hz, 1H), 7.50 (s, 1H), 7.39-7.34 (m, 2H), 7.25 (d, J=7.9 Hz, 1H), 7.14 (t, J=8.9 Hz, 2H), 7.11-7.05 (m, 1H), 6.04 (s, 2H), 4.75-4.66 (m, 1H), 4.61-4.33 (m, 3H), 2.35 (s, 3H), 1.76 (t, J=6.6 Hz, 2H); $^{19}$F NMR (471 MHz, DMSO-d$_6$) δ−73.62, −116.20, −121.84.
MS ESI m/z 470.4 (M+H)$^+$

Example 29: 3-(2-amino-[1,2,4]triazolo[1,5-a]pyridin-7-yl)-N-(3-(4-chlorophenyl)-2,2-difluoro-3-hydroxypropyl)-2-fluoro-6-methylbenzamide

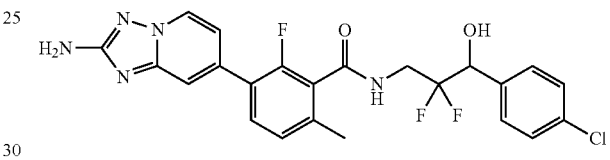

29A: 3-amino-1-(4-chlorophenyl)-2,2-difluoropropan-1-ol (Ref. Org. Lett. 2010, 12, 4648-4651): To a solution of 3-(4-chlorophenyl)-3-oxopropanenitrile (1.08 g, 6.00 mmol) in THF (20 mL) was slowly added NaH (317 mg, 13.19 mmol) and the mixture was stirred for 2 h. Selectfluor (4.67 g, 13.2 mmol) was added. The resulting mixture was stirred at RT for 20 h. LAH, 1M in THF (18.0 mL, 18.0 mmol) was slowly added, and the reaction mixture was stirred under nitrogen for 20 h. Saturated aqueous Na$_2$SO$_4$ was added, and the reaction was carefully quenched by dropwise addition of water. The resulting suspension was diluted with EtOAc, stirred and filtered, and the filtrate was washed with a mixture of EtOAc and MeOH. The combined organic solution was concentrated to a tan foam (2.55 g, 5.74 mmol, 96% yield with ~50% purity). The material was used as is in the next step.
MS ESI m/z 222.2 (M+H)$^+$ 29: A mixture of lithium 3-(2-amino-[1,2,4]triazolo[1,5-a]pyridin-7-yl)-2-fluoro-6-methylbenzoate (29.2 mg, 0.100 mmol), BOP (66.3 mg, 0.150 mmol), 3-amino-1-(4-chlorophenyl)-2,2-difluoropropan-1-ol (33.2 mg, 0.150 mmol) and Hünig's Base (0.07 mL, 0.400 mmol) in DMF (0.5 mL) was stirred at RT for 3 h. The mixture was diluted with MeOH and filtered, and the crude filtrate was purified via preparative LCMS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-min hold at 18% B, 18-58% B over 20 minutes, then a 0-min hold at 100% B; Flow Rate: 20 mL/min; Column Temperature: 25 C. Fraction collection was triggered by MS signals. Fractions containing the desired product were combined and dried via centrifugal evaporation to afford 3-(2-amino-[1,2,4]triazolo[1,5-a]pyridin-7-yl)-N-(3-(4-chlorophenyl)-2,2-difluoro-3-hydroxypropyl)-2-fluoro-6-methylbenzamide (10.9 mg, 0.021 mmol, 21% yield).

$^1$H NMR (500 MHz, DMSO-$d_6$) δ 8.95 (t, J=6.0 Hz, 1H), 8.62 (d, J=7.0 Hz, 1H), 7.60 (t, J=8.1 Hz, 1H), 7.52-7.43 (m, 5H), 7.23 (d, J=7.9 Hz, 1H), 7.05 (d, J=6.9 Hz, 1H), 4.95 (d, J=16.2 Hz, 1H), 3.98-3.80 (m, 2H), 2.56 (s, 3H); $^{19}$F NMR (471 MHz, DMSO-$d_6$) δ−110.63 (d, J=245.0 Hz), −116.66 (d, J=245.1 Hz), −121.34.

MS ESI m/z 490.3 (M+H)$^+$

Example 30: (S)-3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide enantiomer 1

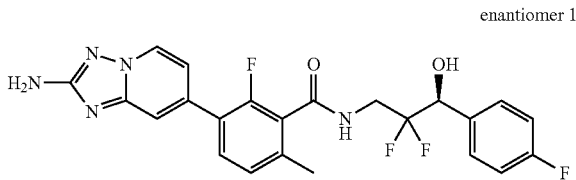 [SMILES: Cc1ccc(-c2ccn3nc(N)nc3c2)c(F)c1C(=O)NCC(F)(F)[C@@H](O)c1ccc(F)cc1]

enantiomer 1

30A: 3-amino-2,2-difluoro-1-(4-fluorophenyl)propan-1-ol: To a solution of 3-(4-fluorophenyl)-3-oxopropanenitrile (1.34 g, 8.21 mmol) in THF (25 mL) was added NaH (0.434 g, 18.1 mmol) slowly and the mixture was stirred at RT for 1.5 h. Selectfluor (6.40 g, 18.1 mmol) was added. The resulting mixture was stirred at RT for 20 h. LAH, 1.0M in THF (24.6 mL, 24.6 mmol) was slowly added and the reaction mixture was stirred under nitrogen for 20 h. Saturated aqueous $Na_2SO_4$ was added, and the reaction was carefully quenched by dropwise addition of water. The resulting suspension was diluted with EtOAc, stirred, and filtered, and the filtrate was washed with a mixture of EtOAc and MeOH. The combined organic solution was concentrated to give 3-amino-2,2-difluoro-1-(4-fluorophenyl)propan-1-ol as a colorless oil (1.47 g, 7.14 mmol, 87%).

The material was used as-is in the next step.

MS ESI m/z 206.1 (M+H)$^+$

30: A mixture of 3-(2-amino-[1,2,4]triazolo[1,5-a]pyridin-7-yl)-2-fluoro-6-methylbenzoic acid (63.0 mg, 0.22 mmol), BOP (146 mg, 0.330 mmol), 3-amino-2,2-difluoro-1-(4-fluorophenyl)propan-1-ol (90.0 mg, 0.440 mmol) and Hünig's Base (0.15 mL, 0.880 mmol) in DMF (1 mL) was stirred at RT for 3 h. The reaction mixture was diluted with MeOH, filtered and purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 12% B, 12-52% B over 25 min, then a 0-min hold at 100% B; Flow Rate: 20 mL/min; Column Temperature: 25 C. Fraction collection was triggered by MS and UV signals. Fractions containing the desired product were combined and dried via centrifugal evaporation. The isolate was then subjected to chiral SFC separation with the following conditions. Analytical chromatographic conditions (prior to preparative SFC separation): Instrument: Shimadzu Nexera UC SFC; Column: Chiral IC, 4.6×150 mm, 5 micron; Mobile Phase: 75% CO2/25% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 30×250 mm. 5 micron; Mobile Phase: 75% CO2/25% MeOH w/0.1% DEA; Flow Rate: 60 mL/min; Detector Wavelength: 220 nm; Injection details: 2500 μL 22.5 mg dissolved in 6 mL MeOH/MeCN. Fractions containing the first eluting isomer were combined and dried to afford (S)-3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide enantiomer 1 (8.6 mg, 0.018 mmol, >95% ee, 8% yield).

$^1$H NMR (500 MHz, DMSO-$d_6$) δ 8.98 (s, 1H), 8.58 (d, J=7.0 Hz, 1H), 7.58 (t, J=8.1 Hz, 1H), 7.48 (d, J=8.0 Hz, 3H), 7.22 (q, J=9.4, 6.8 Hz, 3H), 7.07 (d, J=7.1 Hz, 1H), 6.54 (d, J=5.5 Hz, 1H), 6.04 (s, 1H), 4.91 (d, J=15.5 Hz, 1H), 2.30 (s, 3H) (missing $CH_2$ and partially suppressed $NH_2$ signals due to water suppression); $^{19}$F NMR (471 MHz, DMSO-d6) δ−110.75 (d, J=245.4 Hz), −114.23, −116.83 (d, J=244.4 Hz), −121.57.

MS ESI m/z 474.4 (M+H)$^+$

Example 31: (R)-3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide enantiomer 2

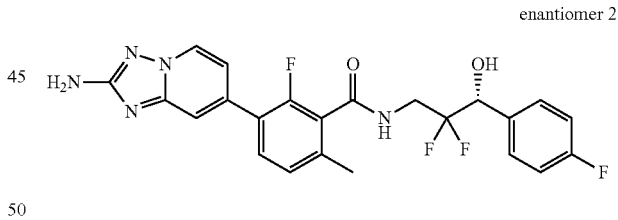

enantiomer 2

The title compound (R)-3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide enantiomer 2 (8.5 mg, 0.018 mmol, 8% yield) was obtained as the second eluting isomer from the chiral SFC purification described for example 30.

$^1$H NMR (500 MHz, DMSO-$d_6$) δ 8.99 (t, J=6.3 Hz, 1H), 8.60 (d, J=7.0 Hz, 1H), 7.59 (t, J=8.0 Hz, 1H), 7.49 (d, J=7.6 Hz, 3H), 7.23 (dt, J=12.1, 5.6 Hz, 3H), 7.08 (d, J=7.0 Hz, 1H), 6.54 (d, J=5.3 Hz, 1H), 6.06 (s, 2H), 4.93 (dd, J=16.1, 6.6 Hz, 1H), 2.31 (s, 3H) (missing CH2 due to solvent suppression); $^{19}$F NMR (471 MHz, DMSO-d6) δ−110.75 (d, J=245.4 Hz), −114.23, −116.83 (d, J=244.4 Hz), −121.57.

MS ESI m/z 474.4 (M+H)$^+$

TABLE 2

Compounds in Table 2 were prepared in a similar fashion to examples 11, 12 and 13.

| Ex No | Name | R | M + H⁺ | ¹H NMR (500 MHz, DMSO-d6) δ |
|---|---|---|---|---|
| 32 | 3-(2-amino-[1,2,4]-triazolo[1,5-a]-pyridin-7-yl)-N-(3-(3,4-dichlorophenyl)-3-hydroxy-propyl)-2-fluoro-6-methylbenzamide | racemate | 488.2 | 8.63-8.59 (m, 2H), 7.63-7.56 (m, 3H), 7.49 (s, 1H), 7.36 (dd, J = 8.2, 1.5 Hz, 1H), 7.23 (d, J = 7.9 Hz, 1H), 7.04 (br d, J = 7.0 Hz, 1H), 4.72-4.66 (m, 1H), 3.33-3.25 (m, 2H), 2.32 (s, 3H), 1.84 (q, J = 7.0 Hz, 2H) |
| 33 | 3-(2-amino-[1,2,4]-triazolo[1,5-a]-pyridin-7-yl)-N-(3-(3,4-dichlorophenyl)-3-hydroxy-propyl)-2-fluoro-6-methylbenzamide enantiomer 1 | enantiomer 1 first eluted | 488.0 | 8.63 (br t, J = 5.3 Hz, 1H), 8.60 (d, J = 7.0 Hz, 1H), 7.62-7.55 (m, 3H), 7.49 (s, 1H), 7.35 (dd, J = 8.2, 1.8 Hz, 1H), 7.23 (d, J = 7.9 Hz, 1H), 7.05 (br d, J = 7.0 Hz, 1H), 4.71-4.66 (m, 1H), 3.40-3.24 (m, 2H), 2.31 (s, 3H), 1.84 (q, J = 6.8 Hz, 2H) |
| 34 | 3-(2-amino-[1,2,4]-triazolo[1,5-a]-pyridin-7-yl)-N-(3-(3,4-dichlorophenyl)-3-hydroxy-propyl)-2-fluoro-6-methylbenzamide enantiomer 2 | enantiomer 2 second eluted | 488.3 | 8.63 (br t, J = 5.3 Hz, 1H), 8.60 (d, J = 7.0 Hz, 1H), 7.62-7.55 (m, 3H), 7.49 (s, 1H), 7.35 (dd, J = 8.2, 1.8 Hz, 1H), 7.23 (d, J = 7.9 Hz, 1H), 7.05 (br d, J = 7.0 Hz, 1H), 4.71-4.66 (m, 1H), 3.40-3.24 (m, 2H), 2.31 (s, 3H), 1.83 (q, J = 6.8 Hz, 2H) |
| 35 | 3-(2-amino-[1,2,4]-triazolo[1,5-a]-pyridin-7-yl)-2-fluoro-N-(4-(4-fluorophenyl)-4-hydroxybutan-2-yl)-6-methylbenzamide | diastereomer mixture | 452.1 | 8.75 (d, J = 6.7 Hz, 1H), 8.60 (br d, J = 8.2 Hz, 1H), 7.68 (s, 1H), 7.60 (br t, J = 7.8 Hz, 1H), 7.42-7.36 (m, 2H), 7.32 (br d, J = 7.0 Hz, 1H), 7.25 (br d, J = 8.2 Hz, 1H), 7.15 (br t, J = 8.7 Hz, 2H), 4.69-4.61 (m, 1H), 4.00-3.92 (m, 1H), 2.34 (s, 3H), 1.99-1.91 (m, 1H), 1.65 (dt, J = 13.4, 6.6 Hz, 1H), 1.17 (br d, J = 6.7 Hz, 3H) |
| 36 | 3-(2-amino-[1,2,4]-triazolo[1,5-a]-pyridin-7-yl)-2-fluoro-N-(4-(4-fluorophenyl)-4-hydroxybutan-2-yl)-6-methylbenzamide diastereomer 1 | diastereomer 1 first eluted | 452.1 | 8.60 (d, J = 7.0 Hz, 1H), 8.57 (d, J = 7.9 Hz, 1H), 7.57 (t, J = 7.9 Hz, 1H), 7.49 (s, 1H), 7.39 (dd, J = 8.5, 5.8 Hz, 2H), 7.22 (d, J = 8.2 Hz, 1H), 7.15 (t, J = 8.9 Hz, 2H), 7.06 (br d, J = 6.7 Hz, 1H), 6.06 (s, 2H), 4.65-4.60 (m, 1H), 3.95 (dt, J = 14.3, 7.1 Hz, 1H), 2.33 (s, 3H), 1.97-1.90 (m, 1H), 1.63 (dt, J = 13.4, 6.6 Hz, 1H), 1.16 (d, J = 6.7 Hz, 3H) |
| 37 | 3-(2-amino-[1,2,4]-triazolo[1,5-a]-pyridin-7-yl)-2-fluoro-N-(4-(4-fluorophenyl)-4-hydroxybutan-2-yl)-6-methylbenzamide diastereomer 2 | diastereomer 2 second eluted | 451.9 | 8.61 (d, J = 7.0 Hz, 1H), 8.56 (br d, J = 7.9 Hz, 1H), 7.59 (t, J = 7.9 Hz, 1H), 7.50 (s, 1H), 7.36 (dd, J = 8.2, 5.8 Hz, 2H), 7.24 (d, J = 8.2 Hz, 1H), 7.14 (t, J = 8.9 Hz, 2H), 7.06 (br d, J = 7.0 Hz, 1H), 6.06 (s, 2H), 4.66 (dt, J = 8.8, 4.3 Hz, 1H), 4.27-4.18 (m, 1H), 2.36 (s, 3H), 1.78-1.64 (m, 2H), 1.18 (d, J = 6.7 Hz, 3H) |

TABLE 2-continued

Compounds in Table 2 were prepared in a similar fashion to examples 11, 12 and 13.

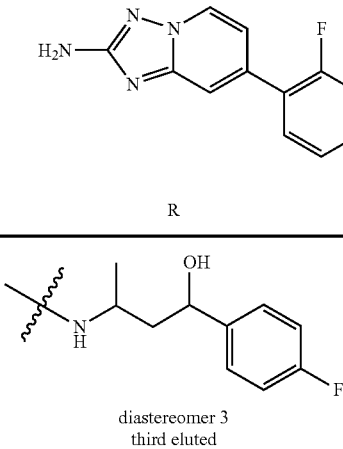

| Ex No | Name | R | M + H⁺ | $^1$H NMR (500 MHz, DMSO-d6) δ |
|---|---|---|---|---|
| 38 | 3-(2-amino-[1,2,4]-triazolo[1,5-a]-pyridin-7-yl)-2-fluoro-N-(4-(4-fluorophenyl)-4-hydroxybutan-2-yl)-6-methylbenzamide diastereomer 3 | 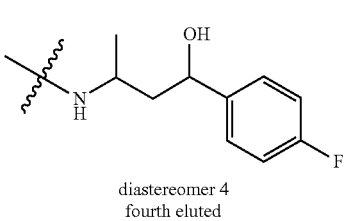 [SMILES: *NC(C)CC(O)c1ccc(F)cc1]<br>diastereomer 3<br>third eluted | 452.1 | 8.61 (d, J = 7.0 Hz, 1H), 8.56 (br d, J = 7.9 Hz, 1H), 7.59 (t, J = 8.2 Hz, 1H), 7.50 (s, 1H), 7.37 (dd, J = 8.1, 6.0 Hz, 2H), 7.24 (d, J = 7.9 Hz, 1H), 7.14 (br t, J = 8.9 Hz, 2H), 7.06 (br d, J = 7.0 Hz, 1H), 6.07 (s, 2H), 4.69-4.63 (m, 1H), 4.27-4.19 (m, 1H), 2.36 (s, 3H), 1.77-1.63 (m, 3H), 1.19 (d, J = 6.7 Hz, 3H) |
| 39 | 3-(2-amino-[1,2,4]-triazolo[1,5-a]-pyridin-7-yl)-2-fluoro-N-(4-(4-fluorophenyl)-4-hydroxybutan-2-yl)-6-methylbenzamide diastereomer 4 | 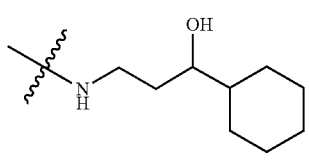<br>diastereomer 4<br>fourth eluted | 452.1 | 8.60 (d, J = 6.7 Hz, 1H), 8.57 (br d, J = 8.2 Hz, 1H), 7.57 (t, J = 7.9 Hz, 1H), 7.49 (s, 1H), 7.39 (dd, J = 8.2, 5.8 Hz, 2H), 7.22 (d, J = 7.9 Hz, 1H), 7.15 (t, J = 8.9 Hz, 2H), 7.06 (br d, J = 7.0 Hz, 1H), 6.06 (s, 2H), 4.66-4.60 (m, 1H), 3.95 (dt, J = 14.3, 7.4 Hz, 1H), 2.33 (s, 3H), 1.94 (dt, J = 14.0, 7.2 Hz, 1H), 1.63 (dt, J = 13.4, 6.7 Hz, 1H), 1.16 (d, J = 6.7 Hz, 3H) |
| 40 | 3-(2-amino-[1,2,4]-triazolo[1,5-a]-pyridin-7-yl)-N-(3-cyclohexyl-3-hydroxypropyl)-2-fluoro-6-methyl-benzamide | 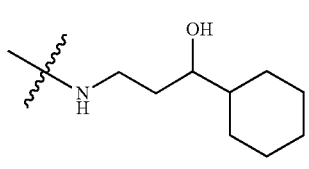<br>racemate | 426.1 | 8.60 (d, J = 7.0 Hz, 1H), 8.54 (br t, J = 5.2 Hz, 1H), 7.56 (t, J = 8.1 Hz, 1H), 7.48 (s, 1H), 7.22 (d, J = 8.2 Hz, 1H), 7.05 (br d, J = 7.0 Hz, 1H), 3.56-3.24 (m, 2H), 2.31 (s, 3H), 1.79-1.56 (m, 6H), 1.53-1.43 (m, 1H), 1.29-0.89 (m, 6H) |
| 41 | 3-(2-amino-[1,2,4]-triazolo[1,5-a]-pyridin-7-yl)-N-(3-cyclohexyl-3-hydroxypropyl)-2-fluoro-6-methyl-benzamide enantiomer 1 | 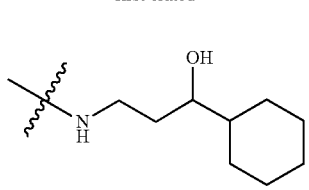<br>enantiomer 1<br>first eluted | 426.1 | 8.61 (d, J = 7.0 Hz, 1H), 8.54 (br t, J = 5.3 Hz, 1H), 7.57 (t, J = 8.1 Hz, 1H), 7.48 (s, 1H), 7.22 (d, J = 7.9 Hz, 1H), 7.05 (br d, J = 7.0 Hz, 1H), 6.06 (s, 2H), 4.42 (d, J = 5.8 Hz, 1H), 3.52-3.25 (m, 2H), 2.31 (s, 3H), 1.79-1.58 (m, 6H), 1.54-1.44 (m, 1H), 1.29-0.91 (m, 6H) |
| 42 | 3-(2-amino-[1,2,4]-triazolo[1,5-a]-pyridin-7-yl)-N-(3-cyclohexyl-3-hydroxypropyl)-2-fluoro-6-methyl-benzamide enantiomer 2 | 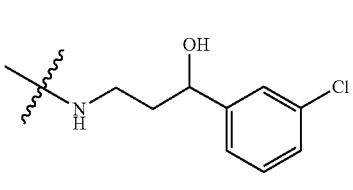<br>enantiomer 2<br>second eluted | 426.1 | 8.61 (d, J = 6.7 Hz, 1H), 8.54 (br t, J = 5.5 Hz, 1H), 7.57 (t, J = 7.9 Hz, 1H), 7.49 (s, 1H), 7.22 (d, J = 7.9 Hz, 1H), 7.05 (br d, J = 1.0 Hz, 1H), 6.07 (s, 2H), 4.41 (d, J = 5.5 Hz, 1H), 3.49-3.25 (m, 2H), 2.32 (s, 3H), 1.79-1.58 (m, 6H), 1.54-1.44 (m 1H), 1.29-0.91 (m, 6H) |
| 43 | 3-(2-amino-[1,2,4]-triazolo[1,5-a]-pyridin-7-yl)-N-(3-(3-chlorophenyl)-3-hydroxypropyl)-2-fluoro-6-methyl-benzamide | <br>racemate | 454.1 | 8.66-8.57 (m, 2H), 7.59 (t, J = 8.1 Hz, 1H), 7.48 (s, 1H), 7.41 (s, 1H), 7.39-7.35 (m, 1H), 7.33-7.28 (m, 2H), 7.22 (d, J = 8.1 Hz, 1H), 7.03 (br d, J = 6.6 Hz, 1H), 6.09 (s, 2H), 5.47 (d, J = 4.4 Hz, 1H), 4.67 (q, J = 5.7 Hz, 1H), 2.56-2.48 (m, 2H), 2.32 (s, 3H), 1.82 (q, J = 6.7 Hz, 2H). |

TABLE 2-continued

Compounds in Table 2 were prepared in a similar fashion to examples 11, 12 and 13.

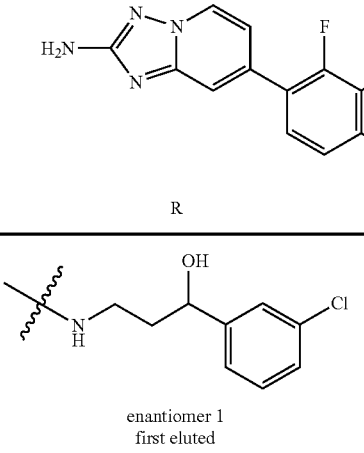

| Ex No | Name | R | M + H⁺ | ¹H NMR (500 MHz, DMSO-d6) δ |
|---|---|---|---|---|
| 44 | 3-(2-amino-[1,2,4]-triazolo[1,5-a]-pyridin-7-yl)-N-(3-(3-chlorophenyl)-3-hydroxypropyl)-2-fluoro-6-methyl-benzamide enantiomer 1 | 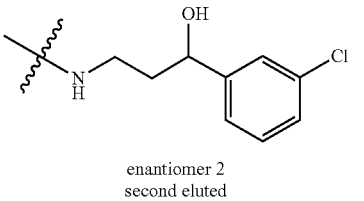 [SMILES: *NCCC(O)c1cccc(Cl)c1]<br>enantiomer 1<br>first eluted | 454.1 | 8.64 (br t, J = 5.0 Hz, 1H), 8.59 (d, J = 7.0 Hz, 1H), 7.57 (t, J = 8.1 Hz, 1H), 7.49 (s, 1H), 7.41-7.35 (m, 2H), 7.33-7.28 (m, 2H), 7.23 (d, J = 7.9 Hz, 1H), 7.06 (br d, J = 7.0 Hz, 1H), 6.05 (s, 2H), 5.54 (d, J = 4.9 Hz, 1H), 4.70-4.65 (m, 1H), 3.40-3.25 (m, 2H), 2.32 (s, 3H), 1.84 (q, J = 6.5 Hz, 2H) |
| 45 | 3-(2-amino-[1,2,4]-triazolo[1,5-a]-pyridin-7-yl)-N-(3-(3-chlorophenyl)-3-hydroxypropyl)-2-fluoro-6-methyl-benzamide enantiomer 2 | 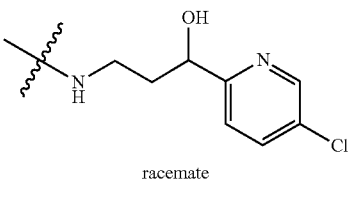 [SMILES: *NCCC(O)c1ccc(Cl)cn1]<br>enantiomer 2<br>second eluted | 454.1 | 8.64 (br t, J = 5.2 Hz, 1H), 8.59 (d, J = 6.7 Hz, 1H), 7.57 (t, J = 8.1 Hz, 1H), 7.49 (s, 1H), 7.41-7.35 (m, 2H), 7.33-7.28 (m, 2H), 7.23 (d, J = 7.9 Hz, 1H), 7.05 (br d, J = 7.0 Hz, 1H), 6.05 (s, 2H), 5.54 (d, J = 4.6 Hz, 1H), 4.70-4.65 (m, 1H), 3.40-3.25 (m, 2H), 2.32 (s, 3H), 1.84 (q, J = 6.8 Hz, 2H) |
| 46 | 3-(2-amino-[1,2,4]-triazolo[1,5-a]-pyridin-7-yl)-N-(3-(5-chloropyridin-2-yl)-3-hydroxy-propyl)-2-fluoro-6-methylbenzamide | 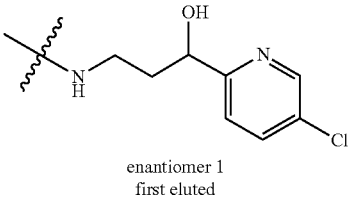 [SMILES: *NCCC(O)c1ccc(Cl)cn1]<br>racemate | 455.2 | 8.64 (br t, J = 5.6 Hz, 1H), 8.61 (d, J = 7.0 Hz, 1H), 8.55 (d, J = 2.1 Hz, 1H), 7.93 (dd, J = 8.5, 2.4 Hz, 1H), 7.60-7.55 (m, 2H), 7.49 (s, 1H), 7.22 (d, J = 7.9 Hz, 1H), 7.05 (br d, J = 7.0 Hz, 1H), 4.73-4.68 (m, 1H), 3.54-3.30 (m, 2H), 2.32 (s, 3H), 2.09-2.00 (m, 1H), 1.85-1.77 (m, 1H) |
| 47 | 3-(2-amino-[1,2,4]-triazolo[1,5-a]-pyridin-7-yl)-N-(3-(5-chloropyridin-2-yl)-3-hydroxy-propyl)-2-fluoro-6-methylbenzamide enantiomer 1 | 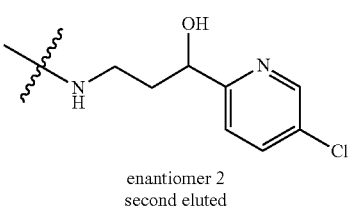 [SMILES: *NCCC(O)c1ccc(Cl)cn1]<br>enantiomer 1<br>first eluted | 455.3 | 8.64 (br t, J = 5.5 Hz, 1H), 8.59 (d, J = 7.0 Hz, 1H), 8.53 (d, J = 2.4 Hz, 1H), 7.92 (dd, J = 8.5, 2.4 Hz, 1H), 7.59-7.53 (m, 2H), 7.48 (s, 1H), 7.21 (d, J = 7.9 Hz, 1H), 7.04 (br d, J = 7.0 Hz, 1H), 6.06 (s, 1H), 5.68 (br d, J = 4.9 Hz, 1H), 4.70 (dt, J = 8.7, 4.2 Hz, 1H), 3.60-3.51 (m, 1H), 3.45-3.32 (m, 1H), 2.31 (s, 3H), 2.08-1.99 (m, 1H), 1.85-1.76 (m, 1H) |
| 48 | 3-(2-amino-[1,2,4]-triazolo[1,5-a]-pyridin-7-yl)-N-(3-(5-chloropyridin-2-yl)-3-hydroxy-propyl)-2-fluoro-6-methylbenzamide enantiomer 2 | 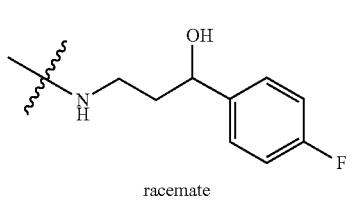 [SMILES: *NCCC(O)c1ccc(F)cc1]<br>enantiomer 2<br>second eluted | 455.1 | 8.64 (br t, J = 5.3 Hz, 1H), 8.59 (d, J = 6.7 Hz, 1H), 8.54 (d, J = 2.1 Hz, 1H), 7.92 (dd, J = 8.2, 2.4 Hz, 1H), 7.59-7.53 (m, 2H), 7.48 (s, 1H), 7.22 (d, J = 8.2 Hz, 1H), 7.05 (br d, J = 7.0 Hz, 1H), 6.06 (s, 1H), 5.68 (d, J = 5.2 Hz, 1H), 4.70 (dt, J = 8.7, 4.5 Hz, 1H), 3.60-3.51 (m, 1H), 3.45-3.32 (m, 1H), 2.31 (s, 3H), 2.08-1.99 (m, 1H), 1.85-1.76 (m, 1H) |
| 49 | 3-(2-amino-[1,2,4]-triazolo[1,5-a]-pyridin-7-yl)-2-fluoro-N-(3-(4-fluorophenyl)-3-hydroxypropyl)-6-methylbenzamide | <br>racemate | 438.3 | 8.67 (d, J = 7.0 Hz, 1H), 8.63 (br t, J = 5.5 Hz, 1H), 7.59 (t, J = 8.1 Hz, 1H), 7.55 (s, 1H), 7.39 (dd, J = 8.4, 5.6 Hz, 2H), 7.24 (d, J = 8.2 Hz, 1H), 7.19-7.13 (m, 3H), 4.67 (br t, J = 6.4 Hz, 1H), 3.37-3.27 (m, 2H), 2.32 (s, 3H), 1.87-1.78 (m, 2H) |

TABLE 2-continued

Compounds in Table 2 were prepared in a similar fashion to examples 11, 12 and 13.

| Ex No | Name | R | M + H+ | ¹H NMR (500 MHz, DMSO-d6) δ |
|---|---|---|---|---|
| 50 | 3-(2-amino-[1,2,4]-triazolo[1,5-a]-pyridin-7-yl)-2-fluoro-N-(3-(4-fluorophenyl)-3-hydroxypropyl)-6-methylbenzamide enantiomer 1 | enantiomer 1 first eluted | 438.2 | 8.64 (br t, J = 5.6 Hz, 1H), 8.59 (d, J = 6.7 Hz, 1H), 7.57 (t, J = 8.1 Hz, 1H), 7.48 (s, 1H), 7.38 (dd, J = 8.4, 5.6 Hz, 2H), 7.22 (d, J = 7.9 Hz, 1H), 7.18-7.12 (m, 2H), 7.06 (br d, J = 7.3 Hz, 1H), 4.66 (br t, J = 6.3 Hz, 1H), 3.31 (dquin, J = 12.8, 6.3 Hz, 2H), 2.31 (s, 3H), 1.87-1.78 (m, 2H) |
| 51 | 3-(2-amino-[1,2,4]-triazolo[1,5-a]-pyridin-7-yl)-2-fluoro-N-(3-(4-fluorophenyl)-3-hydroxypropyl)-6-methylbenzamide enantiomer 2 | enantiomer 2 second eluted | 438.1 | 8.63 (br t, J = 5.5 Hz, 1H), 8.59 (d, J = 7.0 Hz, 1H), 7.57 (t, J = 7.9 Hz, 1H), 7.49 (s, 1H), 7.38 (dd, J = 8.2, 5.8 Hz, 2H), 7.23 (d, J = 7.9 Hz, 1H), 7.18-7.12 (m, 2H), 7.06 (br d, J = 7.0 Hz, 1H), 4.66 (br t, J = 7.8 Hz, 1H), 3.32 (dquin, J = 12.8, 6.4 Hz, 2H), 2.31 (s, 3H), 1.87-1.79 (m, 2H) |
| 52 | 3-(2-amino-[1,2,4]-triazolo[1,5-a]-pyridin-7-yl)-N-(3-cyclohexylpropyl)-2-fluoro-6-methyl-benzamide |  | 410.1 | 8.65-8.53 (m, 2H), 7.56 (td, J = 7.9, 3.7 Hz, 1H), 7.47 (s, 1H), 7.21 (d, J = 8.1 Hz, 1H), 7.03 (br d, J = 5.9 Hz, 1H), 6.08 (br s, 2H), 3.22 (q, J = 6.4 Hz, 2H), 2.30 (s, 3H), 1.72-1.46 (m, 7H), 1.28-1.06 (m, 6H), 0.91-0.79 (m, 2H) |
| 53 | 3-(2-amino-[1,2,4]-triazolo[1,5-a]-pyridin-7-yl)-N-(3-(4-chlorophenyl)-3-hydroxypropyl-1,1,3-d₃)-2-fluoro-6-methylbenzamide enantiomer 1 | enantiomer 1 first eluted | 457.1 | 8.70-8.54 (m, 2H), 7.61 (t, J = 8.1 Hz, 1H), 7.52 (s, 1H), 7.46-7.35 (m, 4H), 7.25 (d, J = 7.9 Hz, 1H), 7.07 (br d, J = 7.0 Hz, 1H), 2.34 (s, 3H), 1.83 (s, 2H) |
| 54 | 3-(2-amino-[1,2,4]-triazolo[1,5-a]-pyridin-7-yl)-N-(3-(4-chlorophenyl)-3-hydroxypropyl-1,1,3-d₃)-2-fluoro-6-methylbenzamide enantiomer 2 | enantiomer 2 second eluted | 457.1 | 8.63-8.58 (m, 2H), 7.58 (t, J = 8.1 Hz, 1H), 7.49 (s, 1H), 7.42-7.35 (m, 4H), 7.23 (d, J = 7.9 Hz, 1H), 7.05 (br d, J = 6.7 Hz, 1H), 2.32 (s, 3H), 1.81 (s, 2H) |
| 55 | 3-(2-amino-[1,2,4]-triazolo[1,5-a]-pyridin-7-yl)-2-fluoro-N-(3-hydroxy-3-(4-(trifluoromethyl)-phenyl)propyl)-6-methylbenzamide | racemate | 488.1 | 8.67 (br t, J = 5.5 Hz, 1H), 8.59 (d, J = 7.0 Hz, 1H), 7.71 (br d, J = 7.9 Hz, 2H), 7.61-7.55 (m, 3H), 7.49 (s, 1H), 7.23 (br d, J = 7.9 Hz, 1H), 7.07 (br d, J = 7.0 Hz, 1H), 4.77 (br t, J = 5.6 Hz, 1H), 3.43-3.28 (m, 2H), 2.32 (s, 3H), 1.91-1.82 (m, 2H) |

TABLE 2-continued

Compounds in Table 2 were prepared in a similar fashion to examples 11, 12 and 13.

| Ex No | Name | R | M + H⁺ | ¹H NMR (500 MHz, DMSO-d6) δ |
|---|---|---|---|---|
| 56 | 3-(2-amino-[1,2,4]-triazolo[1,5-a]-pyridin-7-yl)-2-fluoro-N-(3-hydroxy-3-(4-(trifluoromethyl)-phenyl)propyl)-6-methylbenzamide enantiomer 1 | -NH-CH2CH2-CH(OH)-C6H4-CF3 (enantiomer 1, first eluted) | 488.3 | 8.66 (br d, J = 4.6 Hz, 1H), 8.61 (br d, J = 7.0 Hz, 1H), 7.72 (br d, J = 7.9 Hz, 2H), 7.63-7.56 (m, 3H), 7.50 (s, 1H), 7.24 (br d, J = 7.9 Hz, 1H), 7.07 (br d, J = 6.4 Hz, 1H), 6.07 (br s, 2H), 5.61 (br d, J = 4.3 Hz, 1H), 4.81-4.74 (m, 1H), 3.43-3.29 (m, 2H), 2.33 (s, 3H), 1.92-1.82 (m, 2H) |
| 57 | 3-(2-amino-[1,2,4]-triazolo[1,5-a]-pyridin-7-yl)-2-fluoro-N-(3-hydroxy-3-(4-(trifluoromethyl)-phenyl)propyl)-6-methylbenzamide enantiomer 2 | -NH-CH2CH2-CH(OH)-C6H4-CF3 (enantiomer 2, second eluted) | 488.0 | 8.66 (br t, J = 5.2 Hz, 1H), 8.61 (d, J = 7.0 Hz, 1H), 7.72 (br d, J = 7.6 Hz, 2H), 7.63-7.56 (m, 3H), 7.50 (s, 1H), 7.24 (br d, J = 7.9 Hz, 1H), 7.07 (br d, J = 6.4 Hz, 1H), 6.07 (s, 2H), 5.62 (br d, J = 4.3 Hz, 1H), 4.81-4.74 (m, 1H), 3.44-3.29 (m, 2H), 2.33 (s, 3H), 1.91-1.82 (m, 2H) |
| 58 | 3-(2-amino-[1,2,4]-triazolo[1,5-a]-pyridin-7-yl)-2-fluoro-6-methyl-N-(3-methyl-3-phenylbutyl)benzamide | -NH-CH2CH2-C(CH3)2-C6H5 | 432.0 | 8.59 (dd, J = 6.6, 4.0 Hz, 1H), 8.55-8.48 (m, 1H), 7.59-7.52 (m, 1H), 7.46 (s, 1H), 7.40 (br d, J = 8.1 Hz, 2H), 7.33 (t, J = 7.7 Hz, 2H), 7.23-7.16 (m, 2H), 7.02 (br d, J = 5.5 Hz, 1H), 6.08 (br s, 2H), 3.04-2.97 (m, 2H), 2.51 (br s, 6H), 2.27 (s, 3H), 1.90-1.82 (m, 2H), 1.32 (s, 6H). |
| 59 | 3-(2-amino-[1,2,4]-triazolo[1,5-a]-pyridin-7-yl)-N-(3-(4-chlorophenyl)-3-hydroxybutyl)-2-fluoro-6-methyl-benzamide enantiomer 1 | -NH-CH2CH2-C(CH3)(OH)-C6H4-Cl (enantiomer 1, first eluted) | 468.3 | 8.62 (d, J = 6.7 Hz, 1H), 8.46 (br t, J = 5.3 Hz, 1H), 7.58 (br t, J = 8.1 Hz, 1H), 7.54-7.46 (m, 3H), 7.40 (br d, J = 8.2 Hz, 2H), 7.21 (br d, J = 7.9 Hz, 1H), 7.04 (br d, J = 7.0 Hz, 1H), 6.08 (s, 2H), 3.41-3.25 (m, 1H), 3.04-2.92 (m, 1H), 2.29 (s, 3H), 2.03-1.91 (m, 2H) |
| 60 | 3-(2-amino-[1,2,4]-triazolo[1,5-a]-pyridin-7-yl)-N-(3-(4-chlorophenyl)-3-hydroxybutyl)-2-fluoro-6-methyl-benzamide enantiomer 2 | -NH-CH2CH2-C(CH3)(OH)-C6H4-Cl (enantiomer 2, second eluted) | 468.3 | 8.61 (d, J = 7.0 Hz, 1H), 8.47 (br t, J = 5.6 Hz, 1H), 7.57 (t, J = 7.9 Hz, 1H), 7.53-7.46 (m, 3H), 7.40 (d, J = 8.2 Hz, 2H), 7.22 (d, J = 7.6 Hz, 1H), 7.05 (br d, J = 7.0 Hz, 1H), 6.07 (s, 2H), 3.36-3.24 (m, 1H), 3.04-2.93 (m, 1H), 2.29 (s, 3H), 2.03-1.90 (m, 2H) |
| 61 | 3-(2-amino-[1,2,4]-triazolo[1,5-a]-pyridin-7-yl)-N-(2,2-difluoro-3-(4-fluorophenyl)-3-hydroxybutyl)-2-fluoro-6-methyl-benzamide enantiomer 1 | -NH-CF2-C(CH3)(OH)-C6H4-F (enantiomer 1, first eluted) | 488.3 | 8.80 (br t, J = 5.9 Hz, 1H), 8.58 (br d, J = 7.0 Hz, 1H), 7.62-7.53 (m, 3H), 7.45 (s, 1H), 7.20 (br t, J = 7.0 Hz, 3H), 7.01 (br d, J = 7.0 Hz, 1H), 4.02-3.86 (m, 2H), 2.26 (s, 3H), 1.62 (s, 3H) |

TABLE 2-continued

Compounds in Table 2 were prepared in a similar fashion to examples 11, 12 and 13.

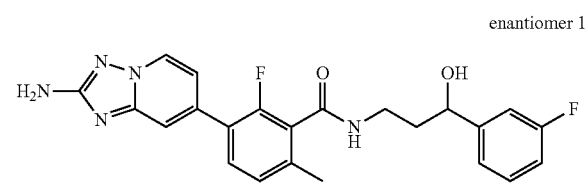 [SMILES: Cc1ccc(-c2ccn3nc(N)nc3c2)c(F)c1C(=O)NCCC(O)c1cccc(F)c1]

| Ex No | Name | R | M + H+ | 1H NMR (500 MHz, DMSO-d6) δ |
|---|---|---|---|---|
| 62 | 3-(2-amino-[1,2,4]-triazolo[1,5-a]-pyridin-7-yl)-N-(2,2-difluoro-3-(4-fluorophenyl)-3-hydroxybutyl)-2-fluoro-6-methyl-benzamide enantiomer 2 | enantiomer 2 second eluted | 488.3 | 8.80 (br t, J = 6.0 Hz, 1H), 8.58 (d, J = 7.0 Hz, 1H), 7.62-7.53 (m, 3H), 7.45 (s, 1H), 7.24-7.15 (m, 3H), 7.01 (br d, J = 6.7 Hz, 1H), 4.01-3.85 (m, 2H), 2.26 (s, 3H), 1.63 (s, 3H) |

Example 63: 3-(2-amino-[1,2,4]triazolo[1,5-a]pyridin-7-yl)-2-fluoro-N-(3-(3-fluorophenyl)-3-hydroxypropyl)-6-methylbenzamide enantiomer 1 enantiomer 1

63A: 3-(3-fluorophenyl)-3-oxopropanenitrile: Sodium hydride 60% dispersion in mineral oil (0.520 g, 13.0 mmol) was carefully added to a solution of methyl 3-fluorobenzoate (1.00 g, 6.50 mmol) in dry toluene (6 mL) at RT under nitrogen. The mixture was then heated to 80° C. and treated with anhydrous acetonitrile (1.6 mL, 30.9 mmol) via dropwise addition. After heating ON, the mixture was allowed to cool to RT and was diluted with hexanes. A solid was isolated by filtration and rinsed with clean hexanes. The solid was dissolved in water (30 mL) and the resulting solution was slowly treated with 1N aqueous HCl with stirring until a precipitate occurred and pH=4-5 was achieved. The precipitate was isolated by filtration and allowed to air-dry. The filtrate was then placed under high vacuum for several hours to afford 3-(3-fluorophenyl)-3-oxopropanenitrile (776 mg, 4.76 mmol, 73% yield) as a slightly off-white solid. 1H NMR (500 MHz, CDCl3) δ 7.73 (d, J=7.6 Hz, 1H), 7.66 (dt, J=9.0, 2.1 Hz, 1H), 7.55 (td, J=8.0, 5.4 Hz, 1H), 7.40 (t, J=8.2 Hz, 1H), 4.09 (s, 2H), no water suppression.

63B: 3-amino-1-(3-fluorophenyl)propan-1-ol, TFA salt: Under a blanket of nitrogen, a solution of 3-(3-fluorophenyl)-3-oxopropanenitrile (300 mg, 1.839 mmol) in anhydrous THF (9.19 mL) was cautiously treated with borane dimethyl sulfide complex, 5M in diethyl ether (1.8 mL, 9.19 mmol). The reaction mixture was heated to 70° C. for 16 h. Methanol (5 mL) was added to the mixture dropwise, and the solution was stirred for 30 min at RT. Solvent was removed in vacuo. The crude mixture was dissolved in MeOH and purified by reverse phase preparative HPLC (Waters Sunfire C18, 50×250 mm, 10 micron, Solvent A=90% H2O, 10% acetonitrile, 0.1% TFA; Solvent B=90% acetonitrile, 10% H2O, 0.1% TFA; 100 mL/min, gradient 0-100% B over 15 min, hold 100% B for 4 min). Fractions containing desired product were combined and concentrated in vacuo, then the residue was placed under high vacuum overnight to provide 3-amino-1-(3-fluorophenyl)propan-1-ol, TFA salt (224 mg, 1.32 mmol, 43% yield) as a clear, colorless oil.

MS ESI m/z 169.9 (M+H)+

63: To a solution of 3-(2-amino-[1,2,4]triazolo[1,5-a]pyridin-7-yl)-2-fluoro-6-methylbenzoic acid, HCl (25 mg, 0.077 mmol) and 3-amino-1-(3-fluorophenyl)propan-1-ol, TFA salt (28.5 mg, 0.101 mmol) in DMF (1 mL) was added BOP (44.5 mg, 0.101 mmol) followed by DIPEA (0.068 mL, 0.387 mmol). The mixture was stirred at RT for 2 h, then the mixture was filtered and purified via preparative LCMS with the following conditions: Column: XBridge C18, 19×200 mm, 5 μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 13% B, 13-53% B over 25 minutes, then a 4-min hold at 100% B; Flow Rate: 20 mL/min; Column Temperature: 25 C. Fractions containing the racemate product were combined and dried via centrifugal evaporation to a residue. The residue was further purified to separate the individual enantiomers using SFC-chiral chromatography with the following conditions: Column: Chiral OD 30×250 mm, 5 μm particles; Mobile Phase: 65% CO2/35% IPA with 0.1% DEA; Flow Rate: 100 mL/min; Injection Details: 1 mL injections of residue dissolved in 3 mL MeOH. Thus was obtained 3-(2-amino-[1,2,4]triazolo[1,5-a]pyridin-7-yl)-2-fluoro-N-(3-(3-fluorophenyl)-3-hydroxypropyl)-6-methylbenzamide enantiomer 1 (5.3 mg, 0.0121 mmol, 14.9% yield) as the first eluting isomer from the described preparative SFC purification.

1H NMR (500 MHz, DMSO-d6) δ 8.67-8.58 (m, 2H), 7.61 (br t, J=8.1 Hz, 1H), 7.51 (s, 1H), 7.45-7.32 (m, 1H), 7.27-7.16 (m, 3H), 7.14-6.99 (m, 2H), 6.09 (s, 2H), 5.46 (d, J=4.7 Hz, 1H), 4.75-4.65 (m, 1H), 2.34 (s, 3H), 1.86 (q, J=6.7 Hz, 2H), no water suppression. Two protons were likely obscured by water peak.

MS ESI m/z 438.3 (M+H)+

Example 64: 3-(2-amino-[1,2,4]triazolo[1,5-a]pyridin-7-yl)-2-fluoro-N-(3-(3-fluorophenyl)-3-hydroxypropyl)-6-methylbenzamide enantiomer 2

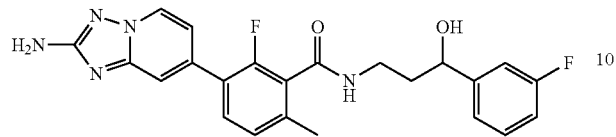

enantiomer 2

The title compound 3-(2-amino-[1,2,4]triazolo[1,5-a]pyridin-7-yl)-2-fluoro-N-(3-(3-fluorophenyl)-3-hydroxypropyl)-6-methylbenzamide enantiomer 2 (5.4 mg, 0.0123 mmol, 15.9% yield) was obtained as the second eluting isomer from the chiral SFC purification described for example 63.

$^1$H NMR (500 MHz, DMSO-d6) δ 8.61 (br d, J=6.9 Hz, 2H), 7.59 (t, J=8.1 Hz, 1H), 7.50 (s, 1H), 7.43-7.34 (m, 1H), 7.27-7.14 (m, 3H), 7.10-7.01 (m, 2H), 6.07 (s, 2H), 5.47 (d, J=4.4 Hz, 1H), 4.74-4.65 (m, 1H), 2.33 (s, 3H), 1.85 (q, J=6.5 Hz, 2H).

MS ESI m/z 438.3 (M+H)$^+$

TABLE 3

Compounds in Table 3 were prepared in a similar fashion to examples 63 and 64. Various alkyl benzoates were used in place of methyl 3-fluorobenzoate in the first step.

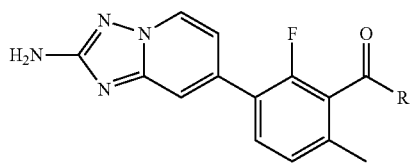

| Ex No | Name | R | M + H$^+$ | 1H NMR (500 MHz, DMSO-d6) δ |
|---|---|---|---|---|
| 65 | 3-(2-amino-[1,2,4]triazolo[1,5-a]pyridin-7-yl)-N-(3-(4-chloro-2-methoxyphenyl)-3-hydroxypropyl)-2-fluoro-6-methylbenzamide enantiomer 1 | enantiomer 1 first eluted | 484.0 | 8.61 (d, J = 7.0 Hz, 1H), 8.58 (t, J = 6.1 Hz, 1H), 7.58 (br t, J = 8.0 Hz, 1H), 7.49 (s, 1H), 7.44 (br d, J = 8.8 Hz, 1H), 7.22 (br d, J = 7.7 Hz, 1H), 7.07-7.00 (m, 3H), 6.08 (s, 2H), 5.23 (br s, 1H), 4.98-4.90 (m, 1H), 3.84-3.75 (m, 3H), 2.33 (s, 3H), 1.91-1.81 (m, 1H), 1.77-1.63 (m, 1H), no water suppression. Two protons were likely obscured by water peak. |
| 66 | 3-(2-amino-[1,2,4]triazolo[1,5-a]pyridin-7-yl)-N-(3-(3,4-difluorophenyl)-3-hydroxypropyl)-2-fluoro-6-methylbenzamide enantiomer 1 | enantiomer 1 first eluted | 456.1 | 8.69-8.54 (m, 2H), 7.59 (br t, J = 8.0 Hz, 1H), 7.50 (s, 1H), 7.45-7.34 (m, 2H), 7.28-7.16 (m, 2H), 7.05 (br d, J = 6.9 Hz, 1H), 6.18-5.97 (m, 2H), 5.51 (br s, 1H), 4.68 (br t, J = 5.9 Hz, 1H), 2.33 (s, 3H), 1.84 (q, J = 6.7 Hz, 2H), no water suppression. Two protons were likely obscured by water peak. |
| 67 | 3-(2-amino-[1,2,4]triazolo[1,5-a]pyridin-7-yl)-N-(3-(3,4-difluorophenyl)-3-hydroxypropyl)-2-fluoro-6-methylbenzamide enantiomer 2 | enantiomer 2 second eluted | 456.1 | 8.64-8.57 (m, 2H), 7.59 (t, J = 8.0 Hz, 1H), 7.49 (s, 1H), 7.44-7.35 (m, 2H), 7.23 (br d, J = 8.0 Hz, 2H), 7.05 (br d, J = 6.9 Hz, 1H), 6.08 (br s, 2H), 5.51 (br s, 1H), 4.72-4.63 (m, 1H), 2.33 (s, 3H), 1.84 (q, J = 7.1 Hz, 2H), no water suppression. Two protons were likely obscured by water peak. |

TABLE 3-continued

Compounds in Table 3 were prepared in a similar fashion to examples 63 and 64.
Various alkyl benzoates were used in place of methyl 3-fluorobenzoate in the first step.

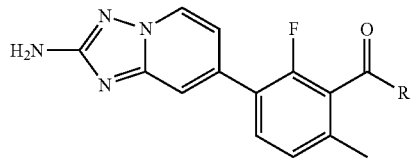

| Ex No | Name | R | M + H⁺ | 1H NMR (500 MHz, DMSO-d6) δ |
|---|---|---|---|---|
| 68 | 3-(2-amino-[1,2,4]triazolo[1,5-a]pyridin-7-yl)-N-(3-(4-chloro-2-fluorophenyl)-3-hydroxypropyl)-2-fluoro-6-methylbenzamide enantiomer 1 | enantiomer 1 first eluted | 472.2 | 8.65 (br t, J = 5.5 Hz, 1H), 8.61 (d, J = 7.2 Hz, 1H), 7.56 (dt, J = 13.7, 8.1 Hz, 2H), 7.49 (s, 1H), 7.36 (d, J = 9.4 Hz, 1H), 7.32 (br d, J = 8.3 Hz, 1H), 7.23 (d, J = 8.0 Hz, 1H), 7.05 (br d, J = 6.9 Hz, 1H), 6.07 (s, 2H), 5.56 (d, J = 4.7 Hz, 1H), 4.93 (dt, J = 8.7, 4.2 Hz, 1H), 3.39-3.35 (m, 2H), 2.32 (s, 3H), 1.93-1.75 (m, 2H), no water suppression. |
| 69 | 3-(2-amino-[1,2,4]triazolo[1,5-a]pyridin-7-yl)-N-(3-(4-chloro-2-fluorophenyl)-3-hydroxypropyl)-2-fluoro-6-methylbenzamide enantiomer 2 | enantiomer 2 second eluted | 472.2 | 8.65 (br t, J = 5.5 Hz, 1H), 8.61 (d, J = 7.2 Hz, 1H), 7.56 (dt, J = 13.7, 8.1 Hz, 2H), 7.49 (s, 1H), 7.36 (d, J = 9.4 Hz, 1H), 7.32 (br d, J = 8.3 Hz, 1H), 7.23 (d, J = 8.0 Hz, 1H), 7.05 (br d, J = 6.9 Hz, 1H), 6.07 (s, 2H), 5.56 (d, J = 4.7 Hz, 1H), 4.93 (dt, J = 8.7, 4.2 Hz, 1H), 3.41-3.36 (m, 2H), 2.32 (s, 3H), 1.89-1.80 (m, 2H), no water suppression. |
| 70 | 3-(2-amino-[1,2,4]triazolo[1,5-a]pyridin-7-yl)-2-fluoro-N-(3-(2-fluorophenyl)-3-hydroxypropyl)-6-methylbenzamide enantiomer 2 | enantiomer 2 second eluted | 438.3 | 8.65 (t, J = 6.2 Hz, 1H), 8.61 (d, J = 7.2 Hz, 1H), 7.61-7.47 (m, 3H), 7.41-7.27 (m, 1H), 7.26-7.20 (m, 2H), 7.14 (br t, J = 9.2 Hz, 1H), 7.05 (br d, J = 6.9 Hz, 1H), 6.07 (s, 2H), 5.46 (d, J = 4.7 Hz, 1H), 5.05-4.86 (m, 1H), 3.41-3.36 (m, 2H), 2.32 (s, 3H), 1.93-1.73 (m, 2H), no water suppression. |
| 71 | 3-(2-amino-[1,2,4]triazolo[1,5-a]pyridin-7-yl)-2-fluoro-N-(3-(2-fluorophenyl)-3-hydroxypropyl)-6-methylbenzamide enantiomer 1 | enantiomer 1 first eluted | 438.0 | 8.67-8.62 (m, 1H), 8.62-8.58 (m, 1H), 7.61-7.51 (m, 2H), 7.50-7.46 (m, 1H), 7.34-7.28 (m, 1H), 7.25-7.19 (m, 2H), 7.17-7.11 (m, 1H), 7.07-7.02 (m, 1H), 6.09-6.04 (m, 2H), 5.48-5.44 (m, 1H), 4.99-4.93 (m, 1H), 3.41-3.36 (m, 2H), 2.35-2.29 (m, 3H), 1.93-1.79 (m, 2H), no water suppression. |

TABLE 3-continued

*Compounds in Table 3 were prepared in a similar fashion to examples 63 and 64.*
*Various alkyl benzoates were used in place of methyl 3-fluorobenzoate in the first step.*

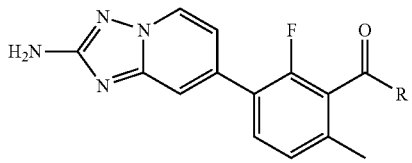

| Ex No | Name | R | M + H⁺ | 1H NMR (500 MHz, DMSO-d6) δ |
|---|---|---|---|---|
| 72 | 3-(2-amino-[1,2,4]triazolo[1,5-a]pyridin-7-yl)-2-fluoro-N-(3-(3-fluoro-2-methoxyphenyl)-3-hydroxypropyl)-6-methylbenzamide enantiomer 1 | [structure: ~NH-CH2-CH2-CH(OH)-(3-fluoro-2-methoxyphenyl)] enantiomer 1 first eluted | 467.9 | 8.67-8.55 (m, 2H), 7.61-7.53 (m, 1H), 7.51-7.45 (m, 1H), 7.31-7.25 (m, 1H), 7.25-7.19 (m, 1H), 7.18-7.08 (m, 2H), 7.08-6.99 (m, 1H), 6.09-6.02 (m, 2H), 5.39-5.33 (m, 1H), 5.02-4.95 (m, 1H), 3.84 (s, 3H), 3.41-3.34 (m, 2H), 2.35-2.29 (m, 3H), 1.91-1.71 (m, 2H), no water suppression. |
| 73 | 3-(2-amino-[1,2,4]triazolo[1,5-a]pyridin-7-yl)-N-(3-(2,6-difluorophenyl)-3-hydroxypropyl)-2-fluoro-6-methylbenzamide enantiomer 1 | [structure: ~NH-CH2-CH2-CH(OH)-(2,6-difluorophenyl)] enantiomer 1 first eluted | 455.8 | ¹H NMR (500 MHz, DMSO-d₆) δ 8.67-8.57 (m, 2H), 7.58 (br t, J = 7.7 Hz, 1H), 7.48 (s, 1H), 7.36 (quin, J = 7.2 Hz, 1H), 7.22 (br d, J = 7.9 Hz, 1H), 7.09-7.00 (m, 3H), 6.07 (s, 2H), 5.48 (br d, J = 4.4 Hz, 1H), 5.07-5.01 (m, 1H), 3.41-3.34 (m, 2H), 2.31 (s, 3H), 2.19 (dq, J = 13.9, 7.0 Hz, 1H), 1.96-1.88 (m, 1H). |
| 74 | 3-(2-amino-[1,2,4]triazolo[1,5-a]pyridin-7-yl)-N-(3-(2,6-difluorophenyl)-3-hydroxypropyl)-2-fluoro-6-methylbenzamide enantiomer 2 | [structure: ~NH-CH2-CH2-CH(OH)-(2,6-difluorophenyl)] enantiomer 2 second eluted | 456.1 | 8.70-8.64 (m, 1H), 8.63-8.58 (m, 1H), 7.61-7.55 (m, 1H), 7.50-7.46 (m, 1H), 7.41-7.33 (m, 1H), 7.25-7.20 (m, 1H), 7.09-7.02 (m, 3H), 6.09-6.04 (m, 2H), 5.57-5.54 (m, 1H), 5.02 (s, 1H), 3.39-3.31 (m, 2H), 2.34-2.28 (m, 3H), 2.25-2.15 (m, 1H), 1.97-1.86 (m, 1H), no water suppression. |

TABLE 4

Compounds in Table 4 were prepared in a similar fashion to examples 11, 12 and 13 where methyl 3-bromo-6-chloro-2-fluorobenzoate was used in place of ethyl 3-bromo-2-fluoro-6-methylbenzoate in the first step.

| Ex No | Name | R | M + H⁺ | ¹H NMR (500 MHz, DMSO-d6) δ |
|---|---|---|---|---|
| 75 | 3-(2-amino-[1,2,4]triazolo[1,5-a]pyridin-7-yl)-6-chloro-N-(3-(4-chlorophenyl)-3-hydroxypropyl-1,1,3-d₃)-2-fluorobenzamide | racemate (D, D, D, OH, 4-Cl-phenyl) | 477.1 | 8.77 (s, 1H), 8.63 (d, J = 6.9 Hz, 1H), 7.72 (t, J = 8.4 Hz, 1H), 7.53-7.48 (m, 2H), 7.40-7.34 (m, 4H), 7.03 (br d, J = 7.0 Hz, 1H), 1.79 (s, 2H) |
| 76 | 3-(2-amino-[1,2,4]triazolo[1,5-a]pyridin-7-yl)-6-chloro-N-(3-(4-chlorophenyl)-3-hydroxypropyl-1,1,3-d₃)-2-fluorobenzamide enantiomer 1 | enantiomer 1 first eluted | 477.3 | 8.77 (s, 1H), 8.63 (d, J = 7.0 Hz, 1H), 7.72 (t, J = 8.2 Hz, 1H), 7.54-7.47 (m, 2H), 7.41-7.34 (m, 4H), 7.03 (br d, J = 6.7 Hz, 1H), 1.79 (s, 2H) |
| 77 | 3-(2-amino-[1,2,4]triazolo[1,5-a]pyridin-7-yl)-6-chloro-N-(3-(4-chlorophenyl)-3-hydroxypropyl-1,1,3-d₃)-2-fluorobenzamide enantiomer 2 | enantiomer 2 second eluted | 477.3 | 8.77 (s, 1H), 8.62 (d, J = 7.0 Hz, 1H), 7.72 (t, J = 8.4 Hz, 1H), 7.53-7.47 (m, 2H), 7.41-7.34 (m, 4H), 7.03 (br d, J = 6.7 Hz, 1H), 1.79 (s, 2H) |
| 78 | 3-(2-amino-[1,2,4]triazolo[1,5-a]pyridin-7-yl)-6-chloro-2-fluoro-N-(3-(4-fluorophenyl)-3-hydroxypropyl)benzamide | racemate | 457.8 | 8.79 (t, J = 5.3 Hz, 1H), 8.64 (d, J = 7.0 Hz, 1H), 7.73 (t, J = 8.4 Hz, 1H), 7.52 (s, 1H), 7.50 (d, J = 8.4 Hz, 1H), 7.38 (dd, J = 8.5, 5.8 Hz, 2H), 7.15 (t, J = 8.9 Hz, 2H), 7.04 (br d, J = 7.0 Hz, 1H), 6.11 (s, 2H), 5.35 (d, J = 4.2 Hz, 1H), 4.70-4.65 (m, 1H), 3.34-3.27 (m, 1H), 1.86-1.77 (m, 2H) |
| 79 | 3-(2-amino-[1,2,4]triazolo[1,5-a]pyridin-7-yl)-6-chloro-2-fluoro-N-(3-(4-fluorophenyl)-3-hydroxypropyl)benzamide enantiomer 1 | enantiomer 1 first eluted | 458.0 | 8.80 (t, J = 5.6 Hz, 1H), 8.62 (d, J = 7.0 Hz, 1H), 7.72 (t, J = 8.5 Hz, 1H), 7.52 (s, 1H), 7.50 (d, J = 8.4 Hz, 1H), 7.37 (dd, J = 8.5, 5.6 Hz, 2H), 7.15 (t, J = 8.9 Hz, 2H), 7.04 (br d, J = 7.0 Hz, 1H), 6.10 (s, 2H), 5.38 (d, J = 4.6 Hz, 1H), 4.69-4.64 (m, 1H), 3.35-3.27 (m, 1H), 1.87-1.76 (m, 2H) |
| 80 | 3-(2-amino-[1,2,4]triazolo[1,5-a]pyridin-7-yl)-6-chloro-2-fluoro-N-(3-(4-fluorophenyl)-3-hydroxypropyl)benzamide enantiomer 2 | enantiomer 2 second eluted | 458.2 | 8.80 (br t, J = 5.4 Hz, 1H), 8.63 (d, J = 6.8 Hz, 1H), 7.72 (t, J = 8.4 Hz, 1H), 7.52 (s, 1H), 7.50 (d, J = 8.5 Hz, 1H), 7.38 (dd, J = 8.5, 5.8 Hz, 2H), 7.15 (t, J = 8.9 Hz, 2H), 7.04 (br d, J = 6.9 Hz, 1H), 6.10 (s, 2H), 5.38 (d, J = 4.1 Hz, 1H), 4.69-4.64 (m, 1H), 3.34-3.27 (m, 1H), 1.87-1.76 (m, 2H) |

TABLE 4-continued

Compounds in Table 4 were prepared in a similar fashion to examples 11, 12 and 13 where methyl 3-bromo-6-chloro-2-fluorobenzoate was used in place of ethyl 3-bromo-2-fluoro-6-methylbenzoate in the first step.

| Ex No | Name | R | M + H⁺ | ¹H NMR (500 MHz, DMSO-d6) δ |
|---|---|---|---|---|
| 81 | 3-(2-amino-[1,2,4]triazolo[1,5-a]pyridin-7-yl)-6-chloro-N-(3-(5-chloropyridin-2-yl)-3-hydroxypropyl)-2-fluorobenzamide | racemate | 475.0 | 8.81 (br t, J = 5.5 Hz, 1H), 8.64 (d, J = 6.7 Hz, 1H), 8.56 (d, J = 2.4 Hz, 1H), 7.94 (dd, J = 8.4, 2.3 Hz, 1H), 7.73 (t, J = 8.2 Hz, 1H), 7.56 (d, J = 8.2 Hz, 1H), 7.53 (s, 1H), 7.51 (d, J = 8.5 Hz, 1H), 7.05 (br d, J = 6.7 Hz, 1H), 4.72 (dt, J = 8.2, 3.8 Hz, 1H), 3.47-3.29 (m, 1H), 2.11-2.01 (m, 1H), 1.86-1.77 (m, 1H) |
| 82 | 3-(2-amino-[1,2,4]triazolo[1,5-a]pyridin-7-yl)-6-chloro-N-(3-(5-chloropyridin-2-yl)-3-hydroxypropyl)-2-fluorobenzamide enantiomer 1 | enantiomer 1 first eluted | 475.2 | 8.82 (br t, J = 5.2 Hz, 1H), 8.64 (d, J = 6.7 Hz, 1H), 8.56 (d, J = 2.1 Hz, 1H), 7.94 (dd, J = 8.5, 2.1 Hz, 1H), 7.73 (t, J = 8.2 Hz, 1H), 7.56 (d, J = 8.2 Hz, 1H), 7.53 (s, 1H), 7.51 (d, J = 8.2 Hz, 1H), 7.05 (br d, J = 6.7 Hz, 1H), 4.72 (dt, J = 8.8, 4.3 Hz, 1H), 3.47-3.32 (m, 1H), 2.10-2.01 (m, 1H), 1.86-1.77 (m, 1H) |
| 83 | 3-(2-amino-[1,2,4]triazolo[1,5-a]pyridin-7-yl)-6-chloro-N-(3-(5-chloropyridin-2-yl)-3-hydroxypropyl)-2-fluorobenzamide enantiomer 2 | enantiomer 2 second eluted | 475.3 | 8.82 (br t, J = 5.3 Hz, 1H), 8.64 (d, J = 7.0 Hz, 1H), 8.57-8.53 (m, 1H), 7.94 (dd, J = 8.4, 2.3 Hz, 1H), 7.73 (t, J = 8.2 Hz, 1H), 7.56 (d, J = 8.2 Hz, 1H), 7.53 (s, 1H), 7.50 (d, J = 8.5 Hz, 1H), 7.05 (br d, J = 7.0 Hz, 1H), 4.72 (dt, J = 8.2, 4.1 Hz, 1H), 3.48-3.33 (m, 1H), 2.10-2.01 (m, 1H), 1.87-1.77 (m, 1H) |
| 84 | 3-(2-amino-[1,2,4]triazolo[1,5-a]pyridin-7-yl)-6-chloro-2-fluoro-N-(2-(1-(4-fluorophenyl)cyclopropyl)ethyl)benzamide | | 468.0 | 8.72 (br t, J = 5.4 Hz, 1H), 8.63 (d, J = 6.9 Hz, 1H), 7.72 (br t, J = 8.3 Hz, 1H), 7.57-7.46 (m, 2H), 7.39 (dd, J = 8.4, 5.7 Hz, 2H), 7.13 (t, J = 8.8 Hz, 2H), 7.03 (br d, J = 7.0 Hz, 1H), 6.11 (s, 2H), 3.25-3.11 (m, 2H), 1.86-1.72 (m, 2H), 0.77 (br d, J = 16.3 Hz, 4H). |
| 85 | 3-(2-amino-[1,2,4]triazolo[1,5-a]pyridin-7-yl)-6-chloro-2-fluoro-N-(3-hydroxy-3-(4-(trifluoromethyl)phenyl)propyl)benzamide enantiomer 1 | enantiomer 1 first eluted | 508.0 | 8.83 (br t, J = 5.5 Hz, 1H), 8.63 (d, J = 6.9 Hz, 1H), 7.76-7.68 (m, 3H), 7.58 (br d, J = 8.0 Hz, 2H), 7.52 (br s, 1H), 7.51 (d, J = 8.5 Hz, 1H), 7.04 (br d, J = 7.1 Hz, 1H), 6.10 (s, 2H), 4.81-4.75 (m, 1H), 3.38 (s, 1H), 1.90-1.80 (m, 2H) |

TABLE 4-continued

Compounds in Table 4 were prepared in a similar fashion to examples 11, 12 and 13 where methyl 3-bromo-6-chloro-2-fluorobenzoate was used in place of ethyl 3-bromo-2-fluoro-6-methylbenzoate in the first step.

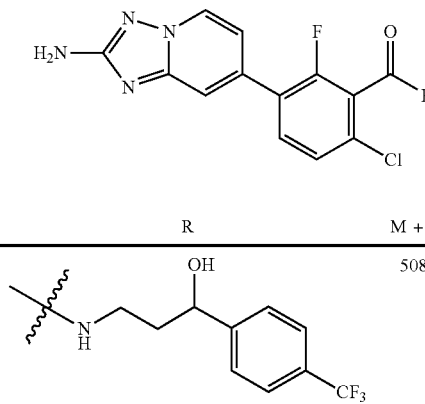

| Ex No | Name | R | M + H+ | 1H NMR (500 MHz, DMSO-d6) δ |
|---|---|---|---|---|
| 86 | 3-(2-amino-[1,2,4]triazolo[1,5-a]pyridin-7-yl)-6-chloro-2-fluoro-N-(3-hydroxy-3-(4-(trifluoromethyl)phenyl)propyl)benzamide enantiomer 2 | enantiomer 2 second eluted | 508.0 | 8.85 (br t, J = 5.3 Hz, 1H), 8.61 (br d, J = 7.0 Hz, 1H), 7.74-7.67 (m, 3H), 7.57 (br d, J = 8.0 Hz, 2H), 7.51 (s, 1H), 7.50 (d, J = 8.5 Hz, 1H), 7.05 (br d, J = 6.8 Hz, 1H), 6.09 (s, 2H), 4.80-4.73 (m, 1H), 3.40-3.29 (m, 1H), 1.88-1.80 (m, 2H) |
| 87 | 3-(2-amino-[1,2,4]triazolo[1,5-a]pyridin-7-yl)-6-chloro-N-(2,2-difluoro-3-(4-fluorophenyl)-3-hydroxybutyl)-2-fluorobenzamide | racemate | 508.1 | 8.99 (br t, J = 5.8 Hz, 1H), 8.66 (d, J = 7.0 Hz, 1H), 7.72 (t, J = 8.4 Hz, 1H), 7.59 (br dd, J = 7.9, 5.8 Hz, 2H), 7.53 (s, 1H), 7.48 (d, J = 8.2 Hz, 1H), 7.20 (t, J = 8.9 Hz, 2H), 7.07 (br d, J = 7.0 Hz, 1H), 4.04-3.83 (m, 2H), 1.63 (s, 3H) |
| 88 | 3-(2-amino-[1,2,4]triazolo[1,5-a]pyridin-7-yl)-6-chloro-N-(2,2-difluoro-3-(4-fluorophenyl)-3-hydroxybutyl)-2-fluorobenzamide enantiomer 1 | enantiomer 1 first eluted | 508.1 | 9.00 (br t, J = 6.0 Hz, 1H), 8.60 (d, J = 7.0 Hz, 1H), 7.70 (t, J = 8.2 Hz, 1H), 7.58 (br dd, J = 1.9, 5.8 Hz, 2H), 7.49 (s, 1H), 7.47 (d, J = 8.5 Hz, 1H), 7.19 (t, J = 8.9 Hz, 2H), 7.02 (br d, J = 7.0 Hz, 1H), 4.01-3.83 (m, 2H), 1.62 (s, 3H) |
| 89 | 3-(2-amino-[1,2,4]triazolo[1,5-a]pyridin-7-yl)-6-chloro-N-(2,2-difluoro-3-(4-fluorophenyl)-3-hydroxybutyl)-2-fluorobenzamide enantiomer 2 | enantiomer 2 second eluted | 508.1 | 9.00 (br t, J = 5.8 Hz, 1H), 8.60 (d, J = 7.0 Hz, 1H), 7.70 (t, J = 8.4 Hz, 1H), 7.58 (br dd, J = 8.2, 5.8 Hz, 2H), 7.49 (s, 1H), 7.47 (d, J = 8.5 Hz, 1H), 7.19 (br t, J = 8.9 Hz, 2H), 7.02 (br d, J = 7.0 Hz, 1H), 4.00-3.84 (m, 2H), 1.62 (s, 3H) |

Example 90: (R)-5-(2-amino-[1,2,4]triazolo[1,5-a]pyridin-7-yl)-2-chloro-N-(3-(4-chlorophenyl)-3-hydroxypropyl)benzamide

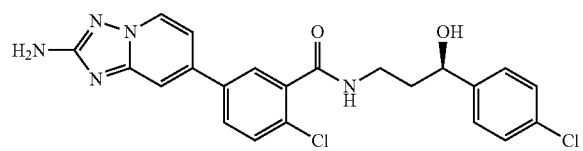 [SMILES: Nc1nc2cc(-c3ccc(Cl)c(C(=O)NCC[C@@H](O)c4ccc(Cl)cc4)c3)ccn2n1]

90A: N,N-bis-Boc-2-amino-7-bromo-[1,2,4]triazolo[1,5-a]pyridine: To a suspension of 7-bromo-[1,2,4]triazolo[1,5-a]pyridin-2-amine (8.00 g, 37.6 mmol) in DCM (80 mL) and MeCN (80 mL) were added (BOC)₂O (21.8 mL, 94.0 mmol) and DMAP (1.84 g, 15.0 mmol). The resulting reaction mixture was stirred at RT for 1.5 h. The mixture was concentrated under reduced pressure to 1/3 volume and diluted with H₂O (50 mL). Further removal of the organic solvents under reduced pressure resulted in a suspension of solid in water. The solid was collected by filtration, washed with water (3×25 mL), and dried under vacuum to afford N,N-bis-Boc-2-amino-7-bromo-[1,2,4]triazolo[1,5-a]pyridine (15.5 g, 37.5 mmol, 100% yield) as a solid.

$^1$H NMR (400 MHz, CDCl₃) δ 8.41 (d, J=7.3 Hz, 1H), 7.91 (d, J=2.0 Hz, 1H), 7.17 (dd, J=7.3, 2.0 Hz, 1H), 1.48 (s, 18H).

MS m/z 412.9 (M+H)⁺

90B: methyl 5-(N,N-bis-Boc-2-amino-[1,2,4]triazolo[1,5-a]pyridin-7-yl)-2-chlorobenzoate and methyl 5-(N-Boc-2-amino-[1,2,4]triazolo[1,5-a]pyridin-7-yl)-2-chlorobenzoate: A mixture of N,N-bis-Boc-2-amino-7-bromo-[1,2,4]triazolo[1,5-a]pyridine (500 mg, 1.21 mmol), (4-chloro-3-

(methoxycarbonyl)phenyl)boronic acid (259 mg, 1.21 mmol), PdCl$_2$(dtbpf) (39.4 mg, 0.060 mmol) and K$_3$PO$_4$ (2M aq.) (1.82 mL, 3.63 mmol) in 1,4-dioxane (6 mL) was purged with N2. The mixture was then stirred at 100° C. for 30 min. The reaction mixture was diluted with EtOAc (50 mL) and filtered. The filtrate was washed with brine (50 mL), dried over anhydrous Na$_2$SO$_4$, filtered and concentrated under reduced pressure. The crude product was purified by flash column chromatography on a silica gel cartridge eluting with 0-50% followed by 50% EtOAc in Hex. The fractions containing the two expected products were collected separately and concentrated under reduced pressure to afford methyl 5-(N,N-bis-Boc-2-amino-[1,2,4]triazolo[1,5-a]pyridin-7-yl)-2-chlorobenzoate (262 mg, 0.521 mmol, 43% yield) and methyl 5-(N-Boc-2-amino-[1,2,4]triazolo[1,5-a]pyridin-7-yl)-2-chlorobenzoate (173 mg, 0.429 mmol, 36% yield).

Methyl 5-(N,N-bis-Boc-2-amino-[1,2,4]triazolo[1,5-a]pyridin-7-yl)-2-chlorobenzoate: $^1$H NMR (500 MHz, CDCl$_3$) δ 8.61 (d, J=7.2 Hz, 1H), 8.14 (d, J=2.3 Hz, 1H), 7.89-7.86 (m, 1H), 7.72 (dd, J=8.3, 2.4 Hz, 1H), 7.62 (d, J=8.3 Hz, 1H), 7.29 (dd, J=7.2, 1.9 Hz, 1H), 4.00 (s, 3H), 1.49 (s, 18H).
MS ESI m/z 503.3 (M+H)$^+$ Methyl 5-(N-Boc-2-amino-[1,2,4]triazolo[1,5-a]pyridin-7-yl)-2-chlorobenzoate: $^1$H NMR (500 MHz, CDCl$_3$) δ 8.61 (d, J=7.0 Hz, 1H), 8.13 (d, J=2.4 Hz, 1H), 7.75 (d, J=1.2 Hz, 1H), 7.70 (dd, J=8.3, 2.4 Hz, 1H), 7.61 (d, J=8.3 Hz, 1H), 7.18 (dd, J=7.1, 2.0 Hz, 1H), 3.99 (s, 3H), 1.57 (s, 9H).
MS ESI m/z 403.2 (M+H)$^+$ 90C: methyl 5-(2-amino-[1,2,4]triazolo[1,5-a]pyridin-7-yl)-2-chlorobenzoate, TFA: To a mixture of methyl 5-(N,N-bis-Boc-2-amino-[1,2,4]triazolo[1,5-a]pyridin-7-yl)-2-chlorobenzoate (262 mg, 0.521 mmol) and methyl 5-(N-Boc-2-amino-[1,2,4]triazolo[1,5-a]pyridin-7-yl)-2-chlorobenzoate (173 mg, 0.429 mmol) in DCM (3 mL) was added TFA (1.20 mL, 15.6 mmol). The resulting solution was stirred at RT ON. The mixture was concentrated under reduced pressure to afford crude methyl 5-(2-amino-[1,2,4]triazolo[1,5-a]pyridin-7-yl)-2-chlorobenzoate, TFA salt as a solid, which was used as-is in next step without further purification.
MS ESI m/z 303.1 (M+H)$^+$ 90D: 5-(2-amino-[1,2,4]triazolo[1,5-a]pyridin-7-yl)-2-chlorobenzoic acid, lithium salt: To a solution of crude methyl 5-(2-amino-[1,2,4]triazolo[1,5-a]pyridin-7-yl)-2-chlorobenzoate, TFA (288 mg, 0.951 mmol) in THF (4 mL) and MeOH (2 mL) was added a solution of LiOH·H$_2$O (140 mg, 3.33 mmol) in H$_2$O (2 mL). The resulting slurry was stirred at RT for 2 h. The mixture was concentrated under reduced pressure and dried under vacuum to afford crude 5-(2-amino-[1,2,4]triazolo[1,5-a]pyridin-7-yl)-2-chlorobenzoic acid, lithium salt as a solid, which was used as-is in next step without further purification.
MS ESI m/z 289.1 (M+H)$^+$ 90: A suspension of crude 5-(2-amino-[1,2,4]triazolo[1,5-a]pyridin-7-yl)-2-chlorobenzoic acid, lithium salt (20 mg, 0.068 mmol), (R)-3-amino-1-(4-chlorophenyl)propan-1-ol hydrochloride (15 mg, 0.068 mmol), BOP (36 mg, 0.081 mmol) and DIPEA (0.060 mL, 0.34 mmol) in DMF (1 mL) was stirred at RT ON. The crude material was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 14% B, 14-54% B over 20 min, then a 0-min hold at 100% B; Flow Rate: 20 mL/min; Column Temperature: 25 C. Fraction collection was triggered by MS and UV signals. Fractions containing the desired product were combined and dried via centrifugal evaporation to afford (R)-5-(2-amino-[1,2,4]triazolo[1,5-a]pyridin-7-yl)-2-chloro-N-(3-(4-chlorophenyl)-3-hydroxypropyl)benzamide (24.5 mg, 0.053 mmol, 79% yield).

$^1$H NMR (500 MHz, DMSO-d$_6$) δ 8.61 (d, J=7.0 Hz, 1H), 8.53 (t, J=5.3 Hz, 1H), 7.87 (dd, J=8.4, 2.4 Hz, 1H), 7.82 (d, J=2.3 Hz, 1H), 7.72 (d, J=1.0 Hz, 1H), 7.60 (d, J=8.4 Hz, 1H), 7.39 (s, 4H), 7.25 (dd, J=6.9, 1.8 Hz, 1H), 4.68 (br t, J=6.2 Hz, 1H), 1.84 (q, J=7.3 Hz, 2H).
MS ESI m/z 455.9 (M+H)$^+$

TABLE 5

Compounds in Table 5 were prepared in a similar fashion to example 90.

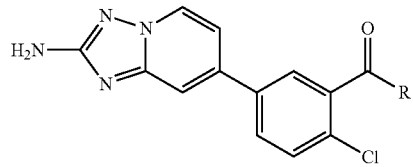

| Ex No | Name | R | M + H$^+$ | 1H NMR (500 MHz, DMSO-d6) δ |
|---|---|---|---|---|
| 91 | (S)-5-(2-amino-[1,2,4]triazolo[1,5-a]pyridin-7-yl)-2-chloro-N-(3-(4-chlorophenyl)-3-hydroxypropyl)benzamide | | 455.9 | 8.59 (d, J = 7.0 Hz, 1H), 8.52 (br t, J = 5.0 Hz, 1H), 7.86 (dd, J = 8.4, 2.3 Hz, 1H), 7.80 (d, J = 2.1 Hz, 1H), 7.70 (d, J = 1.2 Hz, 1H), 7.60 (d, J = 8.5 Hz, 1H), 7.38 (s, 4H), 7.24 (dd, J = 7.0, 1.8 Hz, 1H), 4.72-4.64 (m, 1H), 1.84 (q, J = 6.6 Hz, 2H) |

TABLE 5-continued

Compounds in Table 5 were prepared in a similar fashion to example 90.

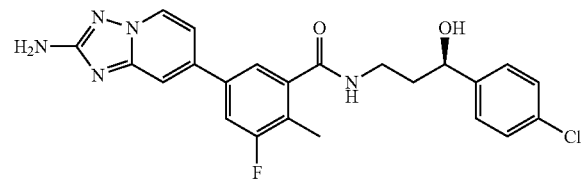 [SMILES: Cc1c(F)cc(-c2ccn3nc(N)nc3c2)cc1C(=O)NCC[C@@H](O)c1ccc(Cl)cc1]

| Ex No | Name | R | M + H⁺ | 1H NMR (500 MHz, DMSO-d6) δ |
|---|---|---|---|---|
| 92 | 5-(2-amino-[1,2,4]triazolo[1,5-a]pyridin-7-yl)-2-chloro-N-(3-phenylbutyl)benzamide | (structure, racemate) | 420.1 | 8.61 (d, J = 7.0 Hz, 1H), 8.50 (br t, J = 5.3 Hz, 1H), 7.86 (dd, J = 8.5, 2.4 Hz, 1H), 7.79 (d, J = 2.4 Hz, 1H), 7.71 (s, 1H), 7.60 (d, J = 8.2 Hz, 1H), 7.34-7.15 (m, 6H), 3.20-3.10 (m, 2H), 2.88-2.79 (m, 1H), 1.81 (q, J = 7.0 Hz, 2H), 1.24 (d, J = 6.7 Hz, 3H) |
| 93 | 5-(2-amino-[1,2,4]triazolo[1,5-a]pyridin-7-yl)-2-chloro-N-(3-hydroxy-3-phenylbutyl)benzamide | (structure, racemate) | 436.0 | 8.66 (d, J = 7.0 Hz, 1H), 8.35 (br t, J = 5.5 Hz, 1H), 7.85 (dd, J = 8.5, 2.1 Hz, 1H), 7.78-7.73 (m, 2H), 7.59 (d, J = 8.2 Hz, 1H), 7.46 (d, J = 7.3 Hz, 2H), 7.37-7.30 (m, 3H), 7.23-7.16 (m, 1H), 3.34-3.23 (m, 1H), 3.06-2.95 (m, 1H), 2.07-1.91 (m, 2H), 1.47 (s, 3H) |

Example 94: (R)-5-(2-amino-[1,2,4]triazolo[1,5-a]pyridin-7-yl)-N-(3-(4-chlorophenyl)-3-hydroxypropyl)-3-fluoro-2-methylbenzamide 94A: N,N-bis-Boc-2-amino-7-(4,4,5,5-tetramethyl-1,3,2-dioxaborolan-2-yl)-[1,2,4]triazolo[1,5-a]pyridine: A mixture of N,N-bis-Boc-2-amino-7-bromo-[1,2,4]triazolo[1,5-a]pyridine (10.0 g, 24.2 mmol), bis(pinacolato)diboron (7.37 g, 29.0 mmol), potassium acetate (7.12 g, 72.6 mmol), and PdCl₂(dppf)-CH₂Cl₂ adduct (0.988 g, 1.21 mmol) in 1,4-dioxane (100 mL) was purged with N2. The mixture was stirred at 100° C. for 1 h, then concentrated under reduced pressure. The residue was diluted with EtOAc (400 mL) and filtered. The filtrate was washed with H₂O (100 mL) followed by brine (100 mL), dried over anhydrous Na₂SO₄, filtered and concentrated under reduced pressure. The crude product was triturated with ether/Hex (10 mL/90 mL). The solid was collected by filtration, rinsed with hexanes (2×10 mL) and dried under vacuum to afford N,N-bis-Boc-2-amino-7-(4,4,5,5-tetramethyl-1,3,2-dioxaborolan-2-yl)-[1,2,4]triazolo[1,5-a]pyridine (10.93 g, 23.7 mmol, 98% yield) as a solid.
¹H NMR (500 MHz, CDCl₃) δ 8.51 (dd, J=6.8, 1.0 Hz, 1H), 8.16 (s, 1H), 7.37 (dd, J=6.8, 1.1 Hz, 1H), 1.45 (s, 18H), 1.38 (s, 12H).
MS ESI m/z 379.4 (M+H)⁺ as boronic acid 94B: methyl 5-(N,N-bis-Boc-2-amino-[1,2,4]triazolo[1,5-a]pyridin-7-yl)-3-fluoro-2-methylbenzoate and methyl 5-(N-Boc-2-amino-[1,2,4]triazolo[1,5-a]pyridin-7-yl)-3-fluoro-2-methylbenzoate: A mixture of N,N-bis-Boc-2-amino-7-(4,4,5,5-tetramethyl-1,3,2-dioxaborolan-2-yl)-[1,2,4]triazolo[1,5-a]pyridine (279 mg, 0.607 mmol), methyl 5-bromo-3-fluoro-2-methylbenzoate (150 mg, 0.61 mmol), PdCl₂(dtbpf) (19.8 mg, 0.030 mmol) and K₃PO₄ (2M aq) (0.91 mL, 1.82 mmol) in 1,4-dioxane (3 mL) was purged with N2. The mixture was stirred at 100° C. for 30 min. The reaction mixture was diluted with EtOAc (20 mL) and filtered. The filtrate was washed with brine (20 mL), dried over Na₂SO₄, filtered and concentrated under reduced pressure. The crude product was purified by flash column chromatography on a silica gel cartridge eluting with 0-50% followed by 50% EtOAc in Hex. The fractions containing the expected products were collected separately and concentrated under reduced pressure to afford methyl 5-(N,N-bis-Boc-2-amino-[1,2,4]triazolo[1,5-a]pyridin-7-yl)-3-fluoro-2-methylbenzoate (183 mg, 0.366 mmol, 60.2% yield) and methyl 5-(N-Boc-2-amino-[1,2,4]triazolo[1,5-a]pyridin-7-yl)-3-fluoro-2-methylbenzoate (73.0 mg, 0.182 mmol, 30% yield).

Methyl 5-(N,N-bis-Boc-2-amino-[1,2,4]triazolo[1,5-a]pyridin-7-yl)-3-fluoro-2-methylbenzoate: ¹H NMR (500 MHz, CDCl₃) δ 8.60 (dd, J=7.2, 0.7 Hz, 1H), 8.01 (s, 1H), 7.88 (d, J=1.0 Hz, 1H), 7.50 (dd, J=10.1, 1.6 Hz, 1H), 7.29 (dd, J=7.2, 1.9 Hz, 1H), 3.97 (s, 3H), 2.57 (d, J=1.9 Hz, 3H), 1.49 (s, 18H).

MS ESI m/z 501.4 (M+H)⁺

Methyl 5-(N-Boc-2-amino-[1,2,4]triazolo[1,5-a]pyridin-7-yl)-3-fluoro-2-methylbenzoate: ¹H NMR (500 MHz, CDCl₃) δ 8.62 (d, J=7.2 Hz, 1H), 8.52 (s, 1H), 8.00 (s, 1H), 7.77 (d, J=1.0 Hz, 1H), 7.48 (dd, J=10.1, 1.7 Hz, 1H), 7.19

(dd, J=7.1, 1.8 Hz, 1H), 3.96 (s, 3H), 2.57 (d, J=1.9 Hz, 3H), 1.57 (s, 9H).
MS ESI m/z 401.3 (M+H)+

94C: methyl 5-(2-amino-[1,2,4]triazolo[1,5-a]pyridin-7-yl)-3-fluoro-2-methylbenzoate, TFA: To a mixture of methyl 5-(N,N-bis-Boc-2-amino-[1,2,4]triazolo[1,5-a]pyridin-7-yl)-3-fluoro-2-methylbenzoate (183 mg, 0.366 mmol) and methyl 5-(N-Boc-2-amino-[1,2,4]triazolo[1,5-a]pyridin-7-yl)-3-fluoro-2-methylbenzoate (73.0 mg, 0.182 mmol) in DCM (2 mL) was added TFA (0.85 mL, 11.0 mmol). The resulting solution was stirred at RT for 2.5 h. The mixture was concentrated under reduced pressure to afford crude methyl 5-(2-amino-[1,2,4]triazolo[1,5-a]pyridin-7-yl)-3-fluoro-2-methylbenzoate, TFA as a solid which was used as-is in next step without further purification.
MS ESI m/z 301.2 (M+H)+

94D: 5-(2-amino-[1,2,4]triazolo[1,5-a]pyridin-7-yl)-3-fluoro-2-methylbenzoic acid, lithium salt: To a solution of crude methyl 5-(2-amino-[1,2,4]triazolo[1,5-a]pyridin-7-yl)-3-fluoro-2-methylbenzoate, TFA (165 mg, 0.549 mmol) in THF (3 mL) and MeOH (1.5 mL) was added a solution of LiOH·H$_2$O (81 mg, 1.92 mmol) in H$_2$O (1.5 mL). The resulting slurry was stirred at 50° C. for 1 h. The mixture was concentrated under reduced pressure and dried under vacuum to afford crude 5-(2-amino-[1,2,4]triazolo[1,5-a]pyridin-7-yl)-3-fluoro-2-methylbenzoic acid, lithium salt as a solid, which was used as-is in next step without further purification.
MS ESI m/z 287.1 (M+H)+

94: A suspension of crude 5-(2-amino-[1,2,4]triazolo[1,5-a]pyridin-7-yl)-3-fluoro-2-methylbenzoic acid, lithium salt (20 mg, 0.068 mmol), (R)-3-amino-1-(4-chlorophenyl)propan-1-ol hydrochloride (15.2 mg, 0.068 mmol), BOP (36 mg, 0.082 mmol) and DIPEA (0.060 mL, 0.341 mmol) in DMF (1 mL) was stirred at RT for 1 h. The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-min hold at 16% B, 16-56% B over 20 min, then a 0-min hold at 100% B; Flow Rate: 20 mL/min; Column Temperature: 25 C. Fraction collection was triggered by MS signals. Fractions containing the desired product were combined and dried via centrifugal evaporation to afford (R)-5-(2-amino-[1,2,4]triazolo[1,5-a]pyridin-7-yl)-N-(3-(4-chlorophenyl)-3-hydroxypropyl)-3-fluoro-2-methylbenzamide (10.2 mg, 0.022 mmol, 33% yield).

$^1$H NMR (500 MHz, DMSO-d$_6$) δ 8.59 (d, J=7.0 Hz, 1H), 8.46 (br t, J=5.2 Hz, 1H), 7.76-7.71 (m, 2H), 7.57 (s, 1H), 7.38 (s, 4H), 7.30-7.23 (m, 1H), 6.05 (s, 2H), 4.70-4.63 (m, 1H), 2.27 (s, 3H), 1.85 (q, J=6.8 Hz, 2H).
MS ESI m/z 454.0 (M+H)+

TABLE 6

Compounds in Table 6 were prepared in a similar fashion to example 94.

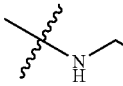

| Ex No | Name | R | M + H+ | 1H NMR (500 MHz, DMSO-d6) δ |
|---|---|---|---|---|
| 95 | 5-{2-amino-[1,2,4]triazolo[1,5-a]pyridin-7-yl}-3-fluoro-2-methyl-N-(3-phenylbutyl)benzamide | racemate | 418.3 | 8.59 (d, J = 7.0 Hz, 1H), 8.45 (t, J = 5.4 Hz, 1H), 7.76-7.70 (m, 2H), 7.55 (s, 1H), 7.34-7.28 (m, 2H), 7.28-7.24 (m, 3H), 7.21-7.16 (m, 1H), 6.06 (s, 2H), 3.22-3.08 (m, 2H), 2.85-2.76 (m, 1H), 2.26 (s, 3H), 1.82 (q, J = 7.3 Hz, 2H), 1.24 (d, J = 6.9 Hz, 3H) |
| 96 | 5-(2-amino-[1,2,4]triazolo[1,5-a]pyridin-7-yl)-3-fluoro-N-(3-hydroxy-3-phenylbutyl)-2-methylbenzamide | racemate | 434.3 | 8.59 (d, J = 7.0 Hz, 1H), 8.30 (br t, J = 5.5 Hz, 1H), 7.74 (br s, 1H), 7.72 (d, J = 12.5 Hz, 1H), 7.52 (s, 1H), 7.47 (d, J = 7.5 Hz, 2H), 7.32 (t, J = 7.7 Hz, 2H), 7.28-7.24 (m, 1H), 7.22-7.17 (m, 1H), 6.07 (s, 2H), 3.06-2.95 (m, 1H), 2.24 (s, 3H), 2.08-1.92 (m, 2H), 1.48 (s, 3H) |

Example 97: 5-(2-amino-[1,2,4]triazolo[1,5-a]pyridin-7-yl)-N-(2,2-difluoro-3-(4-fluorophenyl)-3-hydroxypropyl)-4-fluoro-2-methylbenzamide enantiomer 1

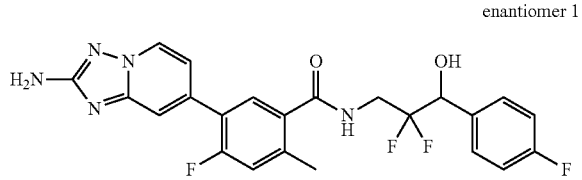 [SMILES: Cc1cc(F)c(-c2ccn3nc(N)nc3c2)cc1C(=O)NCC(F)(F)C(O)c1ccc(F)cc1]

enantiomer 1

97A: 4-fluoro-5-iodo-2-methylbenzoic acid: To a mixture of 4-fluoro-2-methylbenzoic acid (5.00 g, 32.4 mmol) in AcOH (40 mL) was added I2 (9.06 g, 35.7 mmol), sodium periodate (3.47 g, 16.2 mmol) and sulfuric acid (0.259 mL, 4.87 mmol). The mixture was stirred at 110-120° C. for 6 h. Additional I2 (4.00 g, 15.8 mmol) was added, and the mixture was stirred at 120° C. for 4 h. LCMS indicated that the additional $I_2$ did not appear to benefit the progress of the reaction. The mixture was poured into wet ice while stirring. Aqueous $Na_2S_2O_3$ was added until the color turned to light yellow. The resulting solid was isolated by filtration and then dissolved in EtOAc. The organic phase was washed with aqueous $Na_2S_2O_3$ solution, followed by water, then concentrated in vacuo. The residue was crystalized from IPA/water (approximately 10:1) with refrigeration. The solid was isolated by filtration to give 2.2 g of a solid which was significantly contaminated with unreacted 4-fluoro-2-methylbenzoic acid starting material as observed by LCMS. This solid was set aside. The mother liquors from the recrystallization were concentrated in vacuo to give impure 4-fluoro-5-iodo-2-methylbenzoic acid (3.50 g, 12.5 mmol, 39% yield, ~50% purity). The crude material was directly used directly in the next step without further purification or characterization.

97B: 5-(N,N-bis-Boc-2-amino-[1,2,4]triazolo[1,5-a]pyridin-7-yl)-4-fluoro-2-methylbenzoic acid: In a 5 ml pressure vial, a mixture of N,N-bis-Boc-2-amino-7-(4,4,5,5-tetramethyl-1,3,2-dioxaborolan-2-yl)-[1,2,4]triazolo[1,5-a]pyridine (250 mg, 0.543 mmol), 4-fluoro-5-iodo-2-methylbenzoic acid (319 mg, 1.14 mmol) (approx. 50% purity), $PdCl_2$(dtbpf) (17.7 mg, 0.0270 mmol) and $K_3PO_4$, 2M aqueous (1.09 mL, 2.17 mmol) in 1,4-dioxane (2 mL) was degassed by bubbling nitrogen through the mixture. The pressure vial was sealed and the mixture was stirred at 80° C. for 1 h, then cooled to RT. LCMS of the mixture showed the desired bis-Boc product (M+H=486.2), but the mono-Boc product (M+H=387.2) was the major product. The reaction mixture was diluted with EtOAc and water. An off-white precipitate was isolated by filtration and rinsed with water and EtOAc. LCMS of this gray solid isolate showed m/z which was consistent with the mono-Boc product (98.5 mg, 0.255 mmol, 47% yield). This material was set aside as Isolate 1. The organic filtrate was concentrated in vacuo and labeled as Isolate 2; LCMS of Isolate 2 showed m/z consistent with the desired product 5-(N,N-bis-Boc-2-amino-[1,2,4]triazolo[1,5-a]pyridin-7-yl)-4-fluoro-2-methylbenzoic acid (97 mg, 0.20 mmol, 37% yield), slightly contaminated with the aforementioned mono-Boc product. Isolate 2 was used as-is in the next step.
MS ESI m/z 387.2, 486.2 (M+H)+

97C: 5-(N,N-bis-Boc-2-amino-[1,2,4]triazolo[1,5-a]pyridin-7-yl)-N-(2,2-difluoro-3-(4-fluorophenyl)-3-hydroxypropyl)-4-fluoro-2-methylbenzamide: A mixture of 5-(N,N-bis-Boc-2-amino-[1,2,4]triazolo[1,5-a]pyridin-7-yl)-4-fluoro-2-methylbenzoic acid (0.097 g, 0.20 mmol), BOP (0.133 g, 0.300 mmol). 3-amino-2,2-difluoro-1-(4-fluorophenyl)propan-1-ol (0.082 g, 0.40 mmol) and Hünig's Base (0.140 mL, 0.800 mmol) in DMF (1 mL) was stirred at RT for 24 h. The reaction mixture was diluted with EtOAc and water, shaken, and the layers were separated. The aqueous layer was extracted with EtOAc. The combined organic layers were washed with water twice, then with brine, dried with $Na_2SO_4$, filtered and concentrated in vacuo to provide 5-(N,N-bis-Boc-2-amino-[1,2,4]triazolo[1,5-a]pyridin-7-yl)-N-(2,2-difluoro-3-(4-fluorophenyl)-3-hydroxypropyl)-4-fluoro-2-methylbenzamide (135 mg, 0.20 mmol, 100% crude yield) as a tan oil. This material was directly carried on to next reaction without further purification.
MS ESI m/z 674.5 (M+H)+

97: To a solution of 5-(N,N-bis-Boc-2-amino-[1,2,4]triazolo[1,5-a]pyridin-7-yl)-N-(2,2-difluoro-3-(4-fluorophenyl)-3-hydroxypropyl)-4-fluoro-2-methylbenzamide (135 mg, 0.200 mmol) in $CH_2Cl_2$ (1 mL) was added TFA (0.60 mL, 7.8 mmol). The mixture was stirred at RT for 2 h. Volatiles were removed in vacuo. The residue was dissolved in MeOH and was purified via preparative LCMS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-min hold at 12% B, 12-52% B over 25 min, then a 0-min hold at 100% B; Flow Rate: 20 mL/min; Column Temperature: 25 C. Fraction collection was triggered by MS and UV signals. Fractions containing the desired product were combined and dried via centrifugal evaporation. The isolated racemate was further subjected to SFC chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 60% CO2/40% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 60% CO2/40% MeOH w/0.1% DEA; Flow Rate: 60 mL/min; Detector Wavelength: 220 nm; Injection details: 1500 µL 10.6 mg dissolved in 3 mL MeOH. Fractions containing the first eluting isomer were combined and dried to afford 3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide enantiomer 1 (2.2 mg, 4.43 µmol, >95% ee, 2% yield). The absolute stereochemistry was not determined.

$^1$H NMR (500 MHz, DMSO-d6) δ 8.72 (t, J=6.1 Hz, 1H), 8.64 (d, J=7.0 Hz, 1H), 7.66-7.57 (m, 2H), 7.52 (dd, J=8.3, 5.5 Hz, 2H), 7.31 (d, J=12.0 Hz, 1H), 7.22 (t, J=8.7 Hz, 2H), 7.11 (d, J=7.1 Hz, 1H), 6.44 (d, J=5.3 Hz, 1H), 6.09 (s, 2H), 5.04-4.88 (m, 1H), 3.98-3.75 (m, 2H), 2.42 (s, 3H); $^{19}$F NMR (471 MHz, DMSO-d6) δ−110.25 (d, J=245.5 Hz), −114.46, −115.49--116.84 (m).
MS ESI m/z 474.4 (M+H)+

Example 98: 5-(2-amino-[1,2,4]triazolo[1,5-a]pyridin-7-yl)-N-(2,2-difluoro-3-(4-fluorophenyl)-3-hydroxypropyl)-4-fluoro-2-methylbenzamide enantiomer 2 enantiomer 2

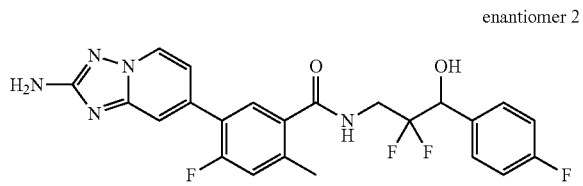 [SMILES: Cc1cc(F)c(-c2ccn3nc(N)nc3c2)cc1C(=O)NCC(F)(F)C(O)c1ccc(F)cc1]

The title compound 5-(2-amino-[1,2,4]triazolo[1,5-a]pyridin-7-yl)-N-(2,2-difluoro-3-(4-fluorophenyl)-3-hydroxypropyl)-4-fluoro-2-methylbenzamide enantiomer 2 (3.4 mg, 7.0 µmol, 4% yield) was obtained as the second eluting isomer from the chiral SFC purification described for example 97.

$^1$H NMR (500 MHz, DMSO-d$_6$) δ 8.71 (t, J=5.7 Hz, 1H), 8.63 (d, J=7.0 Hz, 1H), 7.65-7.57 (m, 2H), 7.56-7.48 (m, 2H), 7.31 (d, J=11.8 Hz, 1H), 7.22 (t, J=8.7 Hz, 2H), 7.11 (d,

J=6.9 Hz, 1H), 6.45 (d, J=5.2 Hz, 1H), 6.08 (s, 2H), 4.95 (d, J=14.9 Hz, 1H), 3.97-3.75 (m, 2H), 2.41 (s, 3H); $^{19}$F NMR (471 MHz, DMSO-d6) δ −110.25 (d, J=245.5 Hz), −114.46, −115.49--116.84 (m).

MS ESI m/z 474.4 (M+H)$^+$

Example 99: (S)-5-(2-amino-[1,2,4]triazolo[1,5-a]pyridin-7-yl)-N-(3-(4-chlorophenyl)-3-hydroxypropyl)-3,4-difluoro-2-methylbenzamide

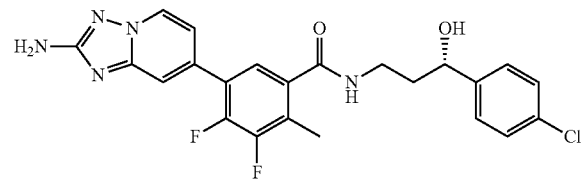 [SMILES: Cc1c(C(=O)NCC[C@H](O)c2ccc(Cl)cc2)cc(-c2ccn3nc(N)nc3c2)c(F)c1F]

99A: 5-bromo-3,4-difluoro-2-methylbenzoic acid: 3,4-Difluoro-2-methylbenzoic acid (1.72 g, 9.99 mmol) was dissolved in concentrated sulfuric acid (7.0 mL, 131 mmol). The mixture was cooled in an ice water bath and 1,3-dibromo-5,5-dimethylhydantoin (1.43 g, 5.00 mmol) was added slowly to the mixture. The mixture was stirred at 0-10° C. for 30 min, which resulted in a heavy precipitate. Ice was added to the mixture. The off white solid was isolated by filtration and rinsed with water, then allowed to air dry ON to give crude 5-bromo-3,4-difluoro-2-methylbenzoic acid (3.0 g, 11.9 mmol, 120% yield). The material was used as-is in the next step.

MS ESI m/z 251.1 (M+H)$^+$

99B: methyl 5-bromo-3,4-difluoro-2-methylbenzoate: To a solution of crude 5-bromo-3,4-difluoro-2-methylbenzoic acid (3.0 g, 11.9 mmol) in DMF (15 mL) was added potassium carbonate (2.76 g, 20.0 mmol) followed by iodomethane (1.6 mL, 25.0 mmol). The mixture was stirred at RT for 2 h. 50 mL of EtOAc was added and the mixture was washed with water, then concentrated in vacuo. The residue was purified via flash column chromatography (40 g silica, gradient 100% Hex to 5% EtOAc in Hex). Fractions containing clean product were combined and concentrated to give methyl 5-bromo-3,4-difluoro-2-methylbenzoate (560 mg, 2.11 mmol, 18% yield).

$^1$H NMR (499 MHz, CHLOROFORM-d) δ 8.06-7.85 (m, 1H), 3.93 (s, 3H), 2.53 (d, J=2.9 Hz, 3H).

99C: methyl 3,4-difluoro-2-methyl-5-(4,4,5,5-tetramethyl-1,3,2-dioxaborolan-2-yl)benzoate: To a mixture of methyl 5-bromo-3,4-difluoro-2-methylbenzoate (0.530 g, 2.00 mmol) in dioxane (10 mL) was added 4,4,4',4',5,5,5',5'-octamethyl-2,2'-bi(1,3,2-dioxaborolane) (0.609 g, 2.40 mmol), PdCl$_2$(dppf)-CH$_2$Cl$_2$ adduct (0.114 g, 0.140 mmol) and potassium acetate (0.491 g, 5.00 mmol). The mixture was sparged with N2 gas then stirred at 115° C. for 4 h. To the crude rxn mixture containing methyl 3,4-difluoro-2-methyl-5-(4,4,5,5-tetramethyl-1,3,2-dioxaborolan-2-yl)benzoate (624 mg, 2.00 mmol) was added 1,4-dioxane (11 mL) (1 mL), 7-bromo-[1,2,4]triazolo[1,5-a]pyridin-2-amine (426 mg, 2.00 mmol), PdCl$_2$(dppf)-CH$_2$Cl$_2$ adduct (65.3 mg, 0.080 mmol) and 2M aqueous K$_3$PO$_4$ (2.50 mL, 5.00 mmol). After the mixture was sparged with N2 gas for 5 min, the mixture was stirred at 115° C. for 5 h. The reaction mixture was diluted with EtOAc and water. A solid precipitate was isolated by filtration and washed with water and EtOAc to afford crude methyl 5-(2-amino-[1,2,4]triazolo[1,5-a]pyridin-7-yl)-3,4-difluoro-2-methylbenzoate (390 mg) as Isolate 1 which was set aside. The filtrate layers were separated, and the organic layer was dried over Na$_2$SO$_4$ and concentrated in vacuo. The residue was purified by silica gel flash column chromatography (gradient 100% DCM to 10% MeOH in DCM) to afford additional methyl 5-(2-amino-[1,2,4]triazolo[1,5-a]pyridin-7-yl)-3,4-difluoro-2-methylbenzoate (110 mg) as a dark solid, labeled Isolate 2. Isolates 1 and 2 were combined to provide the desired methyl 5-(2-amino-[1,2,4]triazolo[1,5-a]pyridin-7-yl)-3,4-difluoro-2-methylbenzoate (500 mg total, 1.57 mmol, 79% yield).

MS ESI m/z 319.1 (M+H)$^+$

99D: 5-(2-amino-[1,2,4]triazolo[1,5-a]pyridin-7-yl)-3,4-difluoro-2-methylbenzoic acid: To a mixture of methyl 5-(2-amino-[1,2,4]triazolo[1,5-a]pyridin-7-yl)-3,4-difluoro-2-methylbenzoate (500 mg, 1.57 mmol) in THF (4 mL) was added LiOH, 2M aqueous solution (3.20 mL, 6.40 mmol), and MeOH (4 mL). The mixture was stirred at RT for 18 h. The reaction mixture was filtered and the filtered solid was rinsed with water and EtOAc to afford a dark solid (143 mg) labeled as Isolate 1, which was set aside. The filtrate was neutralized with TN HCl (4 mL) which caused a precipitation event. The resulting gray solid was isolated by filtration and rinsed with water and EtOAc to provide Isolate 2 (267 mg). The filtrate phases were separated, and the organic layer was dried with Na$_2$SO$_4$, filtered and concentrated in vacuo to afford Isolate 3 (36 mg) as a tan solid. Isolates 1, 2 and 3 were combined to provide total crude 5-(2-amino-[1,2,4]triazolo[1,5-a]pyridin-7-yl)-3,4-difluoro-2-methylbenzoic acid (446 mg, 1.46 mmol, 93% yield) which was used as-is in the next step.

MS ESI m/z 304.9 (M+H)$^+$

99: A mixture of 5-(2-amino-[1,2,4]triazolo[1,5-a]pyridin-7-yl)-3,4-difluoro-2-methylbenzoic acid (30 mg, 0.099 mmol). BOP (65.4 mg, 0.148 mmol), (S)-3-amino-1-(4-chlorophenyl)propan-1-ol hydrochloride (26.3 mg, 0.118 mmol) and Hünig's Base (0.086 mL, 0.49 mmol) in DMF (0.5 mL) was stirred at RT ON. The mixture was diluted with MeOH, and the crude material was purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 17% B, 17-57% B over 20 min, then a 0-min hold at 100% B; Flow Rate: 20 mL/min; Column Temperature: 25 C. Fraction collection was triggered by MS and UV signals. Fractions containing the desired product were combined and dried via centrifugal evaporation to afford (S)-5-(2-amino-[1,2,4]triazolo[1,5-a]pyridin-7-yl)-N-(3-(4-chlorophenyl)-3-hydroxypropyl)-3,4-difluoro-2-methylbenzamide (8.7 mg, 0.018 mmol, 19% yield).

$^1$H NMR (500 MHz, DMSO-d6) δ 8.65 (d, J=7.0 Hz, 1H), 8.47 (t, J=5.5 Hz, 1H), 7.62 (s, 1H), 7.42 (d, J=6.8 Hz, 1H), 7.38 (s, 4H), 7.13 (d, J=7.0 Hz, 1H), 6.11 (s, 2H), 5.43 (d, J=4.6 Hz, 1H), 4.66 (q, J=6.0 Hz, 1H), 3.43-3.26 (m, 2H), 2.35 (d, J=2.3 Hz, 3H), 1.86 (q, J=7.0 Hz, 2H); $^{19}$F NMR (471 MHz, DMSO-d6) δ −140.05, −141.17.

MS ESI m/z 472.4 (M+H)$^+$

Example 100: 5-(2-amino-[1,2,4]triazolo[1,5-a]pyridin-7-yl)-N-(4-(4-chlorophenyl)-4-hydroxybutan-2-yl)-3,4-difluoro-2-methylbenzamide racemate 1

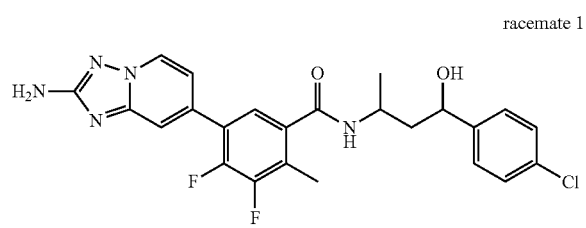 [SMILES: Cc1c(C(=O)NC(C)CC(O)c2ccc(Cl)cc2)cc(-c2ccn3nc(N)nc3c2)c(F)c1F]

racemate 1

A mixture of 5-(2-amino-[1,2,4]triazolo[1,5-a]pyridin-7-yl)-3,4-difluoro-2-methylbenzoic acid (30.4 mg, 0.100 mmol), BOP (66.3 mg, 0.150 mmol), 3-amino-1-(4-chlorophenyl)butan-1-ol (19B, 23.9 mg, 0.120 mmol) and Hünig's Base (0.070 mL, 0.40 mmol) in DMF (0.5 mL) was stirred at RT for 5 h. The mixture was diluted with MeOH and filtered, and the crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 17% B, 17-55% B over 28 min, then a 0-min hold at 100% B; Flow Rate: 20 mL/min; Column Temperature: 25 C. Fraction collection was triggered by MS signals. Fractions containing the first eluting peak with LCMS m/z signal consistent with the desired product were combined and dried via centrifugal evaporation to afford 5-(2-amino-[1,2,4]triazolo[1,5-a]pyridin-7-yl)-N-(4-(4-chlorophenyl)-4-hydroxybutan-2-yl)-3,4-difluoro-2-methylbenzamide racemate 1 (5.4 mg, 10.9 μmol, 11% yield). The absolute stereochemistry was not determined.

$^1$H NMR (500 MHz, DMSO-d6) δ 8.66 (d, J=6.9 Hz, 1H), 8.34 (d, J=8.3 Hz, 1H), 7.63 (s, 1H), 7.38 (d, J=1.6 Hz, 5H), 7.13 (d, J=7.0 Hz, 1H), 6.12 (s, 2H), 5.37 (d, J=4.5 Hz, 1H), 4.64 (q, J=5.9 Hz, 1H), 4.02 (dt, J=16.2, 8.0 Hz, 1H), 2.36 (d, J=2.2 Hz, 3H), 1.96 (dq, J=15.5, 7.8 Hz, 1H), 1.68 (dt, J=13.0, 6.4 Hz, 1H), 1.18 (d, J=6.6 Hz, 3H); $^{19}$F NMR (471 MHz, DMSO-d6) δ−140.19 (d, J=21.8 Hz), −141.36 (d, J=21.8 Hz).
MS ESI m/z 486.2 (M+H)$^+$

Example 101: 5-(2-amino-[1,2,4]triazolo[1,5-a]pyridin-7-yl)-N-(4-(4-chlorophenyl)-4-hydroxybutan-2-yl)-3,4-difluoro-2-methylbenzamide racemate 2

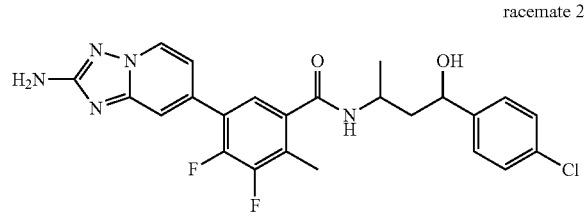 [SMILES: Cc1c(C(=O)NC(C)CC(O)c2ccc(Cl)cc2)cc(-c2ccn3nc(N)nc3c2)c(F)c1F]

racemate 2

The title compound 5-(2-amino-[1,2,4]triazolo[1,5-a]pyridin-7-yl)-N-(4-(4-chlorophenyl)-4-hydroxybutan-2-yl)-3,4-difluoro-2-methylbenzamide racemate 2 (3.9 mg, 7.6 μmol, 8% yield) was obtained as the second eluting peak with LCMS m/z signal consistent with the desired product from the preparative HPLC purification described for example 100.

$^1$H NMR (500 MHz, DMSO-d6) δ 8.67 (d, J=6.9 Hz, 1H), 8.36 (d, J=8.0 Hz, 1H), 7.63 (s, 1H), 7.37 (d, J=1.5 Hz, 4H), 7.13 (d, J=7.0 Hz, 1H), 6.12 (s, 2H), 4.70-4.61 (m, 1H), 4.23-4.07 (m, 1H), 2.37 (d, J=2.3 Hz, 3H), 1.86-1.78 (m, 1H), 1.76-1.68 (m, 1H), 1.20 (d, J=6.6 Hz, 3H); $^{19}$F NMR (471 MHz, DMSO-d$_6$) δ−140.09 (d, J=21.0 Hz), −141.35 (d, J=21.1 Hz).
MS ESI m/z 486.2 (M+H)$^+$

Example 102: 5-(2-amino-[1,2,4]triazolo[1,5-a]pyridin-7-yl)-N-(4-(4-chlorophenyl)-1-fluoro-4-hydroxybutan-2-yl)-3,4-difluoro-2-methylbenzamide racemate 1

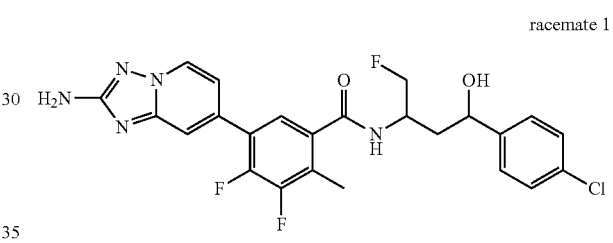

racemate 1

A mixture of 5-(2-amino-[1,2,4]triazolo[1,5-a]pyridin-7-yl)-3,4-difluoro-2-methylbenzoic acid (30.4 mg, 0.100 mmol), BOP (66.3 mg, 0.150 mmol). 3-amino-1-(4-chlorophenyl)-4-fluorobutan-1-ol (21B, 43.5 mg, 0.200 mmol) and Hünig's Base (0.070 mL, 0.400 mmol) in DMF (0.5 mL) was stirred at RT for 4 h. The mixture was diluted with MeOH and filtered, and the crude material was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 12% B, 12-52% B over 23 min, then a 0-min hold at 100% B; Flow Rate: 20 mL/min; Column Temperature: 25 C. Fraction collection was triggered by MS signals. Fractions containing the first eluting peak with LCMS m/z signal consistent with the desired product were combined and dried via centrifugal evaporation to provide 5-(2-amino-[1,2,4]triazolo[1,5-a]pyridin-7-yl)-N-(4-(4-chlorophenyl)-1-fluoro-4-hydroxybutan-2-yl)-3,4-difluoro-2-methylbenzamide racemate 1 (1.1 mg, 2.2 μmol, 2% yield). Absolute stereochemistry was not determined.

$^1$H NMR (500 MHz, DMSO-d6) δ 8.67 (d, J=7.0 Hz, 1H), 8.57 (d, J=8.4 Hz, 1H), 7.64 (s, 1H), 7.41-7.31 (m, 5H), 7.13 (d, J=7.0 Hz, 1H), 6.12 (s, 2H), 4.72 (t, J=6.7 Hz, 1H), 4.48 (dd, J=47.4, 4.9 Hz, 2H), 4.19 (d, J=13.8 Hz, 1H), 2.36 (d, J=2.2 Hz, 3H), 1.98 (dt, J=14.7, 7.5 Hz, 1H), 1.89 (dt, J=13.5, 6.0 Hz, 1H); $^{19}$F NMR (471 MHz, DMSO-d6) δ−73.45, −140.02, −140.92.
MS ESI m/z 504.3 (M+H)$^+$

Example 103: 5-(2-amino-[1,2,4]triazolo[1,5-a]pyridin-7-yl)-N-(4-(4-chlorophenyl)-1-fluoro-4-hydroxybutan-2-yl)-3,4-difluoro-2-methylbenzamide racemate 2

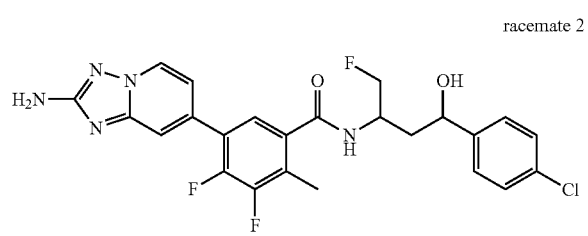 [SMILES: Cc1c(C(=O)NC(CF)CC(O)c2ccc(Cl)cc2)cc(-c2ccn3nc(N)nc3c2)c(F)c1F]

racemate 2

The title compound 5-(2-amino-[1,2,4]triazolo[1,5-a]pyridin-7-yl)-N-(4-(4-chlorophenyl)-1-fluoro-4-hydroxybutan-2-yl)-3,4-difluoro-2-methylbenzamide racemate 2 (1.4 mg, 2.73 μmol, 3% yield) was obtained as the second eluting peak with LCMS m/z signal consistent with the desired product from the preparative HPLC purification described for example 102.

$^1$H NMR (500 MHz, DMSO-d6) δ 8.67 (d, J=6.9 Hz, 1H), 8.57 (d, J=8.4 Hz, 1H), 7.64 (s, 1H), 7.38 (d, J=2.3 Hz, 4H), 7.33 (d, J=6.8 Hz, 1H), 7.13 (d, J=7.0 Hz, 1H), 6.12 (s, 2H), 4.72 (dt, J=8.1, 4.6 Hz, 1H), 4.53 (d, J=4.9 Hz, 1H), 4.43 (d, J=4.8 Hz, 1H), 4.28-4.11 (m, 1H), 2.36 (d, J=2.2 Hz, 3H), 1.97 (q, J=7.2 Hz, 1H), 1.94-1.85 (m, 1H); $^{19}$F NMR (471 MHz, DMSO-d6) δ−73.44, −140.07, −140.99.
MS ESI m/z 504.3 (M+H)$^+$

Example 104: 5-(2-amino-[1,2,4]triazolo[1,5-a]pyridin-7-yl)-N-(3-(4-chlorophenyl)-2,2-difluoro-3-hydroxypropyl)-3,4-difluoro-2-methylbenzamide enantiomer 1 enantiomer 1

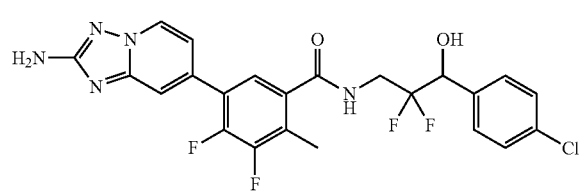

A mixture of 5-(2-amino-[1,2,4]triazolo[1,5-a]pyridin-7-yl)-3,4-difluoro-2-methylbenzoic acid (45.6 mg, 0.150 mmol), BOP (100 mg, 0.225 mmol), 3-amino-1-(4-chlorophenyl)-2,2-difluoropropan-1-ol (29A, 49.9 mg, 0.225 mmol) and Hünig's Base (0.105 mL, 0.600 mmol) in DMF (0.8 mL) was stirred at RT for 18 h. The reaction mixture was diluted with MeOH and filtered, and the crude material was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 19% B, 19-59% B over 20 min, then a 0-min hold at 100% B; Flow Rate: 20 mL/min; Column Temperature: 25 C. Fraction collection was triggered by MS and UV signals. Fractions containing the desired product were combined and dried via centrifugal evaporation. The racemate was then subjected to chiral SFC separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 55% CO2/45% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 55% CO2/45% MeOH w/0.1% DEA; Flow Rate: 60 mL/min; Detector Wavelength: 220 nm; Injection details: 1500 μL 7.4 mg dissolved in 3 mL MeOH. Fractions containing the first eluting isomer were combined and dried to afford 5-(2-amino-[1,2,4]triazolo[1,5-a]pyridin-7-yl)-N-(3-(4-chlorophenyl)-2,2-difluoro-3-hydroxypropyl)-3,4-difluoro-2-methylbenzamide enantiomer 1 (1.4 mg, 2.8 μmol, >95% ee, 2% yield). The absolute stereochemistry was not determined.

$^1$H NMR (500 MHz, DMSO-d6) δ 8.80 (t, J=6.3 Hz, 1H), 8.67 (d, J=6.9 Hz, 1H), 7.64 (s, 1H), 7.55-7.43 (m, 4H), 7.13 (d, J=7.0 Hz, 1H), 6.48 (d, J=5.3 Hz, 1H), 6.12 (s, 2H), 5.02-4.91 (m, 1H), 3.91-3.79 (m, 2H), 2.35 (s, 3H); $^{19}$F NMR (471 MHz, DMSO-d6) δ−109.98 (d, J=246.9 Hz), −115.93 (d, J=246.2 Hz), −139.87 (d, J=22.3 Hz), −140.66 (d, J=20.8 Hz).
MS ESI m/z 508.2 (M+H)$^+$

Example 105: 5-(2-amino-[1,2,4]triazolo[1,5-a]pyridin-7-yl)-N-(3-(4-chlorophenyl)-2,2-difluoro-3-hydroxypropyl)-3,4-difluoro-2-methylbenzamide enantiomer 2 enantiomer 2

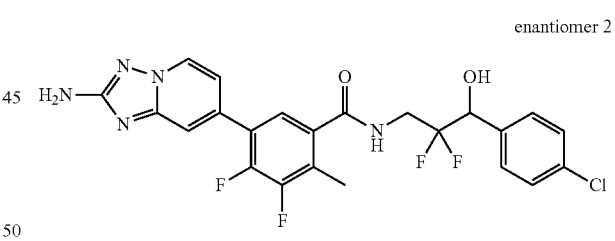

The title compound 5-(2-amino-[1,2,4]triazolo[1,5-a]pyridin-7-yl)-N-(3-(4-chlorophenyl)-2,2-difluoro-3-hydroxypropyl)-3,4-difluoro-2-methylbenzamide enantiomer 2 (1.7 mg, 3.1 μmol, 2% yield) was obtained as the second eluting isomer from the chiral SFC purification described for example 104.

$^1$H NMR (500 MHz, DMSO-d$_6$) δ 8.81 (t, J=6.0 Hz, 1H), 8.66 (d, J=7.1 Hz, 1H), 7.63 (s, 1H), 7.50 (d, J=8.4 Hz, 2H), 7.46 (d, J=8.1 Hz, 2H), 7.13 (d, J=7.0 Hz, 1H), 6.51 (d, J=5.5 Hz, 1H), 6.12 (s, 1H), 5.03-4.92 (m, 1H), 3.86 (td, J=16.3, 13.5, 8.9 Hz, 2H), 2.35 (d, J=2.2 Hz, 3H); $^{19}$F NMR (471 MHz, DMSO-d$_6$) δ−109.98 (d, J=246.9 Hz), −115.93 (d, J=246.2 Hz), −139.87 (d, J=22.3 Hz), −140.66 (d, J=20.8 Hz).
MS ESI m/z 508.2 (M+H)$^+$

Example 106: 5-(2-amino-[1,2,4]triazolo[1,5-a]pyridin-7-yl)-N-(2,2-difluoro-3-(4-fluorophenyl)-3-hydroxypropyl)-3,4-difluoro-2-methylbenzamide enantiomer 1

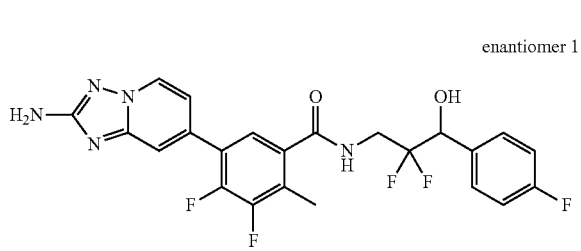 [SMILES: Cc1c(C(=O)NCC(F)(F)C(O)c2ccc(F)cc2)cc(-c2ccn3nc(N)nc3c2)c(F)c1F]

enantiomer 1

A mixture of 5-(2-amino-[1,2,4]triazolo[1,5-a]pyridin-7-yl)-3,4-difluoro-2-methylbenzoic acid (45.6 mg, 0.150 mmol), BOP (100 mg, 0.225 mmol), 3-amino-2,2-difluoro-1-(4-fluorophenyl)propan-1-ol (30A, 61.6 mg, 0.300 mmol) and Hünig's Base (0.105 mL, 0.600 mmol) in DMF (0.8 mL) was stirred at RT for 18 h. The reaction mixture was diluted with MeOH and filtered, and the crude material was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 15% B, 15-55% B over 25 min, then a 0-min hold at 100% B; Flow Rate: 20 mL/min; Column Temperature: 25 C. Fraction collection was triggered by MS and UV signals. Fractions containing the desired product were combined and dried via centrifugal evaporation. The racemate was then subject to SFC chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 55% CO2/45% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 55% CO2/45% MeOH w/0.1% DEA; Flow Rate: 60 mL/min; Detector Wavelength: 220 nm; Injection details: 3000 μL 39.2 mg dissolved in 6 mL MeOH/MeCN. Fractions containing the first eluting isomer were combined and dried to afford 5-(2-amino-[1,2,4]triazolo[1,5-a]pyridin-7-yl)-N-(3-(4-fluorophenyl)-2,2-difluoro-3-hydroxypropyl)-3,4-difluoro-2-methylbenzamide enantiomer 1 (10 mg, 0.020 mmol, >95% ee, 13% yield). The absolute stereochemistry was not determined.

$^1$H NMR (500 MHz, DMSO-d6) δ 8.81 (t, J=6.3 Hz, 1H), 8.65 (d, J=7.0 Hz, 1H), 7.63 (s, 1H), 7.51 (dd, J=8.6, 5.6 Hz, 2H), 7.45 (d, J=6.7 Hz, 1H), 7.21 (t, J=8.7 Hz, 2H), 7.13 (d, J=7.0 Hz, 1H), 6.46 (d, J=5.3 Hz, 1H), 6.11 (s, 2H), 5.01-4.89 (m, 1H), 3.92-3.79 (m, 2H), 2.34 (d, J=2.4 Hz, 3H); $^{19}$F NMR (471 MHz, DMSO-d6) δ−110.21 (d, J=245.7 Hz), −114.42, −116.11 (d, J=245.6 Hz), −139.86 (d, J=21.3 Hz), −140.68 (d, J=21.1 Hz).
MS ESI m/z 492.2 (M+H)$^+$

Example 107: 5-(2-amino-[1,2,4]triazolo[1,5-a]pyridin-7-yl)-N-(2,2-difluoro-3-(4-fluorophenyl)-3-hydroxypropyl)-3,4-difluoro-2-methylbenzamide enantiomer 2

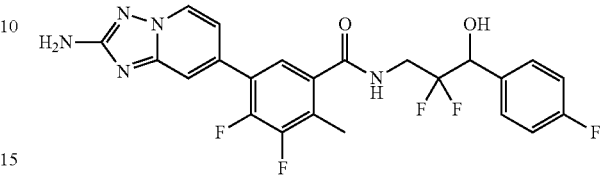

enantiomer 2

The title compound 5-(2-amino-[1,2,4]triazolo[1,5-a]pyridin-7-yl)-N-(2,2-difluoro-3-(4-fluorophenyl)-3-hydroxypropyl)-3,4-difluoro-2-methylbenzamide enantiomer 2 (12 mg, 0.024 mmol, 16% yield) was obtained as the second eluting isomer from the chiral SFC purification described for example 106.

$^1$H NMR (500 MHz, DMSO-d$_6$) δ 8.81 (t, J=6.2 Hz, 1H), 8.66 (d, J=6.9 Hz, 1H), 7.63 (s, 1H), 7.51 (dd, J=8.5, 5.6 Hz, 2H), 7.45 (d, J=6.7 Hz, 1H), 7.21 (t, J=8.7 Hz, 2H), 7.13 (d, J=7.0 Hz, 1H), 6.45 (d, J=5.2 Hz, 1H), 6.11 (s, 2H), 4.99-4.90 (m, 1H), 3.91-3.79 (m, 2H), 2.34 (d, J=2.1 Hz, 3H); $^{19}$F NMR (471 MHz, DMSO-d$_6$) δ−110.21 (d, J=245.7 Hz), −114.42, −116.11 (d, J=245.6 Hz), −139.86 (d, J=21.3 Hz), −140.68 (d, J=21.1 Hz).
MS ESI m/z 492.2 (M+H)$^+$

Example 108: (S)-3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide enantiomer 1

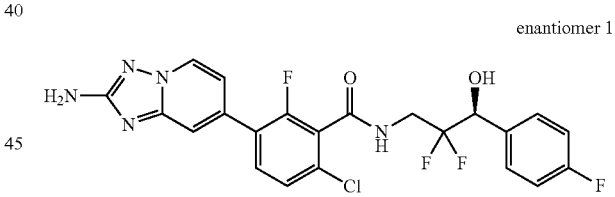

enantiomer 1

A mixture of 3-(2-amino-[1,2,4]triazolo[1,5-a]pyridin-7-yl)-6-chloro-2-fluorobenzoic acid (67.5 mg, 0.220 mmol), BOP (146 mg, 0.330 mmol). 3-amino-2,2-difluoro-1-(4-fluorophenyl)propan-1-ol (30A, 90 mg, 0.44 mmol) and Hünig's Base (0.154 mL, 0.880 mmol) in DMF (1 mL) was stirred at RT for 24 h. The crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 12% B, 12-52% B over 25 min, then a 0-min hold at 100% B; Flow Rate: 20 mL/min; Column Temperature: 25 C. Fraction collection was triggered by MS and UV signals. Fractions containing the desired product were combined and dried via centrifugal evaporation to provide the racemic 3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide. The racemate was then subject to SFC chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 75% CO2/25% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 30×250 mm. 5 micron; Mobile Phase: 75% CO2/25% MeOH w/0.1% DEA; Flow Rate: 60 mL/min; Detector Wavelength: 220 nm; Injection details: 3000 μL 21.2 mg dissolved in 6 mL MeOH/MeCN. Fractions containing the first eluting isomer were combined and dried to afford (S)-3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide (8.3 mg, 0.016 mmol, >95% ee, 7% yield).

$^1$H NMR (500 MHz, DMSO-$d_6$) δ 9.16 (t, J=6.4 Hz, 1H), 8.65 (d, J=7.0 Hz, 1H), 7.76 (t, J=8.3 Hz, 1H), 7.57-7.44 (m, 4H), 7.24 (t, J=8.6 Hz, 2H), 7.06 (d, J=7.1 Hz, 1H), 6.12 (s, 2H), 5.02-4.86 (m, 1H), 3.98-3.77 (m, 2H); $^{19}$F NMR (471 MHz, DMSO-d6) δ−110.76 (d, J=245.4 Hz), −114.36, −116.81 (d, J=245.0 Hz), −117.27.
MS ESI m/z 494.3 (M+H)$^+$

Example 109: (R)-3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide enantiomer 2

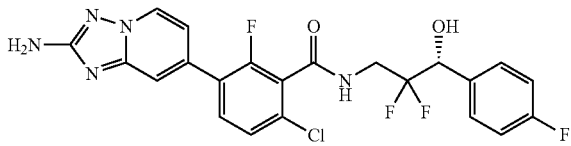

enantiomer 2

The title compound (R)-3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide enantiomer 2 (7.7 mg, 0.015 mmol, 7% yield) was obtained as the second eluting isomer from the chiral SFC purification described for example 108.

$^1$H NMR (500 MHz, DMSO-$d_6$) δ 9.15 (t, J=6.2 Hz, 1H), 8.64 (d, J=6.9 Hz, 1H), 7.75 (t, J=8.4 Hz, 1H), 7.57-7.44 (m, 4H), 7.23 (t, J=8.7 Hz, 2H), 7.06 (d, J=7.0 Hz, 1H), 6.45 (d, J=5.4 Hz, 1H), 6.12 (s, 2H), 4.95 (d, J=16.0 Hz, 1H), 4.01-3.76 (m, 2H); $^{19}$F NMR (471 MHz, DMSO-$d_6$) δ−110.76 (d, J=245.4 Hz), −114.36, −116.81 (d, J=245.0 Hz), −117.27.
MS ESI m/z 494.3 (M+H)$^+$

Example 110: 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide

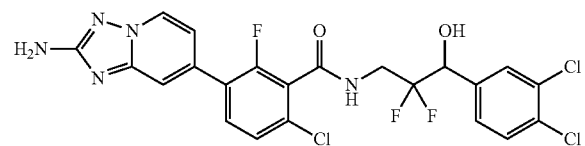 [SMILES: Nc1nc2cc(-c3ccc(Cl)c(C(=O)NCC(F)(F)C(O)c4ccc(Cl)c(Cl)c4)c3F)ccn2n1]

110A: ethyl 3-(3,4-dichlorophenyl)-2,2-difluoro-3-hydroxypropanoate: In a 40 mL sealed glass pressure vessel were combined 3,4-dichlorobenzaldehyde (1.00 g, 5.71 mmol), THF (15 mL) and zinc (0.478 g, 7.31 mmol). The mixture was heated at 85° C. for 30 min and then ethyl bromodifluoroacetate (1.28 mL, 9.75 mmol) was added portionwise over 10 min. The reaction mixture was heated at 85° C. ON. After cooling to RT, the reaction mixture was filtered through a celite pad. The filtrate was acidified by addition of aqueous 1N HCl dropwise while stirring. The acidified filtrate was diluted with EtOAc (30 mL). The organic layer was washed with brine (20 mL), dried with anhydrous Na$_2$SO$_4$, filtered and concentrated under reduced pressure to an orange oil. The residue was subjected to flash column chromatography using a 24 g silica column eluting with 0-40% EtOAc in Hex gradient. The pure fractions were concentrated to afford ethyl 3-(3,4-dichlorophenyl)-2,2-difluoro-3-hydroxypropanoate (1.30 g, 4.40 mmol, 76% yield) as an off-white solid.

$^1$H NMR (400 MHz, CDCl$_3$) δ 7.59 (d, J=1.8 Hz, 1H), 7.50 (d, J=8.2 Hz, 1H), 7.31 (d, J=8.1 Hz, 1H), 5.21-5.14 (m, 1H), 4.45-4.32 (m, 2H), 2.80 (d, J=5.1 Hz, 1H), 1.43-1.21 (m, 3H).

110B: tert-butyl(3-(3,4-dichlorophenyl)-2,2-difluoro-3-hydroxypropyl)carbamate:

To a solution of ethyl 3-(3,4-dichlorophenyl)-2,2-difluoro-3-hydroxypropanoate (1.20 g, 4.01 mmol) in MeOH (6 mL) was added ammonia (7M in MeOH, 6.0 mL, 42 mmol). The resulting solution was stirred at RT for 20 h. The solvent was evaporated to give the crude 3-(3,4-dichlorophenyl)-2,2-difluoro-3-hydroxypropanamide.

To a 50 mL round bottom flask was added 3-(3,4-dichlorophenyl)-2,2-difluoro-3-hydroxypropanamide (600 mg, 2.22 mmol) and THF (6 mL). Borane dimethyl sulfide complex solution (2.0 M in THF, 4.4 mL, 8.89 mmol) was added portionwise at RT over 5 min. The reaction was stirred at 60° C. for 2 h. The mixture was then cooled to RT and was quenched by slow dropwise addition of methanol (5 mL). The mixture was stirred for 30 min and solvent was removed in vacuo to give a clear colorless thick oil. The oily residue was dissolved in 1M aqueous HCl solution (10 mL) and heated at 60° C. for 1 h. The cloudy mixture became clear by the end of the hour. The mixture was concentrated in vacuo to give the crude 3-amino-1-(3,4-dichlorophenyl)-2,2-difluoropropan-1-ol as a white solid. The crude 3-amino-1-(3,4-dichlorophenyl)-2,2-difluoropropan-1-ol was then mixed with THF (10 ml) and triethylamine (0.97 ml, 6.7 mmol). Di-tert-butyldicarbonate (0.61 mL, 2.7 mmol) was added and the mixture was stirred at RT for 1 h. Solvent was removed in vacuo to give a thick oil. The residue was subjected to flash column chromatography using a 24 g silica gel column eluting with 0-20% EtOAc in Hex gradient. The pure fractions were concentrated to afford tert-butyl (3-(3,4-dichlorophenyl)-2,2-difluoro-3-hydroxypropyl)carbamate (600 mg, 1.68 mmol, 76% yield) as a white solid.

110: tert-Butyl (3-(3,4-dichlorophenyl)-2,2-difluoro-3-hydroxypropyl)carbamate (34.8 mg, 0.098 mmol) was dissolved in DCM (1 mL) and TFA (0.2 mL). The solution was stirred at RT for 2 h. The solvent was evaporated to give crude 3-amino-1-(3,4-dichlorophenyl)-2,2-difluoropropan-1-ol, TFA salt. The residue was mixed with 3-(2-amino-[1,2,4]triazolo[1,5-a]pyridin-7-yl)-6-chloro-2-fluorobenzoic acid (30 mg, 0.098 mmol), DIPEA (0.068 mL, 0.39 mmol) and DMF (1 mL). BOP (47.6 mg, 0.108 mmol) was added and the reaction mixture was stirred at RT for 1 h. The crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 27% B, 27-67% B over 20 min, then a 0-min hold at 100% B; Flow Rate: 20 mL/min; Column Temperature: 25° C. Fraction collection was triggered by MS signals. Fractions containing the desired product were combined and dried via centrifugal evaporation to afford racemic 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide (44.7 mg, 0.0820 mmol, 84% yield).

$^1$H NMR (500 MHz, DMSO-d$_6$) δ 9.16 (br t, J=6.1 Hz, 1H), 8.65 (d, J=7.0 Hz, 1H), 7.76 (t, J=8.4 Hz, 1H), 7.68 (s, 1H), 7.69 (d, J=6.7 Hz, 1H), 7.57-7.49 (m, 2H), 7.45 (br d, J=7.9 Hz, 1H), 7.05 (br d, J=7.0 Hz, 1H), 6.64 (d, J=5.5 Hz, 1H), 6.12 (s, 2H), 5.07-4.88 (m, 1H), 4.00-3.80 (m, 2H).

MS ESI m/z 544.2 (M+H)$^+$

TABLE 7

Compounds in Table 7 were prepared in a similar fashion to example 110. In cases of undefined stereochemistry, compounds were isolated as racemic or diastereomeric mixtures unless otherwise noted.

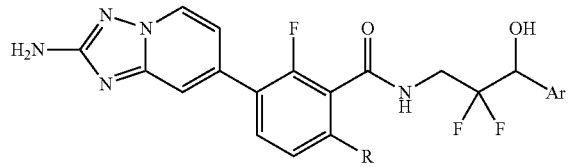

| Ex No | Name | Ar & R | M + H$^+$ | 1H NMR (500 MHz, DMSO-d6) δ |
|---|---|---|---|---|
| 111 | 3-{2-amino-[1,2,4]triazolo[1,5-a]pyridin-7-yl}-N-[3-(3,4-dichlorophenyl)-2,2-difluoro-3-hydroxypropyl]-2-fluoro-6-methoxybenzamide | 3,4-dichlorophenyl racemate R = OMe | 540.3 | 8.87 (br t, J = 6.0 Hz, 1H), 8.59 (d, J = 7.0 Hz, 1H), 7.78-7.62 (m, 3H), 7.52-7.37 (m, 2H), 7.07 (d, J = 8.5 Hz, 1H), 7.03 (d, J = 7.0 Hz, 1H), 6.62 (d, J = 5.5 Hz, 1H), 6.05 (s, 2H), 5.06-4.87 (m, 1H), 3.91 (br s, 3H), 4.01-3.66 (m, 1H), 3.50-3.40 (m, 1H) |
| 112 | 3-{2-amino-[1,2,4]triazolo[1,5-a]pyridin-7-yl}-N-[3-(3,4-dichlorophenyl)-2,2-difluoro-3-hydroxypropyl]-2-fluoro-6-methylbenzamide enantiomer 1 | 3,4-dichlorophenyl enantiomer 1 first eluted R = Me | 524.0 | 8.95 (br t, J = 6.0 Hz, 1H), 8.61 (d, J = 7.0 Hz, 1H), 7.72-7.64 (m, 2H), 7.60 (t, J = 8.1 Hz, 1H), 7.48 (s, 1H), 7.45 (d, J = 8.2 Hz, 1H), 7.23 (d, J = 7.9 Hz, 1H), 7.03 (br d, J = 6.9 Hz, 1H), 6.62 (d, J = 5.4 Hz, 1H), 6.07 (s, 2H), 5.05-4.86 (m, 1H), 3.94-3.81 (m, 2H), 2.31 (s, 3H) |
| 113 | 3-{2-amino-[1,2,4]triazolo[1,5-a]pyridin-7-yl}-N-[3-(3,4-dichlorophenyl)-2,2-difluoro-3-hydroxypropyl]-2-fluoro-6-methylbenzamide enantiomer 2 | 3,4-dichlorophenyl enantiomer 2 second eluted R = Me | 524.2 | 8.95 (br t, J = 6.0 Hz, 1H), 8.61 (d, J = 7.0 Hz, 1H), 7.72-7.64 (m, 2H), 7.60 (t, J = 8.1 Hz, 1H), 7.48 (s, 1H), 7.45 (d, J = 8.2 Hz, 1H), 7.23 (d, J = 7.9 Hz, 1H), 7.03 (br d, J = 6.9 Hz, 1H), 6.62 (d, J = 5.4 Hz, 1H), 6.07 (s, 2H), 5.05-4.86 (m, 1H), 3.94-3.81 (m, 2H), 2.31 (s, 3H) |
| 114 | 3-{2-amino-[1,2,4]triazolo[1,5-a]pyridin-7-yl}-N-[3-(5,6-dichloropyridin-2-yl)-2,2-difluoro-3-hydroxypropyl]-2-fluoro-6-methoxybenzamide | 5,6-dichloropyridin-2-yl R = OMe | 541.0 | 8.87 (br t, J = 5.9 Hz, 1H), 8.58 (d, J = 7.0 Hz, 1H), 8.44 (s, 1H), 8.12 (s, 1H), 7.69 (br t, J = 8.9 Hz, 1H), 7.45 (s, 1H), 7.07 (d, J = 8.6 Hz, 1H), 7.02 (d, J = 7.3 Hz, 1H), 5.09 (br d, J = 16.6 Hz, 1H), 3.99-3.86 (m, 3H), 4.05-3.76 (m, 1H), 3.50-3.32 (m, 1H) |

TABLE 7-continued

Compounds in Table 7 were prepared in a similar fashion to example 110. In cases of undefined stereochemistry, compounds were isolated as racemic or diastereomeric mixtures unless otherwise noted.

| Ex No | Name | Ar & R | M + H⁺ | 1H NMR (500 MHz, DMSO-d6) δ |
|---|---|---|---|---|
| 115 | 3-{2-amino-[1,2,4]triazolo[1,5-a]pyridin-7-yl}-N-[2,2-difluoro-3-(5-fluoropyridin-2-yl)-3-hydroxypropyl]-2-fluoro-6-methylbenzamide | R = Me | 525.0 | 8.98 (br t, J = 6.1 Hz, 1H), 8.61 (d, J = 7.0 Hz, 1H), 8.46 (s, 1H), 8.15 (s, 1H), 7.60 (t, J = 8.0 Hz, 1H), 7.49 (s, 1H), 7.23 (d, J = 8.0 Hz, 1H), 7.03 (br d, J = 7.0 Hz, 1H), 5.27-5.06 (m, 1H), 4.01-3.82 (m, 2H), 2.31 (s, 3H) |
| 116 | 3-{2-amino-[1,2,4]triazolo[1,5-a]pyridin-7-yl}-6-chloro-N-[2,2,-difluoro-3-(5-fluoropyridin-2-yl)-3-hydroxypropyl]-2-fluorobenzamide | R = Cl | 494.9 | 9.17 (br t, J = 6.1 Hz, 1H), 8.64 (d, J = 6.7 Hz, 1H), 8.57 (d, J = 2.7 Hz, 1H), 7.81 (t, J = 8.4 Hz, 1H), 7.75 (t, J = 8.1 Hz, 1H), 7.67 (dd, J = 8.9, 4.6 Hz, 1H), 7.57-7.48 (m, 2H), 7.06 (br d, J = 7.0 Hz, 1H), 6.11 (s, 2H), 5.00 (br dd, J = 15.1, 7.8 Hz, 1H), 3.98-3.86 (m, 2H) |
| 117 | 3-{2-amino-[1,2,4]triazolo[1,5-a]pyridin-7-yl}-N-[2,2-difluoro-3-(5-fluoropyridin-2-yl)-3-hydroxypropyl]-2-fluoro-6-methoxybenzamide | R = OMe | 491.3 | 8.86 (br t, J = 6.3 Hz, 1H), 8.69 (d, J = 7.0 Hz, 1H), 8.56 (d, J = 2.7 Hz, 1H), 7.80 (t, J = 8.4 Hz, 1H), 7.75-7.63 (m, 2H), 7.56 (s, 1H), 7.22-7.14 (m, 1H), 7.13-7.04 (m, 1H), 7.28-6.97 (m, 1H), 4.99 (br dd, J = 15.7, 7.2 Hz, 1H), 4.06-3.89 (m, 2H), 4.14-3.73 (m, 3H) |
| 118 | 3-{2-amino-[1,2,4]triazolo[1,5-a]pyridin-7-yl}-N-[2,2-difluoro-3-(5-fluoropyridin-2-yl)-3-hydroxypropyl]-2-fluoro-6-methylbenzamide | R = Me | 475.3 | 8.98 (br t, J = 6.1 Hz, 1H), 8.67 (d, J = 6.7 Hz, 1H), 8.57 (d, J = 2.7 Hz, 1H), 7.81 (td, J = 8.8, 2.9 Hz, 1H), 7.71-7.57 (m, 2H), 7.55 (s, 1H), 7.25 (br d, J = 7.6 Hz, 1H), 7.15 (br d, J = 4.3 Hz, 1H), 7.05 (s, 2H), 4.99 (br dd, J = 14.8, 7.8 Hz, 1H), 4.06-3.87 (m, 2H), 2.32 (s, 3H) |

Example 119: 3-{2-amino-[1,2,4]triazolo[1,5-a]pyridin-7-yl}-N-[2,2-difluoro-3-(5-fluoropyridin-2-yl)-3-hydroxypropyl]-6-ethyl-2-fluorobenzamide

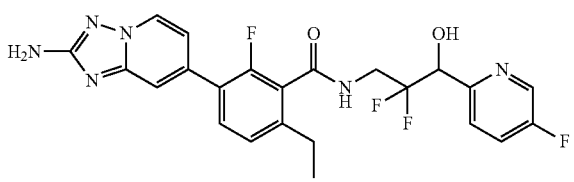 [SMILES: CCc1ccc(-c2ccn3nc(N)nc3c2)c(F)c1C(=O)NCC(F)(F)C(O)c1ccc(F)cn1]

119A: methyl 3-(2-amino-[1,2,4]triazolo[1,5-a]pyridin-7-yl)-6-ethyl-2-fluorobenzoate: A 40 mL vial equipped with a magnetic stir bar was charged with methyl 3-bromo-6-ethyl-2-fluorobenzoate (0.800 g, 3.06 mmol), 4,4,4',4',5,5,5',5'-octamethyl-2,2'-bi(1,3,2-dioxaborolane) (1.01 g, 3.98 mmol), PdCl₂(dppf)-CH₂Cl₂ adduct (0.125 g, 0.153 mmol), 1,4-dioxane (15.3 mL), and potassium acetate (0.601 g, 6.13 mmol). The vial was evacuated and back-filled with nitrogen 3 times, then fitted with a condenser and heated to 110° C. under nitrogen atmosphere for 4 h. To the mixture was added 7-bromo-[1,2,4]triazolo[1,5-a]pyridin-2-amine (0.653 g, 3.06 mmol) and potassium phosphate tribasic, 2.0M aqueous (2.0 mL, 6.13 mmol). The vial was evacuated and backfilled with nitrogen 3 times and heated to 90° C. for 1 h. The mixture was allowed to cool to RT and was adsorbed onto silica gel. The crude, dry-loaded material was purified by flash column silica chromatography (40 g silica, elution gradient 50 to 100% EtOAc in hexanes). Product fractions were combined and concentrated to give a solid which was triturated with EtOAc (15 mL) and isolated by filtration to give methyl 3-(2-amino-[1,2,4]triazolo[1,5-a]pyridin-7-yl)-6-ethyl-2-fluorobenzoate (0.600 g, 1.91 mmol, 62% yield).

¹H NMR (499 MHz, DMSO-d₆) δ 8.61 (d, J=6.9 Hz, 1H), 7.73 (t, J=8.1 Hz, 1H), 7.52 (s, 1H), 7.33 (d, J=8.1 Hz, 1H), 7.04 (dt, J=7.0, 1.7 Hz, 1H), 6.08 (s, 2H), 3.92 (s, 3H), 2.68 (q, J=7.6 Hz, 2H), 1.19 (t, J=7.5 Hz, 3H)
MS ESI m/z 315.1 (M+H)⁺

119B: lithium 3-(2-amino-[1,2,4]triazolo[1,5-a]pyridin-7-yl)-6-ethyl-2-fluorobenzoate: An 8 mL vial was charged with a stir bar, methyl 3-(2-amino-[1,2,4]triazolo[1,5-a]pyridin-7-yl)-6-ethyl-2-fluorobenzoate (0.200 g, 0.636 mmol), THF (2 mL), MeOH (2 mL) and 1M aqueous NaOH (0.127 mL, 1.27 mmol). The resulting mixture was stirred at 60° C. for 16 h. Solvent was removed in vacuo to provide a solid residue which was used directly in the next step, assumed 100% yield.
MS ESI m/z 301.3 (M+H)⁺

119: The title compound was prepared by a similar procedure to that described for the last step of the preparation of example 110, where tert-butyl (2,2-difluoro-3-(5-fluoropyridin-2-yl)-3-hydroxypropyl)carbamate was used in place of tert-Butyl (3-(3,4-dichlorophenyl)-2,2-difluoro-3-hydroxypropyl)carbamate, and where lithium 3-(2-amino-[1,2,4]triazolo[1,5-a]pyridin-7-yl)-6-ethyl-2-fluorobenzoate was used in place of 3-(2-amino-[1,2,4]triazolo[1,5-a]pyridin-7-yl)-6-chloro-2-fluorobenzoic acid to provide the desired product 3-(2-amino-[1,2,4]triazolo[1,5-a]pyridin-7-yl)-N-(2,2-difluoro-3-(5-fluoropyridin-2-yl)-3-hydroxypropyl)-6-ethyl-2-fluorobenzamide (10.7 mg, 0.022 mmol, 33% yield).
¹H NMR (499 MHz, DMSO-d₆) δ 8.99 (br t, J=6.0 Hz, 1H), 8.61 (d, J=7.1 Hz, 1H), 8.57 (s, 1H), 7.81 (td, J=8.8, 2.6 Hz, 1H), 7.68 (t, J=6.9 Hz, 1H), 7.63 (t, J=7.8 Hz, 1H), 7.50 (s, 1H), 7.27 (d, J=7.9 Hz, 1H), 7.06 (br d, J=7.0 Hz, 1H), 6.61 (d, J=5.8 Hz, 1H), 6.07 (s, 1H), 5.07-4.91 (m, 1H), 4.06-3.86 (m, 2H), 3.46 (br s, 1H), 2.64 (q, J=7.2 Hz, 2H), 1.19 (t, J=7.6 Hz, 3H).
MS ESI m/z 489.1 (M+H)⁺

Example 120: 3-(2-amino-[1,2,4]triazolo[1,5-a]pyridin-7-yl)-N-(2,2-difluoro-3-(4-fluorophenyl)-3-hydroxypropyl)-6-ethyl-2-fluorobenzamide

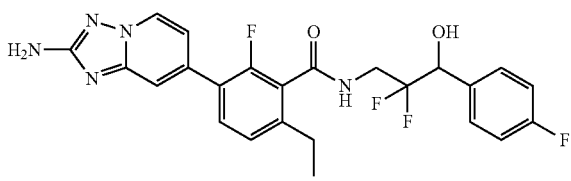 [SMILES: CCc1ccc(-c2ccn3nc(N)nc3c2)c(F)c1C(=O)NCC(F)(F)C(O)c1ccc(F)cc1]

A mixture of 3-(2-amino-[1,2,4]triazolo[1,5-a]pyridin-7-yl)-6-chloro-N-(2,2-difluoro-3-(4-fluorophenyl)-3-hydroxypropyl)-2-fluorobenzamide (30 mg, 0.061 mmol), dicyclohexyl(2',6'-dimethoxy-[1,1'-biphenyl]-2-yl)phosphine [S-Phos] (6.23 mg, 0.0150 mmol), palladium acetate (2.73 mg, 0.0120 mmol) and 6-methyl-2-vinyl-1,3,6,2-dioxazaborocane-4,8-dione (22.2 mg, 0.121 mmol) in 1,4-dioxane (1 mL) was purged with nitrogen for 1 min. Potassium phosphate, tribasic, 2M aqueous (0.17 mL, 0.334 mmol) was added and the reaction mixture was heated to 115° C. for 1.5 h. The mixture was filtered through a pad of celite and washed with EtOAc (2×). The filtrate was concentrated in vacuo and the residue was dissolved in MeOH (3 mL). 25 mg of 10% Pd on C (wet) was added, and the mixture was evacuated and back-filled with H2 from a balloon. The mixture was stirred at RT ON. The reaction mixture was filtered and concentrated in vacuo to give the crude product. The material was dissolved in DMF (2 mL) and was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 18% B, 18-58% B over 21 min, then a 0-min hold at 100% B; Flow Rate: 20 mL/min; Column Temperature: 25 C. Fraction collection was triggered by MS and UV signals. Fractions containing the desired product were combined and dried via centrifugal evaporation. The material was further separated into individual enantiomers through SFC chiral chromatography as follows: Instrument: Waters 100 Prep SFC, Column: Chiral OJ, 30×250 mm. 5 micron, Mobile Phase: 80% CO2/20% MeOH w/0.1% DEA, Flow Conditions: 100 mL/min, Detector Wavelength: 220 nm, Injection Details: 1000 μL 11.3 mg dissolved in 3 mL MeOH to recover the first eluting peak as the desired homochiral product, 3-(2-amino-[1,2,4]triazolo[1,5-a]pyridin-7-yl)-N-(2,2-difluoro-3-(4-fluorophenyl)-3-hydroxypropyl)-6-ethyl-2-fluorobenzamide (2.80 mg, 5.74 μmol, 9% yield), with >95% chiral purity. The absolute stereochemistry was not determined.
¹H NMR (500 MHz, DMSO-d₆) δ 8.98 (br t, J=6.3 Hz, 1H), 8.62 (d, J=7.0 Hz, 1H), 7.64 (t, J=8.1 Hz, 1H), 7.55-7.44 (m, 3H), 7.31-7.18 (m, 3H), 7.05 (br d, J=6.7 Hz, 1H), 6.07 (s, 2H), 4.94 (br d, J=15.0 Hz, 1H), 4.00-3.80 (m, 2H), 2.64 (q, J=7.4 Hz, 2H), 2.58-2.54 (m, 1H), 1.19 (t, J=7.5 Hz, 3H).
MS ESI m/z 488.1 (M+H)⁺

TABLE 8

Compounds in Table 8 were prepared in a similar fashion to example 120. In cases of undefined sterochemistry, compounds were isolated as racemic or diasteromeric mixtures unless otherwise noted.

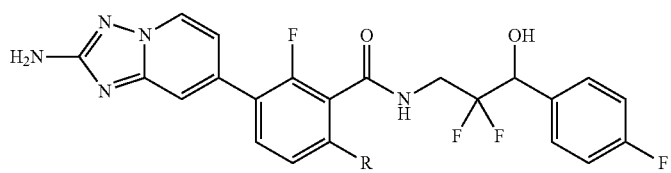

| Ex No | Name | R | M + H⁺ | 1H NMR (500 MHz, DMSO-d6) δ |
|---|---|---|---|---|
| 121 | 3-(2-amino-[1,2,4]triazolo[1,5-a]pyridin-7-yl)-N-(2,2-difluoro-3-(4-fluorophenyl)-3- | | 488.1 | 8.99 (br t, J = 6.1 Hz, 1H), 8.61 (d, J = 7.0 Hz, 1H), 7.64 (t, J = 8.1 Hz, 1H), 7.55-7.44 (m, 3H), 7.31-7.18 (m, 3H), 7.06 (br d, J = 7.0 Hz, 1H), 6.07 (s, 2H), 4.94 (br dd, |

TABLE 8-continued

Compounds in Table 8 were prepared in a similar fashion to example 120. In cases of undefined sterochemistry, compounds were isolated as racemic or diasteromeric mixtures unless otherwise noted.

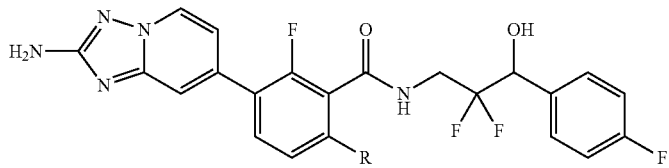

| Ex No | Name | R | M + H+ | 1H NMR (500 MHz, DMSO-d6) δ |
|---|---|---|---|---|
| | hydroxypropyl)-6-ethyl-2-fluorobenzamide | | | J = 16.0, 6.3 Hz, 1H), 3.97-3.80 (m, 2H), 2.64 (q, J = 7.3 Hz, 2H), 2.58-2.54 (m, 1H), 1.19 (t, J = 7.5 Hz, 3H) |
| 122 | 3-(2-amino-[1,2,4]triazolo[1,5-a]pyridin-7-yl)-6-cyclopropyl-N-(2,2-difluoro-3-(4-fluorophenyl)-3-hydroxypropyl)-2-fluorobenzamide | cyclopropyl | 500.1 | 9.01 (br t, J = 6.1 Hz, 1H), 8.59 (d, J = 7.0 Hz, 1H), 7.57 (t, J = 8.3 Hz, 1H), 7.52-7.43 (m, 3H), 7.28-7.16 (m, 2H), 7.03 (br d, J = 6.7 Hz, 1H), 6.87 (d, J = 8.3 Hz, 1H), 6.43 (t, J = 3.9 Hz, 1H), 6.13-5.98 (m, 2H), 4.99-4.86 (m, 1H), 3.96-3.79 (m, 2H), 2.01-1.85 (m, 1H), 1.05-0.90 (m, 2H), 0.85-0.69 (m, 2H) |
| 123 | 3-(2-amino-[1,2,4]triazolo[1,5-a]pyridin-7-yl)-N-(2,2-difluoro-3-(4-fluorophenyl)-3-hydroxypropyl)-2-fluoro-6-(methyl-d3)benzamide | CD3 | 477.4 | 8.95 (br t, J = 5.8 Hz, 1H), 8.63 (d, J = 7.0 Hz, 1H), 7.61 (br t, J = 7.9 Hz, 1H), 7.53-7.45 (m, 3H), 7.27-7.19 (m, 3H), 7.09-7.03 (m, 1H), 4.99-4.86 (m, 1H), 3.94-3.78 (m, 2H) |

Example 124: 3-(2-amino-[1,2,4]triazolo[1,5-a]pyridin-7-yl)-N-(2,2-difluoro-3-(4-fluorophenyl)-3-hydroxypropyl)-2-fluoro-6-methoxybenzamide enantiomer 1

enantiomer 1

124A: 3-bromo-N-(2,2-difluoro-3-(4-fluorophenyl)-3-hydroxypropyl)-2-fluoro-6-methoxybenzamide: To a mixture of 3-bromo-2-fluoro-6-methoxybenzoic acid (20 mg, 0.080 mmol), 3-amino-2,2-difluoro-1-(4-fluorophenyl)propan-1-ol (16.5 mg, 0.0800 mmol) and BOP (39.1 mg, 0.0880 mmol) in DMF (5 mL) was added Hünig's base (0.0280 mL, 0.161 mmol). The mixture was stirred at RT for 1 h. The mixture was diluted with EtOAc (20 mL) and washed with saturated aqueous NaHCO3 (2×20 mL) and brine (20 mL). The organic layer was dried over anhydrous Na2SO4, filtered and concentrated in vacuo. The crude product was used in the next step without further purification.
MS ESI m/z 436.1 (M+H)+
124: A mixture of 7-bromo-[1,2,4]triazolo[1,5-a]pyridin-2-amine (25.0 mg, 0.117 mmol), 4,4,4',4',5,5,5',5'-octamethyl-2,2'-bi(1,3,2-dioxaborolane) (35.8 mg, 0.141 mmol), potassium acetate (34.6 mg, 0.352 mmol) and PdCl2(dppf)-CH2Cl2 adduct (4.79 mg, 5.87 μmol) in 1,4-dioxane (2 mL) was purged with N2 and stirred at 110° C. for 3 h. To the mixture was added 3-bromo-N-(2,2-difluoro-3-(4-fluorophenyl)-3-hydroxypropyl)-2-fluoro-6-methoxybenzamide (46.1 mg, 0.106 mmol), 1,1'-bis(di-tert-butylphosphino)ferrocene palladium dichloride (3.82 mg, 5.87 μmol), and 2.0 M aqueous tripotassium phosphate (0.18 mL, 0.352 mmol). The mixture was stirred at 110° C. for 1.5 h. EtOAc (10 mL) and Et2O (10 mL) were added. The organics were washed with 1N NaOH (2×10 mL). The combined aqueous layer was acidified with concentrated HCl to pH=4-5 to precipitate product. The solid was isolated by filtration, washed with water and dried to give the crude product which was dissolved in DMF and purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 8% B, 8-48% B over 20 min, then a 0-min hold at 100% B; Flow Rate: 20 mL/min; Column Temperature: 25° C. Fraction collection was triggered by MS signals. Fractions containing the desired product were combined and dried via centrifugal evaporation. The material was further purified by SCP using SFC chiral chromatography. Waters 100 Prep SFC, Column: Chiral OJ, 30×250 mm. 5 micron, Mobile Phase: 80% CO2/20% MeOH w/0.1% DEA, Flow Conditions: 100 mL/min, Detector Wavelength: 220 nm, Injection Details: 1000 μL 39.9 mg dissolved in 30 mL MeOH/ACN to recover the first eluting peak as the desired homochiral product, 3-(2-amino-[1,2,4]triazolo[1,5-a]pyridin-7-yl)-N-(2,2-difluoro-3-(4-fluorophenyl)-3-hydroxypropyl)-2-fluoro-6-methoxybenzamide enantiomer 1 (7.4 mg, 0.015 mmol, 13% yield), with >95% of chiral purity). The absolute stereochemistry was not determined.

$^1$H NMR (500 MHz, DMSO-d$_6$) δ 8.91-8.75 (m, 1H), 8.58 (d, J=7.0 Hz, 1H), 7.72-7.63 (m, 1H), 7.56-7.37 (m, 3H), 7.26-7.16 (m, 2H), 7.10-6.95 (m, 2H), 6.04 (s, 2H), 5.05-4.77 (m, 1H), 4.04-3.50 (m, 5H).

MS ESI m/z 488.1 (M+H)$^+$

Example 125: 3-(2-amino-[1,2,4]triazolo[1,5-a]pyridin-7-yl)-N-(2,2-difluoro-3-(4-fluorophenyl)-3-hydroxypropyl)-2-fluoro-6-methoxybenzamide enantiomer 2

enantiomer 2

The title compound 3-(2-amino-[1,2,4]triazolo[1,5-a]pyridin-7-yl)-N-(2,2-difluoro-3-(4-fluorophenyl)-3-hydroxypropyl)-2-fluoro-6-methoxybenzamide enantiomer 2 (5.9 mg, 0.012 mmol, 10% yield) was obtained as the second eluting isomer from the chiral SFC purification described for example 124. The absolute stereochemistry was not determined.

1H NMR (500 MHz, DMSO-d6) δ 8.94-8.79 (m, 1H), 8.66-8.44 (m, 1H), 7.69 (quin, J=8.7 Hz, 1H), 7.52-7.38 (m, 3H), 7.29-7.16 (m, 2H), 7.12-6.97 (m, 2H), 6.14-5.94 (m, 2H), 4.92 (br dd, J=16.7, 6.8 Hz, 1H), 3.97-3.63 (m, 5H).

MS ESI m/z 490.2 (M+H)$^+$

Example 126: 3-(2-amino-8-fluoro-[1,2,4]triazolo[1,5-a]pyridin-7-yl)-N-(2,2-difluoro-3-(4-fluorophenyl)-3-hydroxypropyl)-6-ethyl-2-fluorobenzamide

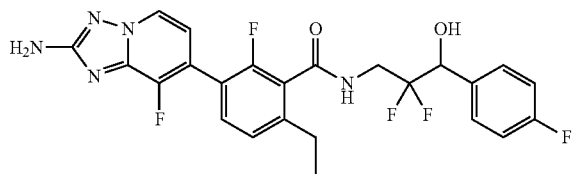 [SMILES: CCc1ccc(-c2ccn3nc(N)nc3c2F)c(F)c1C(=O)NCC(F)(F)C(O)c1ccc(F)cc1]

126A: 3-bromo-6-chloro-N-(2,2-difluoro-3-(4-fluorophenyl)-3-hydroxypropyl)-2-fluorobenzamide: To a mixture of 3-bromo-6-chloro-2-fluorobenzoic acid (150 mg, 0.592 mmol), 3-amino-2,2-difluoro-1-(4-fluorophenyl)propan-1-ol (121 mg, 0.592 mmol), BOP (288 mg, 0.651 mmol) in DMF (5 mL) was added Hünig's base (0.207 mL, 1.18 mmol). The mixture was stirred at RT for 1 h. The mixture was diluted with EtOAc (20 mL) and washed with saturated aqueous NaHCO$_3$ (2×20 mL) and brine (20 mL). The organic layer was dried over anhydrous Na$_2$SO$_4$, filtered and concentrated in vacuo. The crude product was purified by flash column chromatography (12 g silica, gradient EtOAc in Hex=0-10%, gradient time=12 min, with flow rate of 25 mL/min) to afford 3-bromo-6-chloro-N-(2,2-difluoro-3-(4-fluorophenyl)-3-hydroxypropyl)-2-fluorobenzamide (240 mg, 0.545 mmol, 92% yield).

$^1$H NMR (499 MHz, CDCl$_3$) δ 7.62 (dd, J=8.7, 7.3 Hz, 1H), 7.53-7.45 (m, 2H), 7.20 (dd, J=8.6, 1.4 Hz, 1H), 7.15-7.08 (m, 2H), 6.36-6.26 (m, 1H), 5.04-4.92 (m, 1H), 4.55-4.39 (m, 1H), 4.02 (br dd, J=15.1, 10.4 Hz, 1H), 3.67-3.54 (m, 1H).

MS ESI m/z 442.2 (M+H)$^+$

126B: 3-(2-amino-3-fluoropyridin-4-yl)-6-chloro-N-(2,2-difluoro-3-(4-fluorophenyl)-3-hydroxypropyl)-2-fluorobenzamide: A mixture of 3-bromo-6-chloro-N-(2,2-difluoro-3-(4-fluorophenyl)-3-hydroxypropyl)-2-fluorobenzamide (88 mg, 0.20 mmol), 4,4,4',4',5,5,5',5'-octamethyl-2,2'-bi(1,3,2-dioxaborolane) (60.9 mg, 0.240 mmol), potassium acetate (58.9 mg, 0.600 mmol) and PdCl$_2$(dppf)-CH$_2$Cl$_2$ adduct (16.3 mg, 0.0200 mmol) in 1,4-dioxane (2 mL) was purged with N2 and stirred at 110° C. for 3 h. To the above mixture was added 3-fluoro-4-iodopyridin-2-amine (57.1 mg, 0.240 mmol), [1,1'-bis(di-tert-butylphosphino)ferrocene]palladium(II) dichloride (13.0 mg, 0.0200 mmol) and 2M aqueous potassium phosphate tribasic (300 µl, 0.600 mmol). The resulting mixture was degassed by bubbling N2 through the mixture for 2 min, then the mixture was stirred at 110° C. for 1.5 h. The reaction mixture was distributed between EtOAc (20 mL) and H$_2$O (10 mL). The organic phase was dried over anhydrous Na$_2$SO$_4$, filtered and concentrated in vacuo. The residue was purified by flash column chromatography (12 g silica gel, gradient EtOAc/Hex=0-100%) to afford 3-(2-amino-3-fluoropyridin-4-yl)-6-chloro-N-(2,2-difluoro-3-(4-fluorophenyl)-3-hydroxypropyl)-2-fluorobenzamide (78.0 mg, 0.165 mmol, 83% yield).

$^1$H NMR (500 MHz, DMSO-d$_6$) δ 9.18 (br t, J=6.0 Hz, 1H), 7.87 (d, J=5.5 Hz, 1H), 7.64-7.42 (m, 4H), 7.28-7.19 (m, 2H), 7.17-7.00 (m, 1H), 6.65 (t, J=4.9 Hz, 1H), 4.93 (br dd, J=16.2, 6.7 Hz, 1H), 3.97-3.76 (m, 2H).

MS ESI m/z 472.3 (M+H)$^+$

126C: 3-(2-amino-3-fluoropyridin-4-yl)-N-(2,2-difluoro-3-(4-fluorophenyl)-3-hydroxypropyl)-6-ethyl-2-fluorobenzamide: A mixture of 3-(2-amino-3-fluoropyridin-4-yl)-6-chloro-N-(2,2-difluoro-3-(4-fluorophenyl)-3-hydroxypropyl)-2-fluorobenzamide (74.0 mg, 0.157 mmol), dicyclohexyl(2',6'-dimethoxy-[1,1'-biphenyl]-2-yl)phosphine [S-Phos] (12.9 mg, 0.0310 mmol), palladium acetate (3.52 mg, 0.0160 mmol) and 6-methyl-2-vinyl-1,3,6,2-dioxazaborocane-4,8-dione (57.4 mg, 0.314 mmol) in 1,4-dioxane (2 mL) was purged with nitrogen for 1 min. Potassium phosphate, tribasic, 2M aqueous (0.43 mL, 0.863 mmol) was added and the reaction mixture was heated to 115° C. for 1.5 h. The mixture was cooled to RT and filtered through a pad of celite which was washed with EtOAc (20 mL). The filtrate and washes were concentrated in vacuo and the residue was dissolved in MeOH (3 mL). 10% Pd on C (wet, 25 mg) was added, and the mixture was evacuated and back-filled with a balloon of H2. The mixture was stirred at RT ON. The mixture was filtered and concentrated to afford crude 3-(2-amino-3-fluoropyridin-4-yl)-N-(2,2-difluoro-3-(4-fluorophenyl)-3-hydroxypropyl)-6-ethyl-2-fluorobenzamide (68.0 mg, 0.146 mmol, 93% yield) which was used in the next step without further purification.

$^1$H NMR (500 MHz, DMSO-d$_6$) δ 8.97 (t, J=6.2 Hz, 1H), 7.81 (d, J=5.1 Hz, 1H), 7.53-7.33 (m, 3H), 7.31-7.18 (m, 3H), 6.54 (t, J=4.8 Hz, 1H), 6.41 (br d, J=5.5 Hz, 1H), 6.30 (s, 2H), 4.97-4.84 (m, 1H), 3.95-3.76 (m, 2H), 2.63 (q, J=7.6 Hz, 2H), 1.18 (t, J=7.5 Hz, 3H).

MS ESI m/z 466.5 (M+H)$^+$

126: An 8 mL reaction vial was charged with a stir bar and 3-(2-amino-3-fluoropyridin-4-yl)-N-(2,2-difluoro-3-(4-fluorophenyl)-3-hydroxypropyl)-6-ethyl-2-fluorobenzamide (40 mg, 0.086 mmol). The vessel was evacuated and backfilled with nitrogen, followed by the addition of 1,4-dioxane (1 mL), DCM (1 mL) and ethoxylcarbonyl isothiocyanate (0.015 mL, 0.129 mmol) dropwise at RT. The resulting mixture was stirred at RT for 2 h, then at 45° C. for 2 h. The mixture was concentrated in vacuo and the residue containing the desired intermediate (MS ESI m/z 597.5 (M+H$^+$)) was purified by flash column chromatography (4 g silica, gradient MeOH in DCM=0-6%, gradient time=10 min at rate of 15 mL/min). In an 8 mL vial, the purified thiourea intermediate thus obtained (51.3 mg, 0.0860 mmol) was combined with hydroxylamine hydrochloride (29.9 mg, 0.430 mmol). The flask was evacuated and backfilled with nitrogen, followed by the addition of ethanol (1 mL) and Hunig's base (0.0450 mL, 0.258 mmol). The resulting mixture was stirred at RT for 15 min and then at 80° C. ON. A solid was collected by filtration and washed with water. The material was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 8% B, 8-48% B over 20 min, then a 0-min hold at 100% B; Flow Rate: 20 mL/min; Column Temperature: 25° C. Fraction collection was triggered by MS signals. Fractions containing the desired product were combined and dried via centrifugal evaporation to afford the desired racemic product (30 mg, 0.059 mmol, 69% yield). $^1$H NMR (500 MHz, DMSO-d$_6$) δ 9.47-9.13 (m, 1H), 8.94-8.48 (m, 1H), 7.92-7.12 (m, 6H), 6.83-6.30 (m, 2H), 5.38-4.90 (m, 1H), 4.39-3.86 (m, 1H), 3.67-3.20 (m, 2H), 3.01-2.75 (m, 3H), 1.68-1.07 (m, 3H).

MS ESI m/z 506.4 (M+H)$^+$

Example 127: 3-(2-amino-8-fluoro-[1,2,4]triazolo[1,5-a]pyridin-7-yl)-N-(2,2-difluoro-3-(4-fluorophenyl)-3-hydroxypropyl)-6-ethyl-2-fluorobenzamide

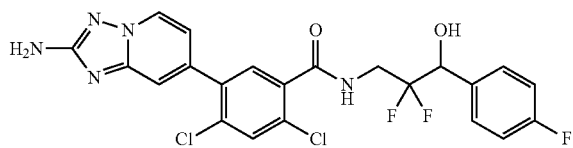 [SMILES: Nc1nc2cc(-c3cc(C(=O)NCC(F)(F)C(O)c4ccc(F)cc4)c(Cl)cc3Cl)ccn2n1]

Example 127 was prepared in a similar fashion to example 124 where 3-bromo-2-fluoro-6-methoxybenzoic acid was substituted with 5-bromo-2,4-dichlorobenzoic acid in the first step, and chiral SFC purification was not performed on the racemate desired product in the final step. Thus, racemic 3-(2-amino-8-fluoro-[1,2,4]triazolo[1,5-a]pyridin-7-yl)-N-(2,2-difluoro-3-(4-fluorophenyl)-3-hydroxypropyl)-6-ethyl-2-fluorobenzamide was obtained (5.6 mg, 0.011 mmol, 24% yield).

$^1$H NMR (500 MHz, DMSO-d$_6$) δ 8.90 (br t, J=6.0 Hz, 1H), 8.64 (d, J=7.0 Hz, 1H), 7.88 (s, 1H), 7.56-7.42 (m, 4H), 7.21 (t, J=7.3 Hz, 2H), 6.97 (dd, J=6.9, 1.7 Hz, 1H), 6.11 (s, 2H), 5.00-4.89 (m, 1H), 3.91 (s, 1H), 3.88-3.67 (m, 2H).

MS ESI m/z 510.1 (M+H)$^+$

Example 128: 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide enantiomeric mixture 1

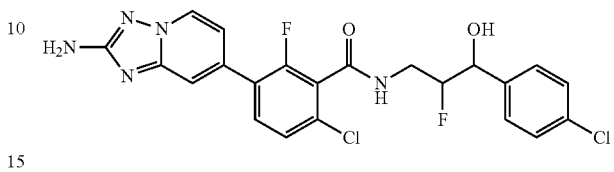

enantiomeric mixture 1

128A: ethyl 3-(4-chlorophenyl)-2-fluoro-3-hydroxypropanoate: To a suspension of zinc (5.58 g, 85.0 mmol) in THF (85 mL) was added a solution of ethyl 2-bromo-2-fluoroacetate (6.0 mL, 51.2 mmol) and 4-chlorobenzaldehyde (6.00 g, 42.7 mmol) in THF (15 mL) dropwise with a dropping funnel over 15 min. The reaction mixture was heated to reflux for 30 min. After filtration, 1N aqueous HCl and ether were added. The aqueous layer was extracted with ethyl acetate three times. The combined organic layers were washed with brine and dried over anhydrous sodium sulfate. The mixture was filtered, and the filtrate was evaporated in vacuo to give the crude product. The crude product was purified by silica gel chromatography eluting with 0-15% ethyl acetate/hexanes to give ethyl 3-(4-chlorophenyl)-2-fluoro-3-hydroxypropanoate (6.50 g, 26.4 mmol, 62% yield).

$^1$H NMR (500 MHz, CDCl$_3$) δ 7.40-7.25 (m, 4H), 5.20-5.08 (m, 1H), 5.08-4.94 (m, 1H), 4.31-4.20 (m, 2H), 2.19 (s, 1H), 1.25 (dt, J=11.8, 7.2 Hz, 3H).

128B: 3-(4-chlorophenyl)-2-fluoro-3-hydroxypropanamide: To a solution of ethyl 3-(4-chlorophenyl)-2-fluoro-3-hydroxypropanoate (1.37 g, 5.55 mmol) in MeOH (13.9 mL) at RT was added 7M ammonia in methanol (4.0 mL, 27.8 mmol), and the reaction mixture was stirred at RT for 12 h. The solvents were removed to give 3-(4-chlorophenyl)-2-fluoro-3-hydroxypropanamide (1.21 g, 5.56 mmol, 100% yield) as a white solid. This material was used directly for the next step.

MS ESI/APCI m/z 216.1 [M−H]$^−$

128C: 3-amino-1-(4-chlorophenyl)-2-fluoropropan-1-ol: To a solution of 3-(4-chlorophenyl)-2-fluoro-3-hydroxypropanamide (158 mg, 0.726 mmol) in THF (1.45 mL) at RT was added borane-dimethylsulfide complex, 2M in THF (1.09 mL, 2.178 mmol), and the reaction mixture was heated to reflux for 2 h. Methanol was added, and the reaction mixture was stirred at RT for 20 min. The residue was azeotroped with methanol (5×) to remove boric acid to give 3-amino-1-(4-chlorophenyl)-2-fluoropropan-1-ol (149 mg, 0.732 mmol, 101% yield) as a colorless oil. This material was used directly for the next step.

MS ESI/APCI m/z 203.8 [M+H]$^+$ 128D-1: 3-bromo-6-chloro-N-(3-(4-chlorophenyl)-2-fluoro-3-hydroxypropyl)-2-fluorobenzamide enantiomeric mixture 1: A mixture of 3-bromo-6-chloro-2-fluorobenzoic acid (20 mg, 0.079 mmol), 3-amino-1-(4-chlorophenyl)-2-fluoropropan-1-ol (17.7 mg, 0.0870 mmol), BOP (41.9 mg, 0.0950 mmol) and diisopropylethylamine (21 μL, 0.118 mmol) in DCM (158 μL) was stirred at RT for 3 h. The solvents were removed in vacuo and the residue was purified by preparative TLC on silica gel (0.50 mm thickness, elution 30% ethyl acetate in hexanes) to provide two separated mixtures of enantiomers. 3-Bromo-6-chloro-N-(3-(4-chlorophenyl)-2-fluoro-3-hydroxypropyl)-2-fluorobenzamide enantiomeric mixture 1 (11 mg, 0.025 mmol, 32% yield) was isolated as the less polar, faster eluting material on preparative silica TLC.

$^1$H NMR (500 MHz, CDCl$_3$) δ 7.59 (t, J=7.7 Hz, 1H), 7.43-7.34 (m, 4H), 7.19 (d, J=8.4 Hz, 1H), 6.38 (br s, 1H), 4.84 (t, J=7.3 Hz, 1H), 4.69-4.53 (m, 1H), 4.30-4.15 (m, 1H), 3.95 (br s, 1H), 3.70 (dddd, J=17.7, 14.9, 5.6, 3.2 Hz, 1H).

MS ESI/APCI m/z 437.8 [M+H]$^+$ 128D-2: 3-bromo-6-chloro-N-(3-(4-chlorophenyl)-2-fluoro-3-hydroxypropyl)-2-fluorobenzamide enantiomeric mixture 2: 3-bromo-6-chloro-N-(3-(4-chlorophenyl)-2-fluoro-3-hydroxypropyl)-2-fluorobenzamide enantiomeric mixture 2 (11 mg, 0.025 mmol, 32% yield) was isolated as the more polar, slower eluting material on preparative silica TLC from the preparative TLC separation described for intermediate 128D-1.

$^1$H NMR (500 MHz, CDCl$_3$) δ 7.54 (dd, J=8.6, 7.3 Hz, 1H), 7.42-7.31 (m, 4H), 7.13 (dd, J=8.6, 1.4 Hz, 1H), 6.28 (br s, 1H), 4.88 (dd, J=18.1, 5.0 Hz, 1H), 4.81 (dt, J=7.0, 4.7 Hz, 1H), 3.96-3.50 (m, 2H).

MS ESI/APCI m/z 437.8 [M+H]$^+$

128: In a 1 dram vial equipped with a stir bar were combined 3-bromo-6-chloro-N-(3-(4-chlorophenyl)-2-fluoro-3-hydroxypropyl)-2-fluorobenzamide enantiomeric mixture 1 (23 mg, 0.052 mmol), N,N-bis-Boc-2-amino-7-(4,4,5,5-tetramethyl-1,3,2-dioxaborolan-2-yl)-[1,2,4]triazolo[1,5-a]pyridine (28.9 mg, 0.063 mmol), potassium phosphate tribasic (79.0 μL, 0.157 mmol), and [1,1'-bis(diphenylphosphino)ferrocene]dichloropalladium(II), complex with dichloromethane (2.0 mg, 2.5 umol) in 1,4-dioxane (250 μL) to give a brown suspension. The reaction mixture was degassed by evacuating and backfilling with nitrogen 3×. The vial was sealed and heated to 60° C. for 2 h. Hydrogen chloride solution (4M in 1,4-dioxane, 196 μL, 0.79 mmol) was added and the mixture was stirred at RT ON. The reaction mixture was concentrated under a gentle stream of nitrogen, dissolved in DMF and filtered through a 0.45 m PTFE frit. The crude material was purified via preparative LCMS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 10% B, 10-50% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide enantiomeric mixture 1, 2 TFA (3.5 mg, 0.0049 mmol, 8% yield).

$^1$H NMR (500 MHz, DMSO-d$_6$) δ 9.01 (s, 1H), 8.61 (br d, J=6.7 Hz, 1H), 7.71 (br t, J=8.1 Hz, 1H), 7.54-7.45 (m, 2H), 7.43 (s, 3H), 7.25 (s, 1H), 7.15 (s, 1H), 7.05 (br s, 2H), 4.79 (br s, 1H), 4.72-4.55 (m, 1H).

MS ESI/APCI m/z 491.9 [M+H]$^+$

Example 129: 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide enantiomeric mixture 2

enantiomeric mixture 2

In a 1 dram vial equipped with a stir bar were combined 3-bromo-6-chloro-N-(3-(4-chlorophenyl)-2-fluoro-3-hydroxypropyl)-2-fluorobenzamide enantiomeric mixture 2 (22 mg, 0.050 mmol), N,N-bis-Boc-2-amino-7-(4,4,5,5-tetramethyl-1,3,2-dioxaborolan-2-yl)-[1,2,4]triazolo[1,5-a]pyridine (27.7 mg, 0.060 mmol), potassium phosphate tribasic (75.0 μL, 0.150 mmol) and [1,1'-bis(diphenylphosphino)ferrocene]dichloropalladium(II), complex with dichloromethane (2.0 mg, 2.5 μmol) in 1,4-dioxane (250 μL) to give a brown suspension. The reaction mixture was degassed by evacuating and backfilling with nitrogen 3×. The vial was sealed and heated to 60° C. for 2 h. Hydrogen chloride solution (4M in 1,4-dioxane, 188 μL, 0.75 mmol) was added, and the mixture was stirred at RT ON. The reaction mixture was concentrated under a gentle stream of nitrogen, dissolved in DMF, and filtered through a 0.45 m PTFE frit. The crude material was purified via preparative LCMS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 9% B, 9-49% B over 20 min, then a 0-mine hold at 100% B; Flow Rate: 20 mL/min; Column Temperature: 25° C. Fraction collection was triggered by MS and UV signals. Fractions containing the desired product were combined and dried via centrifugal evaporation to yield 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide enantiomeric mixture 2, 2 TFA (6.8 mg, 0.0094 mmol, 19% yield).

$^1$H NMR (500 MHz, DMSO-d$_6$) δ 9.03 (br t, J=5.3 Hz, 1H), 8.61 (d, J=7.0 Hz, 1H), 7.71 (t, J=8.4 Hz, 1H), 7.52-7.47 (m, 2H), 7.42 (s, 4H), 7.04 (br d, J=6.9 Hz, 1H), 6.06 (s, 2H), 4.86-4.76 (m, 1H), 4.75-4.57 (m, 1H), 3.61 (br s, 2H).

MS ESI/APCI m/z 491.9 [M+H]$^+$

Example 130: 3-(2-amino-[1,2,4]triazolo[1,5-a]pyridin-7-yl)-6-chloro-N-(3-(4-fluorophenyl)-2-fluoro-3-hydroxypropyl)-2-fluorobenzamide enantiomeric mixture 1

enantiomeric mixture 1

130A: A mixture of ethyl 2-chloro-2-fluoroacetate (5.1 mL, 44.3 mmol), 4-fluorobenzaldehyde (4.3 mL, 40.3 mmol) and zinc (3.69 g, 56.4 mmol) in DMF (101 mL) was heated to 80° C. in an oil bath for 12 h. The reaction mixture was filtered through a pad of celite, and 1 N HCl was added. The aqueous layer was extracted with ethyl acetate 3×. The combined organic layers were washed with brine, dried over anhydrous sodium sulfate, filtered and concentrated in vacuo to a residue. The residue was purified by silica gel flash column chromatography (elution gradient 0-15% ethyl acetate in hexanes) to give ethyl 2-fluoro-3-(4-fluorophenyl)-3-hydroxypropanoate (2.00 g, 8.69 mmol, 22% yield).

$^1$H NMR (500 MHz, CDCl$_3$) δ 7.42-7.34 (m, 2H), 7.11-7.03 (m, 2H), 5.18-5.08 (m, 1H), 5.08-4.92 (m, 1H), 4.30-4.16 (m, 2H), 2.87-2.65 (m, 1H), 1.61-1.57 (m, 1H), 1.29-1.19 (m, 3H).

130B: 2-fluoro-3-(4-fluorophenyl)-3-hydroxypropanamide: To a solution of ethyl 2-fluoro-3-(4-fluorophenyl)-3-hydroxypropanoate (850 mg, 3.69 mmol) in methanol (9.2 mL) at RT was added ammonia, 7M solution in methanol (2.6 mL, 18.5 mmol), and the resulting mixture was stirred at RT for 12 h. Solvents were removed in vacuo to give 2-fluoro-3-(4-fluorophenyl)-3-hydroxypropanamide (750 mg, 3.73 mmol, 101% yield) as a white solid. A 1:1 a mixture of two diastereomers was obtained. This material was used directly for the next step.

MS ESI/APCI m/z 200.1 [M−H]$^-$

130C: 3-amino-1-(4-fluorophenyl)-2-fluoropropan-1-ol: To a solution of 2-fluoro-3-(4-fluorophenyl)-3-hydroxypropanamide (160 mg, 0.795 mmol) in THF (1.6 mL) was added borane-dimethylsulfide complex, 2M in THF (1.2 mL, 2.386 mmol), and the reaction mixture was heated under reflux for 2 h. After cooling, methanol was added, and the reaction mixture was stirred at RT for 30 min. Methanol was removed in vacuo, and the residue was azeotroped with methanol (3×) to remove boric acid to give 3-amino-2-fluoro-1-(4-fluorophenyl)propan-1-ol (150 mg, 0.801 mmol, 101% yield) as a colorless oil. This material was used directly for the next step.

MS ESI/APCI m/z 187.9 [M+H]$^+$ 130D-1: 3-bromo-6-chloro-N-(3-(4-fluorophenyl)-2-fluoro-3-hydroxypropyl)-2-fluorobenzamide enantiomeric mixture 1: A solution of 3-bromo-6-chloro-2-fluorobenzoic acid (190 mg, 0.748 mmol), 3-amino-2-fluoro-1-(4-fluorophenyl)propan-1-1 (140 mg, 0.748 mmol), diisopropylethyl amine (196 μl, 1.12 mmol) and (benzotriazol-1-yloxytris(dimethylamino)phosphonium hexafluorophosphate) (397 mg, 0.897 mmol) in dichloromethane (2.5 mL) was stirred at RT for 3 h. The crude product was purified by preparative TLC on silica gel (0.50 mm thickness, elution 30% ethyl acetate in hexanes) to provide two separated mixtures of enantiomers. 3-Bromo-6-chloro-2-fluoro-N-(2-fluoro-3-(4-fluorophenyl)-3-hydroxypropyl)benzamide enantiomeric mixture 1 (63.0 mg, 0.149 mmol, 20% yield) was isolated as the less polar, faster eluting material on preparative silica TLC.

$^1$H NMR (500 MHz, CDCl$_3$) δ 7.60 (dd, J=8.6, 7.3 Hz, 1H), 7.44 (dd, J=8.7, 5.4 Hz, 2H), 7.19 (dd, J=8.6, 1.4 Hz, 1H), 7.10 (t, J=8.3 Hz, 2H), 6.36-6.27 (m, 1H), 4.89-4.82 (m, 1H), 4.71-4.55 (m, 1H), 4.31-4.16 (m, 1H), 3.88-3.81 (m, 1H), 3.78-3.67 (m, 1H).

MS ESI/APCI m/z 419.9 [M−H]$^-$ 130D-2: 3-bromo-6-chloro-N-(3-(4-fluorophenyl)-2-fluoro-3-hydroxypropyl)-2-fluorobenzamide enantiomeric mixture 2: 3-bromo-6-chloro-N-(3-(4-fluorophenyl)-2-fluoro-3-hydroxypropyl)-2-fluorobenzamide enantiomeric mixture 2 (67.0 mg, 0.159 mmol, 21% yield) was isolated as the more polar, slower eluting material on preparative silica TLC from the preparative TLC separation described for intermediate 130D-1.

$^1$H NMR (500 MHz, CDCl$_3$) δ 7.56 (t, J=7.9 Hz, 1H), 7.43 (t, J=6.7 Hz, 2H), 7.19-7.02 (m, 3H), 6.28 (br s, 1H), 4.90 (dd, J=17.5, 5.3 Hz, 1H), 4.86-4.69 (m, 1H), 3.94-3.49 (m, 2H).

MS ESI/APCI m/z 419.8 [M−H]$^-$

130: In a 1 dram vial equipped with a stir bar were combined 3-bromo-6-chloro-N-(3-(4-fluorophenyl)-2-fluoro-3-hydroxypropyl)-2-fluorobenzamide enantiomeric mixture 1 (23 mg, 0.054 mmol), N,N-bis-Boc-2-amino-7-(4,4,5,5-tetramethyl-1,3,2-dioxaborolan-2-yl)-[1,2,4]triazolo[1,5-a]pyridine (30.1 mg, 0.065 mmol), potassium phosphate tribasic, 2M aqueous solution (82.1 μL, 0.163 mmol), and [1,1'-bis(diphenylphosphino)ferrocene]dichloropalladium(II) complex with dichloromethane (2.2 mg, 2.7 μmol) in 1,4-dioxane (270 μL) to give a brown suspension. The reaction mixture was degassed by evacuating and backfilling with nitrogen (3×). The vial was sealed and heated to 60° C. for 2 h. Hydrogen chloride solution (4M in 1,4-dioxane, 204 μL, 0.82 mmol) was added and the resulting mixture was stirred at RT ON. The reaction mixture was concentrated under a gentle stream of nitrogen. The residue was dissolved in DMF and filtered through a 0.45 um PTFE frit. The crude material was purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 9% B, 9-49% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield 3-(2-amino-[1,2,4]triazolo[1,5-a]pyridin-7-yl)-6-chloro-2-fluoro-N-(2-fluoro-3-(4-fluorophenyl)-3-hydroxypropyl)benzamide enantiomeric mixture 1 (8.4 mg, 0.018 mmol, 32% yield).

$^1$H NMR (500 MHz, DMSO-d$_6$) δ 9.05-8.99 (m, 1H), 8.61 (br d, J=7.0 Hz, 1H), 7.71 (br t, J=8.2 Hz, 1H), 7.54-7.42 (m, 4H), 7.18 (t, J=8.3 Hz, 2H), 7.04 (br d, J=7.0 Hz, 1H), 6.06 (s, 2H), 4.87-4.71 (m, 1H), 4.71-4.51 (m, 1H).

MS ESI/APCI m/z 475.9 [M+H]$^+$

Example 131: 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide enantiomeric mixture 2

enantiomeric mixture 2

In a 1 dram vial equipped with a stir bar were combined 3-bromo-6-chloro-N-(3-(4-fluorophenyl)-2-fluoro-3-hydroxypropyl)-2-fluorobenzamide enantiomeric mixture 2 (23 mg, 0.054 mmol), N,N-bis-Boc-2-amino-7-(4,4,5,5-tetramethyl-1,3,2-dioxaborolan-2-yl)-[1,2,4]triazolo[1,5-a]pyridine (30.1 mg, 0.065 mmol), potassium phosphate tribasic, 2M aqueous solution (82.1 µL, 0.163 mmol) and 1,1'-bis(diphenylphosphino)ferrocene]dichloropalladium(II) complex with dichloromethane (2.2 mg, 2.7 µmol) in 1,4-dioxane (270 µL) to give a brown suspension. The reaction mixture was degassed by evacuating and backfilling with nitrogen (3×). The vial was sealed and heated to 60° C. for 2 h. Hydrogen chloride solution (4M in 1,4-dioxane, 204 µL, 0.82 mmol) was added and the resulting mixture was stirred at RT ON. The reaction mixture was concentrated under a gentle stream of nitrogen, dissolved in DMF and filtered through a 0.45 um PTFE frit. The crude material was purified via preparative LCMS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.10% trifluoroacetic acid; Gradient: a 0-min hold at 5% B, 5-45% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield 3-(2-amino-[1,2,4]triazolo[1,5-a]pyridin-7-yl)-6-chloro-2-fluoro-N-(2-fluoro-3-(4-fluorophenyl)-3-hydroxypropyl)benzamide enantiomeric mixture 2, 2 TFA (4.8 mg, 0.0068 mmol, 11% yield).

$^1$H NMR (500 MHz, DMSO-d$_6$) δ 9.03 (br s, 1H), 8.63 (d, J=7.0 Hz, 1H), 7.71 (t, J=8.2 Hz, 1H), 7.57-7.39 (m, 4H), 7.25 (d, J=3.6 Hz, 1H), 7.22-7.13 (m, 3H), 7.12-7.00 (m, 2H), 4.84-4.76 (m, 1H), 4.74-4.57 (m, 1H).

MS ESI/APCI m/z 475.9 [M+H]$^+$

Example 132: (S)-3-(2-amino-8-fluoro-[1,2,4]triazolo[1,5-a]pyridin-7-yl)-N-(3-(4-chlorophenyl)-3-hydroxypropyl)-2-fluoro-6-methylbenzamide

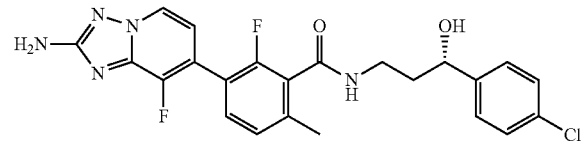 [SMILES: Cc1ccc(-c2ccn3nc(N)nc3c2F)c(F)c1C(=O)NCC[C@H](O)c1ccc(Cl)cc1]

132A: (S)-3-bromo-N-(3-(4-chlorophenyl)-3-hydroxypropyl)-2-fluoro-6-methylbenzamide: An 8 mL reaction vial was charged with a stir bar and BOP (197 mg, 0.446 mmol). The flask was evacuated and backfilled with nitrogen, followed by the addition of DMF (3.43 mL), N,N-diisopropylethylamine (239 µl, 1.37 mmol), 3-bromo-2-fluoro-6-methylbenzoic acid (80.0 mg, 0.343 mmol) and (S)-3-amino-1-(4-chlorophenyl)propan-1-ol, HCl (91.0 mg, 0.412 mmol). The resulting mixture was stirred at RT for 3 d. The reaction mixture was diluted with aqueous LiCl (30 mL, 10% w/w), and extracted with EtOAc (30 mL×2). The combined organic phase was washed with H$_2$O (50 mL×2) and brine (50 mL), dried with anhydrous MgSO$_4$ and filtered through celite. The crude mixture was concentrated in vacuo. A 12 g silica gel cartridge was prewetted with 4% Et$_3$N in hexane (50 mL). The crude material was purified by flash column chromatography (gradient EtOAc in Hex 0% to 50%, then 50% hold, 12 g pretreated silica), affording (S)-3-bromo-N-(3-(4-chlorophenyl)-3-hydroxypropyl)-2-fluoro-6-methylbenzamide (120 mg, 0.299 mmol, 87% yield).

$^1$H NMR (500 MHz, CDCl$_3$) δ 7.46 (dd, J=8.0, 7.3 Hz, 1H), 7.32 (m, 4H), 6.92 (d, J=8.1 Hz, 1H), 6.32 (br s, 1H), 4.84 (dt, J=9.3, 3.5 Hz, 1H), 3.95-3.87 (m, 1H), 3.43 (dq, J=14.1, 5.2 Hz, 1H), 3.10 (d, J=3.5 Hz, 1H), 2.37 (s, 3H), 2.03-1.87 (m, 2H).

MS ESI m/z 382.00 and 384.00 (M-OH)$^+$

132B: 8-fluoro-7-iodo-[1,2,4]triazolo[1,5-a]pyridin-2-amine: A 20 mL reaction vial was charged with a stir bar and 3-fluoro-4-iodopyridin-2-amine (1.00 g, 4.20 mmol). The flask was evacuated and backfilled with nitrogen, followed by the addition of 1,4-dioxane (10.5 mL), DCM (10.5 mL) and ethoxycarbonyl isothiocyanate (0.74 ml, 6.30 mmol). The resulting mixture was stirred at RT for 3 d. The mixture was concentrated in vacuo. The crude was purified by flash column chromatography (gradient EtOAc in Hex, 0% to 100%; 12 g silica), affording a thiourea intermediate (1.50 g, 4.06 mmol).

A 250 mL round-bottom flask was charged with a stir bar, the thiourea intermediate (1.50 g, 4.06 mmol) and hydroxyamine hydrochloride (1.41 g, 20.3 mmol). The flask was evacuated and backfilled with nitrogen, followed by the addition of ethanol (27 mL) and DIPEA (2.1 mL, 12.2 mmol). The resulting mixture was stirred at RT for 15 min and then at 80° C. for 16 h. The reaction mixture was concentrated in vacuo, diluted with 10 mL of DMSO, filtered, and the filtrate was purified by reverse phase HPLC column chromatography (Solvent A: 10% acetonitrile, 90% H$_2$O, 0.10% NH$_4$OAc; Solvent B: 90% acetonitrile, 10% H$_2$O, 0.1% NH$_4$OAc; gradient 0% to 50% B, then hold 100% B) to afford 8-fluoro-7-iodo-[1,2,4]triazolo[1,5-a]pyridin-2-amine (0.500 g, 1.80 mmol, 44% yield).

$^1$H NMR (500 MHz, DMSO-d$_6$) δ 8.25 (d, J=6.9 Hz, 1H), 7.18 (dd, J=6.9, 5.5 Hz, 1H), 6.26 (s, 2H).

MS ESI m/z 278.85 (M+H)$^+$

132C: (2-amino-8-fluoro-[1,2,4]triazolo[1,5-a]pyridin-7-yl)boronic acid: A 20 mL reaction vial was charged with a stir bar, 8-fluoro-7-iodo-[1,2,4]triazolo[1,5-a]pyridin-2-amine (0.100 g, 0.360 mmol), [1,1' bis(diphenylphosphino)ferrocene]dichloro-palladium(II), complex with dichloromethane (0.030 g, 0.036 mmol), bis(pinacolato)diboron (0.240 g, 0.936 mmol) and potassium acetate (0.212 g, 2.16 mmol). The vial was evacuated and backfilled with nitrogen, followed by the addition of 1,4-dioxane (3.6 mL). The resulting mixture was stirred at 80° C. for 4 d. The mixture was diluted with 1,4-dioxane (to give a total volume of 7.2 mL) and directly used in the next step without further purification.

132: An 8 mL reaction vial was charged with a stir bar, (S)-3-bromo-N-(3-(4-chlorophenyl)-3-hydroxypropyl)-2-fluoro-6-methylbenzamide (26.4 mg, 0.0660 mmol), PdCl$_2$(dtbpf) (3.91 mg, 6.00 µmol), and (2-amino-8-fluoro-[1,2,4]triazolo[1,5-a]pyridin-7-yl)boronic acid (1/6 aliquot from the crude mixture, 1.2 mL, 0.060 mmol assumed) in 1,4-dioxane, followed by the addition of potassium phosphate (150 µL, 2M in H$_2$O, 0.300 mmol). The resulting mixture was degassed by bubbling N2 through the solution for 5 min, then the mixture was stirred at 80° C. for 3 h. The mixture was concentrated in vacuo, diluted with 2 mL DMSO and filtered. The crude filtrate was purified via preparative LCMS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 12% B, 12-52% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (S)-3-(2-amino-8-fluoro-[1,2,4]triazolo[1,5-a]pyridin-7-yl)-N-(3-(4-chlorophenyl)-3-hydroxypropyl)-2-fluoro-6-methylbenzamide (7.0 mg, 0.015 mmol, 25% yield).

¹H NMR (500 MHz, DMSO-d₆) δ 8.63 (br t, J=5.3 Hz, 1H), 8.53 (d, J=6.9 Hz, 1H), 7.48 (t, J=7.8 Hz, 1H), 7.43-7.33 (m, 4H), 7.25 (d, J=8.0 Hz, 1H), 6.88 (t, J=6.7 Hz, 1H), 6.36-6.18 (m, 2H), 5.39 (d, J=4.5 Hz, 1H), 4.72-4.58 (m, 1H), 3.40-3.31 (m, 1H), 2.33 (s, 3H), 1.81 (q, J=6.9 Hz, 2H).

MS ESI m/z 471.93 (M+H)⁺

TABLE 9

Compounds in Table 9 were prepared in a similar fashion to example 132.

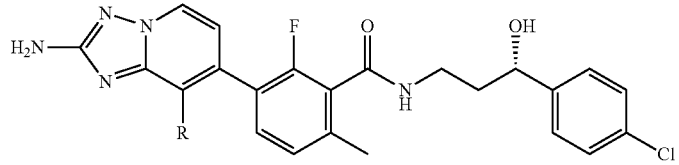

| Ex No | Name | R | M + H⁺ | ¹H NMR (500 MHz, DMSO-d6) δ |
|---|---|---|---|---|
| 133 | 3-{2-amino-8-methoxy-[1,2,4]triazolo[1,5-a]pyridin-7-yl}-N-[(3S)-3-(4-chlorophenyl)-3-hydroxypropyl]-2-fluoro-6-methylbenzamide | OMe | 484.0 | 8.60 (br t, J = 5.0 Hz, 1H), 8.36 (d, J = 7.0 Hz, 1H), 7.44-7.31 (m, 5H), 7.18 (d, J = 7.9 Hz, 1H), 6.73 (d, J = 6.7 Hz, 1H), 6.11 (s, 2H), 4.66 (br s, 1H), 4.09 (s, 3H), 3.39-3.24 (m, 2H), 2.32 (s, 3H), 1.81 (q, J = 6.8 Hz, 2H) |
| 134 | 3-{2-amino-8-methyl-[1,2,4]triazolo[1,5-a]pyridin-7-yl}-N-[(3S)-3-(4-chlorophenyl)-3-hydroxypropyl]-2-fluoro-6-methylbenzamide | Me | 468.0 | 8.63 (br t, J = 5.3 Hz, 1H), 8.44 (d, J = 7.0 Hz, 1H), 7.45-7.28 (m, 5H), 7.21 (d, J = 7.7 Hz, 1H), 6.71 (d, J = 7.0 Hz, 1H), 6.05 (s, 2H), 4.65 (br s, 1H), 3.44-3.22 (m, 2H), 2.33 (s, 3H), 2.25 (s, 3H), 1.80 (q, J = 6.7 Hz, 2H) |

TABLE 10

Compounds in Table 10 were prepared in a similar fashion to example 132. 3-amino-2,2-difluoro-1-(4-fluorophenyl)propan-1-ol was substituted for (S)-3-amino-1-(4-chlorophenyl)propan-1-ol, HCl in the first step of the sequence (formation of intermediate 132A). Additionally, examples 135 and 136 were separated from a racemate via chiral SFC chromatography (Waters 100 Prep SFC, Column: Chiral OJ, 30 × 250 mm. 5 micron, Mobile Phase: 80% CO2/20% MeOH w/0.1% DEA, Flow Conditions: 100 mL/min, Detector Wavelength: 220 nm). Also, examples 137 and 138 were separated from a racemate via chiral SFC chromatography (Waters 100 Prep SFC, Column: Chiral IC, 21 × 250 mm. 5 micron, Mobile Phase: 65% CO2/35% MeOH w/0.1% DEA, Flow Conditions: 60 mL/min, Detector Wavelength: 220 nm).

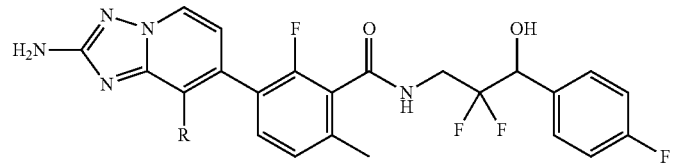

| Ex No | Name | R | M + H⁺ | ¹H NMR (500 MHz, DMSO-d6) δ |
|---|---|---|---|---|
| 135 | 3-(2-amino-8-methoxy-[1,2,4]triazolo[1,5-a]pyridin-7-yl)-N-(2,2-difluoro-3-(4-fluorophenyl)-3-hydroxypropyl]-2-fluoro-6-methylbenzamide enantiomer 1 | R = OMe first eluting enantiomer | 504.1 | 8.93 (br t, J = 6.1 Hz, 1H), 8.35 (d, = 6.7 Hz, 1H), 7.47 (br dd, J = 7.9, 6.1 Hz, 2H), 7.35 (t, J = 7.6 Hz, 1H), 7.25-7.12 (m, 3H), 6.71 (d, J = 6.7 Hz, 1H), 6.38 (d, J = 5.5 Hz, 1H), 6.09 (s, 2H), 5.00-4.82 (m, 1H), 4.08 (s, 3H), 3.95-3.73 (m, 2H), 2.30 (s, 3H) |
| 136 | 3-(2-amino-8-methoxy-[1,2,4]triazolo[1,5- | R = OMe second eluting enantiomer | 504.1 | 8.99-8.87 (m, 1H), 8.35 (d, J = 6.7 Hz, 1H), 7.47 (br t, J = 6.7 Hz, 2H), 7.35 (br t, |

TABLE 10-continued

Compounds in Table 10 were prepared in a similar fashion to example 132. 3-amino-2,2-difluoro-1-(4-fluorophenyl)propan-1-ol was substituted for (S)-3-amino-1-(4-chlorophenyl)propan-1-ol, HCl in the first step of the sequence (formation of intermediate 132A). Additionally, examples 135 and 136 were separated from a racemate via chiral SFC chromatography (Waters 100 Prep SFC, Column: Chiral OJ, 30 × 250 mm. 5 micron, Mobile Phase: 80% CO2/20% MeOH w/0.1% DEA, Flow Conditions: 100 mL/min, Detector Wavelength: 220 nm). Also, examples 137 and 138 were separated from a racemate via chiral SFC chromatography (Waters 100 Prep SFC, Column: Chiral IC, 21 × 250 mm. 5 micron, Mobile Phase: 65% CO2/35% MeOH w/0.1% DEA, Flow Conditions: 60 mL/min, Detector Wavelength: 220 nm).

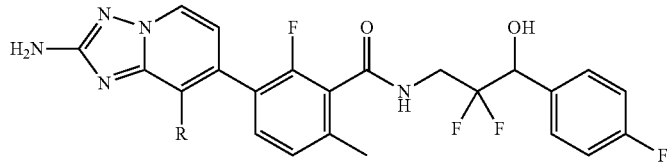

| Ex No | Name | R | M + H+ | 1H NMR (500 MHz, DMSO-d6) δ |
|---|---|---|---|---|
| | a]pyridin-7-yl)-N-(2,2-difluoro-3-(4-fluorophenyl)-3-hydroxypropyl]-2-fluoro-6-methylbenzamide enantiomer 2 | | | J = 7.9 Hz, 1H), 7.28-7.10 (m, 3H), 6.72 (br d, J = 6.7 Hz, 1H), 6.40 (br d, J = 4.9 Hz, 1H), 6.09 (s, 2H), 4.99-4.82 (m, 1H), 4.07 (s, 3H), 3.95-3.72 (m, 2H), 2.30 (s, 3H) |
| 137 | 3-(2-amino-8-fluoro-[1,2,4]triazolo[1,5-a]pyridin-7-yl)-N-(2,2-difluoro-3-(4-fluorophenyl)-3-hydroxypropyl]-2-fluoro-6-methylbenzamide enantiomer 1 | R = F first eluting enantiomer | 492.0 | 9.15 (br s, 1H), 8.71 (br dd, J = 6.9, 2.9 Hz, 1H), 7.66 (br d, J = 4.9 Hz, 3H), 7.51-7.28 (m, 3H), 7.14-6.97 (m, 1H), 6.58 (br dd, J = 5.0, 2.3 Hz, 1H), 6.46 (br s, 2H), 5.21-4.97 (m, 1H), 4.19-3.98 (m, 2H) |
| 138 | 3-{2-amino-8-methyl-[1,2,4]triazolo[1,5-a]pyridin-7-yl}-N-[(3S)-3-(4-chlorophenyl)-3-hydroxypropyl]-2-fluoro-6-methylbenzamide enantiomer 2 | R = F second eluting enantiomer | 492.0 | 9.15 (br t, J = 6.0 Hz, 1H), 8.71 (d, J = 6.7 Hz, 1H), 7.73-7.61 (m, 3H), 7.50-7.33 (m, 3H), 7.06 (t, J = 6.6 Hz, 1H), 6.58 (d, J = 4.9 Hz, 1H), 6.46 (s, 2H), 5.20-4.95 (m, 1H), 4.15-3.88 (m, 2H) |

Example 139: 3-{2-amino-[1,2,4]triazolo[1,5-a]pyridin-7-yl}-N-[(3S)-3-(4-cyanophenyl)-3-hydroxypropyl]-2-fluoro-6-methylbenzamide

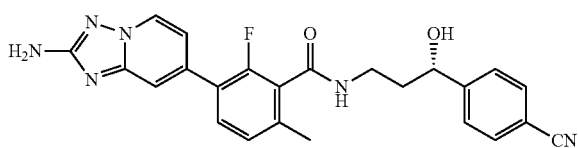 [SMILES: Cc1ccc(-c2ccn3nc(N)nc3c2)c(F)c1C(=O)NCC[C@H](O)c1ccc(C#N)cc1]

A 8 mL reaction vial was charged with a stir bar, (S)-3-(2-amino-[1,2,4]triazolo[1,5-a]pyridin-7-yl)-N-(3-(4-chlorophenyl)-3-hydroxypropyl)-2-fluoro-6-methylbenzamide (22.7 mg, 0.050 mmol), potassium ferrocyanide trihydrate (10.6 mg, 0.0250 mmol), 2nd generation XPhos precatalyst (3.93 mg, 5.00 µmol) and XPhos (2.38 mg, 5.00 µmol). The flask was evacuated and backfilled with nitrogen three times, followed by the addition of degassed 1,4-dioxane (0.3 mL) and degassed aqueous potassium acetate solution (0.30 mL, 0.1M in H$_2$O, 0.030 mmol). The resulting mixture was stirred at 100° C. for 1 h. The reaction mixture was diluted with DCM (10 mL) and iPrOH (5 mL), washed with H$_2$O (10 mL) and brine (10 mL), dried with anhydrous MgSO$_4$ and filtered through celite. The crude mixture was concentrated in vacuo, redissolved in 2 mL DMF and filtered. The crude filtrate was purified via preparative LCMS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-46% B over 20 minutes, then a 0-minute hold at 100% B; Flow Rate: 20 mL/min; Column Temperature: 25 C. Fraction collection was triggered by UV signals. Fractions containing the desired product were combined and dried via centrifugal evaporation to afford (S)-3-(2-amino-[1,2,4]triazolo[1,5-a]pyridin-7-yl)-N-(3-(4-cyanophenyl)-3-hydroxypropyl)-2-fluoro-6-methylbenzamide (11.8 mg, 0.0265 mmol, 51% yield).

$^1$H NMR (600 MHz, DMSO-d$_6$) δ 8.69 (br t, J=5.1 Hz, 1H), 8.56 (d, J=7.0 Hz, 1H), 7.77 (d, J=7.7 Hz, 2H), 7.58-7.49 (m, 3H), 7.47 (s, 1H), 7.21 (d, J=8.1 Hz, 1H), 7.06 (br d, J=6.6 Hz, 1H), 6.03 (s, 2H), 5.83-5.71 (m, 1H), 4.78-4.67 (m, 1H), 3.41-3.25 (m, 2H), 2.28 (s, 3H), 1.91-1.74 (m, 2H).

MS ESI m/z 445.3 (M+H)+

TABLE 11

Compounds in Table 11 were prepared in a similar fashion to example 139 from corresponding aryl chlorides.

![Core structure with H2N-triazolopyridine-phenyl(F)(methyl)-C(O)NH-CH2CH2-R]

| Ex No | Name | R | M + H+ | 1H NMR (600 MHz, DMSO-d6) δ |
|---|---|---|---|---|
| 140 | 3-{2-amino-[1,2,4]triazolo[1,5-a]pyridin-7-yl}-N-[3-(3-cyanophenyl)-3-hydroxypropyl]-2-fluoro-6-methylbenzamide | CH(OH)-(3-cyanophenyl), racemate | 445.1 | 8.70-8.54 (m, 2H), 7.77 (br s, 1H), 7.74-7.65 (m, 2H), 7.60-7.53 (m, 2H), 7.48 (br s, 1H), 7.22 (br dd, J = 7.7, 4.0 Hz, 1H), 7.04 (br d, J = 5.1 Hz, 1H), 6.07 (br s, 2H), 5.68-5.58 (m, 1H), 4.72 (br d, J = 4.8 Hz, 1H), 3.31-3.21 (m, 2H), 2.30 (br d, J = 4.0 Hz, 3H), 1.89-1.79 (m, 2H) |
| 141 | 3-{2-amino-[1,2,4]triazolo[1,5-a]pyridin-7-yl}-N-[3-(4-cyanophenyl)-3-hydroxybutyl]-2-fluoro-6-methylbenzamide | C(CH3)(OH)-(4-cyanophenyl), racemate | 459.1 | 8.58 (d, J = 7.0 Hz, 1H), 8.48 (br t, J = 5.5 Hz, 1H), 7.80 (d, J = 8.4 Hz, 2H), 7.66 (d, J = 8.4 Hz, 2H), 7.54 (br t, J = 8.1 Hz, 1H), 7.46 (s, 1H), 7.19 (d, J = 8.1 Hz, 1H), 7.02 (br d, J = 7.0 Hz, 1H), 6.07 (s, 2H), 2.98-2.88 (m, 2H), 2.25 (s, 3H), 2.04-1.91 (m, 2H), 1.48 (s, 3H) |

Example 142: 3-{2-amino-[1,2,4]triazolo[1,5-a]pyridin-7-yl}-N-[(3S)-3-(4-ethynylphenyl)-3-hydroxypropyl]-2-fluoro-6-methylbenzamide

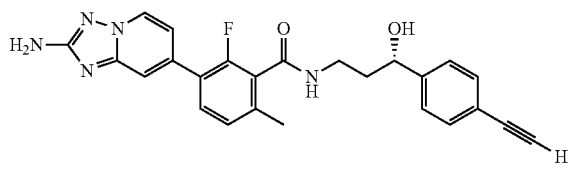 [SMILES: C#Cc1ccc([C@@H](O)CCNC(=O)c2c(C)ccc(-c3ccn4nc(N)nc4c3)c2F)cc1]

An 8 mL vial was charged with a stir bar, (S)-3-(2-amino-[1,2,4]triazolo[1,5-a]pyridin-7-yl)-N-(3-(4-chlorophenyl)-3-hydroxypropyl)-2-fluoro-6-methylbenzamide (22 mg, 0.048 mmol), cesium carbonate (39.5 mg, 0.121 mmol), XPhos (6.93 mg, 0.0150 mmol), and Xphos 2nd generation Pd catalyst (7.63 mg, 9.69 μmol). The flask was evacuated and backfilled with nitrogen, followed by the addition of acetonitrile (969 μl) and trimethylsilylacetylene (68.0 μL, 0.485 mmol). The resulting mixture was stirred at RT for 5 min and then at 90° C. for 3 h. LCMS showed di-silylated alkyne product as the major component. The mixture was concentrated and purified by preparative TLC (elution 5% MeOH in EtOAc). The product was not stable on silica and decomposed to two components. The crude material was recovered and purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 9% B, 9-49% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (S)-3-(2-amino-[1,2,4]triazolo[1,5-a]pyridin-7-yl)-N-(3-(4-ethynylphenyl)-3-hydroxypropyl)-2-fluoro-6-methylbenzamide (0.70 mg, 0.0016 mmol, 3.3% yield).

MS ESI m/z 444.0 (M+H)+

Example 143: 3-{2-amino-[1,2,4]triazolo[1,5-a]pyridin-7-yl}-N-[3-(4-chlorophenyl)-3-oxopropyl]-2-fluoro-6-methylbenzamide

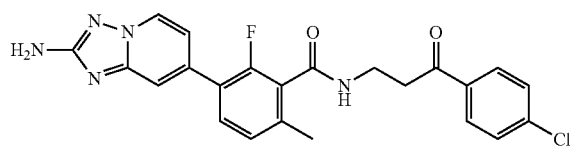 [SMILES: Cc1ccc(-c2ccn3nc(N)nc3c2)c(F)c1C(=O)NCCC(=O)c1ccc(Cl)cc1]

An 8 mL-reaction vial was charged with a stir bar and sulfur trioxide pyridine complex (75.0 mg, 0.474 mmol). The flask was evacuated and backfilled with nitrogen, followed by the addition of DMSO (1.4 mL). The resulting mixture was stirred at RT for 30 min. A separate 8 mL reaction vial was charged with a stir bar, (S)-3-(2-amino-[1,2,4]triazolo[1,5-a]pyridin-7-yl)-N-(3-(4-chlorophenyl)-3-hydroxypropyl)-2-fluoro-6-methylbenzamide (43 mg, 0.095 mmol), triethylamine (0.13 mL, 0.947 mmol), and DMSO (0.6 mL), followed by addition of the prepared solution of SO3-pyridine in DMSO slowly via a syringe. The resulting mixture was stirred at RT for 2.5 h. The reaction was quenched by addition of iPrOH. The mixture was diluted with EtOAc (50 mL), washed with H2O (50 mL) and brine (50 mL), dried with anhydrous MgSO4 and filtered through celite. The crude was concentrated in vacuo and purified by preparative TLC (5% MeOH in DCM) to afford 3-(2-amino-[1,2,4]triazolo[1,5-a]pyridin-7-yl)-N-(3-(4- chlorophenyl)-3-oxopropyl)-2-fluoro-6-methylbenzamide (13.7 mg, 0.0300 mmol, 32% yield).

¹H NMR (500 MHz, DMSO-d6) δ 8.67 (s, 1H), 8.60 (d, J=7.0 Hz, 1H), 8.03-7.95 (m, 2H), 7.65-7.59 (m, 2H), 7.59-7.54 (m, 1H), 7.47 (s, 1H), 7.19 (d, J=8.2 Hz, 1H), 7.01 (d, J=7.0 Hz, 1H), 6.07 (s, 2H), 4.62-4.56 (m, 4H), 2.27 (s, 3H).

MS ESI m/z 452.0 (M+H)⁺

Example 144: (S)-5-(2-amino-[1,2,4]triazolo[1,5-a]pyridin-7-yl)-4-chloro-N-(3-(4-chlorophenyl)-3-hydroxypropyl)-2-methylbenzamide

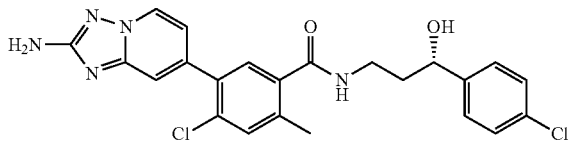 [SMILES: Cc1cc(Cl)c(-c2ccn3nc(N)nc3c2)cc1C(=O)NCC[C@H](O)c1ccc(Cl)cc1]

144A: methyl 5-(2-amino-[1,2,4]triazolo[1,5-a]pyridin-7-yl)-4-chloro-2-methylbenzoate: A mixture of 7-bromo-[1,2,4]triazolo[1,5-a]pyridin-2-amine (256 mg, 1.20 mmol), 4,4,4',4',5,5,5',5'-octamethyl-2,2'-bi(1,3,2-dioxaborolane) (366 mg, 1.44 mmol), PdCl₂(dppf)-CH₂Cl₂ adduct (49.0 mg, 0.0600 mmol) and potassium acetate (294 mg, 3.00 mmol) in 1,4-dioxane (5 mL) was stirred at 110-115° C. for 2 h. To the mixture was added methyl 4-chloro-5-iodo-2-methylbenzoate (298 mg, 0.960 mmol) followed by PdCl₂(dppf)-CH₂Cl₂ adduct (49.0 mg, 0.0600 mmol) and 2.0 M tripotassium phosphate/water (1.50 mL, 3.00 mmol). The mixture was refluxed for 2 h. Water was added, and the solid was collected by to give methyl 5-(2-amino-[1,2,4]triazolo[1,5-a]pyridin-7-yl)-4-chloro-2-methylbenzoate (300 mg, 0.947 mmol, 79% yield).

MS ESI m/z 317.2 (M+H)⁺

144B: lithium 5-(2-amino-[1,2,4]triazolo[1,5-a]pyridin-7-yl)-4-chloro-2-methylbenzoate: To a solution of methyl 5-(2-amino-[1,2,4]triazolo[1,5-a]pyridin-7-yl)-4-chloro-2-methylbenzoate (300 mg, 0.947 mmol) in THF (5 mL) was added a solution of lithium hydroxide hydrate (50 mg, 1.2 mmol) in water (1 mL). The mixture was stirred at RT ON. The mixture was concentrated under reduced pressure to give a crude lithium salt of 5-(2-amino-[1,2,4]triazolo[1,5-a]pyridin-7-yl)-4-chloro-2-methylbenzoic acid (242 mg, 0.947 mmol, 100% yield). The material was used as-is in the next step.

MS ESI m/z 303.2 (M+H)⁺

144: To a mixture of crude lithium 5-(2-amino-[1,2,4]triazolo[1,5-a]pyridin-7-yl)-4-chloro-2-methylbenzoate (30.3 mg, 0.100 mmol) in DMF (0.5 mL) was added BOP (53.1 mg, 0.120 mmol) followed by DIPEA (0.035 mL, 0.200 mmol). After stirring at RT for 10 min, (S)-3-amino-1-(4-chlorophenyl)propan-1-ol hydrochloride (26.7 mg, 0.120 mmol) was added. The mixture was stirred at RT ON. DMF/MeOH was added and solids were filtered away and discarded. The crude filtrate was purified via preparative LCMS with the following conditions: Column: XBridge C18, 200 mm×30 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 14% B, 14-54% B over 20 min, then a 0-min hold at 100% B; Flow Rate: 45 mL/min; Column Temperature: 25° C. Fraction collection was triggered by MS signals. Fractions containing the desired product were combined and dried via centrifugal evaporation to give (S)-5-(2-amino-[1,2,4]triazolo[1,5-a]pyridin-7-yl)-4-chloro-N-(3-(4-chlorophenyl)-3-hydroxypropyl)-2-methylbenzamide (18.8 mg, 0.040 mmol, 40% yield).

¹H NMR (500 MHz, DMSO-d₆) δ 8.63 (d, J=7.0 Hz, 1H), 8.39 (br t, J=5.0 Hz, 1H), 7.52 (s, 1H), 7.45 (s, 1H), 7.41 (s, 1H), 7.37 (s, 4H), 7.02 (dd, J=6.7, 1.5 Hz, 1H), 4.64 (br t, J=6.3 Hz, 1H), 3.33-3.26 (m, 2H), 2.39 (s, 3H), 1.83 (q, J=6.7 Hz, 2H).

MS ESI m/z 470.2 (M+H)⁺

Example 145: (S)-3-(2-amino-[1,2,4]triazolo[1,5-a]pyridin-7-yl)-2-chloro-N-(3-(4-chlorophenyl)-3-hydroxypropyl)-6-methylbenzamide

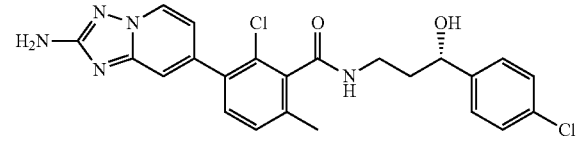

145A: 3-bromo-6-chloro-2-methylbenzoic acid and 3-bromo-2-chloro-6-methylbenzoic acid: 2-chloro-6-methylbenzoic acid (0.341 g, 2.0 mmol) was dissolved in concentrated sulfuric acid (2 mL). The mixture was chilled in an ice/brine water bath and 1,3-dibromo-5,5-dimethylhydantoin (0.286 g, 1.00 mmol) was added slowly. After the mixture was stirred at 0° C. for 30 min, ice was added to the mixture, and the resulting mixture was extracted with EtOAc. The organic layer was washed with water, dried over anhydrous sodium sulfate, then concentrated to give a crude mixture of 3-bromo-2-chloro-6-methylbenzoic acid and 3-bromo-6-chloro-2-methylbenzoic acid. The material was used as-is for the next step.

145B: methyl 3-bromo-2-chloro-6-methylbenzoate and methyl 3-bromo-6-chloro-2-methylbenzoate: To a solution of the crude mixture of 3-bromo-6-chloro-2-methylbenzoic acid and 3-bromo-2-chloro-6-methylbenzoic acid (499 mg, 2.00 mmol) in DMF (6 mL) was added potassium carbonate (553 mg, 4.00 mmol) followed by MeI (0.38 mL, 6.00 mmol). The mixture was stirred at RT ON. EtOAc (50 mL) was added and the organic phase was washed with brine and water, dried over anhydrous sodium sulfate, filtered and concentrated in vacuo. The residue was purified via silica gel flash column chromatography (24 g silica, gradient hexanes-10% EtOAc) to give an inseparable 4:1 ratio of mixture of methyl 3-bromo-6-chloro-2-methylbenzoate (360 mg, 1.37 mmol, 68% yield) and methyl 3-bromo-2-chloro-6-methylbenzoate (90 mg, 0.342 mmol, 17% yield), according to ¹H NMR analysis.

methyl 3-bromo-6-chloro-2-methylbenzoate: ¹H NMR (499 MHz, CDCl₃) δ 7.54 (d, J=8.6 Hz, 1H), 7.13 (d, J=8.6 Hz, 1H), 3.98 (s, 3H), 2.38 (s, 3H).

methyl 3-bromo-2-chloro-6-methylbenzoate: ¹H NMR (499 MHz, CDCl₃) δ 7.56 (d, J=8.2 Hz, 1H), 7.01 (d, J=8.2 Hz, 1H), 3.98 (s, 3H), 2.30 (s, 3H).

MS ESI m/z 265.1 (M+H)⁺

145C: methyl 2-chloro-6-methyl-3-(4,4,5,5-tetramethyl-1,3,2-dioxaborolan-2-yl)benzoate and methyl 6-chloro-2-methyl-3-(4,4,5,5-tetramethyl-1,3,2-dioxaborolan-2-yl)benzoate: To a solution of methyl 3-bromo-2-chloro-6-methylbenzoate (360 mg, 1.37 mmol) and methyl 3-bromo-6-chloro-2-methylbenzoate (90 mg, 0.342 mmol) in 1,4-dioxane (5 mL) was added 4,4,4',4',5,5,5',5'-octamethyl-2, 2'-bi(1,3,2-dioxaborolane) (520 mg, 2.05 mmol), PdCl$_2$(dppf)-CH$_2$Cl$_2$ adduct (112 mg, 0.137 mmol) and potassium acetate (402 mg, 4.10 mmol). The mixture was flushed with nitrogen then stirred at 110-115° C. for 3 h until LCMS indicated the starting material was consumed, and the desired boronate products were formed. The reaction mixture was used as-is for the next step.
MS ESI m/z 311.3 (M+H)$^+$ 145D: methyl 3-(2-amino-[1,2,4]triazolo[1,5-a]pyridin-7-yl)-2-chloro-6-methylbenzoate and methyl 3-(2-amino-[1,2,4]triazolo[1,5-a]pyridin-7-yl)-6-chloro-2-methylbenzoate:
To the reaction mixture of methyl 2-chloro-6-methyl-3-(4,4,5,5-tetramethyl-1,3,2-dioxaborolan-2-yl)benzoate (424 mg, 1.366 mmol) and methyl 6-chloro-2-methyl-3-(4,4,5,5-tetramethyl-1,3,2-dioxaborolan-2-yl)benzoate (106 mg, 0.342 mmol) was added 7-bromo-[1,2,4]triazolo[1,5-a]pyridin-2-amine (364 mg, 1.71 mmol), PdCl$_2$(dppf)-CH$_2$Cl$_2$ adduct (44.6 mg, 0.055 mmol) and 2M aqueous K$_3$PO$_4$ (2.1 mL, 4.10 mmol). After flushing with nitrogen for 5 min, the mixture was stirred at 115° C. for 1 h. Water (50 mL) was added, and the mixture was extracted with EtOAc (2×50 mL). The organic layer was dried over anhydrous sodium sulfate, filtered and concentrated under reduced pressure. The residue was purified via silica gel flash column chromatography (24 g silica, gradient DCM-10% MeOH in DCM) to give an inseparable mixture of methyl 3-(2-amino-[1,2,4]triazolo[1,5-a]pyridin-7-yl)-6-chloro-2-methylbenzoate (350 mg, 1.11 mmol, 81% yield) and methyl 3-(2-amino-[1,2,4]triazolo[1,5-a]pyridin-7-yl)-2-chloro-6-methylbenzoate (80 mg, 0.253 mmol, 18% yield).
MS ESI m/z 317.2 (M+H)$^+$ 145E: lithium 3-(2-amino-[1,2,4]triazolo[1,5-a]pyridin-7-yl)-2-chloro-6-methylbenzoate and lithium 3-(2-amino-[1,2,4]triazolo[1,5-a]pyridin-7-yl)-6-chloro-2-methylbenzoate:
To the mixture of methyl 3-(2-amino-[1,2,4]triazolo[1,5-a]pyridin-7-yl)-6-chloro-2-methylbenzoate (350 mg, 1.11 mmol) and methyl 3-(2-amino-[1,2,4]triazolo[1,5-a]pyridin-7-yl)-2-chloro-6-methylbenzoate (88 mg, 0.276 mmol) in THF (4 mL) was added a solution of LiOH (66.2 mg, 2.76 mmol) in water (1 mL). The reaction was stirred at RT ON, at 60° C. for 3 d, then at 85° C. for 1 d. The reaction mixture was concentrated to dryness under reduced pressure to give the crude mixture of the two lithium carboxylates. The crude residue was used as-is for the next step.
MS ESI m/z 303.2 (M+H)$^+$ 145: To a mixture of lithium 3-(2-amino-[1,2,4]triazolo[1,5-a]pyridin-7-yl)-6-chloro-2-methylbenzoate (30.3 mg, 0.1 mmol) and lithium 3-(2-amino-[1,2,4]triazolo[1,5-a]pyridin-7-yl)-2-chloro-6-methylbenzoate (7.57 mg, 0.025 mmol) in DMF (1 mL) was added BOP (88 mg, 0.200 mmol) followed by DIPEA (0.070 mL, 0.400 mmol). After stirring at RT for 10 min, (S)-3-amino-1-(4-chlorophenyl)propan-1-ol hydrochloride (44.4 mg, 0.200 mmol) was added. The reaction was stirred at RT ON. The reaction mixture was dissolved in DMF and filtered. The filtrate containing crude product was purified via preparative LCMS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-min hold at 18% B, 18-48% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation. The material was further purified via preparative LCMS with the following conditions: Column: XBridge C18, 200 mm×19 mm, 5-µm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 10% B, 10-50% B over 25 min, then a 0-min hold at 100% B; Flow Rate: 20 mL/min; Column Temperature: 25° C. Fraction collection was triggered by MS signals. Fractions containing the desired product were combined and dried via centrifugal evaporation to give the desired (S)-3-(2-amino-[1,2,4]triazolo[1,5-a]pyridin-7-yl)-2-chloro-N-(3-(4-chlorophenyl)-3-hydroxypropyl)-6-methylbenzamide (2.3 mg, 4.9 µmol, 5% yield).
$^1$H NMR (500 MHz, DMSO-d$_6$) δ 8.64 (d, J=6.7 Hz, 1H), 8.59 (t, J=5.5 Hz, 1H), 7.44-7.34 (m, 7H), 6.94 (dd, J=6.9, 1.7 Hz, 1H), 4.68 (t, J=6.4 Hz, 1H), 3.36-3.26 (m, 1H), 3.39-3.25 (m, 2H), 2.31 (s, 3H), 1.83 (q, J=6.6 Hz, 2H).
MS ESI m/z 470.0 (M+H)$^+$ Example 146: (S)-5-(2-amino-[1,2,4]triazolo[1,5-a]pyridin-7-yl)-N-(3-(4-chlorophenyl)-3-hydroxypropyl)-2,4-dimethylbenzamide

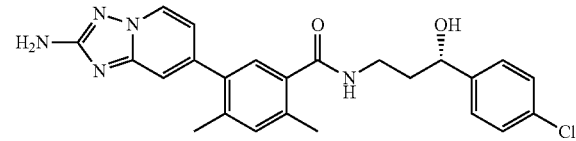

146A: (2-amino-[1,2,4]triazolo[1,5-a]pyridin-7-yl)boronic acid: In a sealable glass medium pressure vessel, to a mixture of 7-bromo-[1,2,4]triazolo[1,5-a]pyridin-2-amine (250 mg, 1.17 mmol), bis(pinacolato)diboron (447 mg, 1.76 mmol) and potassium acetate (346 mg, 3.52 mmol) in 1,4-dioxane (5 mL) was added PdCl$_2$(dppf)-CH$_2$Cl$_2$ adduct (48 mg, 0.059 mmol). The mixture was heated at 100° C. for 45 min, and the crude mixture was used directly in the next step without purification, assumed 100% yield.
MS ESI m/z 178.9 (M+H)$^+$ 146B: methyl 5-(2-amino-[1,2,4]triazolo[1,5-a]pyridin-7-yl)-2,4-dimethylbenzoate: In a sealable glass medium pressure vessel, to the crude mixture described in 146A was added methyl 5-iodo-2,4-dimethylbenzoate (250 mg, 0.862 mmol) and 1,1'-bis(di-tert-butylphosphino)ferrocene palladium dichloride (28 mg, 0.043 mmol). The mixture was degassed and treated with aqueous 2M K$_3$PO$_4$ (1.3 mL, 2.59 mmol). The vessel was sealed and heated at 100° C. for 15 min. The crude reaction was concentrated onto celite and purified via silica gel flash column chromatography (elution with ethyl acetate in hexanes) to afford methyl 5-(2-amino-[1,2,4]triazolo[1,5-a]pyridin-7-yl)-2,4-dimethylbenzoate (222 mg, 0.712 mmol, 95% yield).
MS ESI m/z 297.1 (M+H)$^+$ 146C: lithium 5-(2-amino-[1,2,4]triazolo[1,5-a]pyridin-7-yl)-2,4-dimethylbenzoate: To a solution of methyl 5-(2-amino-[1,2,4]triazolo[1,5-a]pyridin-7-yl)-2,4-dimethylbenzoate (222 mg, 0.749 mmol) in THF (8 mL) and a few drops of methanol was added a solution of lithium hydroxide monohydrate (39.3 mg, 0.936 mmol) in water (1.5 mL). The resulting mixture was stirred at 55° C. for 18 h. The solvent was removed in vacuo to afford crude lithium 5-(2-amino-[1,2,4]triazolo[1,5-a]pyridin-7-yl)-2,4-dimethylbenzoate (217 mg, 0.692 mmol, 92% yield) which was used as-is without further purification in the next step.

146: To a mixture of crude lithium 5-(2-amino-[1,2,4]triazolo[1,5-a]pyridin-7-yl)-2,4-dimethylbenzoate (13 mg, 0.046 mmol), (S)-3-amino-1-(4-chlorophenyl)propan-1-ol (7.8 mg, 0.042 mmol) and N,N-diisopropylethylamine (0.040 mL, 0.23 mmol) in DMF (1.0 mL) was added BOP (31 mg, 0.069 mmol) and the reaction was stirred at 44° C. for 72 h. The mixture was diluted with methanol (2 mL), filtered and purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10 mM ammonium acetate; Gradient: a 0-min hold at 17% B, 17-57% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (S)-5-(2-amino-[1,2,4]triazolo[1,5-a]pyridin-7-yl)-N-(3-(4-chlorophenyl)-3-hydroxypropyl)-2,4-dimethylbenzamide (11.1 mg, 0.0250 mmol, 54% yield).

$^1$H NMR (500 MHz, DMSO-d$_6$) δ 8.57 (d, J=6.8 Hz, 1H), 8.26 (t, J=5.3 Hz, 1H), 7.37 (s, 4H), 7.32 (s, 1H), 7.22 (d, J=19.6 Hz, 2H), 6.89 (dd, J=6.9, 1.8 Hz, 1H), 6.03 (s, 2H), 5.41 (d, J=4.5 Hz, 1H), 4.71-4.57 (m, 1H), 3.53-3.45 (m, 1H), 3.35-3.23 (m, 1H), 2.36 (s, 3H), 2.29 (s, 3H), 1.88-1.77 (m, 2H).
MS ESI m/z 450.28 (M+H)$^+$

Example 147: (S)-3-(2-amino-[1,2,4]triazolo[1,5-a]pyridin-7-yl)-N-(3-(4-chlorophenyl)-3-hydroxypropyl)-2-fluoro-6-methoxybenzamide

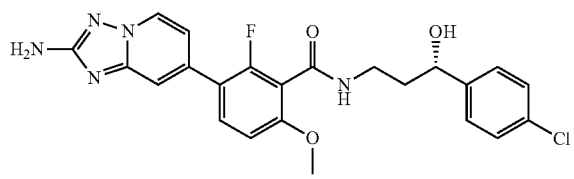

147A: 3-(2-amino-[1,2,4]triazolo[1,5-a]pyridin-7-yl)-2-fluoro-6-methoxybenzoic acid: In a sealable glass medium pressure vessel, a mixture of (2-amino-[1,2,4]triazolo[1,5-a]pyridin-7-yl)boronic acid (180 mg, 1.01 mmol) and 3-bromo-2-fluoro-6-methoxybenzoic acid (233 mg, 0.936 mmol) in 1,4-dioxane (10 mL) was treated with 1,1'-bis(di-tert-butylphosphino)ferrocene palladium dichloride (31 mg, 0.047 mmol). The mixture was degassed and treated with aqueous 2M K$_3$PO$_4$ (1.40 mL, 2.81 mmol). The vessel was then sealed and heated at 100° C. for 18 h. Additional 3-bromo-2-fluoro-6-methoxybenzoic acid (250 mg, 1.00 mmol), aqueous 2M K$_3$PO$_4$ (2.0 mL, 4.0 mmol) and 1,1'-bis(di-tert-butylphosphino)ferrocene palladium dichloride (50 mg, 0.080 mmol) were added and the resulting mixture was heated at 100° C. for 3 h. The mixture was diluted with aqueous phosphate buffer (2 mL), extracted with ethyl acetate, and the aqueous layer was acidified with 6N HCl which caused precipitation of a solid. The resulting solid was collected by filtration to afford 3-(2-amino-[1,2,4]triazolo[1,5-a]pyridin-7-yl)-2-fluoro-6-methoxybenzoic acid (202 mg, 0.601 mmol, 64% yield).
MS ESI m/z 302.99 (M+H)$^+$ 147: To a mixture of 3-(2-amino-[1,2,4]triazolo[1,5-a]pyridin-7-yl)-2-fluoro-6-methoxybenzoic acid (22 mg, 0.073 mmol), (S)-3-amino-1-(4-chlorophenyl)propan-1-ol (7.8 mg, 0.042 mmol) and N,N-diisopropylethylamine (0.064 mL, 0.36 mmol) in DMF (1.0 mL) was added BOP (48.3 mg, 0.109 mmol) and the resulting mixture was stirred at 44° C. for 18 h. The reaction was diluted with methanol (2 mL), filtered and purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 11% B, 11-51% B over 24 min, then a 0-min hold at 100% B; Flow Rate: 20 mL/min; Column Temperature: 25° C. Fraction collection was triggered by MS signals. Fractions containing the desired product were combined and dried via centrifugal evaporation to afford (S)-3-(2-amino-[1,2,4]triazolo[1,5-a]pyridin-7-yl)-N-(3-(4-chlorophenyl)-3-hydroxypropyl)-2-fluoro-6-methoxybenzamide (14.9 mg, 0.032 mmol, 43% yield).

$^1$H NMR (500 MHz, DMSO-d$_6$) δ 8.57 (d, J=7.1 Hz, 1H), 8.53 (t, J=5.9 Hz, 1H), 7.66 (br t, J=9.0 Hz, 1H), 7.44 (s, 1H), 7.42-7.34 (m, 4H), 7.09-7.00 (m, 2H), 6.05 (s, 2H), 4.66 (br d, J=4.8 Hz, 1H), 3.85 (s, 3H), 3.61-3.54 (m, 1H), 3.33-3.16 (m, 2H), 1.79 (q, J=6.7 Hz, 2H).
MS ESI m/z 469.98 (M+H)$^+$

Example 148: (R)-3-(2-amino-[1,2,4]triazolo[1,5-a]pyridin-7-yl)-N-(3-(4-chlorophenyl)-3-hydroxypropyl)-2-fluoro-6-methoxybenzamide

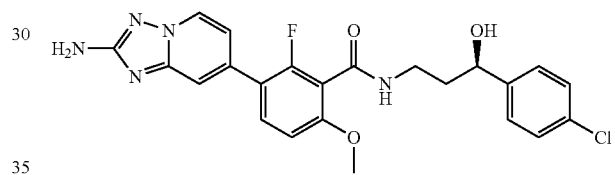

The title compound was prepared in a similar manner as 147, substituting (S)-3-amino-1-(4-chlorophenyl)propan-1-ol with (R)-3-amino-1-(4-chlorophenyl)propan-1-ol in the last step to give (R)-3-(2-amino-[1,2,4]triazolo[1,5-a]pyridin-7-yl)-N-(3-(4-chlorophenyl)-3-hydroxypropyl)-2-fluoro-6-methoxybenzamide (15.1 mg, 0.031 mmol, 43% yield).

$^1$H NMR (500 MHz, DMSO-d$_6$) δ 8.60-8.52 (m, 2H), 7.65 (t, J=9.0 Hz, 1H), 7.44 (s, 1H), 7.42-7.33 (m, 4H), 7.09-7.01 (m, 2H), 6.04 (s, 2H), 4.66 (br d, J=3.3 Hz, 1H), 3.98 (br s, 1H), 3.84 (s, 3H), 3.38-3.21 (m, 2H), 1.86-1.74 (m, 2H).
MS ESI m/z 469.98 (M+H)$^+$

Example 149: (S)-5-(2-amino-[1,2,4]triazolo[1,5-a]pyridin-7-yl)-N-(3-(4-chlorophenyl)-3-hydroxypropyl)-2-methylbenzamide

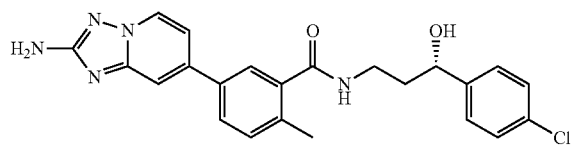 [SMILES: Cc1ccc(-c2ccn3nc(N)nc3c2)cc1C(=O)NCC[C@H](O)c1ccc(Cl)cc1]

149A: methyl 2-methyl-5-(4,4,5,5-tetramethyl-1,3,2-dioxaborolan-2-yl)benzoate: To a mixture of methyl 5-bromo-2-methylbenzoate (2.00 g, 8.73 mmol) in 1,4-dioxane (30 mL) was added 4,4,4',4',5,5,5',5'-octamethyl-2,2'-bi(1,3,2- dioxaborolane) (2.66 g, 10.5 mmol), PdCl₂(dppf)-CH₂Cl₂ adduct (0.356 g, 0.437 mmol) and potassium acetate (2.57 g, 26.2 mmol). The mixture was sparged with nitrogen gas for several minutes, then stirred at 110° C. for 1 h. The mixture was used as-is the next step and 100% yield was assumed.

MS ESI m/z 277.1 (M+H)⁺

149B: methyl 5-(2-amino-[1,2,4]triazolo[1,5-a]pyridin-7-yl)-2-methylbenzoate: To the crude mixture containing methyl 2-methyl-5-(4,4,5,5-tetramethyl-1,3,2-dioxaborolan-2-yl)benzoate (2.41 g, 8.69 mmol) was added 7-bromo-[1,2,4]triazolo[1,5-a]pyridin-2-amine (1.85 g, 8.69 mmol), PdCl₂(dppf)-CH₂Cl₂ adduct (0.284 g, 0.348 mmol) and 2M aqueous K₃PO₄ (10.9 mL, 21.8 mmol). The reaction was degassed and heated at 110° C. for 1 h. The mixture was diluted with water (50 mL) and the aqueous layer was extracted with ethyl acetate (2×150 mL). The combined organics were dried over anhydrous sodium sulfate, filtered and concentrated to a residue. The desired product was crystallized from a mixture of hexanes and ethyl acetate to afford methyl 5-(2-amino-[1,2,4]triazolo[1,5-a]pyridin-7-yl)-2-methylbenzoate (2.30 g, 8.15 mmol, 94% yield).

MS ESI m/z 283.1 (M+H)⁺

149C: lithium 5-(2-amino-[1,2,4]triazolo[1,5-a]pyridin-7-yl)-2-methylbenzoate: To a solution of methyl 5-(2-amino-[1,2,4]triazolo[1,5-a]pyridin-7-yl)-2-methylbenzoate (261 mg, 0.925 mmol) in THF (5 mL) and a few drops of methanol was added a solution of lithium hydroxide monohydrate (48.5 mg, 1.16 mmol) in water (1.5 mL). The resulting mixture was stirred at 60° C. for 3 h. Solvent was removed in vacuo to afford crude lithium 5-(2-amino-[1,2,4]triazolo[1,5-a]pyridin-7-yl)-2-methylbenzoate (245 mg) which was used as-is in the next step.

MS ESI m/z 269.11 (M+H)⁺

149: To a mixture of lithium 5-(2-amino-[1,2,4]triazolo[1,5-a]pyridin-7-yl)-2-methylbenzoate (20 mg, 0.075 mmol), (S)-3-amino-1-(4-chlorophenyl)propan-1-ol, HCl (21 mg, 0.093 mmol) and N,N-diisopropylethylamine (0.078 mL, 0.45 mmol) in DMF (1 mL) was added BOP (49.5 mg, 0.112 mmol) and the reaction was stirred at 44° C. for 18 h. The mixture was diluted with methanol (2 mL), filtered and purified via preparative LCMS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 15% B, 15-55% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (S)-5-(2-amino-[1,2,4]triazolo[1,5-a]pyridin-7-yl)-N-(3-(4-chlorophenyl)-3-hydroxypropyl)-2-methylbenzamide (9.8 mg, 0.022 mmol, 30% yield).

¹H NMR (500 MHz, DMSO-d₆) δ 8.59 (d, J=7.0 Hz, 1H), 8.39 (t, J=5.4 Hz, 1H), 7.76 (dd, J=7.9, 1.9 Hz, 1H), 7.70 (d, J=9.5 Hz, 2H), 7.42-7.36 (m, 5H), 7.24 (dd, J=7.0, 1.8 Hz, 1H), 6.04 (s, 2H), 5.43 (d, J=4.5 Hz, 1H), 4.71-4.65 (m, 1H), 3.46-3.29 (m, 1H), 2.39 (s, 3H), 1.86 (q, J=6.8 Hz, 2H).

MS ESI m/z 436.08 (M+H)⁺

Example 150: (S)-5-(2-amino-[1,2,4]triazolo[1,5-a]pyridin-7-yl)-N-(3-(4-chlorophenyl)-3-hydroxypropyl)-2-ethylbenzamide

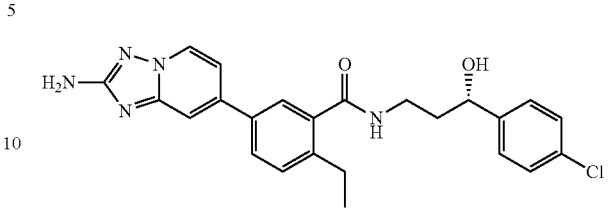

150A: methyl 5-(2-amino-[1,2,4]triazolo[1,5-a]pyridin-7-yl)-2-ethylbenzoate: In a sealable glass medium pressure vessel, to a mixture of (2-amino-[1,2,4]triazolo[1,5-a]pyridin-7-yl)boronic acid (142 mg, 0.800 mmol) and methyl 5-bromo-2-ethylbenzoate (180 mg, 0.740 mmol) in 1,4-dioxane (5 mL) was added 1,1'-bis(di-tert-butylphosphino)ferrocene palladium dichloride (24 mg, 0.037 mmol) and the resulting mixture was degassed. The mixture was treated with aqueous 2M K₃PO₄ (1.1 mL, 2.2 mmol), and the vessel was sealed and heated at 100° C. for 30 min. The crude mixture was dry-load adsorbed onto celite and purified via silica gel flash column chromatography (eluent methanol in dichloromethane) to afford methyl 5-(2-amino-[1,2,4]triazolo[1,5-a]pyridin-7-yl)-2-ethylbenzoate (205 mg, 0.692 mmol, 93% yield).

MS ESI m/z 297.0 (M+H)⁺

150B: lithium 5-(2-amino-[1,2,4]triazolo[1,5-a]pyridin-7-yl)-2-ethylbenzoate: To a solution of methyl 5-(2-amino-[1,2,4]triazolo[1,5-a]pyridin-7-yl)-2-ethylbenzoate (205 mg, 0.692 mmol) in THF (5 mL) and a few drops of methanol was added a solution of lithium hydroxide monohydrate (36.3 mg, 0.865 mmol) in water (1 mL). The mixture was stirred at 60° C. for 18 h. Solvent was removed in vacuo to afford crude lithium 5-(2-amino-[1,2,4]triazolo[1,5-a]pyridin-7-yl)-2-ethylbenzoate (189 mg) which was used as-is in the next step.

MS ESI m/z 283.09 (M+H)⁺

150: To a mixture of crude lithium 5-(2-amino-[1,2,4]triazolo[1,5-a]pyridin-7-yl)-2-ethylbenzoate (17 mg, 0.060 mmol), (S)-3-amino-1-(4-chlorophenyl)propan-1-ol (7.8 mg, 0.042 mmol) and N,N-diisopropylethylamine (0.053 mL, 0.30 mmol) in DMF (1.0 mL) was added BOP (40 mg, 0.090 mmol) and the mixture was stirred at 44° C. for 3 d. The mixture was diluted with methanol (2 mL) and filtered, and the crude filtrate was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 16% B, 16-56% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (S)-5-(2-amino-[1,2,4]triazolo[1,5-a]pyridin-7-yl)-N-(3-(4-chlorophenyl)-3-hydroxypropyl)-2-ethylbenzamide (12.7 mg, 0.028 mmol, 46% yield).

¹H NMR (500 MHz, DMSO-d₆) δ 8.59 (d, J=7.0 Hz, 1H), 8.40 (t, J=5.3 Hz, 1H), 7.79 (dd, J=8.1, 2.0 Hz, 1H), 7.68 (s, 1H), 7.68 (d, J=4.1 Hz, 1H), 7.42-7.38 (m, 5H), 7.24 (dd, J=7.0, 1.8 Hz, 1H), 6.03 (s, 2H), 5.41 (d, J=4.6 Hz, 1H), 4.76-4.59 (m, 1H), 2.77 (q, J=7.3 Hz, 2H), 1.86 (q, J=7.2 Hz, 2H), 1.18 (t, J=7.5 Hz, 3H).

MS ESI m/z 450.09 (M+H)⁺

Example 151: (S)-3-(2-amino-[1,2,4]triazolo[1,5-a]pyridin-7-yl)-N-(3-(4-chlorophenyl)-3-hydroxypropyl)-2-fluoro-6-methylbenzamide

151A: methyl 3-bromo-2-fluoro-6-methylbenzoate: To a solution of 3-bromo-2-fluoro-6-methylbenzoic acid (307 mg, 1.32 mmol) in DMF (6 mL) was added potassium carbonate (455 mg, 3.29 mmol) and the resulting solution was stirred at RT for 10 min. Iodomethane (0.12 mL, 1.98 mmol) was added and the resulting mixture was stirred ON. The mixture was partitioned between EtOAc and saturated aqueous sodium bicarbonate. The EtOAc layer was washed with 10% aqueous LiCl (2×) followed by brine (1x), dried over anhydrous sodium sulfate, filtered and concentrated in vacuo to afford methyl 3-bromo-2-fluoro-6-methylbenzoate (277 mg, 1.11 mmol, 84% yield) as yellow oil which became a solid over time under high vacuum.

151B: N,N-bis-Boc-(2-amino-[1,2,4]triazolo[1,5-a]pyridin-7-yl)boronic acid: A mixture of bis-Boc-7-bromo-[1,2,4]triazolo[1,5-a]pyridin-2-amine (500 mg, 1.210 mmol), bis(pinacolato)diboron (384 mg, 1.51 mmol), potassium acetate (356 mg, 3.63 mmol) and PdCl$_2$(dppf)-CH$_2$Cl$_2$ adduct (49 mg, 0.060 mmol) in 1,4-dioxane (6 mL) was heated at 100° C. for 45 min. The crude reaction mixture was used directly in the next step: assumed 100% yield.
MS ESI m/z 379.2 (M+H)$^+$ 151C: methyl 3-(N,N-bis-Boc-2-amino-[1,2,4]triazolo[1,5-a]pyridin-7-yl)-2-fluoro-6-methylbenzoate: To the crude reaction mixture described in 151B containing N,N-bis-Boc-(2-amino-[1,2,4]triazolo[1,5-a]pyridin-7-yl)boronic acid was added methyl 3-bromo-2-fluoro-6-methylbenzoate (275 mg, 1.11 mmol) and 1,1'-bis(di-tert-butylphosphino)ferrocene palladium dichloride (36 mg, 0.056 mmol). The mixture was degassed by bubbling nitrogen through for 5 min. 2 M aqueous K$_3$PO$_4$ (1.7 mL, 3.34 mmol) was quickly added and the reaction mixture was heated at 100° C. with stirring for 15 min. The crude reaction mixture was concentrated onto celite and dry-load purified by flash silica column chromatography (elution gradient 0-100% EtOAc in Hex) to afford methyl 3-(N,N-bis-Boc-2-amino-[1,2,4]triazolo[1,5-a]pyridin-7-yl)-2-fluoro-6-methylbenzoate (475 mg, 0.949 mmol, 85% yield) as a crystalline beige solid.
MS ESI m/z 501.3 (M+H)$^+$ 151D: methyl 3-(2-amino-[1,2,4]triazolo[1,5-a]pyridin-7-yl)-2-fluoro-6-methylbenzoate: A solution of methyl 3-(N,N-bis-Boc-2-amino-[1,2,4]triazolo[1,5-a]pyridin-7-yl)-2-fluoro-6-methylbenzoate (475 mg, 0.949 mmol) in TFA (5 mL) was stirred at RT ON. The reaction mixture was concentrated to afford methyl 3-(2-amino-[1,2,4]triazolo[1,5-a]pyridin-7-yl)-2-fluoro-6-methylbenzoate (285 mg, 0.902 mmol, 95% yield) as a tan solid.
MS ESI m/z 301.1 (M+H)$^+$ 151E: lithium 3-(2-amino-[1,2,4]triazolo[1,5-a]pyridin-7-yl)-2-fluoro-6-methylbenzoate: To a solution of methyl 3-(2-amino-[1,2,4]triazolo[1,5-a]pyridin-7-yl)-2-fluoro-6-methylbenzoate (175 mg, 0.583 mmol) in THF (8 mL) and a few drops of methanol was added a solution of lithium hydroxide monohydrate (30.6 mg, 0.728 mmol) in water (1.5 mL). The resulting mixture was stirred at 60° C. ON and then concentrated to afford crude lithium 3-(2-amino-[1,2,4]triazolo[1,5-a]pyridin-7-yl)-2-fluoro-6-methylbenzoate (163 mg, 0.512 mmol, 88% yield) as a solid which was used as-is in the next step.
MS ESI m/z 287.2 (M+H)$^+$ 151: A mixture of crude lithium 3-(2-amino-[1,2,4]triazolo[1,5-a]pyridin-7-yl)-2-fluoro-6-methylbenzoate (15 mg, 0.052 mmol) and BOP (35 mg, 0.079 mmol), (S)-3-amino-1-(4-chlorophenyl)propan-1-ol (7.8 mg, 0.042 mmol) and Hünig's Base (0.046 mL, 0.26 mmol) in DMF (1.0 mL) was stirred at 42° C. for 3 h. The crude material was purified via preparative LCMS with the following conditions: Column: XBridge C18, 200 mm×19 mm, 5-μm particles; Mobile Phase A: 5:95 acetonitrile:water with 0.10% trifluoroacetic acid; Mobile Phase B: 95:5 acetonitrile:water with 0.1% trifluoroacetic acid; Gradient: a 0-min hold at 10% B, 10-50% B over 20 min, then a 4-min hold at 100% B; Flow Rate: 20 mL/min; Column Temperature: 25° C. Fraction collection was triggered by MS and UV signals. Fractions containing the desired product were combined and dried via centrifugal evaporation to afford (S)-3-(2-amino-[1,2,4]triazolo[1,5-a]pyridin-7-yl)-N-(3-(4-chlorophenyl)-3-hydroxypropyl)-2-fluoro-6-methylbenzamide (14.1 mg, 0.031 mmol, 59.3% yield).
$^1$H NMR (500 MHz, DMSO-d$_6$) δ 8.65 (br t, J=4.5 Hz, 1H), 8.59 (br d, J=7.0 Hz, 1H), 7.57 (br t, J=8.0 Hz, 1H), 7.48 (s, 1H), 7.42-7.33 (m, 4H), 7.22 (d, J=8.0 Hz, 1H), 7.05 (br d, J=7.0 Hz, 1H), 4.66 (br t, J=6.2 Hz, 1H), 3.39-3.24 (m, 2H), 2.30 (s, 3H), 1.81 (q, J=7.0 Hz, 2H).
MS ESI m/z 454.0 (M+H)$^+$ Example 152: (R)-3-(2-amino-[1,2,4]triazolo[1,5-a]pyridin-7-yl)-N-(3-(4-chlorophenyl)-3-hydroxypropyl)-2-fluoro-6-methylbenzamide

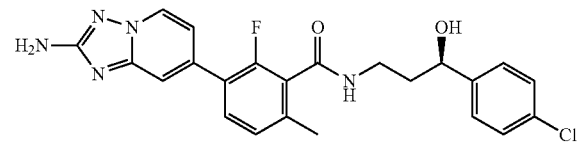 [SMILES: Cc1ccc(-c2ccn3nc(N)nc3c2)c(F)c1C(=O)NCC[C@@H](O)c1ccc(Cl)cc1]

152A: 3-bromo-2-fluoro-6-methylbenzoic acid: A mixture of 2.0 M LDA in THF/heptane/ethylbenzene (34.9 mL, 69.8 mmol) and THF (127 ml) was cooled to −78° C. To the cooled mixture was added 4-bromo-3-fluorotoluene (8.03 mL, 63.5 mmol) dropwise with stirring. When the addition was complete, the mixture was allowed to stir at −78° C. for 20 min. Solid, pulverized carbon dioxide (5.59 g, 127 mmol) was then added in one portion. The yellow mixture quickly became red in color and faded to a light yellow color again just as quickly. The resulting mixture was stirred at −78° C. for 20 min. The reaction was quenched by the addition of water and allowed to warm to RT. The mixture was diluted with additional water and extracted with EtOAc (2×). The basic aqueous layer was brought to pH 1 by the addition of 1 N aqueous HCl. The resulting suspension was filtered and the solid was dried under vacuum to give 3-bromo-2-fluoro-6-methylbenzoic acid (3.44 g, 14.8 mmol, 23% yield).
$^1$H NMR (400 MHz, DMSO-d$_6$) δ 7.72-7.61 (m, 1H), 7.11 (d, J=8.2 Hz, 1H), 2.32 (s, 3H).

152B: (2-amino-[1,2,4]triazolo[1,5-a]pyridin-7-yl)boronic acid: A stirred mixture of potassium acetate (691 mg, 7.04 mmol), 7-bromo-[1,2,4]triazolo[1,5-a]pyridin-2-amine (500 mg, 2.35 mmol), $PdCl_2(dppf)\text{-}CH_2Cl_2$ adduct (96.0 mg, 0.117 mmol) and bis(pinacolato)diboron (894 mg, 3.52 mmol) in 1,4-dioxane (10 mL) was heated at 100° C. for 1 h. The mixture was used directly in the next step as-is. 100% yield was assumed.

MS ESI m/z 179.0 $(M+H)^+$

152C: 3-(2-amino-[1,2,4]triazolo[1,5-a]pyridin-7-yl)-2-fluoro-6-methylbenzoic acid: To the stirred crude mixture described in 152B containing (2-amino-[1,2,4]triazolo[1,5-a]pyridin-7-yl)boronic acid was added 3-bromo-2-fluoro-6-methylbenzoic acid (750 mg, 3.22 mmol) and 1,1'-bis(di-tert-butylphosphino)ferrocene palladium dichloride (120 mg, 0.183 mmol). The mixture was degassed by bubbling nitrogen through for 5 min. 2 M aqueous $K_3PO_4$ (5.22 mL, 10.4 mmol) was quickly added and the reaction mixture was heated at 100° C. for 3 h. The mixture was cooled to RT, then diluted with 1 N aqueous NaOH (50 mL) and extracted with EtOAc (lx). The aqueous layer was acidified with 6 N HCl whereupon the product precipitated out of solution. The solid was isolated by filtration and dried to afford 3-(2-amino-[1,2,4]triazolo[1,5-a]pyridin-7-yl)-2-fluoro-6-methylbenzoic acid (515 mg, 1.62 mmol, 75% yield) as a tan solid.

MS ESI m/z 287.1 $(M+H)^+$

152: A mixture of 3-(2-amino-[1,2,4]triazolo[1,5-a]pyridin-7-yl)-2-fluoro-6-methylbenzoic acid (20 mg, 0.070 mmol), BOP (46.3 mg, 0.105 mmol), (R)-3-amino-1-(4-chlorophenyl)propan-1-ol, HCl (19.4 mg, 0.087 mmol) and Hünig's Base (0.073 mL, 0.42 mmol) in DMF (1 mL) was stirred at 44° C. for 3 d. The crude material was purified via preparative LCMS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 15% B, 15-55% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to afford (R)-3-(2-amino-[1,2,4]triazolo[1,5-a]pyridin-7-yl)-N-(3-(4-chlorophenyl)-3-hydroxypropyl)-2-fluoro-6-methylbenzamide (10.6 mg, 0.023 mmol, 33% yield).

$^1$H NMR (500 MHz, DMSO-$d_6$) δ 8.63 (br d, J=6.7 Hz, 2H), 7.58 (br t, J=7.9 Hz, 1H), 7.52 (s, 1H), 7.44-7.32 (m, 4H), 7.29-7.19 (m, 1H), 7.18-7.08 (m, 1H), 7.10-6.96 (m, 1H), 4.66 (br t, J=6.4 Hz, 1H), 3.39-3.25 (m, 2H), 2.31 (s, 3H), 1.82 (q, J=7.1 Hz, 2H).

MS ESI m/z 454.3 $(M+H)^+$

TABLE 12

Compounds in Table 12 were prepared in a similar fashion to example 152, where 3-bromo-6-chloro-2-fluorobenzoic acid was used in place of 3-bromo-2-fluoro-6-methylbenzoic acid in the third step.

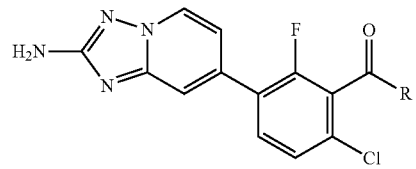

| Ex No | Name | R | M + H$^+$ | 1H NMR (500 MHz, DMSO-d6) δ |
|---|---|---|---|---|
| 153 | (S)-3-(2-amino-[1,2,4]triazolo[1,5-a]pyridin-7-yl)-6-chloro-N-(3-(4-chlorophenyl)-3-hydroxypropyl)-2-fluorobenzamide | (structure) | 474.2 | 8.81 (br t, J = 5.2 Hz, 1H), 8.64 (d, J = 7.0 Hz, 1H), 7.73 (t, J = 8.4 Hz, 1H), 7.53 (s, 1H), 7.52-7.49 (m, 1H), 7.43-7.35 (m, 4H), 7.05 (br d, J = 7.0 Hz, 1H), 6.11 (s, 2H), 5.43 (d, J = 4.6 Hz, 1H), 4.76-4.60 (m, 1H), 3.41 (br s, 1H), 3.32 (br d, J = 7.0 Hz, 1H), 1.90-1.75 (m, 2H) |
| 154 | (R)-3-(2-amino-[1,2,4]triazolo[1,5-a]pyridin-7-yl)-6-chloro-N-(3-(4-chlorophenyl)-3-hydroxypropyl)-2-fluorobenzamide | (structure) | 474.2 | 8.81 (br t, J = 5.5 Hz, 1H), 8.68 (d, J = 7.0 Hz, 1H), 7.75 (t, J = 8.4 Hz, 1H), 7.62-7.47 (m, 2H), 7.45-7.34 (m, 4H), 7.18-6.99 (m, 1H), 4.69 (t, J = 6.4 Hz, 1H), 3.44-3.23 (m, 1H), 1.83 (q, J = 6.8 Hz, 2H) |

Example 155: (S)-3-(2-amino-[1,2,4]triazolo[1,5-a]pyridin-7-yl)-N-(3-(4-chlorophenyl)-3-hydroxypropyl)-6-ethyl-2-fluorobenzamide

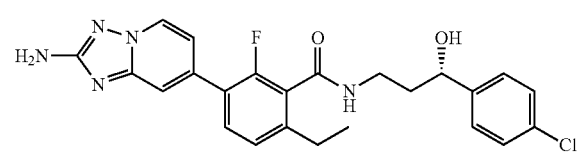 [SMILES: CCc1ccc(-c2ccn3nc(N)nc3c2)c(F)c1C(=O)NCC[C@H](O)c1ccc(Cl)cc1]

155A: methyl 3-(2-amino-[1,2,4]triazolo[1,5-a]pyridin-7-yl)-6-chloro-2-fluorobenzoate: A stirred mixture of potassium acetate (380 mg, 3.87 mmol), 7-bromo-[1,2,4]triazolo

[1,5-a]pyridin-2-amine (275 mg, 1.29 mmol), [1,1'-bis(diphenylphosphino)ferrocene]dichloropalladium(II), complex with dichloromethane (53 mg, 0.065 mmol), and bis(pinacolato)diboron (492 mg, 1.94 mmol) in 1,4-dioxane (5 mL) was heated at 100° C. for 1 h. To the reaction mixture was added methyl 3-bromo-6-chloro-2-fluorobenzoate (300 mg, 1.12 mmol) and 1,1'-bis(di-tert-butylphosphino)ferrocene palladium (II) dichloride (37 mg, 0.056 mmol). To degas the reaction, nitrogen was bubbled through the mixture for 5 min. Aqueous 2 M potassium phosphate, tribasic (1.68 mL, 3.36 mmol) was quickly added and the reaction mixture stirred at RT ON. The crude reaction mixture was concentrated onto celite and purified by flash column chromatography (24 g silica, elution gradient 0-100% ethyl acetate in Hex followed by 0-10% methanol in dichloromethane). The pure fractions were combined and concentrated under reduced pressure to yield methyl 3-(2-amino-[1,2,4]triazolo[1,5-a]pyridin-7-yl)-6-chloro-2-fluorobenzoate (335 mg, 0.992 mmol, 88% yield) as a beige solid.
MS ESI m/z 321.2 (M+H)+

155B: methyl 3-(2-amino-[1,2,4]triazolo[1,5-a]pyridin-7-yl)-2-fluoro-6-vinylbenzoate: A mixture of methyl 3-(2-amino-[1,2,4]triazolo[1,5-a]pyridin-7-yl)-6-chloro-2-fluorobenzoate (350 mg, 1.09 mmol), dicyclohexyl(2',6'-dimethoxy-[1,1'-biphenyl]-2-yl)phosphine (49.3 mg, 0.120 mmol), palladium (II) acetate (12.3 mg, 0.055 mmol) and 6-methyl-2-vinyl-1,3,6,2-dioxazaborocane-4,8-dione (399 mg, 2.18 mmol) in 1,4-dioxane (6.5 mL) was purged with nitrogen for 1 min. Aqueous 2 M potassium phosphate tribasic (3.00 mL, 6.00 mmol) was added, and the reaction mixture was heated to 100° C. for 1 h. The yellow reaction mixture turned orange within 40 min at 100° C. The crude reaction mixture was concentrated onto celite and purified by flash column chromatography (24 g silica, elution gradient 0-100% ethyl acetate in Hex followed by 0-10% methanol in dichloromethane). The pure fractions were combined and concentrated under reduced pressure to afford methyl 3-(2-amino-[1,2,4]triazolo[1,5-a]pyridin-7-yl)-2-fluoro-6-vinylbenzoate (217 mg, 0.695 mmol, 64% yield).
MS ESI m/z 313.2 (M+H)+

155C: methyl 3-(2-amino-[1,2,4]triazolo[1,5-a]pyridin-7-yl)-6-ethyl-2-fluorobenzoate: To a solution of methyl 3-(2-amino-[1,2,4]triazolo[1,5-a]pyridin-7-yl)-2-fluoro-6-vinylbenzoate (217 mg, 0.695 mmol) in ethanol (6.5 mL) was added 10% palladium on carbon (73.9 mg, 0.069 mmol). The resulting mixture was degassed by placing the vessel under vacuum for 5 min and then refilling with hydrogen gas. The mixture was stirred ON at RT under a hydrogen atmosphere. The reaction mixture was filtered and concentrated under reduced pressure to yield solid methyl 3-(2-amino-[1,2,4]triazolo[1,5-a]pyridin-7-yl)-6-ethyl-2-fluorobenzoate (220 mg, 0.630 mmol, 91% yield). The product was used as-is without further purification.
MS ESI m/z 315.2 (M+H)+

155D: lithium-3-(2-amino-[1,2,4]triazolo[1,5-a]pyridin-7-yl)-6-ethyl-2-fluorobenzoate: To a solution of methyl 3-(2-amino-[1,2,4]triazolo[1,5-a]pyridin-7-yl)-6-ethyl-2-fluorobenzoate (220 mg, 0.700 mmol) in tetrahydrofuran (5 mL) and a few drops of methanol was added a solution of lithium hydroxide monohydrate (36.7 mg, 0.875 mmol) in 1 mL water. The resulting mixture was stirred at 65° C. ON. The mixture was concentrated to a solid to afford crude lithium-3-(2-amino-[1,2,4]triazolo[1,5-a]pyridin-7-yl)-6-ethyl-2-fluorobenzoate. This material was used as-is without further purification.
MS ESI m/z 301.2 (M+H)+

155: A mixture of crude lithium 3-(2-amino-[1,2,4]triazolo[1,5-a]pyridin-7-yl)-6-ethyl-2-fluorobenzoate (15 mg, 0.050 mmol), benzotriazol-1-yloxytris(dimethylamino)phosphonium hexafluorophosphate (33 mg, 0.075 mmol), (S)-3-amino-1-(4-chlorophenyl)propan-1-ol (7.8 mg, 0.042 mmol) and diisopropylethyl amine (0.044 mL, 0.25 mmol) in dimethylformamide (1.0 mL) was stirred at 40° C. for 3 d. The crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 17% B, 17-57% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield (S)-3-(2-amino-[1,2,4]triazolo[1,5-a]pyridin-7-yl)-N-(3-(4-chlorophenyl)-3-hydroxypropyl)-6-ethyl-2-fluorobenzamide (11.8 mg, 0.025 mmol, 51% yield).
1H NMR (500 MHz, DMSO-d6) δ 8.66 (t, J=5.7 Hz, 1H), 8.61 (d, J=7.1 Hz, 1H), 7.62 (t, J=8.1 Hz, 1H), 7.49 (s, 1H), 7.42-7.36 (m, 4H), 7.26 (d, J=8.0 Hz, 1H), 7.05 (d, J=7.0 Hz, 1H), 6.09 (s, 2H), 5.44 (d, J=4.5 Hz, 1H), 4.69-4.63 (m, 1H), 3.38-3.26 (m, 1H), 2.64 (q, J=7.5 Hz, 2H), 1.81 (q, J=7.0 Hz, 2H), 1.20 (t, J=7.6 Hz, 3H). Some proton signals were masked by water suppression.
MS ESI m/z 468.1 (M+H)+

Example 156: (R)-3-(2-amino-[1,2,4]triazolo[1,5-a]pyridin-7-yl)-N-(3-(4-chlorophenyl)-3-hydroxypropyl)-6-ethyl-2-fluorobenzamide

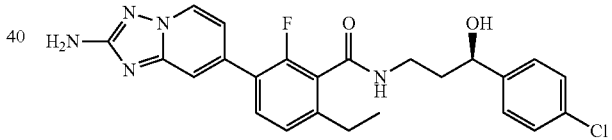

A mixture of crude lithium 3-(2-amino-[1,2,4]triazolo[1,5-a]pyridin-7-yl)-6-ethyl-2-fluorobenzoate (22 mg, 0.073 mmol), benzotriazol-1-yloxytris(dimethylamino)phosphonium hexafluorophosphate (48.6 mg, 0.110 mmol), (R)-3-amino-1-(4-chlorophenyl)propan-1-ol hydrochloride (20 mg, 0.092 mmol) and diisopropylethyl amine (0.077 mL, 0.440 mmol) in dimethylformamide (1.0 mL) was stirred at 44° C. for 3 d. The crude material was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 15% B, 15-52% B over 25 min, then a 0-min hold at 100% B; Flow Rate: 20 mL/min; Column Temperature: 25° C. Fraction collection was triggered by MS signals. Fractions containing the desired product were combined and dried via centrifugal evaporation to yield (R)-3-(2-amino-[1,2,4]triazolo[1,5-a]pyridin-7-yl)-N-(3-(4-chlorophenyl)-3-hydroxypropyl)-6-ethyl-2-fluorobenzamide (10.6 mg, 0.023 mmol, 31% yield).
1H NMR (500 MHz, DMSO-d6) δ 8.65-8.60 (m, 2H), 7.62 (t, J=8.1 Hz, 1H), 7.50 (s, 1H), 7.42-7.36 (m, 4H), 7.26

(d, J=7.9 Hz, 1H), 7.05 (br d, J=7.0 Hz, 1H), 6.07 (s, 2H), 5.40 (d, J=4.6 Hz, 1H), 4.73-4.60 (m, 1H), 2.65 (q, J=7.3 Hz, 2H), 1.92-1.77 (m, 1H), 1.82 (br d, J=6.7 Hz, 1H), 1.21 (t, J=7.6 Hz, 3H).
MS ESI m/z 468.3 (M+H)+

Example 157: (S)-5-(2-amino-[1,2,4]triazolo[1,5-a]pyridin-7-yl)-N-(3-(4-chlorophenyl)-3-hydroxypropyl)-2-ethyl-4-fluorobenzamide

157A: methyl 5-(2-amino-[1,2,4]triazolo[1,5-a]pyridin-7-yl)-2-chloro-4-fluorobenzoate: A stirred mixture of potassium acetate (380 mg, 3.87 mmol), 7-bromo-[1,2,4]triazolo[1,5-a]pyridin-2-amine (275 mg, 1.29 mmol), [1,1'-bis(diphenylphosphino)ferrocene]dichloropalladium(II), complex with dichloromethane (53 mg, 0.065 mmol) and bis(pinacolato)diboron (492 mg, 1.94 mmol) in 1,4-dioxane (5 mL) was heated at 100° C. for 1 h. To the reaction mixture was added methyl 5-bromo-2-chloro-4-fluorobenzoate (300 mg, 1.12 mmol) and 1,1'-bis(di-tert-butylphosphino)ferrocene palladium (II) dichloride (37 mg, 0.056 mmol). To degas the reaction, nitrogen was bubbled through the mixture for 5 min. Aqueous 2 M potassium phosphate tribasic (1.7 mL, 3.36 mmol) was quickly added and the reaction mixture was stirred at RT ON. The crude reaction mixture was concentrated onto celite and purified by flash column chromatography (24 g silica, elution gradient 0-100% ethyl acetate in Hex followed by 0-10% methanol in dichloromethane). The pure fractions were concentrated under reduced pressure to yield methyl 5-(2-amino-[1,2,4]triazolo[1,5-a]pyridin-7-yl)-2-chloro-4-fluorobenzoate (293 mg, 0.868 mmol, 77% yield) as a beige solid.
MS ESI m/z 321.2 (M+H)+

157B: methyl 5-(2-amino-[1,2,4]triazolo[1,5-a]pyridin-7-yl)-4-fluoro-2-vinylbenzoate: A mixture of methyl 5-(2-amino-[1,2,4]triazolo[1,5-a]pyridin-7-yl)-2-chloro-4-fluorobenzoate (293 mg, 0.914 mmol), dicyclohexyl(2',6'-dimethoxy-[1,1'-biphenyl]-2-yl)phosphine (41.3 mg, 0.100 mmol), palladium (II) acetate (10 mg, 0.046 mmol) and 6-methyl-2-vinyl-1,3,6,2-dioxazaborocane-4,8-dione (334 mg, 1.83 mmol) in 1,4-dioxane (5 mL) was purged with nitrogen for 1 min. Aqueous 2 M potassium phosphate tribasic (2.51 mL, 5.02 mmol) was added and the reaction mixture was heated to 100° C. for 1 h. The yellow reaction mixture turned orange within 40 min at 100° C. The crude reaction mixture was concentrated onto celite and purified by flash column chromatography (24 g silica, elution gradient 0-100% ethyl acetate in Hex followed by 0-10% methanol in dichloromethane). The pure fractions were combined and concentrated under reduced pressure to afford methyl 5-(2-amino-[1,2,4]triazolo[1,5-a]pyridin-7-yl)-4-fluoro-2-vinylbenzoate (111 mg, 0.355 mmol, 39% yield).
MS ESI m/z 313.1 (M+H)+

157C: methyl 5-(2-amino-[1,2,4]triazolo[1,5-a]pyridin-7-yl)-2-ethyl-4-fluorobenzoate: To a solution of methyl 5-(2-amino-[1,2,4]triazolo[1,5-a]pyridin-7-yl)-4-fluoro-2-vinylbenzoate (111 mg, 0.355 mmol) in ethanol (6.5 mL) was added 10% palladium on carbon (38 mg, 0.036 mmol). The resulting mixture was degassed by vacuum for 5 min, then the vessel was refilled with hydrogen gas and stirred for 3 d at RT under a hydrogen atmosphere. The reaction mixture was filtered and concentrated under reduced pressure to yield solid methyl 5-(2-amino-[1,2,4]triazolo[1,5-a]pyridin-7-yl)-2-ethyl-4-fluorobenzoate (79 mg, 0.25 mmol, 71% yield). The product was used as-is without further purification.
MS ESI m/z 315.2 (M+H)+

157D: lithium 5-(2-amino-[1,2,4]triazolo[1,5-a]pyridin-7-yl)-2-ethyl-4-fluorobenzoate: To a solution of methyl 5-(2-amino-[1,2,4]triazolo[1,5-a]pyridin-7-yl)-2-ethyl-4-fluorobenzoate (79 mg, 0.25 mmol) in tetrahydrofuran (5 mL) and a few drops of methanol was added a solution of lithium hydroxide monohydrate (13.2 mg, 0.314 mmol) in 1 mL of water. The resulting mixture was stirred at 60° C. ON. The mixture was concentrated in vacuo to a solid to afford crude lithium 5-(2-amino-[1,2,4]triazolo[1,5-a]pyridin-7-yl)-2-ethyl-4-fluorobenzoate (75 mg, 0.25 mmol, 99% yield). The material was used as-is without further purification.
MS ESI m/z 301.1 (M+H)+

157: A mixture of crude lithium 5-(2-amino-[1,2,4]triazolo[1,5-a]pyridin-7-yl)-2-ethyl-4-fluorobenzoate (13 mg, 0.043 mmol), benzotriazol-1-yloxytris(dimethylamino)phosphonium hexafluorophosphate (29 mg, 0.065 mmol), (S)-3-amino-1-(4-chlorophenyl)propan-1-ol (7.8 mg, 0.042 mmol) and diisopropylethyl amine (0.038 mL, 0.22 mmol) in dimethylformamide (1.0 mL) was stirred at 40° C. for 3 d. The crude mixture was purified via preparative LCMS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-min hold at 20% B, 20-60% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield (S)-5-(2-amino-[1,2,4]triazolo[1,5-a]pyridin-7-yl)-N-(3-(4-chlorophenyl)-3-hydroxypropyl)-2-ethyl-4-fluorobenzamide (8.1 mg, 0.017 mmol, 39% yield).
1H NMR (500 MHz, DMSO-d6) δ 8.62 (d, J=6.9 Hz, 1H), 8.41 (t, J=5.4 Hz, 1H), 7.58 (s, 1H), 7.55 (d, J=8.0 Hz, 1H), 7.38 (s, 4H), 7.30 (d, J=12.1 Hz, 1H), 7.10 (br d, J=7.0 Hz, 1H), 6.09 (s, 2H), 5.43 (d, J=4.5 Hz, 1H), 4.71-4.61 (m, 1H), 3.36-3.25 (m, 1H), 2.78 (q, J=7.3 Hz, 2H), 1.84 (q, J=6.8 Hz, 2H), 1.18 (t, J=7.5 Hz, 3H).
MS ESI m/z 468.1 (M+H)+

Example 158: (S)-5-(2-amino-[1,2,4]triazolo[1,5-a]pyridin-7-yl)-N-(3-(4-chlorophenyl)-3-hydroxypropyl)-3-fluoro-2-methylbenzamide 158A: methyl 5-(2-amino-[1,2,4]triazolo[1,5-a]pyridin-7-yl)-3-fluoro-2-methylbenzoate: A stirred mixture of potassium acetate (691 mg, 7.04 mmol), 7-bromo-[1,2,4]triazolo[1,5-a]pyridin-2-amine (500 mg, 2.35 mmol), [1,1'-bis (diphenylphosphino)ferrocene]dichloropalladium(II), complex with dichloromethane (96 mg, 0.12 mmol) and bis(pinacolato)diboron (894 mg, 3.52 mmol) in 1,4-dioxane (10 mL) was heated at 100° C. for 1 h. To the reaction mixture was added methyl 5-bromo-3-fluoro-2-methylbenzoate (600 mg, 2.43 mmol) and 1,1'-bis(di-tert-butylphosphino)ferrocene palladium (II) dichloride (79 mg, 0.12 mmol). To degas the reaction, nitrogen was bubbled through the mixture for 5 min. Aqueous 2 M potassium phosphate tribasic (3.64 mL, 7.29 mmol) was quickly added and the reaction mixture heated to 100° C. for 30 min. The crude reaction mixture was concentrated onto celite and purified by flash column chromatography (40 g silica, elution gradient 0-100% ethyl acetate in Hex followed by 0-10% methanol in dichloromethane). The pure fractions were combined and concentrated under reduced pressure to yield methyl 5-(2-amino-[1,2,4]triazolo[1,5-a]pyridin-7-yl)-3-fluoro-2-methylbenzoate (677 mg, 2.21 mmol, 91% yield). MS ESI m/z 301.1 (M+H)+

158B: lithium 5-(2-amino-[1,2,4]triazolo[1,5-a]pyridin-7-yl)-3-fluoro-2-methylbenzoate: To a solution of methyl 5-(2-amino-[1,2,4]triazolo[1,5-a]pyridin-7-yl)-3-fluoro-2-methylbenzoate (677 mg, 2.21 mmol) in tetrahydrofuran (10 mL) and a few drops of methanol was added a solution of lithium hydroxide monohydrate (114 mg, 2.71 mmol) in 1.5 mL water. The resulting mixture was stirred at 60° C. for 3 d. An additional 5 mg of lithium hydroxide monohydrate in 0.5 ml of water was added and the reaction stirred at 60° C. for 6 h. The mixture was concentrated in vacuo to afford crude lithium 5-(2-amino-[1,2,4]triazolo[1,5-a]pyridin-7-yl)-3-fluoro-2-methylbenzoate (599 mg, 1.99 mmol, 88% yield) as a beige solid. The material was used as-is without further purification.

158: A mixture of lithium 5-(2-amino-[1,2,4]triazolo[1,5-a]pyridin-7-yl)-3-fluoro-2-methylbenzoate (22 mg, 0.077 mmol), benzotriazol-1-yloxytris(dimethylamino)phosphonium hexafluorophosphate (51 mg, 0.115 mmol), (S)-3-amino-1-(4-chlorophenyl)propan-1-ol hydrochloride (21.3 mg, 0.096 mmol) and diisopropylethyl amine (0.081 mL, 0.461 mmol) in dimethylformamide (1.0 mL) was stirred at 44° C. ON. The crude mixture was purified via preparative LCMS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 15% B, 15-55% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield (S)-5-(2-amino-[1,2,4]triazolo[1,5-a]pyridin-7-yl)-N-(3-(4-chlorophenyl)-3-hydroxypropyl)-3-fluoro-2-methylbenzamide (8.1 mg, 0.018 mmol, 23% yield).

$^1$H NMR (500 MHz, DMSO-$d_6$) δ 8.60 (d, J=7.3 Hz, 1H), 8.47 (br t, J=5.2 Hz, 1H), 7.76 (s, 1H), 7.74 (d, J=11.4 Hz, 1H), 7.58 (s, 1H), 7.40 (s, 4H), 7.28 (dd, J=7.0, 1.8 Hz, 1H), 6.06 (s, 2H), 5.43 (d, J=4.6 Hz, 1H), 4.76-4.65 (m, 1H), 3.33 (br s, 1H), 2.31-2.26 (m, 3H), 1.92-1.83 (m, 2H). MS ESI m/z 454.0 (M+H)+

Example 159: (R)-5-(2-amino-[1,2,4]triazolo[1,5-a]pyridin-7-yl)-N-(3-(4-chlorophenyl)-3-hydroxypropyl)-2-methylbenzamide

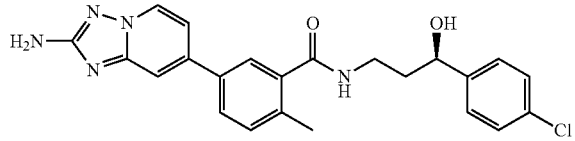 [SMILES: Cc1ccc(-c2ccn3nc(N)nc3c2)cc1C(=O)NCC[C@@H](O)c1ccc(Cl)cc1]

159A: ethyl 5-bromo-2-methylbenzoate: A solution of 5-bromo-2-methylbenzoic acid (1.50 g, 6.98 mmol) in ethanol (20 mL) and sulfuric acid (0.558 mL, 10.5 mmol) was heated to reflux and stirred ON. The ethanol was removed under reduced pressure and the remaining mixture was neutralized by careful addition of 10% aqueous sodium bicarbonate. The crude residue was extracted twice with 100 mL of ethyl acetate. The combined organic layers were washed with brine and dried over anhydrous sodium sulfate, filtered and concentrated in vacuo to afford ethyl 5-bromo-2-methylbenzoate (1.45 g, 5.67 mmol, 81% yield) as an oil.

159B: methyl 5-(2-amino-[1,2,4]triazolo[1,5-a]pyridin-7-yl)-2-methylbenzoate: A stirred mixture of potassium acetate (346 mg, 3.52 mmol), 7-bromo-[1,2,4]triazolo[1,5-a]pyridin-2-amine (250 mg, 1.17 mmol), [1,1'-bis(diphenylphosphino)ferrocene]dichloropalladium(II), complex with dichloromethane (48 mg, 0.059 mmol) and bis(pinacolato)diboron (447 mg, 1.76 mmol) in 1,4-dioxane (5 mL) was heated at 100° C. for 45 min. To the reaction mixture was added ethyl 5-bromo-2-methylbenzoate (310 mg, 1.275 mmol) and 1,1'-bis(di-tert-butylphosphino)ferrocene palladium (II) dichloride (42 mg, 0.064 mmol). To degas the reaction, nitrogen was bubbled through the mixture for 5 min. Aqueous 2 M potassium phosphate tribasic (1.9 mL, 3.83 mmol) was quickly added and the reaction mixture was heated to 100° C. for 30 min. The crude reaction mixture was concentrated onto celite and purified by flash column chromatography (24 g silica, elution gradient 0-100% ethyl acetate in Hex followed by 0-10% methanol in dichloromethane). The pure fractions were combined and concentrated under reduced pressure to yield ethyl 5-(2-amino-[1,2,4]triazolo[1,5-a]pyridin-7-yl)-2-methylbenzoate (261 mg, 0.872 mmol, 68% yield) as a beige solid. MS ESI m/z 297.3 (M+H)+

159C: lithium 5-(2-amino-[1,2,4]triazolo[1,5-a]pyridin-7-yl)-2-methylbenzoate: To a solution of ethyl 5-(2-amino-[1,2,4]triazolo[1,5-a]pyridin-7-yl)-2-methylbenzoate (261 mg, 0.872 mmol) in tetrahydrofuran (5 mL) and a few drops of methanol was added a solution of lithium hydroxide monohydrate (48.5 mg, 1.16 mmol) in 1.5 mL water. The resulting mixture was stirred at 60° C. for 3 h. The reaction mixture was concentrated under reduced pressure to afford crude lithium 5-(2-amino-[1,2,4]triazolo[1,5-a]pyridin-7-yl)-2-methylbenzoate (245 mg, 0.822 mmol, 89% yield) as a light brown solid. The material was used as-is without further purification. MS ESI m/z 269.1 (M+H)+

159: A mixture of crude lithium 5-(2-amino-[1,2,4]triazolo[1,5-a]pyridin-7-yl)-2-methylbenzoate (20 mg, 0.075 mmol), benzotriazol-1-yloxytris(dimethylamino)phosphonium hexafluorophosphate (49.5 mg, 0.112 mmol), (R)-3-amino-1-(4-chlorophenyl)propan-1-ol hydrochloride (21 mg, 0.093 mmol) and diisopropylethyl amine (0.078 mL, 0.48 mmol) in dimethylformamide (1.0 mL) was stirred at 44° C. for 3 d. The crude mixture was purified via preparative LCMS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-min hold at 10% B, 10-50% B over 20 min, then a 0-min hold at 100% B; Flow Rate: 20 mL/min; Column Temperature: 25° C. Fraction collection was triggered by MS and UV signals. Fractions containing the desired product were combined and dried via centrifugal evaporation to yield (R)-5-(2-amino-[1,2,4]triazolo[1,5-a]pyridin-7-yl)-N-(3-(4-chlorophenyl)-3-hydroxypropyl)-2-methylbenzamide (17.4 mg, 0.038 mmol, 51% yield).

$^1$H NMR (500 MHz, DMSO-$d_6$) δ 8.66 (d, J=7.0 Hz, 1H), 8.39 (br t, J=5.3 Hz, 1H), 7.78 (br d, J=7.9 Hz, 1H), 7.75-7.68 (m, 2H), 7.42-7.35 (m, 7H), 4.68 (t, J=6.6 Hz, 1H), 3.33 (br d, J=7.0 Hz, 1H), 2.39 (s, 3H), 1.87 (q, J=6.8 Hz, 2H).

MS ESI m/z 436.1 (M+H)$^+$

Example 160: 3-(2-amino-[1,2,4]triazolo[1,5-a]pyridin-7-yl)-N-(3-(4-chlorophenyl)-3-fluoropropyl)-2-fluoro-6-methylbenzamide

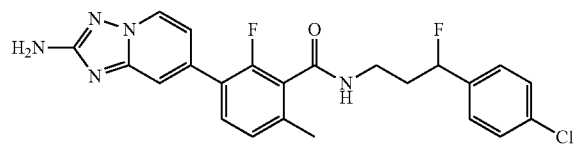 [SMILES: Cc1ccc(-c2ccn3nc(N)nc3c2)c(F)c1C(=O)NCCC(F)c1ccc(Cl)cc1]

Under nitrogen atmosphere, a 0° C. mixture of (S)-3-(2-amino-[1,2,4]triazolo[1,5-a]pyridin-7-yl)-N-(3-(4-chlorophenyl)-3-hydroxypropyl)-2-fluoro-6-methylbenzamide (25 mg, 0.055 mmol) in DCM (1 mL) was treated with a solution of deoxo-fluor (0.015 mL, 0.083 mmol) in DCM (1 mL) via syringe pump over 30 min. The resulting mixture was stirred at 0° C. for 1 h and was then allowed to warm to RT. The mixture was quenched by addition of several drops of methanol. The resulting crude mixture was concentrated in vacuo, then redissolved in methanol. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 23% B, 23-63% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give 3-(2-amino-[1,2,4]triazolo[1,5-a]pyridin-7-yl)-N-(3-(4-chlorophenyl)-3-fluoropropyl)-2-fluoro-6-methylbenzamide (5.2 mg, 0.011 mmol, 21% yield).

1H NMR (600 MHz, DMSO-d6) δ 8.70 (t, J=5.5 Hz, 1H), 8.56 (d, J=6.6 Hz, 1H), 7.54 (t, J=8.1 Hz, 1H), 7.47-7.42 (m, 3H), 7.41-7.36 (m, 2H), 7.18 (d, J=8.1 Hz, 1H), 6.98 (br d, J=7.0 Hz, 1H), 6.04 (s, 2H), 5.71-5.53 (m, 1H), 3.46-3.20 (m, 2H), 2.26 (s, 3H), 2.19-1.92 (m, 2H).

MS ESI m/z 456.0 (M+H)$^+$.

Example 161: 3-(3-(2-amino-[1,2,4]triazolo[1,5-a]pyridin-7-yl)-2-fluoro-6-methylbenzamido)-2,2-difluoro-1-(4-fluorophenyl)propyl dihydrogen phosphate, racemate

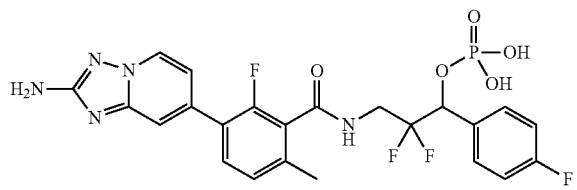 [SMILES: Cc1ccc(-c2ccn3nc(N)nc3c2)c(F)c1C(=O)NCC(F)(F)C(OP(=O)(O)O)c1ccc(F)cc1]

To a solution of 3-(2-amino-[1,2,4]triazolo[1,5-a]pyridin-7-yl)-N-(2,2-difluoro-3-(4-fluorophenyl)-3-hydroxypropyl)-2-fluoro-6-methylbenzamide (47 mg, 0.099 mmol) and di-tert-butyl diisopropylphosphoramidite (0.066 ml, 0.208 mmol) in DMF (1 ml) at 0 C was added 1H-tetrazole (14.60 mg, 0.208 mmol) and the reaction mixture was stirred from 0 C to rt overnight. The reaction mixture was partitioned between EtOAc (30 ml) and water (25 ml). The organic layer was washed with 10% LiCl solution (2×20 ml) and brine (20 ml). After drying over anhydrous sodium sulfate, the organic layer was concentrated and the residue was chromatographed on a 4 gm silica gel cartridge, eluting with a 0-9% MeOH/CH$_2$Cl$_2$ gradient. The product containing fractions were concentrated to afford 55 mg of a mixture of 3-(3-(2-amino-[1,2,4]triazolo[1,5-a]pyridin-7-yl)-2-fluoro-6-methylbenzamido)-2,2-difluoro-1-(4-fluorophenyl)propyl di-tert-butyl phosphate and di-tert-butyl (7-(3-((3-((di-tert-butoxyphosphoryl)oxy)-2,2-difluoro-3-(4-fluorophenyl)propyl)carbamoyl)-2-fluoro-4-methylphenyl)-[1,2,4]triazolo[1,5-a]pyridin-2-yl)phosphoramidate as a white solid. The mixture was dissolved in 1 ml of TFA and was allowed to stand at rt for 1.5 hr. The volatiles were removed in vacuo and the residue was dissolved in DMF and purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 0% B, 0-46% B over 23 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford 3-(3-(2-amino-[1,2,4]triazolo[1,5-a]pyridin-7-yl)-2-fluoro-6-methylbenzamido)-2,2-difluoro-1-(4-fluorophenyl)propyl dihydrogen phosphate, racemate (12.7 mg, 0.023 mmol, 35% yield).

$^1$H NMR (400 MHz, DMSO-$d_6$) δ 9.27-8.88 (m, 1H), 8.60 (d, J=7.0 Hz, 1H), 7.60 (t, J=8.0 Hz, 1H), 7.54-7.46 (m, 3H), 7.30-7.20 (m, 3H), 7.03 (dt, J=7.0, 1.6 Hz, 1H), 6.07 (br s, 2H), 5.63-5.27 (m, 1H), 4.11-3.98 (m, 1H), 3.79-3.71 (m, 1H), 2.30 (s, 3H) phosphate protons missing.

MS ESI m/z 554.3 (M+H)$^+$

Intermediate 1: (S)-3-amino-2,2-difluoro-1-(4-fluorophenyl)propan-1-ol

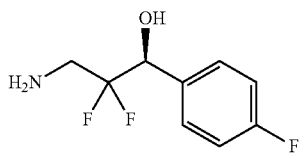 [SMILES: NCC(F)(F)[C@@H](O)c1ccc(F)cc1]

Intermediate 1A: ethyl 2,2-difluoro-3-(4-fluorophenyl)-3-hydroxypropanoate: A mixture of Zn (95.9 g, 1.47 mol) in THF (840 mL) was treated dropwise with a solution of 4-fluorobenzaldehyde (140 g, 1.13 mol) in THF (100 mL). After addition, the resulting mixture was heated to 65° C. with stirring, and then ethyl 2-bromo-2,2-difluoroacetate (275 g, 1.35 mol) was added dropwise to the heated mixture. The resulting mixture was stirred at 65° C. for 1 h The mixture was cooled and then quenched by the addition of saturated aqueous $NaHSO_4$ (1 L). The residue was extracted with EtOAc (300 mL×2), the organic layer was washed with brine (300 mL), dried with anhydrous $Na_2SO_4$, filtered and concentrated under reduced pressure to give a residue. The residue was purified by column chromatography ($SiO_2$, elution gradient petroleum ether/ethyl acetate=50/1 to 3/1) to give ethyl 2,2-difluoro-3-(4-fluorophenyl)-3-hydroxypropanoate (195 g, 786 mmol, 70% yield) as a colorless oil.

$^1$H NMR (400 MHz, $CDCl_3$) δ 7.42-7.46 (m, 2H), 7.07-7.12 (m, 2H), 5.17 (dd, J=15.2 Hz, 8.0 Hz, 1H), 4.32 (q, J=7.2 Hz, 2H), 2.74 (s, 1H), 1.31 (t, J=7.2 Hz 3H).

Intermediate 1B: (S)-2,2-difluoro-3-(4-fluorophenyl)-3-hydroxypropanamide: To a solution of ethyl 2,2-difluoro-3-(4-fluorophenyl)-3-hydroxypropanoate (180 g, 725 mmol) in MeOH (1.2 L) was added $NH_3$/MeOH solution (7 M, 414 mL) at 0° C. The mixture was stirred at 20° C. for 1 h. Silica TLC (petroleum ether:ethyl acetate=5:1, Rf-sm=0.46, Rf-product=0.00) showed the starting material was consumed completely. The reaction mixture was concentrated in vacuo, and the residue (100 g) was separated by chiral SFC (column: Daicel Chiralpak AS (250 mm×50 mm, 10 um particles); mobile phase A: $CO_2$; mobile phase B: 0.1% ammonium hydroxide in MeOH; elution isocratic 15 B %, run time: 11 min). (S)-2,2-difluoro-3-(4-fluorophenyl)-3-hydroxypropanamide (32 g, 146 mmol, 20% yield) was the first isomer to elute from the SFC chromatography and was obtained as a light yellow solid after concentration in vacuo. Absolute stereochemistry of this material was determined through X-Ray crystallography experiments.

$^1$H NMR (400 MHz, DMSO-$d_6$) δ 8.03 (s, 1H), 7.88 (s, 1H), 7.42-7.48 (m, 2H), 7.17-7.24 (m, 2H), 6.42 (d, J=5.6 Hz, 1H), 5.06-5.14 (m, 1H).

Intermediate 1: To a solution of (S)-2,2-difluoro-3-(4-fluorophenyl)-3-hydroxypropanamide (45 g, 205 mmol) in THF (280 mL) was added dropwise 10M $BH_3$-$Me_2$S in THF (71.9 mL, 719 mmol) at 0° C. The mixture was then heated to 65° C. and stirred for 1 hr. Silica TLC (petroleum ether:ethyl acetate=0:1, Rf-sm=0.71, Rf-product=0.00) showed the starting material was consumed completely. The reaction mixture was quenched by addition MeOH (100 mL) at 0° C. The result was stirred for 0.5 h and then concentrated in vacuo. The resulting white solid was charged with 1 L of 1N aqueous HCl. The resulting suspension was then stirred at 65-70° C. for 30 min during which time a colorless solution resulted. The aqueous acidic solution was cooled to RT and then washed in a separatory funnel with EtOAc (200 mL, 100 mL) and the layers were separated. In a separatory funnel, the aqueous acidic layer was made basic with 1N aqueous NaOH until pH=8 was achieved. The aqueous phase was then extracted with ethyl acetate (2×100 mL). The combined organic phase was washed with brine (100 mL), dried with anhydrous $Na_2SO_4$, filtered and concentrated under reduced pressure to give (S)-3-amino-2,2-difluoro-1-(4-fluorophenyl)propan-1-ol (33 g, 158 mmol, 77% yield, 98% purity) as a white solid.

$^1$H NMR (400 MHz, MeOD) δ 7.45-7.48 (m, 2H), 7.05-7.11 (m, 2H), 4.91 (dd, J=15.2 Hz, 7.6 Hz, 1H), 3.04-3.10 (m, 1H), 2.91-3.01 (m, 1H).

Intermediate 2: (R)-3-amino-2,2-difluoro-1-(4-fluorophenyl)propan-1-ol

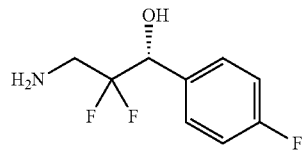 [SMILES: NCC(F)(F)[C@H](O)c1ccc(F)cc1]

Intermediate 2A: (R)-2,2-difluoro-3-(4-fluorophenyl)-3-hydroxypropanamide: The title compound was obtained as the second isomer to elute from the preparative chiral SFC separation described in the preparation of Intermediate 1B. (R)-2,2-difluoro-3-(4-fluorophenyl)-3-hydroxypropanamide (44 g, 201 mmol, 28% yield) was thus obtained as a white solid.

1H NMR (400 MHz, DMSO-d6) δ 8.03 (s, 1H), 7.88 (s, 1H), 7.42-7.48 (m, 2H), 7.17-7.24 (m, 2H), 6.42 (d, J=5.6 Hz, 1H), 5.06-5.14 (m, 1H).

Intermediate 2: To a solution of (R)-2,2-difluoro-3-(4-fluorophenyl)-3-hydroxypropanamide (32 g, 146 mmol) in THF (210 mL) was added dropwise 10M $BH_3$-$Me_2$S in THF (51.1 mL, 511 mmol) at 0° C. The mixture was then heated to 65° C. and stirred for 1 hr. Silica TLC (petroleum ether:ethyl acetate=0:1, Rf-sm=0.71, Rf-product=0.00) showed the starting material was consumed completely. The reaction mixture was quenched by addition MeOH (100 mL) at 0° C. The result was stirred for 0.5 h and then concentrated in vacuo. The resulting white solid was charged with 1 L of 1N aqueous HCl. The resulting suspension was then stirred at 65-70° C. for 30 min during which time a colorless solution resulted. The aqueous acidic solution was cooled to RT and then washed in a separatory funnel with EtOAc (200 mL, 100 mL) and the layers were separated. In a separatory funnel, the aqueous acidic layer was made basic with 1N aqueous NaOH until pH=8 was achieved. The aqueous phase was then extracted with ethyl acetate (2×100 mL). The combined organic phase was washed with brine (100 mL), dried with anhydrous $Na_2SO_4$, filtered and concentrated under reduced pressure to give (R)-3-amino-2,2-difluoro-1-(4-fluorophenyl)propan-1-ol (22 g, 106 mmol, 72% yield, 99% purity) as a white solid.

$^1$H NMR (400 MHz, MeOD) δ 7.45-7.49 (m, 2H), 7.06-7.11 (m, 2H), 4.91 (dd, J=15.2 Hz, 7.6 Hz, 1H), 2.99-3.10 (m, 1H), 2.90-2.97 (m, 1H).

Intermediate 3: 3-bromo-2-fluoro-6-methylbenzoic acid

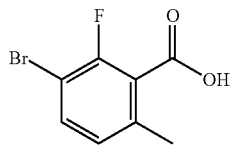

To a solution of 2,2,6,6-tetramethylpiperidine (5.94 mL, 34.9 mmol) in THF (50 mL) at −10° C. was added n-butyllithium (21.82 mL, 34.9 mmol) dropwise and the mixture was stirred at same temperature for 1.5 h. The temperature was reduced to −78° C. and 1-bromo-2-fluoro-4-methylbenzene (3.69 mL, 29.1 mmol) was added dropwise and the mixture stirred for 30 mins. Dry ground up carbon dioxide (2.56 g, 58.2 mmol) was then added in one portion and the mixture stirred for 20 min. LCMS showed good conversion of the starting material to a peak with the desired mass. The reaction mixture was quenched with 1.5N HCl (50 mL) at −78° C. to achieve pH ∼1 and the reaction was allowed to warm to room temperature. The organic layer was separated, and the aqueous layer was extracted with EtOAc (2×30 mL). The combined organic layer was washed with water (50 mL), brine (50 mL), dried over sodium sulphate and concentrated. The crude residue was dissolved in MeOH (25 mL), heated to −40° C. and water 75 (mL) was added slowly during which time a solid precipitated out. The mixture was stirred for 20 min and allowed to reach room temperature. The solid was collected by filtration, washed with water (30 mL) and dried to give 3-bromo-2-fluoro-6-methylbenzoic acid (6.1 g, 25.8 mmol, 89% yield) as an off-white solid.

$^1$H NMR (400 MHz, DMSO-$d_6$) δ 13.80 (br s, 1H), 7.57 (dd, J=8.0, 7.2 Hz, 1H), 7.11 (d, J=8.0 Hz, 1H), 2.31 (s, 3H).

Intermediate 4: tert-butyl (7-bromo-[1,2,4]triazolo[1,5-a]pyridin-2-yl)(tert-butoxycarbonyl)carbamate

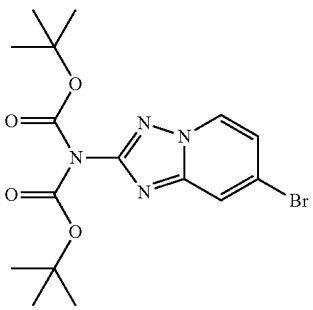 [SMILES: CC(C)(C)OC(=O)N(C(=O)OC(C)(C)C)c1nc2cc(Br)ccn2n1]

A 2 L, single necked, round bottomed flask was charged with 7-bromo-[1,2,4]triazolo[1,5-a]pyridin-2-amine (46 g, 216 mmol) and DCM (700 mL) at room temperature to give a white slurry. To the flask was added TEA (105 mL, 756 mmol) and DMAP (2.64 g, 21.59 mmol). The mixture was stirred for 10 min, then Boc-anhydride (150 mL, 648 mmol) was slowly added over 30 min. A brisk exotherm was observed during the addition. The white slurry was heated to reflux at 40° C. and maintained overnight. The brown solution was concentrated to dryness under vacuum. The yellow semi-solid was purified by silica gel chromatography using a 750 g Redisep Silica column and petroleum ether/EtOAc as solvent to obtain tert-butyl (7-bromo-[1,2,4]triazolo[1,5-a]pyridin-2-yl)(tert-butoxycarbonyl)carbamate (76.8 g, 180 mmol, 83% yield).

$^1$H NMR (499 MHz, CHLOROFORM-d) Shift 8.42 (dd, J=7.3, 0.7 Hz, 1H), 7.92 (dd, J=2.0, 0.7 Hz, 1H), 7.18 (dd, J=7.3, 2.0 Hz, 1H), 1.49 (s, 18H).
MS ESI m/z 413.0 (M+H)$^+$ Intermediate 5: tert-butyl (7-bromo-[1,2,4]triazolo[1,5-a]pyridin-2-yl)(tert-butoxycarbonyl)carbamate

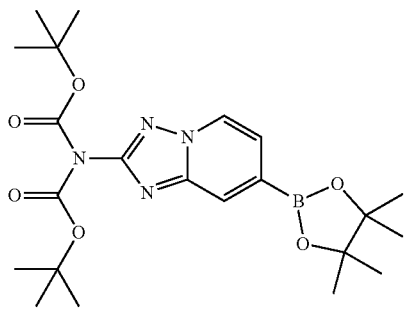 [SMILES: CC(C)(C)OC(=O)N(C(=O)OC(C)(C)C)c1nc2cc(B3OC(C)(C)C(C)(C)O3)ccn2n1]

A dry 3-necked 3 L round bottomed flask equipped with a magnetic stir bar was charged with tert-butyl (7-bromo-[1,2,4]triazolo[1,5-a]pyridin-2-yl)(tert-butoxycarbonyl)carbamate (100 g, 242 mmol) and 1,4-dioxane (968 mL). Potassium acetate (71.2 g, 726 mmol), 4,4,4',4',5,5,5',5'-octamethyl-2,2'-bi(1,3,2-dioxaborolane) (67.6 g, 266 mmol), X-Phos (4.61 g, 9.68 mmol) and X-Phos-Pd-G2 (3.80 g, 4.84 mmol) were added under N2. The reaction mixture was purged with nitrogen and was heated to 95° C. under N2. Progress of the reaction was monitored by HPLC and LC/MS. After LC/MS indicated complete consumption of starting material, the reaction was allowed to cool to room temperature and filtered through celite. The cake was washed with DCM and the filtrate was collected and evaporated in vacuo. The crude product was purified by silica gel chromatography eluting with hexanes/ethyl acetate to give tert-butyl (tert-butoxycarbonyl)(7-(4,4,5,5-tetramethyl-1,3,2-dioxaborolan-2-yl)-[1,2,4]triazolo[1,5-a]pyridin-2-yl)carbamate (87.1 g, 188 mmol, 78% yield).

$^1$H NMR (499 MHz, CHLOROFORM-d) δ 8.53 (dd, J=6.7, 1.0 Hz, 1H), 8.17 (t, J=1.1 Hz, 1H), 7.38 (dd, J=6.8, 1.2 Hz, 1H), 1.57 (s, 4H), 1.47 (s, 18H), 1.40 (s, 12H).

Example 162: 3-(2-amino-[1,2,4]triazolo[1,5-a]pyridin-7-yl)-6-chloro-N-(3-(4-chloro-2-fluorophenyl)-2,2-difluoro-3-hydroxypropyl)-2-fluorobenzamide

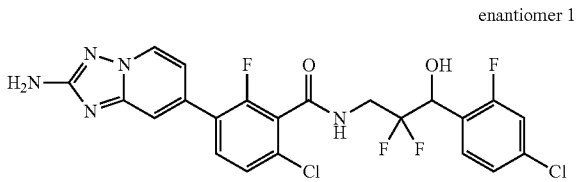 [SMILES: Nc1nc2cc(-c3ccc(Cl)c(C(=O)NCC(F)(F)C(O)c4ccc(Cl)cc4F)c3F)ccn2n1]

enantiomer 1

162A: methyl 3-bromo-6-chloro-2-fluorobenzoate: In a 250 mL round bottom flask equipped with magnetic stir bar were combined 3-bromo-6-chloro-2-fluorobenzoic acid (10.4 g, 40.8 mmol) and potassium carbonate (14.1 g, 102 mmol) in anhydrous DMF (136 mL). To the stirred suspension was added iodomethane (3.83 mL, 61.3 mmol). The mixture was stirred at RT for 24 h. The reaction mixture was diluted with EtOAc (400 mL) and solids were filtered away and rinsed with EtOAc. The filtrate was concentrated in vacuo to a residue then diluted with EtOAc (175 mL), and the organic was washed with water (3×50 mL) and then with brine (50 mL). The organic was dried over anhydrous $MgSO_4$, filtered and concentrated in vacuo. The residue was placed under high vacuum for 1 h to provide methyl 3-bromo-6-chloro-2-fluorobenzoate (11.0 g, 40.8 mmol, quantitative) as a yellow oil. No further purification was performed.

$^1$H NMR (500 MHz, CHLOROFORM-d) δ 7.57 (dd, J=8.6, 7.2 Hz, 1H), 7.15 (dd, J=8.6, 1.5 Hz, 1H), 4.00 (s, 3H).

162B: methyl 3-(2-amino-[1,2,4]triazolo[1,5-a]pyridin-7-yl)-6-chloro-2-fluorobenzoate: In a 500 mL round bottom flask with a magnetic stir bar and under a blanket of nitrogen gas were combined methyl 3-bromo-6-chloro-2-fluorobenzoate (10.9 g, 40.8 mmol) with 4,4,4',4',5,5,5',5'-octamethyl-2,2'-bi(1,3,2-dioxaborolane) (10.9 g, 42.8 mmol), potassium acetate (6.01 g, 61.2 mmol) and 1,1'-bis(diphenyllphosphino)ferrocene palladium dichloride-$CH_2Cl_2$ adduct (1.67 g, 2.04 mmol). The mixture was suspended in 1,4-dioxane (136 mL). The vessel was then fitted with a reflux condenser, and while stirring rapidly, the suspension was iteratively evacuated and then purged with nitrogen five times to degas. The mixture was then heated to 85° C. for 3 h. After the mixture cooled to room temperature, 7-bromo-[1,2,4]triazolo[1,5-a]pyridin-2-amine (8.69 g, 40.8 mmol), tripotassium phosphate (2 M in water) (61.2 mL, 122 mmol) and 1,1'-bis(diphenyllphosphino)ferrocene palladium dichloride-$CH_2Cl_2$ adduct (1.67 g, 2.04 mmol) were added and the resulting mixture was stirred at 75° C. for 14.5 h. The reaction mixture was concentrated in vacuo to remove organic solvent, and to the residue was added EtOAc (600 mL) and the result was filtered to give a biphasic filtrate (labeled Filtrate 1) along with isolated solids. The solids were triturated several times with EtOAc (600 mL, then 2×100 mL) and then DCM (2×100 mL) until the residual solids no longer contained desired product as evidenced by LCMS. The residual solid was discarded. The organic triturants were combined and put aside. The phases of Filtrate 1 were separated, and the separated organic phase was combined with the organic triturants. The Filtrate 1 aqueous phase was diluted with water (100 mL) and extracted with EtOAc (2×100 mL). These EtOAc extracts were combined with the other organic phases. The combined organics was diluted to 1500 mL total volume with EtOAc and then washed with brine (250 mL, then 2×100 mL), dried over anhydrous $MgSO_4$, filtered and concentrated in vacuo. The crude residue was suspended as a solid with heating in DCM (150 mL), and to the stirred suspension was added hexanes (100 mL). 100 mL of organic was removed from the suspension gently via rotary evaporation and the result was chilled in an ice bath and filtered to give a brown powder which was rinsed with diethyl ether and allowed to air-dry to provide Crop 1 of methyl 3-(2-amino-[1,2,4]triazolo[1,5-a]pyridin-7-yl)-6-chloro-2-fluorobenzoate (5.86 g, 18.3 mmol, 45% yield). The filtrate from the Crop 1 isolation was concentrated and the residue was purified by silica gel column chromatography (330 g silica cartridge, elution gradient 0-100% hexanes:EtOAc followed by elution with 30:1 DCM:MeOH) to provide Crop 2 of methyl 3-(2-amino-[1,2,4]triazolo[1,5-a]pyridin-7-yl)-6-chloro-2-fluorobenzoate (1.14 g, 3.50 mmol, 9% yield) as an off-white powder.

Crops 1 and 2 were combined and carried into the next step as-is.

MS ESI m/z 320.8 (M+H)$^+$

162C: 3-(2-amino-[1,2,4]triazolo[1,5-a]pyridin-7-yl)-6-chloro-2-fluorobenzoic acid: A solution of methyl 3-(2-amino-[1,2,4]triazolo[1,5-a]pyridin-7-yl)-6-chloro-2-fluorobenzoate (7.00 g, 21.8 mmol) and sodium hydroxide 1M aqueous solution (32.7 mL, 32.7 mmol) in MeOH (100 mL) was heated to 85° C. for 3.5 h. The dark brown reaction mixture was concentrated to remove methanol, then 100 mL of water was added. The resulting suspension was filtered to remove a small quantity of brown powder solid which was discarded. The brown clear filtrate was stirred rapidly and acidified by slow addition of concentrated 12M HCl (approximately 2.7 mL) until pH measured about 2 to 3 by pH paper. A heavy precipitate occurred during the acid addition. The mixture was chilled in an ice bath and the solid was collected by suction filtration (Buchner funnel and filter paper), rinsed with cold deionized water, and allowed to air-dry overnight and then placed under high vacuum for several hours to give 3-(2-amino-[1,2,4]triazolo[1,5-a]pyridin-7-yl)-6-chloro-2-fluorobenzoic acid (6.39 g, 20.8 mmol, 95% yield) as a brown powder.

$^1$H NMR (500 MHz, DMSO-d6) δ 8.64 (d, J=7.0 Hz, 1H), 7.76 (t, J=8.4 Hz, 1H), 7.55 (s, 1H), 7.54 (d, J=10.5 Hz, 2H), 7.05 (d, J=7.1 Hz, 1H), 6.11 (s, 2H).

162D: ethyl 3-(4-chloro-2-fluorophenyl)-2,2-difluoro-3-hydroxypropanoate: In a 2-neck 100 mL round bottom flask equipped with a magnetic stir bar and a reflux condenser, a stirred suspension of powdered zinc (0.785 g, 12.0 mmol) in THF (20.0 mL) was heated in an oil bath at 70° C. To the hot stirred zinc suspension was added ethyl 2-bromo-2,2-difluoroacetate (1.54 mL, 12.0 mmol) over 2 min. Mild frothing was observed. After 1 min, 4-chloro-2-fluorobenzaldehyde (1.59 g, 10 mmol) was added all at once and the mixture was heated at 70° C. for 20 h. The reaction mixture was allowed to come to room temperature and the reaction was quenched by addition of 10% aqueous $NaHCO_3$ which caused a heavy precipitation to occur. The mixture was neutralized by slow careful addition of concentrated HCl with stirring. The reaction mixture was concentrated in vacuo to remove some of the organic, then the residue was taken up in a mixture of EtOAc (100 mL) and water (50 mL), the mixture was shaken, and phases were separated. The organic was washed iteratively with water until pH of the wash was approximately =5. The organic was washed with brine (25 mL), dried over anhydrous $MgSO_4$, filtered and concentrated in vacuo to a residue. The crude residue was loaded in minimum DCM onto a 120 g silica cartridge which was pre-equilibrated with hexanes. Elution gradient 100% hexanes to 40% EtOAc in hexanes over 10 column volumes. Note: This material had very poor UV absorbance and fractions needed to be checked by TLC visualized with Hanessian's stain and heating. Like product fractions were combined and concentrated in vacuo to give ethyl 3-(4-chloro-2-fluorophenyl)-2,2-difluoro-3-hydroxypropanoate (2.22 g, 7.85 mmol, 79% yield) as a yellow oil.

$^1$H NMR (500 MHz, CHLOROFORM-d) δ 7.54 (t, J=8.0 Hz, 1H), 7.23 (dd, J=8.4, 1.8 Hz, 1H), 7.14 (dd, J=9.9, 2.0 Hz, 1H), 5.56-5.48 (m, 1H), 4.40-4.34 (m, 2H), 3.12-3.00 (m, 1H), 1.36 (t, J=7.2 Hz, 3H).

162E: 3-(4-chloro-2-fluorophenyl)-2,2-difluoro-3-hydroxypropanamide: A 20 mL scintillation vial containing ethyl 3-(4-chloro-2-fluorophenyl)-2,2-difluoro-3-hydroxypropanoate (2.22 g, 7.85 mmol) was charged with methanol (10 mL), followed by the addition of ammonia solution, 7N in methanol (4.49 mL, 31.4 mmol) at 0° C. The resulting mixture was stirred at RT for 2.5 h. The mixture was concentrated in vacuo and the crude 3-(4-chloro-2-fluorophenyl)-2,2-difluoro-3-hydroxypropanamide (1.99 g, 7.85 mmol, 100% yield) thus obtained was carried directly into the next step as-is.

MS ESI m/z 252.05 (M−H)$^-$

162F: 3-amino-1-(4-chloro-2-fluorophenyl)-2,2-difluoropropan-1-ol hydrochloride: Under nitrogen atmosphere, a 100 mL round bottom flask fitted with a stir bar and a reflux condenser was charged with crude 3-(4-chloro-2-fluorophenyl)-2,2-difluoro-3-hydroxypropanamide (1.99 g, 7.85 mmol) and THF (26.2 mL). Borane dimethyl sulfide complex solution, 2M in THF (15.7 mL, 31.4 mmol) was added with stirring, causing vigorous effervescing. The resulting mixture was stirred at 72° C. for 24 h. The mixture was allowed to cool to RT and was then treated dropwise through the top of the reflux condenser with methanol very slowly to cause immediate effervescence and significant exotherm. MeOH was added until all effervescing ceased, then another 4 mL of MeOH was added and the mix was stirred for an additional 30 min and then stood at RT overnight. The mixture was concentrated in vacuo and the residue was dissolved in 1M aqueous HCl (75 mL). The resulting slightly flocculent mixture was heated to 65° C. for 1 hour with stirring. The clear colorless solution was filtered to remove any particulates. The mixture was concentrated in vacuo to a nearly white solid foam residue and the residue was placed under high vacuum for several days to provide 3-amino-1-(4-chloro-2-fluorophenyl)-2,2-difluoropropan-1-ol hydrochloride (1.81 g, 6.61 mmol, 84% yield) as a white foam solid HCl salt.

$^1$H NMR (500 MHz, DMSO-d6) δ 8.59 (br s, 2H), 7.60 (t, J=7.8 Hz, 1H), 7.48 (dd, J=9.8, 1.5 Hz, 1H), 7.43-7.33 (m, 1H), 6.88 (br s, 1H), 5.29 (br d, J=18.5 Hz, 1H), 3.64-3.41 (m, 2H).

MS ESI m/z 239.75 (M+H)$^+$

162: In a 1 dram vial with PTFE screwcap were combined 3-(2-amino-[1,2,4]triazolo[1,5-a]pyridin-7-yl)-6-chloro-2-fluorobenzoic acid (60.0 mg, 0.196 mmol) with 3-amino-1-(4-chloro-2-fluorophenyl)-2,2-difluoropropan-1-ol, HCl (81.0 mg, 0.293 mmol) and BOP (95.0 mg, 0.215 mmol) in DMF (1 mL), followed by addition of DIPEA (0.171 mL, 0.978 mmol). The resulting mixture was stirred at RT for 1 h. The crude mixture was filtered and purified by reverse phase preparative HPLC with the following conditions: Column: XBridge C18, 19 mm×200 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-min hold at 20% B, 20-60% B over 20 minutes, then a 0-min hold at 100% B; Flow Rate: 20 mL/min; Column Temperature: 25 C. Fraction collection was triggered by MS and UV signals. Fractions containing the racemate product were combined and dried via centrifugal evaporation to a residue. The residue was further purified to separate the individual enantiomers using SFC-chiral chromatography with the following conditions: Instrument: Waters 100 Prep SFC; Column: Chiral IC, 21×250 mm, 5 μm particles; Mobile Phase: 60% CO$_2$/40% MeOH with 0.1% DEA; Flow Rate: 60 mL/min; Injection Details: 0.5 mL injections of 80.7 mg residue dissolved in 6 mL DMSO. Thus, was obtained 3-(2-amino-[1,2,4]triazolo[1,5-a]pyridin-7-yl)-6-chloro-N-(3-(4-chloro-2-fluorophenyl)-2,2-difluoro-3-hydroxypropyl)-2-fluorobenzamide enantiomer 1 (23.2 mg, 0.0431 mmol, 22% yield) as the first eluting isomer from the described preparative SFC purification.

$^1$H NMR (500 MHz, DMSO-d6) δ 9.22 (br t, J=6.1 Hz, 1H), 8.61 (d, J=7.0 Hz, 1H), 7.72 (t, J=8.4 Hz, 1H), 7.61 (t, J=8.1 Hz, 1H), 7.53-7.47 (m, 2H), 7.44-7.34 (m, 2H), 7.06 (br d, J=7.3 Hz, 1H), 6.67 (br d, J=5.5 Hz, 1H), 6.08 (s, 2H), 5.29-5.16 (m, 1H), 4.10-3.80 (m, 2H).

MS ESI m/z 528.0 (M+H)$^+$

Example 163: 3-(2-amino-[1,2,4]triazolo[1,5-a]pyridin-7-yl)-6-chloro-N-(3-(4-chloro-2-fluorophenyl)-2,2-difluoro-3-hydroxypropyl)-2-fluorobenzamide

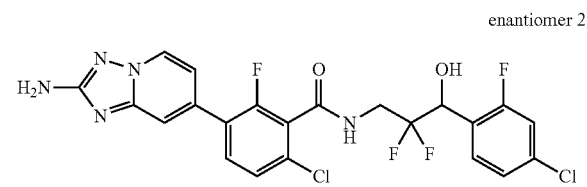 [SMILES: Nc1nc2cc(-c3ccc(Cl)c(C(=O)NCC(F)(F)C(O)c4ccc(Cl)cc4F)c3F)ccn2n1]

enantiomer 2

The title compound 3-(2-amino-[1,2,4]triazolo[1,5-a]pyridin-7-yl)-6-chloro-N-(3-(4-chloro-2-fluorophenyl)-2,2-difluoro-3-hydroxypropyl)-2-fluorobenzamide enantiomer 2 (20.5 mg, 0.0380 mmol, 19% yield) was obtained as the second eluting isomer from the chiral SFC purification described for example 162.

$^1$H NMR (500 MHz, DMSO-d6) δ 9.22 (br t, J=6.1 Hz, 1H), 8.61 (d, J=7.0 Hz, 1H), 7.72 (t, J=8.4 Hz, 1H), 7.62 (t, J=7.9 Hz, 1H), 7.54-7.48 (m, 2H), 7.42 (d, J=10.3 Hz, 1H), 7.36 (d, J=8.0 Hz, 1H), 7.06 (br d, J=7.0 Hz, 1H), 6.08 (s, 2H), 5.22 (br d, J=18.6 Hz, 1H), 4.06-3.85 (m, 2H). One proton is missing, perhaps due to water peak.

MS ESI m/z 528.3 (M+H)$^+$

TABLE 13

Compounds in Table 13 were prepared in a similar fashion to examples 162 and 163. Various substituted benzaldehydes were used in place of 4-chloro-2-fluorobenzaldehyde in the fourth step.

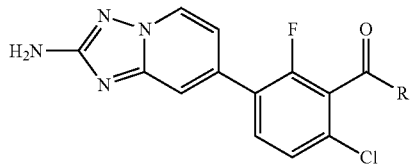

| Ex No | Name | R | M + H⁺ | 1H NMR (500 MHz, DMSO-d6) δ |
|---|---|---|---|---|
| 164 | 3-(2-amino-[1,2,4]triazolo[1,5-a]pyridin-7-yl)-6-chloro-N-(2,2-difluoro-3-(2-fluoro-4-(trifluoromethyl)phenyl)-3-hydroxypropyl)-2-fluorobenzamide | [structure with OH, F, F, CF₃]<br>enantiomer 1<br>first eluted | 562.0 | 9.25 (br t, J = 6.3 Hz, 1H), 8.61 (d, J = 7.0 Hz, 1H), 7.84 (br t, J = 7.5 Hz, 1H), 7.75-7.69 (m, 1H), 7.67 (br d, J = 8.9 Hz, 2H), 7.56-7.46 (m, 2H), 7.06 (br d, J = 7.0 Hz, 1H), 6.08 (s, 2H), 5.33 (br d, J = 18.3 Hz, 1H), 4.12-3.84 (m, 2H). |
| 165 | 3-(2-amino-[1,2,4]triazolo[1,5-a]pyridin-7-yl)-6-chloro-N-(2,2-difluoro-3-(2-fluoro-4-(trifluoromethyl)phenyl)-3-hydroxypropyl)-2-fluorobenzamide | [structure with OH, F, F, CF₃]<br>enantiomer 2<br>second eluted | 562.0 | 9.25 (br t, J = 6.1 Hz, 1H), 8.61 (d, J = 6.7 Hz, 1H), 7.84 (br t, J = 7.0 Hz, 1H), 7.75-7.64 (m, 3H), 7.53-7.48 (m, 2H), 7.10-7.02 (m, 1H), 6.16-6.00 (m, 2H), 5.32 (br d, J = 18.9 Hz, 1H), 4.12-3.85 (m, 2H). |
| 166 | 3-(2-amino-[1,2,4]triazolo[1,5-a]pyridin-7-yl)-6-chloro-N-(3-(2,3-difluorophenyl)-2,2-difluoro-3-hydroxypropyl)-2-fluorobenzamide | [structure with OH, F, F, F]<br>enantiomer 1<br>first eluted | 512.0 | 9.22 (br t, J = 6.1 Hz, 1H), 8.64 (d, J = 6.7 Hz, 1H), 7.75 (t, J = 8.4 Hz, 1H), 7.54-7.49 (m, 2H), 7.48-7.39 (m, 2H), 7.35-7.22 (m, 1H), 7.05 (br d, J = 7.0 Hz, 1H), 6.66 (d, J = 5.5 Hz, 1H), 6.11 (s, 2H), 5.39-5.22 (m, 1H), 4.10-3.87 (m, 2H). |
| 167 | 3-(2-amino-[1,2,4]triazolo[1,5-a]pyridin-7-yl)-6-chloro-N-(3-(2,3-difluorophenyl)-2,2-difluoro-3-hydroxypropyl)-2-fluorobenzamide | [structure with OH, F, F, F]<br>enantiomer 2<br>second eluted | 512.0 | 9.23 (br t, J = 5.8 Hz, 1H), 8.63 (d, J = 7.0 Hz, 1H), 7.74 (br t, J = 8.2 Hz, 1H), 7.56-7.48 (m, 2H), 7.48-7.39 (m, 2H), 7.36-7.18 (m, 1H), 7.05 (br d, J = 6.7 Hz, 1H), 6.10 (s, 2H), 5.36-5.23 (m, 1H), 4.10-3.87 (m, 2H). One proton missing due to water |
| 168 | 3-{2-amino-[1,2,4]triazolo[1,5-a]pyridin-7-yl}-6-chloro-N-[2,2-difluoro-3-(3-fluorophenyl)-3-hydroxypropyl]-2-fluorobenzamide | [structure with OH, F, F]<br>enantiomer 1<br>first eluted | 494.1 | 9.16 (br t, J = 6.0 Hz, 1H), 8.63 (d, J = 7.0 Hz, 1H), 7.74 (t, J = 8.4 Hz, 1H), 7.57-7.41 (m, 3H), 7.33-7.15 (m, 3H), 7.05 (br d, J = 7.0 Hz, 1H), 5.01-4.90 (m, 1H), 3.96-3.78 (m, 2H). Three protons missing due to water |

TABLE 13-continued

Compounds in Table 13 were prepared in a similar fashion to examples 162 and 163. Various substituted benzaldehydes were used in place of 4-chloro-2-fluorobenzaldehyde in the fourth step.

| Ex No | Name | R | M + H⁺ | 1H NMR (500 MHz, DMSO-d6) δ |
|---|---|---|---|---|
| 169 | 3-{2-amino-[1,2,4]triazolo[1,5-a]pyridin-7-yl}-6-chloro-N-[2,2-difluoro-3-(3-fluorophenyl)-3-hydroxypropyl]-2-fluorobenzamide | (structure) enantiomer 2 second eluted | 494.1 | 9.16 (br t, J = 5.8 Hz, 1H), 8.62 (br d, J = 6.7 Hz, 1H), 7.73 (br t, J = 7.9 Hz, 1H), 7.58-7.40 (m, 3H), 7.33-7.14 (m, 3H), 7.05 (br d, J = 6.7 Hz, 1H), 6.57 (br d, J = 5.5 Hz, 1H), 6.10 (s, 2H), 5.04-4.82 (m, 1H), 4.00-3.79 (m, 2H). |
| 170 | 3-(2-amino-[1,2,4]triazolo[1,5-a]pyridin-7-yl)-6-chloro-N-(3-(3-chloro-2-fluorophenyl)-2,2-difluoro-3-hydroxypropyl)-2-fluorobenzamide | (structure) enantiomer 1 first eluted | 527.9 | 9.23 (br t, J = 6.0 Hz, 1H), 8.61 (d, J = 6.7 Hz, 1H), 7.73 (br t, J = 8.4 Hz, 1H), 7.57 (br t, J = 6.7 Hz, 2H), 7.54-7.48 (m, 2H), 7.31 (t, J = 7.6 Hz, 1H), 7.06 (br d, J = 7.0 Hz, 1H), 6.73 (d, J = 5.5 Hz, 1H), 6.08 (s, 2H), 5.38-5.23 (m, 1H), 4.10-3.83 (m, 2H). |
| 171 | 3-(2-amino-[1,2,4]triazolo[1,5-a]pyridin-7-yl)-6-chloro-N-(3-(3-chloro-2-fluorophenyl)-2,2-difluoro-3-hydroxypropyl)-2-fluorobenzamide | (structure) enantiomer 2 second eluted | 528.0 | 9.22 (br t, J = 6.3 Hz, 1H), 8.63 (d, J = 6.7 Hz, 1H), 7.74 (t, J = 8.4 Hz, 1H), 7.59 (t, J = 6.7 Hz, 2H), 7.52 (s, 1H), 7.52 (d, J = 8.5 Hz, 2H), 7.31 (t, J = 7.9 Hz, 1H), 7.05 (br d, J = 7.0 Hz, 1H), 6.10 (s, 2H), 5.29 (br d, J = 18.0 Hz, 1H), 4.10-3.87 (m, 2H). |
| 172 | 3-(2-amino-[1,2,4]triazolo[1,5-a]pyridin-7-yl)-6-chloro-N-(2,2-difluoro-3-hydroxy-3-(p-tolyl)propyl)-2-fluorobenzamide | (structure) enantiomer 1 first eluted | 490.3 | 9.14 (br t, J = 6.0 Hz, 1H), 8.61 (d, J = 7.0 Hz, 1H), 7.72 (br t, J = 8.2 Hz, 1H), 7.59-7.42 (m, 2H), 7.31 (br d, J = 7.9 Hz, 2H), 7.19 (br d, J = 7.6 Hz, 2H), 7.05 (br d, J = 6.7 Hz, 1H), 6.35 (br d, J = 4.9 Hz, 1H), 6.17-5.99 (m, 2H), 4.93-4.78 (m, 1H), 3.92-3.56 (m, 2H), 2.30 (s, 3H). |
| 173 | 3-(2-amino-[1,2,4]triazolo[1,5-a]pyridin-7-yl)-6-chloro-N-(2,2-difluoro-3-hydroxy-3-(p-tolyl)propyl)-2-fluorobenzamide | (structure) enantiomer 2 second eluted | 490.3 | 9.14 (br t, J = 6.1 Hz, 1H), 8.61 (d, J = 7.0 Hz, 1H), 7.72 (t, J = 8.4 Hz, 1H), 7.58-7.43 (m, 2H), 7.35-7.28 (m, J = 7.9 Hz, 2H), 7.22-7.15 (m, J = 7.9 Hz, 2H), 7.05 (br d, J = 7.0 Hz, 1H), 6.17-5.99 (m, 2H), 4.96-4.77 (m, 1H), 3.93-3.51 (m, 2H), 2.30 (s, 3H). One proton missing due to water |

TABLE 13-continued

Compounds in Table 13 were prepared in a similar fashion to examples 162 and 163. Various substituted benzaldehydes were used in place of 4-chloro-2-fluorobenzaldehyde in the fourth step.

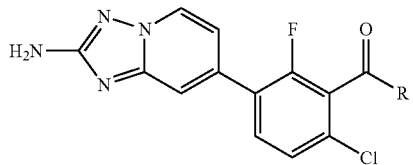

| Ex No | Name | R | M + H⁺ | 1H NMR (500 MHz, DMSO-d6) δ |
|---|---|---|---|---|
| 174 | 3-(2-amino-[1,2,4]triazolo[1,5-a]pyridin-7-yl)-6-chloro-N-(2,2-difluoro-3-hydroxy-3-(m-tolyl)propyl)-2-fluorobenzamide | enantiomer 1 first eluted | 490.4 | 9.12 (br t, J = 5.6 Hz, 1H), 8.64 (d, J = 7.0 Hz, 1H), 7.74 (br t, J = 8.2 Hz, 1H), 7.62-7.42 (m, 2H), 7.31-7.21 (m, 3H), 7.16 (br d, J = 7.0 Hz, 1H), 7.05 (br d, J = 7.0 Hz, 1H), 6.32 (br d, J = 5.2 Hz, 1H), 6.18-6.04 (m, 2H), 4.95-4.76 (m, 1H), 3.96-3.75 (m, 2H), 2.33 (s, 3H). |
| 175 | 3-(2-amino-[1,2,4]triazolo[1,5-a]pyridin-7-yl)-6-chloro-N-(2,2-difluoro-3-hydroxy-3-(m-tolyl)propyl)-2-fluorobenzamide | enantiomer 2 second eluted | 490.3 | 9.12 (br t, J = 6.1 Hz, 1H), 8.63 (d, J = 7.0 Hz, 1H), 7.74 (t, J = 8.4 Hz, 1H), 7.58-7.44 (m, 2H), 7.31-7.20 (m, 3H), 7.16 (br d, J = 7.3 Hz, 1H), 7.05 (br d, J = 6.7 Hz, 1H), 6.32 (d, J = 4.9 Hz, 1H), 6.17-6.05 (m, 2H), 4.93-4.78 (m, 1H), 3.95-3.75 (m, 2H), 2.33 (s, 3H). |
| 176 | 3-(2-amino-[1,2,4]triazolo[1,5-a]pyridin-7-yl)-6-chloro-N-(3-(2,5-difluorophenyl)-2,2-difluoro-3-hydroxypropyl)-2-fluorobenzamide | enantiomer 1 first eluted | 512.3 | 9.22 (br t, J = 6.1 Hz, 1H), 8.63 (d, J = 7.0 Hz, 1H), 7.74 (t, J = 8.4 Hz, 1H), 7.59-7.44 (m, 2H), 7.39-7.23 (m, 3H), 7.05 (br d, J = 7.0 Hz, 1H), 6.67 (br d, J = 5.2 Hz, 1H), 5.24 (br d, J = 18.3 Hz, 1H), 4.09-3.87 (m, 2H). Two protons missing due to water |
| 177 | 3-(2-amino-[1,2,4]triazolo[1,5-a]pyridin-7-yl)-6-chloro-N-(3-(2,5-difluorophenyl)-2,2-difluoro-3-hydroxypropyl)-2-fluorobenzamide | enantiomer 2 second eluted | 512.0 | 9.22 (br t, J = 5.8 Hz, 1H), 8.62 (d, J = 6.7 Hz, 1H), 7.73 (t, J = 8.4 Hz, 1H), 7.58-7.45 (m, 2H), 7.37-7.23 (m, 3H), 7.05 (br d, J = 7.0 Hz, 1H), 6.69 (br d, J = 5.5 Hz, 1H), 5.30-5.16 (m, 1H), 4.08-3.86 (m, 2H). Two protons missing due to water |
| 178 | 3-(2-amino-[1,2,4]triazolo[1,5-a]pyridin-7-yl)-6-chloro-N-(3-(2,4-difluorophenyl)-2,2-difluoro-3-hydroxypropyl)-2-fluorobenzamide | enantiomer 1 first eluted | 512.3 | 9.22 (br t, J = 6.1 Hz, 1H), 8.61 (d, J = 7.0 Hz, 1H), 7.72 (t, J = 8.4 Hz, 1H), 7.68-7.58 (m, 1H), 7.56-7.46 (m, 2H), 7.21 (t, J = 8.8 Hz, 1H), 7.16 (t, J = 8.3 Hz, 1H), 7.06 (br d, J = 7.0 Hz, 1H), 6.67-6.55 (m, 1H), 6.08 (s, 2H), 5.21 (dt, J = 18.3, 4.1 Hz, 1H), 4.06-3.84 (m, 2H). |

TABLE 13-continued

Compounds in Table 13 were prepared in a similar fashion to examples 162 and 163. Various substituted benzaldehydes were used in place of 4-chloro-2-fluorobenzaldehyde in the fourth step.

| Ex No | Name | R | M + H⁺ | 1H NMR (500 MHz, DMSO-d6) δ |
|---|---|---|---|---|
| 179 | 3-(2-amino-[1,2,4]triazolo[1,5-a]pyridin-7-yl)-6-chloro-N-(3-(2,4-difluorophenyl)-2,2-difluoro-3-hydroxypropyl)-2-fluorobenzamide | enantiomer 2 second eluted | 512.3 | 9.26-9.15 (m, 1H), 8.64 (d, J = 6.7 Hz, 1H), 7.74 (t, J = 8.4 Hz, 1H), 7.65 (q, J = 8.0 Hz, 1H), 7.55-7.49 (m, 2H), 7.24 (t, J = 8.9 Hz, 1H), 7.17 (t, J = 8.2 Hz, 1H), 7.05 (br d, J = 7.0 Hz, 1H), 6.54 (br d, J = 5.2 Hz, 1H), 6.11 (s, 2H), 5.22 (br dd, J = 19.2, 4.0 Hz, 1H), 4.08-3.86 (m, 2H). |
| 180 | 3-(2-amino-[1,2,4]triazolo[1,5-a]pyridin-7-yl)-6-chloro-N-(3-(5-chloro-2-fluorophenyl)-2,2-difluoro-3-hydroxypropyl)-2-fluorobenzamide | enantiomer 1 first eluted | 528.1 | 9.23 (br t, J = 6.1 Hz, 1H), 8.62 (d, J = 6.7 Hz, 1H), 7.73 (t, J = 8.4 Hz, 1H), 7.57 (d, J = 6.3 Hz, 1H), 7.54-7.46 (m, 3H), 7.28 (t, J = 9.2 Hz, 1H), 7.05 (br d, J = 7.0 Hz, 1H), 6.72 (d, J = 5.8 Hz, 1H), 6.09 (s, 2H), 5.31-5.19 (m, 1H), 4.08-3.86 (m, 2H). |
| 181 | 3-(2-amino-[1,2,4]triazolo[1,5-a]pryidin-7-yl)-6-chloro-N-(3-(5-chloro-2-fluorophenyl)-2,2-difluoro-3-hydroxypropyl)-2-fluorobenzamide | enantiomer 2 second eluted | 528.1 | 9.23 (br t, J = 6.1 Hz, 1H), 8.62 (d, J = 7.0 Hz, 1H), 7.73 (t, J = 8.4 Hz, 1H), 7.57 (d, J = 6.3 Hz, 1H), 7.54-7.46 (m, 3H), 7.28 (t, J = 9.0 Hz, 1H), 7.05 (br d, J = 6.7 Hz, 1H), 6.72 (d, J = 5.8 Hz, 1H), 6.09 (s, 2H), 5.24 (br d, J = 19.8 Hz, 1H), 4.08-3.87 (m, 2H). |
| 182 | 3-(2-amino-[1,2,4]triazolo[1,5-a]pyridin-7-yl)-6-chloro-N-(2,2-difluoro-3-(2-fluoro-4-methylphenyl)-3-hydroxypropyl)-2-fluorobenzamide | enantiomer 1 first eluted | 508.3 | 9.20 (br t, J = 6.1 Hz, 1H), 8.61 (d, J = 7.0 Hz, 1H), 7.72 (t, J = 8.4 Hz, 1H), 7.56-7.42 (m, 3H), 7.12-6.98 (m, 3H), 6.49 (br d, J = 5.5 Hz, 1H), 6.08 (s, 2H), 5.24-5.05 (m, 1H), 4.03-3.82 (m, 1H), 2.31 (s, 3H). One proton missing due to water |
| 183 | 3-(2-amino-[1,2,4]triazolo[1,5-a]pyridin-7-yl)-6-chloro-N-(2,2-difluoro-3-(2-fluoro-4-methylphenyl)-3-hydroxypropyl)-2-fluorobenzamide | enantiomer 2 second eluted | 508.1 | 9.19 (br t, J = 6.3 Hz, 1H), 8.61 (d, J = 6.7 Hz, 1H), 7.72 (t, J = 8.4 Hz, 1H), 7.58-7.41 (m, 3H), 7.11-6.98 (m, 3H), 6.48 (br d, J = 5.5 Hz, 1H), 6.08 (s, 2H), 5.29-5.08 (m, 1H), 4.07-3.78 (m, 2H), 2.31 (s, 3H). |

TABLE 13-continued

Compounds in Table 13 were prepared in a similar fashion to examples 162 and 163. Various substituted benzaldehydes were used in place of 4-chloro-2-fluorobenzaldehyde in the fourth step.

| Ex No | Name | R | M + H⁺ | 1H NMR (500 MHz, DMSO-d6) δ |
|---|---|---|---|---|
| 184 | 3-(2-amino-[1,2,4]triazolo[1,5-a]pyridin-7-yl)-6-chloro-N-(2,2-difluoro-3-hydroxy-3-(4-methoxyphenyl)propyl)-2-fluorobenzamide | enantiomer 1 first eluted | 505.9 | 9.11 (br t, J = 6.0 Hz, 1H), 8.64 (d, J = 6.7 Hz, 1H), 7.74 (t, J = 8.4 Hz, 1H), 7.57-7.47 (m, 2H), 7.40-7.32 (m, J = 8.5 Hz, 2H), 7.04 (br d, J = 7.0 Hz, 1H), 6.99-6.91 (m, J = 8.5 Hz, 2H), 6.25 (d, J = 5.2 Hz, 1H), 6.11 (s, 2H), 4.90-4.78 (m, 1H), 3.89-3.74 (m, 5H). |
| 185 | 3-(2-amino-[1,2,4]triazolo[1,5-a]pyridin-7-yl)-6-chloro-N-(2,2-difluoro-3-hydroxy-3-(4-methoxyphenyl)propyl)-2-fluorobenzamide | enantiomer 2 second eluted | 506.0 | 9.11 (br t, J = 6.1 Hz, 1H), 8.64 (d, J = 6.7 Hz, 1H), 7.74 (t, J = 8.2 Hz, 1H), 7.59-7.44 (m, 2H), 7.36 (br d, J = 8.2 Hz, 2H), 7.04 (br d, J = 7.0 Hz, 1H), 6.95 (d, J = 8.9 Hz, 2H), 6.25 (br d, J = 5.2 Hz, 1H), 6.11 (s, 2H), 4.86 (br dd, J = 15.3, 6.1 Hz, 1H), 3.89-3.74 (m, 5H). |
| 186 | 3-(2-amino-[1,2,4]triazolo[1,5-a]pyridin-7-yl)-6-chloro-N-(3-(4-(difluoromethoxy)phenyl)-2,2-difluoro-3-hydroxypropyl)-2-fluorobenzamide | enantiomer 1 first eluted | 542.0 | 9.18-9.10 (m, 1H), 8.66-8.60 (m, 1H), 7.78-7.70 (m, 1H), 7.55-7.46 (m, 3H), 7.20 (br d, J = 8.5 Hz, 2H), 7.05 (br d, J = 6.7 Hz, 1H), 6.49-6.40 (m, 1H), 6.15-6.05 (m, 2H), 4.99-4.87 (m, 1H), 3.97-3.77 (m, 2H). |
| 187 | 3-(2-amino-[1,2,4]triazolo[1,5-a]pyridin-7-yl)-6-chloro-N-(3-(4-(difluoromethoxy)phenyl)-2,2-difluoro-3-hydroxypropyl)-2-fluorobenzamide | enantiomer 2 second eluted | 542.1 | 9.14 (br t, J = 6.1Hz, 1H), 8.63 (d, J = 6.7 Hz, 1H), 7.74 (t, J = 8.4 Hz, 1H), 7.54-7.47 (m, 4H), 7.20 (d, J = 8.5 Hz, 2H), 7.24 (t, J = 74.8 Hz, 1H), 7.05 (br d, J = 7.0 Hz, 1H), 6.45 (d, J = 5.2 Hz, 1H), 6.10 (s, 2H), 4.94 (dt, J = 16.3, 5.7 Hz, 1H), 3.96-3.79 (m, 2H). |
| 188 | 3-(2-amino-[1,2,4]triazolo[1,5-a]pyridin-7-yl)-6-chloro-N-(3-(3,5-difluorophenyl)-2,2-difluoro-3-hydroxypropyl)-2-fluorobenzamide | enantiomer 1 first eluted | 512.0 | 9.16 (br t, J = 6.0 Hz, 1H), 8.63 (d, J = 7.0 Hz, 1H), 7.74 (t, J = 8.4 Hz, 1H), 7.56-7.49 (m, 2H), 7.23 (br t, J = 9.3 Hz, 1H), 7.15 (br d, J = 6.7 Hz, 2H), 7.04 (br d, J = 7.0 Hz, 1H), 6.74-6.66 (m, 1H), 6.11 (s, 2H), 5.00 (br d, J = 14.3 Hz, 1H), 3.95-3.81 (m, 2H). |

TABLE 13-continued

Compounds in Table 13 were prepared in a similar fashion to examples 162 and 163. Various substituted benzaldehydes were used in place of 4-chloro-2-fluorobenzaldehyde in the fourth step.

| Ex No | Name | R | M + H⁺ | 1H NMR (500 MHz, DMSO-d6) δ |
|---|---|---|---|---|
| 189 | 3-(2-amino-[1,2,4]triazolo[1,5-a]pyridin-7-yl)-6-chloro-N-(3-(3,5-difluorophenyl)-2,2-difluoro-3-hydroxypropyl)-2-fluorobenzamide | [structure with OH, 3,5-difluorophenyl; enantiomer 2, second eluted] | 512.0 | 9.16 (br t, J = 6.0 Hz, 1H), 8.63 (d, J = 6.7 Hz, 1H), 7.74 (t, J = 8.4 Hz, 1H), 7.55-7.48 (m, 2H), 7.23 (br t, J = 9.2 Hz, 1H), 7.15 (br d, J = 6.7 Hz, 2H), 7.05 (br d, J = 6.7 Hz, 1H), 6.70 (br s, 1H), 6.11 (s, 2H), 5.05-4.95 (m, 1H), 3.94-3.81 (m, 2H). |
| 190 | 3-(2-amino-[1,2,4]triazolo[1,5-a]pyridin-7-yl)-6-chloro-N-(3-(4-chloro-3-fluorophenyl)-2,2-difluoro-3-hydroxypropyl)-2-fluorobenzamide | [structure with OH, 4-chloro-3-fluorophenyl; enantiomer 1, first eluted] | 527.9 | 9.15 (br t, J = 6.0 Hz, 1H), 8.64 (d, J = 6.7 Hz, 1H), 7.74 (t, J = 8.4 Hz, 1H), 7.62 (t, J = 7.9 Hz, 1H), 7.55-7.48 (m, 2H), 7.45 (br d, J = 11.0 Hz, 1H), 7.32 (br d, J = 7.9 Hz, 1H), 7.04 (br d, J = 7.0 Hz, 1H), 6.64 (d, J = 5.5 Hz, 1H), 6.11 (s, 2H), 4.99 (dt, J = 16.0, 6.0 Hz, 1H), 3.96-3.80 (m, 2H). |
| 191 | 3-(2-amino-[1,2,4]triazolo[1,5-a]pyridin-7-yl)-6-chloro-N-(3-(4-chloro-3-fluorophenyl)-2,2-difluoro-3-hydroxypropyl)-3-fluorobenzamide | [structure with OH, 4-chloro-3-fluorophenyl; enantiomer 2, second eluted] | 527.9 | 9.15 (br t, J = 6.1 Hz, 1H), 8.64 (d, J = 7.0 Hz, 1H), 7.75 (t, J = 8.2 Hz, 1H), 7.62 (t, J = 7.9 Hz, 1H), 7.55-7.48 (m, 2H), 7.45 (br d, J = 9.8 Hz, 1H), 7.32 (br d, J = 7.9 Hz, 1H), 7.04 (br d, J = 7.0 Hz, 1H), 6.63 (d, J = 5.2 Hz, 1H), 6.11 (s, 2H), 5.03-4.94 (m, 1H), 3.95-3.80 (m, 2H). |
| 192 | 3-(2-amino-[1,2,4]triazolo[1,5-a]pyridin-7-yl)-6-chloro-N-(3-(3-chlorophenyl)-2,2-difluoro-3-hydroxypropyl)-2-fluorobenzamide | [structure with OH, 3-chlorophenyl; enantiomer 1, first eluted] | 510.3 | 9.16 (br t, J = 6.3 Hz, 1H), 8.63 (d, J = 6.7 Hz, 1H), 7.74 (t, J = 8.4 Hz, 1H), 7.58-7.46 (m, 3H), 7.43-7.32 (m, 3H), 7.05 (br d, J = 7.0 Hz, 1H), 6.11 (s, 2H), 5.06-4.88 (m, 1H), 4.00-3.77 (m, 2H), 1.90 (s, 1H) |
| 193 | 3-(2-amino-[1,2,4]triazolo[1,5-a]pyridin-7-yl)-6-chloro-N-(3-(3-chlorophenyl)-2,2-difluoro-3-hydroxypropyl)-2-fluorobenzamide | [structure with OH, 3-chlorophenyl; enantiomer 2, second eluted] | 510.3 | 9.16 (br t, J = 5.8 Hz, 1H), 8.63 (d, J = 7.0 Hz, 1H), 7.74 (t, J = 8.4 Hz, 1H), 7.59-7.47 (m, 3H), 7.46-7.28 (m, 3H), 7.05 (br d, J = 7.0 Hz, 1H), 6.11 (s, 2H), 4.96 (br dd, J = 16.2, 5.8 Hz, 1H), 4.02-3.72 (m, 2H), 1.89 (s, 1H) |

Example 194: 3-(2-amino-[1,2,4]triazolo[1,5-a]pyridin-7-yl)-6-(difluoromethyl)-2-fluoro-N-(2-fluoro-3-(4-fluorophenyl)-3-hydroxybutyl-4,4,4-d3)benzamide

194A: ethyl 2-fluoro-3-(4-fluorophenyl)-3-hydroxybutanoate-4,4,4-d3: A 40 mL reaction vial was charged with a stir bar, 1-(4-fluorophenyl)ethan-1-one-2,2,2-d3 (0.6 g, 4.25 mmol), iron (0.712 g, 12.75 mmol), iodine (0.216 g, 0.850 mmol), THF (8.50 mL) followed by the addition of ethyl 2-bromo-2-fluoroacetate (2.36 g, 12.75 mmol). The resulting mixture was degassed by bubbling N2 through the solution for 5 min and then stirred at 60° C. for 12 h. The mixture was cooled to rt, and Celite was added. The crude mixture was concentrated in vacuo, and dry loaded onto a silica gel column. The crude was purified by flash column chromatography (EtOAc in hexane, 0% to 20%; 20 g ISCO column), affording ethyl 2-fluoro-3-(4-fluorophenyl)-3-hydroxybutanoate-4,4,4-d3 (480 mg, 1.941 mmol, 46% yield) as a 1:1 mixture of diastereomers.

1H NMR (400 MHz, CHLOROFORM-d) δ 7.39 (ddd, J=7.8, 6.1, 1.6 Hz, 2H), 6.97 (q, J=8.6 Hz, 2H), 5.03-4.65 (m, 1H), 4.14-3.95 (m, 2H), 1.04 (dt, J=17.1, 7.1 Hz, 3H).

194B: 2-fluoro-3-(4-fluorophenyl)-3-hydroxybutanamide-d3: A 40 mL reaction vial was charged with a stir bar, ethyl 2-fluoro-3-(4-fluorophenyl)-3-hydroxybutanoate-4,4,4-d3 (480 mg, 1.941 mmol) and MeOH (3883 µL), followed by addition of ammonia in MeOH (1664 µL, 11.65 mmol). The resulting mixture was stirred at 40° C. for 20 h. The reaction mixture was concentrated in vacuo and used directly in the next step without further purification.

MS ESI m/z 219.4 (M+H)+ (two diastereomers observed in LC-MS)

194C: 4-amino-3-fluoro-2-(4-fluorophenyl)butan-1,1,1-d3-2-ol: A 40 mL reaction vial was charged with a stir bar, 2-fluoro-3-(4-fluorophenyl)-3-hydroxybutanamide (423 mg, 1.94 mmol) and THF (9700 µL), followed by the addition of BH3·DMS (2910 µL, 5.82 mmol). The resulting mixture was stirred at 70° C. for 3 h. The reaction was quenched by methanol and concentrated in vacuo to afford crude 4-amino-3-fluoro-2-(4-fluorophenyl)butan-1,1,1-d3-2-ol (245 mg, 1.200 mmol, 62% yield). The crude was used directly in the next step without further purification.

194D: 3-bromo-6-(difluoromethyl)-2-fluoro-N-(2-fluoro-3-(4-fluorophenyl)-3-hydroxybutyl-4,4,4-d3)benzamide: A 40 mL reaction vial was charged with a stir bar, 3-bromo-6-(difluoromethyl)-2-fluorobenzoic acid (0.151 g, 0.560 mmol), 4-amino-3-fluoro-2-(4-fluorophenyl)butan-1,1,1-d3-2-ol (0.082 g, 0.4 mmol) and ((1H-benzo[d][1,2,3]triazol-1-yl)oxy)tris(dimethylamino)phosphonium hexafluorophosphate(V) (0.248 g, 0.560 mmol), followed by the addition of DCM (4.00 mL) and DIPEA (0.279 mL, 1.600 mmol). The crude mixture was stirred at rt for 2 h. The crude was purified by flash column chromatography (EtOAc in hexane, 0-50%; 12 g ISCO column), affording 3-bromo-6-(difluoromethyl)-2-fluoro-N-(2-fluoro-3-(4-fluorophenyl)-3-hydroxybutyl-4,4,4-d3)benzamide (0.11 g, 0.242 mmol, 60% yield). The crude was used in the next step without further purification.

MS ESI m/z 455.1 (M+H)+

194E: Bis-Boc 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide: A 100 mL round-bottom flask was charged with a stir bar, 3-bromo-6-(difluoromethyl)-2-fluoro-N-(2-fluoro-3-(4-fluorophenyl)-3-hydroxybutyl-4,4,4-d3)benzamide (0.11 g, 0.242 mmol), Bis-Boc 7-(4,4,5,5-tetramethyl-1,3,2-dioxaborolan-2-yl)-[1,2,4]triazolo[1,5-a]pyridin-2-amine (0.133 g, 0.290 mmol) and [1,1'-Bis(diphenylphosphino)ferrocene]dichloropalladium(II), complex with dichloromethane (0.020 g, 0.024 mmol). The flask was evacuated and backfilled with nitrogen, followed by the addition of 1,4-dioxane (1.208 mL) and tripotassium phosphate (0.362 mL, 0.725 mmol). The resulting mixture was stirred at 60° C. for 16 h. The crude was purified by flash column chromatography via dry load on Celite (EtOAc in hexane, 0% to 100%; 80 g ISCO column), affording Bis-Boc 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide (168 mg, 0.237 mmol, 98% yield) as a diastereomeric mixture.

MS ESI m/z 709.4 (M+H)+

194F: 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide: A 40 mL reaction vial was charged with a stir bar, Bis-Boc 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide (168 mg, 0.237 mmol) and Ethanol (2371 µL), followed by the addition of HCl (593 µL, 2.371 mmol). The resulting mixture was stirred at 40° C. for 16 h. LC-MS indicated the completion of reaction (desired product MW+1=509.15). The reaction mixture was concentrated in vacuo, diluted with 1.5 mL DMF, and filtered. The crude material was purified via preparative LC/MS using an XBridge C18 column eluting with acetonitrile:water with ammonium acetate. Fractions containing the desired product were combined and dried via centrifugal evaporation. The material was further purified by SCP using SFC-chiral chromatography.

First eluting isomer: 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide (7.3 mg, 0.014 mmol, 6% yield).

1H NMR (500 MHz, DMSO-d6) δ 8.98 (br t, J=5.5 Hz, 1H), 8.66 (d, J=7.0 Hz, 1H), 7.86 (br t, J=7.8 Hz, 1H), 7.65-7.47 (m, 4H), 7.23-6.88 (m, 4H), 6.12 (s, 2H), 4.76-4.45 (m, 1H), 3.85-3.63 (m, 1H), 3.08-2.89 (m, 1H).

MS ESI m/z 509.2 (M+H)+

Example 195: 3-(2-amino-[1,2,4]triazolo[1,5-a]pyridin-7-yl)-6-(difluoromethyl)-2-fluoro-N-(2-fluoro-3-(4-fluorophenyl)-3-hydroxybutyl-4,4,4-d3)benzamide

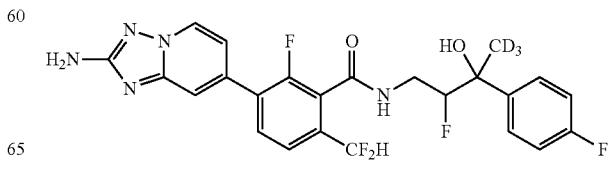

Second eluting isomer from Example 194F: 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3) benzamide (5.8 mg, 0.011 mmol, 5% yield).

1H NMR (500 MHz, DMSO-d6) δ 8.95 (br t, J=5.5 Hz, 1H), 8.66 (d, J=7.0 Hz, 1H), 7.85 (t, J=7.8 Hz, 1H), 7.65-7.50 (m, 4H), 7.23-6.87 (m, 4H), 6.12 (s, 2H), 4.80-4.55 (m, 1H), two protons obscured by solvent.

MS ESI m/z 509.2 (M+H)+

Example 196: 3-(2-amino-[1,2,4]triazolo[1,5-a]pyridin-7-yl)-6-(difluoromethyl)-2-fluoro-N-(2-fluoro-3-(4-fluorophenyl)-3-hydroxybutyl-4,4,4-d3)benzamide

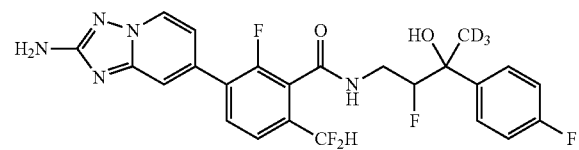 [SMILES: [2H]C([2H])([2H])C(O)(c1ccc(F)cc1)C(F)CNC(=O)c1c(C(F)F)ccc(-c2ccn3nc(N)nc3c2)c1F]

Third eluting isomer from Example 194F: 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3)benzamide (9.5 mg, 0.019 mmol, 8% yield).

1H NMR (500 MHz, DMSO-d$_6$) δ 8.95 (br t, J=5.5 Hz, 1H), 8.66 (d, J=7.0 Hz, 1H), 7.85 (t, J=7.9 Hz, 1H), 7.65-7.51 (m, 4H), 7.24-6.87 (m, 4H), 6.12 (s, 2H), 4.80-4.53 (m, 1H), two protons obscured by solvent.

MS ESI m/z 509.2 (M+H)+

Example 197: 3-(2-amino-[1,2,4]triazolo[1,5-a]pyridin-7-yl)-6-(difluoromethyl)-2-fluoro-N-(2-fluoro-3-(4-fluorophenyl)-3-hydroxybutyl-4,4,4-d3)benzamide

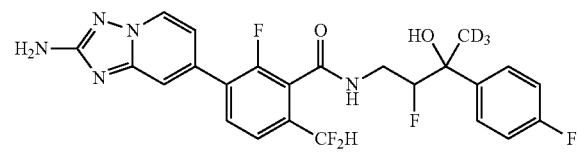 [SMILES: [2H]C([2H])([2H])C(O)(c1ccc(F)cc1)C(F)CNC(=O)c1c(C(F)F)ccc(-c2ccn3nc(N)nc3c2)c1F]

Fourth eluting isomer from Example 194F: 3-(2-amino-[1,2,4]triazolo[1,5-a]pyridin-7-yl)-2-fluoro-N-(2-fluoro-3-(4-fluorophenyl)-3-hydroxybutyl-4,4,4-d3)-6-(methyl-d3) benzamide (8.8 mg, 0.017 mmol, 7% yield).

1H NMR (500 MHz, DMSO-d6) δ 8.99 (br t, J=5.6 Hz, 1H), 8.66 (d, J=7.0 Hz, 1H), 7.86 (t, J=7.9 Hz, 1H), 7.67-7.49 (m, 4H), 7.23-6.89 (m, 4H), 6.12 (s, 2H), 4.74-4.50 (m, 1H), 3.82-3.62 (m, 1H), 3.09-2.90 (m, 1H).

MS ESI m/z 509.2 (M+H)+

Example 198: 3-(2-amino-[1,2,4]triazolo[1,5-a]pyridin-7-yl)-N-(3-(3,4-difluorophenyl)-2,2-difluoro-3-hydroxypropyl)-2-fluoro-6-methylbenzamide

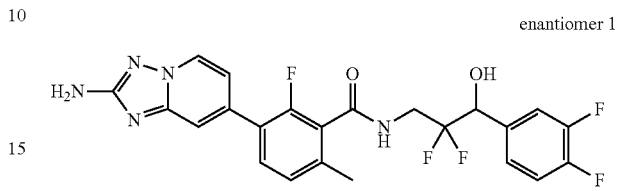

enantiomer 1

198A: methyl 3-bromo-2-fluoro-6-methylbenzoate: In a 250 mL round-bottomed flask, a mixture of 3-bromo-2-fluoro-6-methylbenzoic acid (4.95 g, 21.3 mmol) and potassium carbonate (5.88 g, 42.5 mmol) in DMF (42.5 mL) was treated with iodomethane (2.37 ml, 25.5 mmol). The mixture was stirred overnight, then diluted with ethyl acetate (200 mL) and filtered to remove solids. The filtrate was washed with water three times, then with brine, and then dried over anhydrous sodium sulfate, filtered and concentrated under reduced pressure to yield methyl 3-bromo-2-fluoro-6-methylbenzoate (4.99 g, 20.2 mmol, 95% yield) as a clear oil.

$^1$H NMR (500 MHz, CHLOROFORM-d) δ 7.51 (t, J=7.6 Hz, 1H), 6.93 (d, J=8.2 Hz, 1H), 4.00-3.94 (m, 3H), 2.38 (s, 3H).

198B: methyl 3-(2-amino-[1,2,4]triazolo[1,5-a]pyridin-7-yl)-2-fluoro-6-methylbenzoate: In a 250 mL round-bottomed flask were combined 7-(4,4,5,5-tetramethyl-1,3,2-dioxaborolan-2-yl)-[1,2,4]triazolo[1,5-a]pyridin-2-amine (4.78 g, 18.4 mmol), methyl 3-bromo-2-fluoro-6-methylbenzoate (4.99 g, 20.2 mmol), 2M aqueous potassium phosphate tribasic (27.6 mL, 55.1 mmol), and Pd(dppf)Cl$_2$, DCM adduct (0.750 g, 0.919 mmol) in 1,4-dioxane (117 mL) to give a brown suspension. The reaction mixture was degassed by evacuating and backfilling with nitrogen 3 times. The flask was fitted with a reflux condenser and heated to 80° C. under a nitrogen atmosphere overnight. The mixture was allowed to cool to room temperature and was then concentrated under reduced pressure. The crude residue was diluted in ethyl acetate and filtered through a pad of celite. The celite was rinsed with ethyl acetate, and the filtrate was concentrated under reduced pressure. The residue was dissolved in dichloromethane and purified by silica gel flash chromatography (gradient 50-100% ethyl acetate in hexanes followed by gradient 0-20% methanol in dichloromethane). Product fractions were pooled and concentrated to yield methyl 3-(2-amino-[1,2,4]triazolo[1,5-a]pyridin-7-yl)-2-fluoro-6-methylbenzoate (2.50 g, 8.33 mmol, 45% yield) as an orange solid.

MS ESI m/z 300.95 [M+H]+

198C: 3-(2-amino-[1,2,4]triazolo[1,5-a]pyridin-7-yl)-2-fluoro-6-methylbenzoic acid: A mixture of methyl 3-(2-amino-[1,2,4]triazolo[1,5-a]pyridin-7-yl)-2-fluoro-6-methylbenzoate (0.66 g, 2.2 mmol) and LiOH, 1M aqueous (0.223 g, 9.32 mmol) in MeOH (10 mL) and THF (10 mL) was stirred at RT overnight. The mixture was then heated to 60 degrees C. for 7 h. The mixture was concentrated in vacuo to remove all organic solvent, then to the aqueous residue was added aqueous 1M HCl (9.32 mL, 9.32 mmol) with stirring which caused precipitation of a solid The resulting suspended mixture was concentrated in vacuo directly to a solid residue and dried under high vacuum overnight to provide crude 3-(2-amino-[1,2,4]triazolo[1,5- a]pyridin-7-yl)-2-fluoro-6-methylbenzoic acid (0.888 g, 2.20 mmol, assumed quantitative conversion, approximately 57% desired material by weight). This material was used in the next step as-is.

MS ESI m/z 286.85 [M+H]+

198D: 3-(3,4-difluorophenyl)-2,2-difluoro-3-hydroxy-propanamide: In a 100 mL two-neck round bottom flask fitted with a reflux condenser and under nitrogen atmosphere, a stirred suspension of zinc powder, −140+325 mesh (0.981 g, 15.0 mmol) in THF (20.0 mL) was heated in an oil bath at 70° C. Ethyl 2-bromo-2,2-difluoroacetate (1.54 mL, 12.0 mmol) was added over 2 min at 70° C. Within a few moments, the contents of the flask exothermed such that the reflux condenser was nearly overwhelmed with vapor. After 2 min, 3,4-difluorobenzaldehyde (1.10 mL, 10.0 mmol) was added all at once and the mixture was heated at 70° C. for 16 h to provide a slightly cloudy yellow solution. The mixture was filtered to remove solids, the solids were rinsed with a small quantity of EtOAc, and the filtrate was concentrated in vacuo to an oil. The residue was taken up in EtOAc (75 mL) and the organic was washed with 1M aqueous HCl (30 mL) and then with brine (30 mL), dried over anhydrous $MgSO_4$, filtered and concentrated to an oil. The residue was then dissolved in MeOH (50 mL) and treated with ammonia, 7M in MeOH (5.71 mL, 40.0 mmol) with stirring overnight. The mixture was concentrated in vacuo to provide crude 3-(3,4-difluorophenyl)-2,2-difluoro-3-hydroxypropanamide (2.90 g, 10 mmol, overweight but assumed quantitative conversion, so approximately 82% purity) as a yellow solid which was used as-is in the next step.

$^1$H NMR (500 MHz, DMSO-d6) δ 8.04 (br s, 1H), 7.91 (br s, 1H), 7.49-7.37 (m, 2H), 7.29-7.17 (m, 1H), 6.59 (br s, 1H), 5.14 (br dd, J=17.9, 7.3 Hz, 1H), 4.09 (br s, 1H).

MS ESI m/z 236.00 [M−H]−

198E: 3-amino-1-(3,4-difluorophenyl)-2,2-difluoropropan-1-ol hydrochloride: Under nitrogen atmosphere, a round bottom flask fitted with a stir bar and a reflux condenser was charged with 3-(3,4-difluorophenyl)-2,2-difluoro-3-hydroxypropanamide (2.89 g, 10.0 mmol), THF (50.0 mL) and borane dimethyl sulfide complex solution, 2.0 M in THF (20.0 mL, 40.0 mmol). The resulting mixture was stirred at 80° C. for 2 h. The reaction was quenched by slow dropwise addition of methanol through the top of the reflux condenser (CAUTION: slow addition required, approximately 1-2 mL per minute initially, and then faster while keeping the reaction under control), which caused vigorous effervescence and warming of the mixture to at or near boiling point. A total of 15 mL of MeOH was added in this fashion until effervescence ceased. The mixture was refluxed for 15 min in an 80° C. oil bath. Solvent was removed in vacuo to give a clear colorless thick oil. The colorless thick oil residue was then treated with 1M aqueous HCl (20 mL) at 65 degrees C. for 1 h with swirling. The initially cloudy mixture became clear by the end of the hour. The mixture was then extracted with EtOAc (75 mL), and the EtOAc extract was back-extracted with 1M HCl (20 mL). The combined aqueous phases were concentrated in vacuo to give a slightly off-white solid which was placed under high vacuum for 2 h. Thus, was obtained 3-amino-1-(3,4-difluorophenyl)-2,2-difluoropropan-1-ol hydrochloride (2.54 g, 9.80 mmol, 98% yield) as a beige solid.

$^1$H NMR (500 MHz, DMSO-d6) δ 8.64 (br s, 2H), 7.54-7.37 (m, 2H), 7.29 (br s, 1H), 5.08 (br dd, J=17.1, 6.0 Hz, 1H), 3.53-3.32 (m, 2H).

MS ESI m/z 300.95 [M+H]+

198: In a 1 dram vial with PTFE screwcap were combined 3-(2-amino-[1,2,4]triazolo[1,5-a]pyridin-7-yl)-2-fluoro-6-methylbenzoic acid (70.0 mg, 0.139 mmol) with 3-amino-1-(3,4-difluorophenyl)-2,2-difluoropropan-1-ol, HCl (85.0 mg, 0.279 mmol) and BOP (80.0 mg, 0.181 mmol) in DMF (1 mL), followed by addition of DIPEA (0.243 mL, 1.39 mmol). The resulting mixture was stirred at RT overnight. The crude reaction mixture was then filtered and purified by reverse phase preparative HPLC with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 17% B, 17-57% B over 20 minutes, then a 0-minute hold at 100% B; Flow Rate: 20 mL/min; Column Temperature: 25 C. Fraction collection was triggered by MS and UV signals. Fractions containing the racemate product were combined and dried via centrifugal evaporation to a residue. The residue was further purified to separate the individual enantiomers using SFC-chiral chromatography with the following conditions: Instrument: Waters 100 Prep SFC; Column: Chiral IC, 21×250 mm, 5 μm particles; Mobile Phase: 60% $CO_2$/40% MeOH with 0.1% DEA; Flow Rate: 60 mL/min; Injection Details: 0.5 mL injections of 30.2 mg residue dissolved in 3 mL MeOH. Thus, was obtained 3-(2-amino-[1,2,4]triazolo[1,5-a]pyridin-7-yl)-N-(3-(3,4-difluorophenyl)-2,2-difluoro-3-hydroxypropyl)-2-fluoro-6-methylbenzamide enantiomer 1 (8.7 mg, 0.0176 mmol, 13% yield) as the first eluting isomer from the described preparative SFC purification.

$^1$H NMR (500 MHz, DMSO-d6) δ 8.96 (br t, J=6.1 Hz, 1H), 8.61 (d, J=6.7 Hz, 1H), 7.60 (t, J=7.9 Hz, 1H), 7.53-7.42 (m, 3H), 7.31 (d, J=8.0 Hz, 1H), 7.23 (d, J=7.9 Hz, 1H), 7.05 (br d, J=6.7 Hz, 1H), 5.09-4.90 (m, 1H), 3.87 (ddd, J=19.3, 13.2, 6.0 Hz, 2H), 2.31 (s, 3H).

MS ESI m/z 492.4 (M+H)+

Example 199: 3-(2-amino-[1,2,4]triazolo[1,5-a]pyridin-7-yl)-N-(3-(3,4-difluorophenyl)-2,2-difluoro-3-hydroxypropyl)-2-fluoro-6-methylbenzamide

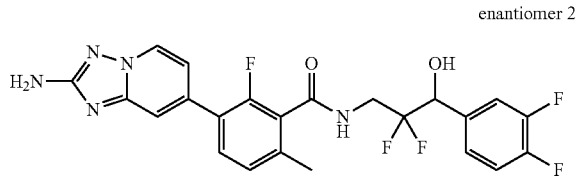

enantiomer 2

The title compound 3-(2-amino-[1,2,4]triazolo[1,5-a]pyridin-7-yl)-N-(3-(3,4-difluorophenyl)-2,2-difluoro-3-hydroxypropyl)-2-fluoro-6-methylbenzamide enantiomer 2 (8.5 mg, 0.0172 mmol, 12% yield) was obtained as the second eluting isomer from the chiral SFC purification described for example 198.

$^1$H NMR (500 MHz, DMSO-d6) δ 8.96 (br t, J=6.1 Hz, 1H), 8.61 (d, J=7.0 Hz, 1H), 7.60 (t, J=8.1 Hz, 1H), 7.53-7.42 (m, 3H), 7.31 (br s, 1H), 7.23 (d, J=7.8 Hz, 1H), 7.04 (br d, J=6.4 Hz, 1H), 5.00-4.92 (m, 1H), 3.97-3.81 (m, 2H), 2.31 (s, 3H).

MS ESI m/z 492.1 (M+H)+

Example 200: 3-(2-amino-[1,2,4]triazolo[1,5-a]pyridin-7-yl)-N-(2,2-difluoro-3-hydroxy-3-(4-(methyl-d₃)phenyl)propyl)-2-fluoro-6-(methyl-d₃)benzamide

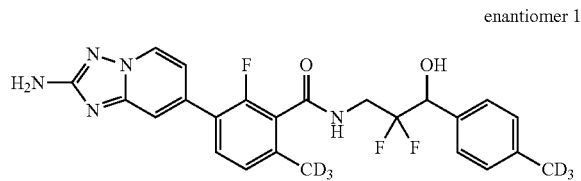 [SMILES: [2H]C([2H])([2H])c1ccc(C(O)C(F)(F)CNC(=O)c2c(C([2H])([2H])[2H])ccc(-c3ccn4nc(N)nc4c3)c2F)cc1]

enantiomer 1

200A: ethyl 3-(4-chlorophenyl)-2,2-difluoro-3-hydroxypropanoate: In a 2-neck 100 mL round bottom flask equipped with a magnetic stir bar and a reflux condenser, a stirred suspension of powdered zinc (0.981 g, 15.0 mmol) in THF (20.0 mL) was heated in an oil bath at 80° C. To the hot stirred zinc suspension was added ethyl 2-bromo-2,2-difluoroacetate (1.54 mL, 12.0 mmol) over 2 min. A significant exotherm resulted which caused vigorous boiling of the mixture. After 2 min, 4-chlorobenzaldehyde (1.18 mL, 10 mmol) was added all at once and the mixture was heated at 80° C. overnight. The reaction mixture was allowed to come to room temperature and was filtered to remove residual solids. The filtrate was concentrated in vacuo to an oil, then the residue was taken up in EtOAc (150 mL) and the organic was washed with 1M aqueous HCl (2×40 mL) and then with brine (30 mL), dried over anhydrous MgSO₄, filtered and concentrated in vacuo to a residue. The crude residue was loaded in minimum DCM onto a 120 g silica cartridge which was preequilibrated with hexanes. Elution gradient 100% hexanes to 50% EtOAc in hexanes over 7 column volumes. Note: This material had very poor UV absorbance and fractions needed to be checked by TLC. Like product fractions were combined and concentrated in vacuo to give ethyl 3-(4-chlorophenyl)-2,2-difluoro-3-hydroxypropanoate (2.60 g, 7.85 mmol, 98% yield) as a pale yellow oil.

¹H NMR (500 MHz, CHLOROFORM-d) δ 7.43-7.36 (m, 4H), 5.18 (dd, J=15.2, 7.7 Hz, 1H), 4.34 (q, J=7.2 Hz, 2H), 2.86 (br s, 1H), 1.35-1.31 (m, 3H).

200B: 3-(4-chlorophenyl)-2,2-difluoro-3-hydroxypropanamide: A solution of ethyl 3-(4-chlorophenyl)-2,2-difluoro-3-hydroxypropanoate (2.55 g, 9.64 mmol) in methanol (15 mL) was treated with ammonia solution, 7N in methanol (13.8 mL, 96 mmol) at RT. The resulting mixture was stirred at RT for 1 h. The mixture was concentrated in vacuo to a slightly yellow powder, and the crude 3-(4-chlorophenyl)-2,2-difluoro-3-hydroxypropanamide (2.08 g, 8.84 mmol, 92% yield) thus obtained was carried directly into the next step as-is.

¹H NMR (500 MHz, DMSO-d6) δ 8.00 (br s, 1H), 7.86 (br s, 1H), 7.46-7.40 (m, 4H), 6.45 (d, J=5.7 Hz, 1H), 5.15-5.06 (m, 1H).

MS ESI m/z 233.80, 235.70 (M+H)⁺

200C: 3-amino-1-(4-chlorophenyl)-2,2-difluoropropan-1-ol hydrochloride: Under nitrogen atmosphere, a 250 mL round bottom flask fitted with a stir bar and a reflux condenser was charged with crude 3-(4-chlorophenyl)-2,2-difluoro-3-hydroxypropanamide (2.07 g, 8.79 mmol) and THF (43.9 mL). Borane dimethyl sulfide complex solution, 2M in THF (17.6 mL, 35.2 mmol) was added with stirring, causing vigorous effervescing. The resulting mixture was stirred at 85° C. for 5 h. The mixture was allowed to cool to RT and was then treated dropwise through the top of the reflux condenser with methanol very slowly to cause immediate effervescence and significant exotherm. A total of 15 mL of MeOH was added in this fashion. The mixture was concentrated in vacuo and the residue was redissolved in MeOH (50 mL) and again concentrated in vacuo to a residue. This methanol azeotrope was repeated once more. The colorless thick oil was treated with 1M aqueous HCl (100 mL), and the resulting slightly flocculent mixture was heated to 65 degrees C. for 1 hour with stirring. The resulting clear mixture was concentrated in vacuo to a white solid which was placed under high vacuum for 2 h to provide 3-amino-1-(4-chlorophenyl)-2,2-difluoropropan-1-ol hydrochloride (2.22 g, 8.59 mmol, 98% yield) as a white solid HCl salt.

¹H NMR (500 MHz, DMSO-d6) δ 8.59 (br s, 2H), 7.52-7.40 (m, 4H), 6.85-6.67 (m, 1H), 5.11-5.00 (m, 1H), 3.55-3.33 (m, 2H).

MS ESI m/z 221.90 (M+H)⁺

200D: 3-(2-amino-[1,2,4]triazolo[1,5-a]pyridin-7-yl)-6-chloro-N-(3-(4-chlorophenyl)-2,2-difluoro-3-hydroxypropyl)-2-fluorobenzamide: In a 1 dram vial with PTFE screwcap were combined 3-(2-amino-[1,2,4]triazolo[1,5-a]pyridin-7-yl)-6-chloro-2-fluorobenzoic acid (63.1 mg, 0.245 mmol) with 3-amino-1-(4-chlorophenyl)-2,2-difluoropropan-1-ol, HCl (81.0 mg, 0.293 mmol) and BOP (95.0 mg, 0.215 mmol) in DMF (1 mL), followed by addition of DIPEA (0.171 mL, 0.978 mmol). The resulting mixture was stirred at RT for 1 h. The crude mixture was filtered and purified by reverse phase preparative HPLC with the following conditions: Column Waters XBridge C18, 30 mm×100 mm, 5 μm particles; Mobile Phase A: 5:95 acetonitrile:water with 10 mM ammonium acetate; Mobile Phase B: 95:5 acetonitrile:water with 10 mM ammonium acetate; Gradient: 0-100% B over 15 minutes, then a 3-min hold at 100% B; Flow Rate: 42.5 mL/min; Column Temperature: 25 C. Fraction collection was triggered by UV signals. Fractions containing the racemate product were combined and concentrated in vacuo. Thus, was obtained racemic 3-(2-amino-[1,2,4]triazolo[1,5-a]pyridin-7-yl)-6-chloro-N-(3-(4-chlorophenyl)-2,2-difluoro-3-hydroxypropyl)-2-fluorobenzamide (80.6 mg, 0.158 mmol, 81% yield) as a white powder.

¹H NMR (600 MHz, DMSO-d6) δ 9.18-9.11 (m, 1H), 8.64 (br s, 1H), 7.77-7.71 (m, 1H), 7.54-7.49 (m, 2H), 7.46 (br s, 4H), 7.04 (br s, 1H), 6.48 (br s, 1H), 6.12 (br s, 2H), 4.95 (br d, J=12.9 Hz, 1H), 3.94-3.79 (m, 2H).

MS ESI m/z 509.90, 510.85, 511.85, 512.85, 513.90 (M+H)⁺

200E: (methyl-d₃)boronic acid: A 500 mL round-bottom flask with stir bar was charged with THF (100 mL) and trimethyl borate (10.03 ml, 90 mmol). The resulting mixture was cooled to −78° C., followed by slow addition of methyl-d₃-magnesium iodide solution, 1.0 M in diethyl ether, 99 atom % D (50.0 mL, 50 mmol). The resulting mixture was stirred at −78° C. for 2 h. The reaction was then quenched by addition of 25 mL 1N aq. HCl and warmed up to rt. The mixture was diluted with diethyl ether, washed with brine, and dried over anhydrous magnesium sulfate. The crude mixture was concentrated in vacuo to provide (methyl-d₃)boronic acid (4.20 g, quantitative yield assumed, material can only be 75% maximum by weight) as a yellow oil. The resulting material was stored in a freezer and was carried directly into the next step as-is and as soon as possible.

200: A 4 mL Chemglass pressure vial was charged with a stir bar, racemic 3-(2-amino-[1,2,4]triazolo[1,5-a]pyridin-7-yl)-6-chloro-N-(3-(4-chlorophenyl)-2,2-difluoro-3-hydroxypropyl)-2-fluorobenzamide (75.0 mg, 0.147 mmol), 1,1′-Bis(di-tert-butylphosphino) ferrocene palladium chloride (38.3 mg, 0.0590 mmol) and (methyl-d₃)boronic acid (123 mg, 1.47 mmol), followed by the addition of dioxane (735 µL) and tripotassium phosphate, 2M aqueous solution (735 µL, 1.47 mmol). The resulting mixture was degassed by bubbling nitrogen through the mixture for 5 min. The vessel was capped, and the mixture was stirred at 115° C. overnight. The crude mixture was then diluted with DMF and filtered to give a 2 mL sample which was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 16% B, 16-56% B over 25 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give racemic 3-(2-amino-[1,2,4]triazolo[1,5-a]pyridin-7-yl)-N-(2,2-difluoro-3-hydroxy-3-(4-(methyl-d₃)phenyl)propyl)-2-fluoro-6-(methyl-d₃)benzamide (43.8 mg, 0.0921 mmol, 62.7% yield). The isolated racemate was further purified to separate the individual enantiomers using SFC-chiral chromatography with the following conditions: Instrument: Waters 100 Prep SFC; Column: Chiral OJ, 30×250 mm, 5 µm particles; Mobile Phase: 70% CO₂/300% MeOH with 0.1% DEA; Flow Rate: 100 mL/min; Injection Details: 3.0 mL injections of 42 mg residue dissolved in 9 mL MeOH/ACN. Thus, was obtained 3-(2-amino-[1,2,4]triazolo[1,5-a]pyridin-7-yl)-N-(2,2-difluoro-3-hydroxy-3-(4-(methyl-d₃)phenyl)propyl)-2-fluoro-6-(methyl-d₃)benzamide enantiomer 1 (11.0 mg, 0.0231 mmol, 16% yield) as the first eluting isomer from the described preparative SFC purification.

¹H NMR (500 MHz, DMSO-d6) δ 8.91 (br t, J=6.1 Hz, 1H), 8.61 (d, J=7.2 Hz, 1H), 7.59 (t, J=8.1 Hz, 1H), 7.48 (s, 1H), 7.34 (br d, J=8.0 Hz, 2H), 7.24-7.17 (m, 3H), 7.04 (br d, J=6.9 Hz, 1H), 6.28 (d, J=5.5 Hz, 1H), 6.07 (s, 2H), 4.86 (dt, J=14.6, 6.3 Hz, 1H), 3.90-3.75 (m, 2H).
MS ESI m/z 476.20 (M+H)⁺

Example 201: 3-(2-amino-[1,2,4]triazolo[1,5-a]pyridin-7-yl)-N-(2,2-difluoro-3-hydroxy-3-(4-(methyl-d₃)phenyl)propyl)-2-fluoro-6-(methyl-d₃)benzamide enantiomer 2

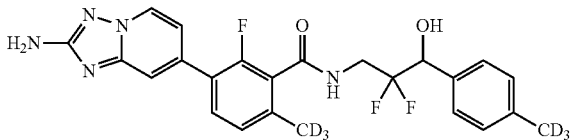

The title compound 3-(2-amino-[1,2,4]triazolo[1,5-a]pyridin-7-yl)-N-(2,2-difluoro-3-hydroxy-3-(4-(methyl-d₃)phenyl)propyl)-2-fluoro-6-(methyl-d₃)benzamide enantiomer 2 (10.5 mg, 0.0221 mmol, 15% yield) was obtained as the second eluting isomer from the chiral SFC purification described for example 200.

¹H NMR (500 MHz, DMSO-d6) δ 8.91 (br t, J=6.2 Hz, 1H), 8.61 (d, J=6.9 Hz, 1H), 7.59 (t, J=8.0 Hz, 1H), 7.48 (s, 1H), 7.34 (br d, J=8.0 Hz, 2H), 7.25-7.16 (m, 3H), 7.04 (br d, J=6.6 Hz, 1H), 6.28 (d, J=5.2 Hz, 1H), 6.10-6.02 (m, 2H), 4.90-4.81 (m, 1H), 3.89-3.74 (m, 2H).
MS ESI m/z 476.20 (M+H)⁺

Example 202: 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 1

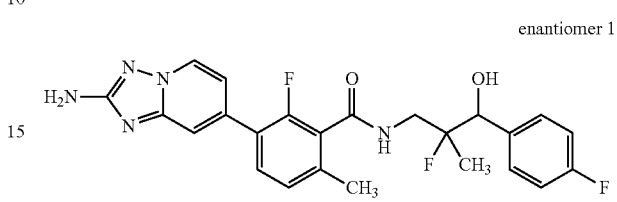

202A: methyl 2-fluoro-3-(4-fluorophenyl)-3-hydroxy-2-methylpropanoate: A stirred suspension of powdered zinc (1.11 g, 17.0 mmol) in anhydrous THF (2.6 mL) was treated with TMS-Cl (0.174 mL, 1.37 mmol) and the resulting mixture was stirred at RT for 10 min. The mixture was then heated to 57° C., whereupon a mixture of methyl 2-bromo-2-fluoropropanoate (3.15 g, 17.0 mmol) and 4-fluorobenzaldehyde (0.912 mL, 8.50 mmol) in THF (1.64 mL) was added dropwise via syringe very slowly to the warm suspension over 10 min. Shortly after the start of the addition, the mixture came to a very vigorous boil. With approximately 90% of the mixture added, there was no longer any visible zinc metal in the vial. Addition of the last 10% of the added mixture did not cause vigorous boiling. At the end of the addition, the mixture appeared as a slightly yellow homogeneous solution with little or no zinc metal visibly present in the flask. The mixture was stirred for an additional 30 min at 57° C. The crude reaction mixture was slowly added to stirred saturated aqueous ammonium chloride (50 mL). The resulting mixture was stirred at RT for 15 min. The crude mixture was extracted with ethyl acetate (3×50 mL), then the combined EtOAc extracts were washed with brine (30 mL), dried over anhydrous magnesium sulfate, filtered and concentrated in vacuo to a residue. The resulting nearly colorless oil was loaded in minimum DCM atop a hexanes preequilibrated 120 g silica cartridge. Elution 100% hexanes for 1 column volume, then gradient to 30% EtOAc in hexanes over 10 column volumes, hold 30% EtOAc in hexanes for 4 column volumes. The product had very little UV chromophore, but silica gel TLC using 2:1 hexanes:EtOAc as eluent visualized by staining of the TLC plate with Hanessian's stain and heating showed that reasonably good separation of two major products occurred. Isolate 1 was the first to elute, rf=0.45 by TLC, and Isolate 2 was the second to elute, rf=0.4 by TLC. Like fractions were combined and concentrated in vacuo to give two colorless oils. After several hours standing at RT, Isolate 2 solidified to a white waxy solid.

Isolate 1 (the first isolate to elute from the silica column) was a racemic mixture of (2S,3S)-methyl 2-fluoro-3-(4-fluorophenyl)-3-hydroxy-2-methylpropanoate and (2R,3R)-methyl 2-fluoro-3-(4-fluorophenyl)-3-hydroxy-2-methylpropanoate (0.697 g, 3.03 mmol, 36% yield) isolated as a colorless oil. The stereochemistry of Isolate 1 was determined by X-Ray crystallography of the product obtained in the next step of the sequence.

Isolate 1 $^1$H NMR (500 MHz, CHLOROFORM-d) δ 7.38 (br dd, J=7.6, 5.8 Hz, 2H), 7.10-7.02 (m, 2H), 5.00 (dd, J=15.0, 4.7 Hz, 1H), 3.76-3.71 (m, 3H), 2.84-2.79 (m, 1H), 1.64-1.56 (m, 3H).

Isolate 1 MS ESI m/z 230.95 (M+H)$^+$

Isolate 2 (the second isolate to elute from the silica column) was a racemic mixture of (2S,3R)-methyl 2-fluoro-3-(4-fluorophenyl)-3-hydroxy-2-methylpropanoate and (2R,3S)-methyl 2-fluoro-3-(4-fluorophenyl)-3-hydroxy-2-methylpropanoate (0.793 g, 3.44 mmol, 41% yield) isolated as a white waxy solid. The stereochemistry of Isolate 2 was determined by X-Ray crystallography of the product obtained in the next step of the sequence.

Isolate 2 $^1$H NMR (500 MHz, CHLOROFORM-d) δ 7.39 (dd, J=7.9, 5.4 Hz, 2H), 7.15-7.02 (m, 2H), 5.00-4.90 (m, 1H), 3.85 (s, 3H), 2.68 (br s, 1H), 1.42 (dd, J=21.7, 1.0 Hz, 3H).

Isolate 2 MS ESI m/z 230.90 (M+H)$^+$

202B: racemic mixture of (2S,3S)-2-fluoro-3-(4-fluorophenyl)-3-hydroxy-2-methylpropanamide and (2R,3R)-2-fluoro-3-(4-fluorophenyl)-3-hydroxy-2-methylpropanamide: A racemic mixture of (2S,3S)-methyl 2-fluoro-3-(4-fluorophenyl)-3-hydroxy-2-methylpropanoate and (2R,3R)-methyl 2-fluoro-3-(4-fluorophenyl)-3-hydroxy-2-methylpropanoate (0.662 g, 2.88 mmol) was treated with a solution of ammonia, 7M in MeOH (12.3 mL, 86.3 mmol) for 3 d. The mixture was concentrated to give the desired product (554 mg, 2.57 mmol, 89% yield) as a slightly off-white powder. This material was determined by X-Ray crystallography to be a racemic mixture of (2S,3S) and (2R,3R) isomers.

$^1$H NMR (500 MHz, DMSO-d$_6$) δ 7.34 (dd, J=8.3, 5.9 Hz, 2H), 7.16 (br d, J=4.8 Hz, 2H), 7.11 (t, J=8.9 Hz, 2H), 5.84 (d, J=5.7 Hz, 1H), 4.87-4.79 (m, 1H), 1.49 (d, J=22.1 Hz, 3H).

MS ESI m/z 213.85 (M–H)$^-$

202C: racemic mixture of (1R,2S)-3-amino-2-fluoro-1-(4-fluorophenyl)-2-methylpropan-1-ol hydrochloride and (1S,2R)-3-amino-2-fluoro-1-(4-fluorophenyl)-2-methylpropan-1-ol hydrochloride: Under nitrogen atmosphere, a 100 mL two neck round bottom flask was charged with a stir bar, a 1:1 racemic mixture of (2S,3S)-2-fluoro-3-(4-fluorophenyl)-3-hydroxy-2-methylpropanamide and (2R,3R)-2-fluoro-3-(4-fluorophenyl)-3-hydroxy-2-methylpropanamide (510 mg, 2.37 mmol), THF (11.8 mL) and borane dimethyl sulfide complex solution, 2.0 M in THF (4.74 mL, 9.48 mmol). The resulting mixture was stirred in an oil bath set at 85° C. for 4.5 h. The reaction was quenched by slow dropwise addition of methanol (CAUTION . . . slow addition required, approximately 1-2 mL per minute initially, and then faster while keeping the reaction under control), which caused vigorous effervescence and warming of the mixture to at or near boiling point. A total of 15 mL of MeOH was added in this fashion until effervescence ceased. Solvent was removed in vacuo to give a clear colorless thick oil. More methanol (50 mL) was added, and the mixture was again concentrated in vacuo. The methanol azeotrope was repeated once more. The resulting colorless thick oily residue was then treated with 1M aqueous HCl (100 mL) at 65 degrees C. for 1 h. The initially cloudy mixture became clear by the end of the hour. The mixture was filtered and concentrated in vacuo to give a racemic mixture of (1R,2S)-3-amino-2-fluoro-1-(4-fluorophenyl)-2-methylpropan-1-ol hydrochloride and (1S,2R)-3-amino-2-fluoro-1-(4-fluorophenyl)-2-methylpropan-1-ol hydrochloride (559 mg, 2.35 mmol, 99% yield) as a slightly yellow sticky foam.

$^1$H NMR (600 MHz, DMSO-d$_6$) δ 8.35 (br s, 2H), 7.44-7.37 (m, 2H), 7.20 (br s, 2H), 6.25 (br s, 1H), 4.85 (br s, 1H), 3.26-3.03 (m, 2H), 1.20-1.10 (m, 3H).

MS ESI m/z 201.90 (M+H)$^+$

202: In a 1 dram vial were combined 3-(2-amino-[1,2,4]triazolo[1,5-a]pyridin-7-yl)-2-fluoro-6-methylbenzoic acid (38 mg, 0.133 mmol) with a racemic mixture of (1R,2S)-3-amino-2-fluoro-1-(4-fluorophenyl)-2-methylpropan-1-ol hydrochloride and (1S,2R)-3-amino-2-fluoro-1-(4-fluorophenyl)-2-methylpropan-1-ol hydrochloride (44.8 mg, 0.166 mmol) and BOP (64.6 mg, 0.146 mmol) in DMF (1 mL), followed by addition of DIPEA (0.116 mL, 0.664 mmol). The resulting mixture was stirred at RT for 3 h. The mixture was concentrated under nitrogen stream, then the residue was dissolved in a mixture of 1:1 DCM:TFA (1.0 mL) and stirred for 1 h at RT. The mixture was concentrated under a stream of nitrogen, then redissolved in 2 mL of DMF and filtered. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 15% B, 15-55% B over 25 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give a racemic mixture of 3-(2-amino-[1,2,4]triazolo[1,5-a]pyridin-7-yl)-2-fluoro-N-((2R,3S)-2-fluoro-3-(4-fluorophenyl)-3-hydroxy-2-methylpropyl)-6-methylbenzamide and 3-(2-amino-[1,2,4]triazolo[1,5-a]pyridin-7-yl)-2-fluoro-N-((2S,3R)-2-fluoro-3-(4-fluorophenyl)-3-hydroxy-2-methylpropyl)-6-methylbenzamide (19.3 mg, 0.0411 mmol, 29% yield). The isolated racemate was further separated into individual enantiomers using SFC-chiral chromatography with the following conditions: Instrument: Waters 100 Prep SFC; Column: Chiral OJ, 30×250 mm, 5 μm particles; Mobile Phase: 85% CO$_2$/15% MeOH with 0.1% DEA; Flow Rate: 100 mL/min; Injection Details: 1.0 mL injections of 18.2 mg residue dissolved in 3 mL MeOH. Thus, was obtained 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 1 (4.3 mg, 0.0091 mmol. 7% yield) as the first eluting isomer from the described preparative SFC purification.

$^1$H NMR (500 MHz, DMSO-d6) δ 8.80 (br t, J=5.9 Hz, 1H), 8.61 (d, J=6.9 Hz, 1H), 7.59 (t, J=8.0 Hz, 1H), 7.49 (s, 1H), 7.43 (t, J=6.5 Hz, 2H), 7.26-7.14 (m, 3H), 7.04 (br d, J=6.9 Hz, 1H), 6.06 (s, 2H), 5.91 (d, J=5.0 Hz, 1H), 4.76 (br dd, J=10.2, 5.0 Hz, 1H), 3.82-3.69 (m, 1H), 3.58-3.51 (m, 1H), 2.33 (s, 3H), 1.16 (d, J=22.0 Hz, 3H).

MS ESI m/z 470.10 (M+H)$^+$

Example 203: 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide

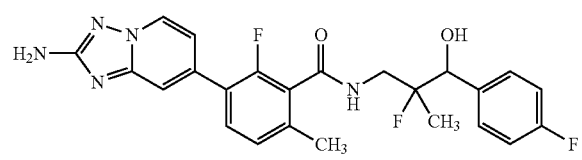

enantiomer 2

The title compound 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 2 (4.3 mg, 0.0091 mmol, 7% yield) was obtained as the second eluting isomer from the chiral SFC purification described for example 202.

Example 204: 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 3

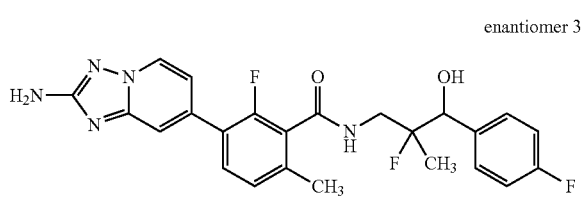 [SMILES: Cc1ccc(-c2ccn3nc(N)nc3c2)c(F)c1C(=O)NCC(C)(F)C(O)c1ccc(F)cc1]

204A: racemic mixture of (2S,3R)-2-fluoro-3-(4-fluorophenyl)-3-hydroxy-2-methylpropanamide and (2R,3S)-2-fluoro-3-(4-fluorophenyl)-3-hydroxy-2-methylpropanamide: A racemic mixture of (2S,3S)-methyl 2-fluoro-3-(4-fluorophenyl)-3-hydroxy-2-methylpropanoate and (2R,3R)-methyl 2-fluoro-3-(4-fluorophenyl)-3-hydroxy-2-methylpropanoate (0.747 g, 3.25 mmol) was treated with a solution of ammonia, 7M in MeOH (13.9 mL, 97.3 mmol) for 3 d. The mixture was concentrated to give the desired product (652 mg, 3.03 mmol, 93% yield) as a slightly off-white powder. This material was determined by X-Ray crystallography to be a racemic mixture of (2S,3R) and (2R,3S) isomers.

$^1$H NMR (500 MHz, DMSO-d6) δ 7.46-7.37 (m, 3H), 7.20-7.14 (m, 2H), 5.77 (d, J=5.5 Hz, 1H), 4.90-4.77 (m, 1H), 1.11 (d, J=21.9 Hz, 3H). One proton missing possibly due to water.

MS ESI m/z 213.90 (M−H)$^-$

204B: racemic mixture of (1R,2R)-3-amino-2-fluoro-1-(4-fluorophenyl)-2-methylpropan-1-ol hydrochloride and (1S,2S)-3-amino-2-fluoro-1-(4-fluorophenyl)-2-methylpropan-1-ol hydrochloride: Under nitrogen atmosphere, a 100 mL two neck round bottom flask was charged with a stir bar, a 1:1 racemic mixture of (2S,3S)-2-fluoro-3-(4-fluorophenyl)-3-hydroxy-2-methylpropanamide and (2R,3R)-2-fluoro-3-(4-fluorophenyl)-3-hydroxy-2-methylpropanamide (589 mg, 2.74 mmol), THF (13.7 mL) and borane dimethyl sulfide complex solution, 2.0 M in THF (5.47 mL, 10.9 mmol). The resulting mixture was stirred in an oil bath set at 85° C. for 4.5 h. The reaction was quenched by slow dropwise addition of methanol (CAUTION . . . slow addition required, approximately 1-2 mL per minute initially, and then faster while keeping the reaction under control), which caused vigorous effervescence and warming of the mixture to at or near boiling point. A total of 15 mL of MeOH was added in this fashion until effervescence ceased. Solvent was removed in vacuo to give a clear colorless thick oil. More methanol (50 mL) was added, and the mixture was again concentrated in vacuo. The methanol azeotrope was repeated once more. The resulting colorless thick oily residue was then treated with 1M aqueous HCl (100 mL) at 65 degrees C. for 1 h. The initially cloudy mixture became clear by the end of the hour. The mixture was filtered and concentrated in vacuo to give a racemic mixture of (1R,2R)-3-amino-2-fluoro-1-(4-fluorophenyl)-2-methylpropan-1-ol hydrochloride and (1S,2S)-3-amino-2-fluoro-1-(4-fluorophenyl)-2-methylpropan-1-ol hydrochloride (855 mg, overweight, quantitative, 76% purity maximum) as a slightly yellow waxy wet semisolid. This material was crude but was used as-is in the next step.

$^1$H NMR (600 MHz, DMSO-d6) δ 8.31 (br s, 2H), 7.41 (br s, 2H), 7.19 (br s, 2H), 4.72 (br d, J=19.1 Hz, 1H), 4.54 (br s, 9H), 3.06-2.94 (m, 1H), 1.30-1.21 (m, 3H).

MS ESI m/z 201.95 (M+H)$^+$

204: In a 1 dram vial were combined 3-(2-amino-[1,2,4]triazolo[1,5-a]pyridin-7-yl)-2-fluoro-6-methylbenzoic acid (38 mg, 0.133 mmol) with a racemic mixture of (1R,2R)-3-amino-2-fluoro-1-(4-fluorophenyl)-2-methylpropan-1-ol hydrochloride and (1S,2S)-3-amino-2-fluoro-1-(4-fluorophenyl)-2-methylpropan-1-ol hydrochloride (62.6 mg, 0.166 mmol) and BOP (64.6 mg, 0.146 mmol) in DMF (1 mL), followed by addition of DIPEA (0.116 mL, 0.664 mmol). The resulting mixture was stirred at RT for 3 h. The mixture was concentrated under nitrogen stream, then the residue was dissolved in a mixture of 1:1 DCM:TFA (1.0 mL) and stirred for 1 h at RT. The mixture was concentrated under a stream of nitrogen, then redissolved in 2 mL of DMF and filtered. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 15% B, 15-55% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give a racemic mixture of 3-(2-amino-[1,2,4]triazolo[1,5-a]pyridin-7-yl)-2-fluoro-N-((2R,3R)-2-fluoro-3-(4-fluorophenyl)-3-hydroxy-2-methylpropyl)-6-methylbenzamide and 3-(2-amino-[1,2,4]triazolo[1,5-a]pyridin-7-yl)-2-fluoro-N-((2S,3S)-2-fluoro-3-(4-fluorophenyl)-3-hydroxy-2-methylpropyl)-6-methylbenzamide (19.2 mg, 0.0407 mmol, 301% yield). The isolated racemate was further separated into individual enantiomers using SFC-chiral chromatography with the following conditions: Instrument: Waters 100 Prep SFC; Column: Chiral IC, 21×250 mm, 5 μm particles; Mobile Phase: 50% CO$_2$/50% MeOH with 0.1% DEA; Flow Rate: 60 mL/min; Injection Details: 1.0 mL injections of 15.1 mg residue dissolved in 3 mL MeOH. Thus, was obtained 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 3 (4.9 mg, 0.0104 mmol, 8% yield) as the first eluting isomer from the described preparative SFC purification.

$^1$H NMR (500 MHz, DMSO-d6) δ 8.71 (br t, J=6.2 Hz, 1H), 8.61 (d, J=6.9 Hz, 1H), 7.58 (t, J=8.0 Hz, 1H), 7.52-7.40 (m, 3H), 7.25-7.14 (m, 3H), 7.04 (br d, J=6.9 Hz, 1H), 6.07 (s, 2H), 5.88 (d, J=5.0 Hz, 1H), 4.71 (br dd, J=15.8, 4.8 Hz, 1H), 3.73-3.59 (m, 1H), 3.49-3.40 (m, 1H), 2.32 (s, 3H), 1.24 (d, J=22.3 Hz, 3H).

MS ESI m/z 470.10 (M+H)$^+$

Example 205: 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide

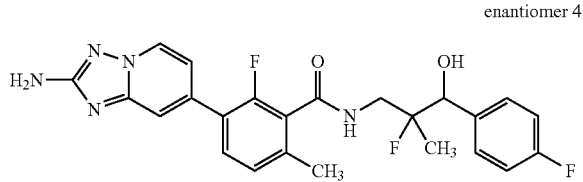

enantiomer 4

The title compound 3-(2-amino-[1,2,4]triazolo[1,5-a]pyridin-7-yl)-2-fluoro-N-(2-fluoro-3-(4-fluorophenyl)-3-hydroxy-2-methylpropyl)-6-methylbenzamide enantiomer 4 (5.1 mg, 0.0109 mmol, 8% yield) was obtained as the second eluting isomer from the chiral SFC purification described for example 204.

Example 206: 3-(2-amino-[1,2,4]triazolo[1,5-a]pyridin-7-yl)-N-(2,2-difluoro-3-(2-fluoro-3-(methyl-d$_3$)phenyl)-3-hydroxypropyl)-2-fluoro-6-(methyl-d$_3$)benzamide

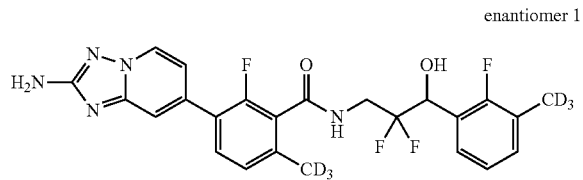 [SMILES: [2H]C([2H])([2H])c1cccc(C(O)C(F)(F)CNC(=O)c2c(C([2H])([2H])[2H])ccc(-c3ccn4nc(N)nc4c3)c2F)c1F]

enantiomer 1

A 1 dram Chemglass pressure vial was charged with a stir bar, 3-(2-amino-[1,2,4]triazolo[1,5-a]pyridin-7-yl)-6-chloro-N-(3-(3-chloro-2-fluorophenyl)-2,2-difluoro-3-hydroxypropyl)-2-fluorobenzamide (4.5 mg, 8.52 μmol), 1,1'-bis(di-tert-butylphosphino) ferrocene palladium chloride (2.22 mg, 3.41 μmol) and (methyl-d$_3$)boronic acid (7.14 mg, 0.085 mmol), followed by the addition of dioxane (500 μl) and 2M aqueous tripotassium phosphate (42.6 μL, 0.085 mmol). The resulting mixture was degassed by bubbling with nitrogen gas for 5 min and then the vessel was capped, and the mixture was stirred at 115° C. overnight. The mixture was then diluted with 1:1 MeOH:dioxane and filtered to give a 2 mL sample for purification. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 13% B, 13-53% B over 20 minutes, then a 0-minute hold at 100% B; Flow Rate 20 mL/min; Column Temperature: 25 C. Fraction collection was triggered by MS and UV signals. Fractions containing the desired product were combined and dried via centrifugal evaporation. Thus, was isolated 3-(2-amino-[1,2,4]triazolo[1,5-a]pyridin-7-yl)-N-(2,2-difluoro-3-(2-fluoro-3-(methyl-d$_3$)phenyl)-3-hydroxypropyl)-2-fluoro-6-(methyl-d$_3$)benzamide enantiomer 1 (0.7 mg, 0.0014 mmol, 16% yield).
MS ESI m/z 494.00 (M+H)$^+$ Example 207: 3-(2-amino-[1,2,4]triazolo[1,5-a]pyridin-7-yl)-6-chloro-N-(2,2-difluoro-3-(4-fluorophenyl)propyl)-2-fluorobenzamide

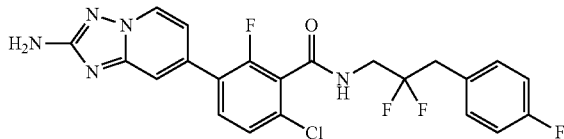 [SMILES: Nc1nc2cc(-c3ccc(Cl)c(C(=O)NCC(F)(F)Cc4ccc(F)cc4)c3F)ccn2n1]

207A: 2,2-difluoro-3-(4-fluorophenyl)propanamide: A mixture of ethyl 2,2-difluoro-2-iodoacetate (3.00 g, 12.0 mmol) and copper powder, dendritic, <45 micron (1.14 g, 18.0 mmol) in DMSO (21 mL) was stirred at RT for 1 h. The mixture was then treated with 1-(bromomethyl)-4-fluorobenzene (0.756 g, 4.00 mmol) and the resulting mixture was stirred at RT overnight. The crude mixture was added via pipet to 200 mL of rapidly stirred EtOAc which caused a sticky, heavy white precipitate to occur. The resulting yellow-green suspension was passed through a plug of celite and the plug was rinsed with ethyl acetate. The yellow-green filtrate (250 mL total) was poured into a separatory funnel with water (100 mL), the funnel was shaken and phases were separated. The organic was washed with a combination of water (100 mL) and brine (20 mL), then once more with brine (50 mL). The organic was dried over anhydrous magnesium sulfate, filtered and concentrated to give a yellow oil. The crude yellow residue was dissolved in 4 mL of 7M ammonia in methanol to immediately give a homogeneous deep blue-green colored solution. After 1 h the color of the ammonia treated mixture was less blue-green and was more lighter teal blue in color, and the mixture had become somewhat cloudy with a small quantity of solid precipitate present. The crude mixture was concentrated in vacuo to a residue. The residue was taken up with shaking into a mixture of EtOAc (75 mL) and water (30 mL) and the phases were separated. The aqueous phase was slightly blue in color and the EtOAc phase was yellow. The EtOAc phase was washed again with water (30 mL). The organic phase was dried over anhydrous magnesium sulfate, filtered and concentrated in vacuo to a residue. TLC on silica with 20:1 DCM:MeOH eluent showed a single major spot at rf=0.55 (visualized with Hanessian's stain and heating). Concentration in vacuo provided a slightly yellow solid. The crude yellow solid was dissolved by warming in minimum DCM (20 mL) and the result was loaded atop a DCM preequilibrated 80 g silica cartridge. Elution gradient 100% DCM to 20:1 DCM:MeOH over 10 column volumes. Product eluted in a band toward the end of the gradient. Product fractions were combined and concentrated in vacuo to give 2,2-difluoro-3-(4-fluorophenyl)propanamide (668 mg, 3.29 mmol, 82% yield) as a slightly yellow powder.
$^1$H NMR (500 MHz, DMSO-d6) δ 8.02 (br s, 1H), 7.84 (br s, 1H), 7.30 (dd, J=8.5, 5.7 Hz, 2H), 7.16 (t, J=8.5 Hz, 2H), 3.43-3.27 (m, 2H).
MS ESI m/z 201.90 (M−H)$^−$ 207B: 2,2-difluoro-3-(4-fluorophenyl)propan-1-amine hydrochloride: Under nitrogen atmosphere, a 50 mL two neck round bottom flask fitted with a reflux condenser was charged with a stir bar, 2,2-difluoro-3-(4-fluorophenyl)propanamide (500 mg, 2.46 mmol), THF (10 mL) and borane dimethyl sulfide complex solution, 2.0 M in THF (4.92 mL, 9.84 mmol). The resulting mixture was stirred at 80° C. After 2.5 h, the reaction was quenched by slow dropwise addition of methanol (CAUTION ... slow addition required, approximately 1-2 mL per minute initially, and then faster while keeping the reaction under control) through the top of the reflux condenser, which caused vigorous effervescence. A total of 15 mL of MeOH was added in this fashion until effervescence slowed significantly. The mixture was refluxed for an additional 15 min, then solvent was removed in vacuo. The resulting colorless thick oil residue was then treated with 2M aqueous HCl (50 mL) at 70 degrees C. for 1 h. The initially cloudy mixture became mostly clear by the end of the hour. The mixture was extracted with EtOAc (50 mL, then 25 mL). The EtOAc extracts were discarded. The aqueous was concentrated in vacuo to give a slightly off-white solid which was placed under high vacuum overnight to give 2,2-difluoro-3-(4-fluorophenyl)propan-1-amine hydrochloride (394.5 mg, 1.75 mmol, 71% yield) as a slightly pink solid.

$^1$H NMR (600 MHz, DMSO-d6) δ 8.65 (br s, 2H), 7.36 (dd, J=8.2, 5.8 Hz, 2H), 7.21 (t, J=8.8 Hz, 2H), 3.50-3.36 (m, 4H).

MS ESI m/z 189.90 (M+H)$^+$

207C: methyl 3-bromo-6-chloro-2-fluorobenzoate: In a 250 mL round bottom flask were combined 3-bromo-6-chloro-2-fluorobenzoic acid (10.4 g, 40.8 mmol) and potassium carbonate (14.1 g, 102 mmol) in anhydrous DMF (136 mL). To the stirred suspension was added iodomethane (3.83 mL, 61.3 mmol). The mixture was stirred at RT overnight. The mixture was diluted with EtOAc (400 mL) and solid was filtered away and rinsed with EtOAc. The filtrate was fully concentrated in vacuo to a residue, then diluted with EtOAc (175 mL) and the organic was washed with water (3×50 mL) and then with brine (50 mL). The organic was dried over anhydrous magnesium sulfate, filtered and concentrated in vacuo to give methyl 3-bromo-6-chloro-2-fluorobenzoate (11.0 g, 40.8 mmol, quantitative) as a yellow oil.

$^1$H NMR (500 MHz, CHLOROFORM-d) δ 7.57 (dd, J=8.6, 7.2 Hz, 1H), 7.15 (dd, J=8.6, 1.5 Hz, 1H), 4.00 (s, 3H).

207D: methyl 3-(2-amino-[1,2,4]triazolo[1,5-a]pyridin-7-yl)-6-chloro-2-fluorobenzoate: In a 500 mL round bottom flask under a blanket of nitrogen gas were combined methyl 3-bromo-6-chloro-2-fluorobenzoate (10.9 g, 40.8 mmol) with 4,4,4',4',5,5,5',5'-octamethyl-2,2'-bi(1,3,2-dioxaborolane) (10.9 g, 42.8 mmol), potassium acetate (6.01 g, 61.2 mmol) and PdCl$_2$(dppf)-CH$_2$Cl$_2$ adduct (1.67 g, 2.04 mmol). The mixture was suspended in 1,4-dioxane (136 mL) and the vessel was then fitted with a reflux condenser. While stirring rapidly, the suspension was iteratively evacuated and then purged with nitrogen five times to degas. The mixture was then heated to 85° C. for 3 h. To the mixture was then added 7-bromo-[1,2,4]triazolo[1,5-a]pyridin-2-amine (8.69 g, 40.8 mmol), tripotassium phosphate (2 M in water) (61.2 ml, 122 mmol) and additional 1,1'-bis(diphenyllphosphino)ferrocene palladium dichloride-CH$_2$Cl$_2$ adduct (1.67 g, 2.04 mmol) and the resulting mixture was sparged with nitrogen gas for 10 min and then stirred with heating at 75° C. for 14.5 h. The mixture was concentrated in vacuo to a residue, then the residue was diluted with EtOAc (600 mL), and the mixture was shaken to give a suspension of solids which was filtered. The collected solids which contained desired product (as determined by LCMS) were treated to successive triturations of EtOAc (2×100 mL) and then DCM (2×100 mL) until finally the solids (approximately 3 g) no longer contained desired product by LCMS. The organic triturants were combined and set aside. The filtrate consisted of two phases which were separated. The organic phase was combined with the already referenced combined organic triturants. The aqueous phase was then diluted with water (100 mL) and extracted with EtOAc twice (100 mL each). The organic extracts were then added to the combined organic. The combined organic phases were diluted to 1.5 L with EtOAc, and saturated brine (250 mL) was added and the mix was shaken and phases were separated. The organic was washed with brine (2×100 mL), then the organic was dried over anhydrous sodium sulfate, filtered and concentrated in vacuo to a dark brown residue. The residue was suspended with gentle heating in DCM (150 mL), and to this brown suspension was added hexanes (100 mL) and the resulting mixture was concentrated in vacuo to remove approximately 100 mL of organic solvent. The resulting suspension was chilled and then filtered to isolate a brown powder which was rinsed with diethyl ether and allowed to air-dry. The brown powder (5.86 g) thus isolated was set aside. The filtrate was concentrated in vacuo to a black oily residue. The black residue was diluted with DCM (40 mL) and loaded onto a hexanes preequilibrated 330 g silica cartridge. Elution gradient 0% hexanes to 100% EtOAc over 5 column volumes, hold 100% EtOAc for 5 column volumes, then elution gradient 100% DCM to 30:1 DCM:MeOH. Desired product fractions were combined and concentrated in vacuo to give a yellow powder: 1.14 g. This yellow powder was combined with the 5.86 g of brown powder previously isolated to give the desired methyl 3-(2-amino-[1,2,4]triazolo[1,5-a]pyridin-7-yl)-6-chloro-2-fluorobenzoate (7.00 g, 21.8 mmol, 54% yield). This material was carried forward as-is into the next experiment.

MS ESI m/z 320.80 (M+H)$^+$

207E: 3-(2-amino-[1,2,4]triazolo[1,5-a]pyridin-7-yl)-6-chloro-2-fluorobenzoic acid: A solution of methyl 3-(2-amino-[1,2,4]triazolo[1,5-a]pyridin-7-yl)-6-chloro-2-fluorobenzoate (7.00 g, 21.8 mmol) and NaOH 1M aqueous solution (32.7 mL, 32.7 mmol) in MeOH (100 mL) was heated to 85° C. for 3.5 h. The dark brown reaction mixture was concentrated to remove methanol, then 100 mL of water was added. The suspension was filtered to remove a brown solid which was found to contain no desired product and was discarded. The brown clear filtrate was stirred rapidly at RT and then acidified by slow addition of concentrated aqueous HCl 12M (approximately 2.7 mL) until pH measured 2 to 3 by pH paper. A heavy precipitate occurred during the acid addition. The resulting solid was collected by filtration, rinsed with cold deionized water, and allowed to air-dry overnight, then placed under high vacuum for several hours to give 3-(2-amino-[1,2,4]triazolo[1,5-a]pyridin-7-yl)-6-chloro-2-fluorobenzoic acid (6.39 g, 20.8 mmol, 95% yield) as a brown powder.

$^1$H NMR (500 MHz, DMSO-d$_6$) δ 8.64 (d, J=7.0 Hz, 1H), 7.76 (t, J=8.4 Hz, 1H), 7.55 (s, 1H), 7.54 (d, J=10.5 Hz, 2H), 7.05 (d, J=7.1 Hz, 1H), 6.11 (s, 2H).

MS ESI m/z 306.80 (M+H)$^+$

207: In a 1 dram vial were combined 3-(2-amino-[1,2,4]triazolo[1,5-a]pyridin-7-yl)-6-chloro-2-fluorobenzoic acid (15.3 mg, 0.0500 mmol) with 2,2-difluoro-3-(4-fluorophenyl)propan-1-amine, HCl (13.5 mg, 0.0600 mmol) and BOP (25.4 mg, 0.0580 mmol) in DMF (1 mL), followed by addition of DIPEA (0.0520 mL, 0.300 mmol). The resulting mixture was stirred at RT overnight. The crude mixture was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 18% B, 18-58% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. Thus, was obtained 3-(2-amino-[1,2,4]triazolo[1,5-a]pyridin-7-yl)-6-chloro-N-(2,2-difluoro-3-(4-fluorophenyl)propyl)-2-fluorobenzamide (12.4 mg, 0.0260 mmol, 52% yield).

$^1$H NMR (500 MHz, DMSO-d6) δ 9.26 (t, J=6.0 Hz, 1H), 8.64 (d, J=6.9 Hz, 1H), 7.76 (t, J=8.1 Hz, 1H), 7.55-7.51 (m, 2H), 7.39-7.34 (m, 2H), 7.19 (br t, J=8.8 Hz, 2H), 7.05 (br d, J=6.8 Hz, 1H), 6.10 (s, 2H), 3.84-3.72 (m, 2H). Two protons missing due to water.
MS ESI m/z 478.00 (M+H)$^+$ Example 208: 3-(2-amino-[1,2,4]triazolo[1,5-a]pyridin-7-yl)-N-(2,2-difluoro-3-(4-fluorophenyl)propyl)-2-fluoro-6-methylbenzamide

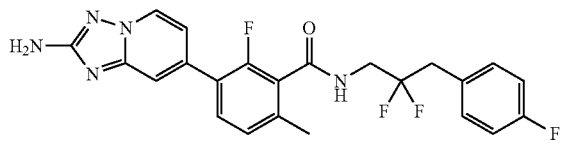 [SMILES: Cc1ccc(-c2ccn3nc(N)nc3c2)c(F)c1C(=O)NCC(F)(F)Cc1ccc(F)cc1]

208A: 6-fluoro-2-methyl-3-nitrobenzoic acid: A stirred solution of 2-fluoro-6-methylbenzoic acid (2.00 g, 13.0 mmol) in sulfuric acid, 18M (14.0 mL, 262 mmol) was chilled in an ice/acetone bath to −10° C. A thermometer was set into the mixture to monitor the temperature of the reaction. To the stirred mixture was slowly added dropwise over 10 min a mixture of nitric acid (1.08 mL, 15.8 mmol) and sulfuric acid (1.00 mL, 18.0 mmol). Addition was controlled such that the temperature of the mixture was maintained between −5 and 0° C. The mixture was stirred for an additional 30 min and was then poured over ice (100 g). A white solid was isolated from the resulting suspension by filtration. The solid was rinsed with ice cold deionized water and allowed to air-dry overnight. The solid was dissolved in EtOAc (50 mL) and the solution was washed with deionized water (3×20 mL) followed by brine (20 mL). The organic was dried over anhydrous magnesium sulfate, filtered and concentrated in vacuo to furnish 6-fluoro-2-methyl-3-nitrobenzoic acid (1.94 g, 9.74 mmol, 75% yield) as a white powder.

$^1$H NMR (500 MHz, CHLOROFORM-d) δ 8.08-8.03 (m, 1H), 7.19 (t, J=8.6 Hz, 1H), 2.67 (s, 3H).
MS ESI m/z 197.70 (M−H)$^-$

208B: 3-bromo-2-fluoro-6-methyl-5-nitrobenzoic acid: To a room temperature solution of 6-fluoro-2-methyl-3-nitrobenzoic acid (1.93 g, 9.69 mmol) in sulfuric acid 18M (10.0 mL, 188 mmol) was added 1,3-dibromo-5,5-dimethylimidazolidine-2,4-dione (2.91 g, 10.2 mmol). The mixture was stirred at RT under nitrogen atmosphere overnight. The mixture was poured into rapidly stirred ice-cold deionized water (100 mL), and the suspension was stirred at RT for 30 min. The suspension was chilled in an ice bath and filtered to isolate a white powder. The solid was dissolved in DMF (5 mL) and loaded onto an Isco Redisep Gold C18 150 g cartridge which was preequilibrated with 100% A solvent. The material was purified by reverse phase MPLC (Solvent A=95% H2O, 5% acetonitrile, 10 mM ammonium acetate; Solvent B=95% acetonitrile, 5% H2O, 10 mM ammonium acetate; 85 mL/min, gradient 0-40% B over 8 column volumes, hold 40% B for 5 column volumes). Product eluted during the gradient as a very broad band. Clean product fractions were combined and concentrated in vacuo to give a white solid. The solid was dissolved in a stirred mixture of EtOAc (100 mL) and water (40 mL) and 1M aqueous HCl was added until pH=1 was achieved. The resulting two phases were separated, the aqueous was extracted with EtOAc (2×50 mL) and the combined organics were washed with brine (25 mL), dried over anhydrous magnesium sulfate, filtered and concentrated in vacuo to give 3-bromo-2-fluoro-6-methyl-5-nitrobenzoic acid (1.90 g, 6.83 mmol, 71% yield) as a white solid.

$^1$H NMR (500 MHz, DMSO-d$_6$) δ 8.47 (d, J=6.4 Hz, 1H), 3.44-3.21 (m, 1H), 2.41 (s, 3H).

208C: 3-amino-5-bromo-6-fluoro-2-methylbenzoic acid: To a solution of 3-bromo-2-fluoro-6-methyl-5-nitrobenzoic acid (1.90 g, 6.83 mmol) in MeOH (70 mL) at RT was added ammonium chloride (3.66 g, 68.3 mmol) followed by deionized water (35 mL). The mixture was heated to 70° C. and then iron (2.29 g, 41.0 mmol) was added. After heating for 3.5 h, the crude mixture was poured over a bed of Celite and eluted with methanol. Concentration of the eluent in vacuo gave a solid which appeared to darken upon standing exposed to air. The solid was suspended in deionized water (100 mL) and the resulting suspension was filtered and the isolated solid was allowed to air dry overnight to give 3-amino-5-bromo-6-fluoro-2-methylbenzoic acid (1.61 g, 6.48 mmol, 95% yield) as a brown powder. No further purification was performed.

$^1$H NMR (500 MHz, DMSO-d6) δ 7.02-6.80 (m, 1H), 5.30-5.07 (m, 1H), 1.98 (br s, 3H).
MS ESI m/z 247.80, 249.80 (M+H)$^+$

208D: 3-bromo-2-fluoro-6-methylbenzoic acid: A stirred suspension of 3-amino-5-bromo-6-fluoro-2-methylbenzoic acid (1.50 g, 6.05 mmol) in AcOH (15 mL) was treated with sulfuric acid 18M (0.672 mL, 12.09 mmol) which caused a thicker but still stirrable suspension. The suspension was treated at RT dropwise very slowly, with stirring, with a concentrated aqueous solution of sodium nitrite (0.438 g, 6.35 mmol) in 3 mL of water over 20 min. Note: The addition rate was approximately one drop every 20 seconds, over a full 20 min. Any faster addition rate risked thermal decomposition of the diazonium salt. The suspension became more reddish in color over time, but still remained a suspension. At the end of the NaNO$_2$ addition, the mixture was stirred for 15 min at RT. The suspension was added all at once via pipet into a stirred solution of ferrous sulfate heptahydrate (1.68 g, 6.05 mmol) and phosphoric acid (1.65 mL, 24.2 mmol) in N,N-dimethylformamide (25 mL, 323 mmol). The resulting mixture effervesced during the addition, and a brown, opaque slightly milky solution resulted. The crude mixture was diluted to 200 mL with water and the resulting mixture was extracted with DCM (3×100 mL). The combined organics were back-extracted with water (100 mL), dried over anhydrous magnesium sulfate, filtered and concentrated in vacuo to give a red oil. The oil was redissolved in EtOAc (175 mL) and the resulting solution was washed with water (4×75 mL) and with brine (25 mL), dried over anhydrous magnesium sulfate, filtered and concentrated in vacuo to give 3-bromo-2-fluoro-6-methylbenzoic acid (1.20 g, 5.15 mmol, 85% yield) as a red/brown solid.

$^1$H NMR (500 MHz, DMSO-d6) δ 7.68 (t, J=7.8 Hz, 1H), 7.11 (d, J=8.2 Hz, 1H), 2.32 (s, 3H).
MS ESI m/z 230.70, 232.60 (M−H)$^-$

208E: 3-(2-amino-[1,2,4]triazolo[1,5-a]pyridin-7-yl)-2-fluoro-6-methylbenzoic acid, hydrochloride: Under nitrogen atmosphere were combined N,N-bis-Boc-2-amino-7-(4,4,5,5-tetramethyl-1,3,2-dioxaborolan-2-yl)-[1,2,4]triazolo[1,5- a]pyridine (1.00 g, 2.17 mmol), 3-bromo-2-fluoro-6-methylbenzoic acid (557 mg, 2.39 mmol), and PdCl$_2$(dtbpf) (70.8 mg, 0.109 mmol) in dioxane (10 mL) to give a brown solution. The solution was quickly treated with potassium phosphate, 2M aqueous (4.34 mL, 8.69 mmol) and the reaction mixture was degassed by bubbling nitrogen gas through for 10 min while stirring rapidly. The solution was heated to 60° C. for 8 h. The mixture was made acidic by slow addition of hydrochloric acid, 3M aqueous (5.79 mL, 17.4 mmol) with stirring. The mixture was transferred to a separatory funnel and diluted with ethyl acetate (50 mL). To the mixture was added solid sodium chloride in order to saturate the aqueous phase with brine. The mixture was shaken and phases were separated. The organic was washed twice more with brine (2×10 mL). The organic was dried over anhydrous sodium sulfate and filtered, then the mixture was concentrated in vacuo to a dark brown residue. The residue was dissolved in minimum DCM and loaded onto a DCM preequilibrated 120 g silica cartridge. Elution gradient, 100% DCM (solvent A) to 60% solvent B (solvent B=EtOAc with 1% acetic acid) over 12 column volumes, hold 60% B for 3 column volumes. Separation of the desired N,N-bis-Boc and the N-mono-Boc products was achieved. The N,N-bis-Boc and N-mono-Boc product fractions were combined into one flask and concentrated in vacuo to approximately 80 mL. The residue was transferred to a separatory funnel and washed with deionized water (4×40 mL) to remove acetic acid, then the organic was washed with brine (30 mL), dried over anhydrous magnesium sulfate, filtered and concentrated in vacuo to give a brown glassy solid. The solid was dissolved in anhydrous 1,4-dioxane (10 mL) and the solution was treated with hydrogen chloride, 4M in dioxane (10.9 mL, 43.4 mmol) for 48 h. The crude mixture was then concentrated under a stream of nitrogen to afford 3-(2-amino-[1,2,4]triazolo[1,5-a]pyridin-7-yl)-2-fluoro-6-methylbenzoic acid, hydrochloride (0.684 g, quantitative, maximum 90% purity) as an off-white powder.

$^1$H NMR (500 MHz, DMSO-d6) δ 8.83 (d, J=7.0 Hz, 1H), 7.72 (s, 1H), 7.68 (t, J=8.1 Hz, 1H), 7.43-7.21 (m, 2H), 2.41 (s, 3H).

MS ESI m/z 286.85 (M+H)$^+$

208: In a 1 dram vial were combined 3-(2-amino-[1,2,4]triazolo[1,5-a]pyridin-7-yl)-2-fluoro-6-methylbenzoic acid, HCl (17.9 mg, 0.0500 mmol) with 2,2-difluoro-3-(4-fluorophenyl)propan-1-amine, HCl (13.5 mg, 0.0600 mmol) and BOP (25.4 mg, 0.0580 mmol) in DMF (1 mL), followed by addition of DIPEA (0.0520 mL, 0.300 mmol). The resulting mixture was stirred at RT overnight. The crude mixture was filtered and was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 16% B, 16-56% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. Thus, was obtained 3-(2-amino-[1,2,4]triazolo[1,5-a]pyridin-7-yl)-N-(2,2-difluoro-3-(4-fluorophenyl)propyl)-2-fluoro-6-methylbenzamide (14.3 mg, 0.0312 mmol, 63% yield).

$^1$H NMR (500 MHz, DMSO-d6) δ 9.06 (t, J=6.1 Hz, 1H), 8.62 (d, J=7.0 Hz, 1H), 7.61 (t, J=7.9 Hz, 1H), 7.50 (s, 1H), 7.37 (t, J=6.6 Hz, 2H), 7.26-7.16 (m, 3H), 7.05 (d, J=7.1 Hz, 1H), 6.28-5.89 (m, 2H), 3.84-3.73 (m, 2H), 2.33 (s, 3H). Two protons missing, possibly obscured by large water peak. MS ESI m/z 458.10 (M+H)$^+$ Example 209: 3-(2-amino-[1,2,4]triazolo[1,5-a]pyridin-7-yl)-6-chloro-2-fluoro-N-((2S,3S)-2-fluoro-3-(4-fluorophenyl)-3-hydroxybutyl)benzamide

209A: ethyl 2-fluoro-3-(4-fluorophenyl)-3-hydroxybutanoate: A mixture of ethyl 2-bromo-2-fluoroacetate (20.8 mL, 176 mmol), 1-(4-fluorophenyl)ethan-1-one (7.09 mL, 58.6 mmol), iron (9.82 g, 176 mmol), and iodine (2.98 g, 11.7 mmol) in THF (117 mL) was heated at 60° C. for 12 h. Water was added and the aqueous layer was extracted with ethyl acetate (×3). The combined organic layers were washed with brine, dried over anhydrous sodium sulfate and filtered, and the filtrate was evaporated in vacuo to give the crude product. The crude product was purified by silica gel chromatography eluting with 0-20% ethyl acetate/hexanes to give ethyl 2-fluoro-3-(4-fluorophenyl)-3-hydroxybutanoate (9.5 g, 39 mmol, 66% yield) as a yellow oil. This material was a mixture of 4 isomers.

$^1$H NMR (500 MHz, CHLOROFORM-d) δ 7.56-7.44 (m, 4H), 7.14-6.98 (m, 4H), 5.08-4.73 (m, 2H), 4.24-3.97 (m, 4H), 3.54 (s, 1H), 3.28 (s, 1H), 1.74-1.64 (m, 6H), 1.23-1.04 (m, 6H).

209B: racemic mixture of (2R,3R)-2-fluoro-3-(4-fluorophenyl)-3-hydroxybutanamide and (2S,3S)-2-fluoro-3-(4-fluorophenyl)-3-hydroxybutanamide and racemic mixture of (2R,3S)-2-fluoro-3-(4-fluorophenyl)-3-hydroxybutanamide and (2S,3R)-2-fluoro-3-(4-fluorophenyl)-3-hydroxybutanamide: A mixture of ethyl 2-fluoro-3-(4-fluorophenyl)-3-hydroxybutanoate (4.00 g, 16.4 mmol) and ammonia, 7M solution in methanol (11.7 mL, 82.0 mmol) and MeOH (32.8 mL) was stirred at RT for 12 h. The crude reaction mixture was purified by reverse phase preparative HPLC on a Sunfire C18 column (10 µM particles, 50×300 mm) eluting with 0-100% B (Solvent A: 95% water/5% acetonitrile/10 mM ammonium acetate, Solvent B: 5% water/95% acetonitrile/10 mM ammonium acetate) over 30 min to give two separated materials. The first product peak to elute from the reverse phase purification provided a racemic mixture of (2R,3R)-2-fluoro-3-(4-fluorophenyl)-3-hydroxybutanamide and (2S,3S)-2-fluoro-3-(4-fluorophenyl)-3-hydroxybutanamide (0.920 g, 4.28 mmol, 26% yield) as a white solid after concentration in vacuo. The stereochemistry of this material was determined by X-Ray crystallography.

$^1$H NMR (500 MHz, METHANOL-d4) δ 7.55 (dd, J=7.7, 5.4 Hz, 2H), 7.13-6.95 (m, 2H), 5.15-5.14 (m, 1H), 4.83 (1H, d, J=50 Hz) 1.68 (d, J=1.7 Hz, 3H).

MS ESI m/z 213.85 (M−H)$^-$

The second product peak to elute from the reverse phase purification provided a racemic mixture of (2R,3S)-2-fluoro-3-(4-fluorophenyl)-3-hydroxybutanamide and (2S,3R)-2-fluoro-3-(4-fluorophenyl)-3-hydroxybutanamide (0.520 g, 2.42 mmol, 15% yield) as white solid. The stereochemistry of this material was determined by X-Ray crystallography.

¹H NMR (500 MHz, CHLOROFORM-d) δ 7.47 (br dd, J=7.3, 5.3 Hz, 2H), 7.04 (t, J=8.8 Hz, 2H), 6.22-6.02 (m, 1H), 5.52-5.27 (m, 1H), 4.95 (1H, d, J=50 Hz), 4.90 (1H, s), 1.71 (d, J=2.0 Hz, 3H).
MS ESI m/z 213.85 (M−H)⁻

209C: Chiral separation of (2R,3S)-2-fluoro-3-(4-fluorophenyl)-3-hydroxybutanamide and (2S,3R)-2-fluoro-3-(4-fluorophenyl)-3-hydroxybutanamide: The racemic mixture of (2R,3S)-2-fluoro-3-(4-fluorophenyl)-3-hydroxybutanamide and (2S,3R)-2-fluoro-3-(4-fluorophenyl)-3-hydroxybutanamide (520 mg total, 2.42 mmol) was resolved into individual enantiomers by chiral SFC with the following conditions: instrument: Waters MGM Prep 150 SFC; Column: Chiral IA, 30×250 mm, 5 micron particles; Mobile Phase: 88% CO₂, 12% MeOH; Flow rate: 85 mL/min; Detector wavelength: 220 nm; Injection details: 1.2 mL injections of 520 mg dissolved in 13 mL of MeOH-ACN. The first peak to elute with these conditions provided (2R,3S)-2-fluoro-3-(4-fluorophenyl)-3-hydroxybutanamide (190 mg, 0.883 mmol, 37% yield). The absolute stereochemistry of this material was determined by X-Ray crystallography. The second peak to elute from the chiral SFC separation gave (2S,3R)-2-fluoro-3-(4-fluorophenyl)-3-hydroxybutanamide (198 mg, 0.920 mmol, 38% yield).

209D: (2S,3S)-4-amino-3-fluoro-2-(4-fluorophenyl)butan-2-ol: Under nitrogen atmosphere in a flask fitted with a reflux condenser and magnetic stir bar, a solution of (2R, 3S)-2-fluoro-3-(4-fluorophenyl)-3-hydroxybutanamide (177 mg, 0.822 mmol) in THF (4.1 mL) was treated with borane dimethyl sulfide complex solution, 2.0 M in THF (1.65 mL, 3.29 mmol). The resulting mixture was stirred at 85° C. overnight. While still heated, the reaction was quenched by slow dropwise addition of methanol (CAUTION . . . dropwise addition required) through the top of the reflux condenser which caused vigorous effervescence and warming of the mixture to at or near the boiling point. Vigorous effervescing ceased after approximately 0.3 mL was added. A total of 2 mL of MeOH was added. The mix was heated for an additional 30 min. Solvent was removed in vacuo to give a clear colorless thick oil. More methanol (50 mL) was added and the mixture was again concentrated in vacuo. The methanol azeotrope was repeated once more and the residue was concentrated in vacuo to give crude (2S,3S)-4-amino-3-fluoro-2-(4-fluorophenyl)butan-2-ol (246 mg, >100% yield) which was used without further purification directly in the next step. Quantitative yield was assumed with crude material purity of approximately 67% by weight.
MS ESI m/z 201.85 (M+H)⁺

209: In a 1 dram vial were combined 3-(2-amino-[1,2,4]triazolo[1,5-a]pyridin-7-yl)-6-chloro-2-fluorobenzoic acid (21 mg, 0.068 mmol) with (2S,3S)-4-amino-3-fluoro-2-(4-fluorophenyl)butan-2-ol (29 mg, 0.096 mmol) and BOP (33 mg, 0.075 mmol) in DMF (1 mL), followed by addition of DIPEA (0.060 mL, 0.34 mmol). The resulting mixture was stirred at RT overnight. The crude reaction was filtered and purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide 3-(2-amino-[1,2,4]triazolo[1,5-a]pyridin-7-yl)-6-chloro-2-fluoro-N-((2S,3S)-2-fluoro-3-(4-fluorophenyl)-3-hydroxybutyl)benzamide (23.7 mg, 0.0483 mmol, 71% yield).
¹H NMR (500 MHz, DMSO-d6) δ 8.93 (t, J=5.7 Hz, 1H), 8.62 (d, J=7.0 Hz, 1H), 7.71 (t, J=8.0 Hz, 1H), 7.55-7.44 (m, 4H), 7.18 (t, J=8.8 Hz, 2H), 7.03 (br d, J=6.9 Hz, 1H), 6.08 (s, 2H), 5.74 (s, 1H), 4.68-4.51 (m, 1H), 3.68 (s, 1H), 3.00-2.90 (m, 1H), 1.56 (s, 3H).
MS ESI m/z 490.00 (M+H)⁺

Example 210: 3-(2-amino-[1,2,4]triazolo[1,5-a]pyridin-7-yl)-6-chloro-2-fluoro-N-((2R,3R)-2-fluoro-3-(4-fluorophenyl)-3-hydroxybutyl)benzamide

210A: (2R,3R)-4-amino-3-fluoro-2-(4-fluorophenyl)butan-2-ol: Under nitrogen atmosphere in a flask fitted with a reflux condenser and magnetic stir bar, a solution of (2S, 3R)-2-fluoro-3-(4-fluorophenyl)-3-hydroxybutanamide (195 mg, 0.906 mmol) in THF (4.5 mL) was treated with borane dimethyl sulfide complex solution, 2.0 M in THF (1.81 mL, 3.62 mmol). The resulting mixture was stirred at 85° C. overnight. While still heated, the reaction was quenched by slow dropwise addition of methanol (CAUTION . . . dropwise addition required) through the top of the reflux condenser which caused vigorous effervescence and warming of the mixture to at or near the boiling point. Vigorous effervescing ceased after approximately 0.3 mL was added. A total of 2 mL of MeOH was added. The mix was heated for an additional 30 min. Solvent was removed in vacuo to give a clear colorless thick oil. More methanol (50 mL) was added and the mixture was again concentrated in vacuo. The methanol azeotrope was repeated once more and the residue was concentrated in vacuo to give crude (2R,3R)-4-amino-3-fluoro-2-(4-fluorophenyl)butan-2-ol (271 mg, >100% yield) as an off-white semisolid which was used without further purification directly in the next step. Quantitative yield was assumed with crude material purity of approximately 67% by weight.
MS ESI m/z 201.90 (M+H)⁺

210: In a 1 dram vial were combined 3-(2-amino-[1,2,4] triazolo[1,5-a]pyridin-7-yl)-6-chloro-2-fluorobenzoic acid (21 mg, 0.068 mmol) with (2R,3R)-4-amino-3-fluoro-2-(4-fluorophenyl)butan-2-ol (29 mg, 0.096 mmol) and BOP (33 mg, 0.075 mmol) in DMF (1 mL), followed by addition of DIPEA (0.060 mL, 0.34 mmol). The resulting mixture was stirred at RT overnight. The crude reaction was filtered and purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide 3-(2-amino-[1,2,4]triazolo[1,5-a]pyridin-7-yl)-6-chloro-2-fluoro-N-((2R,3R)-2-fluoro-3-(4-fluorophenyl)-3-hydroxybutyl)benzamide (25.4 mg, 0.0518 mmol, 76% yield).

¹H NMR (500 MHz, DMSO-d6) δ 8.93 (t, J=5.5 Hz, 1H), 8.62 (d, J=7.0 Hz, 1H), 7.71 (t, J=8.0 Hz, 1H), 7.57-7.44 (m, 4H), 7.18 (t, J=8.3 Hz, 2H), 7.03 (br d, J=7.2 Hz, 1H), 6.14-6.05 (m, 2H), 5.74 (s, 1H), 4.70-4.48 (m, 1H), 3.78-3.64 (m, 1H), 3.04-2.83 (m, 1H), 1.56 (s, 3H).
MS ESI m/z 490.00 (M+H)⁺

Example 211: 3-(2-amino-[1,2,4]triazolo[1,5-a]pyridin-7-yl)-6-chloro-2-fluoro-N-((2S,3R)-2-fluoro-3-(4-fluorophenyl)-3-hydroxybutyl)benzamide

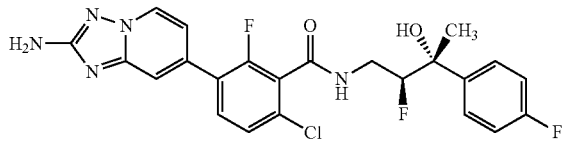 [SMILES: C[C@@](O)(c1ccc(F)cc1)[C@H](F)CNC(=O)c1c(Cl)ccc(-c2ccn3nc(N)nc3c2)c1F]

211A: Chiral separation of (2R,3R)-2-fluoro-3-(4-fluorophenyl)-3-hydroxybutanamide and (2S,3S)-2-fluoro-3-(4-fluorophenyl)-3-hydroxybutanamide: The racemic mixture of (2R,3R)-2-fluoro-3-(4-fluorophenyl)-3-hydroxybutanamide and (2S,3S)-2-fluoro-3-(4-fluorophenyl)-3-hydroxybutanamide (922 mg total, 4.28 mmol) was resolved into individual enantiomers by chiral SFC with the following conditions: Instrument: PIC Prep SFC; Column: Chiral IA, 21×250 mm, 5 micron particles; Mobile Phase: 85% CO₂, 15% MeOH; Flow rate: 45 mL/min; Detector wavelength: 220 nm; Injection details: 0.6 mL injections of 922 mg dissolved in 10 mL of MeOH. The first peak to elute with these conditions provided (2R,3R)-2-fluoro-3-(4-fluorophenyl)-3-hydroxybutanamide (250 mg, 1.16 mmol, 27% yield). The absolute stereochemistry of this material was determined by X-Ray crystallography.

The second peak to elute from the chiral SFC separation gave (2S,3S)-2-fluoro-3-(4-fluorophenyl)-3-hydroxybutanamide (245 mg, 1.14 mmol, 27% yield).

211B: (2R,3S)-4-amino-3-fluoro-2-(4-fluorophenyl)butan-2-ol: Under nitrogen atmosphere in a flask fitted with a reflux condenser and magnetic stir bar, a solution of (2R,3R)-2-fluoro-3-(4-fluorophenyl)-3-hydroxybutanamide (319 mg, 1.48 mmol) in THF (7.4 mL) was treated with borane dimethyl sulfide complex solution, 2.0 M in THF (2.97 mL, 5.93 mmol). The resulting mixture was stirred at 85° C. for 4.5 h. While still heated, the reaction was quenched by slow dropwise addition of methanol (CAUTION . . . dropwise addition required) through the top of the reflux condenser which caused vigorous effervescence and warming of the mixture to at or near the boiling point. A total of 15 mL of MeOH was added. Solvent was removed in vacuo to give a clear colorless thick oil. More methanol (50 mL) was added and the mixture was again concentrated in vacuo. The methanol azeotrope was repeated once more and the residue was concentrated in vacuo to give crude (2R,3S)-4-amino-3-fluoro-2-(4-fluorophenyl)butan-2-ol (348 mg, >100% yield) which was used without further purification directly in the next step. Quantitative yield was assumed with crude material purity of approximately 85% by weight.
MS ESI m/z 201.95 (M+H)⁺

211: In a 1 dram vial were combined 3-(2-amino-[1,2,4]triazolo[1,5-a]pyridin-7-yl)-6-chloro-2-fluorobenzoic acid (21 mg, 0.068 mmol) with (2R,3S)-4-amino-3-fluoro-2-(4-fluorophenyl)butan-2-ol (23 mg, 0.096 mmol) and BOP (33 mg, 0.075 mmol) in DMF (1 mL), followed by addition of DIPEA (0.060 mL, 0.34 mmol). The resulting mixture was stirred at RT overnight The crude reaction was filtered and purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide 3-(2-amino-[1,2,4]triazolo[1,5-a]pyridin-7-yl)-6-chloro-2-fluoro-N-((2S,3R)-2-fluoro-3-(4-fluorophenyl)-3-hydroxybutyl)benzamide (34.5 mg, 0.0680 mmol, quantitative).
¹H NMR (500 MHz, DMSO-d6) δ 8.89 (t, J=5.5 Hz, 1H), 8.62 (d, J=6.3 Hz, 1H), 7.71 (t, J=8.3 Hz, 1H), 7.59-7.45 (m, 4H), 7.18 (t, J=8.6 Hz, 2H), 7.02 (br d, J=7.3 Hz, 1H), 6.08 (s, 2H), 5.75-5.57 (m, 1H), 4.72-4.56 (m, 1H), 1.55 (s, 3H). Two protons missing due to large water peak.
MS ESI m/z 490.00 (M+H)⁺

Example 212: 3-(2-amino-[1,2,4]triazolo[1,5-a]pyridin-7-yl)-6-chloro-2-fluoro-N-((2R,3S)-2-fluoro-3-(4-fluorophenyl)-3-hydroxybutyl)benzamide

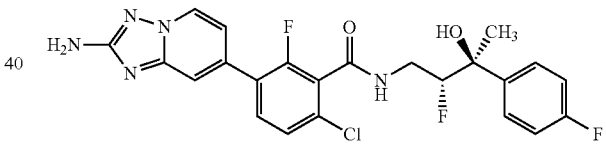

212A: (2S,3R)-4-amino-3-fluoro-2-(4-fluorophenyl)butan-2-ol: Under nitrogen atmosphere in a flask fitted with a reflux condenser and magnetic stir bar, a solution of (2S,3S)-2-fluoro-3-(4-fluorophenyl)-3-hydroxybutanamide (403 mg, 1.87 mmol) in THF (9.4 mL) was treated with borane dimethyl sulfide complex solution, 2.0 M in THF (3.75 mL, 7.49 mmol). The resulting mixture was stirred at 85° C. for 4.5 h While still heated, the reaction was quenched by slow dropwise addition of methanol (CAUTION . . . dropwise addition required) through the top of the reflux condenser which caused vigorous effervescence and warming of the mixture to at or near the boiling point. A total of 15 mL of MeOH was added. Solvent was removed in vacuo to give a clear colorless thick oil. More methanol (50 mL) was added and the mixture was again concentrated in vacuo. The methanol azeotrope was repeated once more and the residue was concentrated in vacuo to give crude (2S,3R)-4-amino-3-fluoro-2-(4-fluorophenyl)butan-2-ol (367 mg, 1.82 mmol, 97% yield) as a thick light brown oil which was used without further purification directly in the next step.
MS ESI m/z 201.85 (M+H)⁺

212: In a 1 dram vial were combined 3-(2-amino-[1,2,4]triazolo[1,5-a]pyridin-7-yl)-6-chloro-2-fluorobenzoic acid (21 mg, 0.068 mmol) with (2S,3R)-4-amino-3-fluoro-2-(4-fluorophenyl)butan-2-ol (19.3 mg, 0.0960 mmol) and BOP (33 mg, 0.075 mmol) in DMF (1 mL), followed by addition of DIPEA (0.060 mL, 0.34 mmol). The resulting mixture was stirred at RT overnight. The crude reaction was filtered and purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide 3-(2-amino-[1,2,4]triazolo[1,5-a]pyridin-7-yl)-6-chloro-2-fluoro-N-((2R,3S)-2-fluoro-3-(4-fluorophenyl)-3-hydroxybutyl)benzamide (30.1 mg, 0.0614 mmol, 90% yield).

$^1$H NMR (500 MHz, DMSO-d6) δ 8.89 (t, J=5.7 Hz, 1H), 8.62 (d, J=7.0 Hz, 1H), 7.71 (t, J=8.2 Hz, 1H), 7.56 (dd, J=7.7, 5.4 Hz, 2H), 7.50 (s, 1H), 7.47 (d, J=8.4 Hz, 1H), 7.18 (t, J=8.8 Hz, 2H), 7.02 (br d, J=7.0 Hz, 1H), 6.10-6.06 (m, 2H), 5.72-5.61 (m, 1H), 4.71-4.57 (m, 1H), 1.55 (s, 3H). Two protons missing due to large water peak.

MS ESI m/z 490.00 (M+H)$^+$

TABLE 14

Compounds in Table 14 were prepared by the same methods described for the preparations of examples 209, 210, 211 and 212, respectively. In each case, 3-(2-amino-[1,2,4]triazolo[1,5-a]pyridin-7-yl)-2-fluoro-6-(methyl-d$_3$)benzoic acid was substituted in place of 3-(2-amino-[1,2,4]triazolo[1,5-a]pyridin-7-yl)-6-chloro-2-fluorobenzoic acid in the final step

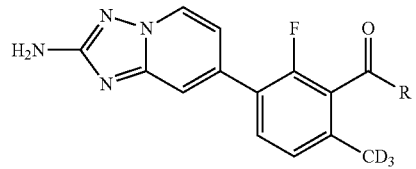

| Ex No | Name | R | M + H$^+$ | 1H NMR (500 MHz, DMSO-d6) δ |
|---|---|---|---|---|
| 213 | 3-(2-amino-[1,2,4]triazolo[1,5-a]pyridin-7-yl)-2-fluoro-N-((2S,3S)-2-fluoro-3-(4-fluorophenyl)-3-hydroxybutyl)-6-(methyl-d$_3$)benzamide | | 473.0 | 8.71 (t, J = 5.5 Hz, 1H), 8.60 (dd, J = 7.0, 3.5 Hz, 1H), 7.60-7.45 (m, 4H), 7.25-7.12 (m, 3H), 7.02 (d, J = 7.0 Hz, 1H), 6.04 (br d, J = 3.6 Hz, 2H), 5.72 (s, 1H), 4.73-4.50 (m, 1H), 3.75-3.56 (m, 1H), 3.06-2.93 (m, 1H), 1.57 (br s, 3H) |
| 214 | 3-(2-amino-[1,2,4]triazolo[1,5-a]pyridin-7-yl)-2-fluoro-N-((2R,3R)-2-fluoro-3-(4-fluorophenyl)-3-hydroxybutyl)-6-(methyl-d$_3$)benzamide | | 473.1 | 8.71 (t, J = 5.7 Hz, 1H), 8.59 (d, J = 7.0 Hz, 1H), 7.61-7.50 (m, 3H), 7.47 (s, 1H), 7.25-7.12 (m, 3H), 7.02 (br d, J = 7.0 Hz, 1H), 6.09-5.99 (m, 2H), 5.73-5.70 (m, 1H), 4.72-4.50 (m, 1H), 3.75-3.58 (m, 1H), 3.05-2.94 (m, 1H), 1.56 (s, 3H) |
| 215 | 3-(2-amino-[1,2,4]triazolo[1,5-a]pyridin-7-yl)-2-fluoro-N-((2S,3R)-2-fluoro-3-(4-fluorophenyl)-3-hydroxybutyl)-6-(methyl-d$_3$)benzamide | | 473.0 | 8.67 (t, J = 5.6 Hz, 1H), 8.60 (d, J = 6.9 Hz, 1H), 7.56 (t, J = 7.1 Hz, 3H), 7.46 (s, 1H), 7.22-7.16 (m, 3H), 7.03-6.98 (m, 1H), 6.12-6.00 (m, 2H), 5.63 (s, 1H), 4.75-4.58 (m, 1H), 1.55 (s, 3H). Two protons missing due to peak. |
| 216 | 3-(2-amino-[1,2,4]triazolo[1,5-a]pyridin-7-yl)-2-fluoro-N-((2R,3S)-2-fluoro-3-(4-fluorophenyl)-3-hydroxybutyl)-6-(methyl-d$_3$)benzamide | | 473.0 | 8.67 (br t, J = 5.6 Hz, 1H), 8.60 (d, J = 7.0 Hz, 1H), 7.56 (t, J =7.3 Hz, 3H), 7.46 (s, 1H), 7.23-7.14 (m, 3H), 7.04-6.99 (m, 1H), 6.12-6.00 (m, 2H), 5.64 (s, 1H), 4.75-4.58 (m, 1H), 1.55 (s, 3H). Two protons missing due to peak. |

Example 217: (S)-3-(2-amino-[1,2,4]triazolo[1,5-a]pyridin-7-yl)-N-(3-(4-chlorophenyl)-3-hydroxypropyl)-2-fluorobenzamide

217A: 3-(2-amino-[1,2,4]triazolo[1,5-a]pyridin-7-yl)-2-fluorobenzoic acid: To a solution of (2-amino-[1,2,4]triazolo[1,5-a]pyridin-7-yl)boronic acid (496 mg, 2.79 mmol) in 1,4-dioxane (10 mL) was added 3-bromo-2-fluorobenzoic acid (565 mg, 2.58 mmol) and 1,1'-bis(di-tert-butylphosphino)ferrocene palladium dichloride (84.0 mg, 0.129 mmol). The mixture was degassed by bubbling nitrogen through the mixture for 5 min. 2M $K_3PO_4$ (a) (3.87 mL, 7.74 mmol) was quickly added and the reaction mixture was heated at 100° C. for 5 min. The mixture was cooled to room temperature, then diluted with 50 mL of 1.5M aqueous potassium phosphate and washed with EtOAc (1×10 mL). The aqueous layer was acidified with 6N aqueous HCl whereupon the product precipitated out of solution. The product was collected by filtration and dried to give 3-(2-amino-[1,2,4]triazolo[1,5-a]pyridin-7-yl)-2-fluorobenzoic acid (497 mg, 1.83 mmol, 71% yield) as a tan solid.

217: A mixture of 3-(2-amino-[1,2,4]triazolo[1,5-a]pyridin-7-yl)-2-fluorobenzoic acid (22 mg, 0.081 mmol), BOP (53.6 mg, 0.121 mmol), (S)-3-amino-1-(4-chlorophenyl)propan-1-ol (7.80 mg, 0.042 mmol), and Hunig's base (0.071 mL, 0.404 mmol) in DMF (1.0 mL) was stirred at 44° C. overnight. The mixture was diluted to 2 mL with methanol, then filtered. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to afford (S)-3-(2-amino-[1,2,4]triazolo[1,5-a]pyridin-7-yl)-N-(3-(4-chlorophenyl)-3-hydroxypropyl)-2-fluorobenzamide (22.1 mg, 0.050 mmol, 62% yield).

$^1$H NMR (500 MHz, DMSO-d6) δ 8.64 (d, J=7.0 Hz, 1H), 8.52-8.39 (m, 1H), 7.74 (br t, J=7.5 Hz, 1H), 7.62 (br t, J=6.4 Hz, 1H), 7.55 (s, 1H), 7.42-7.35 (m, 5H), 7.08 (br d, J=6.9 Hz, 1H), 6.22-6.03 (m, 1H), 4.67 (br s, 1H), 3.48-3.39 (m, 1H), 3.41-3.24 (m, 1H), 1.84 (q, J=6.8 Hz, 2H) [NH$_2$ protons are not observed].
MS ESI m/z 297.3 (M+H)$^+$

Example 218: (R)-3-(2-amino-[1,2,4]triazolo[1,5-a]pyridin-7-yl)-N-(3-(4-chlorophenyl)-3-hydroxypropyl)-2-fluorobenzamide

A mixture of 3-(2-amino-[1,2,4]triazolo[1,5-a]pyridin-7-yl)-2-fluorobenzoic acid (20 mg, 0.073 mmol), BOP (48.7 mg, 0.110 mmol), (R)-3-amino-1-(4-chlorophenyl)propan-1-ol, HCl (20.4 mg, 0.0920 mmol), and Hunig's base (0.077 mL, 0.44 mmol) in DMF (1 mL) was stirred at 44° C. overnight. LCMS indicated complete reaction. The mixture was diluted to 2 mL with methanol, then filtered. The crude material was purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 10% B, 10-46% B over 28 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford (R)-3-(2-amino-[1,2,4]triazolo[1,5-a]pyridin-7-yl)-N-(3-(4-chlorophenyl)-3-hydroxypropyl)-2-fluorobenzamide (17.0 mg, 0.039 mmol, 53% yield).

$^1$H NMR (500 MHz, DMSO-d6) δ 8.63 (d, J=7.0 Hz, 1H), 8.46 (br s, 1H), 7.73 (br t, J=7.1 Hz, 1H), 7.62 (br t, J=6.7 Hz, 1H), 7.54 (s, 1H), 7.42-7.36 (m, 5H), 7.08 (br d, J=7.0 Hz, 1H), 6.09 (s, 2H), 5.46 (br d, J=4.5 Hz, 1H), 4.72-4.62 (m, 1H), 3.57-3.44 (m, 1H), 3.41-3.21 (m, 1H), 1.84 (q, J=6.8 Hz, 2H).
MS ESI m/z 440.03 (M+H)$^+$

Example 219: (S)-3-(2-amino-[1,2,4]triazolo[1,5-a]pyridin-7-yl)-N-(3-(4-chlorophenyl)-3-hydroxypropyl)-2,4-difluorobenzamide

219A: methyl 3-(2-amino-[1,2,4]triazolo[1,5-a]pyridin-7-yl)-2,4-difluorobenzoate: To a solution of (2-amino-[1,2,4]triazolo[1,5-a]pyridin-7-yl)boronic acid (247 mg, 1.39 mmol) in 1,4-dioxane (6 mL) was added methyl 3-chloro-2,4-difluorobenzoate (265 mg, 1.28 mmol) and 1,1'-bis(di-tert-butylphosphino)ferrocene palladium dichloride (42 mg, 0.064 mmol) and the mixture was degassed by bubbling nitrogen through the mixture for 5 min. 2M $K_3PO_4$ (aq) (1.92 mL, 3.85 mmol) was quickly added and the reaction mixture heated at 100° C. for 5 min. LCMS indicated that the reaction was complete. The mixture was cooled to room temperature, concentrated onto Celite, then purified by 24 g silica column, eluting with 0-100% EtOAc in hexanes and then with 0-10% MeOH in DCM to afford methyl 3-(2-amino-[1,2,4]triazolo[1,5-a]pyridin-7-yl)-2,4-difluorobenzoate (390 mg, 1.15 mmol, 90% yield).
MS ESI m/z 305.1 (M+H)+

219B: Lithium 3-(2-amino-[1,2,4]triazolo[1,5-a]pyridin-7-yl)-2,4-difluorobenzoate: To a solution of methyl 3-(2-amino-[1,2,4]triazolo[1,5-a]pyridin-7-yl)-2,4-difluorobenzoate (390 mg, 1.28 mmol) in THF (10 mL) and a few drops of methanol was added a solution of lithium hydroxide monohydrate (64.5 mg, 1.54 mmol) in 0.5 mL water. The mixture was heated to 55° C. and stirred for 3 h. The mixture was cooled to room temperature and concentrated to a solid. The crude material was used as-is in subsequent steps without further purification.
MS ESI m/z 291.0 (M+H)+

219: A mixture of lithium 3-(2-amino-[1,2,4]triazolo[1,5-a]pyridin-7-yl)-2,4-difluorobenzoate (22 mg, 0.076 mmol), BOP (50.3 mg, 0.114 mmol), (S)-3-amino-1-(4-chlorophenyl)propan-1-ol (7.8 mg, 0.042 mmol), and Hunig's base (0.066 mL, 0.38 mmol) in DMF (1.0 mL) was stirred at 44° C. overnight. LCMS indicated complete reaction. The mixture was diluted to 2 mL with methanol, then filtered. The crude material was purified via preparative LCMS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 12% B, 12-52% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to afford (S)-3-(2-amino-[1,2,4]triazolo[1,5-a]pyridin-7-yl)-N-(3-(4-chlorophenyl)-3-hydroxypropyl)-2,4-difluorobenzamide (10.1 mg, 0.022 mmol, 29% yield).
1H NMR (500 MHz, DMSO-d6) δ 8.68 (d, J=7.0 Hz, 1H), 8.41 (br s, 1H), 7.82-7.62 (m, 1H), 7.52 (s, 1H), 7.43-7.32 (m, 4H), 6.98 (br d, J=6.4 Hz, 1H), 6.13 (s, 2H), 4.67 (br s, 1H), 3.33 (br s, 2H), 1.92 (s, 2H), 1.84 (br d, J=6.7 Hz, 2H).
MS ESI m/z 458.3 (M+H)+

Example 220: (R)-3-(2-amino-[1,2,4]triazolo[1,5-a]pyridin-7-yl)-N-(3-(4-chlorophenyl)-3-hydroxypropyl)-2,4-difluorobenzamide

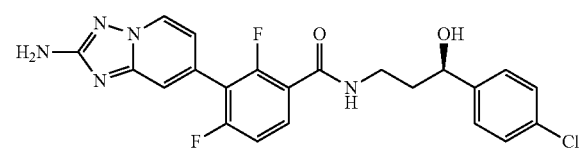 [SMILES: Nc1nc2cc(-c3c(F)ccc(C(=O)NCC[C@@H](O)c4ccc(Cl)cc4)c3F)ccn2n1]

A mixture of lithium 3-(2-amino-[1,2,4]triazolo[1,5-a]pyridin-7-yl)-2,4-difluorobenzoate (22 mg, 0.076 mmol), BOP (50.3 mg, 0.114 mmol), (R)-3-amino-1-(4-chlorophenyl)propan-1-ol (7.8 mg, 0.042 mmol), and Hunig's base (0.066 mL, 0.38 mmol) in DMF (1.0 mL) was stirred at 44° C. overnight. LCMS indicated complete reaction. The mixture was diluted to 2 mL with methanol, then filtered. The crude material was purified via preparative LCMS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 12% B, 12-52% B over 23 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford (R)-3-(2-amino-[1,2,4]triazolo[1,5-a]pyridin-7-yl)-N-(3-(4-chlorophenyl)-3-hydroxypropyl)-2,4-difluorobenzamide (9.3 mg, 0.020 mmol, 27% yield).
1H NMR (500 MHz, DMSO-d6) δ 8.67 (d, J=7.0 Hz, 1H), 8.40 (br s, 1H), 7.80-7.62 (m, 1H), 7.51 (s, 1H), 7.42-7.32 (m, 4H), 6.98 (br d, J=6.7 Hz, 1H), 6.13 (s, 2H), 4.66 (br t, J=6.1 Hz, 1H), 3.43-2.85 (m, 2H), 1.89 (s, 2H), 1.83 (br d, J=6.7 Hz, 2H).
MS ESI m/z 458.01 (M+H)+

Example 221: 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide

enantiomer 1

221A: ethyl 2,2-difluoro-3-(4-chlorophenyl)-3-hydroxybutanoate:
221A Method 1: A mixture of iron (1.08 g, 19.4 mmol), 1-(4-chlorophenyl)ethan-1-one (0.839 mL, 6.47 mmol), ethyl 2-bromo-2,2-difluoroacetate (2.49 mL, 19.4 mmol), and iodine (0.328 g, 1.29 mmol) in THF (13 mL) was purged with nitrogen for 5 min and vigorously stirred at 70° C. for 24 h. Additional ethyl 2-bromo-2,2-difluoroacetate (0.829 mL, 6.47 mmol) and iron (0.361 g, 6.47 mmol) were added. The mixture was purged with nitrogen for 5 min and vigorously stirred at 70° C. for 24 h. The reaction was quenched with saturated aqueous NH4Cl (50 mL). The reaction mixture was extracted with EtOAc (3×50 mL), washed with brine, dried over Na2SO4, filtered and concentrated under reduced pressure. The crude product was purified by column chromatography on a silica gel cartridge eluting with 0-50% EtOAc in hexanes. The fractions containing the expected product were concentrated under reduced pressure to give ethyl 3-(4-chlorophenyl)-2,2-difluoro-3-hydroxybutanoate (1.15 g, 4.13 mmol, 64% yield) as an oil.
1H NMR (500 MHz, CHLOROFORM-d) δ 7.47 (d, J=8.5 Hz, 2H), 7.35 (d, J=8.7 Hz, 2H), 4.20 (q, J=7.1 Hz, 2H), 1.73 (s, 3H), 1.18 (t, J=7.2 Hz, 3H).

221A Method 2: To a stirring mixture of 1-(4-chlorophenyl)ethan-1-one (1.50 g, 9.70 mmol) and indium powder (1.67 g, 14.6 mmol) in THF (20 mL) was added ethyl 2-bromo-2,2-difluoroacetate (2.95 g, 14.6 mmol) dropwise. The resulting mixture was vigorously stirred at 60° C. for 12 h. The reaction was quenched with 1 N aqueous HCl (10 mL). The mixture was diluted with EtOAc (30 mL) and solid was filtered off. The layers of the filtrate were separated. The aqueous layer was extracted with EtOAc (3×50 mL). The combined EtOAc layers were washed with brine (50 mL), dried over Na2SO4, filtered and concentrated under reduced pressure. The crude product was purified by column chromatography on a silica gel cartridge eluting with 0-30% EtOAc in hexane. The fractions containing the expected product were concentrated under reduced pressure to give ethyl 3-(4-chlorophenyl)-2,2-difluoro-3-hydroxybutanoate (2.25 g, 8.07 mmol, 83% yield) as an oil.

$^1$H NMR (400 MHz, CHLOROFORM-d) δ 7.47 (d, J=8.8 Hz, 2H), 7.37-7.33 (m, 2H), 4.20 (q, J=7.2 Hz, 2H), 1.73 (t, J=1.5 Hz, 3H), 1.18 (t, J=7.2 Hz, 3H).

221B: 3-(4-chlorophenyl)-2,2-difluoro-3-hydroxybutanamide: To a solution of ethyl 3-(4-chlorophenyl)-2,2-difluoro-3-hydroxybutanoate (4.84 g, 17.4 mmol) in MeOH (80 mL) at 0° C. was added ammonia (7 M in MeOH) (9.92 mL, 69.5 mmol). The resulting solution was stirred at RT for 2 h. The reaction mixture was concentrated under reduced pressure then dried under vacuum overnight to give crude 3-(4-chlorophenyl)-2,2-difluoro-3-hydroxybutanamide (4.4 g, 17.7 mmol, 96% yield) as a solid which was used as-is in next step without purification.

$^1$H NMR (500 MHz, DMSO-d$_6$) δ 7.78 (br s, 1H), 7.64 (br s, 1H), 7.51 (d, J=8.6 Hz, 2H), 7.40 (d, J=8.7 Hz, 2H), 6.22 (s, 1H), 1.65 (s, 3H).

MS ESI m/z 247.9 (M–H)$^-$

221C: 4-amino-2-(4-chlorophenyl)-3,3-difluorobutan-2-ol: To a solution of 3-(4-chlorophenyl)-2,2-difluoro-3-hydroxybutanamide (1.03 g, 4.13 mmol) in THF (20 mL) was added LAH (2M in THF) (3.09 mL, 6.19 mmol) at −78° C. The mixture was stirred at −78° C. for 30 min, then warmed to RT and stirred overnight. The reaction mixture was cooled to −78° C. Additional LAH (2M in THF) (1.03 mL, 2.06 mmol) was added and the mixture was stirred at RT for 2 h. The reaction was diluted with ether (20 mL) and cooled to 0° C. Water (0.3 mL) was added followed by 15% aqueous NaOH (0.3 mL) and water (0.9 mL). The mixture was warmed to RT and stirred for 15 min. Anhydrous MgSO$_4$ was added and the slurry was stirred for 15 min and then was filtered to remove the salts. The filtrate was concentrated under reduced pressure to give crude 4-amino-2-(4-chlorophenyl)-3,3-difluorobutan-2-ol (832 mg, 3.53 mmol, 86% yield) as a viscous oil which was used as-is in subsequent steps without purification.

$^1$H NMR (400 MHz, DMSO-d$_6$) δ 7.53-7.48 (m, 2H), 7.42-7.37 (m, 2H), 1.64 (s, 3H).

MS ESI m/z 236.0 (M+H)$^+$

221D: N,N-bis-Boc-3-(2-amino-[1,2,4]triazolo[1,5-a]pyridin-7-yl)-2-fluoro-6-methylbenzoic acid and N-Boc-3-(2-amino-[1,2,4]triazolo[1,5-a]pyridin-7-yl)-2-fluoro-6-methylbenzoic acid: A mixture of N,N-bis-Boc-2-amino-7-(4,4,5,5-tetramethyl-1,3,2-dioxaborolan-2-yl)-[1,2,4]triazolo[1,5-a]pyridine (254 mg, 0.552 mmol), 3-bromo-2-fluoro-6-methylbenzoic acid (117 mg, 0.502 mmol), PdCl$_2$(dtbpf) (16.4 mg, 0.0250 mmol) and K$_3$PO$_4$ (2M aq) (0.753 mL, 1.51 mmol) in dioxane (3 mL) was purged with N2 and stirred at 80° C. for 2 h. The reaction mixture was concentrated under reduced pressure. The residue was triturated with Et$_2$O (20 mL). The solid was collected by filtration, dissolved in H$_2$O (20 mL), and acidified to pH ~ 2 by 1N aqueous HCl. The precipitated solid was collected by filtration, washed with H$_2$O (2×10 mL) and dried under vacuum to give a crude mixture of N,N-bis-Boc-3-(2-amino-[1,2,4]triazolo[1,5-a]pyridin-7-yl)-2-fluoro-6-methylbenzoic acid and N-Boc-3-(2-amino-[1,2,4]triazolo[1,5-a]pyridin-7-yl)-2-fluoro-6-methylbenzoic acid (218 mg, 0.448 mmol, 89% yield) as a solid, which was used as-is in subsequent steps without further purification.

MS ESI m/z 487.1 (M+H)$^+$ and 386.9 (M+H)$^+$

221E: 3-(2-amino-[1,2,4]triazolo[1,5-a]pyridin-7-yl)-2-fluoro-6-methylbenzoic acid:

To a mixture of N,N-bis-Boc-3-(2-amino-[1,2,4]triazolo[1,5-a]pyridin-7-yl)-2-fluoro-6-methylbenzoic acid and N-Boc-3-(2-amino-[1,2,4]triazolo[1,5-a]pyridin-7-yl)-2-fluoro-6-methylbenzoic acid (218 mg, 0.448 mmol) in DCM (4 mL) was added TFA (1.04 mL, 13.4 mmol). The resulting solution was stirred at RT for 3 h. The reaction mixture was concentrated under reduced pressure to give crude 3-(2-amino-[1,2,4]triazolo[1,5-a]pyridin-7-yl)-2-fluoro-6-methylbenzoic acid, 2 TFA (213 mg, 0.414 mmol, 92% yield) as a solid, which was used as-is in subsequent steps without further purification.

MS ESI m/z 287.2 (M+H)$^+$

221F: 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide: A solution of crude 3-(2-amino-[1,2,4]triazolo[1,5-a]pyridin-7-yl)-2-fluoro-6-methylbenzoic acid, 2 TFA (51.4 mg, 0.100 mmol), 4-amino-2-(4-chlorophenyl)-3,3-difluorobutan-2-ol (23.6 mg, 0.100 mmol), BOP (66.3 mg, 0.150 mmol), and DIPEA (0.175 mL, 0.999 mmol) in DMF (1 mL) was stirred at RT overnight. Additional 4-amino-2-(4-chlorophenyl)-3,3-difluorobutan-2-ol (23.6 mg, 0.100 mmol) was added. The reaction was continued at RT for 2 h. The reaction mixture was filtered, and the crude material was purified via preparative LCMS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 22% B, 22-62% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give racemic 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide (17.2 mg, 0.034 mmol, 34% yield).

$^1$H NMR (500 MHz, DMSO-d$_6$) δ 8.81 (br t, J=5.8 Hz, 1H), 8.59 (d, J=7.0 Hz, 1H), 7.61-7.54 (m, 3H), 7.47-7.42 (m, 3H), 7.20 (br d, J=7.9 Hz, 1H), 7.01 (br d, J=6.7 Hz, 1H), 6.05 (s, 2H), 4.04-3.84 (m, 2H), 2.27 (s, 3H), 1.62 (s, 3H).

MS ESI m/z 504.2 (M+H)$^+$

221: 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide enantiomer 1: Racemic 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide was separated into individual stereoisomers by SFC-chiral chromatography with the following conditions: Column: Chiral IC 21×250 mm. 5 micron; Mobile Phase: 75% CO$_2$/25% MeOH w/0.1% DEA; Flow Conditions: 60 mL/min; Detector Wavelength: 220 nm; Injection details: 1 mL, 17 mg dissolved in 3 mL MeOH. Thus, was obtained 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide enantiomer 1 (4.9 mg, 0.010 mmol, 9% yield) as the first eluting isomer from the chiral SFC separation. The relative and absolute stereochemistry was not determined.

$^1$H NMR (500 MHz, DMSO-d$_6$) δ 8.82 (br t, J=5.6 Hz, 1H), 8.56 (d, J=7.0 Hz, 1H), 7.60-7.52 (m, 3H), 7.46-7.40 (m, 3H), 7.19 (br d, J=7.9 Hz, 1H), 7.02 (br d, J=7.6 Hz, 1H), 6.03 (s, 2H), 4.00-3.84 (m, 2H), 2.25 (s, 3H), 1.61 (s, 3H).

MS ESI m/z 504.1 (M+H)$^+$

Example 222: 3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide

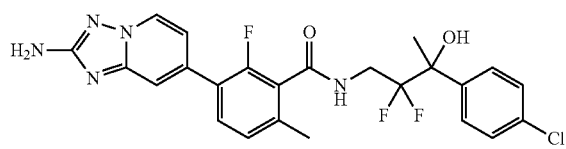

enantiomer 2

3-(2-amino-[1,2,4]triazolo[1,5-a]pyridin-7-yl)-N-(3-(4-chlorophenyl)-2,2-difluoro-3-hydroxybutyl)-2-fluoro-6-methylbenzamide enantiomer 2 (4.9 mg, 0.010 mmol, 9% yield) was obtained as the second eluting isomer from the chiral SFC purification described for example 221. The relative and absolute stereochemistry was not determined.

$^1$H NMR (500 MHz, DMSO-$d_6$) δ 8.81 (br t, J=5.8 Hz, 1H), 8.57 (br d, J=6.7 Hz, 1H), 7.60-7.53 (m, 3H), 7.47-7.41 (m, 3H), 7.19 (br d, J=8.2 Hz, 1H), 7.01 (br d, J=6.4 Hz, 1H), 6.04 (s, 2H), 4.00-3.84 (m, 2H), 2.26 (s, 3H), 1.62 (s, 3H).
MS ESI m/z 504.2 (M+H)$^+$

Example 223: 3-(2-amino-[1,2,4]triazolo[1,5-a]pyridin-7-yl)-6-chloro-N-(3-(4-chlorophenyl)-2,2-difluoro-3-hydroxybutyl)-2-fluorobenzamide

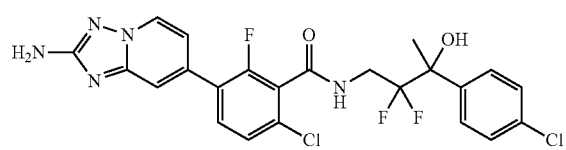

enantiomer 1

The title compound was prepared in a similar fashion described for example 221, substituting 3-bromo-6-chloro-2-fluorobenzoic acid for 3-bromo-2-fluoro-6-methylbenzoic acid in step 221D, to afford 3-(2-amino-[1,2,4]triazolo[1,5-a]pyridin-7-yl)-6-chloro-N-(3-(4-chlorophenyl)-2,2-difluoro-3-hydroxybutyl)-2-fluorobenzamide enantiomer 1 (5.4 mg, 0.010 mmol, 10% yield) as the first eluting isomer from chiral SFC separation. The relative and absolute stereochemistry was not determined.

$^1$H NMR (500 MHz, DMSO-$d_6$) δ 9.01 (br t, J=6.2 Hz, 1H), 8.61 (d, J=7.0 Hz, 1H), 7.70 (t, J=8.5 Hz, 1H), 7.57 (d, J=8.5 Hz, 2H), 7.48 (d, J=6.4 Hz, 2H), 7.47-7.42 (m, 2H), 7.02 (br d, J=7.1 Hz, 1H), 6.08 (s, 2H), 3.99-3.86 (m, 1H), 1.62 (s, 3H).
MS ESI m/z 524.2 (M+H)$^+$

Example 224: 3-(2-amino-[1,2,4]triazolo[1,5-a]pyridin-7-yl)-6-chloro-N-(3-(4-chlorophenyl)-2,2-difluoro-3-hydroxybutyl)-2-fluorobenzamide

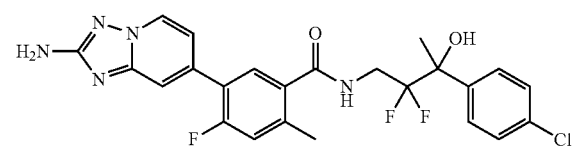

enantiomer 2

The title compound was prepared in a similar fashion described for example 222 to afford 3-(2-amino-[1,2,4]triazolo[1,5-a]pyridin-7-yl)-6-chloro-N-(3-(4-chlorophenyl)-2,2-difluoro-3-hydroxybutyl)-2-fluorobenzamide enantiomer 2 (5.3 mg, 0.010 mmol, 10% yield) as the second eluting isomer from the chiral SFC separation. The relative and absolute stereochemistry was not determined.

$^1$H NMR (500 MHz, DMSO-$d_6$) δ 9.00 (br t, J=6.0 Hz, 1H), 8.61 (d, J=6.8 Hz, 1H), 7.71 (t, J=8.4 Hz, 1H), 7.57 (d, J=8.5 Hz, 2H), 7.49 (d, J=6.6 Hz, 2H), 7.47-7.42 (m, 2H), 7.02 (br d, J=7.0 Hz, 1H), 6.09 (s, 2H), 3.99-3.86 (m, 1H), 1.62 (s, 3H).
MS ESI m/z 524.1 (M+H)$^+$

Example 225: 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide enantiomer 1

225A: 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide: The title compound was prepared in a similar fashion as described for Example 1, substituting 4-amino-2-(4-chlorophenyl)-3,3-difluorobutan-2-ol for (S)-3-amino-1-(4-chlorophenyl)propan-1-ol, HCl in the final step, to afford 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide (59 mg, 0.117 mmol, 47% yield).

225: Racemic 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide was separated by chiral SFC chromatography with the following conditions: Column: Chiral IC 21×250 mm. 5 micron; Mobile Phase: 70% CO$_2$/30% MeOH w/0.1% DEA; Flow Conditions: 60 mL/min; Detector Wavelength: 220 nm; Injection details: 1 mL, 59 mg dissolved in 3 mL MeOH. Thus, was obtained 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide enantiomer 1 (19.6 mg, 0.039 mmol, 16% yield) as the first eluting isomer from the chiral SFC separation. The relative and absolute stereochemistry was not determined.

¹H NMR (500 MHz, DMSO-d₆) δ 8.61 (d, J=7.0 Hz, 1H), 8.54 (br t, J=6.1 Hz, 1H), 7.58 (br d, J=8.5 Hz, 2H), 7.55 (s, 1H), 7.52 (d, J=7.9 Hz, 1H), 7.43 (d, J=8.5 Hz, 2H), 7.26 (d, J=11.9 Hz, 1H), 7.07 (br d, J=6.7 Hz, 1H), 6.28 (s, 1H), 6.06 (s, 2H), 3.98-3.83 (m, 1H), 3.58-3.43 (m, 1H), 2.37 (s, 3H), 1.62 (s, 3H).
MS ESI m/z 504.0 (M+H)⁺

Example 226: 5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide

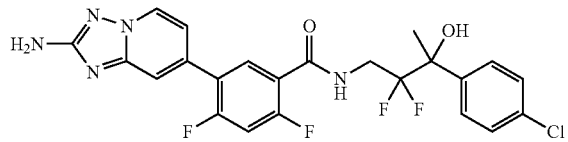

enantiomer 2

5-(2-amino-[1,2,4]triazolo[1,5-a]pyridin-7-yl)-N-(3-(4-chlorophenyl)-2,2-difluoro-3-hydroxybutyl)-4-fluoro-2-methylbenzamide enantiomer 2 (21.7 mg, 0.043 mmol, 17% yield) was obtained as the second eluting isomer from the chiral SFC purification described for example 225. The relative and absolute stereochemistry was not determined.

¹H NMR (500 MHz, DMSO-d₆) δ 8.60 (d, J=7.0 Hz, 1H), 8.54 (br t, J=6.0 Hz, 1H), 7.58 (br d, J=8.9 Hz, 2H), 7.55 (s, 1H), 7.52 (d, J=7.9 Hz, 1H), 7.42 (d, J=8.5 Hz, 2H), 7.26 (d, J=11.9 Hz, 1H), 7.07 (br d, J=7.0 Hz, 1H), 6.28 (s, 1H), 6.06 (s, 2H), 3.98-3.83 (m, 1H), 3.59-3.44 (m, 1H), 2.36 (s, 3H), 1.62 (s, 3H).
MS ESI m/z 504.0 (M+H)⁺

Example 227: 3-(2-amino-[1,2,4]triazolo[1,5-a]pyridin-7-yl)-N-(2,2-difluoro-3-hydroxy-3-(4-(trifluoromethyl)phenyl)butyl)-2-fluoro-6-methylbenzamide

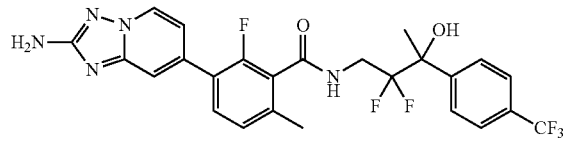 [SMILES: Cc1ccc(-c2ccn3nc(N)nc3c2)c(F)c1C(=O)NCC(F)(F)C(C)(O)c1ccc(C(F)(F)F)cc1]

227A: ethyl 2,2-difluoro-3-hydroxy-3-(4-(trifluoromethyl)phenyl)butanoate: To a suspension of 1-(4-(trifluoromethyl)phenyl)ethan-1-one (5.5 g, 29.2 mmol) and indium powder (5.03 g, 43.8 mmol) in THF (60 mL) was added ethyl 2-bromo-2,2-difluoroacetate (5.62 ml, 43.8 mmol) dropwise via syringe. The suspension was vigorously stirred at 60° C. for 12 h. The mixture changed to orange-red-brown-gray in 5-10 min. The reaction mixture was cooled to room temperature then quenched with 30 mL 1N HCl and diluted with EtOAc (100 mL). The separated aqueous layer was extracted with EtOAc (3×100 mL). The combined organic layer was washed with brine (100 ml), dried over MgSO4, filtered and concentrated under vacuum. The crude product was purified by column chromatography eluting with EtOAc/Hexane. The fractions containing the expected product were concentrated under vacuum to give ethyl 2,2-difluoro-3-hydroxy-3-(4-(trifluoromethyl)phenyl)butanoate (5.39 g, 55% yield) as a viscous oil.

1H NMR (500 MHz, CHLOROFORM-d) δ 7.71-7.61 (m, 4H), 4.19 (qd, J=7.2, 1.0 Hz, 2H), 1.79-1.75 (m, 3H), 1.15 (t, J=7.1 Hz, 3H).

227B: 2,2-difluoro-3-hydroxy-3-(4-(trifluoromethyl)phenyl)butanamide: To a solution of ethyl 2,2-difluoro-3-hydroxy-3-(4-(trifluoromethyl)phenyl)butanoate (5.84 g, 18.70 mmol) in MeOH (80 mL) at 0° C. was added ammonia (7 M in MeOH) (10.69 mL, 74.8 mmol). The resulting orange solution was stirred at RT for 90 min. The reaction mixture was concentrated under vacuum then dried under vacuum overnight to give crude 2,2-difluoro-3-hydroxy-3-(4-(trifluoromethyl)phenyl)butanamide (5.23 g, 96% yield) as a solid which was used as-is in next step without purification.

1H NMR (500 MHz, DMSO-d6) δ 7.80 (br s, 1H), 7.75-7.71 (m, 4H), 7.70 (br s, 1H), 6.36 (s, 1H), 1.69 (s, 3H).
MS ESI m/z 281.8 (M+H)⁻

227C: 4-amino-3,3-difluoro-2-(4-(trifluoromethyl)phenyl)butan-2-ol: To a 500 mL round-bottom flask filled with nitrogen was added a solution of 2,2-difluoro-3-hydroxy-3-(4-(trifluoromethyl)phenyl)butanamide (5.2 g, 18.36 mmol) in THF (100 mL). The mixture was cooled to −78° C. and LAH (2M in THF) (18.36 ml, 36.7 mmol) was added dropwise. The mixture was stirred at −78° C. for 30 min, then at RT overnight. LC/MS showed incomplete reaction, but the reaction was topped. The reaction was diluted with ether (100 mL) and cooled to 0° C. Water (1.4 mL) was slowly added followed by 15% aqueous sodium hydroxide (1.4 mL), water (3×4 mL), then the mixture was warmed to room temperature and stirred for 15 min. Anhydrous magnesium sulfate was added and the mixture stirred for 15 min, then filtered. The filtrate was concentrated under vacuum and the crude product was purified by column chromatography on ISCO 24 g silica gel column cartridge eluting with 20-100% EtOAc/Hexane over 10 CV with ELSD. The fractions containing the expected product were collected and concentrated under vacuum to give 4-amino-3,3-difluoro-2-(4-(trifluoromethyl)phenyl)butan-2-ol (1.06 g, 3.94 mmol, 88% yield) as a solid.

1H NMR (500 MHz, CHLOROFORM-d) δ 7.74 (br d, J=7.6 Hz, 2H), 7.66-7.62 (m, 2H), 3.12-3.02 (m, 1H), 2.98-2.86 (m, 1H), 1.70-1.68 (m, 3H).

227D: 3-bromo-N-(2,2-difluoro-3-hydroxy-3-(4-(trifluoromethyl)phenyl)butyl)-2-fluoro-6-methylbenzamide: To a 50 ml round-bottom flask was added a solution of 3-bromo-2-fluoro-6-methylbenzoic acid (400 mg, 1.716 mmol) and 4-amino-3,3-difluoro-2-(4-(trifluoromethyl)phenyl)butan-2-ol (462 mg, 1.716 mmol) in DCM (15 mL). To this was added BOP (911 mg, 2.060 mmol) and DIPEA (1.499 mL, 8.58 mmol). The resulting yellow solution was stirred at RT for 2 h. The reaction mixture was diluted with DCM (40 mL), washed with H₂O (30 mL) followed by brine (30 mL), dried over Na₂SO₄, filtered and concentrated under vacuum. The crude product was purified by column chromatography on ISCO 40 g silica gel column cartridge eluting with 0-50% EtOAc/Hexane over 15 CV. The fractions containing the expected product were collected and concentrated under vacuum and further dried under high vacuum to give 3-bromo-N-(2,2-difluoro-3-hydroxy-3-(4-(trifluoromethyl)phenyl)butyl)-2-fluoro-6-methylbenzamide (772 mg, 1.59 mmol, 93% yield) as a solid.

1H NMR (500 MHz, CHLOROFORM-d) δ 7.74 (s, 2H), 7.67 (d, J=8.5 Hz, 2H), 7.47 (dd, J=8.2, 7.2 Hz, 1H), 6.91 (d,

J=8.3 Hz, 1H), 6.00 (br s, 1H), 4.11-4.00 (m, 1H), 3.65-3.53 (m, 1H), 2.34 (s, 3H), 1.79 (s, 3H).

227E: 6-methyl-N-(2,2-difluoro-3-(4-trifluoromethylphenyl)-3-hydroxybutyl)-2-fluoro-3-(2-(bis-boc-amino)-[1,2,4]triazolo[1,5-a]pyridin-7-yl)benzamide: To a 15 mL resealable pressure vessel was added a mixture of N,N-Bis-Boc-7-(4,4,5,5-tetramethyl-1,3,2-dioxaborolan-2-yl)-[1,2,4]triazolo[1,5-a]pyridin-2-amine (120 mg, 0.261 mmol), 3-bromo-N-(2,2-difluoro-3-hydroxy-3-(4-(trifluoromethyl)phenyl)butyl)-2-fluoro-6-methylbenzamide (126 mg, 0.261 mmol), PdCl2 (dppf)-CH2Cl2 adduct (12.77 mg, 0.016 mmol) and K3PO4 (2M aq) (0.391 mL, 0.782 mmol) in 1,4-dioxane (2.5 mL). The mixture was cooled in a dry ice-acetone bath and stirred. The mixture was subjected to vacuuming/purging with N2 cycles three times. The vessel was sealed, and the mixture was stirred at 70° C. for 1 h. The reaction mixture was diluted with EtOAc (30 mL), washed with H2O (2×30 mL) followed by brine (30 mL), dried over MgSO4, filtered and concentrated under vacuum. The crude product was purified by column chromatography using Biotage system (ISCO 12 g silica gel column; 30-70% (12 CV), EtOAc/Hexane). The fractions containing the expected product were collected and concentrated under vacuum to give 6-methyl-N-(2,2-difluoro-3-(4-trifluoromethylphenyl)-3-hydroxybutyl)-2-fluoro-3-(2-(bis-boc-amino)-[1,2,4]triazolo[1,5-a]pyridin-7-yl)benzamide (174 mg, 0.236 mmol, 90% yield) as a solid.

1H NMR (600 MHz, CHLOROFORM-d) δ 8.57 (d, J=7.1 Hz, 1H), 7.80 (s, 1H), 7.75 (br d, J=8.2 Hz, 2H), 7.67 (d, J=8.4 Hz, 2H), 7.44 (t, J=7.9 Hz, 1H), 7.22 (br d, J=7.3 Hz, 1H), 7.17 (d, J=7.8 Hz, 1H), 6.11 (br t, J=6.4 Hz, 1H), 4.16-4.05 (m, 1H), 3.67-3.56 (m, 1H), 2.44 (s, 3H), 1.80 (s, 3H), 1.49 (s, 18H).

227: 3-(2-amino-[1,2,4]triazolo[1,5-a]pyridin-7-yl)-N-(2,2-difluoro-3-hydroxy-3-(4-(trifluoromethyl)phenyl)butyl)-2-fluoro-6-methylbenzamide: To a solution of 6-methyl-N-(2,2-difluoro-3-(4-trifluoromethylphenyl)-3-hydroxybutyl)-2-fluoro-3-(2-(bis-boc-amino)-[1,2,4]triazolo[1,5-a]pyridin-7-yl)benzamide (170 mg, 0.230 mmol) in 1,4-dioxane (2 mL) was added HCl (4 M in dioxane) (0.576 mL, 2.304 mmol). The resulting mixture was stirred at RT overnight. The product precipitated, the reaction mixture became suspension. LC/MS showed the reaction was incomplete, so the reaction mixture was stirred at 70° C. for 2 h. LC/MS indicated the reaction was complete. The mixture was concentrated under vacuum and the residue was dissolved in DMF and filtered. The crude material was purified via preparative LC/MS using an XBridge C18 column eluting with acetonitrile:water with 0.10% trifluoroacetic acid. Fractions containing the desired product were combined and dried via centrifugal evaporation to give 63-(2-amino-[1,2,4]triazolo[1,5-a]pyridin-7-yl)-N-(2,2-difluoro-3-hydroxy-3-(4-(trifluoromethyl)phenyl)butyl)-2-fluoro-6-methylbenzamide (58.3 mg, 0.107 mmol, 47% yield) as a solid.

1H NMR (600 MHz, DMSO-d6) δ 8.84 (t, J=6.3 Hz, 1H), 8.62 (d, J=7.0 Hz, 1H), 7.82-7.78 (m, 2H), 7.77-7.74 (m, 2H), 7.58 (t, J=8.0 Hz, 1H), 7.48 (s, 1H), 7.20 (d, J=8.0 Hz, 1H), 7.07-7.04 (m, 1H), 4.02-3.91 (m, 1H), 3.58-3.45 (m, 1H), 2.27 (s, 3H), 1.67 (s, 3H).

MS ESI m/z 538.2 (M+H)+

Example 228: 3-(2-amino-[1,2,4]triazolo[1,5-a]pyridin-7-yl)-N-(3-(4-chlorophenyl)-3-fluorobutyl)-2-fluoro-6-methylbenzamide

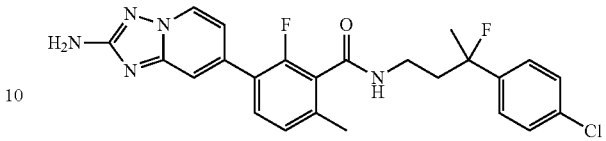

A 8 mL reaction vial was charged with a stir bar and 3-(2-amino-[1,2,4]triazolo[1,5-a]pyridin-7-yl)-N-(3-(4-chlorophenyl)-3-hydroxybutyl)-2-fluoro-6-methylbenzamide (21 mg, 0.045 mmol). The vial was evacuated and back-filled with nitrogen, and then DCM (1.0 mL) was introduced. A solution of Deoxo-Fluor (0.017 mL, 0.090 mmol) in DCM (1.0 mL) was slowly added to the mixture at 0° C. in two portions. The resulting mixture was stirred at 0° C. for 1 h and then at RT for 3 h. Volatiles were removed in vacuo, and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 24% B, 24-64% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide 3-(2-amino-[1,2,4]triazolo[1,5-a]pyridin-7-yl)-N-(3-(4-chlorophenyl)-3-fluorobutyl)-2-fluoro-6-methylbenzamide (4.3 mg, 0.009 mmol, 13% yield).

$^1$H NMR (600 MHz, DMSO-d6) δ 8.62-8.57 (m, 1H), 7.61-7.39 (m, 7H), 7.23-7.17 (m, 1H), 7.04-6.98 (m, 1H), 6.08 (s, 2H), 3.11-3.02 (m, 1H), 2.73 (t, J=7.0 Hz, 1H), 2.27 (s, 3H), 2.25-2.14 (m, 2H), 1.74-1.61 (m, 3H).

MS ESI m/z 470.0 (M+H)+

Example 229: 3-(2-amino-[1,2,4]triazolo[1,5-a]pyridin-7-yl)-6-chloro-N-(2,2-difluoro-3-(4-fluorophenyl)-3-hydroxypropyl-1,1-d₂)-2-fluorobenzamide enantiomer 1

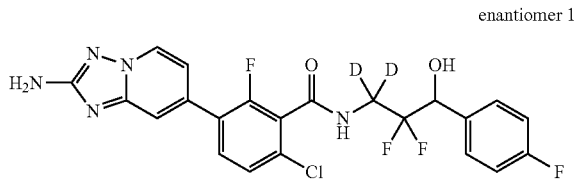 [SMILES: [2H]C([2H])(NC(=O)c1c(Cl)ccc(-c2ccn3nc(N)nc3c2)c1F)C(F)(F)C(O)c1ccc(F)cc1]

229A: 3-amino-2,2-difluoro-1-(4-fluorophenyl)propan-3,3-d₂-1-ol: A 40 mL reaction vial was charged with a stir bar, 2,2-difluoro-3-(4-fluorophenyl)-3-hydroxypropanamide (0.438 g, 2.00 mmol) and THF (10 mL), followed by the addition of lithium aluminum deuteride, 98% isotopic purity (0.252 g, 6.00 mmol) at −78° C. as solid in one portion. The resulting mixture was stirred at −78° C. for 30 min and then at room temperature for 16 h. The reaction mixture was then diluted with ether and cooled to 0° C., followed by slow addition of H₂O (0.5 mL), 15% aqueous sodium hydroxide (0.5 mL), and H₂O (1.5 mL) sequentially. The resulting mixture was warmed up to room temperature and stirred vigorously for 15 min. Anhydrous magnesium sulfate was added and the mixture was stirred for additional 15 min. The crude was filtered to remove salts, affording crude 3-amino-2,2-difluoro-1-(4-fluorophenyl)propan-3,3-d$_2$-1-ol (0.346 g, 1.670 mmol, 83% yield), which was used as-is in the next step.

MS ESI m/z 208.05 (M+H)$^+$

229: A 8 mL reaction vial was charged with a stir bar, BOP (0.097 g, 0.22 mmol), 3-(2-amino-[1,2,4]triazolo[1,5-a]pyridin-7-yl)-6-chloro-2-fluorobenzoic acid (0.080 g, 0.26 mmol), and 3-amino-2,2-difluoro-1-(4-fluorophenyl)propan-3,3-d2-1-ol (0.041 g, 0.20 mmol), followed by the addition of DMF (2.0 mL) and DIPEA (0.140 mL, 0.800 mmol). The resulting mixture was stirred at RT for 16 h. The crude material was purified via preparative LC/MS with the following conditions: Column: XBridge C18, 200 mm×19 mm, 5 µm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 13% B, 13-53% B over 26 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The racemic material thus isolated was further purified through chiral SFC separation to provide separated enantiomers. Approximately 32.8 mg of sample were resolved into two peaks collected in MeOH with 0.1% DEA. Instrument: Waters 100 Prep SFC; Column: Chiral OJ, 30×250 mm. 5 micron; Mobile Phase: 75% CO2/25% MeOH w/0.1% DEA; Flow Conditions: 100 mL/min; Detector Wavelength: 220 nm; Injection Details: 1500 µL 32.8 mg dissolved in 3 mL MeOH. Thus, was recovered 3-(2-amino-[1,2,4]triazolo[1,5-a]pyridin-7-yl)-6-chloro-N-(2,2-difluoro-3-(4-fluorophenyl)-3-hydroxypropyl-1,1-d$_2$)-2-fluorobenzamide enantiomer 1 (7.4 mg, 0.015 mmol, 7% yield) as the first eluting isomer from the preparative SFC column. The absolute stereochemistry was not determined.

$^1$H NMR (500 MHz, DMSO-d6) δ 9.09 (s, 1H), 8.57 (d, J=6.9 Hz, 1H), 7.67 (t, J=8.4 Hz, 1H), 7.50-7.38 (m, 4H), 7.16 (t, J=8.8 Hz, 2H), 7.00 (br d, J=6.7 Hz, 1H), 6.04 (s, 2H), 4.95-4.79 (m, 1H).

MS ESI m/z 496.0 (M+H)$^+$

Example 230: 3-(2-amino-[1,2,4]triazolo[1,5-a]pyridin-7-yl)-6-chloro-N-(2,2-difluoro-3-(4-fluorophenyl)-3-hydroxypropyl-1,1-d$_2$)-2-fluorobenzamide

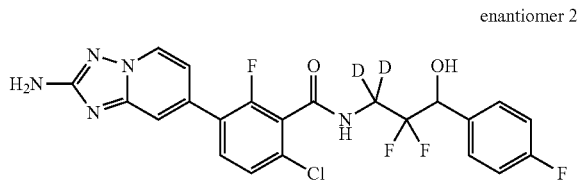 [SMILES: [2H]C([2H])(NC(=O)c1c(Cl)ccc(-c2ccn3nc(N)nc3c2)c1F)C(F)(F)C(O)c1ccc(F)cc1]

enantiomer 2

The title compound 3-(2-amino-[1,2,4]triazolo[1,5-a]pyridin-7-yl)-6-chloro-N-(2,2-difluoro-3-(4-fluorophenyl)-3-hydroxypropyl-1,1-d$_2$)-2-fluorobenzamide enantiomer 2 (7.3 mg, 0.015 mmol, 7% yield) was obtained as the second eluting isomer from the chiral SFC purification described for Example 229.

$^1$H NMR (500 MHz, DMSO-d6) δ 9.09 (s, 1H), 8.56 (br d, J=7.0 Hz, 1H), 7.73-7.62 (m, 1H), 7.51-7.38 (m, 4H), 7.16 (br t, J=8.8 Hz, 2H), 7.00 (br d, J=6.2 Hz, 1H), 6.04 (s, 2H), 4.96-4.78 (m, 1H).

MS ESI m/z 496.0 (M+H)$^+$

Example 231: 5-(2-amino-[1,2,4]triazolo[1,5-a]pyridin-7-yl)-N-(2,2-difluoro-3-(4-fluorophenyl)-3-hydroxypropyl)-3-fluoro-2-methylbenzamide

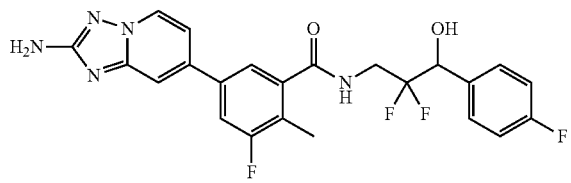

enantiomer 1

A 8 mL reaction vial was charged with a stir bar, BOP (0.097 g, 0.22 mmol), 5-(2-amino-[1,2,4]triazolo[1,5-a]pyridin-7-yl)-3-fluoro-2-methylbenzoic acid (0.115 g, 0.400 mmol), 3-amino-2,2-difluoro-1-(4-fluorophenyl)propan-1-ol (0.041 g, 0.20 mmol), followed by the addition of DMF (2.0 mL) and DIPEA (0.140 mL, 0.800 mmol). The resulting mixture was stirred at RT for 16 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 16% B, 16-56% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The racemic material thus isolated was further purified through chiral SFC separation to provide separated enantiomers. Approximately 24.3 mg of sample were resolved into two peaks collected in MeOH with 0.1% DEA. Instrument: Waters 100 Prep SFC; Column: Chiral OJ, 30×250 mm. 5 micron; Mobile Phase: 80% CO2/20% MeOH w/0.1% DEA; Flow Conditions: 100 mL/min; Detector Wavelength: 220 nm; Injection Details: 500 µL 24.3 mg dissolved in 3 mL MeOH. Thus, was recovered 5-(2-amino-[1,2,4]triazolo[1,5-a]pyridin-7-yl)-N-(2,2-difluoro-3-(4-fluorophenyl)-3-hydroxypropyl)-3-fluoro-2-methylbenzamide enantiomer 1 (5.9 mg, 0.012 mmol, 6% yield) as the first eluting isomer from the preparative SFC column. The absolute stereochemistry was not determined.

$^1$H NMR (500 MHz, DMSO-d6) δ 8.82-8.70 (m, 1H), 8.55 (d, J=7.0 Hz, 1H), 7.77-7.64 (m, 2H), 7.54 (d, J=0.6 Hz, 1H), 7.46 (br dd, J=8.2, 5.8 Hz, 2H), 7.21 (dd, J=7.0, 1.8 Hz, 1H), 7.17 (t, J=8.9 Hz, 2H), 6.40 (d, J=5.5 Hz, 1H), 6.01 (s, 2H), 4.96-4.84 (m, 1H), 3.95-3.70 (m, 2H), 2.22 (s, 3H).

MS ESI m/z 474.1 (M+H)$^+$

Example 232: 5-(2-amino-[1,2,4]triazolo[1,5-a]pyridin-7-yl)-N-(2,2-difluoro-3-(4-fluorophenyl)-3-hydroxypropyl)-3-fluoro-2-methylbenzamide

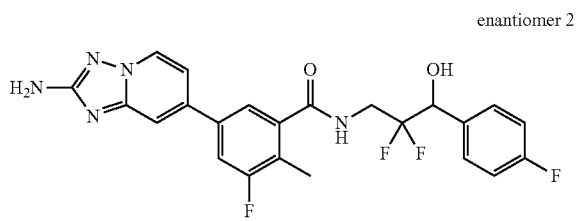 [SMILES: Cc1c(F)cc(-c2ccn3nc(N)nc3c2)cc1C(=O)NCC(F)(F)C(O)c1ccc(F)cc1]

enantiomer 2

The title compound 5-(2-amino-[1,2,4]triazolo[1,5-a]pyridin-7-yl)-N-(2,2-difluoro-3-(4-fluorophenyl)-3-hydroxypropyl)-3-fluoro-2-methylbenzamide enantiomer 2 (6.0 mg, 0.012 mmol, 6% yield) was obtained as the second eluting isomer from the chiral SFC purification described for Example 231.

$^1$H NMR (500 MHz, DMSO-d$_6$) δ 8.75 (br t, J=6.1 Hz, 1H), 8.55 (d, J=7.0 Hz, 1H), 7.75-7.64 (m, 2H), 7.53 (s, 1H), 7.46 (br dd, J=8.2, 5.8 Hz, 2H), 7.25-7.19 (m, 1H), 7.16 (br t, J=8.7 Hz, 2H), 6.40 (d, J=5.2 Hz, 1H), 6.00 (s, 2H), 4.97-4.82 (m, 1H), 3.95-3.71 (m, 2H), 2.22 (s, 3H).
MS ESI m/z 474.0 (M+H)$^+$

Example 233: 3-(2-amino-[1,2,4]triazolo[1,5-a]pyridin-7-yl)-N-(2,2-difluoro-3-(4-fluorophenyl)-3-methoxypropyl)-2-fluoro-6-methylbenzamide

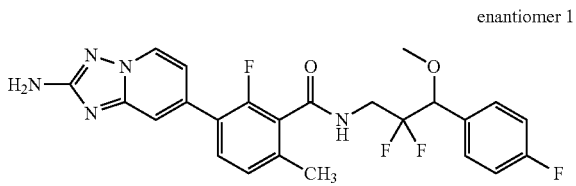 [SMILES: COC(c1ccc(F)cc1)C(F)(F)CNC(=O)c1c(C)ccc(-c2ccn3nc(N)nc3c2)c1F]

enantiomer 1

233A: ethyl 2,2-difluoro-3-(4-fluorophenyl)-3-methoxypropanoate: A 40 mL reaction vial was charged with a stir bar, ethyl 2,2-difluoro-3-(4-fluorophenyl)-3-hydroxypropanoate (200 mg, 0.806 mmol) and silver oxide (280 mg, 1.21 mmol), followed by the addition of methyl iodide (76 µL, 1.2 mmol) and DMF (1.6 mL). The resulting mixture was stirred at 60° C. for 16 h. The reaction mixture was filtered through Celite and diluted with EtOAc, washed with H$_2$O and brine. The crude was dried over Celite and filtered, and the filtrate was concentrated in vacuo to give crude ethyl 2,2-difluoro-3-(4-fluorophenyl)-3-methoxypropanoate which was used directly used in the next step without further purification (100% yield assumed).
MS ESI m/z 233.1 (M-Et)$^-$ 233B: 2,2-difluoro-3-(4-fluorophenyl)-3-methoxypropanamide: A 40 mL reaction vial was charged with a stir bar, ethyl 2,2-difluoro-3-(4-fluorophenyl)-3-methoxypropanoate (0.210 g, 0.800 mmol) and MeOH (4.0 mL), followed by the addition of ammonia solution, 7 N in methanol (0.457 mL, 3.20 mmol). The resulting mixture was stirred at RT for 2 d. The crude mixture was concentrated in vacuo to give crude 2,2-difluoro-3-(4-fluorophenyl)-3-methoxypropanamide (0.187 g, 0.800 mmol, quantitative) which was used directly in the next step without further purification.

233C: 2,2-difluoro-3-(4-fluorophenyl)-3-methoxypropan-1-amine: A 40 mL reaction vial was charged with a stir bar, crude 2,2-difluoro-3-(4-fluorophenyl)-3-methoxypropanamide (0.187 g, 0.800 mmol), and THF (4.00 mL) followed by slow addition of lithium aluminum hydride, 2M in THF (0.800 mL, 1.60 mmol). The resulting mixture was stirred at RT for 16 h. The reaction mixture was then diluted with ether and cooled to 0° C. followed by slow addition of H$_2$O (0.05 mL), 15% aqueous sodium hydroxide (0.05 mL), and H$_2$O (0.15 mL) sequentially. The resulting mixture was warmed up to room temperature and stirred vigorously for 15 min. Anhydrous magnesium sulfate was added and the mixture was stirred for additional 15 min. The crude was filtered to remove salts, affording 2,2-difluoro-3-(4-fluorophenyl)-3-methoxypropan-1-amine (0.150 g, 0.684 mmol, 86% yield), which was used directly in the next step without further purification.
MS ESI m/z 220.27 (M+H)$^+$ 233: A 8 mL reaction vial was charged with a stir bar, 3-(2-amino-[1,2,4]triazolo[1,5-a]pyridin-7-yl)-2-fluoro-6-methylbenzoic acid, HCl (32.3 mg, 0.100 mmol), 2,2-difluoro-3-(4-fluorophenyl)-3-methoxypropan-1-amine (32.9 mg, 0.150 mmol) and BOP (61.9 mg, 0.140 mmol), followed by the addition of DMF (1.0 mL) and DIPEA (105 µL, 0.600 mmol). The resulting mixture was stirred at RT for 2 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 20% B, 20-60% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The racemic material thus isolated was further purified via chiral SFC separation to provide separated enantiomers. Preparative Chromatographic Conditions: Instrument: Waters 100 Prep SFC; Column: Chiral OJ, 30×250 mm. 5 micron; Mobile Phase: 80% CO2/20% MeOH w/0.1% DEA; Flow Conditions: 100 mL/min; Detector Wavelength: 220 nm; Injection Details: 2000 µL 15.3 mg dissolved in 3 mL MeOH. Thus, was isolated 3-(2-amino-[1,2,4]triazolo[1,5-a]pyridin-7-yl)-N-(2,2-difluoro-3-(4-fluorophenyl)-3-methoxypropyl)-2-fluoro-6-methylbenzamide enantiomer 1 (5.0 mg, 0.010 mmol, 10% yield) as the first isomer to elute from the chiral SFC column.

$^1$H NMR (500 MHz, DMSO-d6) δ 8.95 (br t, J=6.0 Hz, 1H), 8.56 (d, J=7.0 Hz, 1H), 7.55 (t, J=8.0 Hz, 1H), 7.46-7.36 (m, 3H), 7.27-7.16 (m, 3H), 6.99 (br d, J=6.8 Hz, 1H), 6.01 (s, 2H), 4.62 (br dd, J=16.8, 5.4 Hz, 1H), 3.99-3.72 (m, 2H), 3.22 (s, 3H), 2.26 (s, 3H).
MS ESI m/z 488.1 (M+H)$^+$

Example 234: 3-(2-amino-[1,2,4]triazolo[1,5-a]pyridin-7-yl)-N-(2,2-difluoro-3-(4-fluorophenyl)-3-methoxypropyl)-2-fluoro-6-methylbenzamide

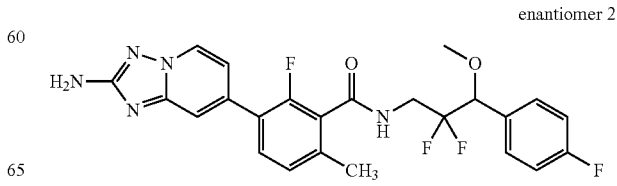

enantiomer 2

The title compound 3-(2-amino-[1,2,4]triazolo[1,5-a]pyridin-7-yl)-N-(2,2-difluoro-3-(4-fluorophenyl)-3-methoxypropyl)-2-fluoro-6-methylbenzamide enantiomer 2 (5.1 mg, 0.011 mmol, 10% yield) was obtained as the second eluting isomer from the chiral SFC purification described for Example 233.

¹H NMR (500 MHz, DMSO-d6) δ 8.95 (br t, J=6.1 Hz, 1H), 8.56 (d, J=7.0 Hz, 1H), 7.55 (t, J=8.1 Hz, 1H), 7.48-7.34 (m, 3H), 7.28-7.14 (m, 3H), 6.99 (br d, J=7.1 Hz, 1H), 6.02 (s, 2H), 4.63 (br dd, J=17.2, 5.7 Hz, 1H), 3.99-3.72 (m, 2H), 3.22 (s, 3H), 2.26 (s, 3H).
MS ESI m/z 488.3 (M+H)⁺

Example 235: 3-(2-amino-[1,2,4]triazolo[1,5-a]pyridin-7-yl)-N-(2,2-difluoro-3-(4-fluorophenyl)-3-(methoxy-d₃)propyl)-2-fluoro-6-methylbenzamide enantimer 1

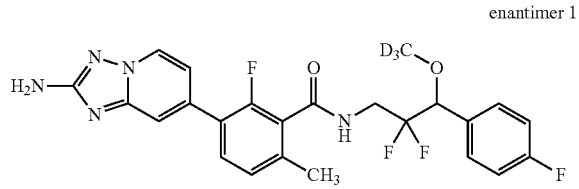 [SMILES: [2H]C([2H])([2H])OC(c1ccc(F)cc1)C(F)(F)CNC(=O)c1c(C)ccc(-c2ccn3nc(N)nc3c2)c1F]

The title compound was prepared in a similar fashion to that described for Example 233, substituting CD₃I for MeI in the first step. Thus, was obtained 3-(2-amino-[1,2,4]triazolo[1,5-a]pyridin-7-yl)-N-(2,2-difluoro-3-(4-fluorophenyl)-3-(methoxy-d₃)propyl)-2-fluoro-6-methylbenzamide enantiomer 1 (5.5 mg, 0.011 mmol, 11% yield) as the first eluting isomer from the chiral SFC purification performed in the final step.

¹H NMR (500 MHz, DMSO-d6) δ 8.95 (br t, J=6.3 Hz, 1H), 8.56 (d, J=7.0 Hz, 1H), 7.55 (t, J=8.1 Hz, 1H), 7.47-7.35 (m, 3H), 7.28-7.14 (m, 3H), 6.99 (br d, J=7.0 Hz, 1H), 6.02 (s, 2H), 4.63 (br dd, J=17.1, 5.8 Hz, 1H), 3.99-3.73 (m, 2H), 2.27 (s, 3H).
MS ESI m/z 491.4 (M+H)⁺

Example 236: 3-(2-amino-[1,2,4]triazolo[1,5-a]pyridin-7-yl)-N-(2,2-difluoro-3-(4-fluorophenyl)-3-(methoxy-d₃)propyl)-2-fluoro-6-methylbenzamide enantiomer 2

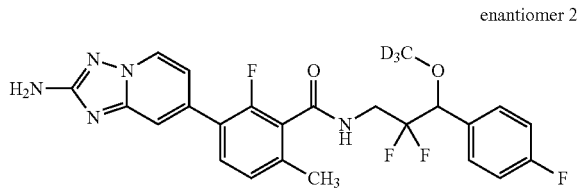 [SMILES: [2H]C([2H])([2H])OC(c1ccc(F)cc1)C(F)(F)CNC(=O)c1c(C)ccc(-c2ccn3nc(N)nc3c2)c1F]

The title compound was prepared in a similar fashion to that described for Example 233, substituting CD₃I for MeI in the first step. Thus, was obtained 3-(2-amino-[1,2,4]triazolo[1,5-a]pyridin-7-yl)-N-(2,2-difluoro-3-(4-fluorophenyl)-3-(methoxy-d₃)propyl)-2-fluoro-6-methylbenzamide enantiomer 2 (5.5 mg, 0.011 mmol, 11I % yield) as the second eluting isomer from the chiral SFC purification performed in the final step.

¹H NMR (500 MHz, DMSO-d6) δ 8.96 (br t, J=6.1 Hz, 1H), 8.55 (d, J=6.7 Hz, 1H), 7.54 (t, J=7.9 Hz, 1H), 7.46-7.33 (m, 3H), 7.28-7.13 (m, 3H), 6.01 (s, 2H), 4.61 (br dd, J=16.9, 5.3 Hz, 1H), 3.96-3.73 (m, 2H), 2.26 (s, 3H).
MS ESI m/z 491.4 (M+H)⁺

Example 237: 3-(2-amino-[1,2,4]triazolo[1,5-a]pyridin-7-yl)-6-chloro-2-fluoro-N-(2-fluoro-3-(4-fluorophenyl)-3-hydroxybutyl-4,4,4-d₃)benzamide diastereomer 1 diastereomer 1

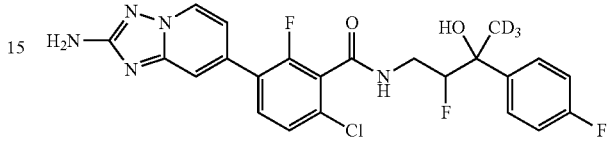

237A: 1-(4-fluorophenyl)ethan-1-one-2,2,2-d₃: A 40 mL reaction vial was charged with a stir bar, 1-(4-fluorophenyl)ethan-1-one (2.0 g, 15 mmol), sodium hydroxide (0.046 g, 1.2 mmol) and D₂O (10 mL). The resulting mixture was degassed by bubbling nitrogen through for 5 min and stirred at RT for 24 h. The mixture was extracted with diethyl ether and the organic phase was concentrated in vacuo. The crude was resubjected to the same condition (NaOH, D₂O) for another 24 h. The mixture was then extracted with diethyl ether, dried over Na₂SO₄, filtered and concentrated in vacuo. The crude was used directly in the next step without further purification. Quantitative yield assumed.

237B: ethyl 2-fluoro-3-(4-fluorophenyl)-3-hydroxybutanoate-4,4,4-d₃: A 40 mL reaction vial was charged with a stir bar, 1-(4-fluorophenyl)ethan-1-one-2,2,2-d₃ (0.600 g, 4.25 mmol), iron (0.712 g, 12.8 mmol), iodine (0.216 g, 0.850 mmol) and THF (8.50 mL) followed by the addition of ethyl 2-bromo-2-fluoroacetate (2.36 g, 12.8 mmol). The resulting mixture was degassed by bubbling nitrogen through for 5 min and then stirred at 60° C. for 12 h. The mixture was then cooled to RT, and Celite was added. The mixture was concentrated in vacuo. The crude was purified by flash column chromatography via dry load onto Celite (eluent=EtOAc in hexane, gradient 0% to 20%; 20 g silica) to afford ethyl 2-fluoro-3-(4-fluorophenyl)-3-hydroxybutanoate-4,4,4-d₃ (480 mg, 1.94 mmol, 46% yield) as a mixture of diastereomers.

¹H NMR (400 MHz, CHLOROFORM-d) δ 7.56-7.40 (m, 2H), 7.15-6.94 (m, 2H), 5.12-4.75 (m, 1H), 4.25-4.07 (m, 2H), 1.21-1.06 (m, 3H).

237C: 2-fluoro-3-(methyl-d₃)-3-(4-fluorophenyl)-3-hydroxypropanamide: A 40 mL reaction vial was charged with a stir bar, ethyl 2-fluoro-3-(4-fluorophenyl)-3-hydroxybutanoate-4,4,4-d₃ (480 mg, 1.94 mmol) and MeOH (3.9 mL), followed by the addition of 7 N ammonia in MeOH (1.66 mL, 11.7 mmol). The resulting mixture was stirred at 40° C. for 20 h. The reaction mixture was concentrated in vacuo, and the crude was used directly in the next step without further purification as a mixture of diastereomers.
MS ESI m/z 219.4 (M+H)⁺

237D: 4-amino-3-fluoro-2-(4-fluorophenyl)butan-1,1,1-d₃-2-ol: A 40 mL reaction vial was charged with a stir bar, 2-fluoro-3-(4-fluorophenyl)-3-hydroxybutanamide (423 mg, 1.94 mmol) and THF (9.7 mL), followed by the addition of BH₃-DMS 2.0M in THF (2.9 mL, 5.8 mmol). The resulting mixture was stirred at 70° C. for 3 h. The reaction was then quenched by slow addition of methanol. The resulting mixture was concentrated in vacuo to afford crude 4-amino-3-fluoro-2-(4-fluorophenyl)butan-1,1,1-$d_3$-2-ol (245 mg, 1.20 mmol, 62% yield). The crude was used directly in the next step without further purification as a mixture of diastereomers.

MS ESI m/z 205.4 $(M+H)^+$

237: A 8 mL reaction vial was charged with a stir bar, 3-(2-amino-[1,2,4]triazolo[1,5-a]pyridin-7-yl)-6-chloro-2-fluorobenzoic acid, HCl (172 mg, 0.3 mmol, 60% pure), 4-amino-3-fluoro-2-(4-fluorophenyl)butan-1,1,1-$d_3$-2-ol (80 mg, 0.390 mmol) as a crude mixture of diastereomers, and BOP (186 mg, 0.420 mmol), followed by the addition of DMF (1.5 mL) and DIPEA (314 µL, 1.80 mmol). The resulting mixture was stirred at RT for 1 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 14% B, 14-54% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. Approximately 57 mg of material thus obtained was further subjected to chiral SFC chromatography (Instrument: Waters 100 Prep SFC; Column: Chiral SB, 30×250 mm. 5 micron; Mobile Phase: 80% $CO_2$/20% MeOH; Flow Conditions: 100 mL/min; Detector Wavelength: 220 nm; Injection Details: 400 µL injections of 57 mg dissolved in 2 mL MeOH). Three separate peaks were collected. The first peak to elute consisted of an unresolved mixture of diastereomers 1 and 2, followed by elution of peak 2 (diastereomer 3) and finally peak 3 (diastereomer 4). The unresolved mixture of diastereomers 1 and 2 thus obtained was further separated into individual isomers via a second preparative chiral SFC separation (Instrument: Waters 100 Prep SFC; Column: Chiral IH, 30×250 mm. 5 micron; Mobile Phase: 80% $CO_2$/20% MeOH; Flow Conditions: 100 mL/min; Detector Wavelength: 220 nm; Injection Details: isolate 1 from SFC step 1 dissolved in 2 mL MeOH). Thus, was obtained 3-(2-amino-[1,2,4]triazolo[1,5-a]pyridin-7-yl)-6-chloro-2-fluoro-N-(2-fluoro-3-(4-fluorophenyl)-3-hydroxybutyl-4,4,4-$d_3$)benzamide diastereomer 1 (9.4 mg, 0.019 mmol, 6% yield). as the first eluting diastereomer from the second chiral preparative SFC separation as described above.

$^1$H NMR (500 MHz, DMSO-$d_6$) δ 8.95 (br t, J=5.3 Hz, 1H), 8.63 (d, J=6.7 Hz, 1H), 7.72 (t, J=8.5 Hz, 1H), 7.57-7.44 (m, 4H), 7.18 (t, J=8.9 Hz, 2H), 7.03 (br d, J=7.0 Hz, 1H), 6.11 (s, 1H), 5.73 (s, 1H), 4.72-4.46 (m, 1H), 3.82-3.63 (m, 1H), 3.06-2.86 (m, 1H).

MS ESI m/z 493.1 $(M+H)^+$

TABLE 15

Examples 238, 239, 240 were obtained from the SFC separations described in the final step of preparation for example 237.

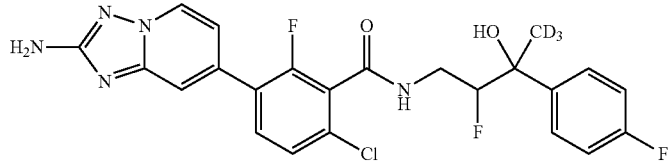 [SMILES: [2H]C([2H])([2H])C(O)(c1ccc(F)cc1)C(F)CNC(=O)c1c(Cl)ccc(-c2ccn3nc(N)nc3c2)c1F]

| Ex No | Name | Note | M + H$^+$ | $^1$H NMR (500 MHz, DMSO-d6) δ |
|---|---|---|---|---|
| 238 | 3-(2-amino-[1,2,4]triazolo[1,5-a]pyridin-7-yl)-6-chloro-2-fluoro-N-(2-fluoro-3-(4-fluorophenyl)-3-hydroxybutyl-4,4,4-d$_3$)benzamide diastereomer 2 | Second eluting isomer from SFC run 2 | 493.1 | 8.91 (br t, J = 5.6 Hz, 1H), 8.63 (d, J = 7.0 Hz, 1H), 7.72 (t, J = 8.4 Hz, 1H), 7.57 (dd, J = 8.4, 5.6 Hz, 2H), 7.53-7.45 (m, 2H), 7.19 (t, J = 8.9 Hz, 2H), 7.02 (br d, J = 7.0 Hz, 1H), 6.11 (s, 1H), 5.66 (s, 1H), 4.75-4.54 (m, 1H), 3.43-3.27 (m, 1H), 2.99-2.87 (m, 1H) |
| 239 | 3-(2-amino-[1,2,4]triazolo[1,5-a]pyridin-7-yl)-6-chloro-2-fluoro-N-(2-fluoro-3-(4-fluorophenyl)-3-hydroxybutyl-4,4,4-d$_3$)benzamide diastereomer 3 | Peak 2 from SFC run 1 | 493.0 | 8.91 (br t, J = 5.6 Hz, 1H), 8.63 (d, J = 7.0 Hz, 1H), 7.72 (t, J = 8.2 Hz, 1H), 7.57 (dd, J = 8.5, 5.5 Hz, 2H), 7.53-7.45 (m, 2H), 7.19 (t, J = 9.0 Hz, 2H), 7.02 (br d, J = 7.0 Hz, 1H), 6.11 (s, 2H), 5.66 (s, 1H), 4.74-4.55 (m, 1H), two protons were obscured by solvent peak. |
| 240 | 3-(2-amino-[1,2,4]triazolo[1,5-a]pyridin-7-yl)-6-chloro-2-fluoro-N-(2-fluoro-3-(4-fluorophenyl)-3-hydroxybutyl-4,4,4-d$_3$)benzamide diastereomer 4 | Peak 3 from SFC run 1 | 493.1 | 8.95 (br t, J = 5.5 Hz, 1H), 8.63 (d, J = 7.0 Hz, 1H), 7.72 (t, J = 8.4 Hz, 1H), 7.58-7.44 (m, 4H), 7.18 (t, J = 8.9 Hz, 2H), 7.03 (br d, J = 6.7 Hz, 1H), 6.11 (s, 2H), 5.74 (s, 1H), 4.69-4.51 (m, 1H), 3.81-3.65 (m, 1H), 3.02-2.88 (m, 1H) |

Example 241: 3-(2-amino-[1,2,4]triazolo[1,5-a]pyridin-7-yl)-N-(2,2-difluoro-3-(4-fluorophenyl)-3-hydroxybutyl)-2-fluoro-6-(methyl-d₃)benzamide

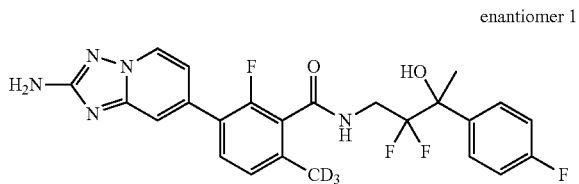 [SMILES: [2H]C([2H])([2H])c1ccc(-c2ccn3nc(N)nc3c2)c(F)c1C(=O)NCC(F)(F)C(C)(O)c1ccc(F)cc1]

enantiomer 1

241A: ethyl 2,2-difluoro-3-(4-fluorophenyl)-3-hydroxybutanoate: A 15 mL pressure vessel was charged with a stir bar, 1-(4-fluorophenyl)ethan-1-one (138 mg, 1.00 mmol), iron (168 mg, 3.00 mmol), iodine (50.8 g, 0.200 mmol) and THF (2 mL) followed by the addition of ethyl 2-bromo-2-fluoroacetate (609 mg, 3.00 mmol). The resulting mixture was degassed by bubbling nitrogen through for 5 min and then stirred at 60° C. for 20 h. The mixture was then cooled to RT, and Celite was added. The mixture was concentrated in vacuo. The crude was purified by flash column chromatography via dry load on Celite (eluent=EtOAc in hexane, gradient 0% to 60%; 24 g silica) to afford ethyl 2,2-difluoro-3-(4-fluorophenyl)-3-hydroxybutanoate (166 mg, 63% yield) as an oil.

$^1$H NMR (500 MHz, CDCl₃) δ 7.51 (dd, J=8.5, 5.5 Hz, 2H), 7.06 (t, J=8.7 Hz, 2H), 4.19 (q, J=7.2 Hz, 2H), 1.74 (t, J=1.5 Hz, 3H), 1.17 (t, J=7.2 Hz, 3H).

241B: 2,2-difluoro-3-(4-fluorophenyl)-3-hydroxybutanamide: A 50 mL round bottom flask was charged with a stir bar, ethyl 2,2-difluoro-3-(4-fluorophenyl)-3-hydroxybutanoate (166 mg, 0.633 mmol) and MeOH (3 mL), followed by the addition of 7 N ammonia in MeOH (0.362 mL, 2.53 mmol). The resulting mixture was stirred at RT for 5 h. The reaction mixture was concentrated in vacuo, and the crude was used directly in the next step without further purification. Quantitative yield was assumed.

MS ESI m/z 231.8 (M−H)⁻

241C: 4-amino-3,3-difluoro-2-(4-fluorophenyl)butan-2-ol: A 15 mL pressure vial was charged with a stir bar, 2,2-difluoro-3-(4-fluorophenyl)-3-hydroxybutanamide (148 mg, 0.635 mmol) and THF (3 mL), followed by addition of BH₃-DMS 2.0M in THF (1.59 mL, 3.17 mmol). The resulting mixture was stirred at 70° C. for 24 h. The reaction was then quenched by slow addition of methanol. The resulting mixture was concentrated in vacuo to afford crude 4-amino-3,3-difluoro-2-(4-fluorophenyl)butan-2-ol, 2 HCl (104 mg, 56.1% yield). The crude was used directly in subsequent steps without further purification.

MS ESI m/z 219.9 (M+H)⁺

241D: methyl 3-(2-amino-[1,2,4]triazolo[1,5-a]pyridin-7-yl)-2-fluoro-6-(methyl-d₃)benzoate: A 40 mL reaction vial was charged with a stir bar, methyl 3-(2-di-((tert-butoxycarbonyl)amino)-[1,2,4]triazolo[1,5-a]pyridin-7-yl)-6-chloro-2-fluorobenzoate (1.00 g, 1.92 mmol), 1,1'-bis(di-tert-butylphosphino) ferrocene palladium chloride (0.250 g, 0.384 mmol) and (methyl-d₃)boronic acid (0.603 g, 9.60 mmol), followed by the addition of dioxane (9.60 mL) and 2M aqueous tripotassium phosphate (5.76 mL, 11.5 mmol).

The resulting mixture was degassed by bubbling with nitrogen for 5 min and the mixture was stirred at 130° C. for 1 d. The crude was purified by flash column chromatography (elution gradient 0% to 8% MeOH in DCM; 12 g silica), affording methyl 3-(2-amino-[1,2,4]triazolo[1,5-a]pyridin-7-yl)-2-fluoro-6-(methyl-d₃)benzoate (447 mg, 1.47 mmol, 77% yield).

$^1$H NMR (500 MHz, DMSO-d₆) δ 8.60 (d, J=6.9 Hz, 1H), 7.68 (t, J=8.1 Hz, 1H), 7.50 (s, 1H), 7.28 (d, J=8.0 Hz, 1H), 7.08-6.98 (m, 1H), 6.05 (s, 2H), 3.91 (s, 3H).

MS ESI m/z 304.3 (M+H)⁺

241E: 3-(2-amino-[1,2,4]triazolo[1,5-a]pyridin-7-yl)-2-fluoro-6-(methyl-d₃)benzoic acid, HCl salt: A 100 mL round-bottom flask was charged with a stir bar, methyl 3-(2-amino-[1,2,4]triazolo[1,5-a]pyridin-7-yl)-2-fluoro-6-(methyl-d₃)benzoate (447 mg, 1.47 mmol) and MeOH (7.4 mL), followed by the addition of sodium hydroxide, 15% aqueous solution (786 mg, 2.95 mmol). The resulting mixture was stirred at 80° C. for 16 h. The mixture was concentrated in vacuo and then acidified by 1N aqueous HCl (2.95 mL, 2.95 mmol). The resulting mixture was concentrated in vacuo to 1 mL and filtered to obtain a brown solid. The crude was used as is in the next step without further purification. Quantitative yield was assumed.

MS ESI m/z 290.1 (M+H)⁺

241: A 4 mL reaction vial was charged with a stir bar, 3-(2-amino-[1,2,4]triazolo[1,5-a]pyridin-7-yl)-2-fluoro-6-(methyl-d₃)benzoic acid, HCl salt (50 mg, 0.15 mmol), 4-amino-3,3-difluoro-2-(4-fluorophenyl)butan-2-ol. 2 HCl salt (76 mg, 0.35 mmol) as crude, and BOP (92 mg, 0.21 mmol), followed by the addition of DMF (0.85 mL) and DIPEA (91 μl, 0.52 mmol). The resulting mixture was stirred at RT for 2 h. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 14% B, 14-54% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. The material thus obtained was further separated into individual stereoisomers via chiral SFC chromatography. Instrument: Waters 100 Prep SFC; Column: Chiral IC, 21×250 mm. 5 micron; Mobile Phase: 70% CO2/30% MeOH with 0.1% DEA; Flow Conditions: 60 mL/min; Detector Wavelength: 220 nm; Injection Details: 500 μL 38.1 mg dissolved in 3 mL MeOH. Thus, was obtained 3-(2-amino-[1,2,4]triazolo[1,5-a]pyridin-7-yl)-N-(2,2-difluoro-3-(4-fluorophenyl)-3-hydroxybutyl)-2-fluoro-6-(methyl-d₃)benzamide enantiomer 1 (10.3 mg, 0.021 mmol, 13% yield) as the first isomer to elute from the chiral SFC purification.

$^1$H NMR (500 MHz, DMSO-d6) δ 8.78 (br t, J=6.0 Hz, 1H), 8.52 (d, J=7.0 Hz, 1H), 7.59-7.46 (m, 3H), 7.41 (s, 1H), 7.19-7.10 (m, 3H), 6.98 (br d, J=7.0 Hz, 1H), 5.98 (s, 2H), 3.98-3.37 (m, 2H), 1.58 (s, 3H).

MS ESI m/z 491.3 (M+H)⁺

225

Example 242: 3-(2-amino-[1,2,4]triazolo[1,5-a]pyridin-7-yl)-N-(2,2-difluoro-3-(4-fluorophenyl)-3-hydroxybutyl)-2-fluoro-6-(methyl-d₃)benzamide

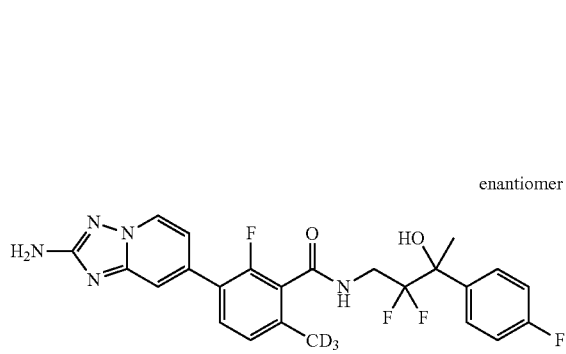

enantiomer 2

The title compound 3-(2-amino-[1,2,4]triazolo[1,5-a]pyridin-7-yl)-N-(2,2-difluoro-3-(4-fluorophenyl)-3-hydroxybutyl)-2-fluoro-6-(methyl-d₃)benzamide enantiomer 2 (10.4 mg, 0.021 mmol, 11% yield) was obtained as the second eluting isomer from the chiral SFC purification described for Example 241.

$^1$H NMR (500 MHz, DMSO-d6) δ 8.78 (br t, J=5.9 Hz, 1H), 8.52 (d, J=7.0 Hz, 1H), 7.58-7.46 (m, 3H), 7.41 (s, 1H), 7.21-7.09 (m, 3H), 6.98 (br d, J=7.0 Hz, 1H), 5.98 (s, 2H), 3.99-3.36 (m, 2H), 1.58 (s, 3H).
MS ESI m/z 491.3 (M+H)⁺

226

Example 245: 3-(2-amino-[1,2,4]triazolo[1,5-a]pyridin-7-yl)-6-chloro-N-(2,2-difluoro-2-(3-(4-fluorophenyl)oxetan-3-yl)ethyl)-2-fluorobenzamide

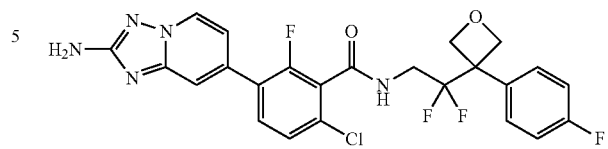

245A: ethyl 2-(3-(4-fluorophenyl)oxetan-3-yl)acetate: A 40 mL reaction vial was charged with a stir bar, KOH (0.197 g, 3.52 mmol) in H₂O (2.64 mL), and dioxane (4.40 mL). The resulting mixture was degassed by bubbling nitrogen through for 5 min followed by addition of chloro(1,5-cyclooctadiene)rhodium(I) dimer (0.087 g, 0.176 mmol), ethyl 2-(oxetan-3-ylidene)acetate (0.50 g, 3.52 mmol) and (4-fluorophenyl)boronic acid (0.541 g, 3.87 mmol). The mixture was stirred at RT for 18 h. The crude was purified by flash column chromatography (EtOAc in hexane, elution gradient 0-20%; 20 g silica), affording ethyl 2-(3-(4-fluorophenyl)oxetan-3-yl)acetate (0.705 g, 2.96 mmol, 84% yield).

$^1$H NMR (400 MHz, CHLOROFORM-d) δ 7.22-7.12 (m, 2H), 7.10-7.00 (m, 2H), 5.00 (d, J=6.1 Hz, 2H), 4.88 (d, J=5.6 Hz, 2H), 4.03 (q, J=7.1 Hz, 2H), 3.13 (s, 2H), 1.15 (td, J=7.1, 0.7 Hz, 3H).
MS ESI m/z 239.3 (M+H)⁺

245B: 2,2-difluoro-2-(3-(4-fluorophenyl)oxetan-3-yl)acetamide: A 4 mL reaction vial was charged with a stir barKHMDS, 1.0M in THF (2.52 mL, 2.52 mmol) and THF (16.8 mL), followed by slow addition of ethyl 2-(3-(4-fluorophenyl)oxetan-3-yl)acetate (0.200 g, 0.839 mmol) at −78° C. The resulting mixture was stirred at −78° C. for 10

TABLE 16

Examples 243 and 244 were prepared in a similar fashion to that described for example 241 and 242, substituting 1-(4-fluorophenyl)ethan-1-one-2,2,2-d₃ in place 1(4-fluorophenyl)ethan-1-one in the first step.

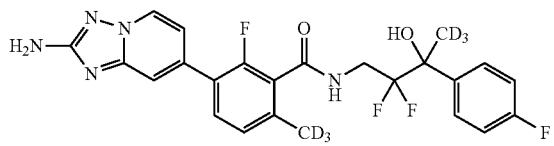

| Ex No | Name | Notes | M + H⁺ | $^1$H NMR (500 MHz, DMSO-d6) δ |
|---|---|---|---|---|
| 243 | 3-(2-amino-[1,2,4]triazolo[1,5-a]pyridin-7-yl)-N-(2,2-difluoro-3-(4-fluorophenyl)-3-hydroxybutyl-4,4,4-d₃)-2-fluoro-6-(methyl-d₃)benzamide | First eluting enantiomer | 494.3 | 8.77 (br, t, J = 6.3 Hz, 1H), 8.53 (d, J = 6.8 Hz, 1H), 7.60-7.46 (m, 3H), 7.41 (s, 1H), 7.21-7.09 (m, 3H), 6.98 (br d, J = 7.1 Hz, 1H), 5.99 (s, 2H), 4.01-3.35 (m, 2H) |
| 244 | 3-(2-amino-[1,2,4]triazolo[1,5-a]pyridin-7-yl)-N-(2,2-difluoro-3-(4-fluorophenyl)-3-hydroxybutyl-4,4,4-d₃)-2-fluoro-6-(methyl-d₃)benzamide | Second eluting enantiomer | 494.3 | 8.77 (br t, J = 6.1 Hz, 1H), 8.52 (br d, J = 7.0 Hz, 1H), 7.60-7.45 (m, 3H), 7.41 (s, 1H), 7.24-7.07 (m, 3H), 6.98 (br d, J = 7.0 Hz, 1H), 5.99 (s, 2H), 4.00-3.33 (m, 2H) | min, then warmed to −20° C. for 20 min, and subsequently N-fluorobenzenesulfonimide (0.794 g, 2.52 mmol) was added in one portion. The resulting mixture was warmed up to RT and stirred for 3 h. The reaction was quenched by addition of saturated NH$_4$Cl and extracted by EtOAc. The organic phase was dried over anhydrous sodium sulfate, filtered via Celite, and concentrated in vacuo. The crude was re-dissolved in MeOH (1.7 mL) in a 40 mL reaction vial, followed by addition of 7M ammonia in methanol (480 μL, 3.36 mmol). The resulting mixture was stirred at 40° C. overnight. The mixture was concentrated in vacuo, affording crude 2,2-difluoro-2-(3-(4-fluorophenyl)oxetan-3-yl)acetamide (142 mg, 0.579 mmol, 69% yield). The crude was used directly in the next step without further purification.
MS ESI m/z 244.0 (M−H)$^-$ 245C: 2,2-difluoro-2-(3-(4-fluorophenyl)oxetan-3-yl) ethan-1-amine: A 40 mL reaction vial was charged with a stir bar, 2,2-difluoro-2-(3-(4-fluorophenyl)oxetan-3-yl)acetamide (140 mg, 0.571 mmol) as crude, and THF (2.9 mL), followed by slow addition of BH$_3$-DMS, 2.0M in THF (856 μL, 1.71 mmol). The resulting mixture was stirred at 70° C. for 3 h. The reaction was quenched by addition of MeOH and aq. HCl (1N) and concentrated in vacuo, affording crude 2,2-difluoro-2-(3-(4-fluorophenyl)oxetan-3-yl)ethan-1-amine (130 mg, 0.562 mmol, 98% yield) mixed with impurities. The crude was used directly in the next step without further purification.
MS ESI m/z 232.3 (M+H)$^+$ 245: A 4 mL reaction vial was charged with a stir bar, 3-(2-amino-[1,2,4]triazolo[1,5-a]pyridin-7-yl)-6-chloro-2-fluorobenzoic acid, HCl salt (34.3 mg, 0.0600 mmol), 2,2-difluoro-2-(3-(4-fluorophenyl)oxetan-3-yl)ethan-1-amine (20.8 mg, 0.090 mmol) and BOP (34.5 mg, 0.078 mmol), followed by the addition of DMF (600 μL) and DIPEA (62.9 μL, 0.360 mmol). The resulting mixture was stirred at RT for 16 h. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 18% B, 18-58% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. Thus, was isolated 3-(2-amino-[1,2,4]triazolo[1,5-a]pyridin-7-yl)-6-chloro-N-(2,2-difluoro-2-(3-(4-fluorophenyl)oxetan-3-yl)ethyl)-2-fluorobenzamide (4.5 mg, 0.009 mmol, 14% yield).
$^1$H NMR (500 MHz, DMSO-d6) δ 9.21-9.12 (m, 1H), 8.64 (d, J=7.0 Hz, 1H), 7.74 (br t, J=8.4 Hz, 1H), 7.55-7.48 (m, 2H), 7.44-7.36 (m, 2H), 7.33-7.25 (m, 2H), 7.04 (br d, J=7.1 Hz, 1H), 6.11 (s, 2H), 5.07 (d, J=6.9 Hz, 2H), 4.90 (br d, J=6.9 Hz, 2H), 3.65 (br d, J=5.8 Hz, 2H).
MS ESI m/z 520.1 (M+H)$^+$ Example 246: 3-(2-amino-[1,2,4]triazolo[1,5-a]pyridin-7-yl)-N-(2,2-difluoro-2-(3-(4-fluorophenyl)oxetan-3-yl)ethyl)-2-fluoro-6-methylbenzamide

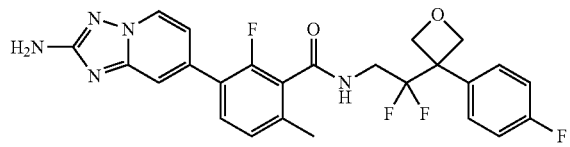 [SMILES: Cc1ccc(-c2ccn3nc(N)nc3c2)c(F)c1C(=O)NCC(F)(F)C1(c2ccc(F)cc2)COC1]

The title compound was prepared in a similar fashion to that described for Example 245, where 3-(2-amino-[1,2,4]triazolo[1,5-a]pyridin-7-yl)-2-fluoro-6-methylbenzoic acid, HCl was substituted for 3-(2-amino-[1,2,4]triazolo[1,5-a]pyridin-7-yl)-6-chloro-2-fluorobenzoic acid, HCl salt in the final step. Thus, was obtained 3-(2-amino-[1,2,4]triazolo[1,5-a]pyridin-7-yl)-N-(2,2-difluoro-2-(3-(4-fluorophenyl)oxetan-3-yl)ethyl)-2-fluoro-6-methylbenzamide (7.3 mg, 0.015 mmol, 24% yield).
MS ESI m/z 500.2 (M+H)$^+$

TABLE 17

Compounds in Table 17 were prepared in a similar fashion to examples 63 and 64. 3-amino-1-cyclopentylpropan-1-ol was used in place of 3-amino-1-(3-fluorophenyl)propan-1-ol TFA salt in the final step.

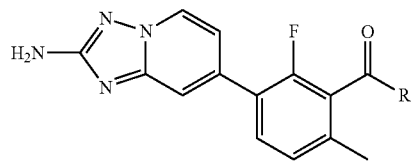

| Ex No | Name | R | M + H$^+$ | $^1$H NMR (500 MHz, DMSO-d6) δ |
|---|---|---|---|---|
| 247 | 3-(2-amino-[1,2,4]triazolo[1,5-a]pyridin-7-yl)-N-(2,2-difluoro-3-(4-fluorophenyl)-3-hydroxybutyl-4,4,4-d$_3$)-2-fluoro-6-(methyl-d$_3$)benzamide | OH, cyclopentyl group (enantiomer 1 first eluted) | 412.2 | 8.59 (d, J = 7.0 Hz, 1H), 8.53 (d, J = 6.8 Hz, 1H), 7.60-7.46 (m, 3H), 7.41 (s, 1H), 7.21-7.09 (m, 3H), 6.98 (br d, J = 7.1 Hz, 1H), 5.99 (s, 2H), 4.01-3.35 (m, 2H) |

TABLE 17-continued

Compounds in Table 17 were prepared in a similar fashion to examples 63 and 64. 3-amino-1-cyclopentylpropan-1-ol was used in place of 3-amino-1-(3-fluorophenyl)propan-1-ol TFA salt in the final step.

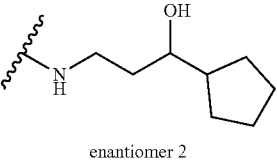

| Ex No | Name | R | M + H⁺ | ¹H NMR (500 MHz, DMSO-d6) δ |
|---|---|---|---|---|
| 248 | 3-(2-amino-[1,2,4]triazolo[1,5-a]pyridin-7-yl)-N-(2,2-difluoro-3-(4-fluorophenyl)-3-hydroxybutyl-4,4,4-d₃)-2-fluoro-6-(methyl-d₃)benzamide | (enantiomer 2, second eluted) | 412.2 | 8.59 (d, J = 7.0 Hz, 1H), 8.52 (br d, J = 7.0 Hz, 1H), 7.60-7.45 (m, 3H), 7.41 (s, 1H), 7.24-7.07 (m, 3H), 6.98 (br d, J = 7.0 Hz, 1H), 5.99 (s, 2H), 4.00-3.33 (m, 2H) |

Example 249: 3-(2-amino-[1,2,4]triazolo[1,5-a]pyridin-7-yl)-2,6-difluoro-N-(2-(1-(4-fluorophenyl)cyclopropyl)ethyl)benzamide

The title compound was prepared in a similar fashion to that described for Example 285, where 2-(1-(4-fluorophenyl)cyclopropyl)ethan-1-amine was substituted for (S)-2,2,3-trifluoro-3-(4-fluorophenyl)propan-1-amine in the final step. Thus, was obtained 3-(2-amino-[1,2,4]triazolo[1,5-a]pyridin-7-yl)-2,6-difluoro-N-(2-(1-(4-fluorophenyl)cyclopropyl)ethyl)benzamide (9.5 mg, 0.021 mmol, 57% yield).

¹H NMR (600 MHz, DMSO-d6) δ 8.75 (t, J=5.3 Hz, 1H), 8.63 (d, J=7.0 Hz, 1H), 7.81-7.72 (m, 1H), 7.50 (s, 1H), 7.39 (dd, J=8.3, 5.7 Hz, 2H), 7.31 (t, J=8.4 Hz, 1H), 7.13 (t, J=8.8 Hz, 2H), 7.02 (br d, J=6.6 Hz, 1H), 6.11 (s, 2H), 3.22-3.13 (m, 1H), 1.79 (br t, J=7.5 Hz, 2H), 0.82-0.71 (m, 4H).

MS ESI m/z 452.3 (M+H)⁺

Example 250: 3-(2-amino-[1,2,4]triazolo[1,5-a]pyridin-7-yl)-N-(3-(4-chlorophenyl)-3-hydroxypropyl-1,1,3-d₃)-2,6-difluorobenzamide enantiomer 1

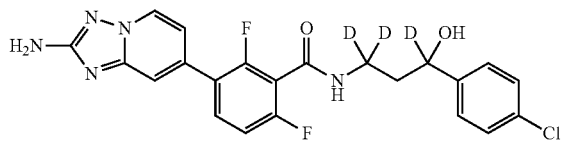

A 8 mL Chemglass reaction vial was charged with a stir bar, BOP (40.6 mg, 0.0920 mmol), 3-amino-1-(4-chlorophenyl)propan-1,3,3-d₃₋₁-ol, HCl salt (20.7 mg, 0.0920 mmol) and 3-(2-amino-[1,2,4]triazolo[1,5-a]pyridin-7-yl)-2,6-difluorobenzoic acid, HCl salt (20 mg, 0.061 mmol). The vial was evacuated and backfilled with nitrogen, followed by the addition of DMF (612 µL) and DIPEA (107 µL, 0.612 mmol). The resulting mixture was stirred at RT for 16 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 13% B, 13-48% B over 25 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The racemic material thus isolated was further purified through chiral SFC separation to provide separated enantiomers. Approximately 28.1 mg of sample were resolved into two peaks collected in IPA with 0.10% DEA. Instrument: Waters 100 Prep SFC; Column: Chiral OD, 30×250 mm. 5 micron; Mobile Phase: 65% CO2/35% IPA w/0.1% DEA; Flow Conditions: 100 mL/min; Detector Wavelength: 220 nm; Injection Details: 3000 µL 28.1 mg dissolved in 3 mL MeOH. Thus, was recovered 3-(2-amino-[1,2,4]triazolo[1,5-a]pyridin-7-yl)-N-(3-(4-chlorophenyl)-3-hydroxypropyl-1,1,3-d₃)-2,6-difluorobenzamide enantiomer 1 (2.1 mg, 0.0045 mmol, 7% yield) as the first eluting isomer from the preparative SFC column. The absolute stereochemistry was not determined.

¹H NMR (500 MHz, DMSO-d₆) δ 8.82 (s, 1H), 8.59 (br d, J=7.3 Hz, 1H), 7.80-7.68 (m, 1H), 7.49 (s, 1H), 7.41-7.32 (m, 4H), 7.29 (br t, J=8.5 Hz, 1H), 7.03 (br d, J=6.4 Hz, 1H), 1.78 (s, 2H).

MS ESI m/z 461.3 (M+H)⁺

Example 251: 3-(2-amino-[1,2,4]triazolo[1,5-a]pyridin-7-yl)-N-(3-(4-chlorophenyl)-3-hydroxypropyl-1,1,3-d₃)-2,6-difluorobenzamide

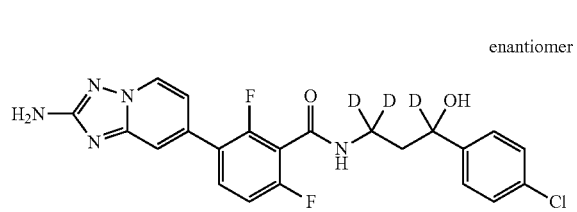
enantiomer 2

The title compound 3-(2-amino-[1,2,4]triazolo[1,5-a]pyridin-7-yl)-N-(3-(4-chlorophenyl)-3-hydroxypropyl-1,1,3-d₃)-2,6-difluorobenzamide enantiomer 2 (2.0 mg, 0.0043 mmol, 7% yield) was obtained as the second eluting isomer from the chiral SFC purification described for Example 250.

¹H NMR (500 MHz, DMSO-d6) δ 8.81 (s, 1H), 8.60 (br d, J=7.0 Hz, 1H), 7.74 (br d, J=6.7 Hz, 1H), 7.49 (s, 1H), 7.40-7.32 (m, 4H), 7.29 (br t, J=8.7 Hz, 1H), 7.03 (br d, J=7.0 Hz, 1H), 1.78 (s, 2H).
MS ESI m/z 461.0 (M+H)⁺

Example 254: 3-(2-amino-[1,2,4]triazolo[1,5-a]pyridin-7-yl)-6-chloro-N-(2,2-difluoro-3-hydroxy-3-(6-(trifluoromethyl)pyridin-2-yl)propyl)-2-fluorobenzamide

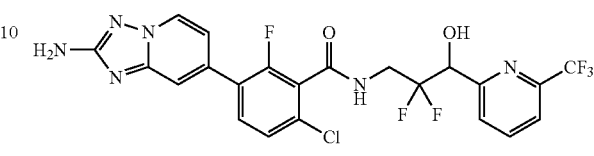
enantiomer 1

254A: ethyl 2,2-difluoro-3-hydroxy-3-(6-(trifluoromethyl)pyridin-2-yl)propanoate: A 40 mL reaction vial was charged with a stir bar, zinc powder (0.560 g, 8.57 mmol), THF (5.71 mL) and 6-(trifluoromethyl)pyridine-2-carboxaldehyde (0.50 g, 2.86 mmol). The mixture was degassed by bubbling nitrogen through for 5 min, followed by the addition of ethyl bromodifluoroacetate (0.439 mL, 3.43 mmol). The resulting mixture was stirred at 70° C. for 16 h. The mixture was then concentrated in vacuo, redissolved in EtOAc and washed with aqueous 1N HCl. The organic phase was dried with MgSO₄, filtered, and concentrated in vacuo, affording ethyl 2,2-difluoro-3-hydroxy-3-(6-(trifluoromethyl)pyridin-2-yl)propanoate (0.557 g, 1.86 mmol, 65% yield). The crude was directly used in the next step without further purification.

TABLE 18

Examples 252 and 253 were prepared in a similar fashion to that described for example 241 and 242, substituting 4-amino-2-(4-chlorophenyl)-3,3-difluorobutan-2-ol in place of 4-amino-3,3-difluoro-2-(4-fluorophenyl)butan-2-ol in the final step.

| Ex No | Name | Notes | M + H⁺ | ¹H NMR (500 MHz, DMSO-d6) δ |
|---|---|---|---|---|
| 252 | 3-(2-amino-[1,2,4]triazolo[1,5-a]pyridin-7-yl)-N-(3-(4-chlorophenyl)-2,2-difluoro-3-hydroxybutyl)-2-fluoro-6-(methyl-d₃)benzamide | First eluting enantiomer | 507.2 | 8.81 (br t, J = 6.1 Hz, 1H), 8.60 (d, J = 7.0 Hz, 1H), 7.59 (br d, J = 8.6 Hz, 3H), 7.51-7.41 (m, 3H), 7.20 (d, J = 7.9 Hz, 1H), 7.01 (br d, J = 6.9 Hz, 1H), 6.29 (s, 1H), 6.06 (s, 2H), 4.03-3.85 (m, 1H), 3.60-3.42 (m, 1H), 1.63 (s, 3H). |
| 253 | 3-(2-amino-[1,2,4]triazolo[1,5-a]pyridin-7-yl)-N-(3-(4-chlorophenyl)-2,2-difluoro-3-hydroxybutyl)-2-fluoro-6-(methyl-d₃)benzamide | Second eluting enantiomer | 507.2 | 8.81 (br t, J = 6.1 Hz, 1H), 8.60 (d, J = 7.0 Hz, 1H), 7.64-7.43 (m, 3H), 7.50-7.41 (m, 3H), 7.20 (d, J = 7.9 Hz, 1H), 7.02 (br d, J = 7.0 Hz, 1H), 6.29 (s, 1H), 6.06 (s, 2H), 4.03-3.86 (m, 1H), 3.59-3.37 (m, 1H), 1.63 (s, 3H). |

¹H NMR (500 MHz, CDCl₃) δ 7.98 (t, J=7.8 Hz, 1H), 7.80-7.63 (m, 2H), 5.34-5.21 (m, 1H), 4.71 (dd, J=7.3, 1.6 Hz, 1H), 4.36 (qd, J=7.1, 2.6 Hz, 2H), 1.44-1.29 (m, 3H).

254B: 2,2-difluoro-3-hydroxy-3-(6-(trifluoromethyl)pyridin-2-yl)propanamide: A 50 mL round bottom flask was charged with a stir bar, ethyl 2,2-difluoro-3-hydroxy-3-(6-(trifluoromethyl)pyridin-2-yl)propanoate (0.300 g, 1.00 mmol) and MeOH (5.0 mL), followed by the addition of 7N ammonia in MeOH (0.573 mL, 4.01 mmol). The resulting mixture was stirred at RT for 16 h. The reaction mixture was concentrated in vacuo, and the crude was used directly in the next step without further purification. Quantitative yield was assumed.
MS ESI m/z 268.8 (M−H)⁻

254C: 3-amino-2,2-difluoro-1-(6-(trifluoromethyl)pyridin-2-yl)propan-1-ol: A 20 mL reaction vial was charged with a stir bar, 2,2-difluoro-3-hydroxy-3-(6-(trifluoromethyl)pyridin-2-yl)propanamide (270 mg, 1.00 mmol) and THF (5.0 mL), followed by the addition of lithium aluminum hydride solution, 2.0 M in THF (1.50 mL, 3.00 mmol) at −78° C. The resulting mixture was stirred at −78° C. for 1 h and then stirred at RT for 3 h. The reaction mixture was then diluted with ether and cooled to 0° C., followed by slow addition of H₂O (0.1 mL), 15% aqueous sodium hydroxide (0.1 mL), and H₂O (0.3 mL) sequentially. The resulting mixture was warmed up to room temperature and stirred vigorously for 15 min. Anhydrous magnesium sulfate was added and the mixture was stirred for additional 15 min. The crude was filtered to remove salts, affording crude 3-amino-2,2-difluoro-1-(6-(trifluoromethyl)pyridin-2-yl)propan-1-ol (204 mg, 0.796 mmol, 80% yield), which was used as-is in the next step without further purification.
MS ESI m/z 256.8 (M+H)⁺

254: A 4 mL reaction vial was charged with a stir bar, 3-(2-amino-[1,2,4]triazolo[1,5-a]pyridin-7-yl)-6-chloro-2-fluorobenzoic acid, HCl salt (34.3 mg, 0.100 mmol), 3-amino-2,2-difluoro-1-(6-(trifluoromethyl)pyridin-2-yl)propan-1-ol (0.031 g, 0.12 mmol) and BOP (0.053 g, 0.120 mmol), followed by the addition of DMF (1.0 mL) and DIPEA (0.070 mL, 0.40 mmol). The resulting mixture was stirred at RT for 1 h. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 13% B, 13-53% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. The material thus obtained was further separated into individual stereoisomers via chiral SFC chromatography. Approximately 14.5 mg of sample were resolved and collected in MeOH with 0.1% DEA. The chiral purity for the isolates were determined using the analytical chromatographic conditions: Instrument: Waters 100 Prep SFC; Column: Chiral IC, 21×250 mm. 5 micron; Mobile Phase: 65% CO2/35% MeOH with 0.1% DEA; Flow Conditions: 60 mL/min; Detector Wavelength: 220 nm; Injection Details: 2000 μL 14.5 mg dissolved in 3 mL MeOH. Thus, was obtained 3-(2-amino-[1,2,4]triazolo[1,5-a]pyridin-7-yl)-6-chloro-N-(2,2-difluoro-3-hydroxy-3-(6-(trifluoromethyl)pyridin-2-yl)propyl)-2-fluorobenzamide enantiomer 1 (4.2 mg, 0.008 mmol, 8% yield) as the first isomer to elute from the preparative chiral SFC separation.

¹H NMR (500 MHz, DMSO-d6) δ 9.20 (br t, J=6.1 Hz, 1H), 8.61 (d, J=7.0 Hz, 1H), 8.22-8.10 (m, 1H), 7.90 (br d, J=7.9 Hz, 2H), 7.72 (t, J=8.4 Hz, 1H), 7.55-7.46 (m, 2H), 7.06 (br d, J=7.0 Hz, 1H), 6.08 (s, 2H), 5.14-4.96 (m, 1H), 4.17-3.85 (m, 2H)
MS ESI m/z 545.3 (M+H)⁺

TABLE 19

Compounds in Table 19 were prepared in a similar fashion to example 254. 255 was prepared as the second eluting isomer from the preparative chiral SFC separation described for 254.

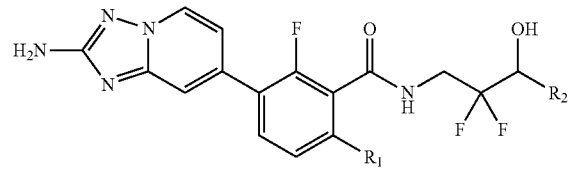

| Ex No | Name | R1 | R2 | M + H⁺ | ¹H NMR (500 MHz, DMSO-d6) δ |
|---|---|---|---|---|---|
| 255 | 3-(2-amino-[1,2,4]triazolo[1,5-a]pyridin-7-yl)-6-chloro-N-(2,2-difluoro-3-hydroxy-3-(6-(trifluoromethyl)pyridin-2-yl)propyl)-2-fluorobenzamide | Cl | 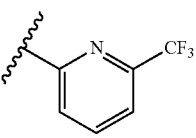

Second eluting enantiomer | 545.3 | 9.20 (br t, J = 6.0 Hz, 1H), 8.60 (d, J = 7.0 Hz, 1H), 8.22-8.10 (m, 1H), 7.90 (d, J = 7.6 Hz, 2H), 7.72 (t, J = 8.4 Hz, 1H), 7.56-7.47 (m, 2H), 7.06 (br d, J = 6.7 Hz, 1H), 6.07 (s, 2H), 5.13-4.99 (m, 1H), 4.10-3.89 (m, 2H) |

TABLE 19-continued

Compounds in Table 19 were prepared in a similar fashion to example 254. 255 was prepared as the second eluting isomer from the preparative chiral SFC separation described for 254.

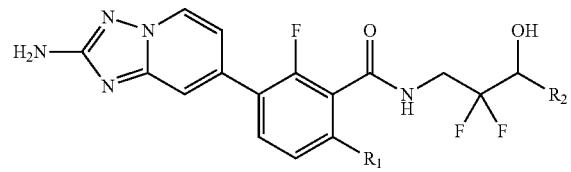

| Ex No | Name | R1 | R2 | M + H⁺ | ¹H NMR (500 MHz, DMSO-d6) δ |
|---|---|---|---|---|---|
| 256 | 3-(2-amino-[1,2,4]triazolo[1,5-a]pyridin-7-yl)-6-chloro-N-(3-(4,4-difluorocyclohexyl)-2,2-difluoro-3-hydroxypropyl)-2-fluorobenzamide | Cl | 4,4-difluorocyclohexyl First eluting enantiomer | 518.1 | 9.14 (br t, J = 6.1 Hz, 1H), 8.63 (d, J = 7.0 Hz, 1H), 7.82-7.68 (m, 1H), 7.58-7.42 (m, 2H), 7.05 (br d, J = 7.0 Hz, 1H), 6.10 (s, 2H), 5.72 (d, J = 6.7 Hz, 1H), 4.05-3.71 (m, 2H), 3.68-3.54 (m, 1H), 2.01 (br d, J = 4.9 Hz, 2H), 1.93-1.67 (m, 5H), 1.60-1.33 (m, 2H). |
| 257 | 3-(2-amino-[1,2,4]triazolo[1,5-a]pyridin-7-yl)-6-chloro-N-(3-(4,4-difluorocyclohexyl)-2,2-difluoro-3-hydroxypropyl)-2-fluorobenzamide | Cl | 4,4-difluorocyclohexyl Second eluting enantiomer | 518.1 | 9.13 (br t, J = 6.0 Hz, 1H), 8.63 (d, J = 6.7 Hz, 1H), 7.74 (t, J = 8.4 Hz, 1H), 7.59-7.44 (m, 2H), 7.05 (br d, J = 6.7 Hz, 1H), 6.10 (s, 2H), 5.71 (d, J = 7.0 Hz, 1H), 4.02-3.75 (m, 2H), 3.70-3.53 (m, 1H), 2.01 (br s, 2H), 1.93-1.65 (m, 5H), 1.59-1.34 (m, 2H). |
| 258 | 3-(2-amino-[1,2,4]triazolo[1,5-a]pyridin-7-yl)-N-(3-(3,3-difluorocyclobutyl)-2,2-difluoro-3-hydroxypropyl)-2-fluoro-6-methylbenzamide | CH₃ | 3,3-difluorocyclobutyl First eluting enantiomer | 470.1 | 8.96 (br t, J = 6.3 Hz, 1H), 8.60 (d, J = 7.0 Hz, 1H), 7.59 (t, J = 7.9 Hz, 1H), 7.48 (s, 1H), 7.23 (d, J = 8.2 Hz, 1H), 7.05 (br d, J = 7.0 Hz, 1H), 6.06 (s, 2H), 3.97-3.71 (m, 3H), 2.69-2.42 (m, 4H), 2.31 (s, 3H). |
| 259 | 3-(2-amino-[1,2,4]triazolo[1,5-a]pyridin-7-yl)-N-(3-(3,3-difluorocyclobutyl)-2,2-difluoro-3-hydroxypropyl)-2-fluoro-6-methylbenzamide | CH₃ | 3,3-difluorocyclobutyl Second eluting enantiomer | 470.2 | 8.97 (br t, J = 6.0 Hz, 1H), 8.60 (d, J = 6.7 Hz, 1H), 7.59 (t, J = 8.1 Hz, 1H), 7.48 (s, 1H), 7.23 (d, J = 7.9 Hz, 1H), 7.05 (br d, J = 7.2 Hz, 1H), 6.06 (s, 2H), 4.00-3.64 (m, 3H), 2.77-2.38 (m, 4H), 2.31 (s, 3H). |
| 260 | 3-(2-amino-[1,2,4]triazolo[1,5-a]pyridin-7-yl)-N-(2,2-difluoro-3-hydroxy-3-(2-(trifluoromethyl)pyridin-4-yl)propyl)-2-fluoro-6-methylbenzamide | CH₃ | 2-(trifluoromethyl)pyridin-4-yl First eluting enantiomer | 525.2 | 9.00 (br t, J = 5.9 Hz, 1H), 8.80 (d, J = 5.0 Hz, 1H), 8.59 (d, J = 6.9 Hz, 1H), 7.92 (s, 1H), 7.79 (br d, J = 4.5 Hz, 1H), 7.58 (t, J = 8.1 Hz, 1H), 7.48 (s, 1H), 7.22 (d, J = 8.0 Hz, 1H), 7.04 (br d, J = 6.8 Hz, 1H), 6.05 (s, 2H), 5.17 (br d, J = 16.5 Hz, 1H), 4.02-3.85 (m, 2H), 2.29 (s, 3H). |

TABLE 19-continued

Compounds in Table 19 were prepared in a similar fashion to example 254. 255 was prepared as the second eluting isomer from the preparative chiral SFC separation described for 254.

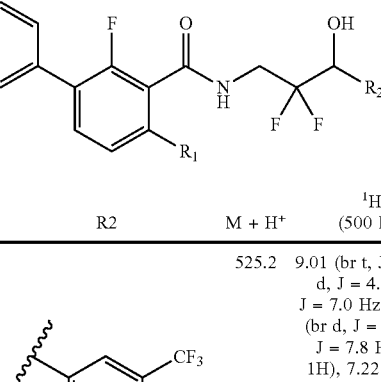

| Ex No | Name | R1 | R2 | M + H+ | 1H NMR (500 MHz, DMSO-d6) δ |
|---|---|---|---|---|---|
| 261 | 3-(2-amino-[1,2,4]triazolo[1,5-a]pyridin-7-yl)-N-(2,2-difluoro-3-hydroxy-3-(2-(trifluoromethyl)pyridin-4-yl)propyl)-2-fluoro-6-methylbenzamide | CH$_3$ | 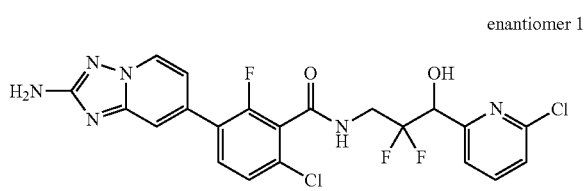<br>Second eluting enantiomer | 525.2 | 9.01 (br t, J = 5.7 Hz, 1H), 8.80 (br d, J = 4.6 Hz, 1H), 8.59 (br d, J = 7.0 Hz, 1H), 7.92 (s, 1H), 7.79 (br d, J = 4.0 Hz, 1H), 7.58 (br t, J = 7.8 Hz, 1H), 7.58-7.42 (m, 1H), 7.22 (br d, J = 8.0 Hz, 1H), 7.04 (br d, J = 6.6 Hz, 1H), 6.05 (br s, 2H), 5.17 (br dd, J = 16.3, 1.7 Hz, 1H), 4.05-3.84 (m, 2H), 2.29 (s, 3H). |

Example 262: 3-(2-amino-[1,2,4]triazolo[1,5-a]pyridin-7-yl)-6-chloro-N-(3-(6-chloropyridin-2-yl)-2,2-difluoro-3-hydroxypropyl)-2-fluorobenzamide

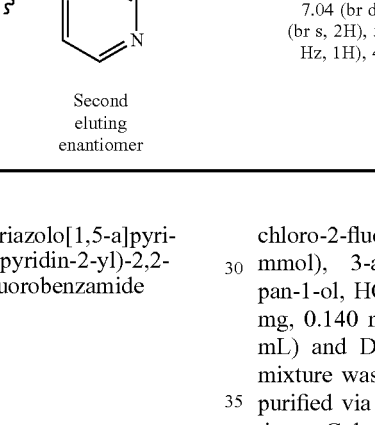
enantiomer 1

262A: 3-(6-chloropyridin-2-yl)-2,2-difluoro-3-hydroxypropanamide: This compound was prepared in similar fashion to 254B.

262B: 3-amino-1-(6-chloropyridin-2-yl)-2,2-difluoropropan-1-ol, HCl salt: A 40 mL reaction vial was charged with a stir bar, 3-(6-chloropyridin-2-yl)-2,2-difluoro-3-hydroxypropanamide (0.521 g, 2.2 mmol), followed by the addition of THF (11.00 ml) and borane dimethyl sulfide complex solution, 2.0 M in THF (3.30 ml, 6.60 mmol) at −78° C. The resulting mixture was stirred at −78° C. for 5 min and then allowed to warm up to RT, and then stirred at 80° C. for 3 h. The reaction was quenched by addition of MeOH (1 mL), and the mixture was concentrated in vacuo. The crude was dissolved in 1N aqueous HCl (5 mL) and stirred at 60° C. for 1 h. The resulting mixture was concentrated in vacuo. The crude was used as is in the next step without further purification. Quantitative yield was assumed.
MS ESI m/z 222.8 (M+H)+

262: A 8 mL Chemglass reaction vial was charged with a stir bar, 3-(2-amino-[1,2,4]triazolo[1,5-a]pyridin-7-yl)-6-chloro-2-fluorobenzoic acid, HCl salt (34.3 mg, 0.100 mmol), 3-amino-1-(6-chloropyridin-2-yl)-2,2-difluoropropan-1-ol, HCl salt (66.8 mg, 0.258 mmol) and BOP (61.9 mg, 0.140 mmol), followed by the addition of DMF (1.0 mL) and DIPEA (69.9 µL, 0.400 mmol). The resulting mixture was stirred at rt for 1 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 10% B, 10-50% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The racemic material thus isolated was further purified through chiral SFC separation to provide separated enantiomers. Approximately 25.7 mg of sample were resolved into two peaks collected in MeOH with 0.1% DEA. Instrument: Waters 100 Prep SFC; Column: Chiral IC, 21×250 mm. 5 micron; Mobile Phase: 60% CO2/40% MeOH w/0.1% DEA; Flow Conditions: 100 mL/min; Detector Wavelength: 220 nm; Injection Details: 600 µL 25.7 mg dissolved in 3 mL DMSO. Thus, was recovered 3-(2-amino-[1,2,4]triazolo[1,5-a]pyridin-7-yl)-6-chloro-N-(3-(6-chloropyridin-2-yl)-2,2-difluoro-3-hydroxypropyl)-2-fluorobenzamide enantiomer 1 (8.5 mg, 0.017 mmol, 17% yield) as the first eluting isomer from the preparative SFC column. The absolute stereochemistry was not determined.

1H NMR (500 MHz, DMSO-d6) δ 9.15 (br t, J=6.0 Hz, 1H), 8.55 (d, J=7.0 Hz, 1H), 7.87 (t, J=7.8 Hz, 1H), 7.66 (t, J=8.4 Hz, 1H), 7.54 (d, J=7.6 Hz, 1H), 7.49-7.40 (m, 3H), 7.01 (br d, J=7.0 Hz, 1H), 6.01 (s, 2H), 4.87 (br dd, J=15.5, 6.6 Hz, 1H), 4.02-3.64 (m, 2H).
MS ESI m/z 511.0 (M+H)+

Example 263: 3-(2-amino-[1,2,4]triazolo[1,5-a]pyridin-7-yl)-6-chloro-N-(3-(6-chloropyridin-2-yl)-2,2-difluoro-3-hydroxypropyl)-2-fluorobenzamide

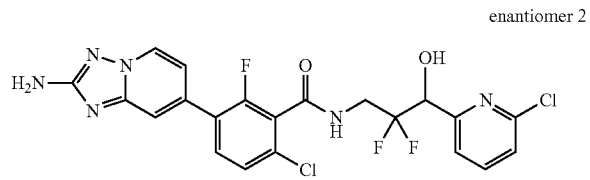 [SMILES: Nc1nc2cc(-c3ccc(Cl)c(C(=O)NCC(F)(F)C(O)c4cccc(Cl)n4)c3F)ccn2n1]

enantiomer 2

The title compound 3-(2-amino-[1,2,4]triazolo[1,5-a]pyridin-7-yl)-6-chloro-N-(3-(6-chloropyridin-2-yl)-2,2-difluoro-3-hydroxypropyl)-2-fluorobenzamide enantiomer 2 (8.3 mg, 0.016 mmol, 16% yield) was obtained as the second eluting isomer from the chiral SFC purification described for Example 262.

$^1$H NMR (500 MHz, DMSO-d6) δ 9.15 (br t, J=6.1 Hz, 1H), 8.55 (d, J=7.0 Hz, 1H), 7.87 (t, J=7.8 Hz, 1H), 7.66 (t, J=8.5 Hz, 1H), 7.54 (d, J=7.6 Hz, 1H), 7.49-7.38 (m, 3H), 7.01 (br d, J=7.0 Hz, 1H), 6.01 (s, 2H), 4.87 (br dd, J=14.9, 6.4 Hz, 1H), 4.03-3.63 (m, 2H).
MS ESI m/z 511.2 (M+H)$^+$

Example 264: 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide

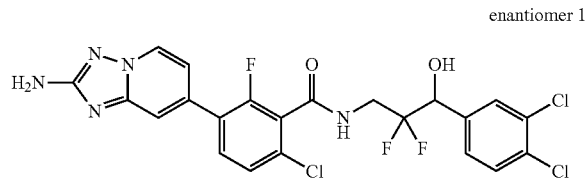 [SMILES: Nc1nc2cc(-c3ccc(Cl)c(C(=O)NCC(F)(F)C(O)c4ccc(Cl)c(Cl)c4)c3F)ccn2n1]

enantiomer 1

264A: ethyl 3-(3,4-dichlorophenyl)-2,2-difluoro-3-hydroxypropanoate: To a 40 mL sealed tube was added 3,4-dichlorobenzaldehyde (1.00 g, 5.71 mmol), THF (15 mL) and zinc (0.478 g, 7.31 mmol). The mixture was heated at 85° C. for 30 min and then ethyl bromodifluoroacetate (1.28 mL, 9.75 mmol) was added portion wise over 10 min. The reaction mixture was heated at 85° C. overnight. After cooling to room temperature, the reaction mixture was vacuum filtered through a celite pad. The filtrate was acidified by adding TN aqueous HCl dropwise while stirring. The acidified filtrate was diluted with EtOAc (30 mL). The organic layer was washed with brine (20 mL), dried with Na$_2$SO$_4$, concentrated, and dried to an orange oil. The residue was subjected to flash chromatography using a 24 g silica column eluting with 0-40% EtOAc in hexanes gradient. The pure fractions were concentrated to afford ethyl 3-(3,4-dichlorophenyl)-2,2-difluoro-3-hydroxypropanoate (1.3 g, 4.4 mmol, 76% yield) as off-white solids.

$^1$H NMR (400 MHz, CDCl3) δ 7.59 (d, J=1.8 Hz, 1H), 7.50 (d, J=8.2 Hz, 1H), 7.31 (d, J=8.1 Hz, 1H), 5.21-5.14 (m, 1H), 4.45-4.32 (m, 2H), 2.80 (d, J=5.1 Hz, 1H), 1.43-1.21 (m, 3H).

264B: tert-butyl(3-(3,4-dichlorophenyl)-2,2-difluoro-3-hydroxypropyl)carbamate: To a solution of ethyl 3-(3,4-dichlorophenyl)-2,2-difluoro-3-hydroxypropanoate (1.20 g, 4.01 mmol) in MeOH (6 mL) was added ammonia (7M in MeOH, 6 mL, 42 mmol). The resulting solution was allowed to stir at room temperature for 20 h. The solvent was evaporated to give the crude 3-(3,4-dichlorophenyl)-2,2-difluoro-3-hydroxypropanamide. To a 50 mL round bottom flask was added 3-(3,4-dichlorophenyl)-2,2-difluoro-3-hydroxypropanamide (600 mg, 2.22 mmol) and THF (6 mL). Borane dimethyl sulfide complex solution (2.0 M in THF, 4.44 mL, 8.89 mmol) was added portion wise at room temperature over 5 min. The reaction was stirred at 60° C. for 2 h. The reaction mixture was then cooled to room temperature and was quenched by slow dropwise addition of methanol (5 ml). The mixture was stirred for 30 min and solvent was removed in vacuo to give a clear colorless thick oil. The oily residue was dissolved in 1M aqueous HCl solution (10 mL) and the result was heated at 60° C. for 1 h. The cloudy mixture became clear by the end of the hour. The mixture was concentrated in vacuo to give the crude 3-amino-1-(3,4-dichlorophenyl)-2,2-difluoropropan-1-ol as white solids. The crude 3-amino-1-(3,4-dichlorophenyl)-2,2-difluoropropan-1-ol was then mixed with THF (10 mL) and triethylamine (0.97 mL, 6.7 mmol) followed by addition of di-tert-butyldicarbonate (0.61 mL, 2.7 mmol). The mixture was stirred at room temperature for 1 h. Solvent was then removed in vacuo to give a thick oil. The residue was subjected to flash chromatography using a 24 g silica column eluting with 0-20% EtOAc in hexanes gradient. Product fractions were concentrated to afford tert-butyl (3-(3,4-dichlorophenyl)-2,2-difluoro-3-hydroxypropyl)carbamate (600 mg, 1.68 mmol, 76% yield) as white solids.
MS ESI m/z 300.0 (M−55)$^+$ 264: tert-butyl (3-(3,4-dichlorophenyl)-2,2-difluoro-3-hydroxypropyl)carbamate (35 mg, 0.098 mmol) was dissolved in DCM (1 mL) and TFA (0.2 mL). The solution was stirred at room temperature for 2 h. The solvent was evaporated to give the crude 3-amino-1-(3,4-dichlorophenyl)-2,2-difluoropropan-1-ol TFA salt. The residue was mixed with 3-(2-amino-[1,2,4]triazolo[1,5-a]pyridin-7-yl)-6-chloro-2-fluorobenzoic acid (30 mg, 0.098 mmol), DIPEA (0.068 mL, 0.391 mmol) and DMF (1 mL). BOP (47.6 mg, 0.108 mmol) was added next and the reaction mixture was stirred at room temperature for 1 h. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 27% B, 27-67% B over 20 minutes, then a 0-minute hold at 100% B; Flow Rate: 20 mL/min; Column Temperature: 25° C. Fraction collection was triggered by MS signals. Fractions containing the desired product were combined and dried via centrifugal evaporation to afford racemic 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide (44.7 mg, 0.082 mmol, 84% yield).
MS ESI m/z 544.2 (M+H)$^+$ $^1$H NMR (500 MHz, DMSO-d$_6$) δ 9.16 (br t, J=6.1 Hz, 1H), 8.65 (d, J=7.0 Hz, 1H), 7.76 (t, J=8.4 Hz, 1H), 7.68 (s, 1H), 7.69 (d, J=6.7 Hz, 1H), 7.57-7.49 (m, 2H), 7.45 (br d, J=7.9 Hz, 1H), 7.05 (br d, J=7.0 Hz, 1H), 6.64 (d, J=5.5 Hz, 1H), 6.12 (s, 2H), 5.07-4.88 (m, 1H), 4.00-3.80 (m, 2H).

Racemic 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide was further separated into two individual stereoisomers via chiral SFC chromatography with the following conditions: Column: Chiral OJ 30×250 mm. 5 micron; Mobile Phase: 75% CO$_2$/25% IPA w/0.1% DEA; Flow Conditions: 100 mL/min; Detector Wavelength: 220 nm; Injection details: 1.0 mL injections of 44.7 mg dissolved in 3 mL MeOH. Fractions containing the first eluted peak were concentrated to afford 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide enantiomer 1 (9.1 mg, 0.017 mmol, 17% yield).

$^1$H NMR (500 MHz, DMSO-$d_6$) δ 9.16 (br t, J=6.1 Hz, 1H), 8.65 (d, J=7.0 Hz, 1H), 7.76 (t, J=8.4 Hz, 1H), 7.68 (s, 1H), 7.69 (d, J=6.7 Hz, 1H), 7.57-7.49 (m, 2H), 7.45 (br d, J=7.9 Hz, 1H), 7.05 (br d, J=7.0 Hz, 1H), 6.64 (d, J=5.5 Hz, 1H), 6.12 (s, 2H), 5.07-4.88 (m, 1H), 4.00-3.80 (m, 2H). MS ESI m/z 544.2 (M+H)$^+$

Example 265: 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide

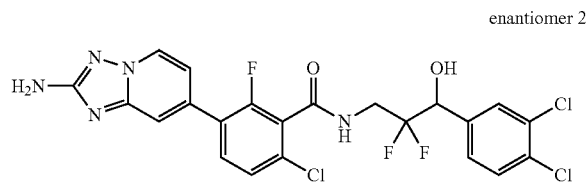 [SMILES: Nc1nc2cc(-c3ccc(Cl)c(C(=O)NCC(F)(F)C(O)c4ccc(Cl)c(Cl)c4)c3F)ccn2n1]

enantiomer 2

The title compound 3-{2-amino-[1,2,4]triazolo[1,5-a]pyridin-7-yl}-6-chloro-N-[3-(3,4-dichlorophenyl)-2,2-difluoro-3-hydroxypropyl]-2-fluorobenzamide enantiomer 2 (8.7 mg, 0.016 mmol, 16% yield) was obtained as the second eluting isomer from the chiral SFC purification described for Example 264.

$^1$H NMR (500 MHz, DMSO-d6) δ 9.16 (br t, J=6.1 Hz, 1H), 8.65 (d, J=7.0 Hz, 1H), 7.76 (t, J=8.4 Hz, 1H), 7.68 (s, 1H), 7.69 (d, J=6.7 Hz, 1H), 7.57-7.49 (m, 2H), 7.45 (br d, J=7.9 Hz, 1H), 7.05 (br d, J=7.0 Hz, 1H), 6.64 (d, J=5.5 Hz, 1H), 6.12 (s, 2H), 5.07-4.88 (m, 1H), 4.00-3.80 (m, 2H). MS ESI m/z 544.2 (M+H)$^+$

Example 266: 3-(2-amino-[1,2,4]triazolo[1,5-a]pyridin-7-yl)-N-(2,2-difluoro-3-(5-fluoropyridin-2-yl)-3-hydroxypropyl)-6-ethyl-2-fluorobenzamide

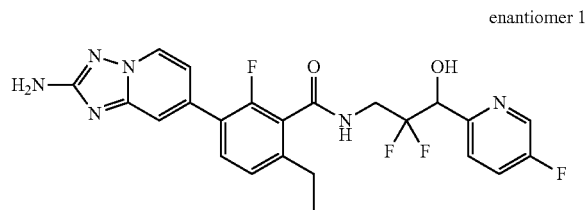 [SMILES: CCc1ccc(-c2ccn3nc(N)nc3c2)c(F)c1C(=O)NCC(F)(F)C(O)c1ccc(F)cn1]

enantiomer 1

266A: methyl 3-bromo-6-ethyl-2-fluorobenzoate: In a 50 mL flask were combined 3-bromo-6-ethyl-2-fluorobenzoic acid (1.90 g, 7.69 mmol), potassium carbonate (2.66 g, 19.2 mmol), and DMF (20 mL). To the stirred suspension was added iodomethane (0.721 mL, 11.5 mmol). The mixture was stirred at room temperature for 20 h. The mixture was then diluted with EtOAc (150 mL), water (100 mL), and brine (25 mL) and thoroughly shaken. The organic layer was collected, dried over anhydrous MgSO$_4$, filtered and concentrated in vacuo to a colorless oil. The residue was subjected to flash chromatography using a 24 g silica column eluting with 0-20% EtOAc in hexanes gradient. The purified fractions were concentrated to afford methyl 3-bromo-6-ethyl-2-fluorobenzoate (1.8 g, 6.55 mmol, 85% yield) as a colorless oil.

$^1$H NMR (499 MHz, CHLOROFORM-d) δ 7.54 (dd, J=8.2, 7.0 Hz, 1H), 6.98-6.93 (m, 1H), 3.97 (s, 3H), 2.72-2.63 (m, 2H), 1.23 (t, J=7.6 Hz, 3H).

266B: methyl 3-(2-amino-[1,2,4]triazolo[1,5-a]pyridin-7-yl)-6-ethyl-2-fluorobenzoate: In a 40 mL pressure vial equipped with a magnetic stir bar were combined methyl 3-bromo-6-ethyl-2-fluorobenzoate (800 mg, 3.06 mmol), 4,4,4',4',5,5,5',5'-octamethyl-2,2'-bi(1,3,2-dioxaborolane) (1.01 g, 3.98 mmol), [1,1'-bis(diphenylphosphino)ferrocene]dichloropalladium(II), complex with dichloromethane (0.125 g, 0.153 mmol), dioxane (15.3 mL), and potassium acetate (0.601 g, 6.13 mmol). The vessel was evacuated and backfilled with nitrogen 3 times, then heated to 110° C. under a nitrogen atmosphere. The mixture was heated for 4 h. The resulting mixture was then charged with 7-bromo-[1,2,4]triazolo[1,5-a]pyridin-2-amine (0.653 g, 3.06 mmol) and 3 M potassium phosphate tribasic aqueous solution (2.04 mL, 6.13 mmol). The vial was evacuated and back-filled with nitrogen 3 times and then heated to 90° C. for 1 h. The crude reaction mixture was subjected to flash chromatography using a 40 g silica column eluting with 50-100% EtOAc in hexanes gradient. The enriched fractions were concentrated to afford crude solids. The crude product was triturated with ethyl acetate (15 mL) to give methyl 3-(2-amino-[1,2,4]triazolo[1,5-a]pyridin-7-yl)-6-ethyl-2-fluorobenzoate (0.600 g, 1.91 mmol, 62% yield) as off white solids.

$^1$H NMR (499 MHz, DMSO-$d_6$) δ 8.61 (d, J=6.9 Hz, 1H), 7.73 (t, J=8.1 Hz, 1H), 7.52 (s, 1H), 7.33 (d, J=8.1 Hz, 1H), 7.04 (dt, J=7.0, 1.7 Hz, 1H), 6.08 (s, 2H), 3.92 (s, 3H), 2.72-2.63 (m, 2H), 1.19 (t, J=7.5 Hz, 3H). MS ESI m/z 315.1 (M+H)+

266C: sodium 3-(2-amino-[1,2,4]triazolo[1,5-a]pyridin-7-yl)-6-ethyl-2-fluorobenzoate: An 8 mL vial equipped with a stir bar was charged with methyl 3-(2-amino-[1,2,4]triazolo[1,5-a]pyridin-7-yl)-6-ethyl-2-fluorobenzoate (0.200 g, 0.636 mmol), THF/MeOH (4:1, 4 mL), and sodium hydroxide, 10M aqueous (0.127 mL, 1.27 mmol). The resulting mixture was stirred at 60° C. for 16 h. After cooling to room temperature, solvent was removed in vacuo. The crude sodium 3-(2-amino-[1,2,4]triazolo[1,5-a]pyridin-7-yl)-6-ethyl-2-fluorobenzoate residue was used as-is directly in subsequent steps. Quantitative yield was assumed. MS ESI m/z 301.3 (M+H)+

266D: tert-butyl (2,2-difluoro-3-(5-fluoropyridin-2-yl)-3-hydroxypropyl)carbamate: Intermediate tert-butyl (2,2-difluoro-3-(5-fluoropyridin-2-yl)-3-hydroxypropyl)carbamate (150 mg, 0.490 mmol, 6% yield over 4 steps) was obtained by a similar procedure as that described for the preparation of tert-butyl(3-(3,4-dichlorophenyl)-2,2-difluoro-3-hydroxypropyl)carbamate (Intermediate 264B), where 5-fluoropicolinaldehyde was substituted in place of 3,4-dichlorobenzaldehyde in the first step. MS ESI m/z 307.3 (M+H)+

266: The title compound was prepared in a similar fashion as described for the final step in the preparation of Example 264, where sodium 3-(2-amino-[1,2,4]triazolo[1,5-a]pyridin-7-yl)-6-ethyl-2-fluorobenzoate was used in place of 3-(2-amino-[1,2,4]triazolo[1,5-a]pyridin-7-yl)-6-chloro-2-fluorobenzoic acid, and where tert-butyl (2,2-difluoro-3-(5- fluoropyridin-2-yl)-3-hydroxypropyl)carbamate was used in place of tert-butyl(3-(3,4-dichlorophenyl)-2,2-difluoro-3-hydroxypropyl)carbamate. The title compound 3-(2-amino-[1,2,4]triazolo[1,5-a]pyridin-7-yl)-N-(2,2-difluoro-3-(5-fluoropyridin-2-yl)-3-hydroxypropyl)-6-ethyl-2-fluorobenzamide enantiomer 1 (1.9 mg, 0.0038 mmol, 6% yield) was the first isomer to elute from the chiral SFC purification.

¹H NMR (500 MHz, DMSO-d6) δ 8.99 (br t, J=6.0 Hz, 1H), 8.61 (d, J=7.1 Hz, 1H), 8.57 (s, 1H), 7.81 (td, J=8.8, 2.6 Hz, 1H), 7.68 (t, J=6.9 Hz, 1H), 7.63 (t, J=7.8 Hz, 1H), 7.50 (s, 1H), 7.27 (d, J=7.9 Hz, 1H), 7.06 (br d, J=7.0 Hz, 1H), 6.61 (d, J=5.8 Hz, 1H), 6.07 (s, 1H), 5.07-4.91 (m, 1H), 4.06-3.86 (m, 2H), 3.46 (br s, 1H), 2.64 (q, J=7.2 Hz, 2H), 1.19 (t, J=7.6 Hz, 3H)).
MS ESI m/z 489.1 (M+H)+

TABLE 20

Compounds in Table 20 were prepared in a similar fashion to examples 264 and 265. In cases of undefined stereochemistry, compounds were isolated as racemic or diastereomeric mixtures unless otherwise noted.

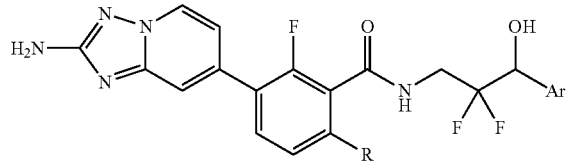

| Ex No | Name | Ar & R | M + H⁺ | 1H NMR (500 MHz, DMSO-d6) δ |
|---|---|---|---|---|
| 267 | 3-{2-amino-[1,2,4]triazolo[1,5-a]pyridin-7-yl}-N-[3-(3,4-dichlorophenyl)-2,2-difluoro-3-hydroxypropyl]-2-fluoro-6-methoxybenzamide | 3,4-dichlorophenyl; R = OMe; enantiomer 1 first eluted | 540.3 | 8.87 (br t, J = 6.0 Hz, 1H), 8.59 (d, J = 7.0 Hz, 1H), 7.78-7.62 (m, 3H), 7.52-7.37 (m, 2H), 7.07 (d, J = 8.5 Hz, 1H), 7.03 (d, J = 7.0 Hz, 1H), 6.62 (d, J = 5.5 Hz, 1H), 6.05 (s, 2H), 5.06-4.87 (m, 1H), 3.91 (br s, 3H), 4.01-3.66 (m, 1H), 3.50-3.40 (m, 1H), |
| 268 | 3-{2-amino-[1,2,4]triazolo[1,5-a]pyridin-7-yl}-N-[3-(3,4-dichlorophenyl)-2,2-difluoro-3-hydroxypropyl]-2-fluoro-6-methoxybenzamide | 3,4-dichlorophenyl; R = OMe; enantiomer 2 second eluted | 540.3 | 8.87 (br t, J = 6.0 Hz, 1H), 8.59 (d, J = 7.0 Hz, 1H), 7.78-7.62 (m, 3H), 7.52-7.37 (m, 2H), 7.07 (d, J = 8.5 Hz, 1H), 7.03 (d, J = 7.0 Hz, 1H), 6.62 (d, J = 5.5 Hz, 1H), 6.05 (s, 2H), 5.06-4.87 (m, 1H), 3.91 (br s, 3H), 4.01-3.66 (m, 1H), 3.50-3.40 (m, 1H), |
| 269 | 3-{2-amino-[1,2,4]triazolo[1,5-a]pyridin-7-yl}-N-[2,2-difluoro-3-(5-fluoropyridin-2-yl)-3-hydroxypropyl]-2-fluoro-6-methylbenzamide | 5-fluoropyridin-2-yl; R = Me; enantiomer 1 first eluted | 475.3 | 8.98 (br t, J = 6.1 Hz, 1H), 8.67 (d, J = 6.7 Hz, 1H), 8.57 (d, J = 2.7 Hz, 1H), 7.71-7.57 (m, 2H), 7.55 (s, 1H), 7.25 (br d, J = 7.6 Hz, 1H), 7.15 (br d, J = 4.3 Hz, 1H), 7.05 (s, 2H), 4.99 (br dd, J = 14.8, 7.8 Hz, 1H), 4.06-3.87 (m, 2H), 2.32 (s, 3H) |
| 270 | 3-{2-amino-[1,2,4]triazolo[1,5-a]pyridin-7-yl}-N-[2,2-difluoro-3-(5-fluoropyridin-2-yl)-3-hydroxypropyl]-2-fluoro-6-methylbenzamide | 5-fluoropyridin-2-yl; R = Me; enantiomer 2 second eluted | 475.3 | 8.98 (br t, J = 6.1 Hz, 1H), 8.67 (d, J = 6.7 Hz, 1H), 8.57 (d, J = 2.7 Hz, 1H), 7.81 (td, J = 8.8, 2.9 Hz, 1H), 7.71-7.57 (br d, J = 7.6 Hz, 1H), 7.15 (br d, J = 4.3 Hz, 1H), 7.05 (s, 2H), 4.99 (br dd, J = 14.8, 7.8 Hz, 1H), 4.06-3.87 (m, 2H), 2.32 (s, 3H) |

TABLE 20-continued

Compounds in Table 20 were prepared in a similar fashion to examples 264 and 265. In cases of undefined stereochemistry, compounds were isolated as racemic or diastereomeric mixtures unless otherwise noted.

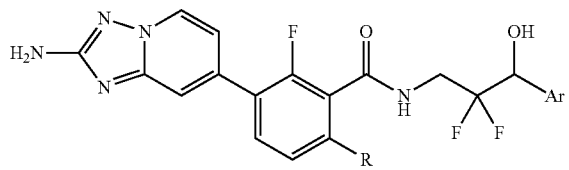

| Ex No | Name | Ar & R | M + H⁺ | 1H NMR (500 MHz, DMSO-d6) δ |
|---|---|---|---|---|
| 271 | 3-(2-amino-[1,2,4]triazolo[1,5-a]pyridin-7-yl)-6-chloro-N-(3-(5,6-dichloropyridin-2-yl)-2,2-difluoro-3-hydroxypropyl)-2-fluorobenzamide | R = Cl<br>enantiomer 1<br>first eluted | 545.0 | 9.17 (t, J = 6.5 Hz, 1H), 8.64 (d, J = 7.0 Hz, 1H), 8.44 (s, 1H), 8.14 (s, 1H), 7.75 (t, J = 8.4 Hz, 1H), 7.55-7.49 (m, 2H), 7.04 (br d, J = 6.9 Hz, 1H), 6.84 (d, J = 5.6 Hz, 1H), 6.11 (s, 2H), 5.15-5.08 (m, 1H), 3.99-3.86 (m, 2H) |
| 272 | 3-(2-amino-[1,2,4]triazolo[1,5-a]pyridin-7-yl)-6-chloro-N-(3-(5,6-dichloropyridin-2-yl)-2,2-difluoro-3-hydroxypropyl)-2-fluorobenzamide | R = Cl<br>enantiomer 2<br>second eluted | 545.3 | 9.17 (t, J = 6.5 Hz, 1H), 8.64 (d, J = 7.0 Hz, 1H), 8.44 (s, 1H), 8.14 (s, 1H), 7.75 (t, J = 8.4 Hz, 1H), 7.55-7.49 (m, 2H), 7.04 (br d, J = 6.9 Hz, 1H), 6.84 (d, J = 5.6 Hz, 1H), 6.11 (s, 2H), 5.15-5.08 (m, 1H), 3.99-3.86 (m, 2H) |

Example 273: methyl 4-(3-(3-(2-amino-[1,2,4]triazolo[1,5-a]pyridin-7-yl)-6-chloro-2-fluorobenzamido)propyl)benzoate

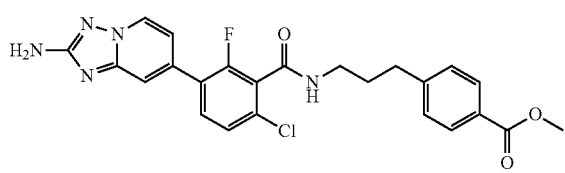 [SMILES: COC(=O)c1ccc(CCCNC(=O)c2c(Cl)ccc(-c3ccn4nc(N)nc4c3)c2F)cc1]

To a solution of 3-(2-amino-[1,2,4]triazolo[1,5-a]pyridin-7-yl)-6-chloro-2-fluorobenzoic acid (39.7 mg, 0.129 mmol) in DMF (1 mL) were added methyl 4-(3-aminopropyl)benzoate (25.0 mg, 0.129 mmol), BOP (68.7 mg, 0.155 mmol) and Hunig's base (0.090 mL, 0.517 mmol). The mixture was stirred at RT for 2 h. The reaction mixture was diluted with water, extracted with EtOAc, and the solvent was concentrated in vacuo. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 15% B, 15-55% B over 20 minutes, then a 0-minute hold at 100% B; Flow Rate: 20 mL/min to afford methyl 4-(3-(3-(2-amino-[1,2,4]triazolo[1,5-a]pyridin-7-yl)-6-chloro-2-fluorobenzamido)propyl)benzoate (14 mg, 0.030 mmol, 23% yield).

¹H NMR (500 MHz, DMSO-d₆) δ 8.90 (br t, J=5.0 Hz, 1H), 8.58 (d, J=6.7 Hz, 1H), 7.96-7.79 (m, J=7.9 Hz, 2H), 7.69 (br t, J=8.5 Hz, 1H), 7.59-7.44 (m, 2H), 7.43-7.29 (m, J=7.9 Hz, 2H), 7.08 (br d, J=7.0 Hz, 1H), 6.05 (s, 2H), 4.02-3.86 (m, 1H), 3.82-3.62 (m, 2H), 3.28 (q, J=6.1 Hz, 2H), 2.73 (br t, J=7.5 Hz, 2H), 1.91-1.72 (m, 2H), 1.39 (s, 1H).

MS ESI m/z 482.11 (M+H)⁺.

Example 274: 3-(2-amino-[1,2,4]triazolo[1,5-a]pyridin-7-yl)-2-fluoro-6-methyl-N-(2,2,4,4-tetrafluoro-3-(4-fluorophenyl)-3-hydroxybutyl)benzamide

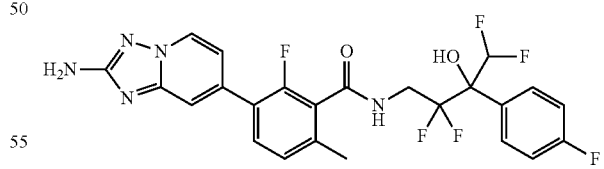

274A: 2,2,4,4-tetrafluoro-3-(4-fluorophenyl)-3-hydroxybutanamide: To a dry 100 mL flask under nitrogen atmosphere was added zinc (122 mg, 1.87 mmol) and anhydrous THF (5 mL). The resulting suspension was heated to reflux. To the refluxing suspension, ethyl 2-bromo-2,2-difluoroacetate (221 μL, 1.72 mmol) was added over 2-3 min. After 4 min, 2,2-difluoro-1-(4-fluorophenyl)ethan-1-one (250 mg, 1.44 mmol) was added in a single portion and the reaction was heated at reflux for 4 h. The reaction mixture was diluted with water and extracted with EtOAc.

The organic layer was collected and concentrated in vacuo to a crude oil which was dissolved in MeOH (4 mL) and treated with ammonia, 7M in MeOH (2.01 mL, 14.1 mmol). The resulting solution was stirred at RT for 4 h. The mixture was concentrated in vacuo to give 2,2,4,4-tetrafluoro-3-(4-fluorophenyl)-3-hydroxybutanamide (250 mg, 65% yield over 2 steps) which was used as-is in the next step.
MS ESI m/z 270.2 (M+H)+.

274B: 4-amino-1,1,3,3-tetrafluoro-2-(4-fluorophenyl)butan-2-ol: A solution of 2,2,4,4-tetrafluoro-3-(4-fluorophenyl)-3-hydroxybutanamide (250 mg, 0.929 mmol) in THF (3 mL) was treated with borane dimethyl sulfide complex, 2M in THF (1.86 mL, 3.72 mmol) and the resulting mixture was heated to 60° C. and stirred for 2 h. The mixture was allowed to come to RT and was treated with MeOH (0.5 mL) and stirred for 30 min. The solvent was removed to give a clear colorless thick oil. The oil was re-dissolved in 1M aqueous HCl solution (0.5 mL) and heated at 60° C. for 1 h. The mixture was concentrated in vacuo to give crude 4-amino-1,1,3,3-tetrafluoro-2-(4-fluorophenyl)butan-2-ol which was used directly in the next step as crude without further purification.
MS ESI m/z 255.9 (M+H)+.

274: To a solution of 3-(2-amino-[1,2,4]triazolo[1,5-a]pyridin-7-yl)-2-fluoro-6-methylbenzoic acid (20 mg, 0.070 mmol) in DMF (1 mL) were added 4-amino-1,1,3,3-tetrafluoro-2-(4-fluorophenyl)butan-2-ol (26.7 mg, 0.105 mmol), BOP (37 mg, 0.084 mmol), Hunig's base (0.049 mL, 0.28 mmol). The mixture was stirred at RT for 2 h. The reaction mixture was then diluted with water, extracted with EtOAc, and the organic was concentrated in vacuo. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 17% B, 17-57% B over 23 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to afford 3-(2-amino-[1,2,4]triazolo[1,5-a]pyridin-7-yl)-2-fluoro-6-methyl-N-(2,2,4,4-tetrafluoro-3-(4-fluorophenyl)-3-hydroxybutyl)benzamide (4.5 mg, 0.008 mmol, 13% yield).
1H NMR (500 MHz, DMSO-d6) δ 8.91 (br t, J=6.1 Hz, 1H), 8.66-8.54 (m, J=7.0 Hz, 1H), 7.70 (br dd, J=7.9, 5.8 Hz, 2H), 7.59 (t, J=7.9 Hz, 1H), 7.47 (s, 1H), 7.37-7.27 (m, 3H), 7.22 (d, J=7.9 Hz, 1H), 7.10-6.94 (m, J=7.0 Hz, 1H), 6.81-6.59 (m, 2H), 4.08-3.86 (m, 1H), 3.62 (br d, J=2.1 Hz, 1H), 3.57 (br d, J=4.3 Hz, 1H), 3.00 (s, 1H), 2.28 (s, 3H).
MS ESI m/z 524.00 (M+H)+.

Example 275: N-(3-amino-2,2-difluoro-3-(4-fluorophenyl)propyl)-3-(2-amino-[1,2,4]triazolo[1,5-a]pyridin-7-yl)-2-fluoro-6-methylbenzamide

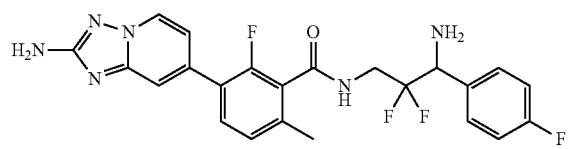 [SMILES: Cc1ccc(-c2ccn3nc(N)nc3c2)c(F)c1C(=O)NCC(F)(F)C(N)c1ccc(F)cc1]

275A: tert-butyl (tert-butoxycarbonyl)(7-(3-((2,2-difluoro-3-(4-fluorophenyl)-3-oxopropyl)carbamoyl)-2-fluoro-4-methylphenyl)-[1,2,4]triazolo[1,5-a]pyridin-2-yl)carbamate: To a solution of oxalyl chloride (42.2 μL, 0.482 mmol) in DCM (1.86 mL) at −78° C. was added DMSO (65.8 μL, 0.928 mmol), and the reaction mixture was stirred at −78° C. for 20 min. A solution of tert-butyl (S)-(tert-butoxycarbonyl)(7-(3-((2,2-difluoro-3-(4-fluorophenyl)-3-hydroxypropyl)carbamoyl)-2-fluoro-4-methylphenyl)-[1,2,4]triazolo[1,5-a]pyridin-2-yl)carbamate (250 mg, 0.371 mmol) in DCM (2 mL) was added to the reaction mixture, and the resulting mixture was stirred at −78° C. for 30 min. Triethylamine (233 μL, 1.67 mmol) was added, and the reaction was warmed up to RT and stirred for 20 min. Water was added and the aqueous layer was extracted with ethyl acetate (×3). The combined organic layers were washed with brine, dried over anhydrous sodium sulfate and filtered, and the filtrate was evaporated in vacuo to give the crude product. The crude product was purified by preparative TLC on silica gel (0.50 mm thickness) eluting with 40% ethyl acetate/hexanes to give tert-butyl (tert-butoxycarbonyl)(7-(3-((2,2-difluoro-3-(4-fluorophenyl)-3-oxopropyl)carbamoyl)-2-fluoro-4-methylphenyl)-[1,2,4]triazolo[1,5-a]pyridin-2-yl)carbamate (220 mg, 0.328 mmol, 88% yield) as a white solid.
1H NMR (500 MHz, CDCl3) δ 8.61-8.55 (m, 1H), 8.27-8.20 (m, 2H), 7.84 (s, 1H), 7.54-7.44 (m, 1H), 7.26-7.13 (m, 4H), 6.36-6.27 (m, 1H), 4.33 (td, J=13.9, 6.5 Hz, 2H), 1.51 (s, 18H).
MS ESI m/z 672.10 (M+H)+

275: To a solution of tert-butyl (tert-butoxycarbonyl)(7-(3-((2,2-difluoro-3-(4-fluorophenyl)-3-oxopropyl)carbamoyl)-2-fluoro-4-methylphenyl)-[1,2,4]triazolo[1,5-a]pyridin-2-yl)carbamate (30 mg, 0.045 mmol) in toluene (298 μL) at RT was added LHMDS (214 μL, 0.107 mmol), and the reaction mixture was stirred at RT for 20 min. Borane-methyl sulfide complex (89.0 μL, 0.179 mmol) was added, and the reaction mixture was stirred at RT for 30 min. MeOH was added carefully to quench excess BH3, and HCl, 4M in dioxane (156 μL, 0.625 mmol) was added. The reaction mixture was heated at 65° C. for 1 h. The reaction mixture was evaporated in vacuo, and the residue was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 8% B, 8-48% B over 20 minutes, then a 0-minute hold at 100% B; Flow Rate: 20 mL/min. This process gave the title compound N-(3-amino-2,2-difluoro-3-(4-fluorophenyl)propyl)-3-(2-amino-[1,2,4]triazolo[1,5-a]pyridin-7-yl)-2-fluoro-6-methylbenzamide (3.0 mg, 0.0063 mmol, 12% yield).
1H NMR (500 MHz, DMSO-d6) δ 9.03-8.90 (m, 1H), 8.61 (d, J=6.7 Hz, 1H), 7.66-7.54 (m, 2H), 7.51-7.44 (m, 3H), 7.28-7.14 (m, 3H), 7.04 (br d, J=6.8 Hz, 1H), 6.06 (s, 2H), 4.26 (br dd, J=18.6, 7.3 Hz, 1H), 4.00-3.74 (m, 3H), 2.32 (3H, s).
MS ESI m/z 473.1 (M+H)+

249

Example 276: (S)-3-(3-(2-amino-[1,2,4]triazolo[1,5-a]pyridin-7-yl)-2-fluoro-6-methylbenzamido)-2,2-difluoro-1-(4-fluorophenyl)propyl carbamate

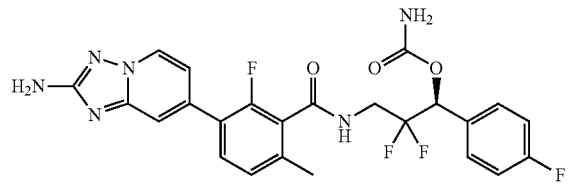 [SMILES: Cc1ccc(-c2ccn3nc(N)nc3c2)c(F)c1C(=O)NCC(F)(F)[C@@H](OC(N)=O)c1ccc(F)cc1]

A mixture of tert-butyl (S)-(tert-butoxycarbonyl)(7-(3-((2,2-difluoro-3-(4-fluorophenyl)-3-hydroxypropyl)carbamoyl)-2-fluoro-4-methylphenyl)-[1,2,4]triazolo[1,5-a]pyridin-2-yl)carbamate (50 mg, 0.074 mmol) and chlorosulfinyl isocyanate (14.8 µL, 0.148 mmol) in DCM (742 µl) was stirred at RT for 2 h. The volatiles were removed in vacuo, and HCl, 4M in 1,4-dioxane (186 µl, 0.742 mmol) was added, and the reaction mixture was heated at 70° C. for 3 h. The solvents were removed in vacuo, and the residue was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 8% B, 8-48% B over 20 minutes, then a 0-minute hold at 100% B; Flow Rate: 20 mL/min. This process gave the title compound (S)-3-(3-(2-amino-[1,2,4]triazolo[1,5-a]pyridin-7-yl)-2-fluoro-6-methylbenzamido)-2,2-difluoro-1-(4-fluorophenyl)propyl carbamate (22 mg, 0.042 mmol, 57% yield).

$^1$H NMR (500 MHz, DMSO-d6) δ 9.10-8.94 (m, 1H), 8.61 (d, J=6.9 Hz, 1H), 7.60 (t, J=8.0 Hz, 1H), 7.53-7.48 (m, 3H), 7.35-7.19 (m, 3H), 7.03 (br d, J=7.0 Hz, 1H), 6.05 (s, 2H), 5.93 (dd, J=14.3, 10.0 Hz, 1H), 4.00-3.79 (m, 2H). MS ESI m/z 517.0 (M+H)$^+$

Example 277: (S)-3-(2-amino-[1,2,4]triazolo[1,5-a]pyridin-7-yl)-N-(3-(4-chlorophenyl)-3-hydroxypropyl)-2,4-difluoro-6-methylbenzamide

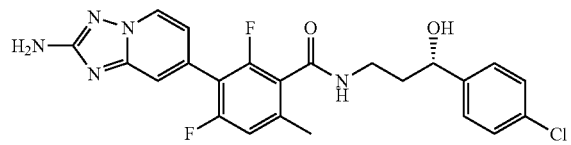 [SMILES: Cc1cc(F)c(-c2ccn3nc(N)nc3c2)c(F)c1C(=O)NCC[C@H](O)c1ccc(Cl)cc1]

277A: 1,3-difluoro-2-iodo-5-methylbenzene: A solution of 1,3-difluoro-5-methylbenzene (2.64 g, 20.6 mmol) in THF (50 mL) was stirred at −75° C. under nitrogen. BuLi, 2.5M solution in hexane (9.50 mL, 23.7 mmol) was added slowly and the mixture was stirred for 1 h before iodine (5.49 g, 21.6 mmol) was added slowly. The reaction was allowed to warm to RT and stirred for 3 h. The reaction was quenched with water and extracted with EtOAc. The organic layer was washed with brine, dried over Na$_2$SO$_4$, filtered and concentrated in vacuo to give a light tan solid (4.38 g, 17.2 mmol, 84% yield).

$^1$H NMR (499 MHz, chloroform-d) δ 6.74 (dt, J=7.8, 0.9 Hz, 2H), 2.37 (s, 3H). $^{19}$F NMR (470 MHz, chloroform-d) δ−94.00.

250

277B: 2,4-difluoro-3-iodo-6-methylbenzoic acid: A solution of diisopropylamine (4.16 mL, 29.2 mmol) in 20 mL THF was stirred at −75° C. under nitrogen. BuLi, 2.5M solution in hexane (10.3 mL, 25.7 mmol) was added slowly and the mixture was stirred for 5 min at RT before it was cannulated into a −75° C. solution of 1,3-difluoro-2-iodo-5-methylbenzene (4.36 g, 17.2 mmol) in THF (20 mL). After stirring for 1 h, carbon dioxide (6.04 g, 137 mmol) (crushed dry ice) was added. The reaction was allowed to warm to RT with stirring. The mixture was quenched by addition of water and neutralized with 60 mL of 1 N aqueous HCl and then diluted with EtOAc. The layers were separated. The aqueous layer was extracted four times with EtOAc. The organic layers were combined and washed with brine, dried over Na$_2$SO$_4$, filtered and concentrated in vacuo to afford a dark tan oil (3.59 g, 12.1 mmol, 70% crude yield). The material was used as-is without further purification in subsequent steps.

277C: methyl 2,4-difluoro-3-iodo-6-methylbenzoate: To a solution of 2,4-difluoro-3-iodo-6-methylbenzoic acid (3.59 g, 12.1 mmol) in DMF (20 mL) was added K$_2$CO$_3$ (3.33 g, 24.1 mmol) followed by MeI (1.13 mL, 18.1 mmol). The mixture was stirred at RT for 24 h. The mixture was diluted with EtOAc and water. The layers were separated. The organic layer was washed with brine, dried over Na$_2$SO$_4$, filtered and concentrated in vacuo to give a tan oil. The material was purified by silica flash chromatography, gradient 100% hexanes to 40% EtOAc in hexanes to afford the desired product (2.67 g, 8.6 mmol, 71% yield) as a light yellow solid.

$^1$H NMR (499 MHz, chloroform-d) δ 6.96 (ddd, J=10.1, 1.7, 0.8 Hz, 1H), 3.97 (s, 3H), 2.52 (s, 3H). $^{19}$F NMR (470 MHz, chloroform-d) δ−111.06, −112.18. MS ESI m/z 313.2 (M+H)$^+$ 277D: methyl 3-(2-amino-[1,2,4]triazolo[1,5-a]pyridin-7-yl)-2,4-difluoro-6-methylbenzoate: In a 150 mL pressure bottle, a mixture of methyl 2,4-difluoro-3-iodo-6-methylbenzoate (825 mg, 2.64 mmol), bis(pinacolato)diboron (839 mg, 3.30 mmol), potassium acetate (778 mg, 7.93 mmol), and [1,1'-bis(diphenylphosphino)ferrocene]dichloropalladium(ii) (97 mg, 0.132 mmol) in 1,4-dioxane (8 mL) (degassed with nitrogen) was stirred at 100° C. After 1 h, LCMS showed that the reaction was complete. To the crude reaction mixture was added dioxane (2 mL), 7-bromo-[1,2,4]triazolo[1,5-a]pyridin-2-amine (562 mg, 2.64 mmol), PdCl$_2$(dppf)-CH$_2$Cl$_2$ adduct (86 mg, 0.106 mmol) and 2 M aqueous K$_3$PO$_4$ (3.30 mL, 6.60 mmol). After nitrogen was bubbled through for 5 min, the mixture was stirred at 100° C. for 11 h. The reaction mixture was diluted with EtOAc and water. The layers were separated. Silica TLC (80% EtOAc/hexane) showed a polar blue spot (Rf ~0.2) with a little tailing. The organic layer was dried over Na$_2$SO$_4$, filtered and concentrated in vacuo. The residue was purified by silica flash chromatography, elution gradient 100% hexanes up to 90% EtOAc in hexanes to afford the desired product (310 mg, 0.974 mmol, 37% yield) as a light yellow solid.

$^1$H NMR (499 MHz, chloroform-d) δ 8.38 (dd, J=6.9, 0.9 Hz, 1H), 7.30 (dd, J=1.8, 0.9 Hz, 1H), 6.94 (ddd, J=10.1, 1.6, 0.8 Hz, 1H), 6.71 (ddd, J=6.9, 1.8, 0.8 Hz, 1H), 4.68 (s, 2H), 3.96 (s, 3H), 2.24 (d, J=0.7 Hz, 3H). $^{19}$F NMR (470 MHz, chloroform-d) δ−110.53, −110.65. MS ESI m/z 319.1 (M+H)$^+$ 277E: 3-(2-amino-[1,2,4]triazolo[1,5-a]pyridin-7-yl)-2,4-difluoro-6-methylbenzoic acid: To a solution of methyl 3-(2-amino-[1,2,4]triazolo[1,5-a]pyridin-7-yl)-2,4-difluoro-6-methylbenzoate (310 mg, 0.974 mmol) in THF (4 mL) was added LiOH, 2M aqueous (1.95 mL, 3.90 mmol), and MeOH (3 mL). The mixture was stirred at RT for 18 h. 1N aqueous HCl (4 mL) was added and volatiles were removed in vacuo to afford a tan solid (600 mg, 0.974 mmol, 100% crude yield assumed with 60% purity). The material was used as-is without further purification in subsequent steps. MS ESI m/z 305.4 (M+H)$^+$ 277: A mixture of 3-(2-amino-[1,2,4]triazolo[1,5-a]pyridin-7-yl)-2,4-difluoro-6-methylbenzoic acid (40 mg, 0.079 mmol), BOP (52.3 mg, 0.118 mmol), (S)-3-amino-1-(4-chlorophenyl)propan-1-ol hydrochloride (21 mg, 0.095 mmol) and Hunig's base (0.069 mL, 0.39 mmol) in DMF (0.5 mL) was stirred at room temperature overnight. The mixture was diluted with a small amount of MeOH and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 14% B, 14-54% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give the title compound (S)-3-(2-amino-[1,2,4]triazolo[1,5-a]pyridin-7-yl)-N-(3-(4-chlorophenyl)-3-hydroxypropyl)-2,4-difluoro-6-methylbenzamide (28.4 mg, 0.060 mmol, 76% yield).

$^1$H NMR (500 MHz, DMSO-d$_6$) δ 8.77 (t, J=5.5 Hz, 1H), 8.61 (dd, J=6.8, 1.0 Hz, 1H), 7.36 (q, J=8.5 Hz, 4H), 7.30 (d, J=1.6 Hz, 1H), 7.19 (d, J=9.8 Hz, 1H), 6.80 (dd, J=6.9, 1.8 Hz, 1H), 4.62 (t, J=6.5 Hz, 1H), 3.28 (hept, J=6.4 Hz, 2H), 2.19 (s, 3H), 1.78 (q, J=6.9 Hz, 2H).
$^{19}$F NMR (471 MHz, DMSO-d$_6$) δ−115.16, −115.28.
MS ESI m/z 472.4 (M+H)$^+$ Example 278: (R)-3-(2-amino-[1,2,4]triazolo[1,5-a]pyridin-7-yl)-N-(3-(4-chlorophenyl)-3-hydroxypropyl)-2,4-difluoro-6-methylbenzamide

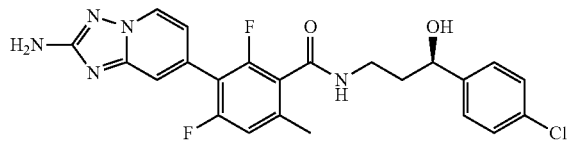

A mixture of 3-(2-amino-[1,2,4]triazolo[1,5-a]pyridin-7-yl)-2,4-difluoro-6-methylbenzoic acid (40 mg, 0.079 mmol), BOP (52.3 mg, 0.118 mmol), (R)-3-amino-1-(4-chlorophenyl)propan-1-ol hydrochloride (21 mg, 0.095 mmol) and Hunig's base (0.069 mL, 0.39 mmol) in DMF (0.5 mL) was stirred at room temperature overnight. The mixture was diluted with a small amount of MeOH and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 14% B, 14-54% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give the title compound (R)-3-(2-amino-[1,2,4]triazolo[1,5-a]pyridin-7-yl)-N-(3-(4-chlorophenyl)-3-hydroxypropyl)-2,4-difluoro-6-methylbenzamide (21.9 mg, 0.046 mmol, 58% yield).

$^1$H NMR (500 MHz, DMSO-d$_6$) δ 8.73 (t, J=5.5 Hz, 1H), 8.61 (d, J=6.7 Hz, 1H), 7.42-7.32 (m, 4H), 7.30 (t, J=1.2 Hz, 1H), 7.20 (d, J=9.7 Hz, 1H), 6.79 (dd, J=7.0, 1.8 Hz, 1H), 4.63 (q, J=6.1 Hz, 1H), 3.29 (hept, J=6.1 Hz, 2H), 2.20 (s, 3H), 1.79 (q, J=7.0 Hz, 2H).
MS ESI m/z 472.4 (M+H)$^+$ Example 279: 3-(2-amino-[1,2,4]triazolo[1,5-a]pyridin-7-yl)-2-fluoro-N-(3-(4-fluorophenyl)-2-hydroxy-2-methyl-3-oxopropyl)-6-methylbenzamide

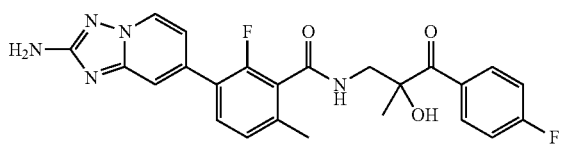 [SMILES: Cc1ccc(-c2ccn3nc(N)nc3c2)c(F)c1C(=O)NCC(C)(O)C(=O)c1ccc(F)cc1]

279A: 1-(4-fluorophenyl)-2-methylprop-2-en-1-ol: In a 250 mL oven-dried round-bottomed flask was dissolved 4-fluorobenzaldehyde (1.24 g, 9.99 mmol) in THF (20 mL) to give a colorless solution. Prop-1-en-2-yl magnesium bromide, 0.5M solution in THF (22.0 mL, 11.0 mmol) was added dropwise at RT. The mixture was stirred at RT for 30 min. The reaction was quenched with saturated aqueous NH$_4$Cl solution and diluted with EtOAc. The layers were separated. The organic layer was dried and concentrated to the crude product as a slightly tan oil (2.12 g, 9.99 mmol, 100% crude yield assumed). The material was used as-is in subsequent steps without further purification.

279B: (4-fluorophenyl)(2-methyloxiran-2-yl)methanol: In a 250 mL oven-dried round-bottomed flask was dissolved 1-(4-fluorophenyl)-2-methylprop-2-en-1-ol (831 mg, 5.00 mmol) in CH$_2$Cl$_2$ (20 mL) to give a colorless solution. m-CPBA (863 mg, 5.00 mmol) was added followed by sodium bicarbonate (420 mg, 5.00 mmol). The mixture was stirred at RT for 16 h. The reaction mixture was diluted with ether and water. The layers were separated. The organic layer was washed three times with saturated aqueous NaHCO$_3$ solution and with brine. The organic solution was then dried over Na$_2$SO$_4$ and concentrated in vacuo to give the crude product as a light yellow oil (836 mg, crude 92% yield over two steps). The material was used as-is in subsequent steps without further purification.

279C: 3-amino-1-(4-fluorophenyl)-2-methylpropane-1,2-diol: In a 20 mL pressure vial were combined (4-fluorophenyl)(2-methyloxiran-2-yl)methanol (274 mg, 1.50 mmol) and ammonia, 7M in MeOH (2.00 mL, 14.0 mmol). The mixture was stirred at RT for 18 h. The reaction was then heated at 65° C. for 5 h. The volatiles were removed in vacuo to leave the crude desired product as a slightly tan dense oil (200 mg, 1.01 mmol, 67% yield). The material was used as-is without further purification.
MS ESI m/z 200.1 (M+H)$^+$ 279D: 3-(2-amino-[1,2,4]triazolo[1,5-a]pyridin-7-yl)-2-fluoro-N-(3-(4-fluorophenyl)-2,3-dihydroxy-2-methylpropyl)-6-methylbenzamide: A mixture of lithium 3-(2-amino-[1,2,4]triazolo[1,5-a]pyridin-7-yl)-2-fluoro-6-methylbenzoate (58.4 mg, 0.200 mmol) and BOP (133 mg, 0.300 mmol), 3-amino-1-(4-fluorophenyl)-2-methylpropane-1,2-diol (39.8 mg, 0.200 mmol) and Hunig's base (0.140 mL, 0.800 mmol) in DMF (1 mL) was stirred at room temperature for 18 h. The mixture was diluted with water and EtOAc. The layers were separated. The organic layer was dried over $Na_2SO_4$, filtered and concentrated in vacuo to give crude 3-(2-amino-[1,2,4]triazolo[1,5-a]pyridin-7-yl)-2-fluoro-N-(3-(4-fluorophenyl)-2,3-dihydroxy-2-methylpropyl)-6-methylbenzamide (0.062 g, 0.133 mmol, 66% yield) which was used directly in the next step without further purification.

MS ESI m/z 468.3 (M+H)$^+$

279: A mixture of 3-(2-amino-[1,2,4]triazolo[1,5-a]pyridin-7-yl)-2-fluoro-N-(3-(4-fluorophenyl)-2,3-dihydroxy-2-methylpropyl)-6-methylbenzamide (0.062 g, 0.133 mmol) and IBX (0.067 g, 0.239 mmol) in DMSO (1 mL) was stirred at room temperature for 22 h. The mixture was diluted with a small amount of methanol and filtered to prepare a sample for reverse phase preparative HPLC purification. The crude material was purified via preparative LC/MS with the following conditions: Column: XBridge C18, 200 mm×19 mm, 5 μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge Phenyl, 200 mm×19 mm, 5 μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 16% B, 16-46% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation. Thus, was obtained 3-(2-amino-[1,2,4]triazolo[1,5-a]pyridin-7-yl)-2-fluoro-N-(3-(4-fluorophenyl)-2-hydroxy-2-methyl-3-oxopropyl)-6-methylbenzamide (2.0 mg, 0.0043 mmol, 3% yield).

$^1$H NMR (500 MHz, DMSO-d$_6$) δ 8.67-8.57 (m, 2H), 8.27 (dd, J=8.6, 5.7 Hz, 2H), 7.55 (t, J=8.0 Hz, 1H), 7.47 (s, 1H), 7.32 (d, J=8.7 Hz, 2H), 7.28 (d, J=10.2 Hz, 1H), 7.17 (d, J=4.9 Hz, 1H), 7.07 (s, 1H), 7.04 (d, J=7.0 Hz, 1H), 2.25 (s, 3H), 1.45 (s, 3H).

MS ESI m/z 466.2 (M+H)$^+$

Example 280: 3-(2-amino-[1,2,4]triazolo[1,5-a]pyridin-7-yl)-6-chloro-N-(2,2-difluoro-3-(4-fluorophenyl)-3-oxopropyl)-2-fluorobenzamide

280A: tert-butyl (tert-butoxycarbonyl)(7-(4-chloro-3-((2,2-difluoro-3-(4-fluorophenyl)-3-oxopropyl)carbamoyl)-2-fluorophenyl)-[1,2,4]triazolo[1,5-a]pyridin-2-yl)carbamate: In a 1 dram pressure vial, a solution of tert-butyl (R)-(tert-butoxycarbonyl)(7-(4-chloro-3-((2,2-difluoro-3-(4-fluorophenyl)-3-hydroxypropyl)carbamoyl)-2-fluorophenyl)-[1,2,4]triazolo[1,5-a]pyridin-2-yl)carbamate (73.0 mg, 0.105 mmol) and Dess-Martin periodinane (134 mg, 0.316 mmol) in $CH_2Cl_2$ (0.8 mL) was stirred at RT for 3 h. The reaction mixture was directly loaded onto a 4 g silica gel cartridge and eluted with EtOAc. The desired product fractions were combined and concentrated to a tan oil (68.6 mg, 94% yield) which was used directly in the next step.

MS ESI m/z 692.6 (M+H)$^+$

280: A solution of tert-butyl (tert-butoxycarbonyl)(7-(4-chloro-3-((2,2-difluoro-3-(4-fluorophenyl)-3-oxopropyl)carbamoyl)-2-fluorophenyl)-[1,2,4]triazolo[1,5-a]pyridin-2-yl)carbamate (68.6 mg, 0.099 mmol) in $CH_2Cl_2$ (0.8 mL) was treated with TFA (500 μL, 6.49 mmol) and the resulting mixture was stirred at RT for 1 h. The reaction mixture was concentrated, the residue was dissolved in DMF and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 17% B, 17-57% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give the title compound 3-(2-amino-[1,2,4]triazolo[1,5-a]pyridin-7-yl)-6-chloro-N-(2,2-difluoro-3-(4-fluorophenyl)-3-oxopropyl)-2-fluorobenzamide (14.3 mg, 0.029 mmol, 29% yield).

$^1$H NMR (500 MHz, DMSO-d$_6$) δ 9.39 (dd, J=13.5, 9.2 Hz, 1H), 8.65 (d, J=7.1 Hz, 1H), 8.18 (t, J=7.1 Hz, 2H), 7.76 (t, J=8.4 Hz, 1H), 7.67-7.58 (m, 1H), 7.50 (dd, J=19.5, 9.9 Hz, 3H), 7.09-7.01 (m, 1H), 4.29-4.13 (m, 2H); $^{19}$F NMR (471 MHz, DMSO-d6) δ−102.47, −103.90, −116.98.

MS ESI m/z 492.4 (M+H)$^+$

Example 281: 3-(2-amino-[1,2,4]triazolo[1,5-a]pyridin-7-yl)-N-(2,2-difluoro-3-(4-fluorophenyl)-3-oxopropyl)-2-fluoro-6-methylbenzamide

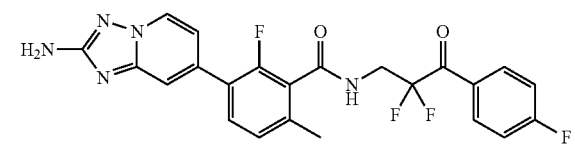

281A: 3-bromo-N-(2,2-difluoro-3-(4-fluorophenyl)-3-hydroxypropyl)-2-fluoro-6-methylbenzamide: To a solution of 3-bromo-2-fluoro-6-methylbenzoic acid (5.23 g, 22.4 mmol) in DMF (30 mL) was added HATU (10.5 g, 27.6 mmol) followed by DIPEA (7.53 mL, 43.1 mmol) at RT. After 10 min, 3-amino-2,2-difluoro-1-(4-fluorophenyl)propan-1-ol (3.54 g, 17.25 mmol) was added to the mixture and the result was stirred at RT for 3 h. EtOAc was added, the mixture was washed with water and the organic phase was concentrated in vacuo. The residue was purified via silica gel chromatography (120 g, elution gradient 100% hexanes to 100% EtOAc) to give 3-bromo-N-(2,2-difluoro-3-(4-fluorophenyl)-3-hydroxypropyl)-2-fluoro-6-methylbenzamide (6.80 g, 16.2 mmol, 94% yield).

MS ESI m/z 422.3 (M+H)$^+$

281B: tert-butyl (7-(3-((2,2-difluoro-3-(4-fluorophenyl)-3-hydroxypropyl)carbamoyl)-2-fluoro-4-methylphenyl)-[1,2,4]triazolo[1,5-a]pyridin-2-yl)carbamate: A pressure vial was charged with a stir bar, N,N-bis-Boc-2-amino-7-(4,4,5,5-tetramethyl-1,3,2-dioxaborolan-2-yl)-[1,2,4]triazolo[1,5-a]pyridine (307 mg, 0.667 mmol), 3-bromo-N-(2,2-difluoro-3-(4-fluorophenyl)-3-hydroxypropyl)-2-fluoro-6-methylbenzamide (233.7 mg, 0.556 mmol), [1,1'-bis(diphenylphosphino)ferrocene]dichloropalladium(II), complex with dichloromethane (27 mg, 0.033 mmol), dioxane (2.8 mL) and tripotassium phosphate 2M aqueous solution (0.834 mL, 1.67 mmol). The mixture was degassed by bubbling with a stream of nitrogen. The vial was sealed and mixture was stirred at 70° C. for 4 h. After cooling to RT, the mixture was diluted with EtOAc and water and the layers were separated. The organic layer was washed with brine, dried over anhydrous sodium sulfate and concentrated in vacuo. The residue was purified by silica flash chromatography (24 g), elution gradient 100% hexanes to 50% EtOAc in hexanes to afford the desired product (336 mg, 0.498 mmol, 90% yield) as a slightly tan oil.

MS ESI m/z 674.4 (M+H)$^+$

281C: tert-butyl (tert-butoxycarbonyl)(7-(3-((2,2-difluoro-3-(4-fluorophenyl)-3-oxopropyl)carbamoyl)-2-fluoro-4-methylphenyl)-[1,2,4]triazolo[1,5-a]pyridin-2-yl)carbamate: In a 1 dram pressure vial, a solution of tert-butyl (tert-butoxycarbonyl)(7-(3-((2,2-difluoro-3-(4-fluorophenyl)-3-hydroxypropyl)carbamoyl)-2-fluoro-4-methylphenyl)-[1,2,4]triazolo[1,5-a]pyridin-2-yl)carbamate (89.0 mg, 0.132 mmol) and Dess-Martin periodinane (84.0 mg, 0.198 mmol) in CH$_2$Cl$_2$ (1 mL) was stirred at RT for 2 h. The reaction mixture was loaded onto a 4 g silica gel cartridge and eluted with EtOAc. The desired product fractions were combined and concentrated to a tan oil (90 mg, 0.132 mmol, 100% crude yield) which was directly used in the next step.

MS ESI m/z 672.3 (M+H)$^+$

281: A solution of tert-butyl (tert-butoxycarbonyl)(7-(3-((2,2-difluoro-3-(4-fluorophenyl)-3-oxopropyl)carbamoyl)-2-fluoro-4-methylphenyl)-[1,2,4]triazolo[1,5-a]pyridin-2-yl)carbamate (89.0 mg, 0.133 mmol) in CH$_2$Cl$_2$ (1.5 mL) was treated with TFA (1.0 mL, 12 mmol) and the resulting mixture was stirred at RT for 1 h. The reaction mixture was concentrated, the residue was dissolved in DMF and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 14% B, 14-54% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to provide the title compound 3-(2-amino-[1,2,4]triazolo[1,5-a]pyridin-7-yl)-N-(2,2-difluoro-3-(4-fluorophenyl)-3-oxopropyl)-2-fluoro-6-methylbenzamide (11.8 mg, 18 μmol, 14% yield).

$^1$H NMR (500 MHz, DMSO-d$_6$) δ 9.21 (t, J=6.3 Hz, 1H), 8.60 (dd, J=7.3, 3.0 Hz, 1H), 8.17 (dd, J=8.6, 5.5 Hz, 2H), 7.60 (dd, J=9.5, 6.5 Hz, 1H), 7.48 (q, J=9.7 Hz, 3H), 7.22 (d, J=8.0 Hz, 1H), 7.03 (d, J=7.0 Hz, 1H), 6.07 (s, 2H), 4.19 (td, J=15.5, 6.1 Hz, 2H), 2.27 (s, 3H).

MS ESI m/z 472.2 (M+H)$^+$

Example 282: (S)-3-(2-amino-[1,2,4]triazolo[1,5-a]pyridin-7-yl)-6-chloro-2-fluoro-N-(2,2,3-trifluoro-3-(4-fluorophenyl)propyl)benzamide

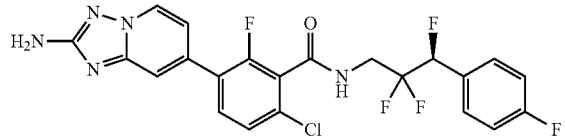 [SMILES: Nc1nc2cc(-c3ccc(Cl)c(C(=O)NCC(F)(F)C(=O)c4ccc(F)cc4)c3F)ccn2n1]

282A: (R)-2-(2,2-difluoro-3-(4-fluorophenyl)-3-hydroxypropyl)isoindoline-1,3-dione: To a mixture of (R)-3-amino-2,2-difluoro-1-(4-fluorophenyl)propan-1-ol (1.30 g, 6.34 mmol) in acetonitrile (60 mL) was added phthalic anhydride (1.15 g, 7.76 mmol). The mixture was stirred at 85° C. for 18 h. The solvent was removed in vacuo and the residue was dissolved in toluene (70 mL), treated with 4A mol sieves and heated at 115° C. for 8.5 h. The reaction was filtered through a small pad of Celite and the solvent was removed in vacuo. The residue was purified via flash column chromatography (40 g silica, gradient 100% dichloromethane to 100% EtOAc). Fractions containing clean product were combined and concentrated to give (R)-2-(2,2-difluoro-3-(4-fluorophenyl)-3-hydroxypropyl)isoindoline-1,3-dione (1.68 g, 5.01 mmol, 79% yield).

$^1$H NMR (500 MHz, CHLOROFORM-d) δ 8.00-7.91 (m, 2H), 7.88-7.78 (m, 2H), 7.47 (dd, J=8.3, 5.4 Hz, 2H), 7.14-7.02 (m, 2H), 4.84 (dt, J=18.4, 4.8 Hz, 1H), 4.40-4.13 (m, 2H), 3.80 (d, J=5.0 Hz, 1H).

282B: (S)-2-(2,2,3-trifluoro-3-(4-fluorophenyl)propyl)isoindoline-1,3-dione:

To a suspension of (R)-2-(2,2-difluoro-3-(4-fluorophenyl)-3-hydroxypropyl)isoindoline-1,3-dione (1.60 g, 4.77 mmol) in dichloromethane (12 mL) was added DAST (3.2 mL, 24 mmol) and the reaction was heated to 50° C. for 2 h. The reaction was quenched with water (10 mL) and diluted with dichloromethane (175 mL). The organic layer was washed with water (2×10 mL), brine (1×10 mL), dried over anhydrous sodium sulfate, filtered and evaporated to dryness. The residue was purified via flash column chromatography (120 g silica, gradient 100% dichloromethane to 100% EtOAc). Fractions containing clean product were combined and concentrated to give (R)-2-(2,2-difluoro-3-(4-fluorophenyl)-3-hydroxypropyl)isoindoline-1,3-dione (406 mg, 1.21 mmol, 25% yield).

$^1$H NMR (500 MHz, CHLOROFORM-d) δ 8.00-7.91 (m, 2H), 7.88-7.78 (m, 2H), 7.47 (dd, J=8.3, 5.4 Hz, 2H), 7.14-7.02 (m, 2H), 4.84 (dt, J=18.4, 4.8 Hz, 1H), 4.40-4.13 (m, 2H), 3.80 (d, J=5.0 Hz, 1H).

$^{19}$F NMR (471 MHz, CHLOROFORM-d) δ-110.69--111.96 (m, 1F), -115.31--116.56 (m, 1F), -191.69 (ddd, J=44.5, 10.6, 8.5 Hz, 1F)

282C: (S)-2,2,3-trifluoro-3-(4-fluorophenyl)propan-1-amine: To a suspension of (S)-2-(2,2,3-trifluoro-3-(4-fluorophenyl)propyl)isoindoline-1,3-dione (406 mg, 1.20 mmol) in ethanol was added hydrazine hydrate, 50-60% (1.00 mL, 17.5 mmol) and the reaction was heated at 80° C. for 10 min. The reaction was diluted with ethanol (3 mL), the resulting white precipitate was filtered off and the filtrate was concentrated in vacuo. The residue was treated with dichloromethane and the resulting white precipitate was filtered off. The filtrate was concentrated in vacuo to give (S)-2,2,3-trifluoro-3-(4-fluorophenyl)propan-1-amine (229 mg, 1.11 mmol, 92% yield).

¹H NMR (500 MHz, CHLOROFORM-d) δ 7.44 (dd, J=8.0, 5.6 Hz, 2H), 7.13 (t, J=8.6 Hz, 2H), 5.79-5.57 (m, 1H), 3.32-3.00 (m, 2H), 1.50-1.18 (m, 2H).
MS ESI m/z 207.8 (M+H)⁺

282: To a solution of 3-(2-amino-[1,2,4]triazolo[1,5-a]pyridin-7-yl)-6-chloro-2-fluorobenzoic acid (20 mg, 0.065 mmol), (S)-2,2,3-trifluoro-3-(4-fluorophenyl)propan-1-amine (15 mg, 0.072 mmol) and N,N-diisopropylethylamine (35 μL, 0.20 mmol) in DMF (1 mL) was added BOP (40 mg, 0.090 mmol). The reaction was stirred at RT for 3 d, then the mixture was filtered and purified via preparative LCMS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 19% B, 19-59% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give the title compound (S)-3-(2-amino-[1,2,4]triazolo[1,5-a]pyridin-7-yl)-6-chloro-2-fluoro-N-(2,2,3-trifluoro-3-(4-fluorophenyl)propyl)benzamide (22.3 mg, 0.045 mmol, 69% yield).

¹H NMR (500 MHz, DMSO-d₆) δ 9.29 (t, J=6.1 Hz, 1H), 8.63 (d, J=7.0 Hz, 1H), 7.75 (t, J=8.4 Hz, 1H), 7.62-7.46 (m, 4H), 7.33 (t, J=8.8 Hz, 2H), 7.05 (br d, J=7.0 Hz, 1H), 6.18-5.88 (m, 3H), 4.05-3.84 (m, 2H).
MS ESI m/z 496.0, 497.9 (M+H)⁺

Example 283: 3-(2-amino-[1,2,4]triazolo[1,5-a]pyridin-7-yl)-N-(2,2-difluoro-3-hydroxy-3-(2,4,6-trifluorophenyl)propyl)-2-fluoro-6-methylbenzamide enantiomer 1

283A: ethyl 2,2-difluoro-3-hydroxy-3-(2,4,6-trifluorophenyl)propanoate: To a dry 500 mL, 3-neck round bottom flask under nitrogen was added zinc (2.50 g, 38.2 mmol) and anhydrous THF (100 mL). The reaction was flushed with nitrogen, placed into a 75° C. oil bath and slowly treated with ethyl bromodifluoroacetate (4.42 mL, 34.5 mmol) over 3-4 min. The reaction was refluxed for 5 min, then treated with 2,4,6-trifluorobenzaldehyde (5.00 g, 31.2 mmol) and heated at 75° C. for 5.5 h. The reaction was filtered through small pad of Celite and the filtrate was evaporated to dryness in vacuo. The residue was redissolved in ethyl acetate and washed 1 N aqueous HCl (2×20 mL), brine (1×10 mL), dried over anhydrous sodium sulfate, filtered and evaporated to dryness. The crude product was purified via flash column chromatography (80 g silica, gradient 100% hexanes to 100% ethyl acetate) to give ethyl 2,2-difluoro-3-hydroxy-3-(2,4,6-trifluorophenyl)propanoate (4.61 g, 16.2 mmol, 52% yield).

¹H NMR (500 MHz, CHLOROFORM-d) δ 6.76 (t, J=8.5 Hz, 2H), 5.52 (ddd, J=19.5, 11.1, 5.1 Hz, 1H), 4.49-4.34 (m, 2H), 3.19 (dt, J=11.0, 4.0 Hz, 1H), 1.40 (t, J=7.2 Hz, 3H).

283B: 2,2-difluoro-3-hydroxy-3-(2,4,6-trifluorophenyl)propanamide: To a solution of ethyl 2,2-difluoro-3-hydroxy-3-(2,4,6-trifluorophenyl)propanoate (2.60 g, 9.15 mmol) in methanol (5 mL) was added ammonia, 7M in methanol (6.80 mL, 47.6 mmol) and the resulting solution was stirred at room temp for 195 min. The solvent was removed in vacuo to give 2,2-difluoro-3-hydroxy-3-(2,4,6-trifluorophenyl)propanamide (2.17 g, 8.51 mmol, 93% yield) which was used without purification in subsequent steps.
MS ESI m/z 253.85 (M−H)⁻

283C: 3-amino-2,2-difluoro-1-(2,4,6-trifluorophenyl)propan-1-ol: To a solution of 2,2-difluoro-3-hydroxy-3-(2,4,6-trifluorophenyl)propanamide (1.26 g, 4.94 mmol) in anhydrous THF (15 mL) was added borane dimethyl sulfide complex solution, 2.0 M in THF (7.50 mL, 15.0 mmol) and the reaction was heated to 80° C. for 3 h. The reaction was cooled to 0° C., quenched with methanol (30 mL), stirred at room temp for 30 min and the volatiles were removed in vacuo. The residue was redissolved in methanol (35 mL) and evaporated to dryness again to give 3-amino-2,2-difluoro-1-(2,4,6-trifluorophenyl)propan-1-ol (1.22 g, 5.0 mmol, quantitative yield).
MS ESI m/z 241.85 (M+H)⁺

283: To a dry reaction vial was added 3-(2-((tert-butoxycarbonyl)amino)-[1,2,4]triazolo[1,5-a]pyridin-7-yl)-2-fluoro-6-methylbenzoic acid (200 mg, 0.518 mmol), 3-amino-2,2-difluoro-1-(2,4,6-trifluorophenyl)propan-1-ol (135 mg, 0.560 mmol), anhydrous CH₂Cl₂ and N,N-diisopropylethylamine (450 μL, 2.58 mmol). The reaction was flushed briefly with nitrogen, then treated with BOP (300 mg, 0.678 mmol) and the result was stirred at RT for 18 h. The volatiles were removed under a gentle stream of nitrogen and the residue was redissolved in methanol (2 mL), treated with 4N HCl in dioxane (4.0 mL, 16 mmol)) and heated at 60° C. for 90 min. The reaction was treated with additional 4N HCl in dioxane (2.0 mL, 8.0 mmol) and heated at 60° C. for 3.5 h. The volatiles were removed in vacuo and the crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient a 0-minute hold at 12% B, 12-52% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The racemate thus isolated was further subjected to SFC chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 60% CO2/40% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 60% CO2/40% MeOH w/0.1% DEA; Flow Rate: 60 mL/min; Detector Wavelength: 220 nm; Injection details: 1500 μL injections of 10.6 mg dissolved in 3 mL MeOH. Fractions containing the first eluting isomer were combined and dried to afford 3-(2-amino-[1,2,4]triazolo[1,5-a]pyridin-7-yl)-N-(2,2-difluoro-3-hydroxy-3-(2,4,6-trifluorophenyl)propyl)-2-fluoro-6-methylbenzamide (28.5 mg, 0.0560 mmol, ee >95%, 34% yield) as the first eluting isomer. The absolute stereochemistry was not determined.

¹H NMR (500 MHz, DMSO-d₆) δ 9.03 (br t, J=6.0 Hz, 1H), 8.59 (d, J=7.0 Hz, 1H), 7.58 (t, J=8.1 Hz, 1H), 7.48 (s,

1H), 7.28-7.12 (m, 3H), 7.05 (br d, J=6.7 Hz, 1H), 5.35-5.17 (m, 1H), 4.09-3.88 (m, 2H), 2.30 (s, 3H).
MS ESI m/z 510.3 (M+H)+

Example 284: 3-(2-amino-[1,2,4]triazolo[1,5-a]pyridin-7-yl)-N-(2,2-difluoro-3-hydroxy-3-(2,4,6-trifluorophenyl)propyl)-2-fluoro-6-methylbenzamide

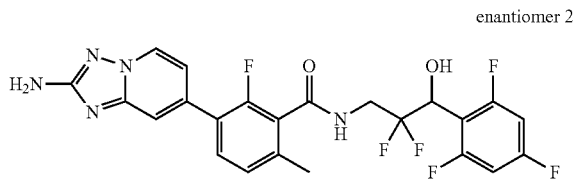 [SMILES: Cc1ccc(-c2ccn3nc(N)nc3c2)c(F)c1C(=O)NCC(F)(F)C(O)c1c(F)cc(F)cc1F]

enantiomer 2

The title compound 3-(2-amino-[1,2,4]triazolo[1,5-a]pyridin-7-yl)-N-(2,2-difluoro-3-hydroxy-3-(2,4,6-trifluorophenyl)propyl)-2-fluoro-6-methylbenzamide enantiomer 2 (29.2 mg, 0.057 mmol, ee >95%, 35% yield) was obtained as the second eluting isomer from the chiral SFC purification described for example 283. The absolute stereochemistry was not determined.
$^1$H NMR (500 MHz, DMSO-d$_6$) δ 9.03 (br t, J=6.1 Hz, 1H), 8.59 (br d, J=6.8 Hz, 1H), 7.58 (br t, J=8.0 Hz, 1H), 7.48 (s, 1H), 7.26-7.11 (m, 3H), 7.09-6.99 (m, 1H), 5.32-5.16 (m, 1H), 4.11-3.89 (m, 2H), 2.30 (s, 3H).
MS ESI m/z 510.3 (M+H)+

Example 285: (S)-3-(2-amino-[1,2,4]triazolo[1,5-a]pyridin-7-yl)-2,6-difluoro-N-(2,2,3-trifluoro-3-(4-fluorophenyl)propyl)benzamide

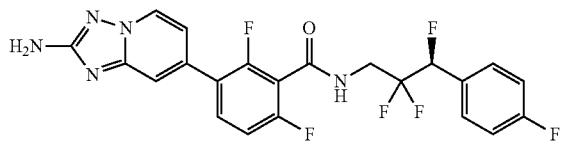 [SMILES: Nc1nc2cc(-c3ccc(F)c(C(=O)NCC(F)(F)[C@@H](F)c4ccc(F)cc4)c3F)ccn2n1]

285A: 3-(2-(di-(tert-butoxycarbonyl)amino)-[1,2,4]triazolo[1,5-a]pyridin-7-yl)-2,6-difluorobenzoic acid: To a solution of N,N-bis-Boc-2-amino-7-(4,4,5,5-tetramethyl-1,3,2-dioxaborolan-2-yl)-[1,2,4]triazolo[1,5-a]pyridine (1.80 g, 3.91 mmol), 3-bromo-2,6-difluorobenzoic acid (1.11 g, 4.69 mmol), and tripotassium phosphate, 2M aqueous solution (9.78 mL, 19.5 mmol) in dioxane (19.5 mL) was added [1,1'-bis(di-tert-butylphosphino)ferrocene]dichloropalladium(II) (0.127 g, 0.196 mmol). The reaction was flushed well with nitrogen and heated at 60° C. for 5 h. The crude mixture was acidified with acetic acid (2.24 mL, 39.1 mmol), concentrated onto Celite and purified via flash column chromatography (80 g silica, gradient 100% dichloromethane to 50% EtOAc/dichloromethane). Fractions containing clean product were combined and concentrated to give 3-(2-(di-(tert-butoxycarbonyl)amino)-[1,2,4]triazolo[1,5-a]pyridin-7-yl)-2,6-difluorobenzoic acid (1.50 g, 3.06 mmol, 78% yield).
MS ESI m/z 491.1 (M+H)+
285B: 3-(2-amino-[1,2,4]triazolo[1,5-a]pyridin-7-yl)-2,6-difluorobenzoic acid: To a solution of 3-(2-(di-(tert-butoxycarbonyl)amino)-[1,2,4]triazolo[1,5-a]pyridin-7-yl)-2,6-difluorobenzoic acid (1.27 g, 2.58 mmol) in dichloromethane was added TFA (6.46 mL, 84.0 mmol) and the reaction was stirred at RT for 16 h. The volatiles were removed in vacuo to give 3-(2-amino-[1,2,4]triazolo[1,5-a]pyridin-7-yl)-2,6-difluorobenzoic acid (0.50 g, 1.7 mmol, 67% yield) which was used without further purification.
MS ESI m/z 290.8 (M+H)+
285: To a dry reaction vial was added 3-(2-amino-[1,2,4]triazolo[1,5-a]pyridin-7-yl)-2,6-difluorobenzoic acid (20 mg, 0.069 mmol), (S)-2,2,3-trifluoro-3-(4-fluorophenyl)propan-1-amine (15 mg, 0.072 mmol), DMF (1.0 mL) and N,N-diisopropylethylamine (35 µL, 0.20 mmol). The reaction was flushed with nitrogen, treated with BOP (40 mg, 0.090 mmol) and allowed to stir at RT for 3.5 days. The crude product was purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate Gradient: a 0-minute hold at 17% B, 17-57% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give (S)-3-(2-amino-[1,2,4]triazolo[1,5-a]pyridin-7-yl)-2,6-difluoro-N-(2,2,3-trifluoro-3-(4-fluorophenyl)propyl)benzamide (14.8 mg, 0.0310 mmol, 45% yield).
$^1$H NMR (500 MHz, DMSO-d$_6$) δ 9.29 (t, J=6.1 Hz, 1H), 8.62 (d, J=7.0 Hz, 1H), 7.89-7.72 (m, 1H), 7.63-7.46 (m, 3H), 7.33 (br t, J=8.7 Hz, 3H), 7.04 (br d, J=7.0 Hz, 1H), 6.18-5.87 (m, 3H), 4.08-3.80 (m, 2H).
MS ESI m/z 480.0 (M+H)+

Example 286: (S)-3-(2-amino-[1,2,4]triazolo[1,5-a]pyridin-7-yl)-2-fluoro-N-(2,2,3-trifluoro-3-(4-fluorophenyl)propyl)-6-(trifluoromethyl)benzamide

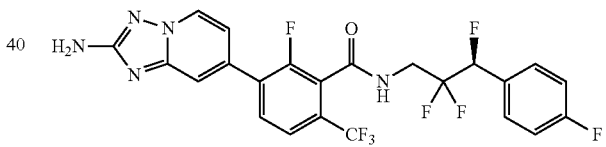

286A: 3-(2-(di-(tert-butoxycarbonyl)amino)-[1,2,4]triazolo[1,5-a]pyridin-7-yl)-2-fluoro-6-trifluoromethylbenzoic acid: To a solution of N,N-bis-Boc-2-amino-7-(4,4,5,5-tetramethyl-1,3,2-dioxaborolan-2-yl)-[1,2,4]triazolo[1,5-a]pyridine (2.00 g, 4.34 mmol), 3-bromo-2-fluoro-6-(trifluoromethyl)benzoic acid (1.30 g, 4.53 mmol), and potassium acetate, 2.0 M in water (6.62 mL, 13.3 mmol) in dioxane (40 mL) was added with [1,1'-bis(diphenylphosphino)ferrocene]dichloropalladium(II), complex with dichloromethane (350 mg, 0.429 mmol). The reaction was purged with argon and heated at 80° C. for 2.5 h. The reaction was treated with additional 3-bromo-2-fluoro-6-(trifluoromethyl)benzoic acid (200 mg, 0.697 mmol) and additional catalyst (50 mg, 0.060 mmol), flushed with nitrogen and heated at 80° C. for 18 h. The solvent was removed in vacuo and the resulting residue was diluted with ethyl acetate (750 mL) and water (50 mL). The water layer was adjusted to pH=4 and washed with ethyl acetate (1×125 mL). The organic layers were combined, washed with water (3×30 mL), brine (2×15 mL), dried over anhydrous Na$_2$SO$_4$, filtered and evaporated to dryness. The crude residue was purified via flash column chromatography (20 g silica, gradient 100% dichloromethane to 35% 1:1 methanol/dichloromethane) and the fractions containing clean product were combined and concentrated to give 3-(2-(di-(tert-butoxycarbonyl)amino)-[1,2,4]triazolo[1, 5-a]pyridin-7-yl)-2-fluoro-6-trifluoromethylbenzoic acid (3.53 g, >100% yield) which was used without further purification.
MS ESI m/z 541 (M+H)$^+$ 286: To a solution of 3-(2-(di-(tert-butoxycarbonyl) amino)-[1,2,4]triazolo[1,5-a]pyridin-7-yl)-2-fluoro-6-trifluoromethylbenzoic acid (25 mg, 0.046 mmol), (S)-2,2,3-trifluoro-3-(4-fluorophenyl)propan-1-amine (14 mg, 0.068 mmol), and N,N-diisopropylethylamine (35 µL, 0.20 mmol) in dichloromethane (1.0 mL) was added BOP (40 mg, 0.090 mmol), and the reaction was stirred at RT for 5.5 h. The volatiles were removed under a gentle stream of nitrogen and the crude product was dissolved in methanol (800 µL), treated with hydrogen chloride, 4.0M solution in 1 4-dioxane (1.5 mL, 6.00 mmol) and heated at 60 C for 3 h. The crude product purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 22% B, 22-62% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give (S)-3-(2-amino-[1,2,4]triazolo[1,5-a]pyridin-7-yl)-2-fluoro-N-(2,2,3-trifluoro-3-(4-fluorophenyl)propyl)-6-(trifluoromethyl)benzamide (9.2 mg, 0.017 mmol, 36% yield).
$^1$H NMR (500 MHz, DMSO-d$_6$) δ 9.33 (t, J=6.1 Hz, 1H), 8.65 (d, J=7.0 Hz, 1H), 7.93 (t, J=7.7 Hz, 1H), 7.83-7.70 (m, 1H), 7.63-7.48 (m, 3H), 7.33 (t, J=8.8 Hz, 2H), 7.09 (br d, J=7.1 Hz, 1H), 6.11 (s, 2H), 6.04-5.83 (m, 1H), 4.03-3.80 (m, 2H)
MS ESI m/z 529.9 (M+H)$^+$ Example 287: (R)-3-(2-amino-[1,2,4]triazolo[1,5-a]pyridin-7-yl)-2,6-difluoro-N-(2,2,3-trifluoro-3-(4-fluorophenyl)propyl)benzamide

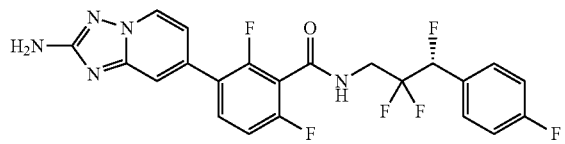 [SMILES: Nc1nc2cc(-c3ccc(F)c(C(=O)NCC(F)(F)[C@H](F)c4ccc(F)cc4)c3F)ccn2n1]

287A: (S)-2-(2,2-difluoro-3-(4-fluorophenyl)-3-hydroxypropyl)isoindoline-1,3-dione: Following the procedure as described in Example 282A, except using (S)-3-amino-2,2-difluoro-1-(4-fluorophenyl)propan-1-ol (1.30 g, 6.34 mmol) as the starting material, (S)-2-(2,2-difluoro-3-(4-fluorophenyl)-3-hydroxypropyl)isoindoline-1,3-dione (1.72 g, 5.00 mmol, 81%) was isolated.
$^1$H NMR (500 MHz, CHLOROFORM-d) δ 7.99-7.89 (m, 2H), 7.82 (dd, J=5.5, 3.0 Hz, 2H), 7.48 (dd, J=8.3, 5.5 Hz, 2H), 7.12-7.01 (m, 2H), 4.84 (dt, J=18.5, 4.6 Hz, 1H), 4.42-4.14 (m, 2H), 3.79 (d, J=5.0 Hz, 1H).
MS ESI m/z 333.9 (M–H)$^-$ 287B: (R)-2-(2,2,3-trifluoro-3-(4-fluorophenyl)propyl)isoindoline-1,3-dione: Following the procedure as described in Example 282B, except using (S)-2-(2,2-difluoro-3-(4-fluorophenyl)-3-hydroxypropyl)isoindoline-1,3-dione (1.72 g, 5.13 mmol) as the starting material, (R)-2-(2,2,3-trifluoro-3-(4-fluorophenyl)propyl)isoindoline-1,3-dione (255 mg, 0.756 mmol, 15% yield) was isolated.
$^1$H NMR (500 MHz, CHLOROFORM-d) δ 7.98-7.86 (m, 2H), 7.84-7.73 (m, 2H), 7.49 (dd, J=8.4, 5.4 Hz, 2H), 7.19-7.10 (m, 2H), 5.72-5.53 (m, 1H), 4.40-4.17 (m, 2H).

287C: (R)-2,2,3-trifluoro-3-(4-fluorophenyl)propan-1-amine: Following the procedure as described in Example 282C, except using (R)-2-(2,2,3-trifluoro-3-(4-fluorophenyl)propyl)isoindoline-1,3-dione (500 mg, 1.48 mmol) as the starting material, (R)-2,2,3-trifluoro-3-(4-fluorophenyl)propan-1-amine (304 mg, 1.47 mmol, 99% yield) was isolated.
$^1$H NMR (400 MHz, CHLOROFORM-d) δ 7.44 (dd, J=8.4, 5.4 Hz, 2H), 7.19-7.08 (m, 2H), 5.81-5.57 (m, 1H), 3.30-3.02 (m, 2H).
MS ESI m/z 207.9 (M+H)$^+$ 287: (R)-3-(2-amino-[1,2,4]triazolo[1,5-a]pyridin-7-yl)-2,6-difluoro-N-(2,2,3-trifluoro-3-(4-fluorophenyl)propyl)benzamide: To a solution of 3-(2-amino-[1,2,4]triazolo[1,5-a]pyridin-7-yl)-2,6-difluorobenzoic acid (15.2 mg, 0.0520 mmol), (R)-2,2,3-trifluoro-3-(4-fluorophenyl)propan-1-amine (11.8 mg, 0.0570 mmol) and N,N-diisopropylethylamine (40 µL, 0.23 mmol) in DMF (750 µL) was added BOP (37 mg, 0.084 mmol) and the reaction was stirred at RT for 5 h. The crude product purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 15% B, 15-55% B over 20 minutes, then a 0-minute hold at 100% B; Flow Rate: 2 0 mL/min; Column Temperature: 25 C. Fraction collection was triggered by MS and UV signals. Fractions containing the desired product were combined and dried via centrifugal evaporation to give (R)-3-(2-amino-[1,2,4]triazolo[1,5-a]pyridin-7-yl)-2,6-difluoro-N-(2,2,3-trifluoro-3-(4-fluorophenyl)propyl)benzamide (12.4 mg, 0.0260 mmol, 49% yield).
$^1$H NMR (500 MHz, DMSO-d$_6$) δ 9.28 (br t, J=5.9 Hz, 1H), 8.63 (d, J=6.9 Hz, 1H), 7.89-7.68 (m, 1H), 7.63-7.46 (m, 3H), 7.33 (br t, J=8.8 Hz, 3H), 7.04 (br d, J=7.0 Hz, 1H), 6.16-5.89 (m, 3H), 4.08-3.80 (m, 2H).
MS ESI m/z 480.0 (M+H)$^+$ Example 288: (R)-3-(2-amino-[1,2,4]triazolo[1,5-a]pyridin-7-yl)-6-chloro-2-fluoro-N-(2,2,3-trifluoro-3-(4-fluorophenyl)propyl)benzamide

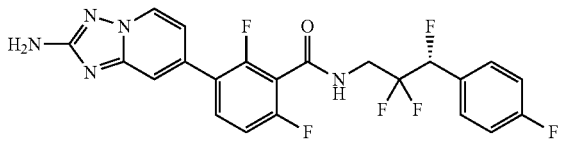 [SMILES: Nc1nc2cc(-c3ccc(F)c(C(=O)NCC(F)(F)[C@H](F)c4ccc(F)cc4)c3F)ccn2n1]

To a solution of 3-(2-amino-[1,2,4]triazolo[1,5-a]pyridin-7-yl)-6-chloro-2-fluorobenzoic acid (17 mg, 0.055 mmol), (R)-2,2,3-trifluoro-3-(4-fluorophenyl)propan-1-amine (12.8 mg, 0.0620 mmol), N,N-diisopropylethylamine (40 µL, 0.23 mmol) in DMF (750 µL) was added BOP (37 mg, 0.084 mmol) and the reaction was stirred at RT for 5 h. The crude product purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 18% B, 18-58% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give (R)-3-(2-amino-[1,2,4]triazolo[1,5-a]pyridin-7-yl)-6-chloro-2-fluoro-N-(2,2,3-trifluoro-3-(4-fluorophenyl)propyl)benzamide (17.4 mg, 0.0350 mmol, 63% yield).

$^1$H NMR (500 MHz, DMSO-$d_6$) δ 9.28 (t, J=6.1 Hz, 1H), 8.64 (d, J=7.0 Hz, 1H), 7.76 (t, J=8.4 Hz, 1H), 7.60-7.47 (m, 4H), 7.34 (t, J=8.7 Hz, 2H), 7.04 (br d, J=7.0 Hz, 1H), 6.15-5.90 (m, 3H), 4.03-3.81 (m, 2H).
MS ESI m/z 495.9, 497.9 (M+H)$^+$

Example 289: (R)-3-(2-amino-[1,2,4]triazolo[1,5-a]pyridin-7-yl)-2-fluoro-N-(2,2,3-trifluoro-3-(4-fluorophenyl)propyl)-6-(trifluoromethyl)benzamide

To a solution of 3-(2-(di-(tert-butoxycarbonyl)amino)-[1,2,4]triazolo[1,5-a]pyridin-7-yl)-2-fluoro-6-trifluoromethylbenzoic acid (30 mg, 0.056 mmol), (R)-2,2,3-trifluoro-3-(4-fluorophenyl)propan-1-amine (12.8 mg, 0.0620 mmol), and N,N-diisopropylethylamine (40 µL, 0.23 mmol) in DMF (750 µL) was added BOP (37 mg, 0.084 mmol) and the reaction was stirred at RT for 5 h. The volatiles were removed under a gentle stream of nitrogen and the residue was dissolved in methanol (500 µL), treated with 4M HCl in dioxane (1.5 mL, 6 mmol) and heated at 65° C. for 18 h. The crude residue was purified via preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 20% B, 20-60% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 18% B, 18-58% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give (R)-3-(2-amino-[1,2,4]triazolo[1,5-a]pyridin-7-yl)-2-fluoro-N-(2,2,3-trifluoro-3-(4-fluorophenyl)propyl)-6-(trifluoromethyl)benzamide (10.7 mg, 0.0200 mmol, 36% yield).

$^1$H NMR (500 MHz, DMSO-$d_6$) δ 9.31 (t, J=6.1 Hz, 1H), 8.69 (d, J=6.9 Hz, 1H), 8.04-7.88 (m, 1H), 7.77 (d, J=8.2 Hz, 1H), 7.62 (s, 1H), 7.55 (br dd, J=7.8, 5.7 Hz, 2H), 7.34 (t, J=8.7 Hz, 2H), 7.22 (s, 1H), 7.17-7.07 (m, 2H), 7.02 (s, 1H), 6.12-5.87 (m, 1H), 4.05-3.81 (m, 2H).
MS ESI m/z 530.0 (M+H)$^+$

Example 290: 3-(2-amino-[1,2,4]triazolo[1,5-a]pyridin-7-yl)-N-(3,3-difluoro-3-(4-fluorophenyl)-2-hydroxypropyl)-2-fluoro-6-methylbenzamide

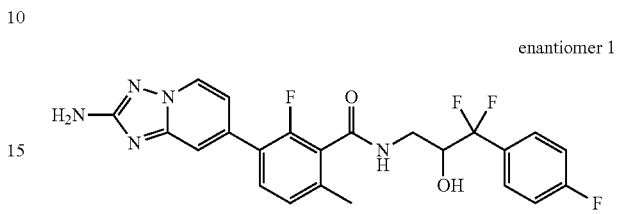

enantiomer 1

290A: ethyl 2,2-difluoro-2-(4-fluorophenyl)acetate: A mixture of 1-fluoro-4-iodobenzene (7.95 mL, 68.9 mmol), ethyl 2-bromo-2,2-difluoroacetate (8.84 mL, 68.9 mmol) and copper (11.4 g, 179 mmol) in DMSO (172 mL) was heated in a 70° C. oil bath for 12 h. Water was added and the aqueous layer was extracted with ether (×3). The combined organic layers were washed with brine, dried over anhydrous sodium sulfate and filtered, and the filtrate was evaporated in vacuo to give crude ethyl 2,2-difluoro-2-(4-fluorophenyl)acetate (13.0 g, 59.6 mmol, 86% yield). This product was used directly in subsequent steps without further purification.

$^1$H NMR (500 MHz, CHLOROFORM-d) δ 7.66-7.61 (m, 3H), 7.22-7.11 (m, 2H), 4.33 (q, J=7.1 Hz, 2H), 1.34-1.29 (m, 3H).

290B: 2,2-difluoro-2-(4-fluorophenyl)ethan-1-ol: To a solution of ethyl 2,2-difluoro-2-(4-fluorophenyl)acetate (0.500 g, 2.29 mmol) in methanol (5.73 mL) at 0° C. was added sodium borohydride (0.130 g, 3.44 mmol) portionwise, and the reaction mixture was stirred at 0° C. for 10 min and then at RT for 30 min. Methanol was removed in vacuo and 1N aqueous HCl was added. The aqueous layer was extracted with ether (×3). The combined organic layers were washed with brine, dried over anhydrous sodium sulfate and filtered, and the filtrate was evaporated in vacuo to give 2,2-difluoro-2-(4-fluorophenyl)ethan-1-ol (0.350 g, 1.99 mmol, 87% yield).

$^1$H NMR (500 MHz, CHLOROFORM-d) δ 7.59-7.51 (m, 2H), 7.16 (t, J=8.5 Hz, 2H), 3.99 (br t, J=13.1 Hz, 2H), 1.95 (br s, 1H).

290C: 2,2-difluoro-2-(4-fluorophenyl)acetaldehyde: To a solution of oxalyl chloride (239 µL, 2.73 mmol) in DCM (9 mL) at −78° C. was added DMSO (403 µL, 5.68 mmol), and the reaction mixture was stirred at −78° C. for 20 min. A solution of 2,2-difluoro-2-(4-fluorophenyl)ethan-1-ol (400 mg, 2.27 mmol) in DCM (2 mL) was added to the reaction mixture, and the resulting mixture was stirred at −78° C. for 30 min. Triethylamine (1.42 mL, 10.2 mmol) was added, and the reaction was allowed to warm to RT and stirred for 20 min. Water was added and the aqueous layer was extracted with DCM (×3). Thus, was obtained crude 2,2-difluoro-2-(4-fluorophenyl)acetaldehyde (0.35 g, 2.0 mmol, 89% yield). This material was used immediately in the next step as-is.

290D: 1,1-difluoro-1-(4-fluorophenyl)-3-nitropropan-2-ol: A mixture of 2,2-difluoro-2-(4-fluorophenyl)acetaldehyde (240 mg, 1.38 mmol), nitromethane (221 µL, 4.14 mmol), and potassium carbonate (57.1 mg, 0.414 mmol) in THF (4.6 mL) was stirred at RT for 3 h. The reaction mixture was filtered through a pad of Celite and washed with EtOAc. The crude product was purified by preparative TLC on silica gel (0.50 mm thickness) eluting with 30% ethyl acetate/hexanes to give 1,1-difluoro-1-(4-fluorophenyl)-3-nitropropan-2-ol (60 mg, 0.255 mmol, 74% yield) as a colorless oil.

$^1$H NMR (500 MHz, CHLOROFORM-d) δ 7.56 (dd, J=8.6, 5.1 Hz, 2H), 7.20 (t, J=8.3 Hz, 2H), 4.85-4.70 (m, 2H), 4.60-4.54 (m, 1H), 2.83-2.70 (m, 1H).

LC/MS ESI/APCI m/z 234.05 (M+H)$^+$

290E: 3-amino-1,1-difluoro-1-(4-fluorophenyl)propan-2-ol: A mixture of 1,1-difluoro-1-(4-fluorophenyl)-3-nitropropan-2-ol (260 mg, 1.11 mmol) and 10% palladium on carbon (118 mg, 0.111 mmol) in MeOH (3.7 mL) was stirred at RT under a hydrogen atmosphere (1 ATM, balloon) for 12 h. After filtration and evaporation, the crude 3-amino-1,1-difluoro-1-(4-fluorophenyl)propan-2-ol (230 mg, 1.12 mmol, 100% yield) was used directly in the next step without further purification.

LC/MS ESI/APCI m/z 205.75 (M+H)$^+$

290F: 3-(N,N-bis-Boc-2-amino-[1,2,4]triazolo[1,5-a]pyridin-7-yl)-N-(3,3-difluoro-3-(4-fluorophenyl)-2-hydroxypropyl)-2-fluoro-6-methylbenzamide: In a 20 mL reaction vial were combined 3-(N,N-bis-Boc-2-amino-[1,2,4]triazolo[1,5-a]pyridin-7-yl)-2-fluoro-6-methylbenzoic acid (156 mg, 0.322 mmol), 3-amino-1,1-difluoro-1-(4-fluorophenyl)propan-2-ol (60 mg, 0.292 mmol), BOP (155 mg, 0.351 mmol), and diisopropylethyl amine (153 μL, 0.877 mmol) in DCM (2.9 mL) to give a brown solution. The reaction was stirred at room temperature overnight. The crude reaction mixture was purified directly by flash silica gel chromatography. The clean fractions were concentrated under reduced pressure to yield 3-(2-N,N-bis-Boc-amino-[1,2,4]triazolo[1,5-a]pyridin-7-yl)-N-(3,3-difluoro-3-(4-fluorophenyl)-2-hydroxypropyl)-2-fluoro-6-methylbenzamide (117 mg, 0.174 mmol, 59% yield).

$^1$H NMR (500 MHz, CHLOROFORM-d) δ 8.59 (d, J=7.2 Hz, 1H), 7.83 (s, 1H), 7.58 (dd, J=8.5, 5.2 Hz, 2H), 7.49-7.44 (m, 1H), 7.26-7.14 (m, 1H), 6.31 (br t, J=5.8 Hz, 1H), 4.26 (br dd, J=13.4, 7.9 Hz, 1H), 4.15 (d, J=7.2 Hz, 1H), 4.00 (ddd, J=14.3, 7.0, 3.2 Hz, 1H), 3.57 (ddd, J=13.9, 8.5, 5.3 Hz, 3H), 3.34 (d, J=4.9 Hz, 1H), 2.48 (s, 3H), 1.53-1.50 (m, 20H), 0.86 (br s, 1H).

LC/MS ESI/APCI m/z 674.10 (M+H)$^+$

290: In a vial were combined 3-(2-N,N-bis-Boc-amino-[1,2,4]triazolo[1,5-a]pyridin-7-yl)-N-(3,3-difluoro-3-(4-fluorophenyl)-2-hydroxypropyl)-2-fluoro-6-methylbenzamide (117 mg, 0.174 mmol) and hydrogen chloride solution, 4 M in dioxane (434 μL, 1.74 mmol) in dioxane (347 μL) to give a tan solution. The reaction was stirred at room temperature overnight. The crude product was concentrated in vacuo. The isolated 3-(2-amino-[1,2,4]triazolo[1,5-a]pyridin-7-yl)-N-(3,3-difluoro-3-(4-fluorophenyl)-2-hydroxypropyl)-2-fluoro-6-methylbenzamide (49.1 mg, 0.104 mmol) was subjected to chiral separation with the following conditions: Analytical chromatographic conditions (prior to preparative SFC separation): Instrument: Shimadzu Nexera UC SFC; Column: Chiral AD, 4.6×100 mm, 5 micron; Mobile Phase: 65% CO2/35% IPA w/0.1% DEA; Flow Conditions: 2 mL/min; Detector Wavelength: 220 nm. Preparative SFC chromatographic conditions: Instrument: Waters 100 Prep SFC Column: Chiral AD, 30×250 mm. 5 micron; Mobile Phase: 65% CO2/35% IPA w/0.1% DEA; Flow Rate: 100 mL/min; Detector Wavelength: 220 nm; Injection details: 3000 μL 49.1 mg dissolved in 9 mL MeOH/ACN. Fractions containing the first eluting isomer were combined and dried to afford 3-(2-amino-[1,2,4]triazolo[1,5-a]pyridin-7-yl)-N-(3,3-difluoro-3-(4-fluorophenyl)-2-hydroxypropyl)-2-fluoro-6-methylbenzamide enantiomer 1 (11.1 mg, 0.023 mmol, >95% ee, 14% yield): The relative and absolute stereochemistry was not determined.

$^1$H NMR (500 MHz, DMSO-d$_6$) δ 8.71 (br t, J=5.6 Hz, 1H), 8.58 (d, J=6.9 Hz, 1H), 7.62-7.53 (m, 3H), 7.47 (s, 1H), 7.33 (br t, J=8.7 Hz, 2H), 7.21 (d, J=8.0 Hz, 1H), 7.05 (br d, J=6.9 Hz, 1H), 6.12 (br d, J=6.1 Hz, 1H), 6.03 (s, 2H), 4.17-4.07 (m, 1H), 3.13-3.06 (m, 1H), 2.30 (s, 3H).

LC/MS ESI/APCI m/z 474.12 (M+H)$^+$

Example 291: 3-(2-amino-[1,2,4]triazolo[1,5-a]pyridin-7-yl)-N-(3,3-difluoro-3-(4-fluorophenyl)-2-hydroxypropyl)-2-fluoro-6-methylbenzamide

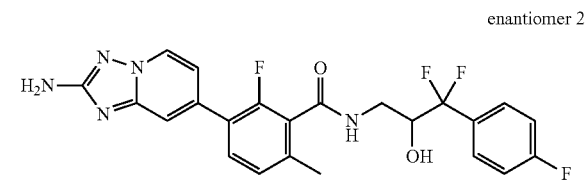

enantiomer 2

The title compound 3-(2-amino-[1,2,4]triazolo[1,5-a]pyridin-7-yl)-N-(3,3-difluoro-3-(4-fluorophenyl)-2-hydroxypropyl)-2-fluoro-6-methylbenzamide enantiomer 2 (9.9 mg, 0.021 mmol, 12% yield) was obtained as the second eluting isomer from the chiral SFC purification described for example 290.

$^1$H NMR (500 MHz, DMSO-d$_6$) δ 8.72 (br t, J=5.6 Hz, 1H), 8.58 (d, J=7.0 Hz, 1H), 7.62-7.53 (m, 3H), 7.47 (s, 1H), 7.33 (br t, J=8.9 Hz, 2H), 7.21 (d, J=7.9 Hz, 1H), 7.05 (br d, J=7.0 Hz, 1H), 6.03 (s, 2H), 4.13 (br s, 1H), 3.66-3.50 (m, 1H), 3.19-3.04 (m, 1H), 2.30 (s, 3H).

LC/MS ESI/APCI m/z 474.12 (M+H)$^+$

Example 292: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide

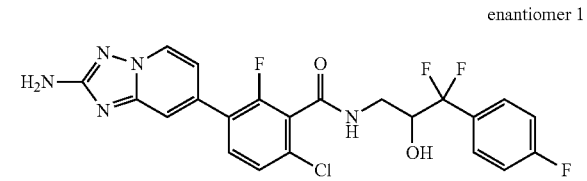 [SMILES: Cc1ccc(-c2ccn3nc(N)nc3c2)c(F)c1C(=O)NCC(O)C(F)(F)c1ccc(F)cc1]

enantiomer 1

292A: ethyl 2,2-difluoro-2-(4-fluorophenyl)acetate: A suspension of ethyl 2-bromo-2,2-difluoroacetate (7.74 mL, 60.4 mmol), 1-fluoro-4-iodobenzene (13.4 g, 60.4 mmol) and copper (9.97 g, 157 mmol) in DMSO (151 mL) was heated at 75° C. for 12 hours. Water was added and the aqueous layer was extracted with ether three times. The combined organic layers were washed with brine, dried over anhydrous sodium sulfate, and filtered. The filtrate was concentrated in vacuo to give ethyl 2,2-difluoro-2-(4-fluorophenyl)acetate (12.0 g, 55.0 mmol, 91% yield). This material was not pure but was used in subsequent steps without further purification.

292B: 2,2-difluoro-2-(4-fluorophenyl)ethan-1-ol: To a solution of ethyl 2,2-difluoro-2-(4-fluorophenyl)acetate (5.67 g, 26.0 mmol) in ether (65.0 mL) at 0° C. was added lithium aluminum hydride (1.48 g, 39.0 mmol) portionwise, and the reaction mixture was stirred at 0° C. for 10 min. Sodium sulfate decahydrate was added, and the reaction mixture was stirred at room temperature until a white suspension was formed. The reaction mixture was filtered to give 2,2-difluoro-2-(4-fluorophenyl)ethan-1-ol (3.00 g, 17.0 mmol, 66% yield) as colorless oil.

$^1$H NMR (500 MHz, CHLOROFORM-d) δ 7.61-7.50 (m, 2H), 7.20-7.10 (m, 2H), 3.99 (td, J=13.2, 6.9 Hz, 2H), 2.07 (br s, 1H).

292C: 2,2-difluoro-2-(4-fluorophenyl)acetaldehyde: To a solution of oxalyl chloride (0.590 mL, 6.74 mmol) in DCM (22.5 mL) at −78° C. was added DMSO (0.997 mL, 14.1 mmol), and the reaction mixture was stirred at −78° C. for 20 min. A solution of 2,2-difluoro-2-(4-fluorophenyl)ethan-1-ol (0.990 g, 5.62 mmol) in DCM (2 mL) was added to the reaction mixture, and the resulting mixture was stirred at −78° C. for 30 min. Triethylamine (3.53 mL, 25.3 mmol) was added, and the reaction was allowed to warm to room temperature and stirred for 20 min. Water was added and the aqueous layer was extracted with DCM three times. The crude product thus obtained was used directly in the next step without further purification.

292D: 1,1-difluoro-1-(4-fluorophenyl)-3-nitropropan-2-ol: A mixture of 2,2-difluoro-2-(4-fluorophenyl)acetaldehyde (0.98 g, 5.63 mmol), nitromethane (0.452 mL, 8.44 mmol) and potassium carbonate (0.156 g, 1.13 mmol) in THF (18.8 mL) was stirred at room temperature for 12 h. The reaction mixture was filtered through a pad of Celite and washed with ethyl acetate. The crude product was purified by preparative TLC on silica gel (0.50 mm thickness) eluting with 30% ethyl acetate/hexanes to give 1,1-difluoro-1-(4-fluorophenyl)-3-nitropropan-2-ol (412 mg, 1.75 mmol, 31% yield) as a colorless oil.

$^1$H NMR (500 MHz, CHLOROFORM-d) δ 7.56 (dd, J=8.6, 5.1 Hz, 2H), 7.20 (t, J=8.4 Hz, 2H), 4.88-4.77 (m, 1H), 4.72 (dd, J=13.9, 2.2 Hz, 1H), 4.61-4.50 (m, 1H), 2.85 (br s, 1H).

LC/MS ESI/APCI m/z: 234.05 (M−H)$^-$

292E: 3-amino-1,1-difluoro-1-(4-fluorophenyl)propan-2-ol: A mixture of 1,1-difluoro-1-(4-fluorophenyl)-3-nitropropan-2-ol (412 mg, 1.75 mmol) and 10% palladium on carbon (186 mg, 0.175 mmol) in MeOH (5.8 mL) was hydrogenated with a hydrogen balloon (1 ATM) for 12 h. The reaction mixture was filtered through a pad of Celite to give 3-amino-1,1-difluoro-1-(4-fluorophenyl)propan-2-ol (335 mg, 1.63 mmol, 93% yield) as a colorless oil. This material was used in subsequent steps without further purification.

LC/MS ESI/APCI m/z 205.80 (M+H)$^+$

292F: 3-(2-amino-[1,2,4]triazolo[1,5-a]pyridin-7-yl)-6-chloro-N-(3,3-difluoro-3-(4-fluorophenyl)-2-hydroxypropyl)-2-fluorobenzamide: A mixture of 3-amino-1,1-difluoro-1-(4-fluorophenyl)propan-2-ol (100 mg, 0.487 mmol), 3-(2-amino-[1,2,4]triazolo[1,5-a]pyridin-7-yl)-6-chloro-2-fluorobenzoic acid (149 mg, 0.487 mmol), BOP (237 mg, 0.536 mmol) and diisopropylethyl amine (128 μL, 0.731 mmol) in DMF (2.4 mL) was stirred at room temperature for 2 h, and the crude product was purified by reverse phase preparative HPLC to give racemic 3-(2-amino-[1,2,4]triazolo[1,5-a]pyridin-7-yl)-6-chloro-N-(3,3-difluoro-3-(4-fluorophenyl)-2-hydroxypropyl)-2-fluorobenzamide (78 mg, 0.158 mmol, 32% yield).

292: The isolated racemic 3-(2-amino-[1,2,4]triazolo[1,5-a]pyridin-7-yl)-6-chloro-N-(3,3-difluoro-3-(4-fluorophenyl)-2-hydroxypropyl)-2-fluorobenzamide (78 mg, 0.158 mmol) was subjected to chiral separation with the following conditions: Analytical chromatographic conditions (prior to preparative SFC separation) Instrument: Shimadzu Nexera UC SFC; Column: Chiral IC, 4.6×150 mm, 5 micron; Mobile Phase: 60% CO2/40% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 60% CO2/40% MeOH w/0.1% DEA; Flow Rate: 60 mL/min; Detector Wavelength: 220 nm; Injection details: 3 00 μL 78 mg dissolved in 3 mL MeOH. Fractions containing the first eluting isomer were combined and dried to afford 3-(2-amino-[1,2,4]triazolo[1,5-a]pyridin-7-yl)-6-chloro-N-(3,3-difluoro-3-(4-fluorophenyl)-2-hydroxypropyl)-2-fluorobenzamide enantiomer 1 (21.2 mg, 0.043 mmol, >95% ee, 27% yield): The relative and absolute stereochemistry was not determined.

$^1$H NMR (500 MHz, DMSO-d$_6$) δ 8.94 (br t, J=5.5 Hz, 1H), 8.63 (d, J=7.0 Hz, 1H), 7.72 (br t, J=8.1 Hz, 1H), 7.63-7.57 (m, 2H), 7.52 (s, 1H), 7.49 (d, J=8.5 Hz, 1H), 7.35 (br t, J=8.7 Hz, 2H), 7.04 (br d, J=7.0 Hz, 1H), 6.10 (s, 2H), 4.11 (br s, 1H), 3.63 (br d, J=11.6 Hz, 1H), 3.45 (br s, 1H), 3.11-3.00 (m, 1H).

LC/MS ESI/APCI m/z 494.05 (M+H)$^+$

Example 293: 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide

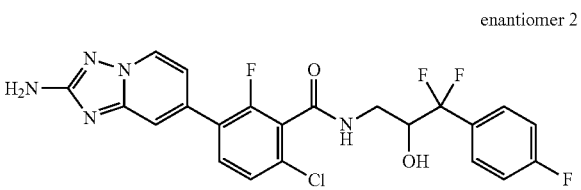 [SMILES: Nc1nc2cc(-c3ccc(Cl)c(C(=O)NCC(O)C(F)(F)c4ccc(F)cc4)c3F)ccn2n1]

enantiomer 2

The title compound 3-(2-amino-[1,2,4]triazolo[1,5-a]pyridin-7-yl)-2-fluoro-N-(1-fluoro-4-(4-fluorophenyl)-4-hydroxybutan-2-yl)-6-methylbenzamide enantiomer 2 (21.7 mg, 0.044 mmol, 27% yield) was obtained as the second eluting isomer from the chiral SFC purification described for example 292.

$^1$H NMR (500 MHz, DMSO-d$_6$) δ 8.94 (br t, J=5.5 Hz, 1H), 8.63 (d, J=7.0 Hz, 1H), 7.72 (t, J=8.4 Hz, 1H), 7.60 (t, J=6.5 Hz, 2H), 7.52 (s, 1H), 7.48 (d, J=7.9 Hz, 1H), 7.35 (br t, J=8.7 Hz, 2H), 7.04 (br d, J=6.7 Hz, 1H), 6.10 (s, 2H), 4.10 (br s, 1H), 3.63 (br d, J=7.6 Hz, 1H), 3.46 (br d, J=15.9 Hz, 1H), 3.11-2.99 (m, 1H).

LC/MS ESI/APCI m/z 494.28 (M+H)$^+$

Example 294: (S)-3-(2-amino-[1,2,4]triazolo[1,5-a]pyridin-7-yl)-N-(2,2-difluoro-3-(4-fluorophenyl)-3-hydroxypropyl)-2-fluoro-6-(fluoromethyl)benzamide

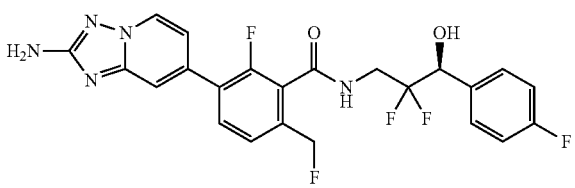 [SMILES: Nc1nc2cc(-c3ccc(CF)c(C(=O)NCC(F)(F)[C@@H](O)c4ccc(F)cc4)c3F)ccn2n1]

294A: (4-bromo-3-fluorophenyl)methanol: To a solution of 4-bromo-3-fluorobenzaldehyde (4.00 g, 19.7 mmol) in methanol (39.4 mL) at 0° C. was added sodium borohydride (0.745 g, 19.7 mmol) portionwise, and the reaction mixture was then stirred at room temperature for 30 min. Methanol was removed in vacuo, water was added, and the aqueous layer was extracted with ethyl acetate three times. The combined organic layers were washed with brine, dried over anhydrous sodium sulfate, and filtered. The filtrate was concentrated in vacuo to give (4-bromo-3-fluorophenyl)methanol (3.86 g, 18.8 mmol, 96% yield) as a white solid. This material was used directly for the subsequent fluorination reaction.

$^1$H NMR (500 MHz, CHLOROFORM-d) δ 7.54 (dd, J=8.1, 7.2 Hz, 1H), 7.21-7.14 (m, 1H), 7.04 (dd, J=8.0, 1.5 Hz, 1H), 4.69 (d, J=4.9 Hz, 2H), 1.83 (br d, J=5.0 Hz, 1H).

294B: 1-bromo-2-fluoro-4-(fluoromethyl)benzene: DAST (2.74 mL, 20.7 mmol) was added dropwise to (4-bromo-3-fluorophenyl)methanol (3.86 g, 18.8 mmol) at 0° C., and the reaction mixture was stirred at room temperature for 2 h. The reaction mixture was poured into ice water, and ether was added. The aqueous layer was extracted with ether three times. The combined organic layers were washed with brine, dried over anhydrous sodium sulfate, and filtered. The filtrate was evaporated in vacuo to give the crude product. The crude product was purified by silica gel chromatography eluting with 0-10% ethyl acetate/hexanes to give 1-bromo-2-fluoro-4-(fluoromethyl)benzene (2.00 g, 9.66 mmol, 51% yield) as a colorless oil.

$^1$H NMR (500 MHz, CHLOROFORM-d) δ 7.65-7.54 (m, 1H), 7.17 (d, J=9.1 Hz, 1H), 7.05 (d, J=8.1 Hz, 1H), 5.45-5.30 (m, 2H).

294C: 3-bromo-2-fluoro-6-(fluoromethyl)benzoic acid: In a 100 mL round-bottomed flask was combined 1-bromo-2-fluoro-4-(fluoromethyl)benzene (0.5 g, 2.415 mmol) and THF (12.1 mL) to give an orange solution. The solution was cooled to −78° C. in a dry ice/acetone bath. 1-bromo-2-fluoro-4-(fluoromethyl)benzene (0.500 g, 2.42 mmol) was added dropwise. The solution changed from orange to dark green color upon addition. The reaction was stirred at −78° C. for 20 min and then was quenched with dry ice. The reaction was allowed to warm to room temperature overnight. An orange precipitate formed. The reaction was diluted in ether and extracted 3 times with 1M sodium hydroxide. The aqueous layer was acidified with concentrated hydrochloric acid and back-extracted into ether 3 times. The combined organic layers were washed with brine and dried over sodium sulfate. The product was concentrated under reduced pressure to yield 3-bromo-2-fluoro-6-(fluoromethyl)benzoic acid (424 mg, 1.69 mmol, 70% yield).

$^1$H NMR (500 MHz, CHLOROFORM-d) δ 7.78 (dd, J=8.3, 6.7 Hz, 1H), 7.32 (d, J=8.3 Hz, 1H), 5.70-5.58 (m, 2H).

LC/MS ESI/APCI m/z 248.65 (M−H)$^-$

294D: (S)-3-bromo-N-(2,2-difluoro-3-(4-fluorophenyl)-3-hydroxypropyl)-2-fluoro-6-(fluoromethyl)benzamide: To a 20 mL reaction vial was added (S)-3-amino-2,2-difluoro-1-(4-fluorophenyl)propan-1-ol (103 mg, 0.504 mmol), 3-bromo-2-fluoro-6-(fluoromethyl)benzoic acid (115 mg, 0.458 mmol), BOP (243 mg, 0.550 mmol), and DIPEA (240 µL, 1.37 mmol) in DCM (2.3 mL) to give a colorless solution. The reaction was stirred at room temperature overnight. The crude reaction mixture was purified directly by silica gel flash chromatography. Product fractions were pooled and concentrated to yield (S)-3-bromo-N-(2,2-difluoro-3-(4-fluorophenyl)-3-hydroxypropyl)-2-fluoro-6-(fluoromethyl)benzamide (158 mg, 0.361 mmol, 79% yield).

$^1$H NMR (500 MHz, CHLOROFORM-d) δ 7.74 (t, J=7.6 Hz, 1H), 7.48 (dd, J=8.3, 5.7 Hz, 2H), 7.30 (s, 1H), 7.10 (t, J=7.8 Hz, 2H), 6.59 (br s, 1H), 5.69-5.45 (m, 2H), 4.92 (dt, J=19.0, 4.3 Hz, 1H), 4.48-4.37 (m, 1H), 4.01 (br d, J=4.2 Hz, 1H), 3.69-3.59 (m, 1H).

LC/MS ESI/APCI m/z 437.85 (M+H)$^+$

294E: 7-(4,4,5,5-tetramethyl-1,3,2-dioxaborolan-2-yl)-[1,2,4]triazolo[1,5-a]pyridin-2-amine: In a 250 mL round bottom flask was combined 7-bromo-[1,2,4]triazolo[1,5-a]pyridin-2-amine (5.00 g, 23.5 mmol), potassium acetate (6.91 g, 70.4 mmol), bis(pinacolato)diboron (8.94 g, 35.2 mmol), and Pd(dppf)Cl$_2$, DCM adduct (0.958 g, 1.173 mmol) in 1,4-dioxane (117 mL) to give an orange solution. The reaction mixture was degassed by evacuating and backfilling with nitrogen 3 times. The reaction flask was fitted with a reflux condenser and heated to 100° C. for 2 hours. After 2 hours, the LC/MS indicated the reaction was complete. The reaction mixture thus provided crude 7-(4,4,5,5-tetramethyl-1,3,2-dioxaborolan-2-yl)-[1,2,4]triazolo[1,5-a]pyridin-2-amine (6.10 g, 23.5 mmol, 100% yield was assumed) which was used as crude mixture in the subsequent reactions as-is.

LC/MS(ESI/APCI) m/z 178.95 [M+H]+

294: A 20 mL reaction vial was charged with 7-(4,4,5,5-tetramethyl-1,3,2-dioxaborolan-2-yl)-[1,2,4]triazolo[1,5-a]pyridin-2-amine (47.6 mg, 0.183 mmol) as a crude reaction mixture, (S)-3-bromo-N-(2,2-difluoro-3-(4-fluorophenyl)-3-hydroxypropyl)-2-fluoro-6-(fluoromethyl)benzamide (80.0 mg, 0.183 mmol), potassium phosphate, tribasic, 2M aqueous (274 µL, 0.548 mmol), and Pd(dppf)Cl$_2$, DCM adduct (7.45 mg, 9.13 µmol) to give a brown suspension. The reaction mixture was degassed by evacuating and backfilling with nitrogen 3 times. The reaction vial was sealed and heated to 100° C. on a heating block for 2 h. The reaction was concentrated under a gentle stream of nitrogen and diluted in ethyl acetate. The ethyl acetate solution was filtered through a pad of celite and concentrated under reduced pressure to yield the crude product. The product was diluted in DMF and filtered through a 0.45 um PTFE frit prior to purification. The crude material was purified via preparative LC/MS with the following conditions: Column: XBridge C18, 200 mm×19 mm, 5-µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 11% B, 11-51% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to afford (S)-3-(2-amino-[1,2,4]triazolo[1,5-a]pyridin-7-yl)-N-(2,2-difluoro-3-(4-fluorophenyl)-3-hydroxypropyl)-2-fluoro-6-(fluoromethyl)benzamide (35 mg, 0.071 mmol, 39% yield).

$^1$H NMR (500 MHz, DMSO-d$_6$) δ 9.05 (t, J=6.0 Hz, 1H), 8.64 (d, J=6.9 Hz, 1H), 7.78 (t, J=7.9 Hz, 1H), 7.55 (s, 1H), 7.52-7.45 (m, 3H), 7.25-7.19 (m, 2H), 7.07 (br d, J=6.9 Hz, 1H), 6.42 (d, J=5.1 Hz, 1H), 6.09 (s, 2H), 5.57-5.42 (m, 2H), 5.00-4.88 (m, 1H), 3.88 (br s, 2H).

LC/MS ESI/APCI m/z 492.01 (M+H)$^+$

Example 295: (S)-3-(2-amino-[1,2,4]triazolo[1,5-a]pyridin-7-yl)-N-(2,2-difluoro-3-(4-fluorophenyl)-3-hydroxypropyl)-6-(difluoromethyl)-2-fluorobenzamide

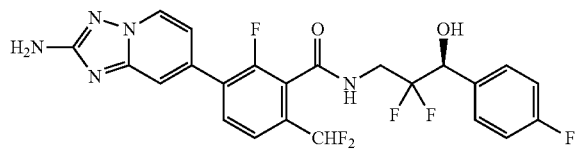 [SMILES: Nc1nc2cc(-c3ccc(C(F)F)c(C(=O)NCC(F)(F)[C@@H](O)c4ccc(F)cc4)c3F)ccn2n1]

295A: 1-bromo-4-(difluoromethyl)-2-fluorobenzene: DAST (4.93 mL, 37.3 mmol) was added dropwise to 4-bromo-3-fluorobenzaldehyde (7.57 g, 37.3 mmol), and the reaction mixture was heated at 60° C. for 1 h. This reaction mixture was poured into ice water, and ether was added. The aqueous layer was extracted with ether three times. The combined organic layers were washed with brine, dried over anhydrous sodium sulfate, and filtered. The filtrate was evaporated in vacuo to give the crude product. The crude product was purified by silica gel chromatography eluting with 0-10% ethyl acetate/hexanes to give 1-bromo-4-(difluoromethyl)-2-fluorobenzene (3.50 g, 15.6 mmol, 42% yield) as a colorless oil.

$^1$H NMR (500 MHz, CHLOROFORM-d) δ 7.68 (dd, J=8.0, 7.0 Hz, 1H), 7.31 (d, J=8.6 Hz, 1H), 7.21 (d, J=8.2 Hz, 1H), 6.77-6.45 (t, J=50 Hz, 1H).

295B: 3-bromo-6-(difluoromethyl)-2-fluorobenzoic acid: In a 100 mL round-bottomed flask were combined lithium diisopropylamide solution, 2M in THF (1.22 mL, 2.44 mmol) and THF (11.1 mL) to give an orange solution. The solution was cooled to −78° C. in a dry ice/acetone bath. A solution of 1-bromo-4-(difluoromethyl)-2-fluorobenzene (0.500 g, 2.22 mmol) in THF was added dropwise. The solution changed color from orange to dark green upon addition. The reaction mixture was stirred for 20 min at −78° C. Dry ice was added to quench the reaction. Gas evolved upon addition of dry ice and the solution turned a light orange color. The mixture was allowed to warm to room temperature overnight. A precipitate formed overnight. The reaction mixture was diluted in ether and extracted with 1M aqueous sodium hydroxide three times. The combined aqueous layers were acidified with concentrated hydrochloric acid. The aqueous mixture was back-extracted with ether 3 times. The combined organic layers were washed with brine and dried over sodium sulfate. The combined organic layers were concentrated under reduced pressure to yield 3-bromo-6-(difluoromethyl)-2-fluorobenzoic acid (299 mg, 1.11 mmol, 50% yield) as an oil.

$^1$H NMR (500 MHz, CHLOROFORM-d) δ 7.90-7.80 (m, 1H), 7.49-7.43 (m, 1H), 7.25-6.98 (m, 1H).

295C: (S)-3-bromo-N-(2,2-difluoro-3-(4-fluorophenyl)-3-hydroxypropyl)-6-(difluoromethyl)-2-fluorobenzamide: In a 10 mL reaction vial were combined (S)-3-amino-2,2-difluoro-1-(4-fluorophenyl)propan-1-ol (137 mg, 0.669 mmol), 3-bromo-6-(difluoromethyl)-2-fluorobenzoic acid (150 mg, 0.558 mmol), BOP (296 mg, 0.669 mmol), and DIPEA (292 µL, 1.67 mmol) in DCM (2.8 mL) to give a colorless solution. The reaction was stirred for 2 h at room temperature. The crude reaction mixture was purified directly by silica gel flash chromatography to yield (S)-3-bromo-N-(2,2-difluoro-3-(4-fluorophenyl)-3-hydroxypropyl)-6-(difluoromethyl)-2-fluorobenzamide (137 mg, 0.300 mmol, 54% yield).

LC/MS ESI/APCI m/z 455.90 (M+H)$^+$ $^1$H NMR (500 MHz, CHLOROFORM-d) δ 7.81 (t, J=7.5 Hz, 1H), 7.50-7.44 (m, 3H), 7.21-6.96 (m, 3H), 6.52 (br s, 1H), 4.93 (dt, J=18.9, 4.2 Hz, 1H), 4.49-4.38 (m, 1H), 3.86 (d, J=4.4 Hz, 1H), 3.71-3.61 (m, 1H).

295: A 20 mL reaction vial was charged with 7-(4,4,5,5-tetramethyl-1,3,2-dioxaborolan-2-yl)-[1,2,4]triazolo[1,5-a]pyridin-2-amine (78.8 mg, 0.303 mmol) as a crude mixture, (S)-3-bromo-N-(2,2-difluoro-3-(4-fluorophenyl)-3-hydroxypropyl)-6-(difluoromethyl)-2-fluorobenzamide (138 mg, 0.303 mmol), potassium phosphate, tribasic, 2M aqueous (413 µL, 0.826 mmol), and Pd(dppf)Cl$_2$, DCM adduct (11.2 mg, 0.014 mmol). The reaction mixture was degassed by evacuating and back-filling with nitrogen 3 times. The reaction was heated to 80° C. on a heating block and stirred overnight. LC/MS indicated the starting material was consumed. The reaction was cooled to room temperature. The crude product was concentrated under a gentle stream of nitrogen and diluted in ethyl acetate. The mixture was filtered through a pad of Celite and washed with more ethyl acetate. The ethyl acetate solution was concentrated under reduced pressure, diluted in DMF, and filtered through a 0.45 um PTFE frit. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 13% B, 13-53% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide (S)-3-(2-amino-[1,2,4]triazolo[1,5-a]pyridin-7-yl)-N-(2,2-difluoro-3-(4-fluorophenyl)-3-hydroxypropyl)-6-(difluoromethyl)-2-fluorobenzamide (75.3 mg, 0.148 mmol, 53% yield).

$^1$H NMR (500 MHz, DMSO-d6) δ 9.18 (br s, 1H), 8.63 (br d, J=6.8 Hz, 1H), 7.86 (br t, J=7.5 Hz, 1H), 7.62 (d, J=8.1 Hz, 1H), 7.56 (s, 1H), 7.51-7.42 (m, 2H), 7.20 (br t, J=8.7 Hz, 2H), 7.12-6.85 (m, 2H), 4.91 (br d, J=15.4 Hz, 1H), 3.93-3.79 (m, 2H), −0.01 (d, J=4.5 Hz, 1H) (one proton peak obscured by water).

LC/MS ESI/APCI m/z 510.01 (M+H)$^+$

Example 296: 3-(2-amino-[1,2,4]triazolo[1,5-a]pyridin-7-yl)-6-chloro-2-fluoro-N-((2S,3S)-2-fluoro-3-(4-fluorophenyl)-3-hydroxypropyl)benzamide

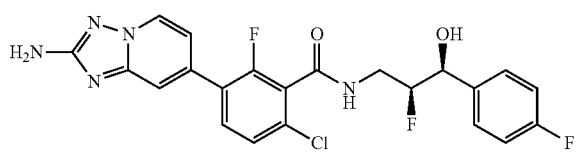 [SMILES: Nc1nc2cc(-c3ccc(Cl)c(C(=O)NC[C@H](F)[C@@H](O)c4ccc(F)cc4)c3F)ccn2n1]

296A: ethyl 2-fluoro-3-(4-fluorophenyl)-3-hydroxypropanoate: A mixture of ethyl 2-chloro-2-fluoroacetate (5.14 mL, 44.3 mmol), 4-fluorobenzaldehyde (4.32 mL, 40.3 mmol) and zinc (3.69 g, 56.4 mmol) in DMF (101 mL) was heated at 80° C. using an oil bath for 12 h. The reaction mixture was filtered through a pad of Celite, and 1 N aqueous HCl was added. The aqueous layer was extracted with ethyl acetate three times. The combined organic layers were washed with brine, dried over anhydrous sodium sulfate, and filtered. The filtrate was evaporated in vacuo to give the crude product. The crude product was purified by silica gel chromatography eluting with 01-15% ethyl acetate/hexanes to give ethyl 2-fluoro-3-(4-fluorophenyl)-3-hydroxypropanoate (2.00 g, 8.69 mmol, 22% yield).

$^1$H NMR (500 MHz, CHLOROFORM-d) δ 7.44-7.37 (m, 2H), 7.13-7.05 (m, 2H), 5.19-5.10 (m, 1H), 5.09-4.94 (m, 1H), 4.30-4.18 (m, 2H), 2.88-2.66 (m, 1H), 1.29-1.21 (m, 3H).

296B: 2-fluoro-3-(4-fluorophenyl)-3-hydroxypropanamide: To a solution ethyl 2-fluoro-3-(4-fluorophenyl)-3-hydroxypropanoate (850 mg, 3.69 mmol) in methanol (9.2 mL) at room temperature was added 7 M ammonia in methanol (2.64 mL, 18.46 mmol). The reaction mixture was stirred at room temperature for 12 h. Solvent was removed in vacuo to give 2-fluoro-3-(4-fluorophenyl)-3-hydroxypropanamide (750 mg, 3.73 mmol, 100% yield) as a white solid. This material was used without further purification.

LC/MS ESI/APCI m/z 200.10 (M−H)⁻

296C: 3-amino-2-fluoro-1-(4-fluorophenyl)propan-1-ol: To a solution of 2-fluoro-3-(4-fluorophenyl)-3-hydroxypropanamide (810 mg, 4.03 mmol) in THF (8.05 mL) was added borane-methyl sulfide complex, 2.0 M in THF (6.04 mL, 12.08 mmol). The reaction mixture was heated under reflux for 2 h. After cooling, methanol was added, and the reaction mixture was stirred at room temperature for 30 min. Methanol was removed in vacuo, and the residue was azeotroped with methanol to remove B(OH)₃ three times to give 3-amino-2-fluoro-1-(4-fluorophenyl)propan-1-ol (760 mg, 4.06 mmol, 100% yield) as a solid. This material was used directly in subsequent steps without further purification.

LC/MS ESI/APCI m/z 187.85 (M+H)⁺

296D: 3-(2-amino-[1,2,4]triazolo[1,5-a]pyridin-7-yl)-6-chloro-2-fluoro-N-(2-fluoro-3-(4-fluorophenyl)-3-hydroxypropyl)benzamide: To a dry 100 mL round bottom flask under nitrogen was added 3-amino-2-fluoro-1-(4-fluorophenyl)propan-1-ol (250 mg, 1.34 mmol), 3-(2-amino-[1,2,4]triazolo[1,5-a]pyridin-7-yl)-6-chloro-2-fluorobenzoic acid (400 mg, 1.30 mmol), dichloromethane (8 mL) and N,N-diisopropylethylamine (350 μL, 2.00 mmol). The reaction was flushed briefly with nitrogen, then treated with BOP (635 mg, 1.44 mmol), then the vessel was sealed and the mixture was stirred overnight at room temperature. Solvent was removed in vacuo. The crude product was redissolved in 4 mL DMF and filtered through a 0.45 um PTFE frit. The crude material was purified via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 8% B, 8-38% B over 30 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation. The purification yielded two separated enantiomeric mixtures of 3-(2-amino-[1,2,4]triazolo[1,5-a]pyridin-7-yl)-6-chloro-2-fluoro-N-(2-fluoro-3-(4-fluorophenyl)-3-hydroxypropyl) benzamide. The first isolate to elute from the preparative reverse phase separation was racemate 296D-01 (133.4 mg, 0.28 mmol, 22% yield). The second isolate to elute from the preparative reverse phase separation was racemate 296D-02 (112.4 mg, 0.24 mmol, 18% yield).

296D-01: LC/MS ESI/APCI m/z 475.96 (M+H)⁺
296D-02: LC/MS ESI/APCI m/z 475.99 (M+H)⁺

296: The isolate 296D-01 (119 mg, 0.25 mmol) was subjected to chiral SFC separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 50% CO2/50% MeOH w/0.1% DEA; Flow Conditions: 2 mL/min; Detector Wavelength: 220 nm. Preparative SFC chromatographic conditions: instrument: Waters 100 Prep SFC; Column: Chiral IC, 21×250 mm. 5 micron; Mobile Phase: 50% CO2/50% MeOH w/0.1% DEA; Flow Rate: 60 mL/min; Detector Wavelength: 220 nm; Injection details: 600 μL 133.4 mg dissolved in 3 mL DMSO. Fractions containing the first eluting isomer were combined and dried to afford 3-(2-amino-[1,2,4]triazolo[1,5-a]pyridin-7-yl)-6-chloro-2-fluoro-N-((2S,3S)-2-fluoro-3-(4-fluorophenyl)-3-hydroxypropyl)benzamide (46.4 mg, 0.098 mmol, >95% ee, 39% yield). The exact (2S,3S) stereochemistry of this material was determined by analytical chiral SFC chromatography retention time compared to standard reference material. The standard reference material (SRM) was synthesized using enantiopure starting materials with absolute stereochemistry that was confirmed via X-Ray crystallography, as described in sections Intermediates 296-SRM-A to 296-SRM-D.

$^1$H NMR (500 MHz, DMSO-d₆) δ 9.04 (br t, J=5.5 Hz, 1H), 8.63 (d, J=7.0 Hz, 1H), 7.73 (t, J=8.4 Hz, 1H), 7.54-7.42 (m, 4H), 7.20 (t, J=9.0 Hz, 2H), 7.05 (br d, J=7.0 Hz, 1H), 6.10 (s, 2H), 5.89 (d, J=5.2 Hz, 1H), 4.86-4.77 (m, 1H), 4.64-4.58 (m, 1H), 4.73-4.56 (m, 1H).

LC/MS ESI/APCI m/z 476.16 (M+H)⁺

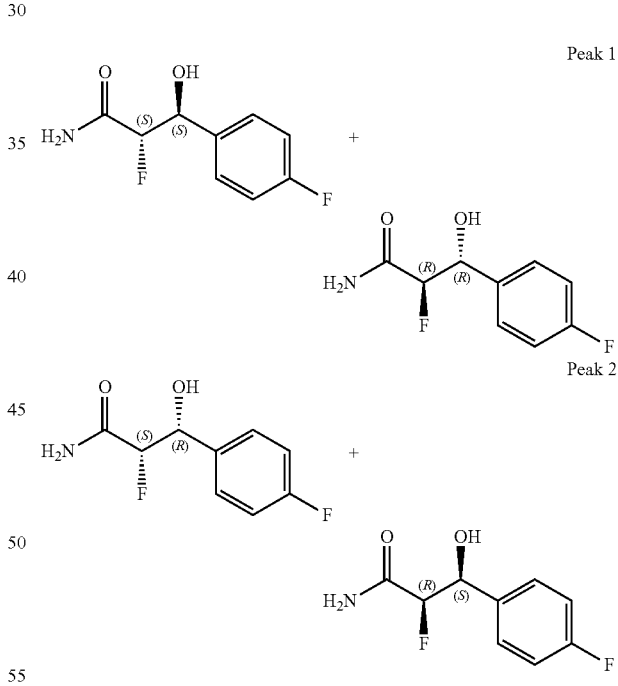

Intermediates 296-SRM-A: racemic mixture of (2S,3S)-2-fluoro-3-(4-fluorophenyl)-3-hydroxypropanamide and (2R,3R)-2-fluoro-3-(4-fluorophenyl)-3-hydroxypropanamide and racemic mixture of (2S,3R)-2-fluoro-3-(4-fluorophenyl)-3-hydroxypropanamide and (2R,3S)-2-fluoro-3-(4-fluorophenyl)-3-hydroxypropanamide: To a solution ethyl 2-fluoro-3-(4-fluorophenyl)-3-hydroxypropanoate (preparation as described in 296A) (2.00 g, 8.69 mmol) in methanol (21.7 mL) at RT was added ammonia, 7M in methanol (6.21 mL, 43.4 mmol) and the reaction mixture was stirred at RT for 12 h. This material was purified by reverse phase preparative HPLC (Column=Waters Sunfire Prep C18 OBD, 50×250 mm, 10 micron particles, Solvent A=95% water, 5% acetonitrile, 10 mM ammonium acetate, Solvent B=5% water, 95% acetonitrile, 10 mM ammonium acetate, Flow rate=100 mL/min, elution gradient 0 to 30% B over 25 minutes) to provide two separate peaks. The first peak to elute was concentrated to give a racemic mixture of (2S,3S)-2-fluoro-3-(4-fluorophenyl)-3-hydroxypropanamide and (2R,3R)-2-fluoro-3-(4-fluorophenyl)-3-hydroxypropanamide (0.67 g, 3.33 mmol, 38% yield) as a white powder, and the second peak to elute was concentrated to give a racemic mixture of (2S,3R)-2-fluoro-3-(4-fluorophenyl)-3-hydroxypropanamide and (2R,3S)-2-fluoro-3-(4-fluorophenyl)-3-hydroxypropanamide (0.70 g, 3.48 mmol, 40% yield) as a white powder. The stereochemistry of both isolates was determined via X-Ray crystallography.

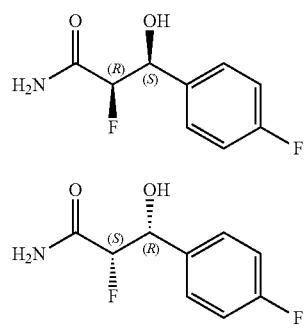

Peak 1

Peak 2

Intermediates 296-SRM-B: (2R,3S)-2-fluoro-3-(4-fluorophenyl)-3-hydroxypropanamide and (2S,3R)-2-fluoro-3-(4-fluorophenyl)-3-hydroxypropanamide: A racemic mixture of (2S,3R)-2-fluoro-3-(4-fluorophenyl)-3-hydroxypropanamide and (2R,3S)-2-fluoro-3-(4-fluorophenyl)-3-hydroxypropanamide (640 mg, 3.18 mmol) was separated into individual isomers via preparative chiral SFC chromatography. Instrument: PIC Prep SFC; Column: Chiral IG, 30×250 mm. 5 micron; Mobile Phase: 90% CO2/10% IPA; Flow Conditions: 85 mL/min; Detector Wavelength: 220 nm; Injection Details: 900 µL of 639 mg material dissolved in 20 mL IPA. Thus, was obtained the separated materials (2R,3S)-2-fluoro-3-(4-fluorophenyl)-3-hydroxypropanamide (200 mg, 0.994 mmol, 31% yield) as the first material to elute from the SFC separation, and (2S,3R)-2-fluoro-3-(4-fluorophenyl)-3-hydroxypropanamide (240 mg, 1.19 mmol, 38% yield) as the second material to elute from the SFC separation. The absolute stereochemistry for both materials was determined via X-Ray crystallography.

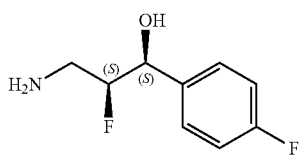

Intermediate 296-SRM-C: (1S,2S)-3-amino-2-fluoro-1-(4-fluorophenyl)propan-1-ol: To a solution of (2R,3S)-2-fluoro-3-(4-fluorophenyl)-3-hydroxypropanamide (234 mg, 1.163 mmol) in anhydrous THF (10 mL) was added borane dimethyl sulfide complex solution, 2.0 M in THF (1.75 mL, 3.50 mmol) over 3-4 min. The mixture was stirred at RT for 5 min and was then heated to 80° C. oil bath for 2 h. Methanol (50 mL) was slowly added and the mixture was stirred at RT overnight. Solvent was removed in vacuo, then the residue was redissolved in MeOH (65 mL) and evaporated to dryness again. This methanol azeotrope was repeated once more. Thus, was obtained (1S,2S)-3-amino-2-fluoro-1-(4-fluorophenyl)propan-1-ol (344 mg, excess weight, assumed 100% yield) as a white solid. The material was used as-is in subsequent steps without further purification. LC/MS ESI/APCI m/z 187.85 (M+H)⁺

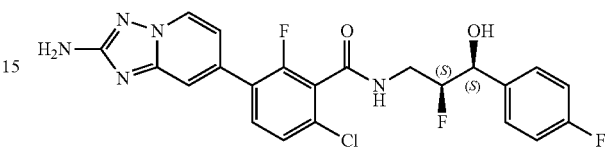

296-SRM-D: In a dry vial under nitrogen were combined 3-(2-amino-[1,2,4]triazolo[1,5-a]pyridin-7-yl)-6-chloro-2-fluorobenzoic acid (12 mg, 0.039 mmol), (1S,2S)-3-amino-2-fluoro-1-(4-fluorophenyl)propan-1-ol (8.8 mg, 0.047 mmol), anhydrous DMF (1.0 mL) and N,N-diisopropylethylamine (35 µL, 0.20 mmol). The reaction was flushed briefly with nitrogen, treated with BOP (26 mg, 0.059 mmol), capped and heated for 2 h. The crude material was purified via preparative LC/MS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 7% B, 7-47% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give 3-(2-amino-[1,2,4]triazolo[1,5-a]pyridin-7-yl)-6-chloro-2-fluoro-N-((2S,3S)-2-fluoro-3-(4-fluorophenyl)-3-hydroxypropyl)benzamide (9.0 mg, mmol, 48% yield). This material was used as a standard reference material to determine the absolute stereochemistry of example 296 and example 297 via analytical chiral SFC chromatography.

Example 297: 3-(2-amino-[1,2,4]triazolo[1,5-a]pyridin-7-yl)-6-chloro-2-fluoro-N-((2R,3R)-2-fluoro-3-(4-fluorophenyl)-3-hydroxypropyl)benzamide

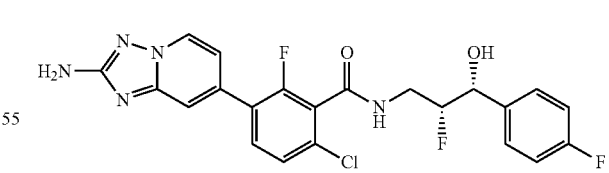

The title compound 3-(2-amino-[1,2,4]triazolo[1,5-a]pyridin-7-yl)-6-chloro-2-fluoro-N-((2R,3R)-2-fluoro-3-(4-fluorophenyl)-3-hydroxypropyl)benzamide (45.8 mg, 0.096 mmol, 39% yield) was obtained as the second eluting isomer from the chiral SFC purification described for example 296. The exact (2R,3R) stereochemistry of this material was determined by analytical chiral SFC chromatography retention time compared to standard reference material. The standard reference material was synthesized using enantiopure starting materials with absolute stereochemistry that was confirmed via X-Ray crystallography, as described in section Intermediates 296-SRM-A to 296-SRM-D.

$^1$H NMR (500 MHz, DMSO-d$_6$) δ 9.03 (br t, J=5.5 Hz, 1H), 8.63 (d, J=7.0 Hz, 1H), 7.73 (t, J=8.1 Hz, 1H), 7.53-7.42 (m, 4H), 7.20 (t, J=8.7 Hz, 2H), 7.04 (br d, J=7.0 Hz, 1H), 6.11 (s, 2H), 5.88 (d, J=5.2 Hz, 1H), 4.86-4.77 (m, 1H), 4.76-4.55 (m, 1H).

LC/MS ESI/APCI m/z 476.18 (M+H)$^+$

Example 298: 3-(2-amino-[1,2,4]triazolo[1,5-a]pyridin-7-yl)-6-chloro-2-fluoro-N-((2R,3S)-2-fluoro-3-(4-fluorophenyl)-3-hydroxypropyl)benzamide

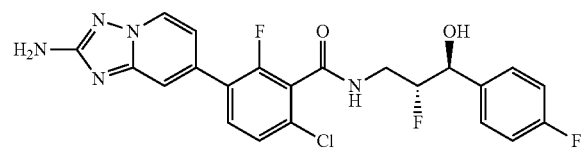 [SMILES: Nc1nc2cc(-c3ccc(Cl)c(C(=O)NC[C@@H](F)[C@@H](O)c4ccc(F)cc4)c3F)ccn2n1]

The isolate 296D-02 (112 mg, 0.24 mmol) was subjected to chiral SFC separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 65% CO2/35% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 65% CO2/35% MeOH w/0.1% DEA; Flow Rate: 60 mL/min; Detector Wavelength: 220 nm; Injection details: 600 μL 112 mg dissolved in 3 mL DMSO. Fractions containing the first eluting isomer were combined and dried to afford 3-(2-amino-[1,2,4]triazolo[1,5-a]pyridin-7-yl)-6-chloro-2-fluoro-N-((2R,3S)-2-fluoro-3-(4-fluorophenyl)-3-hydroxypropyl)benzamide (42.3 mg, 0.089 mmol, >95% ee, 37% yield). The exact (2R,3S) stereochemistry of this material was determined by analytical chiral SFC chromatography retention time compared to standard reference material. The standard reference material was synthesized using enantiopure starting materials with absolute stereochemistry that was confirmed via X-Ray crystallography, as described in section Intermediates 298-SRM-A to 298-SRM-D.

$^1$H NMR (500 MHz, DMSO-d$_6$) δ 9.03 (br t, J=5.6 Hz, 1H), 8.62 (d, J=7.0 Hz, 1H), 7.72 (t, J=8.4 Hz, 1H), 7.53-7.42 (m, 4H), 7.19 (br t, J=8.9 Hz, 2H), 7.05 (br d, J=7.0 Hz, 1H), 6.10 (s, 2H), 4.82-4.73 (m, 1H), 4.72-4.54 (m, 1H).

LC/MS ESI/APCI m/z 475.90 (M+H)$^+$

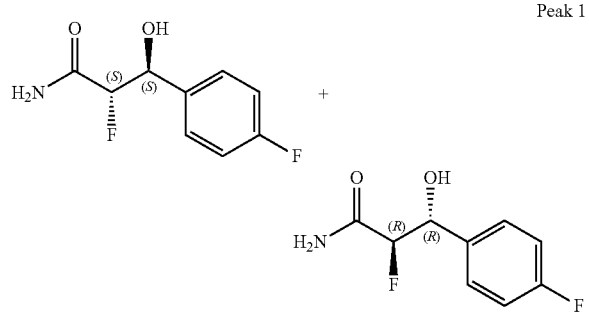

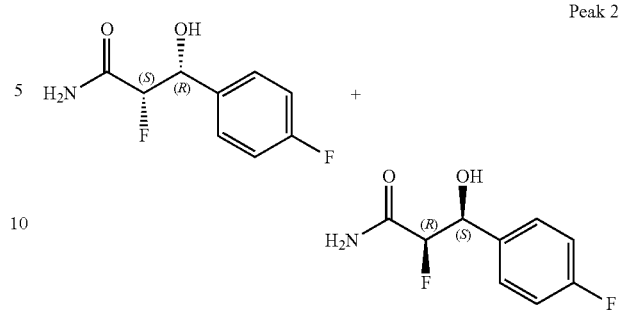

Intermediates 298-SRM-A: racemic mixture of (2S,3S)-2-fluoro-3-(4-fluorophenyl)-3-hydroxypropanamide and (2R,3R)-2-fluoro-3-(4-fluorophenyl)-3-hydroxypropanamide and racemic mixture of (2S,3R)-2-fluoro-3-(4-fluorophenyl)-3-hydroxypropanamide and (2R,3S)-2-fluoro-3-(4-fluorophenyl)-3-hydroxypropanamide: To a solution ethyl 2-fluoro-3-(4-fluorophenyl)-3-hydroxypropanoate (preparation as described in 296A) (2.00 g, 8.69 mmol) in methanol (21.7 mL) at RT was added ammonia, 7M in methanol (6.21 mL, 43.4 mmol) and the reaction mixture was stirred at RT for 12 h. This material was purified by reverse phase preparative HPLC (Column=Waters Sunfire Prep C18 OBD, 50×250 mm, 10 micron particles, Solvent A=95% water, 5% acetonitrile, 10 mM ammonium acetate, Solvent B=5% water, 95% acetonitrile, 10 mM ammonium acetate, Flow rate=100 mL/min, elution gradient 0 to 30% B over 25 minutes) to provide two separate peaks. The first peak to elute was concentrated to give a racemic mixture of (2S,3S)-2-fluoro-3-(4-fluorophenyl)-3-hydroxypropanamide and (2R,3R)-2-fluoro-3-(4-fluorophenyl)-3-hydroxypropanamide (0.67 g, 3.33 mmol, 38% yield) as a white powder, and the second peak to elute was concentrated to give a racemic mixture of (2S,3R)-2-fluoro-3-(4-fluorophenyl)-3-hydroxypropanamide and (2R,3S)-2-fluoro-3-(4-fluorophenyl)-3-hydroxypropanamide (0.70 g, 3.48 mmol, 40% yield) as a white powder. The stereochemistry of both isolates was determined via X-Ray crystallography.

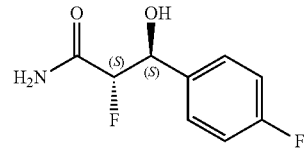

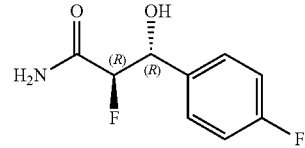

Intermediates 298-SRM-B: (2S,3S)-2-fluoro-3-(4-fluorophenyl)-3-hydroxypropanamide and (2R,3R)-2-fluoro-3-(4-fluorophenyl)-3-hydroxypropanamide: A racemic mixture of (2S,3S)-2-fluoro-3-(4-fluorophenyl)-3-hydroxypropanamide and (2R,3R)-2-fluoro-3-(4-fluorophenyl)-3-hydroxypropanamide (559 mg, 2.78 mmol) was separated into individual isomers via preparative chiral SFC chromatography. Analytical chromatographic conditions (prior to preparative SFC separation): Instrument: Agilent SFC; Column: Chiral IC, 4.6×250 mm, 5 micron; Mobile phase: 90% CO2/10% IPA-ACN; Flow conditions: 2 mL/min; Detector wavelength: 220 nm. Preparative SFC chromatographic conditions: Instrument: Berger Prep SFC; Column: Chiral IC, 30×250 mm, 5 micron; Mobile phase: 90% CO2/10% IPA-ACN; Flow rate: 85 mL/min; Detector wavelength: 220 nm; Injection details: 1500 microliter injections of 559 mg racemate dissolved in 8 mL IPA-ACN. Fractions containing the first eluting isomer were combined and dried to afford (2S,3S)-2-fluoro-3-(4-fluorophenyl)-3-hydroxypropanamide (180 mg, 0.895 mmol, 32% yield).

Fractions containing the second eluting isomer were combined and dried to afford (2R,3R)-2-fluoro-3-(4-fluorophenyl)-3-hydroxypropanamide (230 mg, 1.14 mmol, 41% yield). The absolute stereochemistry of this second eluting material was determined by X-Ray crystallography.

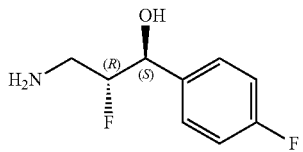

Intermediate 298-SRM-C: (1S,2R)-3-amino-2-fluoro-1-(4-fluorophenyl)propan-1-ol: To a solution of (2S,3S)-2-fluoro-3-(4-fluorophenyl)-3-hydroxypropanamide (100 mg, 0.497 mmol) in anhydrous THF (2.0 mL) was added borane-methyl sulfide complex, 2.0 M in THF (750 µL, 1.50 mmol). The reaction was stirred at room temp for 5 min, then heated at 80° C. for 125 min. The reaction was quenched with methanol (2.5 mL) and the volatiles were removed in vacuo to give (1S,2R)-3-amino-2-fluoro-1-(4-fluorophenyl)propan-1-ol (95 mg, 0.51 mmol, quantitative yield) which was used without further purification in the next step.
MS ESI m/z 187.8 (M+H)$^+$

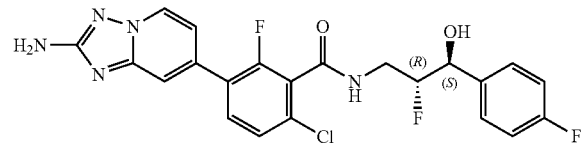

298-SRM-D: 3-(2-amino-[1,2,4]triazolo[1,5-a]pyridin-7-yl)-6-chloro-2-fluoro-N-((2R,3S)-2-fluoro-3-(4-fluorophenyl)-3-hydroxypropyl)benzamide: To a solution of 3-(2-amino-[1,2,4]triazolo[1,5-a]pyridin-7-yl)-6-chloro-2-fluorobenzoic acid (9.0 mg, 0.029 mmol), (1S,2R)-3-amino-2-fluoro-1-(4-fluorophenyl)propan-1-ol (6.1 mg, 0.033 mmol), and N,N-diisopropylethylamine (26 µL, 0.15 mmol) in DMF (1 mL) was added BOP (17 mg, 0.038 mmol). The reaction was stirred at RT for 18 h, then the mixture was filtered and purified via reverse phase preparative LCMS with the following conditions: Column: XBridge C18, 200 mm×19 mm, 5 µm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 9% B, 9-49% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to give 3-(2-amino-[1,2,4]triazolo[1,5-a]pyridin-7-yl)-6-chloro-2-fluoro-N-((2R,3S)-2-fluoro-3-(4-fluorophenyl)-3-hydroxypropyl)benzamide (9.8 mg, 0.020 mmol, 70% yield). This material was used as a standard reference material to determine the absolute stereochemistry of example 298 and example 299 via analytical chiral SFC chromatography.
MS ESI m/z 476.0 (M+H)$^+$ Example 299: 3-(2-amino-[1,2,4]triazolo[1,5-a]pyridin-7-yl)-6-chloro-2-fluoro-N-((2S,3R)-2-fluoro-3-(4-fluorophenyl)-3-hydroxypropyl)benzamide

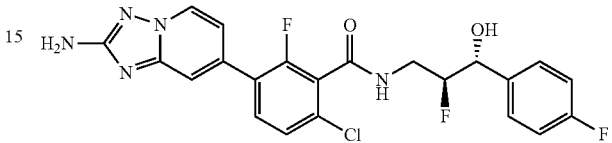

The title compound 3-(2-amino-[1,2,4]triazolo[1,5-a]pyridin-7-yl)-6-chloro-2-fluoro-N-((2S,3R)-2-fluoro-3-(4-fluorophenyl)-3-hydroxypropyl)benzamide (39.0 mg, 0.082 mmol, 35% yield) was obtained as the second eluting isomer from the chiral SFC purification described for example 298. The exact (2S,3R) stereochemistry of this material was determined by analytical chiral SFC chromatography retention time compared to standard reference material. The standard reference material was synthesized using enantiopure starting materials with absolute stereochemistry that was confirmed via X-Ray crystallography, as described in section Intermediates 298-SRM-A to 298-SRM-D.
$^1$H NMR (500 MHz, DMSO-d$_6$) δ 9.04 (br s, 1H), 8.62 (br d, J=6.7 Hz, 1H), 7.72 (br t, J=7.9 Hz, 1H), 7.53-7.42 (m, 4H), 7.19 (br t, J=8.4 Hz, 2H), 7.05 (br d, J=6.4 Hz, 1H), 6.09 (s, 2H), 4.78 (br d, J=11.6 Hz, 1H), 4.73-4.54 (m, 1H), 3.55 (br d, J=6.7 Hz, 1H).
LC/MS ESI/APCI m/z 475.95 (M+H)$^+$ Example 300: 3-(2-amino-[1,2,4]triazolo[1,5-a]pyridin-7-yl)-N-((2R,3S)-3-(4-chlorophenyl)-2-fluoro-3-hydroxypropyl)-2-fluoro-6-methylbenzamide

300A: ethyl 3-(4-chlorophenyl)-2-fluoro-3-hydroxypropanoate: To a suspension of zinc (5.58 g, 85.0 mmol) in THF (85 mL) was added a solution of ethyl 2-bromo-2-fluoroacetate (6.05 mL, 51.2 mmol) and 4-chlorobenzaldehyde (6.00 g, 42.7 mmol) in THF (15 mL) dropwise with an addition funnel over 15 minutes. The reaction mixture was heated under reflux for 30 minutes. After filtration, 1 N aqueous HCl and ether were added. The aqueous layer was extracted with ethyl acetate three times. The combined organic layers were washed with brine, dried over anhydrous sodium sulfate, and filtered. The filtrate was concentrated in vacuo to give the crude product which was purified by silica gel chromatography eluting with 0-15% ethyl acetate/hexanes to give ethyl 3-(4-chlorophenyl)-2-fluoro-3-hydroxypropanoate (6.50 g, 26.4 mmol, 62% yield).

¹H NMR (500 MHz, CHLOROFORM-d) δ 7.42-7.35 (m, 8H), 5.20-5.10 (m, 2H), 5.06 (dd, J=9.7, 4.4 Hz, 1H), 4.96 (dd, J=9.4, 4.4 Hz, 1H), 4.30-4.15 (m, 4H), 3.04-2.90 (m, 1H), 2.77 (br d, J=3.1 Hz, 1H), 1.25 (dt, J=11.8, 7.2 Hz, 6H).

300B: 3-(4-chlorophenyl)-2-fluoro-3-hydroxypropanamide: To a solution of ethyl 3-(4-chlorophenyl)-2-fluoro-3-hydroxypropanoate (2.22 g, 9.00 mmol) in MeOH (18.0 mL) at room temperature was added 7 M ammonia in methanol (6.43 mL, 45.0 mmol), and the reaction mixture was stirred at room temperature for 12 h. Residual solvents were removed under reduced pressure. The crude product was purified by reverse phase preparative HPLC to yield two enantiomeric mixtures. The first eluted isolate from the reverse phase preparative HPLC separation was 300B-01 (0.80 g, 3.68 mmol, 41% yield). The second eluted isolate from the reverse phase preparative HPLC separation was 300B-02 (0.75 g, 3.45 mmol, 38% yield).

300B-01: ¹H NMR (500 MHz, METHANOL-d₄) δ 7.43-7.38 (m, 1H), 7.37-7.33 (m, 1H), 5.13 (s, 1H), 5.10-5.02 (m, 1H).

LC/MS ESI/APCI m/z 215.85 (M−H)⁻

300B-02: ¹H NMR (500 MHz, METHANOL-d₄) δ 7.50-7.44 (m, 2H), 7.42-7.35 (m, 2H), 5.21-5.10 (m, 1H), 5.03-4.90 (m, 1H).

LC/MS ESI/APCI m/z 215.80 (M−H)⁻

300C: 3-amino-1-(4-chlorophenyl)-2-fluoropropan-1-ol: To a solution of isolate 300B-01 (655 mg, 3.01 mmol) in anhydrous THF (10 mL) was added borane dimethyl sulfide complex solution, 2.0 M in THF (4.50 mL, 9.00 mmol). There was much gas evolution during the addition. After the addition was complete, the reaction was flushed briefly with nitrogen, then heated in an 80° C. oil bath for 2.5 hours. The reaction mixture was cooled in an ice bath and methanol (75 mL) was added. The methanol was removed in vacuo. The crude reaction mixture was azeotroped with methanol three times and the product was dried under high vacuum overnight to yield 3-amino-1-(4-chlorophenyl)-2-fluoropropan-1-ol (676 mg, 3.32 mmol, quantitative yield) as a white oil.

LC/MS ESI/APCI m/z 203.80 (M+H)⁺

300D: tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate: In a 20 mL reaction vial were combined 3-(2-((tert-butoxycarbonyl)amino)-[1,2,4]triazolo[1,5-a]pyridin-7-yl)-2-fluoro-6-methylbenzoic acid (200 mg, 0.518 mmol), 300C 3-amino-1-(4-chlorophenyl)-2-fluoropropan-1-ol (116 mg, 0.569 mmol), BOP (275 mg, 0.621 mmol), and DIPEA (271 µL, 1.55 mmol) in DCM (2.6 mL) to give a tan solution. The reaction was stirred at room temperature for 2 h. The crude reaction was purified directly by silica gel flash chromatography. The product fractions were concentrated under reduced pressure to yield tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate (98 mg, 0.171 mmol, 33% yield). The material was used as-is in the next step.

300E: 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA: In a 2 dram reaction vial were combined tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate (98 mg, 0.171 mmol) and hydrogen chloride solution, 4 M in dioxane (214 µL, 0.857 mmol) in dioxane (343 µL) to give a colorless solution. The reaction was stirred at room temperature overnight. The reaction was concentrated under a gentle stream of nitrogen and dissolved in DMF. The sample was filtered through a 0.45 um PTFE frit. The crude material was purified via preparative LC/MS with the following conditions: Column: XBridge C18, 200 mm×19 mm, 5 µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 9% B, 9-49% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to afford 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA (59 mg, 0.10 mmol, 59% yield).

LC/MS ESI/APCI m/z 471.97 (M+H)⁺

300: The isolate 300E 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA (59 mg, 0.10 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 55% CO2/45% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 55% CO2/45% MeOH w/0.1% DEA; Flow Rate: 60 mL/min; Detector Wavelength: 220 nm; Injection details: 500 µL 47.7 mg dissolved in 3 mL MeOH. Fractions containing the first eluting isomer from the preparative SFC separation were combined and dried to afford 3-(2-amino-[1,2,4]triazolo[1,5-a]pyridin-7-yl)-N-((2R,3S)-3-(4-chlorophenyl)-2-fluoro-3-hydroxypropyl)-2-fluoro-6-methylbenzamide (14.8 mg, 0.031 mmol, >95% ee, 31% yield).

¹H NMR (500 MHz, DMSO-d₆) δ 8.82 (br t, J=5.2 Hz, 1H), 8.59 (d, J=6.7 Hz, 1H), 7.57 (t, J=8.1 Hz, 1H), 7.49-7.41 (m, 5H), 7.22 (d, J=8.2 Hz, 1H), 7.04 (br d, J=6.7 Hz, 1H), 6.06 (s, 2H), 4.79 (br d, J=9.2 Hz, 1H), 4.74-4.58 (m, 1H), 2.29 (s, 3H). (Some protons obscured by water suppression). The exact (2R,3S) stereochemistry of this material was determined by analytical chiral SFC chromatography retention time compared to standard reference material. The standard reference material was synthesized using enantiopure starting materials with absolute stereochemistry that was confirmed via X-Ray crystallography. Standard reference materials were prepared in a similar fashion as described for Example 296 beginning in section 296-SRM-A.

LC/MS ESI/APCI m/z 472.06 (M+H)⁺

Example 301: 3-(2-amino-[1,2,4]triazolo[1,5-a]pyridin-7-yl)-N-((2S,3R)-3-(4-chlorophenyl)-2-fluoro-3-hydroxypropyl)-2-fluoro-6-methylbenzamide

The title compound 3-(2-amino-[1,2,4]triazolo[1,5-a]pyridin-7-yl)-N-((2S,3R)-3-(4-chlorophenyl)-2-fluoro-3-hydroxypropyl)-2-fluoro-6-methylbenzamide (14.6 mg, 0.031 mmol, 31% yield) was obtained as the second eluting isomer from the chiral SFC purification described for example 300. The exact (2S,3R) stereochemistry of this material was determined by analytical chiral SFC chromatography retention time compared to standard reference material. The standard reference material was synthesized using enantiopure starting materials with absolute stereochemistry that was confirmed via X-Ray crystallography. Standard reference materials were prepared in a similar fashion as described for Example 296, beginning in section 296-SRM-A.

$^1$H NMR (500 MHz, DMSO-d$_6$) δ 8.82 (br t, J=5.5 Hz, 1H), 8.60 (d, J=6.7 Hz, 1H), 7.58 (t, J=8.1 Hz, 1H), 7.49-7.42 (m, 5H), 7.22 (d, J=8.2 Hz, 1H), 7.03 (br d, J=6.7 Hz, 1H), 6.06 (s, 2H), 4.79 (br dd, J=12.8, 5.2 Hz, 1H), 4.73-4.56 (m, 1H), 3.71-3.57 (m, 1H), 2.30 (s, 3H).

LC/MS ESI/APCI m/z 472.05 (M+H)$^+$

Example 302: 3-(2-amino-[1,2,4]triazolo[1,5-a]pyridin-7-yl)-N-((2S,3S)-3-(4-chlorophenyl)-2-fluoro-3-hydroxypropyl)-2-fluoro-6-methylbenzamide

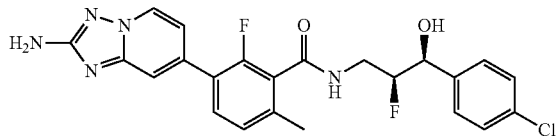 [SMILES: Cc1ccc(-c2ccn3nc(N)nc3c2)c(F)c1C(=O)NC[C@H](F)[C@@H](O)c1ccc(Cl)cc1]

302A: 3-amino-1-(4-chlorophenyl)-2-fluoropropan-1-ol: To a solution of 300B-02 (797 mg, 3.66 mmol) in anhydrous THF (10 mL) was added borane dimethyl sulfide complex solution, 2.0 M in THF (5.50 mL, 11.0 mmol). There was much gas evolution during the addition. After the addition was complete, the reaction was flushed briefly with nitrogen, then heated in an 80° C. oil bath for 2.5 h. The reaction mixture was cooled on an ice bath and methanol (75 mL) was added. The methanol was removed in vacuo. The crude reaction mixture was azeotroped with methanol three times and the product was dried under high vacuum overnight to yield 3-amino-1-(4-chlorophenyl)-2-fluoropropan-1-ol (803 mg, 3.94 mmol, quantitative yield) as a white oil.

LC/MS ESI/APCI m/z 203.85 (M+H)$^+$

302B: tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate: In a 20 mL reaction vial were combined 3-(2-((tert-butoxycarbonyl)amino)-[1,2,4]triazolo[1,5-a]pyridin-7-yl)-2-fluoro-6-methylbenzoic acid (200 mg, 0.518 mmol), 3-amino-1-(4-chlorophenyl)-2-fluoropropan-1-ol (116 mg, 0.569 mmol), BOP (275 mg, 0.621 mmol), and DIPEA (271 μL, 1.55 mmol) in DCM (2.6 mL) to give a tan solution. The reaction was stirred for 2 h. The crude reaction mixture was purified directly by silica gel flash chromatography to afford tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate (123 mg, 0.215 mmol, 42% yield).

302C: 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA: In a 2 dram reaction vial were combined tert-butyl (7-(3-((3-(4-chlorophenyl)-2-fluoro-3-hydroxypropyl)carbamoyl)-2-fluoro-4-methylphenyl)-[1,2,4]triazolo[1,5-a]pyridin-2-yl)carbamate (145 mg, 0.253 mmol) and hydrogen chloride solution, 4 M in 1,4-dioxane (317 μL, 1.27 mmol) in dioxane (507 μL) to give a colorless solution. The reaction was stirred at room temperature overnight. A white precipitate formed. The reaction mixture was concentrated under a gentle stream of nitrogen. The crude material was dissolved in DMF and filtered through a 0.45 um PTFE frit. The crude material was purified via preparative LC/MS with the following conditions: Column: XBridge C18, 200 mm×19 mm, 5 μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 8% B, 8-48% B over 20 minutes, then a 0-minute hold at 100% B; Flow Rate: 20 mL/min; Column Temperature: 25 C. Fraction collection was triggered by MS signals. Fractions containing the desired product were combined and dried via centrifugal evaporation to give ethyl 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA (88.9 mg, 0.152 mmol, 29% yield).

LC/MS ESI/APCI m/z 472.00 (M+H)$^+$

302: The isolate 302C 3-(2-amino-[1,2,4]triazolo[1,5-a]pyridin-7-yl)-N-(3-(4-chlorophenyl)-2-fluoro-3-hydroxypropyl)-2-fluoro-6-methylbenzamide, TFA (89 mg, 0.152 mmol) was subjected to chiral separation with the following conditions: Analytical chromatographic conditions (prior to preparative SFC separation): Instrument: Shimadzu Nexera UC SFC; Column: Chiral IC, 4.6×150 mm, 5 micron; Mobile Phase: 50% CO2/50% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 50% CO2/50% MeOH w/0.1% DEA; Flow Rate: 60 mL/min; Detector Wavelength: 220 nm; Injection details: 2000 μL 71.7 mg dissolved in 3 mL MeOH. Fractions containing the first eluting isomer from the preparative SFC separation were combined and dried to afford 3-(2-amino-[1,2,4]triazolo[1,5-a]pyridin-7-yl)-N-((2S,3S)-3-(4-chlorophenyl)-2-fluoro-3-hydroxypropyl)-2-fluoro-6-methylbenzamide (6.3 mg, 0.013 mmol, >95% ee, 9% yield). The exact (2S,3S) stereochemistry of this material was determined by analytical chiral SFC chromatography retention time compared to standard reference material. The standard reference material was synthesized using enantiopure starting materials with absolute stereochemistry that was confirmed via X-Ray crystallography. Standard reference materials were prepared in a similar fashion as described for Example 296, beginning in section 296-SRM-A.

$^1$H NMR (500 MHz, DMSO-d$_6$) δ 8.83 (t, J=5.9 Hz, 1H), 8.59 (d, J=7.0 Hz, 1H), 7.57 (t, J=8.1 Hz, 1H), 7.47 (s, 1H), 7.43 (s, 4H), 7.22 (d, J=7.9 Hz, 1H), 7.04 (br d, J=6.7 Hz, 1H), 6.05 (s, 2H), 4.86-4.76 (m, 1H), 4.76-4.59 (m, 1H), 2.29 (s, 3H).

LC/MS ESI/APCI m/z 472.01 (M+H)$^+$

Example 303: 3-(2-amino-[1,2,4]triazolo[1,5-a]pyridin-7-yl)-N-((2R,3R)-3-(4-chlorophenyl)-2-fluoro-3-hydroxypropyl)-2-fluoro-6-methylbenzamide

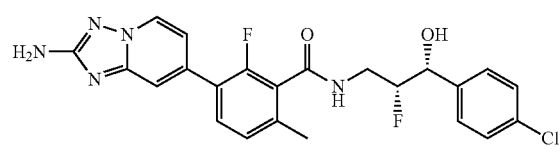 [SMILES: Cc1ccc(-c2ccn3nc(N)nc3c2)c(F)c1C(=O)NC[C@@H](F)[C@H](O)c1ccc(Cl)cc1]

The title compound 3-(2-amino-[1,2,4]triazolo[1,5-a]pyridin-7-yl)-N-((2R,3R)-3-(4-chlorophenyl)-2-fluoro-3-hydroxypropyl)-2-fluoro-6-methylbenzamide (6.1 mg, 0.013 mmol, 9% yield) was obtained as the second eluting isomer from the chiral SFC purification described for example 299. The exact (2R,3R) stereochemistry of this material was determined by analytical chiral SFC chromatography retention time compared to standard reference material. The standard reference material was synthesized using enantiopure starting materials with absolute stereochemistry that was confirmed via X-Ray crystallography. Standard reference materials were prepared in a similar fashion as described for Example 296, beginning in section 296-SRM-A.

$^1$H NMR (500 MHz, DMSO-d$_6$) δ 8.83 (t, J=6.1 Hz, 1H), 8.60 (d, J=6.7 Hz, 1H), 7.58 (t, J=8.1 Hz, 1H), 7.49-7.41 (m, 5H), 7.22 (d, J=8.2 Hz, 1H), 7.04 (br d, J=6.7 Hz, 1H), 6.06 (s, 2H), 4.85-4.77 (m, 1H), 4.76-4.61 (m, 1H), 2.30 (s, 3H).
LC/MS ESI/APCI m/z 472.04 (M+H)$^+$ overnight. The mixture was diluted with EtOAc (20 mL) and washed with saturated NaHCO$_3$ (20 mL) and brine (20 mL), dried over Na$_2$SO$_4$, filtered and concentrated in vacuo to provide methyl 3-bromo-2-fluoro-6-methoxybenzoate (450 mg, 4.30 mmol, 99% yield) which was used to next step without further purification.

$^1$H NMR (499 MHz, CHLOROFORM-d) δ 7.55 (dd, J=8.9, 7.7 Hz, 1H), 6.67 (dd, J=9.0, 1.3 Hz, 1H), 3.96 (s, 3H), 3.88 (s, 3H). MS ESI m/z 263.2 (M+H)$^+$.

306B: methyl 3-bromo-2-fluoro-6-hydroxybenzoate: Methyl 3-bromo-2-fluoro-6-methoxybenzoate (450 mg, 4.30 mmol) was dissolved in DCM (6 mL). Aluminum chloride (460 mg, 3.45 mmol) was added and the mixture was stirred at RT for 30 min. The mixture was poured into ice water (20 mL) and extracted with DCM (20 mL×3). The combined organics were dried over Na$_2$SO$_4$, filtered and concentrated in vacuo to provide methyl 3-bromo-2-fluoro-6-hydroxybenzoate (430 mg, 4.30 mmol, 100% yield) which was used to next step without further purification.

TABLE 21

Compounds in Table 21 were prepared in a similar fashion to example 120.

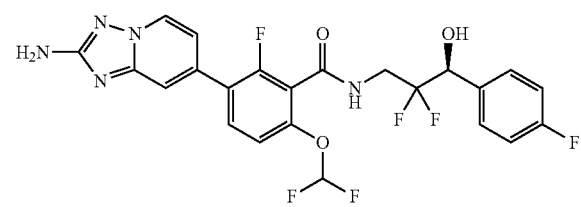 [SMILES: Nc1nc2cc(-c3ccc(OC(F)F)c(C(=O)NCC(F)(F)[C@@H](O)c4ccc(F)cc4)c3F)ccn2n1]

| Ex No | Name | R | M + H$^+$ | $^1$H NMR (500 MHz, DMSO-d6) δ |
|---|---|---|---|---|
| 304 | (S)-3-(2-amino-[1,2,4]triazolo[1,5-a]pyridin-7-yl)-6-cyclopropyl-N-(2,2-difluoro-3-(4-fluorophenyl)-3-hydroxypropyl)-2-fluorobenzamide | cyclopropyl | 499.5 | 9.11-8.94 (m, 1H), 8.61-8.46 (m, 1H), 7.60-7.52 (m, 1H), 7.49-7.38 (m, 2H), 7.20 (br t, J = 8.9 Hz, 2H), 7.06 (br d, J = 7.3 Hz, 1H), 6.86 (br d, J = 8.2 Hz, 1H), 6.60-6.45 (m, 1H), 6.01 (s, 1H), 4.99-4.80 (m, 1H), 2.02-1.83 (m, 1H), 1.02-0.91 (m, 2H), 0.83-0.67 (m, 2H) (no water suppression) |
| 305 | (R)-3-(2-amino-[1,2,4]triazolo[1,5-a]pyridin-7-yl)-6-cyclopropyl-N-(2,2-difluoro-3-(4-fluorophenyl)-3-hydroxypropyl)-2-fluorobenzamide | cyclopropyl | 499.5 | 9.01 (br t, J = 6.1 Hz, 1H), 8.60 (br d, J = 7.0 Hz, 1H), 7.62-7.54 (m, 1H), 7.53-7.42 (m, 3H), 7.22 (br t, J = 8.7 Hz, 2H), 7.03 (br d, J = 6.7 Hz, 1H), 6.87 (d, J = 8.2 Hz, 1H), 6.43 (d, J = 5.2 Hz, 1H), 6.05 (br s, 2H), 4.93 (dt, J = 16.2, 6.0 Hz, 1H), 3.99-3.75 (m, 2H), 2.01-1.85 (m, 1H), 0.97 (br d, J = 8.5 Hz, 2H), 0.77 (br d, J = 3.7 Hz, 2H) |

Example 306: (S)-3-(2-amino-[1,2,4]triazolo[1,5-a]pyridin-7-yl)-N-(2,2-difluoro-3-(4-fluorophenyl)-3-hydroxypropyl)-6-(difluoromethoxy)-2-fluorobenzamide 306A: methyl 3-bromo-2-fluoro-6-methoxybenzoate: To a mixture of 3-bromo-2-fluoro-6-methoxybenzoic acid (430 mg, 1.73 mmol) in MeOH (42 mL) was added 5 drops of concentrated H$_2$SO$_4$. The mixture was stirred at 85° C.

$^1$H NMR (499 MHz, CHLOROFORM-d) δ 11.27 (s, 1H), 7.59 (dd, J=9.0, 7.5 Hz, 1H), 6.76 (dd, J=9.1, 1.7 Hz, 1H), 4.03 (s, 3H).

306C: methyl 3-bromo-6-(difluoromethoxy)-2-fluorobenzoate: A mixture of methyl 3-bromo-2-fluoro-6-hydroxybenzoate (125 mg, 0.502 mmol), acetonitrile (1.0 mL) and 6M aqueous KOH (1.0 mL) was treated with difluoromethyl trifluoromethanesulfonate (301 mg, 1.51 mmol) at RT for 15 min. The mixture was diluted with H$_2$O (8 mL) and extracted with EtOAc (2×8 mL). The combined organics were dried over Na$_2$SO$_4$, filtered and concentrated in vacuo to provide methyl 3-bromo-6-(difluoromethoxy)-2-fluorobenzoate (150 mg, 0.502 mmol, 100% yield) which was used to next step without further purification.

$^1$H NMR (499 MHz, DMSO-d$_6$) δ 7.98 (dd, J=8.9, 8.1 Hz, 1H), 7.54-7.14 (m, 2H), 3.91 (s, 3H).

306D: 3-bromo-6-(difluoromethoxy)-2-fluorobenzoic acid: A mixture of methyl 3-bromo-6-(difluoromethoxy)-2-fluorobenzoate (150 mg, 0.502 mmol) in EtOH (2 mL) and aqueous ION NaOH (0.200 mL, 2.00 mmol) was stirred at 80° C. for 30 min. The solution was acidified with concentrated HCl and the solvent was removed in vacuo to give 3-bromo-6-(difluoromethoxy)-2-fluorobenzoic acid (143 mg, 0.502 mmol, 100% yield) which was used in the next step without further purification.

306E: (S)-3-bromo-N-(2,2-difluoro-3-(4-fluorophenyl)-3-hydroxypropyl)-6-(difluoromethoxy)-2-fluorobenzamide: 3-bromo-6-(difluoromethoxy)-2-fluorobenzoic acid (143 mg, 0.502 mmol) was dissolved in DMF (3 mL) and the solution was treated with BOP (266 mg, 0.602 mmol), Hunig's base (175 µL, 1.00 mmol) and (S)-3-amino-2,2-difluoro-1-(4-fluorophenyl)propan-1-ol (103 mg, 0.502 mmol). The mixture was stirred at RT for 20 min. The mixture was diluted with $H_2O$ (8 mL) and extracted with EtOAc (2×8 mL). The combined organics were dried over $Na_2SO_4$, filtered and concentrated in vacuo to provide (230 mg, 0.487 mmol, 97% yield) which was used in the next step without further purification.

306: A mixture of 7-bromo-[1,2,4]triazolo[1,5-a]pyridin-2-amine (30 mg, 0.141 mmol), $PdCl_2(dppf)$-$CH_2Cl_2$ adduct (5.75 mg, 7.04 µmol), 4,4,4',4',5,5,5',5'-octamethyl-2,2'-bi(1,3,2-dioxaborolane) (42.9 mg, 0.169 mmol) and potassium acetate (41.5 mg, 0.422 mmol) in dioxane (2 mL) was purged with nitrogen and stirred at 105° C. for 2 h. To the mixture was added (S)-3-bromo-N-(2,2-difluoro-3-(4-fluorophenyl)-3-hydroxypropyl)-6-(difluoromethoxy)-2-fluorobenzamide (66.5 mg, 0.141 mmol), $PdCl_2(dtbpf)$ (9.18 mg, 0.014 mmol) and potassium phosphate, 2M aqueous solution (211 µL, 0.422 mmol). The resulting mixture was degassed by bubbling nitrogen through for 2 min and then stirred at 110° C. for 1.5 h. The reaction mixture was filtered and the filtrate was concentrated in vacuo. The crude material was purified via preparative LC/MS with the following conditions: Column: XBridge C18, 200 mm×19 mm, 5 µm particles; Mobile Phase A: 5:95 acetonitrile:water with ammonium acetate; Mobile Phase B: 95:5 acetonitrile:water with ammonium acetate; Gradient: a 0-minute hold at 15% B, 15-55% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation to provide (S)-3-(2-amino-[1,2,4]triazolo[1,5-a]pyridin-7-yl)-N-(2,2-difluoro-3-(4-fluorophenyl)-3-hydroxypropyl)-6-(difluoromethoxy)-2-fluorobenzamide (13.1 mg, 0.0249 mmol, 18% yield)

$^1$H NMR (500 MHz, DMSO-$d_6$) δ 9.05 (br t, J=5.7 Hz, 1H), 8.62 (br d, J=7.1 Hz, 1H), 7.78 (br t, J=8.8 Hz, 1H), 7.54-7.43 (m, 3H), 7.28-7.17 (m, 4H), 7.13-6.99 (m, 1H), 6.50-6.38 (m, 1H), 6.08 (br s, 2H), 4.91 (dt, J=16.6, 5.8 Hz, 1H), 3.94-3.71 (m, 2H).
MS ESI m/z 525.9 (M+H)$^+$

Example 307: 3-(2-amino-[1,2,4]triazolo[1,5-a]pyridin-7-yl)-2-fluoro-N-((1-((4-fluorophenyl)(hydroxy)methyl)cyclopropyl)methyl)-6-(methyl-$d_3$)benzamide enantiomer 1

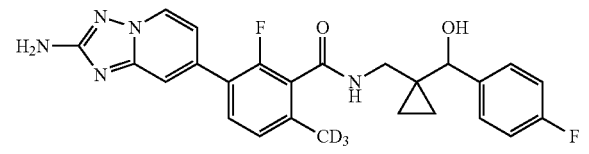

307A: 1-(4-fluorobenzoyl)cyclopropane-1-carboxylic acid: In a 40 mL vial were combined methyl 3-(4-fluorophenyl)-3-oxopropanoate (1.50 g, 7.65 mmol), $K_2CO_3$ (2.11 g, 15.3 mmol), methanol (1.24 mL) and DMSO (15 mL) and the mixture was stirred at room temperature for 30 min. 1,2-dibromoethane (5.75 g, 30.6 mmol) was added in one portion. The mixture was heated to 65° C. for 30 h. The reaction was quenched by addition of 12 mL water. The mixture was extracted with DCM (30 mL×3) and the combined organics were washed with saturated NaCl solution (30 mL×3), dried over anhydrous sodium sulfate, filtered and the filtrate was evaporated under reduced pressure. The product was purified by silica gel column (40 g silica, gradient EtOAc/Hexanes=0-60%, gradient time=15 min at flow rate=30 mL/min). Fractions containing the desired ester product were combined and concentrated, and the residue was dissolved in a mixture of MeOH (5 mL) and water (1 mL) and treated with 12N aqueous NaOH (1.5 mL, 18 mmol). The resulting mixture was stirred at 65° C. for 5 h. The mixture was acidified with concentrated HCl and solvent was removed to give the desired 1-(4-fluorobenzoyl)cyclopropane-1-carboxylic acid (0.80 g, 50% yield). The material was used as-is in the next step without further purification
MS ESI m/z 209.2 (M+H)$^+$ 307B: 1-(4-fluorobenzoyl)cyclopropane-1-carboxamide: To a solution of 1-(4-fluorobenzoyl)cyclopropane-1-carboxylic acid (470 mg, 2.26 mmol), ammonium carbonate (868 mg, 9.03 mmol) and DIPEA (0.789 mL, 4.52 mmol) in DMF (6 mL) was added BOP (1.20 g, 2.71 mmol) and the mixture was stirred at RT for 1 h. The reaction mixture was diluted with water (20 mL) and EtOAc (30 mL), the organic layer was separated and washed with saturated aqueous $NaHCO_3$ solution (20 mL×2) and brine (20 mL), dried over anhydrous $Na_2SO_4$, filtered and concentrated under reduced pressure to provide 1-(4-fluorobenzoyl)cyclopropane-1-carboxamide (470 mg, 2.26 mmol, 100% yield) which was used in subsequent steps without further purification.

$^1$H NMR (499 MHz, CHLOROFORM-d) δ 8.07-7.94 (m, 2H), 7.24-7.12 (m, 2H), 5.80-5.40 (m, 2H), 1.69-1.65 (m, 2H), 1.47-1.41 (m, 2H).
MS ESI m/z 208.2 (M+H)$^+$

307C: (1-(aminomethyl)cyclopropyl)(4-fluorophenyl)methanol: In an 8 mL resealable pressure vessel filled with nitrogen, a solution of 1-(4-fluorobenzoyl)cyclopropane-1-carboxamide (100 mg, 0.483 mmol) in THF (3 mL) was treated with borane-methyl sulfide complex, 5M in THF (0.483 mL, 2.413 mmol) at RT. Effervescence was observed. The vessel was sealed and the mixture was stirred at 80° C. overnight. The reaction was quenched by careful addition of methanol (1 mL) dropwise which caused vigorous effervescence and warming of the mixture. The mixture was stirred at RT for 30 min. The reaction mixture was concentrated in vacuo to give a viscous oil. The crude ketone product (MS ESI m/z=193.3 (M+H)$^+$) thus obtained was then dissolved in a mixture of DCM (4 mL) and MeOH (2 mL), and to the mixture was added $NaBH_4$ (110 mg, 2.90 mmol) in 3 portions over 1 h. The mixture was stirred for another 1 h and then treated with TN aq. HCl (2 mL) and heated to 65° C. for 1 h. Mild effervescence was noticed initially. The cloudy mixture became clear and the color became slightly brown over time. The mixture was concentrated in vacuo, and the crude residue was triturated with $Et_2O$. The residue was dried under vacuum to give crude (1-(aminomethyl)cyclopropyl)(4-fluorophenyl)methanol (70 mg, 0.359 mmol, 74% yield) as a solid which was used in the next step without further purification.

MS ESI m/z 196.3 (M+H)+

307D: 3-(2-amino-[1,2,4]triazolo[1,5-a]pyridin-7-yl)-6-chloro-2-fluoro-N-((1-((4-fluorophenyl)(hydroxy)methyl)cyclopropyl)methyl)benzamide: To a solution of 3-(2-amino-[1,2,4]triazolo[1,5-a]pyridin-7-yl)-6-chloro-2-fluorobenzoic acid (80.0 mg, 0.261 mmol), (1-(aminomethyl)cyclopropyl)(4-fluorophenyl)methanol (61.1 mg, 0.313 mmol) and DIPEA (0.137 mL, 0.783 mmol) in DMF (3 mL) was added BOP (138 mg, 0.313 mmol) and the mixture was stirred at RT for 2 h. The reaction mixture was concentrated in vacuo and the residue was triturated in water (5 mL). The solid was collected and then purified by silica gel column (12 g silica, gradient EtOAc/Hexanes=0-100%, gradient time=12 min, flow rate 25 mL/min) to give racemic 3-(2-amino-[1,2,4]triazolo[1,5-a]pyridin-7-yl)-6-chloro-2-fluoro-N-((1-((4-fluorophenyl)(hydroxy)methyl)cyclopropyl)methyl)benzamide (69 mg, 0.143 mmol, 55% yield). The product was taken directly to next step as-is.

MS ESI m/z 484.5 (M+H)+

307: A mixture of 3-(2-amino-[1,2,4]triazolo[1,5-a]pyridin-7-yl)-6-chloro-2-fluoro-N-((1-((4-fluorophenyl)(hydroxy)methyl)cyclopropyl)methyl)benzamide (35 mg, 0.072 mmol), PdCl$_2$(dtbpf) (4.71 mg, 7.23 μmol) and (methyl-d$_3$)boronic acid (0.310 mL, 0.217 mmol) in dioxane (2 mL) was purged with nitrogen for 1 min. Potassium phosphate, tribasic, 2M aqueous (0.199 mL, 0.398 mmol) was added and the reaction mixture was heated to 130° C. overnight. The crude material was purified directly via preparative LC/MS with the following conditions: Column: XBridge C18, 200 mm×19 mm, 5 μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 15% B, 15-55% B over 20 minutes, then a 0-minute hold at 100% B; Flow Rate: 20 mL/min; Column Temperature: 25 C. Fraction collection was triggered by MS and UV signals. Fractions containing the desired product were combined and dried via centrifugal evaporation. The residue thus obtained was further purified by preparative chiral SFC chromatography to provide separated enantiomers with the following conditions: Analytical chromatographic conditions (prior to preparative SFC separation): Instrument: Shimadzu Nexera UC SFC; Column: Chiral IC, 4.6×150 mm, 5 micron; Mobile Phase: 55% CO2/45% MeOH w/0.1% DEA; Flow Conditions: 2 mL/min; Detector Wavelength: 220 nm. Preparative SFC chromatographic conditions: Instrument: Waters 100 Prep SFC; Column: Chiral IC, 21×250 mm. 5 micron; Mobile Phase: 55% CO2/45% MeOH w/0.1% DEA; Flow Rate: 60 mL/min; Detector Wavelength: 220 nm; Injection details: 1500 μL 7.4 mg dissolved in 3 mL MeOH. Fractions containing the first eluting isomer were combined and dried to afford the title compound 3-(2-amino-[1,2,4]triazolo[1,5-a]pyridin-7-yl)-2-fluoro-N-((1-((4-fluorophenyl)(hydroxy)methyl)cyclopropyl)methyl)-6-(methyl-d$_3$)benzamide enantiomer 1 (2.5 mg, 0.0053 mmol, 9% yield).

$^1$H NMR (500 MHz, DMSO-d$_6$) δ 8.61 (d, J=7.0 Hz, 1H), 8.45 (br t, J=5.5 Hz, 1H), 7.63-7.55 (m, 1H), 7.49 (s, 1H), 7.43 (br dd, J=8.1, 6.0 Hz, 2H), 7.22 (d, J=7.9 Hz, 1H), 7.15 (br t, J=8.9 Hz, 2H), 7.05 (br d, J=7.0 Hz, 1H), 6.06 (s, 2H), 5.38 (d, J=4.6 Hz, 1H), 4.57 (dt, J=4.2, 0.8 Hz, 1H), 3.44 (br d, J=6.7 Hz, 1H), 3.15 (br dd, J=13.7, 6.4 Hz, 1H), 0.65 (br d, J=8.2 Hz, 1H), 0.48 (s, 3H).

MS ESI m/z 467.1 (M+H)+

Example 308: 3-(2-amino-[1,2,4]triazolo[1,5-a]pyridin-7-yl)-2-fluoro-N-((1-((4-fluorophenyl)(hydroxy)methyl)cyclopropyl)methyl)-6-(methyl-d$_3$)benzamide

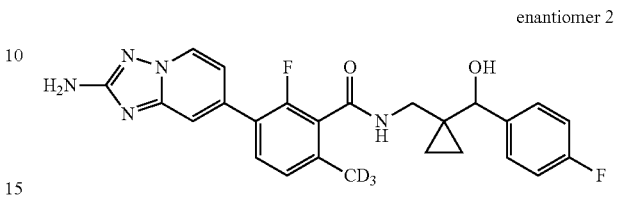

enantiomer 2

The title compound 3-(2-amino-[1,2,4]triazolo[1,5-a]pyridin-7-yl)-2-fluoro-N-((1-((4-fluorophenyl)(hydroxy)methyl)cyclopropyl)methyl)-6-(methyl-d$_3$)benzamide enantiomer 2 (2.6 mg, 0.0055 mmol, 9% yield). was obtained as the second eluting isomer from chiral SFC purification described for example 307.

$^1$H NMR (500 MHz, DMSO-d$_6$) δ 8.61 (d, J=7.0 Hz, 1H), 8.45 (br t, J=5.8 Hz, 1H), 7.57 (t, J=8.1 Hz, 1H), 7.49 (s, 1H), 7.43 (br dd, J=8.1, 6.0 Hz, 2H), 7.22 (d, J=7.9 Hz, 1H), 7.15 (br t, J=8.7 Hz, 2H), 7.05 (br d, J=6.7 Hz, 1H), 6.06 (s, 2H), 5.39 (d, J=4.6 Hz, 1H), 4.56 (br d, J=4.3 Hz, 1H), 3.45 (br d, J=5.8 Hz, 1H), 3.15 (br dd, J=13.7, 6.1 Hz, 1H), 0.68-0.62 (m, 1H), 0.52-0.43 (m, 3H).

MS ESI m/z 467.2 (M+H)+

Example 309: 3-(2-amino-[1,2,4]triazolo[1,5-a]pyridin-7-yl)-2-fluoro-N-((1-((4-fluorophenyl)(hydroxy)methyl-d)cyclopropyl)methyl)-6-(methyl-d$_3$)benzamide

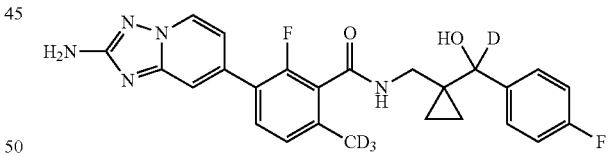

enantiomer 1

The title compound was prepared in a similar fashion to example 307, except NaBD$_4$ was used to replace NaBH$_4$ in Step 307C. Thus, was obtained 3-(2-amino-[1,2,4]triazolo[1,5-a]pyridin-7-yl)-2-fluoro-N-((1-((4-fluorophenyl)(hydroxy)methyl-d)cyclopropyl)methyl)-6-(methyl-d$_3$)benzamide enantiomer 1 (3.3 mg, 0.0070 mmol, 20% yield) as the first eluting isomer from chiral SFC purification.

$^1$H NMR (500 MHz, DMSO-d$_6$) δ 8.62 (d, J=6.7 Hz, 1H), 8.45 (br t, J=5.5 Hz, 1H), 7.59 (t, J=7.9 Hz, 1H), 7.49 (s, 1H), 7.43 (dd, J=8.5, 5.8 Hz, 2H), 7.22 (d, J=7.9 Hz, 1H), 7.15 (br t, J=8.9 Hz, 2H), 7.04 (br d, J=6.7 Hz, 1H), 6.11-6.03 (m, 2H), 0.66 (br d, J=9.5 Hz, 1H), 0.52-0.44 (m, 3H).

MS ESI m/z 468.3 (M+H)+

Example 310: 3-(2-amino-[1,2,4]triazolo[1,5-a]pyridin-7-yl)-2-fluoro-N-((1-((4-fluorophenyl)(hydroxy)methyl-d)cyclopropyl)methyl)-6-(methyl-d₃)benzamide

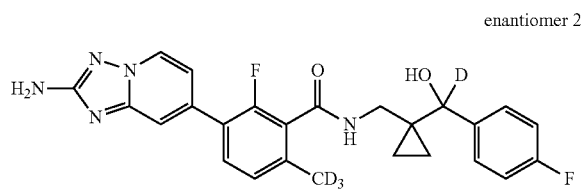

enantiomer 2

The title compound 3-(2-amino-[1,2,4]triazolo[1,5-a]pyridin-7-yl)-2-fluoro-N-((1-((4-fluorophenyl)(hydroxy)methyl-d)cyclopropyl)methyl)-6-(methyl-d₃)benzamide enantiomer 2 (3.1 mg, 0.0066 mmol, 19% yield) was obtained as the second eluting isomer from chiral SFC purification of example 309.

$^1$H NMR (500 MHz, DMSO-d$_6$) δ 8.61 (d, J=7.0 Hz, 1H), 8.45 (br t, J=5.8 Hz, 1H), 7.58 (br t, J=8.1 Hz, 1H), 7.49 (s, 1H), 7.43 (br dd, J=7.9, 6.1 Hz, 2H), 7.22 (d, J=7.9 Hz, 1H), 7.15 (br t, J=8.9 Hz, 2H), 7.05 (br d, J=7.0 Hz, 1H), 6.06 (s, 2H), 0.65 (br d, J=9.8 Hz, 1H), 0.52-0.44 (m, 3H).
MS ESI m/z 468.3 (M+H)$^+$

Example 311: 3-(2-amino-[1,2,4]triazolo[1,5-a]pyridin-7-yl)-6-chloro-N-(3-(4-(difluoromethyl)phenyl)-2,2-difluoro-3-hydroxypropyl-3-d)-2-fluorobenzamide

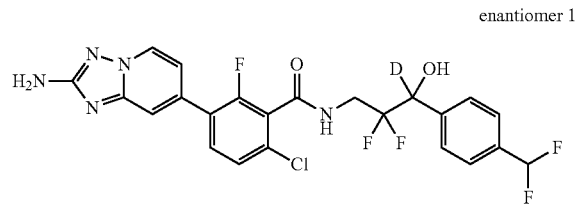 [SMILES: [2H]C(O)(c1ccc(C(F)F)cc1)C(F)(F)CNC(=O)c1c(Cl)ccc(-c2ccn3nc(N)nc3c2)c1F]

enantiomer 1

311A: (4-(difluoromethyl)phenyl)methan-d₂-ol: In a 40 mL sealed tube under nitrogen atmosphere, a mixture of 4-(difluoromethyl)benzoic acid (800 mg, 4.65 mmol) and sodium tetrahydroborate-d₄ (292 mg, 6.97 mmol) in THF (12 mL) was treated with a solution of BF₃OEt₂ (0.383 mL, 3.02 mmol) in THF (5 mL) at RT. The mixture was heated to reflux (65° C.) for 1.5 h until silica TLC indicated the completion of the reaction. The reaction mixture was cooled to 0° C. and quenched with water which resulted in vigorous gas evolution. The reaction mixture was vacuum filtered through a Celite pad. The filtrate was acidified by addition of 1N aqueous HCl dropwise while stirring. The acidified filtrate was diluted with 30 mL of EtOAc. The EtOAc solution was washed with saturated aqueous NaHCO₃ (2×20 mL) and brine (20 mL), dried over anhydrous Na₂SO₄, filtered concentrated under reduced pressure to get (4-(difluoromethyl)phenyl)methan-d₂-ol (650 mg, 4.05 mmol, 87% yield) as a slight green solid which was used in next step without further purification.

$^1$H NMR (499 MHz, CHLOROFORM-d) δ 8.23 (d, J=8.6 Hz, 1H), 7.66 (d, J=8.1 Hz, 1H), 7.58-7.42 (m, 2H), 6.90-6.51 (m, 1H).

311B: 4-difluorobenzaldehyde-di: (4-(difluoromethyl)phenyl)methan-d2-ol (650 mg, 4.06 mmol) was dissolved in DCM (10 mL) and pyridinium chlorochromate (3.01 g, 13.9 mmol) was added at 0° C. The mixture was stirred for 1.5 h from 0° C. to RT. The mixture was quenched by addition of saturated aqueous NaHCO₃ (15 mL) and then extracted with EtOAc (50 mL). The organic was then washed with brine (30 mL), dried over Na₂SO₄, filtered and concentrated under reduced pressure. The mixture was purified by silica gel chromatography (24 g silica, gradient EtOAc/Hexanes=0-50%, gradient time=12 min, flow rate 30 mL/min). Thus, was obtained 4-difluorobenzaldehyde-di (469 mg, 2.61 mmol, 64% yield).

$^1$H NMR (499 MHz, CHLOROFORM-d) δ 8.06-7.92 (m, 2H), 7.72 (d, J=8.0 Hz, 2H), 6.92-6.52 (m, 1H).
MS ESI m/z 158.2 (M+H)$^+$

311: The title compound was prepared in a similar fashion to example 110, where 4-difluorobenzaldehyde-di was used to replace 3,4-dichlorobenzaldehyde in Step 110A. Thus, was obtained 3-(2-amino-[1,2,4]triazolo[1,5-a]pyridin-7-yl)-6-chloro-N-(3-(4-(difluoromethyl)phenyl)-2,2-difluoro-3-hydroxypropyl-3-d)-2-fluorobenzamide enantiomer 1 (28.2 mg, 0.0535 mmol, 33% yield) as the first eluting isomer from chiral SFC purification.

$^1$H NMR (500 MHz, DMSO-d$_6$) δ 9.19 (br t, J=6.0 Hz, 1H), 8.63 (d, J=6.7 Hz, 1H), 8.34 (s, 1H), 7.79-7.70 (m, 1H), 7.60 (s, 4H), 7.55-7.48 (m, 2H), 7.20-6.93 (m, 2H), 6.11 (s, 1H).
MS ESI m/z 527.3 (M+H)$^+$.

Example 312: 3-(2-amino-[1,2,4]triazolo[1,5-a]pyridin-7-yl)-6-chloro-N-(3-(4-(difluoromethyl)phenyl)-2,2-difluoro-3-hydroxypropyl-3-d)-2-fluorobenzamide

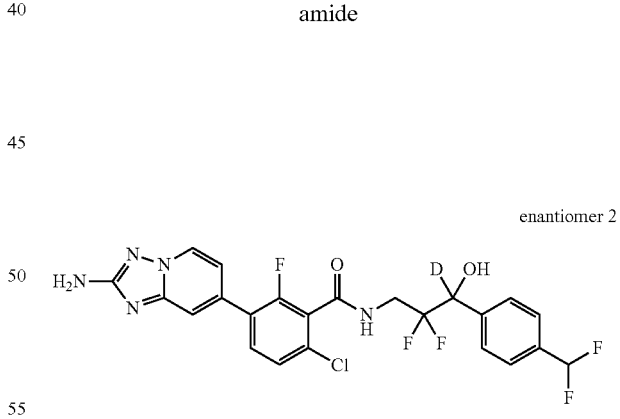

enantiomer 2

The title compound 3-(2-amino-[1,2,4]triazolo[1,5-a]pyridin-7-yl)-6-chloro-N-(3-(4-(difluoromethyl)phenyl)-2,2-difluoro-3-hydroxypropyl-3-d)-2-fluorobenzamide enantiomer 2 (30.8 mg, 0.0584 mmol, 36% yield) was obtained as the second eluting isomer from chiral SFC purification of example 311.

$^1$H NMR (500 MHz, DMSO-d$_6$) δ 9.20 (br t, J=6.0 Hz, 1H), 8.68-8.60 (m, 1H), 8.38 (s, 1H), 7.74 (t, J=8.4 Hz, 1H), 7.59 (s, 4H), 7.55-7.49 (m, 2H), 7.18-6.91 (m, 2H), 6.11 (s, 1H).
MS ESI m/z 527.3 (M+H)$^+$.

293

Example 313: 3-(2-amino-[1,2,4]triazolo[1,5-a]pyridin-7-yl)-6-chloro-N-(2,2-difluoro-3-(4-fluorophenyl)-3-hydroxypentyl)-2-fluorobenzamide enantiomer 1

The title compound was prepared in a similar fashion to example 110 using 1-(4-fluorophenyl)propane-1-one in place of 3,4-dichlorobenzaldehyde in Step 110A. Thus, was obtained 3-(2-amino-[1,2,4]triazolo[1,5-a]pyridin-7-yl)-6-chloro-N-(2,2-difluoro-3-(4-fluorophenyl)-3-hydroxypentyl)-2-fluorobenzamide enantiomer 1 (9.1 mg, 0.0174 mmol, 18% yield) as the first eluting isomer from chiral SFC purification.

$^1$H NMR (500 MHz, DMSO-$d_6$) δ 8.99 (br t, J=6.1 Hz, 1H), 8.63 (d, J=7.0 Hz, 1H), 7.72 (t, J=8.4 Hz, 1H), 7.55 (br dd, J=7.9, 6.1 Hz, 2H), 7.52-7.42 (m, 2H), 7.22 (t, J=8.9 Hz, 2H), 7.03 (br d, J=7.0 Hz, 1H), 6.10 (s, 2H), 4.03-3.82 (m, 1H), 2.19-1.97 (m, 2H), 0.62 (t, J=7.2 Hz, 3H).

MS ESI m/z 522.0 (M+H)$^+$

Example 314: 3-(2-amino-[1,2,4]triazolo[1,5-a]pyridin-7-yl)-6-chloro-N-(2,2-difluoro-3-(4-fluorophenyl)-3-hydroxypentyl)-2-fluorobenzamide enantiomer 2

The title compound 3-(2-amino-[1,2,4]triazolo[1,5-a]pyridin-7-yl)-6-chloro-N-(2,2-difluoro-3-(4-fluorophenyl)-3-hydroxypentyl)-2-fluorobenzamide enantiomer 2 (10.2 mg, 0.0195 mmol, 20% yield) was obtained as the second eluting isomer from chiral SFC purification of example 313.

$^1$H NMR (500 MHz, DMSO-$d_6$) δ 9.03-8.94 (m, 1H), 8.62 (d, J=7.0 Hz, 1H), 7.72 (t, J=8.2 Hz, 1H), 7.59-7.53 (m, 2H), 7.51-7.44 (m, 2H), 7.22 (t, J=8.7 Hz, 2H), 7.03 (br d, J=6.7 Hz, 1H), 6.10 (s, 2H), 4.00-3.84 (m, 1H), 2.20-2.10 (m, 1H), 2.06-1.96 (m, 1H), 0.62 (t, J=7.2 Hz, 3H).

MS ESI m/z 522.1 (M+H)$^+$

294

Example 315: (S)-3-(2-amino-[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide

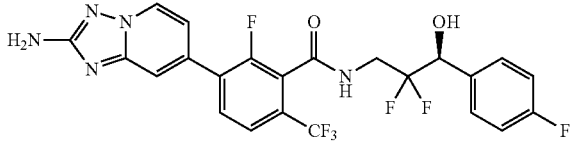 [SMILES: Nc1nc2cc(-c3ccc(C(F)(F)F)c(C(=O)NCC(F)(F)[C@@H](O)c4ccc(F)cc4)c3F)ccn2n1]

315A: (S)-3-(2-amino-[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide: To a dry 100 mL round bottom flask under N2 was added 3-bromo-2-fluoro-6-(trifluoromethyl)benzoic acid (1.0 g, 3.48 mmol), (S)-3-amino-2,2-difluoro-1-(4-fluorophenyl)propan-1-ol (720 mg, 3.51 mmol), anhydrous CH2Cl2 (25 mL) and N,N-diisopropylethylamine (3.0 ml, 17.18 mmol). The reaction (a colorless solution) was flushed briefly with N2, treated with BOP (1.90 g, 4.30 mmol), capped and allowed to stir at room temperature overnight. The mixture was concentrated under vacuum and purified by silica gel chromatography eluting with EtOAc/hexanes to obtain (S)-3-(2-amino-[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide (1.63 g, 3.45 mmol, 99% yield) as a foamy white solid.

1H NMR (500 MHz, DMSO-$d_6$) δ 9.14 (br s, 1H), 8.02 (br t, J=7.6 Hz, 1H), 7.60 (d, J=8.5 Hz, 1H), 7.48 (br t, J=6.5 Hz, 2H), 7.31-7.14 (m, 2H), 6.41 (br s, 1H), 4.91 (br dd, J=16.0, 6.1 Hz, 1H), 3.94-3.71 (m, 2H).

315: (S)-3-(2-amino-[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide: To a dry reaction vial under N2 was added (S)-3-bromo-N-(2,2-difluoro-3-(4-fluorophenyl)-3-hydroxypropyl)-2-fluoro-6-(trifluoromethyl)benzamide (75 mg, 0.158 mmol), (S)-3-bromo-N-(2,2-difluoro-3-(4-fluorophenyl)-3-hydroxypropyl)-2-fluoro-6-(trifluoromethyl)benzamide (75 mg, 0.158 mmol) and anhydrous 1,4-dioxane (1.5 mL). The reaction was flushed well with argon, treated with potassium acetate, 2M in water (240 μL, 0.480 mmol), followed by dichloro 1,1'-bis(diphenylphosphino)ferrocene palladium (II) dichloromethane, 99% (13 mg, 0.016 mmol). The reaction was flushed well with argon, securely capped and placed in an 80° C. oil bath and stirred for 4 h. The mixture was then cooled to room temperature and concentrated under reduced pressure. The residue was dissolve reside in EtOAc (25 mL) and the organic layer washed with water (2×5 mL), brine (1×5 mL), dried over Na2SO4, filter and evaporate to dryness. The residue was purified by silica gel chromatography eluting with EtOAc/CH2Cl2 to obtain bis-Boc (S)-3-(2-amino-[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide.

The material (98 mg) was dissolved in MeOH (1 mL), treated with HCl, 4M in dioxane (2 mL, 8.00 mmol) and placed in a 80° C. sand bath and stirred for 90 min. The mixture was concentrated and the residue purified via preparative LC/MS on a XBridge C18 column eluting with acetonitrile:water with 10-mM ammonium acetate. Fractions containing the desired product were combined and dried via centrifugal evaporation to afford (S)-3-(2-amino-

[1,2,4]triazolo[1,5-a]pyridin-7-yl)-N-(2,2-difluoro-3-(4-fluorophenyl)-3-hydroxypropyl)-2-fluoro-6-(trifluoromethyl)benzamide (43.1 mg, 0.082 mmol, 52% yield over two steps).

1H NMR (500 MHz, DMSO-d6) Shift 9.12 (br t, J=6.1 Hz, 1H), 8.67 (br d, J=7.0 Hz, 1H), 7.93 (br t, J=7.6 Hz, 1H), 7.75 (d, J=8.4 Hz, 1H), 7.59 (s, 1H), 7.48 (br t, J=6.5 Hz, 2H), 7.22 (t, J=8.8 Hz, 2H), 7.08 (br d, J=6.8 Hz, 1H), 6.40 (br d, J=5.1 Hz, 1H), 5.05-4.81 (m, 1H), 3.95-3.72 (m, 2H), 3.14-2.76 (br s, 2H).
MS ESI m/z 528.0 (M+H)+

Example 316: 3-(2-amino-[1,2,4]triazolo[1,5-a]pyridin-7-yl)-N-(3-phenylbutyl)benzamide

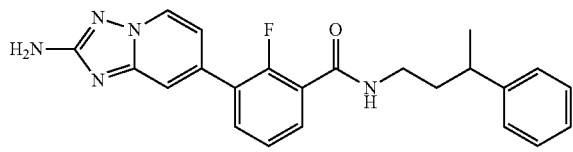 [SMILES: CC(CCNC(=O)c1cccc(-c2ccn3nc(N)nc3c2)c1F)c1ccccc1]

316A: N-(3-phenylbutyl)-3-(4,4,5,5-tetramethyl-1,3,2-dioxaborolan-2-yl)benzamide: To a solution of 3-carboxyphenylboronic acid pinacol ester (1.0 g, 4.03 mmol), 3-phenylbutan-1-amine (0.602 g, 4.03 mmol) and DIPEA (0.880 mL, 5.04 mmol) in DMF (15 mL) was added BOP (2.228 g, 5.04 mmol). The mixture was then stirred at 23° C. for 1 h. The reaction mixture was diluted with 150 mL of EtOAc and washed with 10% LiCl solution (2×50 mL), water (50 mL), brine (50 mL), then and dried over Na2SO4. The mixture was filtered and concentrated under reduced pressure. The crude material was purified via silica gel column chromatography eluting with CH2Cl2/EtOAc (10/1) to afford N-(3-phenylbutyl)-3-(4,4,5,5-tetramethyl-1,3,2-dioxaborolan-2-yl)benzamide (1.13 g, 2.99 mmol, 74% yield).
MS ESI m/z 380.1 (M+H)+

316: 3-(2-amino-[1,2,4]triazolo[1,5-a]pyridin-7-yl)-N-(3-phenylbutyl)benzamide: To a solution of N-(3-phenylbutyl)-3-(4,4,5,5-tetramethyl-1,3,2-dioxaborolan-2-yl)benzamide (15 mg, 0.040 mmol) in dioxane (400 µL) was added 7-bromo-[1,2,4]triazolo[1,5-a]pyridin-2-amine (16.85 mg, 0.079 mmol), PdCl2 (dppf)-CH2Cl2 adduct (3.23 mg, 3.95 µmol), and tripotassium phosphate (25.2 mg, 0.119 mmol). The reaction mixture was capped and degasses and purged with N2. The reaction vessel was then heated to 100° C. for 1 h. The mixture was cooled to room temperature then purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-70% B over 20 minutes, then a 5-minute hold at 100% B; Flow: 20 mL/min. Fractions containing the desired product were combined and dried via centrifugal evaporation to give 3-(2-amino-[1,2,4]triazolo[1,5-a]pyridin-7-yl)-N-(3-phenylbutyl)benzamide (10.6 mg, 0.027 mmol, 70% yield).

$^1$H NMR (500 MHz, DMSO-d$_6$) δ 8.72-8.55 (m, 2H), 8.20 (s, 1H), 7.96 (br d, J=7.7 Hz, 1H), 7.87 (br d, J=7.7 Hz, 1H), 7.75 (s, 1H), 7.59 (t, J=7.7 Hz, 1H), 7.41-7.24 (m, 5H), 7.23-7.15 (m, 1H), 3.31-3.21 (m, 1H), 3.20-3.09 (m, 1H), 2.88-2.75 (m, 1H), 1.86 (q, J=7.3 Hz, 2H), 1.25 (br d, J=6.8 Hz, 3H), 2 exchangeable protons not observed.

WO2018/148626 discloses compounds which are useful as receptor interacting protein kinase 1 (RIPK1) inhibitors. Table 22 shows compounds of the present invention and their activity in the RIPK1 and pMLKL assays. The activity in the RIPK1 and pMLKL assays of representative compounds from WO2018/148626 are shown in Table 23.

Preferred compounds have improved RIPK1 activity, improved pMLKL activity, or a combination of improved activity in both assays.
Tables 22 and 23: Show the pMLKL Activity of Compounds of the Present Invention and Compounds Described in WO2018/148626

TABLE 22

| Structure | Ex | RIPK1 IC$_{50}$ (nM) | pMLKL IC$_{50}$ (nM) |
|---|---|---|---|
| isomer 1 | 9 | 6.2 | 2.4 |
| isomer 2 | 10 | 9.4 | 2.5 |

TABLE 22-continued

| Structure | Ex | RIPK1 IC$_{50}$ (nM) | pMLKL IC$_{50}$ (nM) |
| --- | --- | --- | --- |
| racemate 1 | 19 | | 7.7 |
| racemate 2 | 20 | | 3.6 |
| racemate | 46 | 1.9 | 2.4 |
| racemate | 49 | 2.5 | 2.6 |
| isomer 1 | 66 | | 1.2 |
| isomer 2 | 67 | 4.4 | 1.3 |
| racemate | 78 | 19 | 9.9 |

TABLE 22-continued

| Structure | Ex | RIPK1 IC$_{50}$ (nM) | pMLKL IC$_{50}$ (nM) |
|---|---|---|---|
| (racemate) | 92 | | 11 |
| 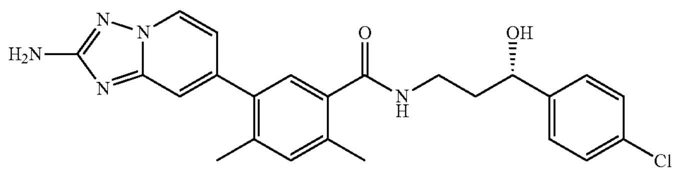 [SMILES: Cc1cc(C)c(-c2ccn3nc(N)nc3c2)cc1C(=O)NCC[C@H](O)c1ccc(Cl)cc1] | 146 | 0.6 | 2.4 |
| 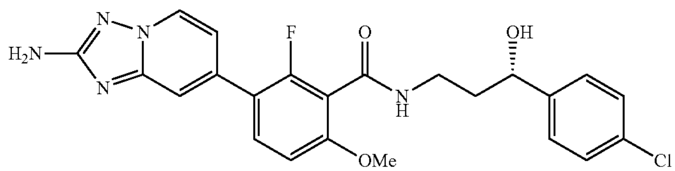 [SMILES: COc1ccc(-c2ccn3nc(N)nc3c2)c(F)c1C(=O)NCC[C@H](O)c1ccc(Cl)cc1] | 147 | 9.4 | 21 |
| 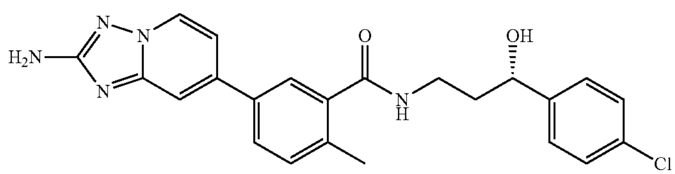 [SMILES: Cc1ccc(-c2ccn3nc(N)nc3c2)cc1C(=O)NCC[C@H](O)c1ccc(Cl)cc1] | 149 | 8.2 | 1.3 |
| 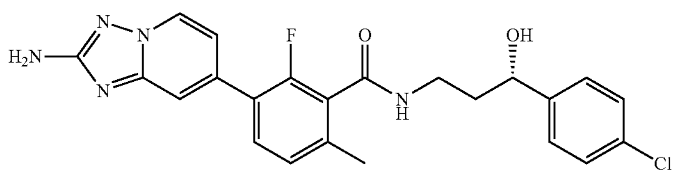 [SMILES: Cc1ccc(-c2ccn3nc(N)nc3c2)c(F)c1C(=O)NCC[C@H](O)c1ccc(Cl)cc1] | 151 | 3.5 | 0.8 |
| 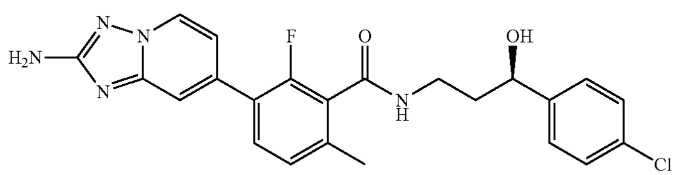 [SMILES: Cc1ccc(-c2ccn3nc(N)nc3c2)c(F)c1C(=O)NCC[C@@H](O)c1ccc(Cl)cc1] | 152 | 2.3 | 0.5 |
| 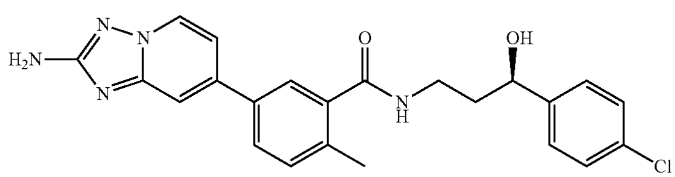 [SMILES: Cc1ccc(-c2ccn3nc(N)nc3c2)cc1C(=O)NCC[C@@H](O)c1ccc(Cl)cc1] | 159 | 2.5 | 1.9 |
| (racemate) | 279 | | 8.3 |

TABLE 22-continued
| Structure | Ex | RIPK1 IC$_{50}$ (nM) | pMLKL IC$_{50}$ (nM) |
|---|---|---|---|
| 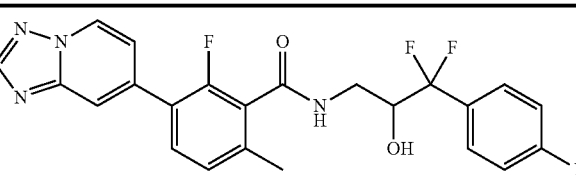 isomer 1 | 290 | 4.8 | 0.5 |
| 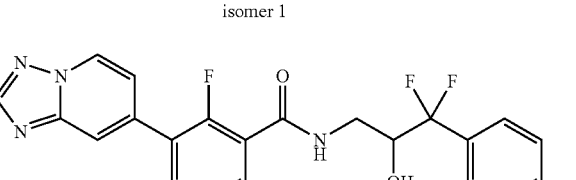 isomer 2 | 291 | 1.0 | 2.4 |
| 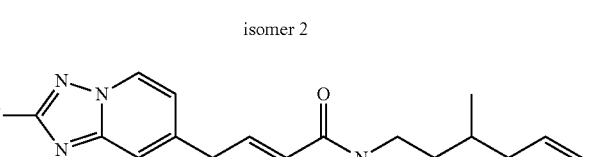 racemate | 316 | 8.5 | 25 |
TABLE 23
| Structure | Compound from WO2018/148626 | RIPK1 IC$_{50}$ (nM) | pMLKL IC$_{50}$ nM) |
|---|---|---|---|
| 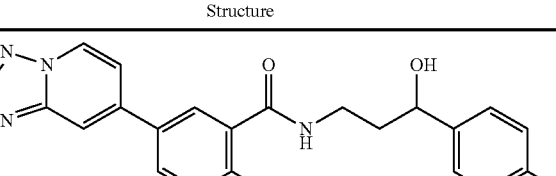 racemate | 78 | 120 | 146 |
| 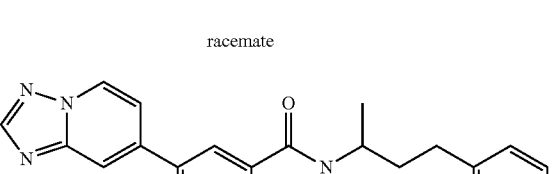 racemate | 101 | | 82 |
| 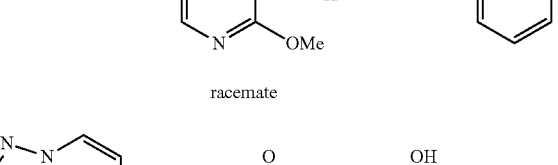 racemate | 75 | 290 | 146 |

TABLE 23-continued

| Structure | Compound from WO2018/ 148626 | RIPK1 IC$_{50}$ (nM) | pMLKL IC$_{50}$ nM) |
|---|---|---|---|
| (racemate, triazolopyridine-aminopyridine-methoxy-carboxamide with 3,4-difluorophenyl-hydroxypropyl) | 77 | 60 | 120 |
| (racemate, triazolopyridine-methylpyridine-carboxamide with 3-phenylbutyl) | 82 | 5.8 | 23 |
| (racemate, triazolopyridine-chloropyridine-carboxamide with 3-phenylbutyl) | 170 | | 48 |
| (triazolopyridine-dimethylpyridine-carboxamide with (S)-hydroxy-4-chlorophenylpropyl) | 179 | 17 | 55 |
| (triazolopyridine-methoxypyridine-carboxamide with (S)-hydroxy-4-chlorophenylpropyl) | 157 | 59 | 115 |
| (triazolopyridine-methyl-methoxypyridine-carboxamide with (S)-hydroxy-4-chlorophenylpropyl) | 193 | 47 | 63 |
| (triazolopyridine-methylpyridine-carboxamide with (S)-hydroxy-4-chlorophenylpropyl) | 225 | 37 | 180 |

TABLE 23-continued

| Structure | Compound from WO2018/ 148626 | RIPK1 IC$_{50}$ (nM) | pMLKL IC$_{50}$ nM) |
|---|---|---|---|
| 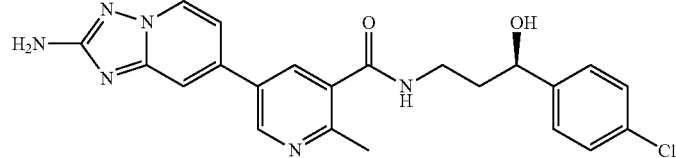 [SMILES: Cc1ncc(-c2ccn3nc(N)nc3c2)cc1C(=O)NCC[C@@H](O)c1ccc(Cl)cc1] | 224 | 17 | 97 |
| 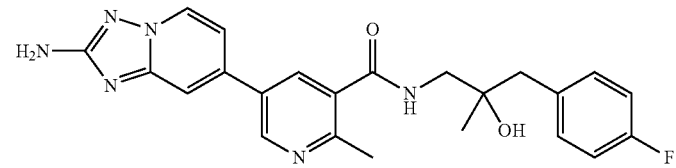 racemate | 421 | 110 | 315 |
| 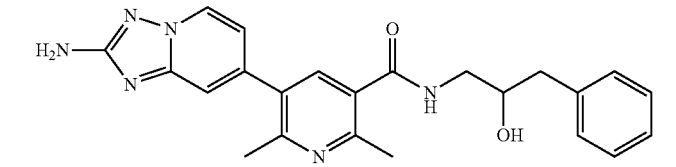 racemate | 174 | 48 | 205 |
| 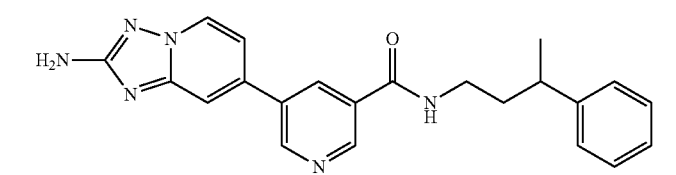 racemate | 73 | 24 | 246 |

What is claimed is:

1. A compound having formula (I), or salt thereof,

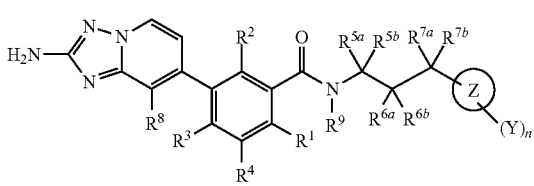

(I)

wherein

R$^1$ is H, C$_{1-3}$ alkyl, C$_{1-3}$ alkoxy, C$_{1-3}$ haloalkyl, C$_{1-3}$ haloalkoxy, C$_{1-3}$ deuteroalkyl, C$_{1-3}$ deuteroalkoxy, halo, or cyclopropyl;
R$^2$ is H, or halo;
R$^3$ is H, halo, C$_{1-3}$ alkyl or C$_{1-3}$ deuteroalkyl;
R$^4$ is H or F;
R$^{5a}$ and R$^{5b}$ are each H;
one of R$^{6a}$ and R$^{6b}$ is H and the other is F;
R$^{7a}$ and R$^{7b}$ are each, independently, H, deuterium, OH, F, C$_{1-2}$ alkyl, or C$_{1-2}$ haloalkyl;

R$^8$ is H, F, Cl, C$_{1-3}$ alkyl, C$_{1-3}$ alkoxy, C$_{1-3}$ deuteroalkyl, or C$_{1-3}$ deuteroalkoxy;
R$^9$ is H or CH$_3$;
ring Z is phenyl;
Y is F, Cl, C$_{1-3}$ alkyl, C$_{1-3}$ alkoxy, CN, C$_{1-3}$ haloalkyl, C$_{1-3}$ haloalkoxy, C$_{1-3}$ deuteroalkyl, C$_{1-3}$ deuteroalkoxy, C(O)OCH$_3$, or C≡CH; and
n is 0, 1, 2, or 3.

2. A compound of claim 1, wherein the compound has formula (II), or salt thereof,

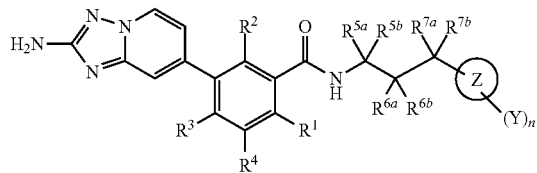

(II)

wherein
R$^1$ is H, C$_{1-3}$ alkyl, C$_{1-3}$ alkoxy, C$_{1-3}$ haloalkyl, C$_{1-3}$ deuteroalkyl, halo, or cyclopropyl;
R$^2$ is H, or halo;

R³ is H, halo, C₁₋₃ alkyl, or C₁₋₃ deuteroalkyl;
R⁴ is H or F;
R⁵ᵃ and R⁵ᵇ are each H;
one of R⁶ᵃ and R⁶ᵇ is H and the other is F;
R⁷ᵃ and R⁷ᵇ are each, independently, H, deuterium, OH, F, C₁₋₂ alkyl or C₁₋₂ haloalkyl;
ring Z is phenyl;
Y is F, Cl, C₁₋₃ alkyl, C₁₋₃ alkoxy, CN, or C₁₋₃ haloalkyl;
n is 0, 1, or 2.

3. A compound of claim 2, or salt thereof, wherein
R¹ is H, C₁₋₂ alkyl, C₁₋₂ alkoxy, CD3, halo, or cyclopropyl;
R² is H, or halo;
R³ is H, halo, or C₁₋₂ alkyl;
R⁴ is H or F;
R⁵ᵃ and R⁵ᵇ are each H;
one R⁶ᵃ and R⁶ᵇ is H and the other is F;
R⁷ᵃ and R⁷ᵇ are each, independently, H, deuterium, OH, F, C₁₋₂ alkyl or C₁₋₂ haloalkyl;
Y is F, Cl, C₁₋₂ alkyl, C₁₋₂ alkoxy, CN, or C₁₋₂ haloalkyl; and
n is 0, 1, or 2.

4. A compound of claim 2, or salt thereof, wherein
R¹ is C₁₋₂ alkyl, C₁₋₂ deuteroalkyl, C₁₋₂ haloalkyl, or halo;
R² is H, or halo;
R³ is H, halo, or C₁₋₂ alkyl;
R⁴ is H or F;
R⁵ᵃ and R⁵ᵇ are each H;
one of R⁶ᵃ and R⁶ᵇ is H and the other is F;
R⁷ᵃ and R⁷ᵇ are each, independently, H, deuterium, OH, F, C₁₋₂ alkyl or C₁₋₂ haloalkyl;
Y is F, Cl, C₁₋₂ alkyl, CN, or C₁₋₂ haloalkyl; and
n is 0, 1, or 2.

5. A compound of claim 3, or salt thereof, wherein
R¹ is Cl or CH₃;
R² is H, or F;
R³ is H, or F;
R⁴ is H;
R⁵ᵃ and R⁵ᵇ are each H;
R⁶ᵃ and R⁶ᵇ are each, independently, H, or F;
R⁷ᵃ and R⁷ᵇ are each, independently, H, methyl, or OH;
Y is F or Cl; and
n is 0, 1, or 2.

6. A compound of claim 3, or salt thereof, wherein

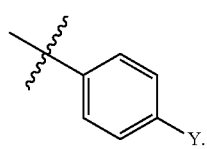

7. A compound of claim 1, or salt thereof, wherein the compound of Formula (I) is a compound of Formula (Ie), (If), or (Ig),

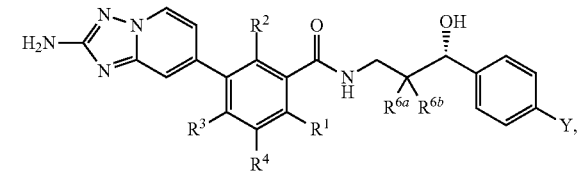

(Ie)

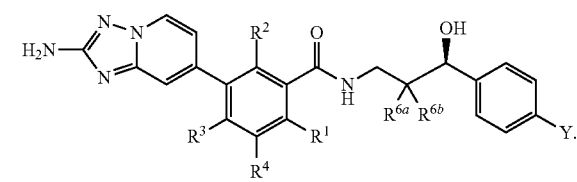

(If)

(Ig)

8. A compound of claim 1, or salt thereof, wherein the compound of Formula (I) is a compound of Formula (Ii), (Ij), (Ik), (Il), or (Im)

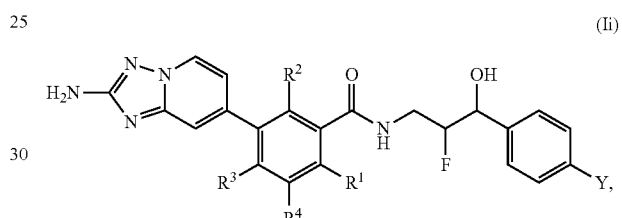

(Ii)

(Ij)

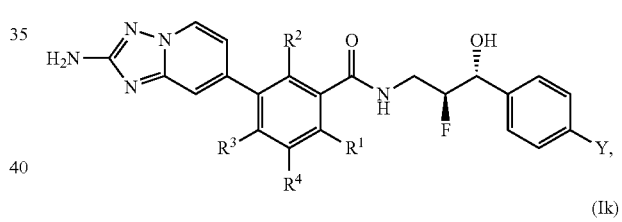

(Ik)

(Il)

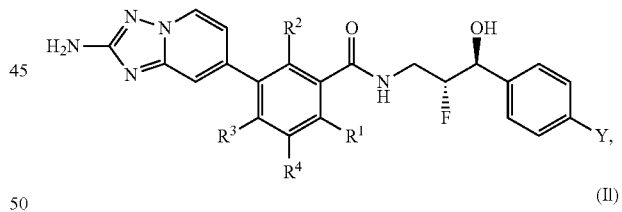

(Im)

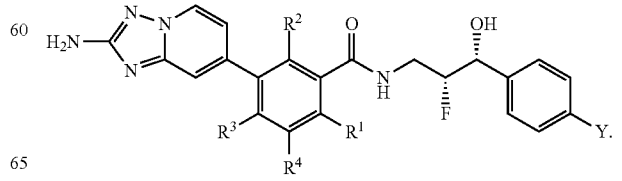

9. A compound, or salt thereof, wherein the compound is selected from

- 3-(2-amino-[1,2,4]triazolo[1,5-a]pyridin-7-yl)-6-chloro-N-(3-(4-chlorophenyl)-2-fluoro-3-hydroxypropyl)-2-fluorobenzamide;
- 3-(2-amino-[1,2,4]triazolo[1,5-a]pyridin-7-yl)-6-chloro-2-fluoro-N-((2S,3S)-2-fluoro-3-(4-fluorophenyl)-3-hydroxybutyl)benzamide;
- 3-(2-amino-[1,2,4]triazolo[1,5-a]pyridin-7-yl)-6-chloro-2-fluoro-N-((2R,3R)-2-fluoro-3-(4-fluorophenyl)-3-hydroxybutyl)benzamide;
- 3-(2-amino-[1,2,4]triazolo[1,5-a]pyridin-7-yl)-6-chloro-2-fluoro-N-((2S,3R)-2-fluoro-3-(4-fluorophenyl)-3-hydroxybutyl)benzamide;
- 3-(2-amino-[1,2,4]triazolo[1,5-a]pyridin-7-yl)-6-chloro-2-fluoro-N-((2R,3S)-2-fluoro-3-(4-fluorophenyl)-3-hydroxybutyl)benzamide;
- 3-(2-amino-[1,2,4]triazolo[1,5-a]pyridin-7-yl)-2-fluoro-N-((2S,3S)-2-fluoro-3-(4-fluorophenyl)-3-hydroxybutyl)-6-(methyl-d$_3$)benzamide;
- 3-(2-amino-[1,2,4]triazolo[1,5-a]pyridin-7-yl)-2-fluoro-N-((2R,3R)-2-fluoro-3-(4-fluorophenyl)-3-hydroxybutyl)-6-(methyl-d$_3$)benzamide;
- 3-(2-amino-[1,2,4]triazolo[1,5-a]pyridin-7-yl)-2-fluoro-N-((2S,3R)-2-fluoro-3-(4-fluorophenyl)-3-hydroxybutyl)-6-(methyl-d$_3$)benzamide;
- 3-(2-amino-[1,2,4]triazolo[1,5-a]pyridin-7-yl)-2-fluoro-N-((2R,3S)-2-fluoro-3-(4-fluorophenyl)-3-hydroxybutyl)-6-(methyl-d$_3$)benzamide;
- 3-(2-amino-[1,2,4]triazolo[1,5-a]pyridin-7-yl)-6-chloro-2-fluoro-N-((2S,3S)-2-fluoro-3-(4-fluorophenyl)-3-hydroxypropyl)benzamide;
- 3-(2-amino-[1,2,4]triazolo[1,5-a]pyridin-7-yl)-6-chloro-2-fluoro-N-((2R,3R)-2-fluoro-3-(4-fluorophenyl)-3-hydroxypropyl)benzamide;
- 3-(2-amino-[1,2,4]triazolo[1,5-a]pyridin-7-yl)-6-chloro-2-fluoro-N-((2R,3S)-2-fluoro-3-(4-fluorophenyl)-3-hydroxypropyl)benzamide;
- 3-(2-amino-[1,2,4]triazolo[1,5-a]pyridin-7-yl)-6-chloro-2-fluoro-N-((2S,3R)-2-fluoro-3-(4-fluorophenyl)-3-hydroxypropyl)benzamide;
- 3-(2-amino-[1,2,4]triazolo[1,5-a]pyridin-7-yl)-N-((2R,3S)-3-(4-chlorophenyl)-2-fluoro-3-hydroxypropyl)-2-fluoro-6-methylbenzamide;
- 3-(2-amino-[1,2,4]triazolo[1,5-a]pyridin-7-yl)-N-((2S,3R)-3-(4-chlorophenyl)-2-fluoro-3-hydroxypropyl)-2-fluoro-6-methylbenzamide;
- 3-(2-amino-[1,2,4]triazolo[1,5-a]pyridin-7-yl)-N-((2S,3S)-3-(4-chlorophenyl)-2-fluoro-3-hydroxypropyl)-2-fluoro-6-methylbenzamide; and
- 3-(2-amino-[1,2,4]triazolo[1,5-a]pyridin-7-yl)-N-((2R,3R)-3-(4-chlorophenyl)-2-fluoro-3-hydroxypropyl)-2-fluoro-6-methylbenzamide.

10. A pharmaceutical composition comprising one or more compounds of claim 1, or pharmaceutically acceptable salt thereof, and a pharmaceutically acceptable carrier.

11. A method of inhibiting casein kinase RIPK1 activity in a patient, comprising administering to the patient in need thereof, a therapeutically effective amount of one or more compounds according to claim 1.

12. A method for treating a disease comprising the administration to a subject in need thereof a therapeutically-effective amount of at least one compound of claim 1, wherein the disease is selected from inflammatory bowel disease, ulcerative colitis, Crohn's disease, psoriasis, rheumatoid arthritis (RA), NASH, and heart failure.

13. A method for treating a disease comprising the administration to a subject in need thereof a therapeutically-effective amount of at least one compound of claim 1, wherein the disease is selected from multiple sclerosis, amyotrophic lateral sclerosis, or alzheimers.

14. A method for treating a disease comprising the administration to a subject in need thereof a therapeutically-effective amount of at least one compound of claim 1, wherein the disease is selected from inflammatory bowel disease, ulcerative colitis, and Crohn's disease.

\* \* \* \* \*